United States Patent
Buesking et al.

(10) Patent No.: US 12,030,885 B2
(45) Date of Patent: Jul. 9, 2024

(54) SUBSTITUTED IMIDAZO[2,1-F][1,2,4]TRIAZINES AS PI3K-GAMMA INHIBITORS

(71) Applicant: Incyte Corporation, Wilmington, DE (US)

(72) Inventors: Andrew W. Buesking, Wilmington, DE (US); Richard B. Sparks, Wilmington, DE (US); Andrew P. Combs, Kennett Square, PA (US); Brent Douty, Fallowfield, PA (US); Nikoo Falahatpisheh, Wilmington, DE (US); Lixin Shao, Wilmington, DE (US); Stacey Shepard, Wilmington, DE (US); Eddy W. Yue, Landenberg, PA (US); Artem Shvartsbart, Kennett Square, PA (US); David M. Burns, Plymouth Meeting, PA (US); Daniel Levy, Philadelphia, PA (US)

(73) Assignee: Incyte Corporation, Wilmington, DE (US)

( * ) Notice: Subject to any disclaimer, the term of this patent is extended or adjusted under 35 U.S.C. 154(b) by 246 days.

(21) Appl. No.: 17/183,253

(22) Filed: Feb. 23, 2021

(65) Prior Publication Data
US 2022/0251087 A1   Aug. 11, 2022

Related U.S. Application Data

(60) Continuation of application No. 16/591,017, filed on Oct. 2, 2019, now Pat. No. 10,975,088, which is a continuation of application No. 16/165,390, filed on Oct. 19, 2018, now Pat. No. 10,479,795, which is a division of application No. 15/631,417, filed on Jun. 23, 2017, now Pat. No. 10,138,248.

(60) Provisional application No. 62/354,509, filed on Jun. 24, 2016.

(51) Int. Cl.
| | |
|---|---|
| *A61K 31/53* | (2006.01) |
| *C07D 471/04* | (2006.01) |
| *C07D 487/04* | (2006.01) |
| *C07D 519/00* | (2006.01) |

(52) U.S. Cl.
CPC ......... *C07D 487/04* (2013.01); *C07D 471/04* (2013.01); *C07D 519/00* (2013.01); *C07B 2200/13* (2013.01)

(58) Field of Classification Search
CPC ............... A61K 31/53; C07D 487/04
USPC ......... 514/243; 544/184
See application file for complete search history.

(56) References Cited

U.S. PATENT DOCUMENTS

| | | |
|---|---|---|
| 4,269,846 A | 5/1981 | Huang et al. |
| 5,521,184 A | 5/1996 | Zimmermann |
| 7,186,832 B2 | 3/2007 | Sun |
| 7,511,145 B2 | 3/2009 | Schmitz et al. |
| 8,680,108 B2 | 3/2014 | Li et al. |
| 8,759,359 B2 | 6/2014 | Combs et al. |
| 8,940,752 B2 | 1/2015 | Li et al. |
| 9,062,055 B2 | 6/2015 | Li et al. |
| 9,096,600 B2 | 8/2015 | Li et al. |
| 9,108,984 B2 | 8/2015 | Combs et al. |
| 9,126,948 B2 | 9/2015 | Combs et al. |
| 9,193,721 B2 | 11/2015 | Combs et al. |
| 9,199,982 B2 | 12/2015 | Li et al. |
| 9,586,949 B2 | 3/2017 | Zou et al. |
| 10,022,387 B2 | 7/2018 | Zou et al. |
| 10,065,963 B2 | 9/2018 | Shvartsbart et al. |
| 10,138,248 B2 | 11/2018 | Buesking et al. |
| 10,472,368 B2 | 11/2019 | Shvartsbart et al. |
| 10,479,795 B2 | 11/2019 | Buesking et al. |
| 10,596,184 B2 | 3/2020 | Zou et al. |
| 10,975,088 B2 | 4/2021 | Buesking et al. |
| 11,091,491 B2 | 8/2021 | Shvartsbart et al. |
| 11,352,340 B2 | 6/2022 | Sparks et al. |

(Continued)

FOREIGN PATENT DOCUMENTS

| | | |
|---|---|---|
| EP | 2044051 | 1/2010 |
| JP | 2015-512940 | 4/2015 |

(Continued)

OTHER PUBLICATIONS

European Office Action in European Application No. 20187907.9, dated Jun. 27, 2022, 3 pages.

(Continued)

*Primary Examiner* — Douglas M Willis
(74) *Attorney, Agent, or Firm* — Fish & Richardson P.C.

(57) ABSTRACT

This application relates to compounds of Formula (I):

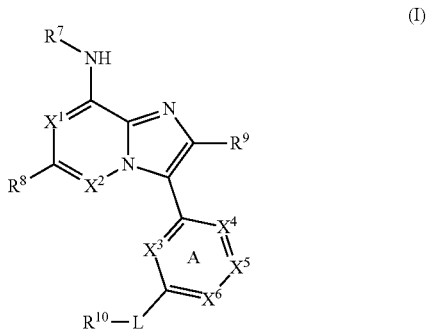

or pharmaceutically acceptable salts or stereoisomers thereof, which are inhibitors of PI3K-γ which are useful for the treatment of disorders such as autoimmune diseases, cancer, cardiovascular diseases, and neurodegenerative diseases.

20 Claims, 9 Drawing Sheets

(56) References Cited

U.S. PATENT DOCUMENTS

| | | | |
|---|---|---|---|
| 2008/0019915 A1 | 1/2008 | Hadida-Ruah et al. |
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0183985 A1 | 7/2011 | Li et al. |
| 2011/0224190 A1 | 9/2011 | Huang et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0238564 A1 | 9/2012 | Luk et al. |
| 2013/0018034 A1 | 1/2013 | Yao et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0121198 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2015/0361094 A1 | 12/2015 | Li et al. |
| 2016/0000795 A1 | 1/2016 | Scherle et al. |
| 2016/0022685 A1 | 1/2016 | Li et al. |
| 2016/0024117 A1 | 1/2016 | Li et al. |
| 2017/0129899 A1 | 5/2017 | Shvartsbart et al. |
| 2017/0190689 A1 | 7/2017 | Sparks et al. |
| 2018/0009816 A1 | 1/2018 | Buesking et al. |
| 2019/0060331 A1 | 2/2019 | Zou et al. |
| 2019/0062336 A1 | 2/2019 | Shvartsbart et al. |
| 2019/0119287 A1 | 4/2019 | Buesking et al. |
| 2019/0359592 A1 | 11/2019 | Sparks et al. |
| 2020/0031837 A1 | 1/2020 | Shvartsbart et al. |
| 2020/0102315 A1 | 4/2020 | Buesking et al. |
| 2022/0227736 A1 | 7/2022 | Sparks et al. |

FOREIGN PATENT DOCUMENTS

| | | |
|---|---|---|
| WO | WO 00/09495 | 2/2000 |
| WO | WO 00/053595 | 9/2000 |
| WO | WO 01/014402 | 3/2001 |
| WO | WO 01/064655 | 9/2001 |
| WO | WO 01/85724 | 11/2001 |
| WO | WO 2002/000196 | 1/2002 |
| WO | WO 03/024967 | 3/2003 |
| WO | WO 03/035065 | 5/2003 |
| WO | WO 03/035644 | 5/2003 |
| WO | WO 03/037347 | 5/2003 |
| WO | WO 03/068225 | 8/2003 |
| WO | WO 03/099771 | 12/2003 |
| WO | WO 04/005281 | 1/2004 |
| WO | WO 04/046120 | 6/2004 |
| WO | WO 04/056786 | 7/2004 |
| WO | WO 04/080980 | 9/2004 |
| WO | WO 2004/078943 | 9/2004 |
| WO | WO 2005/012288 | 2/2005 |
| WO | WO 05/028444 | 3/2005 |
| WO | WO 2005/118580 | 12/2005 |
| WO | WO 2006/056399 | 6/2006 |
| WO | WO 2007/019416 | 2/2007 |
| WO | WO 2007/019417 | 2/2007 |
| WO | WO 2007/028051 | 3/2007 |
| WO | WO 2009/005551 | 1/2009 |
| WO | WO 2009/016118 | 2/2009 |
| WO | WO 2009/024585 | 2/2009 |
| WO | WO 2009/079011 | 6/2009 |
| WO | WO 2009/123776 | 10/2009 |
| WO | WO 2009/133127 | 11/2009 |
| WO | WO 2009/158118 | 12/2009 |
| WO | WO 2010/051245 | 5/2010 |
| WO | WO 2010/061903 | 6/2010 |
| WO | WO 2010/069684 | 6/2010 |
| WO | WO 2010/135014 | 11/2010 |
| WO | WO 2011/099832 | 8/2011 |
| WO | WO 2011/123609 | 10/2011 |
| WO | WO 2011/149856 | 12/2011 |
| WO | WO 2011/149874 | 12/2011 |
| WO | WO 2012/051410 | 4/2012 |
| WO | WO 2012/074126 | 6/2012 |
| WO | WO 2012/143796 | 10/2012 |
| WO | WO 2012/170867 | 12/2012 |
| WO | WO 2013/129674 | 9/2013 |
| WO | WO 2013/154878 | 10/2013 |
| WO | WO 2013/180193 | 12/2013 |
| WO | WO 2014/009295 | 1/2014 |
| WO | WO 2014/149207 | 9/2014 |
| WO | WO 2014/153529 | 9/2014 |
| WO | WO 2014/182954 | 11/2014 |
| WO | WO 2015/008872 | 1/2015 |
| WO | WO 2015/051241 | 4/2015 |
| WO | WO 2015/154878 | 10/2015 |
| WO | WO 2016/044342 | 3/2016 |
| WO | WO 2016/054491 | 4/2016 |
| WO | WO 2016/075130 | 5/2016 |

OTHER PUBLICATIONS

European Search Report in European Application No. 22162035.4, dated Jul. 27, 2022, 9 pages.
Cheung et al., "Future therapeutic targets in rheumatoid arthritis?" Semin Immunopathol., 2017, 39:487-500.
Campa et al., "Inhalation of the prodrug PI3K inhibitor CL27c improves lung function in asthma and fibrosis," Nature Communications, 2018, 9:5232.
Chamcheu et al., "Dual Inhibition of PI3K/Akt and mTOR by the Dietary Antioxidant, Delphinidin, Ameliorates Psoriatic Features In Vitro and in an Imiquimod-Induced Psoriasis-Like Disease in Mice," Antioxidants Redox Signaling, 2017, 26(2):49-69.
Jacot et al., "Potential Therapeutic Roles for Inhibition of the PI3K/Akt/mTOR Pathway in the Pathophysiology of Diabetic Retinopathy," J Ophthalmology, 2011, ID:589813.
U.S. Appl. No. 60/578,491, Ren, filed Jun. 10, 2004.
Ameriks and Venable, "Small Molecule Inhibitors of Phosphoinositide 3-Kinase (PI3K) δ and γ," Curr Topics Med Chem., 2009, 9:738-753.
Bala et al., "Highly efficient water-mediated approach to access benzazoles: metal catalyst and base-free synthesis of 2-substituted benzimidazoles, benzoxazoles, and benzothiazoles," Molecular Diversity, Mar. 2015, 19(2):263-272.
Barber et al., "Class IB-Phosphatidylinositol 3-Kinase (PI3K) Deficiency Ameliorates IA-PI3K-Induces Systemic Lupus but Not T Cell Invasion," J Immunol., 2006, 176:589-593.
Barber et al., "PI3Kgamma inhibition blocks glomerulonephritis and extends lifespan in a mouse model of systemic lupus," Nat Med., Sep. 2005, 11(9):933-5.
Berge, Journal of Pharmaceutical Science, 66, 2 (1977).
Berod et al., "PI3Kγ deficiency delays the onset of experimental autoimmune encephalomyelitis and ameliorates its clinical outcome," Eur J Immunol, Mar. 2011, 41(3):833-44.
Blom et al., "Optimizing Preparative LC/MS Configurations and Methods for Parallel Synthesis Purification," J. Comb. Chem., 2003, 5:670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography-Mass Spectrometry," J. Comb. Chem., 2002, 4: 295-301.
Brock et al., "Roles of G beta gamma in membrane recruitment and activation of p110 gamma/p101 phosphoinositide 3-kinase gamma," J Cell Biol, Jan. 2003, 160(1):89-99.
Camps et al., "Blockade of PI3Kγ suppresses joint inflammation and damage in mouse models of rheumatoid arthritis," Nature Medicine, Sep. 2005, 11(9):936-943.
Cantley, "The phosphoinositide 3-kinase pathway," Science, May 2002, 296(5573):1655-7.
Carter et al., "Prioritization of driver mutations in pancreatic cancer using cancer-specific high-throughput annotation of somatic mutations (CHASM)," Cancer Biol Ther, Sep. 2010, 10(6):582-7.

(56) References Cited

OTHER PUBLICATIONS

Collier et al., "Discovery of Highly Isoform Selective Thiazolopiperidine Inhibitors of Phosphoinositide 3-Kinase γ," Journal of Medicinal Chemistry, 2015, 58:5684-5688.
Collier et al., "Structural Basis for Isoform Selectivity in a Class of Benzothiazole Inhibitors of Phosphoinositide 3-Kinase [gamma]," Journal of Medicinal Chemistry, Jan. 2015, 58(1):517-521.
Comerford et al., "PI3Kγ drives priming and survival of autoreactive CD4(+) T cells during experimental autoimmune encephalomyelitis," PLoS One, 2012, 7(9):e45095.
Cossy et al., "Formation of optically active 3-hydroxypiperidines," Tetrahedron Letters, Jan. 23, 1995, 36(4):549-552.
Cushing et al., "PI3Kδ and PI3Kγ as Targets for Autoimmune and Inflammatory Diseases," Journal of Medicinal Chemistry, 2012, 55:8559-8581.
Database Registry [online], Chemical Abstracts Service, Columbus, OH, US; Aug. 2012, CAS client services: XP002755356, Database accession No. 1391828-67-3.
Database Registry [online], Chemical Abstracts Service, Columbus, OH, US; Dec. 2011, Chemical Catalog; Supplier: Ukrorgsyntez ltd.: XP002755357, Database accession No. 1347088-14-5.
Database Registry [online], Chemical Abstracts Service, Columbus, OH, US; Dec. 2012, Chemical Catalog; Supplier: Aurora Fine Chemicals: XP002755355, Database accession No. 1411464-90-8.
Database Registry [online], Chemical Abstracts Service, Columbus, OH, US; Feb. 2014, Chemical Catalog; Supplier: Aurora Fine Chemicals: XP002755346, Database accession No. 1554931-95-1.
Database Registry [online], Chemical Abstracts Service, Columbus, OH, US; Feb. 2014, Chemical Catalog; Supplier: Aurora Fine Chemicals: XP002755347, Database accession No. 1540856-06-1.
Database Registry [online], Chemical Abstracts Service, Columbus, OH, US; Feb. 2014, Chemical Catalog; Supplier: Aurora Fine Chemicals: XP002755349, Database accession No. 1538237-68-1.
Database Registry [online], Chemical Abstracts Service, Columbus, OH, US; Feb. 2014, Chemical Catalog; Supplier: Aurora Fine Chemicals: XP002755350, Database accession No. 1536955-67-5.
Database Registry [online], Chemical Abstracts Service, Columbus, OH, US; Jan. 2014, Chemical Catalog; Supplier: Aurora Fine Chemicals: XP002755351, Database accession No. 1528719-88-1.
Database Registry [online], Chemical Abstracts Service, Columbus, OH, US; Jan. 2014, Chemical Catalog; Supplier: Aurora Fine Chemicals: XP002755352, Database accession No. 1526778-80-2.
Database Registry [online], Chemical Abstracts Service, Columbus, OH, US; Jan. 2014, Chemical Catalog; Supplier: Aurora Fine Chemicals: XP002755353, Database accession No. 1522493-70-4.
Database Registry [online], Chemical Abstracts Service, Columbus, OH, US; Jan. 2014, Chemical Catalog; Supplier: Aurora Fine Chemicals: XP002755354, Database accession No. 1520181-20-7.
Database Registry [online], Chemical Abstracts Service, Columbus, OH, US; Oct. 2005, Chemical Library; Supplier: interchim: XP002755358, Database accession No. 866138-38-7.
Database Registry [online], Chemical Abstracts Service, Columbus, OH, US; Oct. 2005, Chemical Library; Supplier: interchim: XP002755359, Database accession No. 864939-76-4.
Database Registry [online], Chemical Abstracts Service, Columbus, Ohio, US, Feb. 2010, Chemical Catalog; Supplier: Aurora Fine Chemicals: XP002755348, Database accession No. 1540777-22-7.
Database Registry [online], Chemical Abstracts Service, Columbus, OH, US, May 29, 2015, Chemical Catalog; Supplier: Aurora Fine Chemicals: XP002755360, Database Accession No. 1715195-44-0.
Database Registry [online], Chemical Abstracts Service, Columbus, OH, US, Jun. 1, 2015, Chemical Catalog; Supplier: Aurora Fine Chemicals: XP002755361, Database Accession No. 1770353-29-1.
Database Registry [online], Chemical Abstracts Service, Columbus, OH, US, Jun. 4, 2015, Chemical Catalog; Supplier: Aurora Fine Chemicals: XP002755362, Database Accession No. 1773443-64-3.
Dorwald et al., "Side reactions in Organic Synthesis," Wiley: VCH Weinhenn Preface, 2005, pp. 1-15, Chapter 8, pp. 279-308.
Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther, Mar. 2009, 328(3):758-65.
Doukas et al., "Phosphoinositide 3-kinase gamma/delta inhibition limits infarct size after myocardial ischemia/reperfusion injury," Proc Natl Acad Sci USA, Dec. 2006, 103(52):19866-71.
El Khoury et al., "Ccr2 deficiency impairs microglial accumulation and accelerates progression of Alzheimer-like disease," Nat Med, Apr. 2007, 13(4):432-8.
Elger et al., "Novel alpha-amino-3-hydroxy-5-methyl-4-isoxazole propionate (AMPA) receptor antagonists of 2,3-benzodiazepine type: chemical synthesis, in vitro characterization, and in vivo prevention of acute neurodegeneration," J. Med. Chem., Jul. 2005, 48(14):4618-4627.
European Office Action in European Application No. 16805238.9, dated Mar. 27, 2020, 5 pages.
European Search Report in European Application No. 20187907.9, dated Jan. 20, 2021, 6 pages.
Falasca and Maffucci, "Targeting p110gamma in gastrointestinal cancers: attack on multiple fronts," Frontiers in Physiology, 2014, 5:1-10.
Giri et al., "Mechanism of amyloid peptide induced CCR5 expression in monocytes and its inhibition by siRNA for Egr-1," Am J Physiol Cell Physiol, Aug. 2005, 289(2):C264-76.
Gonzalez-Garcia et al., "Phosphatidylinositol 3-Kinase Inhibition Ameliorates Inflammation and Tumor Growth in a Model of Colitis-Associated Cancer," Gastroenterology, 2010, 138:1373-1384.
Hanahan and Weinberg, "Hallmarks of Cancer: The Next Generation," Cell, 2011, 144:646-674.
Hayer et al., "PI3Kgamma regulates cartilage damage in chronic inflammatory arthritis," Faseb J, Dec. 2009, 23(12):4288-98.
International Search Report and Written Opinion in International Application No. PCT/US2016/017073, dated Apr. 15, 2016, 21 pages.
International Search Report and Written Opinion in International Application No. PCT/US2016/060468, dated Jan. 25, 2017, 14 pages.
International Search Report and Written Opinion in International Application No. PCT/US2017/038955, dated Aug. 8, 2017, 15 pages.
International Search Report and Written Opinion in International Application No. PCT/US2017/012135, dated May 19, 2017, 17 pages.
International Preliminary Report on Patentability in International Application No. PCT/US2017/038955, dated Dec. 25, 2018, 8 pages.
International Preliminary Report on Patentability in International Application No. PCT/US2016/017073, dated Aug. 15, 2017, 11 pages.
International Preliminary Report on Patentability in International Application No. PCT/US2016/060468, dated May 8, 2018, 9 pages.
International Preliminary Report on Patentability in International Application No. PCT/US2017/012135, dated Jul. 19, 2018, 10 pages.
Japanese Office Action in Japanese Application No. 2018-523015, dated Oct. 20, 2020, 7 pages.
Jimenez et al., "The p85 regulatory subunit controls sequential activation of phosphoinositide 3-kinase by Tyr kinases and Ras," J Biol Chem, Nov. 2002, 277(44):41556-62.
Kaneda et al., "Abstract 3650: PI3-kinase gamma controls the macrophage M1-M2 switch, thereby promoting tumor immunosuppression and progression," Cancer Res., Oct. 2014, 74(Suppl 19), 2 pages.
Kumar et al., "Discovery and optimization of a new class of pyruvate kinase inhibitors as potential therapeutics for the treatment of methicillin-resistant *Staphylococcus aureus* infections," Bioorganic & Medicinal Chemistry, Jan. 2014, 22(5):1708-1725.
Laffargue et al., "Phosphoinositide 3-kinase gamma is an essential amplifier of mast cell function," Immunity, Mar. 2002, 16(3):441-51.
Li et al., "PI3Kγ inhibition alleviates symptoms and increases axon No. in experimental autoimmune encephalomyelitis mice," Neuroscience, Dec. 2013, 253:89-99.

(56) References Cited

OTHER PUBLICATIONS

Liu et al., "Discovery of Novel Small Molecule Mer Kinase Inhibitors for the Treatment of Pediatric Acute Lymphoblastic Leukemia," ACS Med. Chem. Lett., Feb. 9, 2012, 3(2):129-134.
Lupia et al., "Ablation of phosphoinositide 3-kinase-gmma reduces the severity of acute pancreatitis," Am J Pathol, Dec. 2004, 165(6):2003-11.
Mamedov et al., "Acid-catalyzed rearrangement of 3-(beta-2-aminostyryl)quinoxalin-2(1H)ones—a new and efficient method for the synthesis of 2-benzimidazol-2-ylquinolines," Tetrahedron Letters, Dec. 2010, 51(50):6503-6506.
Martin et al., "PI3Kγ mediates Kaposi's sarcoma-associated herpesvirus vGPCR-induced sarcomagenesis," Cancer Cell, Jun. 2011, 19(6):805-13.
Mejdrova et al., "Highly selective Phosphatidylinositol 4-Kinase III[beta] Inhibitors and Structural Insight into Their Mode of Action," Journal of Medicinal Chemistry, May 2015, 58(9):3767-3793.
Passos et al., "Involvement of phophoinositide 3-kinase gamma in the neuro-inflammatory response and cognitive impairments induced by beta-amyloid 1-40 peptide in mice," Brain Behav Immun, Mar. 2010, 24(3):493-501.
Park et al., "Homogenous proximity tyrosine kinase assays: scintillation proximity assay versus homogenous time-resolved fluorescence," Anal. Biochem., Apr. 1999, 269(1):94-104.
Pinho et al., "Phosphoinositide-3 kinases critically regulate the recruitment and survival of eosinophils in vivo: importance for the resolution of allergic inflammation," J Leukoc Biol, May 2005, 77(5):800-10.
Pomel et al., "Furan-2-ylmethylene thiazolidinediones as novel, potent, and selective inhibitors of phosphoinositide 3-kinase gamma," J. Med. Chem., Jun. 2006, 49(13):3857-71.
Prete et al., "Defective dendritic cell migration and activation of adaptive immunity in PI3Kgamma-deficient mice," EMBO J, Sep. 2004, 23(17):3505-15.
Randis et al., "Role of PI3Kdelta and PI3Kgamma in inflammatory arthritis and tissue localization of neutrophils," Eur J Immunol, May 2008, 38(5):1215-24.
Remington's Pharmaceutical Sciences, 17th ed., Mack Publishing Company, Easton, Pa., 1985, p. 1418.
Rodrigues et al., "Absence of PI3K gamma leads to increased leukocyte apoptosis and diminished severity of experimental autoimmune encephalomyelitis," J Neuroimmunol, May 2010, 222(1-2):90-4.
Rommel et al., "PI3Kδ and PI3Kγ: partners in crime in inflammation in rheumatoid arthritis and beyond?" Nature Rev Immunol., 2007, 7:191-201.
Ruckle et al., "PI3Kgamma inhibition: towards an 'aspirin of the 21st century'?" Nat Rev Drug Discov, Nov. 2006, 5(11):903-18.
Schmid et al., "Receptor tyrosine kinases and TLR/ILIRs unexpectedly activate myeloid cell PI3Kγ, a single convergent point promoting tumor inflammation and progression," Cancer Cell, Jun. 2011, 19(6):715-27.
Schmidt et al., Cancer Res. 2012, 72 (Suppl 1: Abstract, 411).
Subramaniam et al., "Targeting nonclassical oncogenes for therapy in T-ALL," Cancer Cell, Apr. 2012, 21(4):459-72.
Taiwan Office Action in Taiwan Application No. 105136055, dated Aug. 8, 2020, 14 pages.
T. W. Greene and P. G. M. Wuts, Protective Groups in Organic Synthesis, 3rd Ed., Wiley & Sons, Inc., New York (1999), 799 pages.
Thomas et al., "Airway inflammation: chemokine-induced neutrophilia and the class I phosphoinositide 3-kinases," Eur J Immunol, Apr. 2005, 35(4):1283-91.
Vaillard et al., "Synthesis of 6-substituted 2-pyrrolyl and Indolyl Benzoxazoles by Intramolecular O-Arylation in Photostimulated Reactions," The Journal of Organic Chemistry, Feb. 2012, 77(3):1507-1519.
Vanhaesebroeck et al., "Signalling by PI3K isoforms: insights from gene-targeted mice," Trends Biochem Sci, Apr. 2005, 30(4):194-204.
Vecchione et al., "Protection from angiotensin II-mediated vasculotoxic and hypertensive response in mice lacking PI3Kgamma," J Exp Med, Apr. 2005, 201(8):1217-28.
Venable et al., "Phosphoinositide 3-Kinase Gamma (PI3K[gamma]) Inhibitors for the Treatment of Inflammation and Autoimmune Disease," Recent Patents on Inflammation & Allergy Drug Discovery, Jan. 2010, 4(1):1-15.
Confettura et al., "Neddylation-dependent protein degradation is a nexus between synaptic insulin resistance, neuroinflammation and Alzheimer's disease," Translational Neurodegeneration, 2022, 11(2):1-18.
Office Action in European Appln. No. 20187907.9, dated Mar. 30, 2023, 5 pages.

SUBSTITUTED IMIDAZO[2,1-F][1,2,4]TRIAZINES AS PI3K-GAMMA INHIBITORS

CROSS REFERENCE TO RELATED APPLICATIONS

This application is a continuation of U.S. patent application Ser. No. 16/591,017, filed Oct. 2, 2019, which is a continuation of U.S. patent application Ser. No. 16/165,390, filed Oct. 19, 2018, which is a divisional of U.S. patent application Ser. No. 15/631,417, filed Jun. 23, 2017, which claims the benefit of U.S. Provisional Application No. 62/354,509, filed Jun. 24, 2016, the disclosure of which is incorporated herein by reference in its entirety.

FIELD OF THE INVENTION

The present invention provides heterocyclic compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., *Immunity*, 2002, 16, 441-451; Prete et al., *The EMBO Journal*, 2004, 23, 3505-3515; Pinho et al., *L. Leukocyte Biology*, 2005, 77, 800-810; Thomas et al., *Eur. J. Immunol.* 2005, 35, 1283-1291; Doukas et al., *J. Pharmacol. Exp Ther.* 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., *Am. J. Pathology*, 2004, 165, 2003-2011). PI3Kγ$^{-/-}$ mice were largely protected in four different models of rheumatoid arthritis (CIA, α-CII-IA, K/B×N serum transfer and TNF transgenic) and PI3Kγ inhibition suppressed the progression of joint inflammation and damage in the CIA and α-CII-IA models (see e.g., Camps et al., *Nat. Medicine*, 2005, 11, 939-943; Randis et al., *Eur. J. Immunol*, 2008, 38, 1215-1224; Hayer et al., *FASB J.*, 2009, 4288-4298). In the MRL-lpr mouse model of human systemic lupus erythematous, inhibition of PI3Kγ reduced glomerulonephritis and prolonged life span (Barber et al., *Nat. Medicine*, 2005, 9, 933-935).

There is evidence suggesting that chronic inflammation due to infiltration by myeloid-derived cells is a key component in the progression of neurodegeneration diseases, such as Alzheimer's disease (AD) (Gir et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced cognitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., *J. Neuroimmunol*. 2010, 222, 90-94; Berod et al., *Euro. J. Immunol*. 2011, 41, 833-844; Comerford et al., *PLOS one*, 2012, 7, e45095; Li et al., *Neuroscience*, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., *Cancer Cell*, 2011, 19, 715-727). A further study reported that PI3Kγ deficiency could ameliorate inflammation and tumor growth in mice having colitis-associated colon cancer, (Gonzalez- Garcia et al., *Gastroenterology*, 2010, 138, 1373-1384). Detailed mechanistic analysis indicates that tumor infiltration by CD11b+ myeloid cells can cause protumorigenic inflammation at tumor sites and PI3Kγ in the myeloid cells is critical in mediating signaling of various chemoattractants in bring the cells to the tumor (Schmid et al., *Cancer Cell*, 2011, 19, 715-727). Other studies suggest that PI3Kγ is also required for differentiation of naïve myeloid cells into M2 macrophges at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., *Cancer Res.* 2012, 72 (Suppl 1: Abstract, 411; Kaneda et al., *Cancer Res.*, 74 (Suppl 19: Abstact 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., *Cancer Cell*, 2011, 19, 805-813). PI3Kγ was also suggested to be required for growth of T-ALL (Subramanjam et al., *Cancer Cell*, 2012, 21, 459-472), PDAC and HCC cells (Falasca and Maffucci, Frontiers in Physiology, 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., *J. Exp. Med.* 2005, 201, 1217-1228). In rigorous animal myocardial infarction models, PI3Kγ inhibition provided potent cardioprotection, reducing infarct development and preserving myocardial function (Doukas et al., Proc. Natl. Acad. Sci. USA, 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present invention related to, inter alia, compounds of Formula (I):

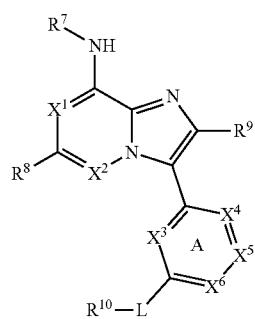

(I)

or pharmaceutically acceptable salts, wherein constituent members are defined herein.

The present invention further provides pharmaceutical compositions comprising a compound of Formula (I), or a pharmaceutically acceptable salt thereof, and a pharmaceutically acceptable carrier.

The present invention further provides pharmaceutically acceptable salt forms of the compounds of Formula (I).

The present invention further provides crystalline forms of the compounds of Formula (I).

The present invention further provides methods of inhibiting an activity of PI3Kγ kinase comprising contacting the kinase with a compound of Formula (I), or a pharmaceutically acceptable salt thereof.

The present invention further provides methods of treating a disease or a disorder associated with abnormal PI3Kγ kinase expression or activity in a patient by administering to a patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

Figure 1:
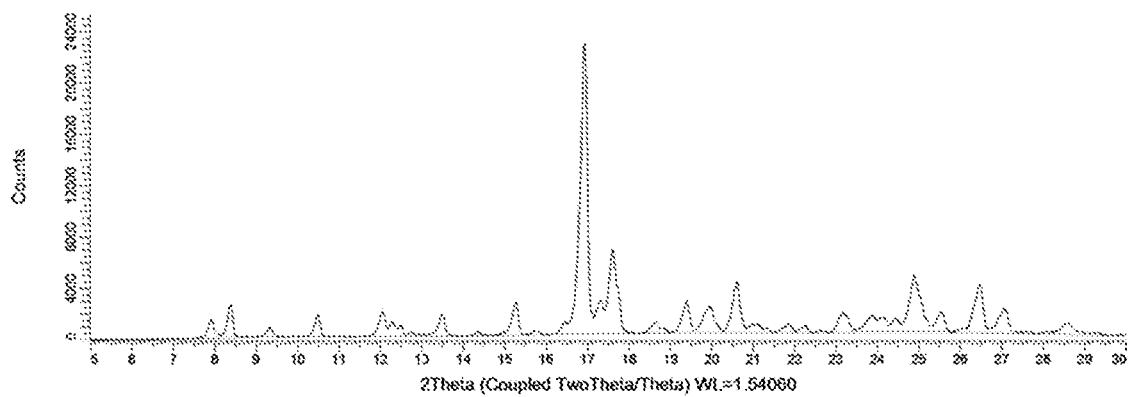
FIG. 1 shows an X-Ray Powder Diffraction (XRPD) pattern characteristic of the crystalline compound of Example 253.

The present application provides, inter alia, a compound of Formula (I):

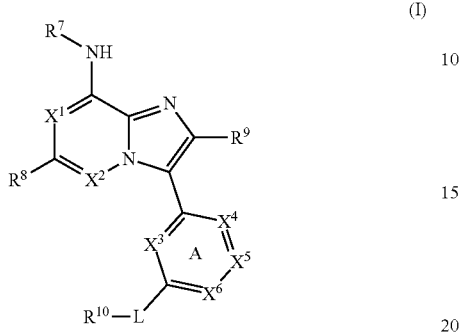

or a pharmaceutically acceptable salt thereof, wherein:
$X^1$ is N or $CR^1$;
$X^2$ is N or $CR^2$;
$X^3$ is N or $CR^3$;
$X^4$ is N or $CR^4$;
$X^5$ is N or $CR^5$;
$X^6$ is N or $CR^6$;
$X^3$, $X^4$, $X^5$ and $X^6$ are not simultaneously N;
$R^7$ is H or $C_{1-6}$ alkyl optionally substituted with 1, 2 or 3 groups independently selected from halo, OH, oxo, CN, $C_{3-6}$ cycloalkyl, 4-6 membered heterocycloalkyl, $C_{6-10}$ aryl, $C_{1-6}$ haloalkyl, $C_{1-6}$ alkoxy, $C_{1-6}$ haloalkoxy, $NH_2$, $C_{1-6}$ alkyl-NH— and $(C_{1-6}$ alkyl$)_2$N—;
$R^1$, $R^2$, $R^3$, $R^4$, $R^5$, $R^6$ and $R^7$ are each independently selected from H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^{a1}$, $SR^{a1}$, $NHOR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NHR^{a1}$, $NR^{a1}R^{a1}$, $NR^{a1}C(O)R^{a1}$, $NR^{a1}C(O)OR^{a1}$, $NR^{a1}C(O)NR^{a1}R^{a1}$, $C(=NR^{a1})R^{a1}$, $C(=NR^{a1})NR^{a1}R^{a1}$, $NR^{a1}C(=NR^{a1})NR^{a1}R^{a1}$, $NR^{a1}C(=NOH)NR^{a1}R^{a1}$ $NR^{a1}C(=NCN)NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$, $S(O)NR^{a1}R^{a1}$, $S(O)_2R^{a1}$, $SF_5$, —$P(O)R^{a1}R^{a1}$, —$P(O)(OR^{a1})(OR^{a1})$, $B(OR^{a1})_2$ and $S(O)_2NR^{a1}R^{a1}$, wherein the $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^1$, $R^2$, R3, R4, $R^5$, $R^6$ and $R^7$ are each optionally substituted with 1, 2, 3, 4 or 5 independently selected $R^b$ substituents;
$R^9$ is H, D, CN, C(O), $NH_2$, —OH, —COOH, —NH($C_{1-6}$ alkyl), —$NH(C_{1-6}$ alkyl$)_2$, $C_{1-6}$ alkyl, $C_{1-6}$ haloalkyl, $C_{1-6}$ alkoxy or $C_{1-6}$ haloalkoxy, wherein the $C_{1-6}$ alkyl is optionally substituted with 1, 2 or 3 independently selected $R^q$ substituents;

$R^{10}$ is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, $OR^{a2}$, $SR^{a2}$, $NHOR^{a2}$, $C(O)R^{a2}$, $C(O)NR^{a2}R^{a2}$, $C(O)OR^{a2}$, $NHR^{a2}$, $NR^{a2}R^{a2}$, $NR^{a2}C(O)R^{a2}$, $NR^{a2}C(O)OR^{a2}$, $NR^{a2}C(O)NR^{a2}R^{a2}$, $C(=NR^{a2})R^{a2}$, $C(=NR^{a2})NR^{a2}R^{a2}$, $NR^{a2}C(=NR^{a2})NR^{a2}R^{a2}$, $NR^{a2}S(O)R^{a2}$, $NR^{a2}S(O)_2R^{a2}$, $NR^{a2}S(O)_2NR^{a2}R^{a2}$, $S(O)R^{a2}$, $S(O)NR^{a2}R^{a2}$, $S(O)_2R^{a2}$, $S(O)_2NR^{a2}R^{a2}$, wherein the $C_{1-6}$ alkyl, $C_{2-6}$ alkenyl, $C_{2-6}$ alkynyl, $C_{1-6}$ alkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{14}$ alkyl-, and (4-14 membered heterocycloalkyl)-$C_{1-4}$ alkyl- of $R^{10}$ are each optionally substituted with 1, 2, 3, 4, 5, 6, 7 or 8 independently selected $R^b$ substituents;

L is

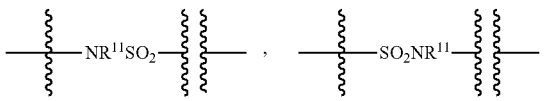

or —$SO_2$—, wherein each $R^{11}$ is independently H, $C_{1-6}$ alkyl, or $C_{3-10}$ cycloalkyl optionally substituted with 1 or 2 $R^q$ substituents and wherein the single wavy line indicates the point of attachment to $R^{10}$ and the double wavy line indicates the point of attachment to the 6-membered ring A;
or when L is

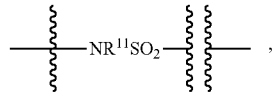

$R^{10}$ and $R^{11}$ optionally taken together with the nitrogen atom to which they are attached, form a 4 to 14 membered heterocycloalkyl or a 4 to 14 membered heterocycloalkyl-$C_{1-4}$ alkyl- having 0 to 4 additional heteroatoms as a ring member, each of which is independently selected from N, O and S, wherein the 4 to 14-membered heterocycloalkyl formed by $R^{10}$, $R^{11}$ and N is optionally substituted with 1, 2, 3, 4, 5, 6, 7 or 8 independently selected $R^b$ substituents;
$R^{a1}$ and $R^{a2}$ are each independently selected from H, D, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-14 membered heterocycloalkyl)-$C_{1-4}$ alkyl- of $R^a$ and $R^{a2}$ are each optionally substituted with 1, 2, 3, 4, or 5 independently selected Rd substituents;

each $R^b$ substituent is independently selected from D, halo, oxo, $C_{1-4}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-14 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, —$P(O)R^cR^c$, —$P(O)(OR^c)(OR^c)$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein the $C_{1-4}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-14 membered heterocycloalkyl)-$C_{1-4}$ alkyl- of $R^b$ are each further optionally substituted with 1, 2, or 3 independently selected Rd substituents;

each $R^c$ is independently selected from H, D, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $NR^gC(=NOH)NR^gR^g$, $NR^gC(=NCN)NR^gR^g$, $SF_5$, —$P(O)R^gR^g$, —$P(O)(OR^g)(OR^g)$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $NR^oC(=NOH)NR^oR^o$, $NR^oC(=NCN)NR^oR^o$, $SF_5$, —$P(O)R^oR^o$, —$P(O)(OR^o)$ $(OR^o)$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$;

each $R^d$ is independently selected from D, oxo, $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{14}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $SF_5$, —$P(O)R^eR^e$, —$P(O)(OR^e)(OR^e)$, $S(O)R^e$, $S(O)NR^eR^e$, $S(O)_2R$, $NR^eS(O)_2R^e$, $NR^eS(O)_2NR^eR^e$, and $S(O)_2NR^eR^e$, wherein the $C_{1-6}$ alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^d$ are each optionally substituted with 1, 2, or 3 independently selected $R^f$ substituents;

each $R^e$ is independently selected from H, D, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^q$ substituents;

each $R^g$ is independently selected from H, D, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2 or 3 independently selected $R^p$ substituents;

each $R^p$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^r$, $SF_5$, —$P(O)R^rR^r$, —$P(O)(OR^r)(OR^r)$, $S(O)R^r$, $S(O)NR^r$, $S(O)_2R^r$, $NR^rS(O)_2R^r$, $NR^rS(O)_2NR^rR^r$, and $S(O)_2NR^rR^r$;

or any two $R^{a1}$ substituents together with the nitrogen atom to which they are attached form a 4-, 5-, 6-, 7-, 8-, 9- or 10-membered heterocycloalkyl group optionally substituted with 1, 2 or 3 independently selected Rh substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $NR^iC(=NOH)NR^iR^i$, $NR^iC(=NCN)NR^iR^i$, $SF_5$, —$P(O)R^iR^i$, —$P(O)(OR^i)(OR^i)$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $NR^kC(=NOH)NR^kR^k$, $NR^kC(=NCN)NR^kR^k$, $SF_5$, —$P(O)R^kR^k$, —$P(O)(OR^k)(OR^k)$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$; or two $R^j$ groups attached to the same carbon atom of the 4- to 10-membered heterocycloalkyl taken together with the carbon atom to which they attach form a $C_{3-6}$ cycloalkyl or 4- to 6-membered heterocycloalkyl having 1-2 heteroatoms as ring members selected from O, N or S;

or any two $R^{a2}$ substituents together with the nitrogen atom to which they are attached form a 4-, 5-, 6-, 7-, 8-, 9- or 10-membered heterocycloalkyl group optionally substituted with 1, 2 or 3 $R^h$ substituents;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents;

or any two $R^r$ substituents together with the nitrogen atom to which they are attached form a 4-, 5-, 6-, or 7-membered heterocycloalkyl group optionally substituted with 1, 2, or 3 independently selected $R^h$ substituents;

each $R^i$, $R^k$, $R^o$ or $R^r$ is independently selected from H, D, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl of R, $R^k$, $R^o$ or $R^r$ are each optionally substituted with 1, 2 or 3 independently selected $R^q$ substituents;

each $R^q$ is independently selected from D, OH, CN, —COOH, $NH_2$, halo, $C_{1-6}$ alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, —$CONHR^{12}$, —$NHC(O)R^2$, —$OC(O)R^{12}$, —$C(O)OR^2$, —$C(O)R^{12}$, —$SO_2R^{12}$, —$NHSO_2R^{12}$, —$SO_2NHR^{12}$ and $NR^{12}R^{12}$, wherein the $C_{1-6}$ alkyl, phenyl, 4-6 membered heterocycloalkyl and 5-6 membered heteroaryl of $R^g$ are each optionally substituted with OH, CN, —COOH, $NH_2$, $C_{1-6}$ alkoxy, $C_{3-6}$ cycloalkyl or 4-6 membered heterocycloalkyl;

and each $R^{12}$ is independently $C_{1-6}$ alkyl;

provided that:
when $R^7$ is $C_{1-6}$ alkyl, $R^{10}$-L- is other than cyclopropylsulfamoyl and methanesulfonamido;
when $R^7$ is cyclopropylmethyl, $R^{10}$-L- is other than methanesulfonamido;
when $R^7$ is 2-(4-morpholino)ethyl, $R^{10}$-L- is other than methanesulfonyl; and
the compound is other than 3-(8-aminoimidazo[1,2-a]pyridin-3-yl)-2-(1H-tetrazol-5-yl)benzenesulfonamide.

In some embodiments:
$X^1$ is N or $CR^1$;
$X^2$ is N or $CR^2$;
$X^3$ is N or $CR^3$;
$X^4$ is N or $CR^4$;
$X^5$ is N or $CR^5$;
$X^6$ is N or $CR^6$;
$X^3$, $X^4$, $X^5$ and $X^6$ are not simultaneously N;
$R^7$ is H or $C_{1-6}$ alkyl optionally substituted with 1, 2 or 3 groups independently selected from halo, OH, oxo, CN, $C_{3-6}$ cycloalkyl, 4-6 membered heterocycloalkyl, $C_{1-6}$ haloalkyl, $C_{1-6}$ alkoxy, $C_{1-6}$ haloalkoxy, $NH_2$, $C_{1-6}$ alkyl-NH— and $(C_{1-6}$ alkyl$)_2$N—; $R^1$, $R^2$, $R^3$, $R^4$, $R^5$, $R^6$ and $R^7$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^{a1}$, $SR^{a1}$, $NHOR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NHR^{a1}$, $NR^{a1}R^{a1}$, $NR^{a1}C(O)R^{a1}$, $NR^{a1}C(O)NR^{a1}R^{a1}$, $NR^{a1}C(O)OR^{a1}$, $C(=NR^{a1})R^{a1mi}$, $C(=NR^{a1})NR^{a1}R^{a1}$, $NR^{a1}C(=NR^{a1})NR^{a1}R^{a1}$, $NR^{a1}C(=NOH)NR^{a1}R^{a1}$, $NR^{a1}C(=NCN)NR^{a1}R^{a1}$, $NR^{a1}S(O)R^{a1}$, $NR^{a1}S(O)_2R^{a1}$, NR$^{a1}$S(O)$_2$NR$^{a1}$R$^{a1}$, S(O)R$^{a1}$, S(O)NR$^{a1}$R$^{a1}$, S(O)$_2$R$^{a1}$, SF$_5$, —P(O)R$^{a1}$R$^{a1}$, —P(O)(OR$^{a1}$)(OR$^{a1}$) and S(O)$_2$NR$^{a1}$R$^{a1}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl- of R$^1$, R$^2$, R$^3$, R$^4$, R$^5$, R$^6$ and R$^7$ are each optionally substituted with 1, 2, 3, 4 or 5 independently selected R$^b$ substituents;

R$^9$ is H, CN, NH$_2$, —OH, —COOH, —NH(C$_{1-6}$ alkyl), —NH(C$_{1-6}$ alkyl)$_2$, C$_{1-6}$ alkyl, C$_{1-6}$ haloalkyl, C$_{1-6}$ alkoxy or C$_{1-6}$ haloalkoxy, wherein the C$_{1-6}$ alkyl is optionally substituted with 1, 2 or 3 independently selected R$^q$ substituents;

R$^{10}$ is selected from H, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, (4-10 membered heterocycloalkyl)-C$_{1-4}$ alkyl-, OR$^{a2}$, SR$^{a2}$, NHOR$^{a2}$, C(O)R$^{a2}$, C(O)NR$^{a2}$R$^{a2}$, C(O)OR$^{a2}$, NHR$^{a2}$, NR$^{a2}$R$^{a2}$, NR$^{a2}$C(O)R$^{a2}$, NR$^{a2}$C(O)NR$^{a2}$R$^{a2}$, C(=NR$^{a2}$)R$^{a2}$, C(=NR$^{a2}$)NR$^{a2}$R$^{a2}$, NR$^{a2}$C(=NR$^{a2}$)NR$^{a2}$R$^{a2}$, NR$^{a2}$S(O)R$^{a2}$, NR$^{a2}$S(O)$_2$R$^{a2}$, NR$^{a2}$S(O)$_2$NR$^{a2}$R$^{a2}$, S(O)R$^{a2}$, S(O)NR$^{a2}$R$^{a2}$, S(O)$_2$R$^{a2}$, and S(O)$_2$NR$^{a2}$R$^{a2}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl- of R$^{10}$ are each optionally substituted with 1, 2, 3, 4 or 5 independently selected R$^b$ substituents;

L is

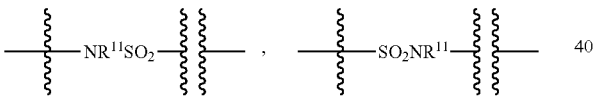

or —SO$_2$—, wherein each R$^{11}$ is independently H or C$_{1-6}$ alkyl optionally substituted with 1 or 2 R$^q$ substituents and wherein the single wavy line indicates the point of attachment to R$^{10}$ and the double wavy line indicates the point of attachment to the 6-membered ring A;

or when L is

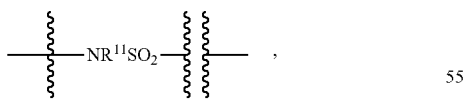

R$^{10}$ and R$^{11}$ optionally taken together with the nitrogen atom to which they are attached, form 4-, 5-, 6- or 7-membered heterocycloalkyl having 0 to 1 additional heteroatom as a ring member selected from N, O and S, wherein the 4-, 5-, 6- or 7-membered heterocycloalkyl formed by R$^{10}$, R$^{11}$ and N is optionally substituted with 1, 2 or 3 independently selected R$^q$ substituents;

or two substituents attached to the same ring carbon atom of the heterocycloalkyl formed by R$^{10}$ and R$^{11}$, taken together with the carbon atom to which they are attached form C$_{3-6}$ cycloalkyl, optionally substituted with 1, 2 or 3 independently selected R$^q$ substituents;

R$^{a1}$ and R$^{a2}$ are each independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^a$ and R$^{a2}$ are each optionally substituted with 1, 2, 3, 4, or 5 independently selected R$^d$ substituents;

each R$^b$ substituent is independently selected from halo, C$_{1-4}$ alkyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, CN, OH, NH$_2$, NO$_2$, NHOR$^c$, OR$^c$, SR, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NR$^c$C(=NOH)NR$^c$R$^c$, NR$^c$C(=NCN)NR$^c$R$^c$, SF$_5$, —P(O)R$^c$R$^c$, —P(O)(OR$^c$)(OR$^c$), NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein the C$_{1-4}$ alkyl, C$_{1-4}$ haloalkyl, C$_{1-4}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{14}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^c$ are each further optionally substituted with 1, 2, or 3 independently selected R$^d$ substituents;

each R$^c$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^c$ are each optionally substituted with 1, 2, 3, 4, or 5 independently selected R$^f$ substituents;

each R$^f$ is independently selected from C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, halo, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, NR$^g$C(=NOH)NR$^g$R$^g$, NR$^g$C(=NCN)NR$^g$R$^g$, SF$_5$, —P(O)R$^g$R$^g$, —P(O)(OR$^g$)(OR$^g$), S(O)R$^g$, S(O)NR$^g$R$^g$, S(O)$_2$R$^g$, NR$^g$S(O)$_2$R$^g$, NR$^g$S(O)$_2$NR$^g$R$^g$, and S(O)$_2$NR$^g$R$^g$; wherein the C$_{1-4}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is independently selected from $C_{1-4}$ alkyl, $C_{1-4}$ haloalkyl, halo, CN, $R^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, NR$^o$C(=NOH)NR$^o$R$^o$, NR$^o$C(=NCN)NR$^o$R$^o$, SF$_5$, —P(O)R$^o$R$^o$, —P(O)(OR$^o$)(OR$^o$), S(O)R$^o$, S(O)NR$^o$R$^o$, S(O)$_2$R$^o$, NR$^o$S(O)$_2$R$^o$, NR$^o$S(O)$_2$NR$^o$R$^o$, and S(O)$_2$NR$^o$R$^o$;

each $R^d$ is independently selected from $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, SF$_5$, —P(O)R$^e$R$^e$, —P(O)(OR$^e$)(OR$^e$), S(O)R$^e$, S(O)NR$^e$R$^e$, S(O)$_2$R, NR$^e$S(O)$_2$R$^e$, NR$^e$S(O)$_2$NR$^e$R$^e$, and S(O)$_2$NR$^e$R$^e$, wherein the $C_{1-6}$ alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^d$ are each optionally substituted with 1, 2, or 3 independently selected $R^f$ substituents;

each $R^e$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^e$ are each optionally substituted with 1, 2 or 3 independently selected $R^g$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{14}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2 or 3 independently selected $R^p$ substituents;

each $R^p$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, SF$_5$, —P(O)R$^r$R$^r$, —P(O)(OR$^r$)(OR$^r$), S(O)R$^r$, S(O)NR$^r$R$^r$, S(O)$_2$R$^r$, NR$^r$S(O)$_2$R$^r$, NR$^r$S(O)$_2$NR$^r$R$^r$, and S(O)$_2$NR$^r$R$^r$;

or any two $R^{a1}$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, NR$^i$C(=NOH)NR$^i$R$^i$, NR$^i$C(=NCN)NR$^i$R$^i$, SF$_5$, —P(O)R$^i$R$^i$, —P(O)(OR$^i$)(OR$^i$), S(O)R$^i$, S(O)NR$^i$R$^i$, S(O)$_2$R$^i$, NR$^i$S(O)$_2$R$^i$, NR$^i$S(O)$_2$NR$^i$R$^i$, and S(O)$_2$NR$^i$R$^i$, wherein the $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, NR$^k$C(=NOH)NR$^k$R$^k$, NR$^k$C(=NCN)NR$^k$R$^k$, SF$_5$, —P(O)R$^k$R$^k$, —P(O)(OR$^k$)(OR$^k$), S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$; or two $R^h$ groups attached to the same carbon atom of the 4- to 10-membered heterocycloalkyl taken together with the carbon atom to which they attach form a $C_{3-6}$ cycloalkyl or 4- to 6-membered heterocycloalkyl having 1-2 heteroatoms as ring members selected from O, N or S;

or any two $R^{a2}$ substituents together with the nitrogen atom to which they are attached form a 4-, 5-, 6-, 7-, 8-, 9- or 10-membered heterocycloalkyl group optionally substituted with 1, 2 or 3 $R^h$ substituents;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents;

or any two $R^r$ substituents together with the nitrogen atom to which they are attached form a 4-, 5-, 6-, or 7-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl of $R^i$, $R^k$, $R^o$ or $R^r$ are each optionally substituted with 1, 2 or 3 independently selected $R^q$ substituents;

each $R^q$ is independently selected from OH, CN, —COOH, $NH_2$, halo, $C_{1-6}$ alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, —$CONHR^{12}$, —$NHC(O)R^{12}$, —$OC(O)R^{12}$, —$C(O)OR^{12}$, —$C(O)R^{12}$, —$SO_2R^{12}$, —$NHSO_2R^{12}$, —$SO_2NHR^{12}$ and $NR^{12}R^{12}$, wherein the $C_{1-6}$ alkyl, phenyl, 4-6 membered heterocycloalkyl and 5-6 membered heteroaryl of $R^q$ are each optionally substituted with OH, CN, —COOH, $NH_2$, $C_{1-6}$ alkoxy, $C_{3-6}$ cycloalkyl or 4-6 membered heterocycloalkyl; and each $R^{12}$ is independently $C_{1-6}$ alkyl;

provided that:

when $R^7$ is $C_{1-6}$ alkyl, $R^{10}$-L- is other than cyclopropylsulfamoyl and methanesulfonamido;

when $R^7$ is cyclopropylmethyl, $R^{10}$-L- is other than methanesulfonamido;

when $R^7$ is 2-(4-morpholino)ethyl, $R^{10}$-L- is other than methanesulfonyl; and the compound is other than 3-(8-aminoimidazo[1,2-a]pyridin-3-yl)-2-(1H-tetrazol-5-yl)benzenesulfonamide.

In some embodiments of the previous embodiment, each $R^b$ is independently selected from $R^q$.

In some embodiments:

$X^1$ is N or $CR^1$;
$X^2$ is N or $CR^2$;
$X^3$ is N or $CR^3$;
$X^4$ is N or $CR^4$;
$X^5$ is N or $CR^5$;
$X^6$ is N or $CR^6$;
$X^3$, $X^4$, $X^5$ and $X^6$ are not simultaneously N;

$R^7$ is H, methyl, or ethyl, wherein said methyl and ethyl are each optionally substituted with 1, 2 or 3 groups independently selected from halo, OH, oxo, CN, $C_{1-6}$ haloalkyl, $C_{1-6}$ alkoxy, $C_{1-6}$ haloalkoxy, $NH_2$, $C_{1-6}$ alkyl-NH—, and $(C_{1-6}$ alkyl$)_2$N—;

$R^1$, $R^2$, $R^4$, $R^5$, $R^6$ and $R^7$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NR^{a1}R^{a1}$, $NR^{a1}C(O)R^{a1}$, $NR^{a1}C(O)OR^{a1}$, $NR^{a1}C(O)NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$ $S(O)NR^{a1}R^{a1}$, $S(O)_2R^{a1}$, and $S(O)_2NR^{a1}R^{a1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^1$, $R^2$, $R^3$, $R^4$, $R^5$, $R^6$ and $R^7$ are each optionally substituted with 1, 2, 3, 4 or 5 independently selected $R^b$ substituents;

$R^3$ is H, halo, $C_{1-6}$ alkyl, $C_{1-6}$ haloalkyl, $C_{1-6}$alkoxy, $C_{1-6}$haloalkoxy, OH, CN, $NH_2$, $C_{1-6}$ alkyl-NH—, or $(C_{1-6}$ alkyl$)_2$N—;

$R^9$ is H, CN, $NH_2$, —OH, —COOH, —$NH(C_{1-6}$ alkyl), —$NH(C_{1-6}$ alkyl$)_2$, $C_{1-6}$ alkyl, $C_{1-6}$ haloalkyl, $C_{1-6}$ alkoxy or $C_{1-6}$ haloalkoxy, wherein the $C_{1-6}$ alkyl is optionally substituted with 1, 2 or 3 independently selected $R^q$ substituents;

$R^{10}$ is selected from $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, $OR^{a2}$, $C(O)R^{a2}$, $C(O)NR^{a2}R^{a2}$, $C(O)OR^{a2}$, $NR^{a2}R^{a2}$, $NR^{a2}C(O)R^{a2}$, $NR^{a2}C(O)OR^{a2}$, $NR^{a2}C(O)NR^{a2}R^{a2}$, $NR^{a2}S(O)R^{a2}$, $NR^{a2}S(O)_2R^{a2}$, $NR^{a2}S(O)_2NR^{a2}R^{a2}$, $S(O)R^{a2}$, $S(O)_2R^{a2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^{10}$ are each optionally substituted with 1, 2, 3, 4 or 5 independently selected $R^b$ substituents;

L is

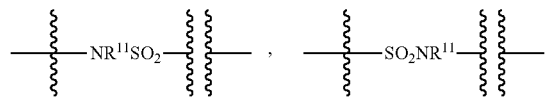

or —$SO_2$—, wherein each $R^{11}$ is independently H or $C_{1-6}$ alkyl optionally substituted with 1 or 2 $R^q$ substituents and wherein the single wavy line indicates the point of attachment to $R^{10}$ and the double wavy line indicates the point of attachment to the 6-membered ring A;

or when L is

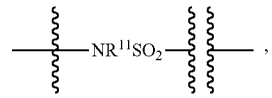

$R^{10}$ and $R^{11}$ optionally taken together with the nitrogen atom to which they are attached, form 4-, 5-, 6-, 7-, 8-, 9-, or 10-membered heterocycloalkyl having 0 to 1 additional heteroatom as a ring member selected from N, O and S, wherein the form 4-, 5-, 6-, 7-, 8-, 9-, or 10-membered heterocycloalkyl formed by $R^{10}$, $R^{11}$ and N is optionally substituted with 1, 2 or 3 independently selected $R^q$ substituents;

$R^{a1}$ and $R^{a2}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{14}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ and $R^{a2}$ are each optionally substituted with 1, 2, 3, 4, or 5 independently selected $R^d$ substituents;

each $R^b$ substituent is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-;

each $R^d$ is independently selected from $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, CN, $OR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)NR^eR^e$, $NR^eC(O)OR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$;

each $R^e$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-;

or any two $R^{a1}$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

or any two $R^{a2}$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{2-6}$ alkenyl, $C_{2-6}$ alkynyl, halo, CN, $OR^i$, $C(O)R^i$, $C(O)NR^iR^i$, $C(O)OR^i$, $OC(O)R^i$, $OC(O)NR^iR^i$, $NR^iR^i$, $NR^iC(O)R^i$, $NR^iC(O)NR^iR^i$, $NR^iC(O)OR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$ each $R^i$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl;

each $R^q$ is independently selected from OH, CN, —COOH, $NH_2$, halo, $C_{1-6}$ alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, —$CONHR^{12}$, —$NHC(O)R^2$, —$OC(O)R^{12}$, —$C(O)OR^{12}$, —$C(O)R^{12}$, —$SO_2R^{12}$, —$NHSO_2R^{12}$, —$SO_2NHR^{12}$ and $NR^{12}R^{12}$; and each $R^{12}$ is independently $C_{1-6}$ alkyl.

In some embodiments of the previous embodiment, one or more hydrogen atoms can be replaced by deuterium atoms (e.g., one or more hydrogen atoms of a $C_{1-6}$ alkyl group can be replaced by deuterium atoms).

In some embodiments:
$X^1$ is N or $CR^1$;
$X^2$ is N or $CR^2$;
$X^3$ is N or $CR^3$;
$X^4$ is N or $CR^4$;
$X^5$ is N or $CR^5$;
$X^6$ is N or $CR^6$;
$X^3$, $X^4$, $X^5$ and $X^6$ are not simultaneously N;
$R^7$ is H, methyl, or ethyl, wherein said methyl and ethyl are each optionally substituted with 1, 2 or 3 groups independently selected from halo, OH, oxo, CN, $C_{1-6}$ haloalkyl, $C_{1-6}$ alkoxy, $C_{1-6}$ haloalkoxy, $NH_2$, $C_{1-6}$ alkyl-NH—, and $(C_{1-6}$ alkyl$)_2$N—;
$R^1$, $R^2$, $R^4$, $R^5$, $R^6$ and $R^7$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{14}$ alkyl-, CN, $NO_2$, $OR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NR^{a1}R^{a1}$, $NR^{a1}C(O)R^{a1}$ $NR^{a1}C(O)OR^{a1}$, $NR^{a1}C(O)NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$ $S(O)NR^{a1}R^{a1}$, $S(O)_2R^{a1}$, and $S(O)_2NR^{a1}R^{a1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^1$, $R^2$, $R^3$, $R^4$, $R^5$, $R^6$ and $R^8$ are each optionally substituted with 1, 2, 3, 4 or 5 independently selected $R^b$ substituents;

$R^3$ is H, halo, $C_{1-6}$ alkyl, $C_{1-6}$ haloalkyl, $C_{1-6}$ alkoxy, $C_{1-6}$ haloalkoxy, OH, CN, NH$_2$, $C_{1-6}$ alkyl-NH—, or $(C_{1-6}$ alkyl)$_2$N—;

$R^9$ is H, CN, NH$_2$, —OH, —COOH, —NH($C_{1-6}$ alkyl), —NH($C_{1-6}$ alkyl)$_2$, $C_{1-6}$ alkyl, $C_{1-6}$ haloalkyl, $C_{1-6}$ alkoxy or $C_{1-6}$ haloalkoxy, wherein the $C_{1-6}$ alkyl is optionally substituted with 1, 2 or 3 independently selected $R^q$ substituents;

$R^{10}$ is selected from $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, $OR^{a2}$, $C(O)R^{a2}$, $C(O)NR^{a2}R^{a2}$, $C(O)OR^{a2}$, $NR^{a2}R^{a2}$, $NR^{a2}C(O)R^{a2}$, $NR^{a2}C(O)OR^{a2}$, $NR^{a2}C(O)NR^{a2}R^{a2}$, $NR^{a2}S(O)R^{a2}$, $NR^{a2}S(O)_2R^{a2}$, $NR^{a2}S(O)_2NR^{a2}R^{a2}$, $S(O)R^{a2}$, $S(O)_2R^{a2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{14}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^{10}$ are each optionally substituted with 1, 2, 3, 4 or 5 independently selected $R^b$ substituents;

L is

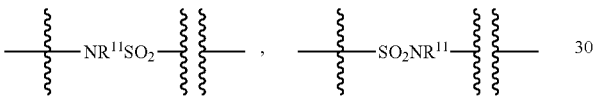

or —SO$_2$—, wherein each $R^{11}$ is independently H or $C_{1-6}$ alkyl optionally substituted with 1 or 2 $R^q$ substituents and wherein the single wavy line indicates the point of attachment to $R^{10}$ and the double wavy line indicates the point of attachment to the 6-membered ring A;

$R^{a1}$ and $R^{a2}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^{a1}$ and $R^{a2}$ are each optionally substituted with 1, 2, 3, 4, or 5 independently selected $R^d$ substituents;

each $R^b$ substituent is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-;

each $R^d$ is independently selected from $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, CN, $OR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)NR^eR^e$, $NR^eC(O)OR$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$;

each $R^e$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-;

or any two $R^{a1}$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

or any two $R^{a2}$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{2-6}$ alkenyl, $C_{2-6}$ alkynyl, halo, CN, OW, C(O)R, $C(O)NR^iR^i$, $C(O)OR^i$, $OC(O)R^i$, $OC(O)NR^iR^i$, $NR^iR^i$, $NR^iC(O)R^i$, $NR^iC(O)NR^iR^i$, $NR^iC(O)OR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$ each $R^i$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl;

each $R^q$ is independently selected from OH, CN, —COOH, NH$_2$, halo, $C_{1-6}$ alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, —CONHR$^{12}$, —NHC(O)R$^{12}$, —OC(O)R$^{12}$, —C(O)OR$^{12}$, —C(O)R$^{12}$, —SO$_2$R$^{12}$, —NHSO$_2$R$^{12}$, —SO$_2$NHR$^{12}$ and NR$^{12}$R$^{12}$; and each R$^{12}$ is independently C$_{1-6}$ alkyl.

In some embodiments, one or more hydrogen atoms in a compound of the present disclosure (e.g., a compound of Formula I, II, III, IV, V, and the like), or a pharmaceutically acceptable salt thereof, can be replaced by one or more deuterium atoms. In some embodiments, one or more hydrogen atoms in a C$_{1-6}$ alkyl group can be replaced by deuterium atoms (e.g., —CD$_3$).

In some embodiments, X$^1$ is N.
In some embodiments, X$^1$ is CR$^1$.
In some embodiments, X$^2$ is N.
In some embodiments, X$^2$ is CR$^2$.
In some embodiments, X$^3$ is N.
In some embodiments, X$^3$ is CR$^3$.
In some embodiments, X$^4$ is N.
In some embodiments, X$^4$ is CR$^4$.
In some embodiments, X$^4$ is CH.
In some embodiments, X$^5$ is N.
In some embodiments, X$^5$ is CR$^5$.
In some embodiments, X$^5$ is CH.
In some embodiments, X$^4$ is CH and X$^5$ is CH or N.
In some embodiments, X$^6$ is N.
In some embodiments, X$^6$ is CR$^6$.

In some embodiments, R$^1$ is H, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl- are each optionally substituted by 1, 2, 3, 4, or 5 independently selected R$^b$ substituents.

In some embodiments, R$^1$ is H, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-10 membered heteroaryl, and 4-10 membered heterocycloalkyl, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl are each optionally substituted by 1, 2, 3, 4, or 5 independently selected R$^b$ substituents.

In some embodiments, R$^1$ is H, halo, C$_{6-10}$ aryl, C$_{3-10}$ cycloalkyl, 5-10 membered heteroaryl, and 4-10 membered heterocycloalkyl, wherein the C$_{6-10}$ aryl, C$_{3-10}$ cycloalkyl, 5-10 membered heteroaryl, and 4-10 membered heterocycloalkyl are each optionally substituted by 1, 2, 3, 4, or 5 independently selected R$^b$ substituents.

In some embodiments, R$^1$ is H, halo, or 5-10 membered heteroaryl, wherein the 5-10 membered heteroaryl is optionally substituted by 1, 2, 3, 4, or 5 independently selected R$^b$ substituents.

In some embodiments, R$^1$ is H, halo, or 5-10 membered heteroaryl, wherein the 5-10 membered heteroaryl is optionally substituted by 1 or 2 independently selected R$^b$ substituents.

In some embodiments, R$^1$ is H, halo, or 5-6 membered heteroaryl, wherein the 5-6 membered heteroaryl is optionally substituted by 1 or 2 independently selected R$^b$ substituents.

In some embodiments, R$^1$ is H, halo, or 5-6 membered heteroaryl, wherein the 5-6 membered heteroaryl is optionally substituted by 1 or 2 independently selected C$_{1-4}$ alkyl groups.

In some embodiments, R$^1$ is H, Cl, or 1-methyl-1H-pyrazol-4-yl.

In some embodiments, R$^2$ is H, halo, C$_{1-6}$ alkyl, C$_{2-6}$ alkenyl, C$_{2-6}$ alkynyl, or C$_{1-6}$ haloalkyl, wherein the C$_{1-6}$ alkyl, C$_{2-6}$ alkenyl, and C$_{2-6}$ alkynyl are each optionally substituted with 1, 2, 3, 4 or 5 independently selected R$^b$ substituents.

In some embodiments, R$^2$ is H.

In some embodiments, R$^3$ is H, halo, C$_{1-6}$ alkyl, C$_{2-6}$ alkenyl, C$_{2-6}$ alkynyl, or C$_{1-6}$ haloalkyl, wherein the C$_{1-6}$ alkyl, C$_{2-6}$ alkenyl, and C$_{2-6}$ alkynyl are each optionally substituted with 1, 2, 3, 4 or 5 independently selected R$^b$ substituents.

In some embodiments, R$^3$ is H.

In some embodiments, R$^4$ is H, halo, C$_{1-6}$ alkyl, C$_{2-6}$ alkenyl, C$_{2-6}$ alkynyl, or C$_{1-6}$ haloalkyl, wherein the C$_{1-6}$ alkyl, C$_{2-6}$ alkenyl, and C$_{2-6}$ alkynyl are optionally substituted by 1, 2, 3, 4, or 5 independently selected R$^b$ substituents.

In some embodiments, R$^4$ is H, halo, C$_{1-6}$ alkyl, or C$_{1-6}$ haloalkyl, wherein the C$_{1-6}$ alkyl is optionally substituted by 1, 2, 3, 4, or 5 independently selected R$^b$ substituents.

In some embodiments, R$^4$ is H, halo, or C$_{1-6}$ alkyl, wherein the C$_{1-6}$ alkyl is optionally substituted by 1, 2, 3, 4, or 5 independently selected R$^b$ substituents.

In some embodiments, R$^4$ is H, D, F, Cl, CD$_3$, or methyl.
In some embodiments, R$^4$ is H, F, Cl, CD$_3$, or methyl.
In some embodiments, R$^4$ is H, F, CD$_3$, or methyl.
In some embodiments, R$^4$ is H, F, or methyl.
In some embodiments, R$^4$ is Cl, CD$_3$, or methyl.
In some embodiments, R$^4$ is CD$_3$, or methyl.

In some embodiments, R$^5$ is H, halo, C$_{1-6}$ alkyl, C$_{2-6}$ alkenyl, C$_{2-6}$ alkynyl, or C$_{1-6}$ haloalkyl, wherein said C$_{1-6}$ alkyl, C$_{2-6}$ alkenyl, and C$_{2-6}$ alkynyl are each optionally substituted by 1, 2, 3, 4, or 5 independently selected R$^b$ substituents.

In some embodiments, R$^5$ is H, C$_{1-6}$ alkyl, C$_{2-6}$ alkenyl, C$_{2-6}$ alkynyl, or C$_{1-6}$ haloalkyl, wherein said C$_{1-6}$ alkyl, C$_{2-6}$ alkenyl, and C$_{2-6}$ alkynyl are each optionally substituted by 1, 2, 3, 4, or 5 independently selected R$^b$ substituents.

In some embodiments, R$^5$ is H, halo, C$_{1-6}$ alkyl, or C$_{1-6}$ haloalkyl, wherein the C$_{1-6}$ alkyl is optionally substituted by 1, 2, 3, 4, or 5 independently selected R$^b$ substituents.

In some embodiments, R$^5$ is H, C$_{1-6}$ alkyl, or C$_{1-6}$ haloalkyl, wherein the C$_{1-6}$ alkyl is optionally substituted by 1, 2, 3, 4, or 5 independently selected R$^b$ substituents.

In some embodiments, R$^5$ is H or C$_{1-6}$alkyl, wherein the C$_{1-6}$ alkyl is optionally substituted by 1, 2, 3, 4, or 5 independently selected R$^b$ substituents.

In some embodiments, R$^5$ is H or C$_{1-6}$ alkyl.
In some embodiments, R$^5$ is H or methyl.
In some embodiments, R$^5$ is H or F.
In some embodiments, R$^4$ is H and R$^5$ is H.

In some embodiments, R$^6$ is H, halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{a1}$, C(O)NR$^{a1}$R$^{a1}$, C(O)OR$^{a1}$, OC(O)R$^{a1}$, OC(O)NR$^{a1}$R$^{a1}$, NR$^{a1}$R$^{a1}$ NR$^{a1}$C(O)R$^{a1}$, NR$^{a1}$C(O)OR$^{a1}$, NR$^{a1}$C(O)NR$^{a1}$R$^{a1}$, C(=NR$^{a1}$)R$^{a1}$, C(=NR$^{a1}$)NR$^{a1}$R$^{a1}$, NR$^{a1}$C(=NR$^{a1}$)NR$^{a1}$R$^{a1}$, NR$^{a1}$C(=NOH)NR$^{a1}$R$^{a1}$, NR$^{a1}$C(=NCN)NR$^{a1}$R$^{a1}$, NR$^{a1}$S(O)R$^{a1}$ NR$^{a1}$S(O)$_2$R$^{a1}$, NR$^{a1}$S(O)$_2$NR$^{a1}$R$^{a1}$, S(O)R$^{a1}$, S(O)NR$^{a1}$R$^{a1}$, S(O)$_2$R$^{a1}$, SF$_5$, —P(O)R$^{a1}$R$^{a1}$, —P(O)(OR$^{a1}$)(OR$^{a1}$) and S(O)$_2$NR$^{a1}$R$^{a1}$, wherein the $C_{1-6}$ alkyl, $C_{2-6}$ alkenyl, and $C_{2-6}$ alkynyl are optionally substituted by 1, 2, 3, 4, or 5 independently selected $R^b$ substituents.

In some embodiments, $R^6$ is H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NR^{a1}R^{a1}$, $NR^{a1}C(O)R^{a1}$, $NR^{a1}C(O)OR^{a1}$, $NR^{a1}C(O)NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$, $S(O)NR^{a1}R^{a1}$, $S(O)_2R^{a1}$, and $S(O)_2NR^{a1}R^{a1}$, wherein the $C_{1-6}$ alkyl, $C_{2-6}$ alkenyl, and $C_{2-6}$ alkynyl are optionally substituted by 1, 2, 3, 4, or 5 independently selected $R^b$ substituents.

In some embodiments, $R^6$ is H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{a1}$, $C(O)NR^{a1}R^{a1}$, $C(O)OR^{a1}$, $OC(O)R^{a1}$, or $OC(O)NR^{a1}R^{a1}$, wherein the $C_{1-6}$ alkyl, $C_{2-6}$ alkenyl, and $C_{2-6}$ alkynyl are optionally substituted by 1, 2, 3, 4, or 5 independently selected $R^b$ substituents.

In some embodiments, $R^6$ is H, halo, $C_{1-6}$ alkyl, $C_{2-6}$ alkenyl, $C_{2-6}$ alkynyl, $C_{1-6}$ haloalkyl, or $OR^a$, wherein said $C_{1-6}$ alkyl, $C_{2-6}$ alkenyl, and $C_{2-6}$ alkynyl are optionally substituted by 1, 2, 3, 4, or 5 independently selected $R^b$ substituents.

In some embodiments, $R^6$ is H, halo, $C_{1-6}$ alkyl, $C_{1-6}$ haloalkyl, or $OR^{a1}$, wherein said $C_{1-6}$ alkyl is optionally substituted by 1, 2, 3, 4, or 5 independently selected $R^b$ substituents.

In some embodiments, $R^6$ is H, halo, $C_{1-6}$ alkyl, or $OR^{a1}$, wherein said $C_{1-6}$ alkyl is optionally substituted by 1, 2, 3, 4, or 5 independently selected $R^b$ substituents.

In some embodiments, $R^6$ is H, halo, $C_{1-6}$ alkyl, or $OR^{a1}$.

In some embodiments, $R^6$ is H, F, Cl, methyl, methoxy, or ethoxy.

In some embodiments, $R^6$ is halo, $C_{1-6}$ alkyl, or CN.

In some embodiments, $R^7$ is H or $C_{1-6}$ alkyl optionally substituted with 1, 2 or 3 groups independently selected from halo, OH, oxo, CN, $C_{1-6}$ alkoxy, and $C_{1-6}$ haloalkoxy.

In some embodiments, $R^7$ is H or $C_{1-6}$ alkyl optionally substituted with 1, 2 or 3 groups independently selected from OH and oxo.

In some embodiments, $R^7$ is H, unsubstituted $C_{1-6}$ alkyl, or $C_{1-6}$ alkyl substituted by oxo.

In some embodiments, $R^7$ is H, unsubstituted $C_{1-2}$ alkyl, or $C_{1-6}$ alkyl substituted by oxo.

In some embodiments, $R^7$ is H, methyl, or ethyl, wherein said methyl or ethyl are optionally substituted with 1, 2 or 3 groups independently selected from halo, OH, oxo, CN, $C_{1-6}$ alkoxy, and $C_{1-6}$ haloalkoxy.

In some embodiments, $R^7$ is H, methyl, or $C(=O)CH_3$.

In some embodiments, $R^7$ is H.

In some embodiments, $R^8$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^8$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, or 3 independently selected $R^q$ substituents.

In some embodiments, $R^8$ is H, halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-C14 alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^8$ is H, halo, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^8$ is H, halo, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, or 3 independently selected $R^q$ substituents.

In some embodiments, $R^8$ is H, halo, $C_{1-6}$ alkyl, $C_{1-6}$ haloalkyl, $C_{6-10}$ aryl, 5-10 membered heteroaryl, 4-10 membered heterocycloalkyl, $C_{6-10}$ aryl-$C_{1-4}$ alkyl-, (5-10 membered heteroaryl)-$C_{1-4}$ alkyl-, or (4-10 membered heterocycloalkyl)-$C_{14}$ alkyl-, wherein the $C_{1-6}$ alkyl, $C_{6-10}$ aryl, 5-10 membered heteroaryl, 4-10 membered heterocycloalkyl, $C_{6-10}$ aryl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^8$ is H, halo, $C_{1-6}$ alkyl, $C_{6-10}$ aryl, 5-10 membered heteroaryl, 4-10 membered heterocycloalkyl, $C_{6-10}$ aryl-$C_{1-4}$ alkyl-, (5-10 membered heteroaryl)-$C_{1-4}$ alkyl-, or (4-10 membered heterocycloalkyl)-$C_{14}$ alkyl-, wherein the $C_{1-6}$ alkyl, $C_{6-10}$ aryl, 5-10 membered heteroaryl, 4-10 membered heterocycloalkyl, $C_{6-10}$ aryl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^8$ is H, halo, $C_{1-6}$ alkyl, $C_{6-10}$ aryl, 5-10 membered heteroaryl, 4-10 membered heterocycloalkyl, $C_{6-10}$ aryl-$C_{1-4}$ alkyl-, (5-10 membered heteroaryl)-$C_{1-4}$ alkyl-, or (4-10 membered heterocycloalkyl)-$C_{14}$ alkyl-, wherein the $C_{1-6}$ alkyl, $C_{6-10}$ aryl, 5-10 membered heteroaryl, 4-10 membered heterocycloalkyl, $C_{6-10}$ aryl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, or 3 independently selected $R^q$ substituents.

In some embodiments, $R^8$ is H, halo, $C_{1-6}$ alkyl, $C_{1-6}$ haloalkyl, $C_{3-6}$ cycloalkyl, phenyl, 5-6 membered heteroaryl, or 5-6 membered heterocycloalkyl, wherein the $C_{1-6}$ alkyl, phenyl, 5-6 membered heteroaryl, and 5-6 membered heterocycloalkyl each optionally substituted with 1, 2, 3, 4 or 5 independently selected $R^b$ substituents.

In some embodiments, $R^8$ is H, halo, $C_{1-6}$ alkyl, phenyl, 5-6 membered heteroaryl, or 5-6 membered heterocycloalkyl, wherein the $C_{1-6}$ alkyl, phenyl, 5-6 membered heteroaryl, and 5-6 membered heterocycloalkyl each optionally substituted with 1, 2, 3, 4 or 5 independently selected $R^b$ substituents.

In some embodiments, $R^8$ is H, halo, $C_{1-6}$ alkyl, phenyl, 5-6 membered heteroaryl, or 5-6 membered heterocycloalkyl, wherein the $C_{1-6}$ alkyl, phenyl, 5-6 membered heteroaryl, and 5-6 membered heterocycloalkyl each optionally substituted with 1, 2, or 3 independently selected $R^g$ substituents.

In some embodiments, $R^8$ is halo, $C_{1-6}$ alkyl, $C_{1-6}$ haloalkyl, $C_{3-6}$ cycloalkyl, $C_{6-10}$ aryl or 5-6 membered heteroaryl, wherein $C_{1-6}$ alkyl, $C_{6-10}$ aryl and 5-6 membered heteroaryl are each optionally substituted with 1, 2 or 3 independently selected $R^b$ substituents.

In some embodiments, $R^8$ is halo, $C_{1-6}$ alkyl, $C_{6-10}$ aryl or 5-6 membered heteroaryl, wherein $C_{1-6}$ alkyl, $C_{6-10}$ aryl and 5-6 membered heteroaryl are each optionally substituted with 1, 2 or 3 independently selected $R^b$ substituents.

In some embodiments, $R^8$ is halo, $C_{1-6}$ alkyl, $C_{6-10}$ aryl or 5-6 membered heteroaryl, wherein $C_{1-6}$ alkyl, $C_{6-10}$ aryl and 5-6 membered heteroaryl are each optionally substituted with 1, 2, or 3 independently selected $R^q$ substituents.

In some embodiments, $R^8$ is halo, $C_{1-6}$ alkyl, $C_{1-6}$ haloalkyl, $C_{3-6}$ cycloalkyl, phenyl, or 5-6 membered heteroaryl, wherein $C_{1-6}$ alkyl, phenyl, and 5-6 membered heteroaryl are each optionally substituted with 1, 2 or 3 $R^b$ substituents.

In some embodiments, $R^8$ is halo, $C_{1-6}$ alkyl, phenyl, or 5-6 membered heteroaryl, wherein $C_{1-6}$ alkyl, phenyl, and 5-6 membered heteroaryl are each optionally substituted with 1, 2 or 3 $R^b$ substituents.

In some embodiments, $R^8$ is halo, $C_{1-6}$ alkyl, phenyl, or 5-6 membered heteroaryl, wherein $C_{1-6}$ alkyl, phenyl, and 5-6 membered heteroaryl are each optionally substituted with 1, 2, or 3 independently selected $R^q$ substituents.

In some embodiments, $R^8$ is H, halo, $C_{1-6}$ alkyl, or $C_{1-6}$ haloalkyl.

In some embodiments, $R^8$ is H, halo, or $C_{1-6}$ alkyl.

In some embodiments, $R^8$ is H, Cl, F, Br, methyl, or ethyl.

In some embodiments, $R^8$ is phenyl, which is optionally substituted with 1, 2, 3, 4 or 5 independently selected $R^b$ substituents.

In some embodiments, $R^8$ is phenyl, which is optionally substituted with 1 or 2 independently selected $R^b$ substituents.

In some embodiments, $R^8$ is phenyl, which is optionally substituted with 1, 2, or 3 independently selected $R^q$ substituents.

In some embodiments, $R^8$ is phenyl, which is optionally substituted with 1 or 2 independently selected $R^b$ substituents selected from halo, $C_{1-4}$ alkyl, $C_{1-4}$ haloalkyl, CN, $NO_2$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $—P(O)R^cR^c$, $—P(O)(OR^c)(OR^c)$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$.

In some embodiments, $R^8$ is phenyl, which is optionally substituted with 1 or 2 independently selected $R^b$ substituents independently selected from halo, $C_{1-4}$ alkyl, $C_{1-4}$ haloalkyl, CN, $NO_2$, $OR^c$, $SR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$.

In some embodiments, $R^8$ is phenyl, which is optionally substituted with 1 or 2 independently selected $R^b$ substituents independently selected from halo, $C_{1-4}$ alkyl, $C_{1-4}$ haloalkyl, CN, $NR^cR^c$, $NO_2$, $OR^c$, $S(O)R^c$, $S(O)_2R^c$, and $S(O)_2NR^cR^c$.

In some embodiments, $R^8$ is phenyl, which is optionally substituted with 1 or 2 independently selected $R^b$ substituents independently selected from halo, $C_{1-4}$ alkyl, CN, $OR^c$, and $S(O)_2R^c$.

In some embodiments, $R^8$ is phenyl, which is optionally substituted with 1 or 2 independently selected $R^b$ substituents independently selected from halo, $C_{1-4}$ alkyl, CN, $OR^c$, and $S(O)_2R^c$, wherein each $R^c$ is an independently selected $C_{1-6}$ alkyl group.

In some embodiments, $R^8$ is phenyl, 2-methylphenyl, 3-methylphenyl, 4-methylphenyl, 2-fluorophenyl, 3-fluorophenyl, 4-fluorophenyl, 4-cyanophenyl, or 2-fluoro-3-methoxyphenyl.

In some embodiments, $R^8$ is a 5-6 membered heteroaryl or 5-6 membered heterocycloalkyl, wherein the 5-6 membered heteroaryl and 5-6 membered heterocycloalkyl are each optionally substituted with 1, 2, 3, 4 or 5 independently selected $R^b$ substituents.

In some embodiments, $R^8$ is a 5-6 membered heteroaryl, which is optionally substituted with 1, 2, 3, 4 or 5 independently selected $R^b$ substituents.

In some embodiments, $R^8$ is a 5-6 membered heteroaryl, which is optionally substituted with 1 or 2 independently selected $R^b$ substituents.

In some embodiments, $R^8$ is a 5-6 membered heteroaryl, which is optionally substituted with 1 or 2 independently selected $R^b$ substituents selected from halo, $C_{1-4}$ alkyl, $C_{1-4}$ haloalkyl, CN, $NO_2$, OR, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $—P(O)R^cR^c$, $—P(O)(OR^c)(OR^c)$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$.

In some embodiments, $R^8$ is a 5-6 membered heteroaryl, which is optionally substituted with 1 or 2 independently selected $R^b$ substituents selected from halo, $C_{1-4}$ alkyl, $C_{1-4}$ haloalkyl, CN, $NO_2$, OR, $SR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$.

In some embodiments, $R^8$ is a 5-6 membered heteroaryl, which is optionally substituted with 1 or 2 independently selected $R^b$ substituents selected from halo, $C_{1-4}$ alkyl, $C_{1-4}$ haloalkyl, CN, $NR^cR^c$, $NO_2$, $OR^c$, $S(O)R^c$, $S(O)_2R^c$, and $S(O)_2NR^cR^c$.

In some embodiments, $R^8$ is a 5-6 membered heteroaryl, which is optionally substituted with 1 or 2 independently selected $R^b$ substituents selected from $C_{1-4}$ alkyl and $C_{1-4}$ haloalkyl.

In some embodiments, $R^8$ is a 5-6 membered heteroaryl, which is optionally substituted with 1 or 2 independently selected $R^b$ substituents selected from $C_{1-4}$ alkyl.

In some embodiments, $R^8$ is 2-fluoro-pyridin-3-yl, pyridin-4-yl, 2-thienyl, 2-fluoro-5-(N-methylaminocarbonyl) phenyl, 3-methylsulfonylphenyl, 2-fluoro-6-methoxyphenyl, 1-methyl-1H-pyrazol-4-yl, 1-methyl-1H-pyrazol-5-yl, pyrimidin-5-yl, or 2-methylthiazol-5-yl.

In some embodiments, $R^8$ is H, Br, Cl, $C_{1-4}$ alkyl, phenyl, 1H-pyrazol-3-yl, 1H-pyrazol-5-yl, 1H-pyrazol-4-yl, 1-methyl-1H-pyrazol-5-yl, 1-methyl-1H-pyrazol-4-yl, thiazol-2-yl, thiazol-4-yl, thiazol-5-yl, pyridyl, thiophenyl or pyrimidinyl, wherein the phenyl, 1H-pyrazol-3-yl, 1H-pyrazol-5-yl, 1H-pyrazol-4-yl, 1-methyl-1H-pyrazol-5-yl, 1-methyl-1H-pyrazol-4-yl, thiazol-2-yl, thiazol-4-yl, thiazol-5-yl, pyridyl, thiophenyl and pyrimidinyl are each optionally substituted with 1 or 2 substituents independently selected from halo, CN, —S(O)$_2$—C$_{1-6}$ alkyl, C$_{1-6}$ alkyl, and —C$_{1-6}$ alkylene-OH.

In some embodiments, $R^8$ is H, Br, Cl, $C_{1-4}$ alkyl, phenyl, 1H-pyrazol-5-yl, 1H-pyrazol-4-yl, 1-methyl-1H-pyrazol-5-yl, 1-methyl-1H-pyrazol-4-yl, thiazol-5-yl, pyridyl, thiophenyl or pyrimidinyl, wherein the phenyl, 1H-pyrazol-5-yl, 1H-pyrazol-4-yl, 1-methyl-1H-pyrazol-5-yl, 1-methyl-1H-pyrazol-4-yl, thiazol-5-yl, pyridyl, thiophenyl and pyrimidinyl are each optionally substituted with 1 or 2 substituents independently selected from halo, CN, —S(O)$_2$—C$_{1-6}$ alkyl, C$_{1-6}$ alkyl, and —C$_{1-6}$ alkylene-OH.

In some embodiments, $R^8$ is H, Br, Cl, $C_{1-4}$ alkyl, $C_{1-4}$ haloalkyl, cyclopropyl, phenyl, 1H-pyrazol-5-yl, 1H-pyrazol-4-yl, 1-methyl-1H-pyrazol-5-yl, 1-methyl-1H-pyrazol-4-yl, thiazol-5-yl, isoxazol-4-yl, isoxazol-5-yl, pyridyl, thiophenyl or pyrimidinyl, wherein the $C_{1-4}$ alkyl, phenyl, 1H-pyrazol-5-yl, 1H-pyrazol-4-yl, 1-methyl-1H-pyrazol-5-yl, 1-methyl-1H-pyrazol-4-yl, thiazol-5-yl, isoxazol-4-yl, isoxazol-5-yl, pyridyl, thiophenyl and pyrimidinyl are each optionally substituted with 1 or 2 independently selected $R^b$ substituents.

In some embodiments, $R^8$ is H, Br, Cl, $C_{1-4}$ alkyl, phenyl, 1H-pyrazol-5-yl, 1H-pyrazol-4-yl, 1-methyl-1H-pyrazol-5-yl, 1-methyl-1H-pyrazol-4-yl, thiazol-5-yl, pyridyl, thiophenyl or pyrimidinyl, wherein the phenyl, 1H-pyrazol-5-yl, 1H-pyrazol-4-yl, 1-methyl-1H-pyrazol-5-yl, 1-methyl-1H-pyrazol-4-yl, thiazol-5-yl, pyridyl, thiophenyl and pyrimidinyl are each optionally substituted with 1 or 2 independently selected $R^b$ substituents.

In some embodiments, $R^8$ is H, Br, Cl, $C_{1-4}$ alkyl, phenyl, 1H-pyrazol-5-yl, 1H-pyrazol-4-yl, 1-methyl-1H-pyrazol-5-yl, 1-methyl-1H-pyrazol-4-yl, thiazol-5-yl, pyridyl, thiophenyl or pyrimidinyl, wherein the phenyl, 1H-pyrazol-5-yl, 1H-pyrazol-4-yl, 1-methyl-1H-pyrazol-5-yl, 1-methyl-1H-pyrazol-4-yl, thiazol-5-yl, pyridyl, thiophenyl and pyrimidinyl are each optionally substituted with 1 or 2 independently selected $R^b$ substituents.

In some embodiments, $R^8$ is H, D, CD$_3$, CF$_3$, methyl, C(O)NR$^{a1}$R$^{a1}$, $C_{3-6}$ cycloalkyl, C6-10 aryl, or 4-10 membered heterocycloalkyl, wherein the $C_{6-10}$ aryl and 4-10 membered heterocycloalkyl are each optionally substituted with 1 or 2 independently selected $R^b$ substituents.

In some embodiments, $R^8$ is H, D, CD$_3$, CF$_3$, methyl, C(O)NR$^{a1}$R$^{a1}$, cyclopropyl, phenyl, 1H-pyrazol-5-yl, 1H-pyrazol-4-yl, 1-methyl-1H-pyrazol-5-yl, 1-methyl-1H-pyrazol-4-yl, thiazol-5-yl, isoxazol-4-yl, isoxazol-5-yl, pyridyl, thiophenyl or pyrimidinyl, wherein the phenyl, 1H-pyrazol-5-yl, 1H-pyrazol-4-yl, 1-methyl-1H-pyrazol-5-yl, 1-methyl-1H-pyrazol-4-yl, thiazol-5-yl, isoxazol-4-yl, isoxazol-5-yl, pyridyl, thiophenyl and pyrimidinyl are each optionally substituted with 1 or 2 independently selected $R^b$ substituents.

In some embodiments, $R^8$ is H, D, CD$_3$, CF$_3$, methyl, C(O)NR$^{a1}$R$^{a1}$, cyclopropyl, phenyl, 1H-pyrazol-5-yl, 1H-pyrazol-4-yl, 1-methyl-1H-pyrazol-5-yl, 1-methyl-1H-pyrazol-4-yl, thiazol-5-yl, isoxazol-4-yl, isoxazol-5-yl, pyridyl, thiophenyl or pyrimidinyl, wherein the phenyl, 1H-pyrazol-5-yl, 1H-pyrazol-4-yl, 1-methyl-1H-pyrazol-5-yl, 1-methyl-1H-pyrazol-4-yl, thiazol-5-yl, isoxazol-4-yl, isoxazol-5-yl, pyridyl, thiophenyl and pyrimidinyl are each optionally substituted with 1 or 2 independently selected $R^b$ substituents.

In some embodiments, $R^8$ is H, D, CD$_3$, CF$_3$, methyl, C(O)NR$^{a1}$R$^{a1}$, $C_{3-6}$ cycloalkyl, $C_{6-10}$ aryl, or 4-10 membered heterocycloalkyl, wherein the $C_{6-10}$ aryl and 4-10 membered heterocycloalkyl are each optionally substituted with 1 or 2 independently selected R substituents.

In some embodiments, $R^8$ is H, CF$_3$, or methyl.

In some embodiments, $R^g$ is H, halo, $C_{1-6}$ alkyl, $C_{2-6}$ alkenyl, $C_{2-6}$ alkynyl, $C_{1-6}$ haloalkyl, wherein the $C_{1-6}$ alkyl, $C_{2-6}$ alkenyl, and $C_{2-6}$ alkynyl, are each optionally substituted with 1, 2, 3, 4 or 5 independently selected $R^b$ substituents.

In some embodiments, $R^9$ is H.

In some embodiments, $R^2$ and $R^3$ are each H.

In some embodiments, $R^2$ and $R^9$ are each H.

In some embodiments, $R^3$ and $R^9$ are each H.

In some embodiments, $R^2$, $R^3$, and $R^9$ are each H.

In some embodiments, $R^{10}$ is H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^{10}$ is $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^{10}$ is $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents.

In some embodiments, $R^{10}$ is $C_{1-6}$ alkyl, phenyl, $C_{3-6}$ cycloalkyl, 5-6 membered heteroaryl, 4-6 membered heterocycloalkyl, phenyl-$C_{1-4}$ alkyl-, $C_{3-6}$ cycloalkyl-$C_{1-4}$ alkyl-, (5-6 membered heteroaryl)-$C_{1-4}$ alkyl-, or (4-6 membered heterocycloalkyl)-$C_{1-4}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-4}$ alkyl-, $C_{3-6}$ cycloalkyl-$C_{1-4}$ alkyl-, (5-6 membered heteroaryl)-$C_{1-4}$ alkyl-, and (4-6 membered heterocycloalkyl)-$C_{1-4}$ alkyl- are each optionally substituted with 1, 2, 3, 4 or 5 independently selected $R^b$ substituents.

In some embodiments, $R^{10}$ is $C_{1-6}$ alkyl, $C_{3-6}$ cycloalkyl, $C_{3-6}$ cycloalkyl-$C_{1-4}$ alkyl-, 4-6 membered heterocycloalkyl or 4-6 membered heterocycloalkyl-$C_{1-4}$ alkyl-, each of which is optionally substituted with 1, 2 or 3 independently selected $R^b$ substituents.

In some embodiments, $R^{10}$ is $C_{1-6}$ alkyl, $C_{3-6}$ cycloalkyl, 4-6 membered heterocycloalkyl, or (4-6 membered heterocycloalkyl)-$C_{1-4}$ alkyl-, wherein the $C_{1-6}$ alkyl, phenyl, $C_{3-6}$ cycloalkyl, 4-6 membered heterocycloalkyl, and (4-6 membered heterocycloalkyl)-$C_{1-4}$ alkyl- are each optionally substituted with 1, 2, 3, 4 or 5 independently selected $R^b$ substituents.

In some embodiments, $R^{10}$ is $C_{1-6}$ alkyl, which is optionally substituted with 1, 2, 3, 4 or 5 independently selected $R^b$ substituents.

In some embodiments, $R^{10}$ is $C_{1-6}$ alkyl, which is optionally substituted with 1 or 2 independently selected $R^b$ substituents.

In some embodiments, $R^{10}$ is $C_{1-6}$ alkyl, which is optionally substituted with 1 or 2 independently selected $R^b$ substituents selected from halo, CN, $NO_2$, OR, $SR^c$, and $NR^cR^c$.

In some embodiments, $R^{10}$ is methyl, ethyl, or 3-hydroxypropyl.

In some embodiments, $R^{10}$ is $C_{3-10}$ cycloalkyl, which is optionally substituted with 1, 2, 3, 4 or 5 independently selected $R^b$ substituents.

In some embodiments, $R^{10}$ is $C_{3-6}$ cycloalkyl, which is optionally substituted with 1 or 2 independently selected $R^b$ substituents.

In some embodiments, $R^{10}$ is $C_{3-6}$ cycloalkyl, which is optionally substituted with 1 or 2 independently selected $R^b$ substituents selected from $C_{1-4}$ alkyl, $C_{1-4}$ haloalkyl, CN, $NO_2$, OR, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $-P(O)R^cR^c$, $-P(O)(OR^c)(OR^c)$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-4}$ alkyl of $R^c$ is further optionally substituted with 1, 2, or 3 independently selected $R^d$ substituents selected from $OR^e$.

In some embodiments, $R^{10}$ is $C_{3-6}$ cycloalkyl, which is optionally substituted with 1 or 2 independently selected $R^b$ substituents selected from $C_{1-4}$ alkyl, $C_{1-4}$ haloalkyl, CN, $NO_2$, OR, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-4}$ alkyl of $R^c$ is further optionally substituted with 1, 2, or 3 independently selected $R^d$ substituents selected from $OR^e$.

In some embodiments, $R^{10}$ is $C_{3-6}$ cycloalkyl, which is optionally substituted with 1 or 2 independently selected $R^b$ substituents selected from $C_{1-4}$ alkyl, $OR^a$, $NR^cR^c$, $NR^cC(O)R^c$, and $NR^cC(O)OR^c$, wherein the $C_{1-4}$ alkyl of $R^b$ is further optionally substituted with 1, 2, or 3 independently selected $R^d$ substituents selected from $OR^e$.

In some embodiments, $R^{10}$ is $C_{3-6}$ cycloalkyl, which is optionally substituted with 1 or 2 independently selected $R^b$ substituents selected from $C_{1-4}$ alkyl, OH, $NH_2$, $NHC(O)R^c$, and $NHC(O)OR^c$, wherein the $C_{1-4}$ alkyl is optionally substituted by OH, and each $R^c$ is an independently selected $C_{1-6}$ alkyl group.

In some embodiments, $R^{10}$ is cyclopropyl, 3-hydroxycyclobutyl, 3-(hydroxymethyl)cyclobutyl, 4-hydroxycyclohexyl, 4-methoxycyclohexyl, 4-aminocyclohexyl, 4-(N-(tert butoxycarbonyl)amino)cyclohexyl, or 4-(N-(methylcarbonyl)amino)cyclohexyl.

In some embodiments, $R^{10}$ is 4-10 membered heterocycloalkyl, or (4-15 membered heterocycloalkyl)-$C_{1-4}$ alkyl-, wherein the 4-10 membered heterocycloalkyl and (4-15 membered heterocycloalkyl)-$C_{1-4}$ alkyl- are each optionally substituted with 1, 2, 3, 4 or 5 independently selected $R^b$ substituents.

In some embodiments, $R^{10}$ is 4-10 membered heterocycloalkyl, or (4-10 membered heterocycloalkyl)-$C_{1-4}$ alkyl-, wherein the 4-10 membered heterocycloalkyl and (4-10 membered heterocycloalkyl)-$C_{1-4}$ alkyl- are each optionally substituted with 1, 2, 3, 4 or 5 independently selected $R^b$ substituents.

In some embodiments, $R^{10}$ is 4-10 membered heterocycloalkyl, or (4-10 membered heterocycloalkyl)-$C_{1-4}$ alkyl-, wherein the 4-10 membered heterocycloalkyl and (4-10 membered heterocycloalkyl)-$C_{1-4}$ alkyl- are each optionally substituted with 1, 2, or 3 independently selected R substituents selected from $C_{1-4}$ alkyl, $C_{1-4}$ haloalkyl, CN, $NO_2$, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$, wherein each $C_{1-4}$ alkyl of $R^c$ is further optionally substituted with 1, 2, or 3 independently selected $R^d$ substituents.

In some embodiments, $R^{10}$ is 4-6 membered heterocycloalkyl or (4-6 membered heterocycloalkyl)-$C_{1-4}$ alkyl-, wherein the 4-6 membered heterocycloalkyl and (4-6 membered heterocycloalkyl)-$C_{1-4}$ alkyl- are each optionally substituted with 1, 2, 3, 4 or 5 independently selected $R^b$ substituents.

In some embodiments, $R^{10}$ is 4-6 membered heterocycloalkyl or (4-6 membered heterocycloalkyl)-$C_{1-4}$ alkyl-, wherein the 4-6 membered heterocycloalkyl and (4-6 membered heterocycloalkyl)-$C_{1-4}$ alkyl- are each optionally substituted with 1 or 2 independently selected $R^b$ substituents selected from $C_{1-4}$ alkyl, $C_{1-4}$ haloalkyl, CN, $NO_2$, OR, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $-P(O)R^cR^c$, $-P(O)(OR^c)(OR^c)$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$, wherein the $C_{1-4}$ alkyl of $R^c$ is further optionally substituted with 1, 2, or 3 independently selected $R^d$ substituents.

In some embodiments, $R^{10}$ is 4-6 membered heterocycloalkyl or (4-6 membered heterocycloalkyl)-$C_{1-4}$ alkyl-, wherein the 4-6 membered heterocycloalkyl and (4-6 membered heterocycloalkyl)-$C_{1-4}$ alkyl- are each optionally substituted with 1 or 2 independently selected $R^b$ substituents selected from $C_{1-4}$ alkyl, $C_{1-4}$ haloalkyl, CN, $NO_2$, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$, wherein the $C_{1-4}$ alkyl of $R^c$ is further optionally substituted with 1, 2, or 3 independently selected $R^d$ substituents.

In some embodiments, $R^{10}$ is 4-6 membered heterocycloalkyl or (4-6 membered heterocycloalkyl)-$C_{1-4}$ alkyl-, wherein the 4-6 membered heterocycloalkyl and (4-6 membered heterocycloalkyl)-$C_{1-4}$ alkyl- are each optionally substituted with 1 or 2 independently selected $R^b$ substituents selected from $C_{1-4}$ alkyl, $OR^a$, $NR^cR^c$, $NR^cC(O)R^c$, and $NR^cC(O)OR^c$, wherein the $C_{1-4}$ alkyl of $R^b$ is further optionally substituted with 1, 2, or 3 independently selected $R^d$ substituents.

In some embodiments, $R^{10}$ is 4-6 membered heterocycloalkyl, or (4-6 membered heterocycloalkyl)-$C_{1-4}$ alkyl-, wherein the 4-6 membered heterocycloalkyl and (4-6 membered heterocycloalkyl)-$C_{1-4}$ alkyl- are each optionally substituted with 1 or 2 independently selected R substituents selected from $C_{1-4}$ alkyl and $OR^{a1}$, wherein the $C_{1-4}$ alkyl of $R^b$ is further optionally substituted with 1, 2, or 3 independently selected $R^d$ substituents selected from $OR^c$.

In some embodiments, $R^{10}$ is 4-6 membered heterocycloalkyl, or (4-6 membered heterocycloalkyl)-$C_{1-4}$ alkyl-, wherein the 4-6 membered heterocycloalkyl and (4-6 membered heterocycloalkyl)-$C_{1-4}$ alkyl- are each optionally substituted with 1 or 2 independently selected $R^b$ substituents selected from $C_{1-4}$ alkyl and OH, wherein the $C_{1-4}$ alkyl is optionally substituted by OH.

In some embodiments, $R^{10}$ is tetrahydro-2H-pyran-4-yl, 4-hydroxypiperidin-1-yl, or 2-(hydroxymethyl)tetrahydro-1H-pyran-5-yl.

In some embodiments, $R^{10}$ is methyl, ethyl, 3-hydroxypropyl, tetrahydrofuran-3-ylmethyl, 2-(3-oxetanyl)prop-1-yl, cyclopropyl, 3-hydroxycyclobutyl, 3-(hydroxymethyl)cyclobutyl, 4-hydroxycyclohexyl, 4-methoxycyclohexyl, 4-aminocyclohexyl, tetrahydro-2H-pyran-4-yl, 4-hydroxypiperidin-1-yl, 4-(N-(tert butoxycarbonyl)amino)cyclohexyl, 4-(N-(methylcarbonyl)amino)cyclohexyl, or 2-(hydroxymethyl)tetrahydro-1H-pyran-5-yl, each of which is optionally substituted with 1, 2 or 3 independently selected $R^g$ substituents.

In some embodiments, $R^{10}$ is methyl, ethyl, 3-hydroxypropyl, tetrahydrofuran-3-ylmethyl, 2-(3-oxetanyl)prop-1-yl, cyclopropyl, 3-hydroxycyclobutyl, 3-(hydroxymethyl)cyclobutyl, 4-hydroxycyclohexyl, 4-methoxycyclohexyl, 4-aminocyclohexyl, tetrahydro-2H-pyran-4-yl, 4-hydroxypiperidin-1-yl, 4-(N-(tert butoxycarbonyl)amino)cyclohexyl, 4-(N-(methylcarbonyl)amino)cyclohexyl, or 2-(hydroxymethyl)tetrahydro-1H-pyran-5-yl.

In some embodiments, $R^{10}$ is methyl, ethyl, propyl, cyclopropyl, cyclobutyl, cyclohexyl, tetrahydrofuranyl, tetrahydropyranyl, or —$CH_2$-oxetanyl, each of which is optionally substituted with 1 or 2 independently selected $R^b$ substituents In some embodiments, $R^{10}$ is methyl, ethyl, propyl, cyclopropyl, cyclobutyl, cyclohexyl, tetrahydrofuranyl, tetrahydropyranyl, or —$CH_2$-oxetanyl, each of which is optionally substituted with 1 or 2 independently selected $R^g$ substituents.

In some embodiments, $R^{10}$ is a bicyclic $C_{4-10}$ cycloalkyl or a bicyclic 4-10 membered heterocycloalkyl, each of which is optionally substituted with 1, 2, 3, 4 or 5 independently selected $R^b$ substituents.

In some embodiments, $R^{10}$ is a spirocyclic $C_{5-10}$ membered cycloalkyl or a spirocyclic 5-10 membered heterocycloalkyl, each of which is optionally substituted with 1, 2, 3, 4 or 5 independently selected $R^b$ substituents.

In some embodiments, $R^{10}$ is a bridged bicyclic $C_{5-10}$ membered cycloalkyl or a bridged bicyclic 6-10 membered heterocycloalkyl, which is optionally substituted with 1, 2, 3, 4 or 5 independently selected $R^b$ substituents.

In some embodiments, $R^{10}$ is selected from:

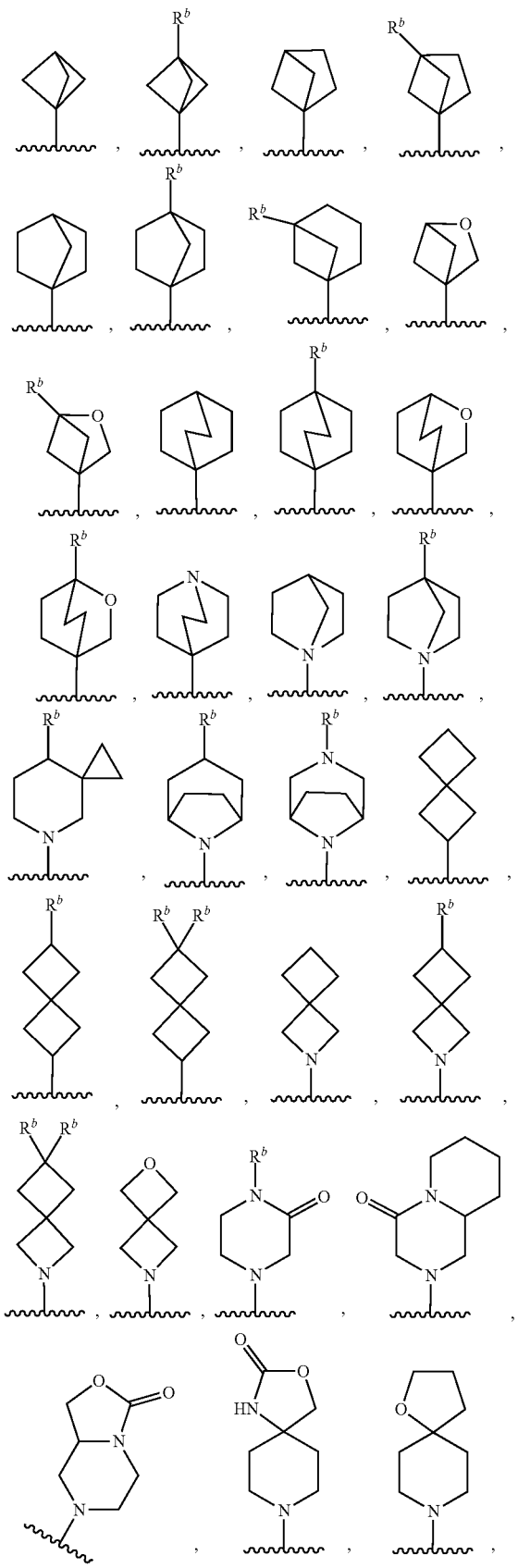

-continued

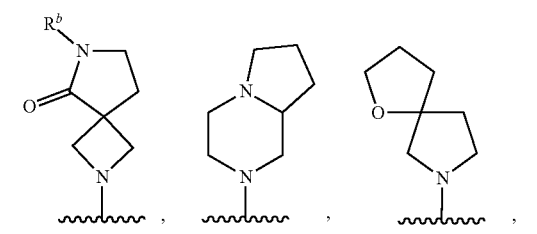

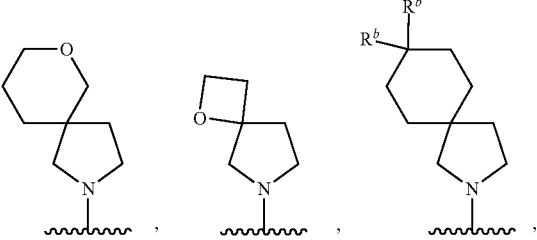

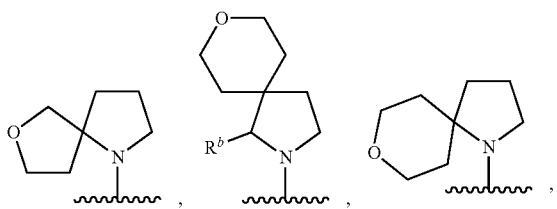

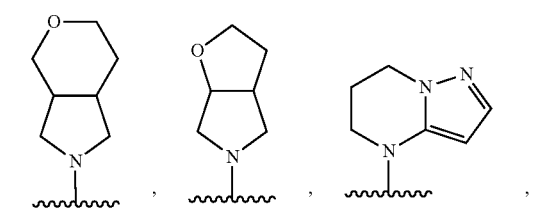

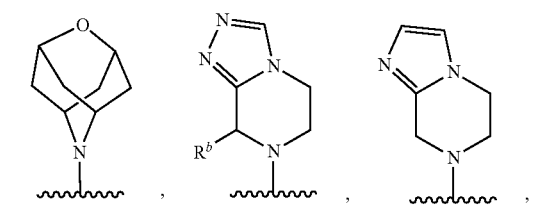

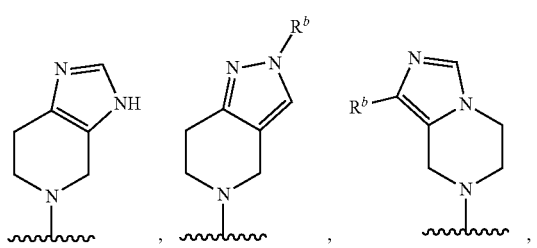

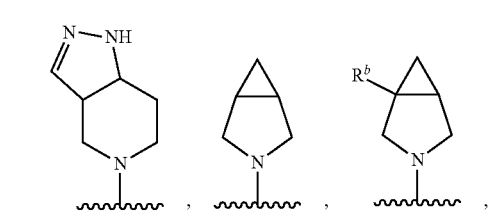

-continued

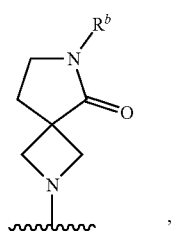

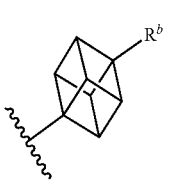

In some embodiments, $R^{10}$ is selected from:

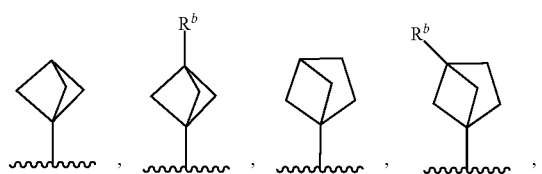

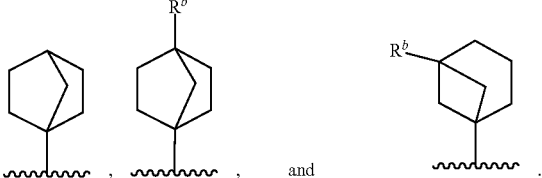

In some embodiments, $R^{10}$ is

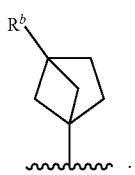

In some embodiments, L is

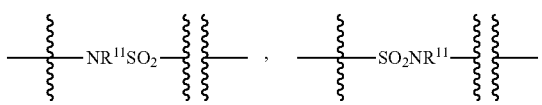

or —SO$_2$—, wherein each $R^{11}$ is independently H or C$_{1-6}$ alkyl optionally substituted with 1 or 2 $R^q$ substituents and wherein the single wavy line indicates the point of attachment to $R^{10}$ and the double wavy line indicates the point of attachment to the 6-membered ring A.

In some embodiments, L is

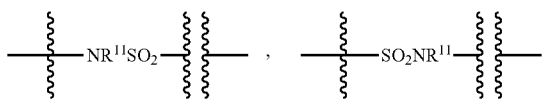

or —SO$_2$—, wherein each R$^{11}$ is independently H or C$_{1-6}$ alkyl.

In some embodiments, L is

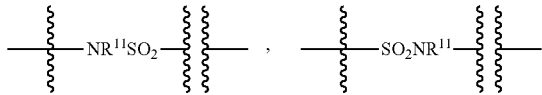

or —SO$_2$—, wherein each R$^{11}$ is H or methyl.

In some embodiments, L is

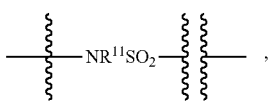

and R$^{11}$ is H or C$_{1-6}$ alkyl.

In some embodiments, L is

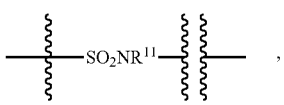

and R$^{11}$ is H or C$_{1-6}$ alkyl.

In some embodiments, L is —SO$_2$—.

In some embodiments, L is

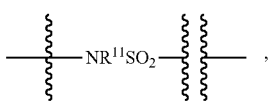

SO$_2$ or

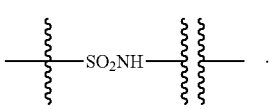

In some embodiments, L is

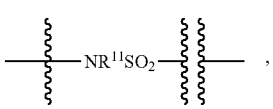

SO$_2$ or

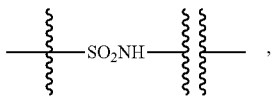

and R$^{11}$ is H or C$_{1-6}$ alkyl.

In some embodiments, -L-R$^{10}$ forms a group selected from:

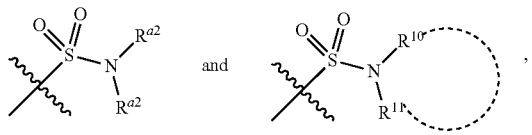

wherein each R$^{a2}$ is independently selected from H, D, halo, oxo, C$_{1-6}$ alkyl, C$_{1-6}$ alkoxy, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-14 membered heterocycloalkyl)-C$_{1-4}$ alkyl-, wherein the C$_{1-6}$ alkyl, C$_{1-6}$ alkoxy, C$_{2-6}$ alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-14 membered heterocycloalkyl)-C$_{1-4}$ alkyl- of R$^{a1}$ and R$^{a2}$ are each optionally substituted with 1, 2, 3, 4, or 5 independently selected R$^{d}$ substituents, and wherein R$^{10}$ and R$^{11}$ taken together with the nitrogen atom to which they are attached, form a 4 to 14-membered heterocycloalkyl (indicated by the dashed ring structure) having 0 to 4 additional heteroatoms as a ring member, each of which is independently selected from N, O and S, wherein the 4 to 14-membered heterocycloalkyl formed by R$^{10}$, R$^{11}$ and N is optionally substituted with 1, 2, or 3 independently selected R$^{b}$ substituents.

In some embodiments, L is

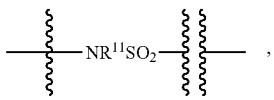

and R$^{10}$ and R$^{11}$ are taken together with the nitrogen atom to which they are attached to form a 4-, 5-, 6-, 7-, 8-, 9-, or 10-membered heterocycloalkyl having 0 to 1 additional heteroatom as a ring member selected from N, O and S, wherein the 4-, 5-, 6-, 7-, 8-, 9-, or 10-membered heterocycloalkyl formed by R$^{10}$, R$^{11}$ and N is optionally substituted with 1, 2 or 3 independently selected R$^{q}$ substituents.

In some embodiments, L is

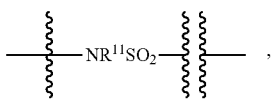

and R$^{10}$ and R$^{11}$ are taken together with the nitrogen atom to which they are attached to form a 8-, 9-, or 10-membered heterocycloalkyl having 0 to 1 additional heteroatom as a ring member selected from N, O, and S, wherein the 8-, 9-, or 10-membered heterocycloalkyl formed by $R^{10}$, $R^{11}$, and N is optionally substituted with 1, 2 or 3 independently selected $R^q$ substituents.

In some embodiments, -L-$R^{10}$ forms a group selected from:

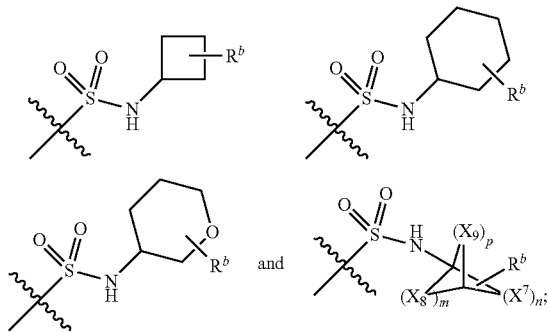

wherein $X^7$, $X^8$, $X^9$ are each independently selected from be C, N, O, or S, wherein p, m and n are each independently 0, 1, 2, 3 or 4; and wherein each formed group is optionally substituted with 0, 1, 2, 3 or 4 independently selected $R^b$ substituents.

In some embodiments, $X^7$, $X^8$, $X^9$ are each independently C, N or O.

In some embodiments, $X^8$ and $X^9$ are C, and $X^7$ is selected from C, N or O.

In some embodiments, $X^8$ and $X^9$ are C, and $X^7$ is selected from C or O.

In some embodiments, p, m, and n are each independently 0, 1 or 2.

In some embodiments, p, m, and n are each independently 1 or 2.

In some embodiments, -L-$R^{10}$ forms a group selected from:

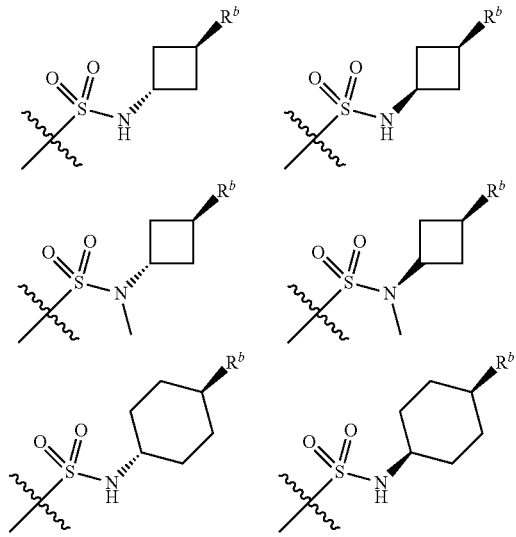

In some embodiments, one or more $R^b$ groups of a compound provided herein is each an independently selected $R^q$ group. In some embodiments, each $R^b$ group of a compound provided herein is an independently selected $R^q$ group.

In some embodiments:
  $X^1$ is N or $CR^1$;
  $X^2$ is N or $CR^2$;
  $X^3$ is $CR^3$;
  $X^4$ is $CR^4$;
  $X^5$ is N or $CR^5$;
  $X^6$ is $CR^6$;
  $R^1$ is H, halo, or 5-10 membered heteroaryl, wherein said 5-10 membered heteroaryl is optionally substituted by 1, 2, 3, 4, or 5 independently selected $R^b$ substituents;
  $R^2$ is H;
  $R^3$ is H;
  $R^4$ is H, halo, $C_{1-6}$ alkyl, $C_{2-6}$ alkenyl, $C_{2-6}$ alkynyl, or $C_{1-6}$ haloalkyl, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;
  $R^5$ is H, $C_{1-6}$ alkyl, $C_{2-6}$ alkenyl, $C_{2-6}$ alkynyl, or $C_{1-6}$ haloalkyl, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;
  $R^6$ is H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{a1}$, $C(O)NR^{a1}R^{a1}$, $C(O)OR^{a1}$, $OC(O)R^{a1}$, or $OC(O)NR^{a1}R^{a1}$, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;
  $R^7$ is H, methyl or ethyl, wherein said methyl and ethyl are each optionally substituted with 1, 2 or 3 groups independently selected from halo, OH, oxo, CN, $C_{1-6}$ alkoxy, and $C_{1-6}$ haloalkoxy;
  $R^8$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{14}$ alkyl- are each optionally substituted with 1, 2, 3, 4 or 5 independently selected $R^b$ substituents;

$R^9$ is H;

$R^{10}$ is $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents;

L is

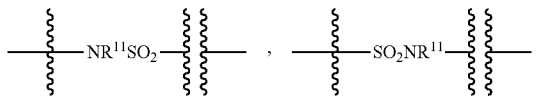

or —SO$_2$—;

each $R^{11}$ is independently H or $C_{1-6}$ alkyl;
or when L is

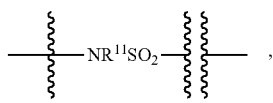

$R^{10}$ and $R^{11}$ optionally taken together with the nitrogen atom to which they are attached, form a 4 to 14-membered heterocycloalkyl or a 4 to 14-membered heterocycloalkyl-$C_{1-4}$ alkyl-, having 0 to 4 additional heteroatoms as a ring member, each of which is independently selected from N, O and S, wherein the 4 to 14-membered heterocycloalkyl formed by $R^{10}$, $R^{11}$ and N is optionally substituted with 1, 2 or 3 independently selected $R^b$ substituents;

each $R^{a1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 $R^d$ substituents;

each $R^b$ substituent is independently selected from D, halo, $C_{1-4}$ alkyl, $C_{1-4}$ haloalkyl, $C_{1-4}$ haloalkoxy, CN, $OR^c$, $C(O)R^c$, $C(O)NR^cR^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$ or $S(O)_2NR^cR^c$; wherein the $C_{1-4}$ alkyl, $C_{1-4}$ haloalkyl, and $C_{1-4}$ haloalkoxy of $R^{a1}$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl;

each $R^d$ is independently selected from $C_{1-6}$ alkyl, $C_{1-6}$ haloalkyl, and $OR^e$; and each $R^e$ is independently selected from H, $C_{1-6}$ alkyl, $C_{1-4}$ haloalkyl, $C_{2-6}$ alkenyl, and $C_{2-6}$ alkynyl.

In some embodiments:

$X^1$ is N or $CR^1$;

$X^2$ is N or $CR^2$;

$X^3$ is $CR^3$;

$X^4$ is $CR^4$;

$X^5$ is N or $CR^5$;

$X^6$ is $CR^6$;

$R^1$ is H, halo, or 5-10 membered heteroaryl, wherein said 5-10 membered heteroaryl is optionally substituted by 1, 2, 3, 4, or 5 independently selected $R^b$ substituents;

$R^2$ is H;

$R^3$ is H;

$R^4$ is H, halo, $C_{1-6}$ alkyl, $C_{2-6}$ alkenyl, $C_{2-6}$ alkynyl, or $C_{1-6}$ haloalkyl, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;

$R^5$ is H, $C_{1-6}$ alkyl, $C_{2-6}$ alkenyl, $C_{2-6}$ alkynyl, or $C_{1-6}$ haloalkyl, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;

$R^6$ is H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{a1}$, $C(O)NR^{a1}R^{a1}$, $C(O)OR^{a1}$, $OC(O)R^{a1}$, or $OC(O)NR^{a1}R^{a1}$, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;

$R^7$ is H, methyl or ethyl, wherein said methyl and ethyl are each optionally substituted with 1, 2 or 3 groups independently selected from halo, OH, oxo, CN, $C_{1-6}$ alkoxy, and $C_{1-6}$ haloalkoxy;

$R^8$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents;

$R^9$ is H;

$R^{10}$ is $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents;

L is

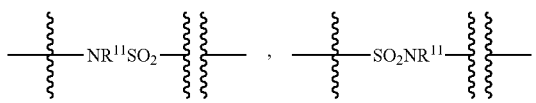

or —SO$_2$—;
each R$^{11}$ is independently H or C$_{1-6}$ alkyl;
or when L is

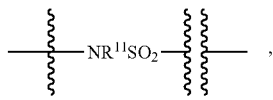

R$^{10}$ and R$^{11}$ optionally taken together with the nitrogen atom to which they are attached, form 4-, 5-, 6- or 7-membered heterocycloalkyl having 0 to 1 additional heteroatom as a ring member, which is selected from N, O and S, wherein the 4-, 5-, 6- or 7-membered heterocycloalkyl formed by R$^{10}$, R$^{11}$ and N is optionally substituted with 1, 2 or 3 independently selected R$^q$ substituents;

each R$^{a1}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^a$ are each optionally substituted with 1, 2, 3, 4, or 5 R$^d$ substituents;

each R$^b$ substituent is independently selected from halo, C$_{1-4}$ alkyl, C$_{1-4}$ haloalkyl, C$_{1-4}$ haloalkoxy, CN, OR$^c$, C(O)R$^c$, C(O)NR$^c$R$^c$, OC(O)NR$^c$R$^c$, NR$^c$R$^c$, NR$^c$C(O)R$^c$, NR$^c$C(O)OR$^c$, NR$^c$C(O)NR$^c$R$^c$, S(O)R$^c$, S(O)NR$^c$R$^c$, S(O)$_2$R$^c$ or S(O)$_2$NR$^c$R$^c$; wherein the C$_{1-4}$ alkyl, C$_{1-4}$ haloalkyl, and C$_{1-4}$ haloalkoxy of R$^b$ are each further optionally substituted with 1, 2, or 3 independently selected R$^d$ substituents;

each R$^c$ is independently selected from H, C$_{1-6}$ alkyl, C$_{1-4}$ haloalkyl, C$_{2-6}$ alkenyl, and C$_{2-6}$ alkynyl;
each R$^d$ is independently selected from C$_{1-6}$ alkyl, C$_{1-6}$ haloalkyl, and OR$^e$; and
each R$^e$ is independently selected from H, C$_{1-6}$ alkyl, C$_{1-4}$ haloalkyl, C$_{2-6}$ alkenyl, and C$_{2-6}$ alkynyl.

In some embodiments:
X$^1$ is N or CR$^1$;
X$^2$ is N or CR$^2$;
X$^3$ is CR$^3$;
X$^4$ is CR$^4$;
X$^5$ is N or CR$^5$;
X$^6$ is CR$^6$;
R$^1$ is H, halo, or 5-6 membered heteroaryl, wherein said 5-6 membered heteroaryl is optionally substituted by 1, 2, 3, 4, or 5 independently selected R$^b$ substituents;
R$^2$ is H;
R$^3$ is H;
R$^4$ is H, halo, C$_{1-6}$ alkyl, or C$_{1-6}$ haloalkyl;
R$^5$ is H, C$_{1-6}$ alkyl, or C$_{1-6}$ haloalkyl;
R$^6$ is H, halo, C$_{1-6}$ alkyl, C$_{1-6}$ haloalkyl, OR$^{a1}$, SR$^{a1}$, C(O)R$^{a1}$, C(O)NR$^{a1}$R$^{a1}$, C(O)OR$^{a1}$, OC(O)R$^{a1}$, or OC(O)NR$^{a1}$R$^{a1}$, wherein said C$_{1-6}$ alkyl, C$_{2-6}$ alkenyl, and C$_{2-6}$ alkynyl are optionally substituted by 1, 2, 3, 4, or 5 independently selected R$^b$ substituents;
R$^7$ is H, methyl or ethyl, wherein said methyl and ethyl are each optionally substituted with 1, 2 or 3 groups independently selected from halo, OH, oxo, CN, C$_{1-6}$ alkoxy, and C$_{1-6}$ haloalkoxy;
R$^8$ is H, halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{14}$ alkyl- are each optionally substituted with 1, 2, 3, 4 or 5 independently selected R$^b$ substituents;
R$^9$ is H;
R$^{10}$ is C$_{1-6}$ alkyl, C$_{2-6}$ alkenyl, C$_{2-6}$ alkynyl, C$_{1-6}$ haloalkyl, C$_{6-10}$ aryl, C$_{3-10}$cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl- are each optionally substituted with 1, 2, 3, 4 or 5 independently selected R$^b$ substituents;
L is

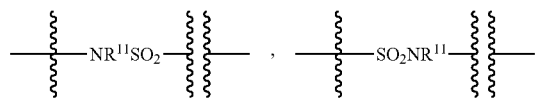

or —SO$_2$—;
each R$^{11}$ is independently H or C$_{1-6}$ alkyl;
or when L is

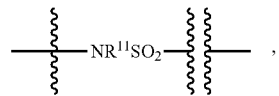

R$^{10}$ and R$^{11}$ optionally taken together with the nitrogen atom to which they are attached, form a 4 to 6-membered heterocycloalkyl or a 4 to 14-membered heterocycloalkyl-C$_{14}$ alkyl-, having 0 to 1 additional heteroatoms as a ring member, each of which is independently selected from N, O and S, wherein the 4 to 6-membered heterocycloalkyl formed by R$^{10}$, R$^{11}$ and N is optionally substituted with 1, 2 or 3 independently selected R$^b$ substituents;
each R$^{a1}$ is independently selected from H and C$_{1-6}$ alkyl;
each R$^b$ is independently selected from halo, C$_{1-4}$ alkyl, C$_{3-6}$ cycloalkyl, CN, OR$^c$, C(O)NR$^c$R$^c$, NR$^c$R$^c$, NR$^c$C (O)OR$^c$, S(O)R$^c$, or S(O)$_2$R$^c$; wherein the C$_{1-4}$ alkyl of R$^b$ is further optionally substituted with 1, 2, or 3 independently selected R$^d$ substituents;

each R$^c$ is independently selected from H, C$_{1-6}$ alkyl, C$_{1-4}$ haloalkyl, C$_{2-6}$ alkenyl, and C$_{2-6}$ alkynyl;

each R$^d$ is independently selected from C$_{1-s}$ alkyl, C$_{1-6}$ haloalkyl, OR$^e$; and each R$^e$ is independently selected from H, C$_{1-6}$ alkyl, C$_{1-4}$ haloalkyl, C$_{2-6}$ alkenyl, and C$_{2-6}$ alkynyl.

In some embodiments:

X$^1$ is N or CR$^1$;
X$^2$ is N or CR$^2$;
X$^3$ is CR$^3$;
X$^4$ is CR$^4$;
X$^5$ is N or CR$^5$;
X$^6$ is CR$^6$;
R$^1$ is H, halo, or 5-6 membered heteroaryl, wherein said 5-6 membered heteroaryl is optionally substituted by 1, 2, 3, 4, or 5 independently selected R$^b$ substituents;
R$^2$ is H;
R$^3$ is H;
R$^4$ is H, halo, C$_{1-6}$ alkyl, or C$_{1-6}$ haloalkyl;
R$^8$ is H, C$_{1-6}$ alkyl, or C$_{1-6}$ haloalkyl;
R$^6$ is H, halo, C$_{1-6}$ alkyl, C$_{1-6}$ haloalkyl, OR$^{a1}$, SR$^{a1}$, C(O)R$^{a1}$, C(O)NR$^{a1}$R$^{a1}$, C(O)OR$^{a1}$, OC(O)R$^{a1}$, or OC(O)NR$^{a1}$R$^{a1}$, wherein said C$_{1-6}$ alkyl, C$_{2-6}$ alkenyl, and C$_{2-6}$ alkynyl are optionally substituted by 1, 2, 3, 4, or 5 independently selected R$^b$ substituents;
R$^7$ is H, methyl or ethyl, wherein said methyl and ethyl are each optionally substituted with 1, 2 or 3 groups independently selected from halo, OH, oxo, CN, C$_{1-6}$ alkoxy, and C$_{1-6}$ haloalkoxy;
R$^8$ is H, halo, C$_{1-6}$ alkyl, C$_{2-6}$ alkenyl, C$_{2-6}$ alkynyl, C$_{1-6}$ haloalkyl, C6-10 aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl- are each optionally substituted with 1, 2, 3, 4 or 5 independently selected R$^b$ substituents;
R$^9$ is H;
R$^{10}$ is C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, or (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-14 membered heteroaryl)-C$_{1-4}$ alkyl-, and (4-10 membered heterocycloalkyl)-C$_{1-4}$ alkyl- are each optionally substituted with 1, 2, 3, 4 or 5 independently selected R$^b$ substituents; L is

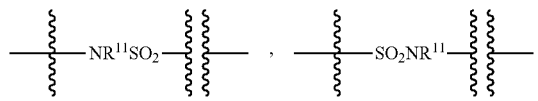

or —SO$_2$—;

each R$^{11}$ is independently H or C$_{1-6}$ alkyl; or when L is

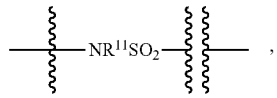

R$^{10}$ and R$^{11}$ optionally taken together with the nitrogen atom to which they are attached, form 4-, 5- or 6-membered heterocycloalkyl having 0 to 1 additional heteroatom as a ring member, which is selected from N, O and S, wherein the 4-, 5- or 6-membered heterocycloalkyl formed by R$^{10}$, R$^{11}$ and N is optionally substituted with 1, 2 or 3 independently selected R$^q$ substituents;

each R$^{a1}$ is independently selected from H and C$_{1-6}$ alkyl;
each R$^b$ is independently selected from halo, C$_{1-4}$ alkyl, C$_{3-6}$ cycloalkyl, CN, OR$^c$, C(O)NR$^c$R$^c$, NR$^c$R$^c$, NR$^c$C(O)OR$^c$, S(O)R$^c$, or S(O)$_2$R$^c$; wherein the C$_{1-4}$ alkyl of R$^b$ is further optionally substituted with 1, 2, or 3 independently selected R$^d$ substituents;
each R$^c$ is independently selected from H, C$_{1-6}$ alkyl, C$_{1-4}$ haloalkyl, C$_{2-6}$ alkenyl, and C$_{2-6}$ alkynyl;
each R$^d$ is independently selected from C$_{1-6}$ alkyl, C$_{1-6}$ haloalkyl, OR$^e$; and
each R$^e$ is independently selected from H, C$_{1-6}$ alkyl, C$_{1-4}$ haloalkyl, C$_{2-6}$ alkenyl, and C$_{2-6}$ alkynyl.

In some embodiments:

X$^1$ is N or CR$^1$;
X$^2$ is N or CR$^2$;
X$^3$ is CR$^3$;
X$^4$ is CR$^4$;
X$^5$ is N or CR$^5$;
X$^6$ is CR$^6$;
R$^1$ is H, halo, or 5-6 membered heteroaryl, wherein said 5-6 membered heteroaryl is optionally substituted by 1 or 2 independently selected C$_{1-4}$ alkyl groups;
R$^2$ is H;
R$^3$ is H;
R$^4$ is H, halo, or C$_{1-6}$ alkyl;
R$^5$ is H or C$_{1-6}$ alkyl;
R$^6$ is H, halo, C$_{1-6}$ alkyl, or OR$^{a1}$;
R$^7$ is H, methyl or ethyl, wherein said methyl and ethyl are each optionally substituted with 1, 2 or 3 groups independently selected from halo, OH, oxo, CN, C$_{1-6}$ alkoxy, and C$_{1-6}$ haloalkoxy;
R$^8$ is halo, C$_{1-6}$ alkyl, phenyl, or 5-6 membered heteroaryl, wherein C$_{1-6}$ alkyl, C$_{6-10}$ aryl and 5-6 membered heteroaryl are each optionally substituted with 1, 2 or 3 independently selected R$^b$ substituents;
R$^9$ is H;
R$^{10}$ is C$_{1-6}$ alkyl, C$_{3-6}$ cycloalkyl, 4-6 membered heterocycloalkyl, or (4-6 membered heterocycloalkyl)-C$_{1-4}$ alkyl-, wherein the C$_{1-6}$ alkyl, phenyl, C$_{3-6}$ cycloalkyl, 4-6 membered heterocycloalkyl, and (4-6 membered heterocycloalkyl)-C$_{1-4}$ alkyl- are each optionally substituted with 1, 2, 3, 4 or 5 independently selected R$^b$ substituents;

L is

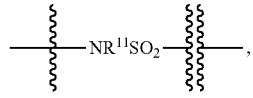

SO$_2$ or

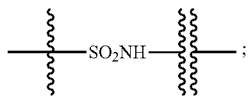

R$^{11}$ is H or C$_{1-6}$ alkyl;
or when L is

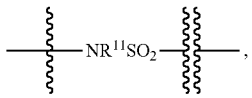

R$^{10}$ and R$^{11}$ optionally taken together with the nitrogen atom to which they are attached, form a 4 to 6-membered heterocycloalkyl or a 4 to 14-membered heterocycloalkyl-C$_{1-4}$ alkyl-, having 0 to 1 additional heteroatoms as a ring member, each of which is independently selected from N, O and S, wherein the 4 to 6-membered heterocycloalkyl formed by R$^{10}$, R$^{11}$ and N is optionally substituted with 1, 2 or 3 independently selected R substituents;

each R$^{a1}$ is H or C$_{1-6}$ alkyl;

each R$^b$ substituent is independently selected from halo, C$_{1-4}$ alkyl, CN, OR$^c$, C(O)NR$^c$R$^c$, NR$^c$R$^c$, NR$^c$C(O)OR$^c$, S(O)R$^c$, or S(O)$_2$R$^c$; wherein the C$_{1-4}$ alkyl of R$^b$ is further optionally substituted with 1, 2, or 3 independently selected R$^d$ substituents;

each R$^c$ is independently selected from H and C$_{1-6}$ alkyl;
each R$^d$ is independently selected from C$_{1-6}$ alkyl and OR$^e$; and
each R$^e$ is independently selected from H and C$_{1-6}$ alkyl.

In some embodiments:
X$^1$ is N or CR$^1$;
X$^2$ is N or CR$^2$;
X$^3$ is CR$^3$;
X$^4$ is CR$^4$;
X$^5$ is N or CR$^5$;
X$^6$ is CR$^6$;
R$^1$ is H, halo, or 5-6 membered heteroaryl, wherein said 5-6 membered heteroaryl is optionally substituted by 1 or 2 independently selected C$_{1-4}$ alkyl groups;
R$^2$ is H;
R$^3$ is H;
R$^4$ is H, halo, or C$_{1-6}$ alkyl;
R$^5$ is H or C$_{1-6}$ alkyl;
R$^6$ is H, halo, C$_{1-6}$ alkyl, or OR$^{a1}$;
R$^7$ is H, methyl or ethyl, wherein said methyl and ethyl are each optionally substituted with 1, 2 or 3 groups independently selected from halo, OH, oxo, CN, C$_{1-6}$ alkoxy, and C$_{1-6}$ haloalkoxy;
R$^8$ is halo, C$_{1-6}$ alkyl, phenyl, or 5-6 membered heteroaryl, wherein C$_{1-6}$ alkyl, C$_{6-10}$ aryl and 5-6 membered heteroaryl are each optionally substituted with 1, 2 or 3 independently selected R substituents;
R$^9$ is H;
R$^{10}$ is C$_{1-6}$ alkyl, C$_{3-6}$ cycloalkyl, 4-6 membered heterocycloalkyl, or (4-6 membered heterocycloalkyl)-C$_{1-4}$ alkyl-, wherein the C$_{1-6}$ alkyl, phenyl, C$_{3-6}$ cycloalkyl, 4-6 membered heterocycloalkyl, and (4-6 membered heterocycloalkyl)-C$_{1-4}$ alkyl- are each optionally substituted with 1, 2, 3, 4 or 5 independently selected R$^b$ substituents;

L is

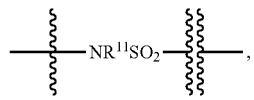

SO$_2$ or

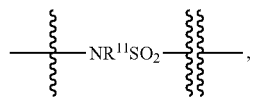

R$^{11}$ is H or C$_{1-6}$ alkyl;
or when L is

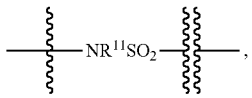

R$^{10}$ and R$^{11}$ optionally taken together with the nitrogen atom to which they are attached, form a 4-, 5- or 6-membered heterocycloalkyl having 0 to 1 additional heteroatom as a ring member, which is selected from N, O and S, wherein the 4-, 5- or 6-membered heterocycloalkyl formed by R$^{10}$, R$^{11}$ and N is optionally substituted with 1, 2 or 3 independently selected R$^q$ substituents;

each R$^{a1}$ is H or C$_{1-6}$ alkyl;

each R$^b$ substituent is independently selected from halo, C$_{1-4}$ alkyl, CN, OR$^c$, C(O)NR$^c$R$^c$, NR$^c$R$^c$, NR$^c$C(O)OR$^c$, S(O)R$^c$, or S(O)$_2$R$^c$; wherein the C$_{1-4}$ alkyl of R$^b$ is further optionally substituted with 1, 2, or 3 independently selected R$^d$ substituents;

each R$^c$ is independently selected from H and C$_{1-6}$ alkyl;
each R$^d$ is independently selected from C$_{1-6}$ alkyl and OR$^e$; and
each R$^e$ is independently selected from H and C$_{1-6}$ alkyl.

In some embodiments:
X$^1$ is N or CR$^1$;
X$^2$ is N or CR$^2$;
X$^3$ is CR$^3$;
X$^4$ is CR$^4$;
X$^5$ is N or CR$^5$;
X$^6$ is CR$^6$;
R$^1$ is H, halo, or pyrazolyl, wherein said pyrazolyl is optionally substituted by 1 or 2 independently selected C$_{1-4}$ alkyl groups;
R$^2$ is H;
R$^3$ is H;
R$^4$ is H, F, CD$_3$, or methyl;
R$^5$ is H or methyl;
R$^6$ is H, F, Cl, methyl, methoxy, or ethoxy;
R$^7$ is H, methyl, or —C(O)-methyl;
R$^8$ is H, Br, Cl, C$_{1-4}$ alkyl, phenyl, 1H-pyrazol-5-yl, pyrazol-4-yl, thiazol-5-yl, pyridyl, thiophenyl or pyrimidinyl, wherein the phenyl, 1H-pyrazol-5-yl, 1H-pyrazol-4-yl, thiazol-5-yl, pyridyl, thiophenyl and pyrimidinyl are each optionally substituted with 1 or 2 independently selected R$^b$ substituents;
R$^9$ is H;

$R^{10}$ is methyl, ethyl, propyl, cyclopropyl, cyclobutyl, cyclohexyl, tetrahydrofuranyl, tetrahydropyranyl, or —CH$_2$-oxetanyl, each of which is optionally substituted with 1 or 2 independently selected $R^b$ substituents;

L is

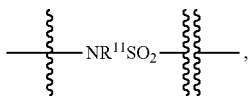

SO$_2$ or

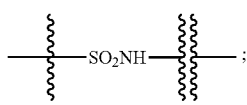

$R^{11}$ is H or methyl;
or when L is

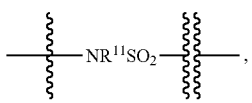

$R^{10}$ and $R^{11}$ optionally taken together with the nitrogen atom to which they are attached, form 4-, 5- or 6-membered heterocycloalkyl having 0 to 1 additional heteroatom as a ring member, which is selected from N, O and S, wherein the 4-, 5- or 6-membered heterocycloalkyl formed by $R^{10}$, $R^{11}$ and N is optionally substituted with 1, 2 or 3 independently selected $R^q$ substituents;
each $R^{a1}$ is H or C$_{1-6}$ alkyl;
each $R^b$ substituent is independently selected from halo, C$_{1-4}$ alkyl, CN, OR$^c$, C(O)NR$^c$R$^c$, NR$^c$R$^c$, NR$^c$C(O)OR$^c$, or S(O)$_2$R$^c$; wherein the C$_{1-4}$ alkyl of $R^b$ is further optionally substituted with 1, 2, or 3 independently selected $R^d$ substituents;
each $R^c$ is independently selected from H and C$_{1-6}$ alkyl;
each $R^d$ is independently OR$^e$; and
each $R^e$ is independently selected from H and C$_{1-6}$ alkyl.
In some embodiments:
$X^1$ is N or CR$^1$;
$X^2$ is N or CR$^2$;
$X^3$ is CR$^3$;
$X^4$ is CR$^4$;
$X^5$ is N or CR$^5$;
$X^6$ is CR$^6$;
$R^1$ is H, halo, or pyrazolyl, wherein said pyrazolyl is optionally substituted by 1 or 2 independently selected C$_{1-4}$ alkyl groups;
$R^2$ is H;
$R^3$ is H;
$R^4$ is H, F, or methyl;
$R^5$ is H or methyl;
$R^6$ is H, F, Cl, methyl, methoxy, or ethoxy;
$R^7$ is H, methyl, or —C(O)-methyl;
$R^8$ is H, Br, Cl, C$_{1-4}$ alkyl, phenyl, 1H-pyrazol-5-yl, pyrazol-4-yl, thiazol-5-yl, pyridyl, thiophenyl or pyrimidinyl, wherein the phenyl, 1H-pyrazol-5-yl, 1H-pyrazol-4-yl, thiazol-5-yl, pyridyl, thiophenyl and pyrimidinyl are each optionally substituted with 1 or 2 independently selected $R^b$ substituents;
$R^9$ is H;
$R^{10}$ is methyl, ethyl, propyl, cyclopropyl, cyclobutyl, cyclohexyl, tetrahydrofuranyl, tetrahydropyranyl, or —CH$_2$-oxetanyl, each of which is optionally substituted with 1 or 2 independently selected $R^b$ substituents;

L is

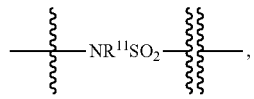

SO$_2$ or

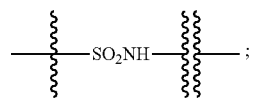

$R^{11}$ is H or methyl;
or when L is

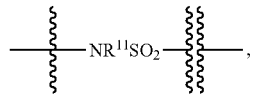

$R^{10}$ and $R^{11}$ optionally taken together with the nitrogen atom to which they are attached, form 4-, 5- or 6-membered heterocycloalkyl having 0 to 1 additional heteroatom as a ring member, which is selected from N, O and S, wherein the 4-, 5- or 6-membered heterocycloalkyl formed by $R^{10}$, $R^{11}$ and N is optionally substituted with 1, 2 or 3 independently selected $R^q$ substituents;
each $R^{a1}$ is H or C$_{1-6}$ alkyl;
each $R^b$ substituent is independently selected from halo, C$_{1-4}$ alkyl, CN, OR$^c$, C(O)NR$^c$R$^c$, NR$^c$R$^c$, NR$^c$C(O)OR$^c$, or S(O)$_2$R$^c$; wherein the C$_{1-4}$ alkyl of $R^b$ is further optionally substituted with 1, 2, or 3 independently selected $R^d$ substituents;
each $R^c$ is independently selected from H and C$_{1-6}$ alkyl;
each $R^d$ is independently OR$^e$; and
each $R^e$ is independently selected from H and C$_{1-6}$ alkyl.
In some embodiments:
$X^1$ is N or CR$^1$;
$X^2$ is N or CR$^2$;
$X^3$ is CR$^3$;
$X^4$ is CR$^4$;
$X^5$ is N or CR$^5$;
$X^6$ is CR$^6$;
$R^1$ is H, halo, or 5-10 membered heteroaryl, wherein said 5-10 membered heteroaryl is optionally substituted by 1, 2, 3, 4, or 5 independently selected $R^b$ substituents;
$R^2$ is H;
$R^3$ is H;
$R^4$ is H, halo, C$_{1-6}$ alkyl, C$_{2-6}$ alkenyl, C$_{2-6}$ alkynyl, or C$_{1-6}$ haloalkyl, wherein said C$_{1-6}$ alkyl, C$_{2-6}$ alkenyl, and C$_{2-6}$ alkynyl are optionally substituted by 1, 2, 3, 4, or 5 independently selected $R^b$ substituents;
$R^5$ is H, C$_{1-6}$ alkyl, C$_{2-6}$ alkenyl, C$_{2-6}$ alkynyl, or C$_{1-6}$ haloalkyl, wherein said C$_{1-6}$ alkyl, C$_{2-6}$ alkenyl, and $C_{2-6}$ alkynyl are optionally substituted by 1, 2, 3, 4, or 5 independently selected $R^b$ substituents;

$R^6$ is H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{a1}$, $C(O)NR^{a1}R^{a1}$, $C(O)OR^{a1}$, $OC(O)R^{a1}$, or $OC(O)NR^{a1}R^{a1}$, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;

$R^7$ is H, methyl or ethyl, wherein said methyl and ethyl are each optionally substituted with 1, 2 or 3 groups independently selected from halo, OH, oxo, CN, $C_{1-6}$ alkoxy, and $C_{1-6}$ haloalkoxy;

$R^8$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents;

$R^9$ is H;

$R^{10}$ is $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents;

L is or —SO$_2$—;

each $R^{11}$ is independently H or $C_{1-6}$ alkyl;

each $R^{a1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^b$ substituent is independently selected from halo, $C_{1-4}$ alkyl, $C_{1-4}$ haloalkyl, $C_{1-4}$ haloalkoxy, CN, $OR^c$, $C(O)R^c$, $C(O)NR^cR^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$ or $S(O)_2NR^cR^c$; wherein the $C_{1-4}$ alkyl, $C_{1-4}$ haloalkyl, and $C_{1-4}$ haloalkoxy of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl;

each $R^d$ is independently selected from $C_{1-6}$ alkyl, $C_{1-6}$ haloalkyl, and $OR^e$; and each $R^e$ is independently selected from H, $C_{1-6}$ alkyl, $C_{1-4}$ haloalkyl, $C_{2-6}$ alkenyl, and $C_{2-6}$ alkynyl.

In some embodiments:

$X^1$ is N or $CR^1$;

$X^2$ is N or $CR^2$;

$X^3$ is $CR^3$;

$X^4$ is $CR^4$;

$X^5$ is N or $CR^5$;

$X^6$ is $CR^6$;

$R^1$ is H, halo, or 5-6 membered heteroaryl, wherein said 5-6 membered heteroaryl is optionally substituted by 1, 2, 3, 4, or 5 independently selected $R^b$ substituents;

$R^2$ is H;

$R^3$ is H;

$R^4$ is H, halo, $C_{1-6}$ alkyl, or $C_{1-6}$ haloalkyl;

$R^5$ is H, $C_{1-6}$ alkyl, or $C_{1-6}$ haloalkyl;

$R^6$ is H, halo, $C_{1-6}$ alkyl, $C_{1-6}$ haloalkyl, $OR^{a1}$, $SR^{a1}$, $C(O)R^{a1}$, $C(O)NR^{a1}R^{a1}$, $C(O)OR^{a1}$, $OC(O)R^{a1}$, or $OC(O)NR^{a1}R^{a1}$, wherein said $C_{1-6}$ alkyl, $C_{2-6}$ alkenyl, and $C_{2-6}$ alkynyl are optionally substituted by 1, 2, 3, 4, or 5 independently selected $R^b$ substituents;

$R^7$ is H, methyl or ethyl, wherein said methyl and ethyl are each optionally substituted with 1, 2 or 3 groups independently selected from halo, OH, oxo, CN, $C_{1-6}$ alkoxy, and $C_{1-6}$ haloalkoxy;

$R^8$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents;

$R^9$ is H;

$R^{10}$ is $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- are each optionally substituted with 1, 2, 3, 4 or 5 independently selected $R^b$ substituents;

L is or —SO$_2$—;

each $R^{11}$ is independently H or $C_{1-6}$ alkyl;
each $R^{a1}$ is independently selected from H and $C_{1-6}$ alkyl;
each $R^b$ is independently selected from halo, $C_{1-4}$ alkyl, CN, $OR^c$, $C(O)NR^cR^c$, $NR^cR^c$, $NR^cC(O)OR^c$, $S(O)R^c$, or $S(O)_2R^c$; wherein the $C_{1-4}$ alkyl of $R^b$ is further optionally substituted with 1, 2, or 3 independently selected $R^d$ substituents;
each $R^c$ is independently selected from H, $C_{1-6}$ alkyl, $C_{1-4}$ haloalkyl, $C_{2-6}$ alkenyl, and $C_{2-6}$ alkynyl;
each $R^d$ is independently selected from $C_{1-6}$ alkyl, $C_{1-6}$ haloalkyl, $OR^e$; and
each $R^e$ is independently selected from H, $C_{1-6}$ alkyl, $C_{1-4}$ haloalkyl, $C_{2-6}$ alkenyl, and $C_{2-6}$ alkynyl.

In some embodiments:
$X^1$ is N or $CR^1$;
$X^2$ is N or $CR^2$;
$X^3$ is $CR^3$;
$X^4$ is $CR^4$;
$X^5$ is N or $CR^5$;
$X^6$ is $CR^6$;
$R^1$ is H, halo, or 5-6 membered heteroaryl, wherein said 5-6 membered heteroaryl is optionally substituted by 1 or 2 independently selected $C_{1-4}$ alkyl groups;
$R^2$ is H;
$R^3$ is H;
$R^4$ is H, halo, or $C_{1-6}$ alkyl;
$R^5$ is H or $C_{1-6}$ alkyl;
$R^6$ is H, halo, $C_{1-6}$ alkyl, or $OR^{a1}$;
$R^7$ is H, methyl or ethyl, wherein said methyl and ethyl are each optionally substituted with 1, 2 or 3 groups independently selected from halo, OH, oxo, CN, $C_{1-6}$ alkoxy, and $C_{1-6}$ haloalkoxy;
$R^8$ is halo, $C_{1-6}$ alkyl, phenyl, or 5-6 membered heteroaryl, wherein $C_{1-6}$ alkyl, $C_{6-10}$ aryl and 5-6 membered heteroaryl are each optionally substituted with 1, 2 or 3 independently selected R substituents;
$R^9$ is H;
$R^{10}$ is $C_{1-6}$ alkyl, $C_{3-6}$ cycloalkyl, 4-6 membered heterocycloalkyl, or (4-6 membered heterocycloalkyl)-$C_{1-4}$ alkyl-, wherein the $C_{1-6}$ alkyl, phenyl, $C_{3-6}$ cycloalkyl, 4-6 membered heterocycloalkyl, and (4-6 membered heterocycloalkyl)-$C_{1-4}$ alkyl- are each optionally substituted with 1, 2, 3, 4 or 5 independently selected $R^b$ substituents;
L is

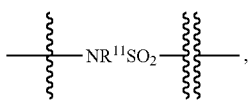

$SO_2$ or

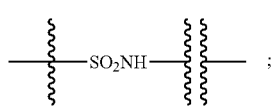

$R^{11}$ is H or $C_{1-6}$ alkyl;
each $R^{a1}$ is independently H or $C_{1-6}$ alkyl;
each $R^b$ substituent is independently selected from halo, $C_{1-4}$ alkyl, CN, $OR^c$, $C(O)NR^cR^c$, $NR^cR^c$, $NR^cC(O)OR^c$, $S(O)R^c$, or $S(O)_2R^c$; wherein the $C_{1-4}$ alkyl of $R^b$ is further optionally substituted with 1, 2, or 3 independently selected $R^d$ substituents;
each $R^c$ is independently selected from H and $C_{1-6}$ alkyl;
each $R^d$ is independently selected from $C_{1-6}$ alkyl and $OR^e$; and
each $R^e$ is independently selected from H and $C_{1-6}$ alkyl.

In some embodiments:
$X^1$ is N or $CR^1$;
$X^2$ is N or $CR^2$;
$X^3$ is $CR^3$;
$X^4$ is $CR^4$;
$X^5$ is N or $CR^5$;
$X^6$ is $CR^6$;
$R^1$ is H, halo, or pyrazolyl, wherein said pyrazolyl is optionally substituted by 1 or 2 independently selected $C_{1-4}$ alkyl groups;
$R^2$ is H;
$R^3$ is H;
$R^4$ is H, F, or methyl;
$R^5$ is H or methyl;
$R^6$ is H, F, Cl, methyl, methoxy, or ethoxy;
$R^7$ is H, methyl, or —C(O)-methyl;
$R^8$ is H, Br, Cl, $C_{1-4}$ alkyl, phenyl, 1H-pyrazol-5-yl, pyrazol-4-yl, thiazol-5-yl, pyridyl, thiophenyl or pyrimidinyl, wherein the phenyl, 1H-pyrazol-5-yl, 1H-pyrazol-4-yl, thiazol-5-yl, pyridyl, thiophenyl and pyrimidinyl are each optionally substituted with 1 or 2 independently selected $R^b$ substituents;
$R^9$ is H;
$R^{10}$ is methyl, ethyl, propyl, cyclopropyl, cyclobutyl, cyclohexyl, tetrahydrofuranyl, tetrahydropyranyl, or —CH$_2$-oxetanyl, each of which is optionally substituted with 1 or 2 independently selected $R^b$ substituents;
L is

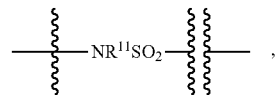

$SO_2$ or

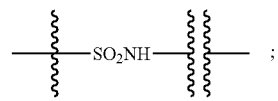

$R^{11}$ is H or methyl;
each $R^{a1}$ is independently H or $C_{1-6}$ alkyl;
each $R^b$ substituent is independently selected from halo, $C_{1-4}$ alkyl, CN, $OR^c$, $C(O)NR^cR^c$, $NR^cR^c$, $NR^cC(O)OR^c$, or $S(O)_2R^c$; wherein the $C_{1-4}$ alkyl of $R^b$ is further optionally substituted with 1, 2, or 3 independently selected $R^d$ substituents;
each $R^c$ is independently selected from H and $C_{1-6}$ alkyl;
each $R^d$ is independently $OR^e$; and
each $R^e$ is independently selected from H and $C_{1-6}$ alkyl.

In the last four embodiments, L is preferably

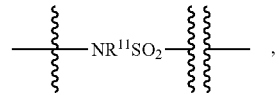

wherein $R^{11}$ is H or methyl.

In some embodiments:
$X^1$ is N;
$X^2$ is N;
$X^3$ is CH;
$X^4$ is $CR^4$;
$X^5$ is CH;
$X^6$ is CH;
$R^4$ is H, D, F, or $C_{1-6}$ alkyl, wherein one or more hydrogen atoms of the $C_{1-6}$ alkyl group are replaced with deuterium atoms;
$R^7$ is H;
$R^8$ is H, Br, Cl, $C_{1-4}$ alkyl, phenyl, 1H-pyrazol-5-yl, pyrazol-4-yl, thiazol-5-yl, pyridyl, thiophenyl or pyrimidinyl, wherein the phenyl, 1H-pyrazol-5-yl, 1H-pyrazol-4-yl, thiazol-5-yl, pyridyl, thiophenyl and pyrimidinyl are each optionally substituted with 1 or 2 independently selected $R^b$ substituents;
$R^9$ is H;
$R^{10}$ is 4-10 membered heterocycloalkyl or (4-10 membered heterocycloalkyl)-$C_{1-4}$ alkyl-, each of which may be optionally substituted with 1 or 2 independently selected $R^b$ substituents;
L is

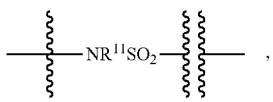

$SO_2$ or

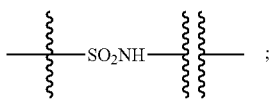

;

$R^{11}$ is H or $C_{1-6}$ alkyl;
each $R^b$ substituent is independently selected from halo, $C_{1-4}$ alkyl, CN, $OR^c$, $C(O)NR^cR^c$, $NR^cR^c$, $NR^cC(O)OR^c$, and $S(O)_2R^c$; wherein the $C_{1-4}$ alkyl of $R^b$ is further optionally substituted with 1, 2, or 3 independently selected $R^d$ substituents;
each $R^c$ is independently selected from H and $C_{1-6}$ alkyl;
each $R^d$ is independently $OR^e$; and
each $R^e$ is independently selected from H and $C_{1-6}$ alkyl.
In some embodiments:
$X^1$ is N;
$X^2$ is N;
$X^3$ is CH;
$X^4$ is $CR^4$;
$X^5$ is CH;
$X^6$ is CH;
$R^4$ is H, D, F, or $C_{1-6}$ alkyl, wherein one or more hydrogen atoms of the $C_{1-6}$ alkyl group are replaced with deuterium atoms;
$R^7$ is H;
$R^8$ is H, Br, Cl, $C_{1-4}$ alkyl, phenyl, 1H-pyrazol-5-yl, pyrazol-4-yl, thiazol-5-yl, pyridyl, thiophenyl or pyrimidinyl, wherein the phenyl, 1H-pyrazol-5-yl, 1H-pyrazol-4-yl, thiazol-5-yl, pyridyl, thiophenyl and pyrimidinyl are each optionally substituted with 1 or 2 independently selected $R^b$ substituents;
$R^9$ is H;
$R^{10}$ is a bicyclic 6-10 membered heterocycloalkyl, which is optionally substituted with 1 or 2 independently selected $R^b$ substituents;
L is

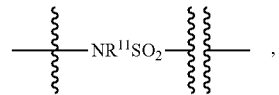

$SO_2$ or

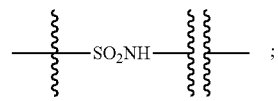

;

$R^{11}$ is H or $C_{1-6}$ alkyl;
each $R^b$ substituent is independently selected from halo, $C_{1-4}$ alkyl, CN, $OR^c$, $C(O)NR^cR^c$, $NR^cR^c$, $NR^cC(O)OR^c$, and $S(O)_2R^c$; wherein the $C_{1-4}$ alkyl of $R^b$ is further optionally substituted with 1, 2, or 3 independently selected $R^d$ substituents;
each $R^c$ is independently selected from H and $C_{1-6}$ alkyl;
each $R^d$ is independently $OR^e$; and
each $R^e$ is independently selected from H and $C_{1-6}$ alkyl.
In some embodiments:
$X^1$ is N;
$X^2$ is N;
$X^3$ is CH;
$X^4$ is $CR^4$;
$X^5$ is CH;
$X^6$ is CH;
$R^4$ is H, D, F, or $C_{1-6}$ alkyl, wherein one or more hydrogen atoms of the $C_{1-6}$ alkyl group are replaced with deuterium atoms;
$R^7$ is H;
$R^8$ is H, Br, Cl, $C_{1-4}$ alkyl, phenyl, 1H-pyrazol-5-yl, pyrazol-4-yl, thiazol-5-yl, pyridyl, thiophenyl or pyrimidinyl, wherein the phenyl, 1H-pyrazol-5-yl, 1H-pyrazol-4-yl, thiazol-5-yl, pyridyl, thiophenyl and pyrimidinyl are each optionally substituted with 1 or 2 independently selected $R^b$ substituents;
$R^9$ is H;
$R^{10}$ is a bicyclic 6-10 membered heterocycloalkyl, which is optionally substituted with 1 or 2 independently selected $R^b$ substituents;
L is

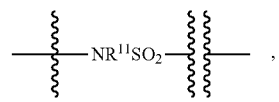

$SO_2$ or

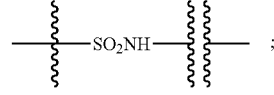

;

$R^{11}$ is H or $C_{1-6}$ alkyl;

each $R^b$ substituent is independently selected from halo, $C_{1-4}$ alkyl, CN, $OR^c$, $C(O)NR^cR^c$, $NR^cR^c$, $NR^cC(O)OR^c$, and $S(O)_2R$; and each $R^e$ is independently selected from H and $C_{1-6}$ alkyl.

In some embodiments:

$X^1$ is N;

$X^2$ is N;

$X^3$ is CH;

$X^4$ is $CR^4$;

$X^5$ is CH;

$X^6$ is CH;

$R^4$ is H, D, F, or $C_{1-6}$ alkyl, wherein one or more hydrogen atoms of the $C_{1-6}$ alkyl group are replaced with deuterium atoms;

$R^7$ is H;

$R^8$ is H, Br, Cl, $C_{1-4}$ alkyl, phenyl, 1H-pyrazol-5-yl, pyrazol-4-yl, thiazol-5-yl, pyridyl, thiophenyl or pyrimidinyl, wherein the phenyl, 1H-pyrazol-5-yl, 1H-pyrazol-4-yl, thiazol-5-yl, pyridyl, thiophenyl and pyrimidinyl are each optionally substituted with 1 or 2 independently selected $R^b$ substituents;

$R^9$ is H;

$R^{10}$ is a bicyclic 6-10 membered heterocycloalkyl, which is optionally substituted with 1 or 2 independently selected $R^b$ substituents;

L is

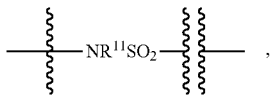

$SO_2$ or

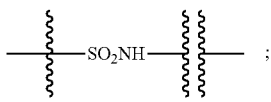

$R^{11}$ is H or $C_{1-6}$ alkyl;

each $R^b$ substituent is independently selected from halo, $C_{1-4}$ alkyl, CN, $OR^c$, $C(O)NR^cR^c$, $NR^cR^c$, $NR^cC(O)OR^c$, and $S(O)_2R^c$; and each $R^c$ is independently selected from H and $C_{1-6}$ alkyl;

In some embodiments, L is preferably

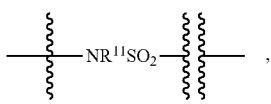

wherein $R^{11}$ is H or methyl.

In some embodiments, the compound is a compound of Formula (II):

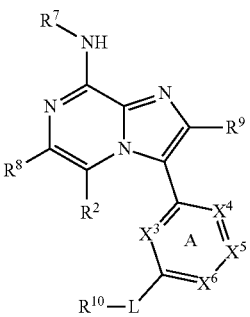

(II)

or a pharmaceutically acceptable salt thereof.

In some embodiments, the compound is a compound of Formula (III):

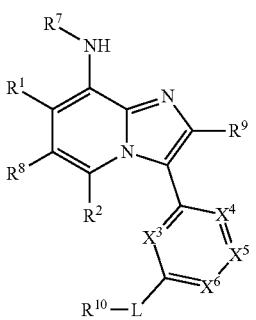

(III)

or a pharmaceutically acceptable salt thereof.

In some embodiments, the compound is a compound of Formula (IV):

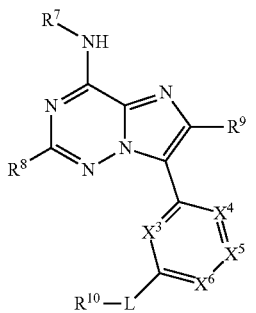

(IV)

or a pharmaceutically acceptable salt thereof.

In some embodiments, the compound is a compound of Formula (V):

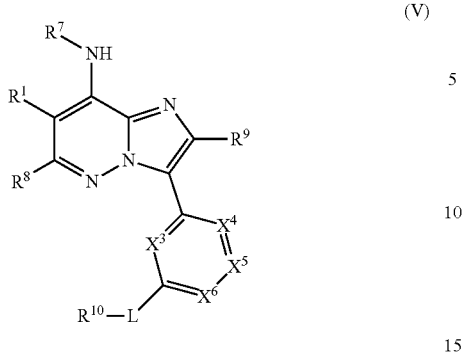
(V)
or a pharmaceutically acceptable salt thereof.
In some embodiments, the compound is a compound of Formula (IIa), (IIb), (IIc), (IId), (IIe), (IIf), (IIIa), (IIIb), (IIIc), (IIId), (IIIe), (IIIf), (IVa), (IVb), (IVc), (IVd), (IVe), (Va), (Vb), (Vc), (Vd), or (Ve):
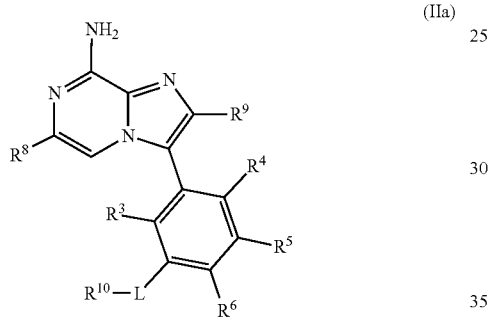
(IIa)
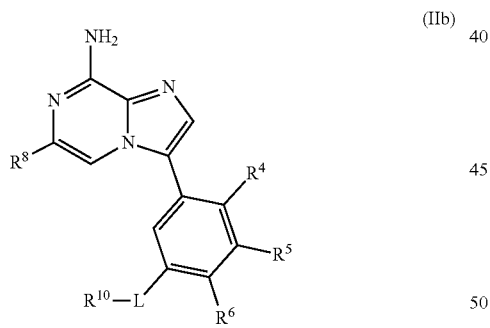
(IIb)
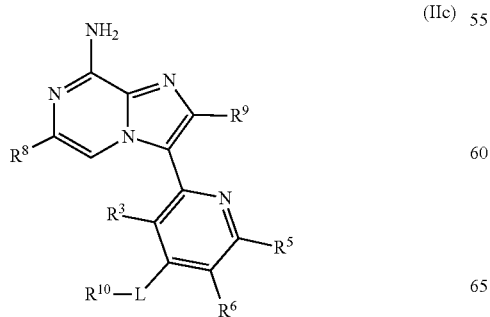
(IIc)
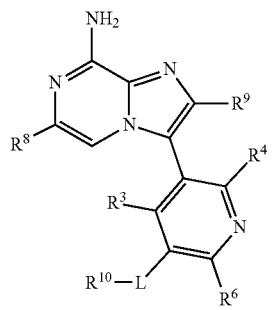
(IId)
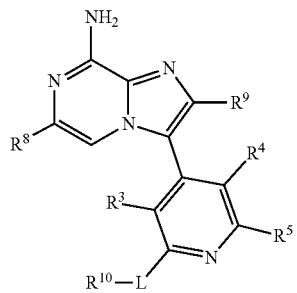
(IIe)
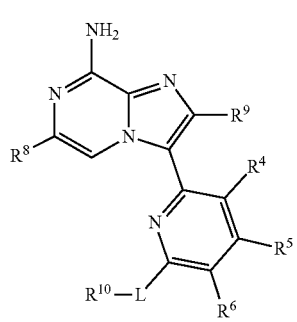
(IIf)
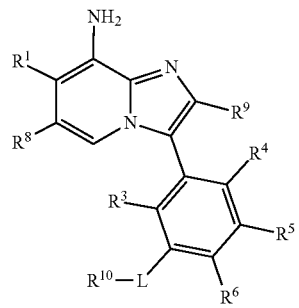
(IIIa)
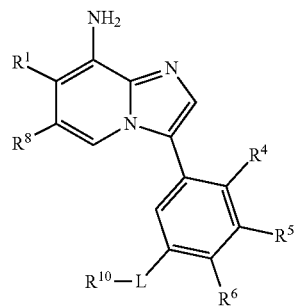
(IIIb)

-continued
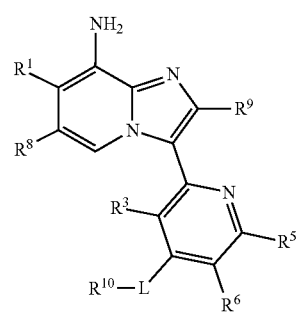
(IIIc)
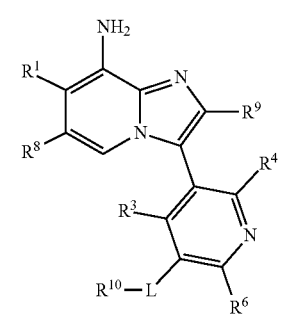
(IIId)
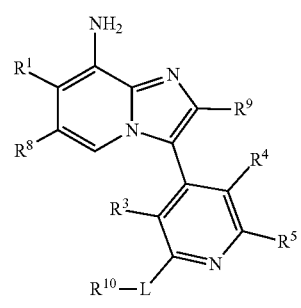
(IIIe)
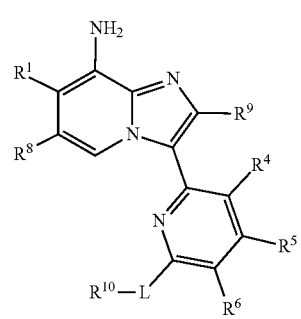
(IIIf)
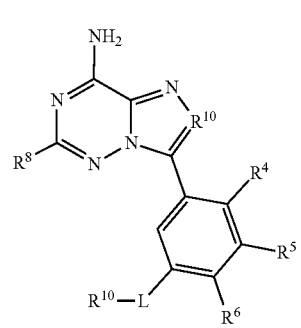
(IVa)
-continued
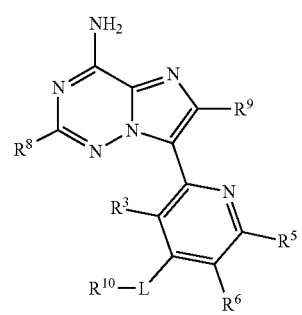
(IVb)
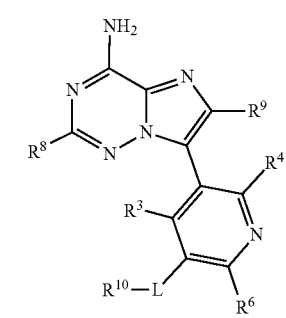
(IVc)
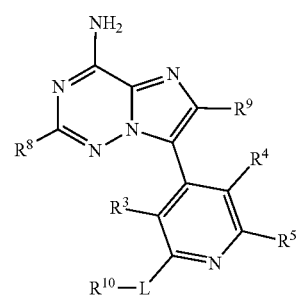
(IVd)
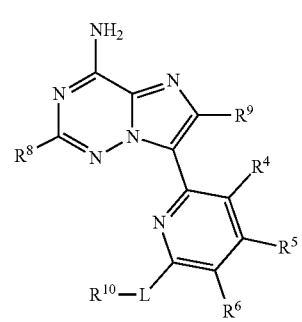
(IVe)
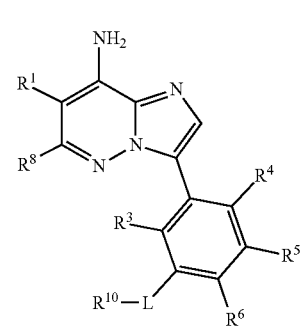
(Va)

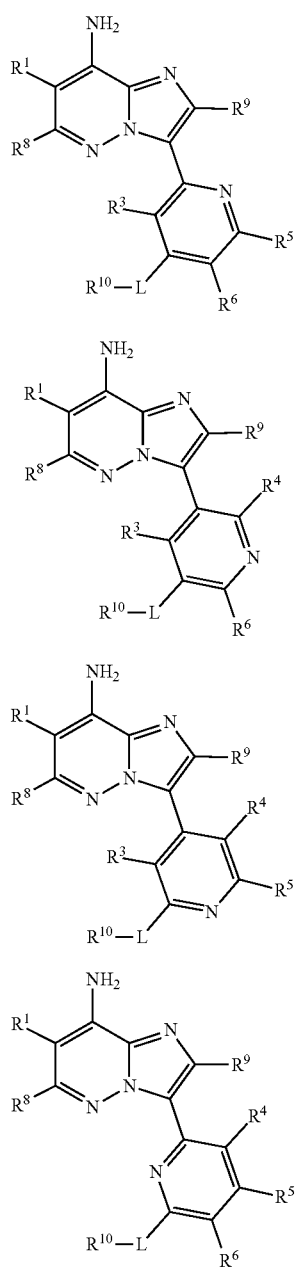

(Vb)

(Vc)

(Vd)

(Ve)

or a pharmaceutically acceptable salt thereof.

In the each of the subformulas (II), (III), (IV), (V), (IIa), (IIb), (IIc), (IId), (IIe), (IIf), (IIIa), (IIIb), (IIIc), (IIId), (IIIe), (IIIf), (IVa), (IVb), (IVc), (IVd), (IVe), (Va), (Vb), (Vc), (Vd), or (Ve), L is preferably

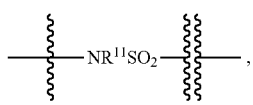

wherein $R^{11}$ is H or methyl.

In some embodiments, the compound is a compound of Formula IIg, IIh, IVg, or IVh:

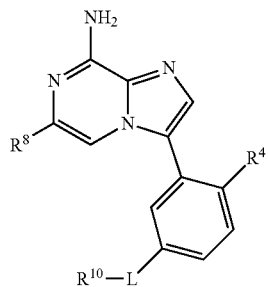

(IIg)

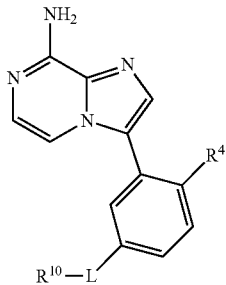

(IIh)

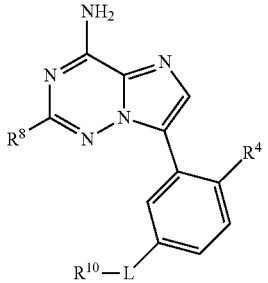

(IVg)

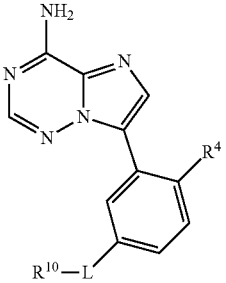

(IVh)

or a pharmaceutically acceptable salt or a tautomer thereof.

In some embodiments of Formulas (IIg), (IIh), (IVg), and (IVh), L is

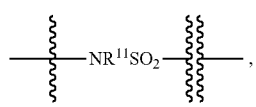

wherein $R^{11}$ is H or methyl.

In some embodiments of Formulas (IIg), (IIh), (IVg), and (IVh), $R^4$ is H, D, F, or $C_{1-6}$ alkyl, wherein one or more hydrogen atoms of the $C_{1-6}$ alkyl group are replaced with deuterium atoms.

In some embodiments of Formulas (IIg), (IIh), (IVg), and (IVh), $R^4$ is H, D, F, $CD_3$, or $CH_3$.

In some embodiments, the compound is a compound of Formula (VI):

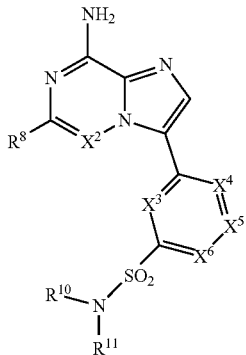

(VI)

or a pharmaceutically acceptable salt or a tautomer thereof.

In some embodiments, the compound is a compound of Formula (VII):

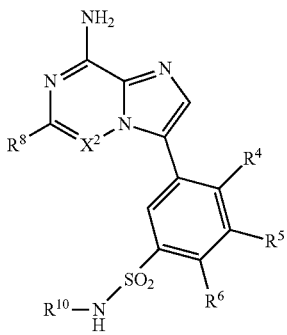

(VII)

or a pharmaceutically acceptable salt or a tautomer thereof.

In some embodiments, the compound is a compound of Formula (VII), wherein
  $R^4$ is selected from H, D, F, Cl, $CD_3$, and methyl; and
  $R^8$ is selected H, D, $CD_3$, $CF_3$, methyl, $C(O)NR^{a1}R^{a1}$, $C_{6-10}$ aryl, and 4-10 membered heterocycloalkyl, wherein the $C_{6-10}$ aryl and 4-10 membered heterocycloalkyl are each optionally substituted with 1 or 2 independently selected $R^q$ substituents.

In some embodiments, the compound is a compound of Formula (VII), wherein
  $R^4$ is selected from Cl, $CD_3$, or methyl;
  $R^5$ is selected from H or F; and
  $R^6$ is selected CN, halo or $C_{1-6}$ alkyl.

In some embodiments, the compound is a compound of Formula (VIII):

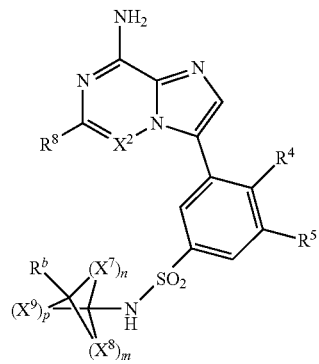

(VIII)

or a pharmaceutically acceptable salt or a tautomer thereof.

In some embodiments, the compound is a compound of Formula (VIII), wherein
  $R^4$ is selected from Cl, $CD_3$, or methyl;
  $R^5$ is selected from H or F;
  $R^8$ is selected H, $CF_3$ or methyl;
  $X^7$, $X^8$, and $X^9$ are each independently selected from C, O, N or S; and
  m, n, p are each independently 0, 1, 2, 3 or 4.

In some embodiments, the compound is a compound of Formula (IX):

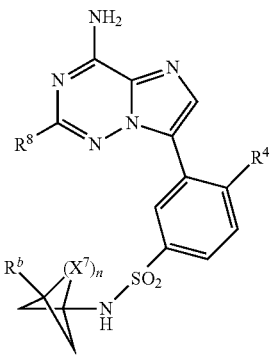

(IX)

or a pharmaceutically acceptable salt or a tautomer thereof.

In some embodiments, the compound is a compound of Formula (IX), wherein
  $R^4$ is selected from $CD_3$, or methyl;
  $R^8$ is selected H, $CF_3$ or methyl;
  $X^7$ is selected from C, O, N or S; and
  N is 0, 1, 2, 3 or 4.

In some embodiments, the compound is a compound of Formula (X):

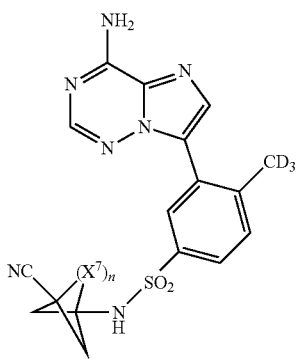

or a pharmaceutically acceptable salt or a tautomer thereof.

In some embodiments, the compound is a compound of Formula (X), wherein
$X^7$ is selected from C or O; and
N is 1, 2 or 3.

In some embodiments, the compound is a compound of Formula (X), wherein
$X^7$ is C; and
N is 1 or 2.

In some embodiments, the compound or pharmaceutically acceptable salt of the compound of Formula (I) provided herein is crystalline. As used herein, "crystalline" or "crystalline form" is meant to refer to a certain lattice configuration of a crystalline substance.

Different crystalline forms of the same substance typically have different crystalline lattices (e.g., unit cells) which are attributed to different physical properties that are characteristic of each of the crystalline forms. In some instances, different lattice configurations have different water or solvent content.

Different crystalline forms of the same compound or salt can have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

The different crystalline forms can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 5% of the maximum peak height/intensity.

Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

The present invention provides crystalline forms of certain compounds, or salts thereof. In some embodiments, the compound of Formula I is 3-(4-aminoimidazo[2,1-f][1,2,4]triazin-7-yl)-N-(4-cyanobicyclo[2.1.1]hexan-1-yl)-4-(methyl-d₃)benzenesulfonamide, or a pharmaceutically acceptable salt thereof.

In some embodiments, the present invention provides crystalline 3-(4-aminoimidazo[2,1-f][1,2,4]triazin-7-yl)-N-(4-cyanobicyclo[2.1.1]hexan-1-yl)-4-(methyl-d₃)benzenesulfonamide characterized, for example, by an XRPD profile substantially as shown in FIG. 1.

In some embodiments, crystalline 3-(4-aminoimidazo[2,1-f][1,2,4]triazin-7-yl)-N-(4-cyanobicyclo[2.1.1]hexan-1-yl)-4-(methyl-d₃)benzenesulfonamide has at least one, at least two, at least three, at least four, or at least five XRPD peaks, in terms of 2-theta, selected from about 8.4°, about 15.3°, about 16.9°, about 17.3°, about 17.4°, about 17.6°, about 19.4°, about 20.6°, about 24.9°, and about 26.5°.

In some embodiments, crystalline 3-(4-aminoimidazo[2,1-f][1,2,4]triazin-7-yl)-N-(4-cyanobicyclo[2.1.1]hexan-1-yl)-4-(methyl-d₃)benzenesulfonamide is characterized by a DSC thermogram having an endothermic peak at about 234° C.

Figure 3:
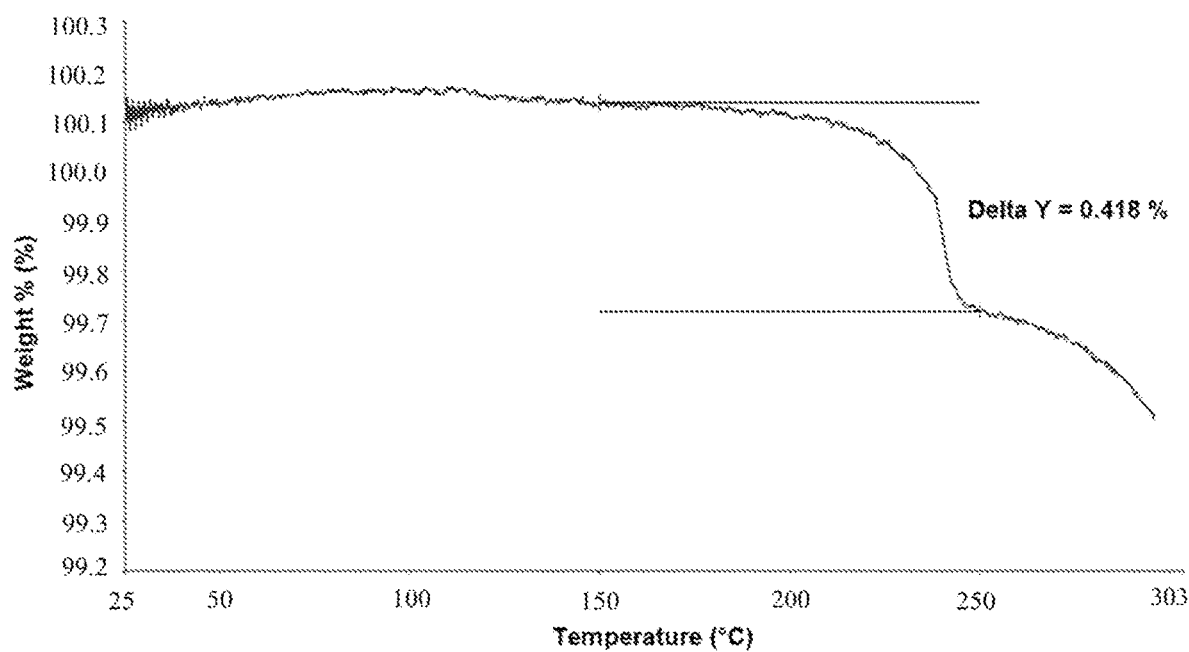
FIG. 3 shows a TGA thermogram characteristic of the crystalline compound of Example 253.

In some embodiments, crystalline 3-(4-aminoimidazo[2,1-f][1,2,4]triazin-7-yl)-N-(4-cyanobicyclo[2.1.1]hexan-1-yl)-4-(methyl-d₃)benzenesulfonamide is characterized by a thermographic analysis (TGA) substantially as shown in FIG. 3.

In some embodiments, the 3-(4-aminoimidazo[2,1-f][1,2,4]triazin-7-yl)-N-(4-cyanobicyclo[2.1.1]hexan-1-yl)-4-(methyl-d₃)benzenesulfonamide can be isolated as a hydrochloric acid salt, which can be crystalline.

Figure 4:
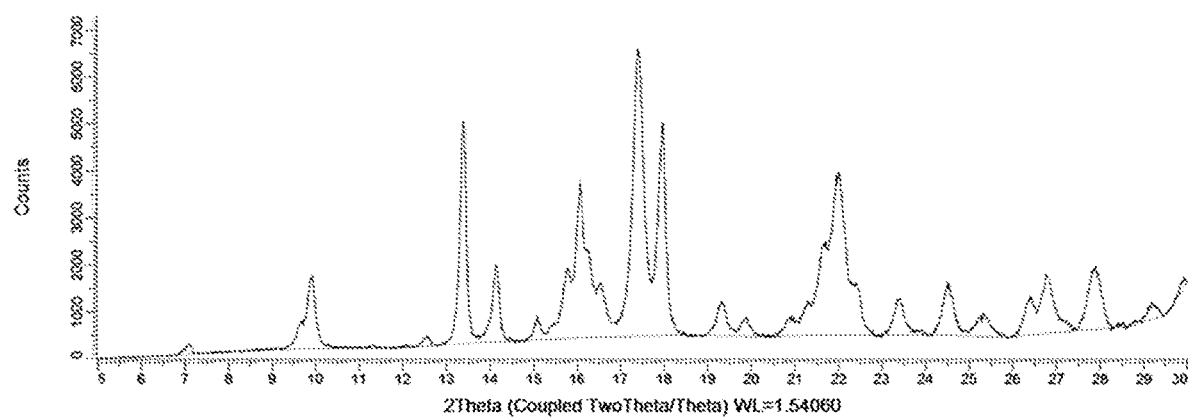
FIG. 4 shows an X-Ray Powder Diffraction (XRPD) pattern characteristic of the crystalline hydrochloric acid salt of Example 254.

In some embodiments, the crystalline form of the 3-(4-aminoimidazo[2,1-f][1,2,4]triazin-7-yl)-N-(4-cyanobicyclo[2.1.1]hexan-1-yl)-4-(methyl-d₃)benzenesulfonamide hydrochloric acid salt has an XRPD profile substantially as shown in FIG. 4.

In some embodiments, the crystalline form of the 3-(4-aminoimidazo[2,1-f][1,2,4]triazin-7-yl)-N-(4-cyanobicyclo[2.1.1]hexan-1-yl)-4-(methyl-d₃)benzenesulfonamide hydrochloric acid salt has at least one, at least two, at least three, at least four, or at least five XRPD peaks, in terms of 2-theta, selected from about 9.9°, about 13.4°, about 14.10, about 15.8°, about 16.10, about 16.2°, about 17.4°, about 18.0°, about 21.7°, about 22.0°, about 22.4°, about 23.4°, about 24.5°, about 25.3°, about 26.4°, about 26.8°, and about 27.9°.

In some embodiments, the crystalline form of the 3-(4-aminoimidazo[2,1-f][1,2,4]triazin-7-yl)-N-(4-cyanobicyclo[2.1.1]hexan-1-yl)-4-(methyl-d₃)benzenesulfonamide hydrochloric acid salt has at least one, at least two, at least three, at least four, or at least five XRPD peaks, in terms of 2-theta, selected from about 9.9°, about 13.4°, about 14.10, about 15.8°, about 16.10, about 16.2°, about 17.4°, about 18.0°, about 21.7°, about 22.0°, about 26.8°, and about 27.9°.

In some embodiments, the crystalline form of the 3-(4-aminoimidazo[2,1-f][1,2,4]triazin-7-yl)-N-(4-cyanobicyclo [2.1.1]hexan-1-yl)-4-(methyl-d$_3$)benzenesulfonamide hydrochloric acid salt is characterized by a DSC thermogram having an endothermic peak at about 233.4° C.

Figure 6:
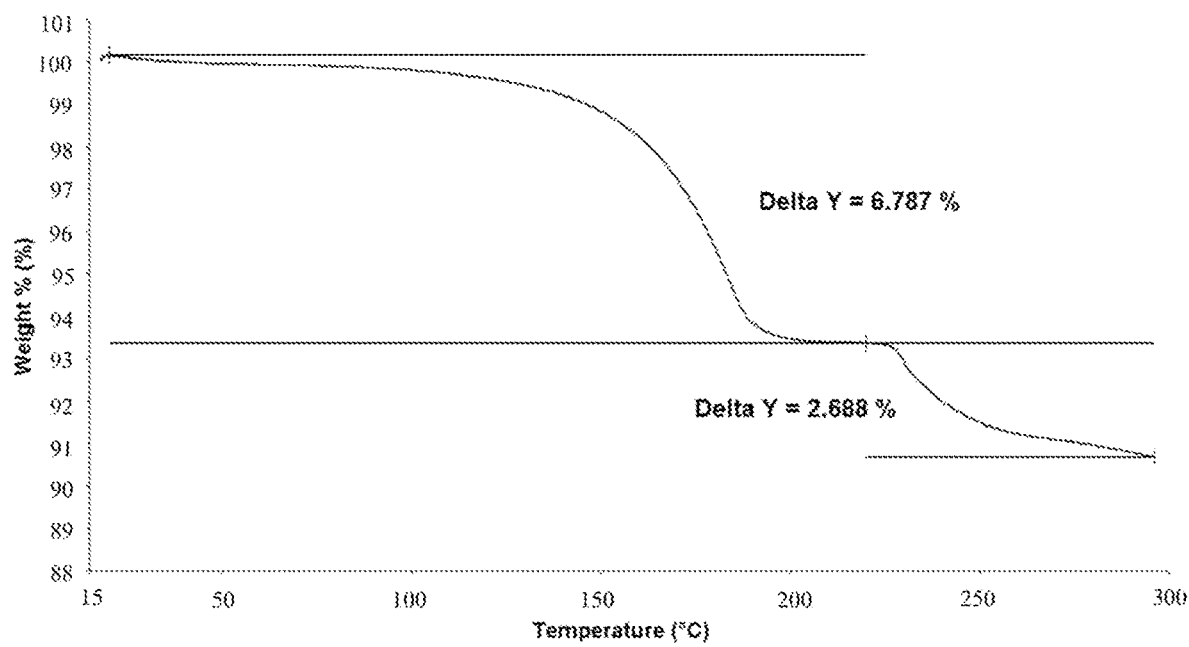
FIG. 6 shows a TGA thermogram characteristic of the crystalline hydrochloric acid salt of Example 254.

In some embodiments, the crystalline form of the 3-(4-aminoimidazo[2,1-f][1,2,4]triazin-7-yl)-N-(4-cyanobicyclo [2.1.1]hexan-1-yl)-4-(methyl-d$_3$)benzenesulfonamide hydrochloric acid salt is characterized by a thermographic analysis (TGA) substantially as shown in FIG. 6.

In some embodiments, the 3-(4-aminoimidazo[2,1-f][1,2, 4]triazin-7-yl)-N-(4-cyanobicyclo[2.1.1]hexan-1-yl)-4-(methyl-d$_3$)benzenesulfonamide can be isolated as a benzenesulfonic acid salt, which can be crystalline.

Figure 7:
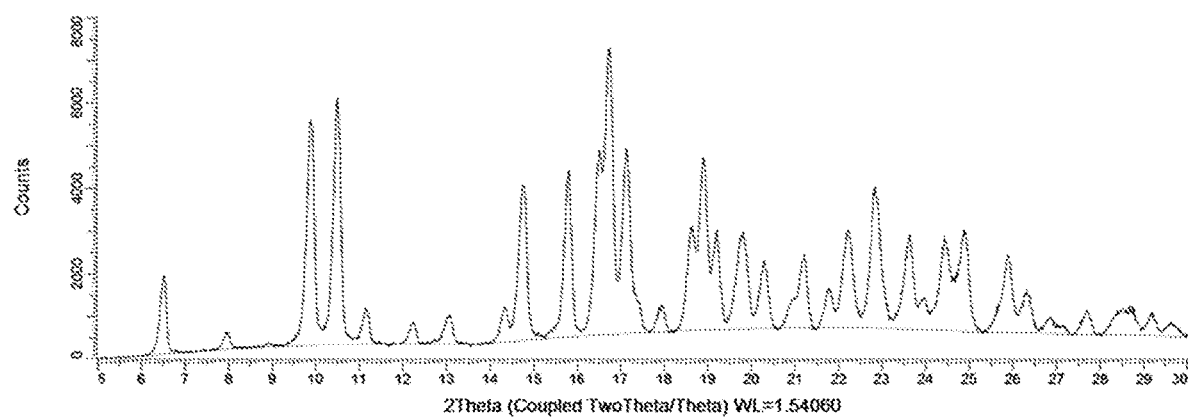
FIG. 7 shows an X-Ray Powder Diffraction (XRPD) pattern characteristic of the crystalline benzenesulfonic acid salt of Example 255.

In some embodiments, the crystalline form of the 3-(4-aminoimidazo[2,1-f][1,2,4]triazin-7-yl)-N-(4-cyanobicyclo [2.1.1]hexan-1-yl)-4-(methyl-d$_3$)benzenesulfonamide benzenesulfonic acid salt has an XRPD profile substantially as shown in FIG. 7.

In some embodiments, the crystalline form of the 3-(4-aminoimidazo[2,1-f][1,2,4]triazin-7-yl)-N-(4-cyanobicyclo [2.1.1]hexan-1-yl)-4-(methyl-d$_3$)benzenesulfonamide benzenesulfonic acid salt has at least one, at least two, at least three, at least four, or at least five XRPD peaks, in terms of 2-theta, selected from about 14.8°, about 15.8°, about 16.5°, about 16.7°, about 17.1°, about 18.6°, about 18.9°, about 19.2°, about 19.8°, about 22.2°, about 22.8°, about 23.6°, about 24.5°, about 24.9°, and about 25.9°.

In some embodiments, the crystalline form of the 3-(4-aminoimidazo[2,1-f][1,2,4]triazin-7-yl)-N-(4-cyanobicyclo [2.1.1]hexan-1-yl)-4-(methyl-d$_3$)benzenesulfonamide benzenesulfonic acid salt is characterized by a DSC thermogram having an endothermic peak at about 213.8° C.

Figure 9:
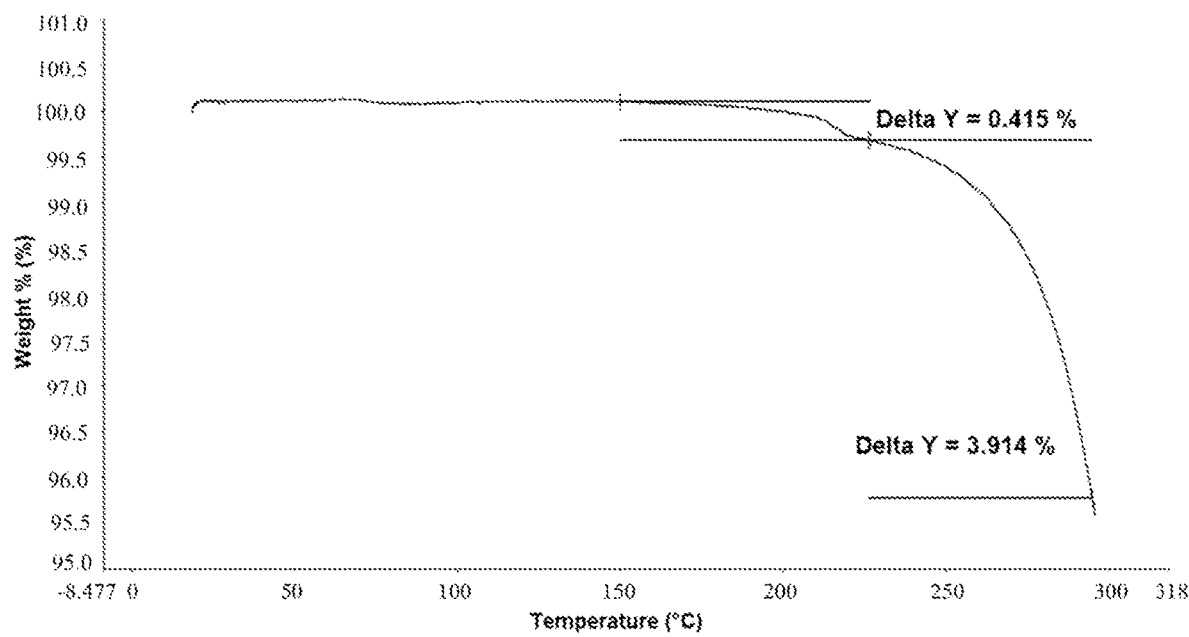
FIG. 9 shows a TGA thermogram characteristic of the crystalline benzenesulfonic acid salt of Example 255.

In some embodiments, the crystalline form of the 3-(4-aminoimidazo[2,1-f][1,2,4]triazin-7-yl)-N-(4-cyanobicyclo [2.1.1]hexan-1-yl)-4-(methyl-d$_3$)benzenesulfonamide benzenesulfonic acid salt is characterized by a thermographic analysis (TGA) substantially as shown in FIG. 9.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl.

As used herein, the term "di($C_{n-m}$ alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, or Br.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups, spirocycles, and bridged rings. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cyclocalkyl. In some embodiments, the cycloalkyl is a C3-7 monocyclic cyclocalkyl. In some embodiments, the cycloalkyl is a $C_{4-10}$ spirocycle or bridged cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-14-membered heterocycloalkyl groups. Heterocycloalkyl groups can also include spirocycles and bridged rings, e.g., a 5-8 membered bridged heterocycloalkyl ring optionally substituted with 0 to 2 additional heteroatoms independently selected from nitrogen, oxygen and sulfur. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O), or attached to a nitrogen or sulfur heteroatom forming a nitroso, sulfinyl or sulfonyl group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Formulas (I)-(XII) herein include stereoisomers of the compounds. In some embodiments, the carbon atom to which $R^1$ is attached is in the (R)-configuration. In some embodiments, the carbon atom to which $R^1$ is attached is in the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and $R^b$ forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated, the compounds provided herein, including salts and stereoisomers thereof, can be prepared using known organic synthesis techniques and can be synthesized according to any of numerous possible synthetic routes.

Compounds of Formula (I) can be prepared from optionally protected (e.g., P=acetyl) bicycles 1-1 where $Y^1$ is halogen (e.g., Cl, Br, or I) or pseudohalogen (e.g., OTf or OMs) as shown in Scheme I. Bicycle 1-1 can be coupled with 1-2, where $M^1$ is a boronic acid, boronate ester, potassium trifluoroborate, or an appropriately substituted metal, such as $Sn(Bu)_3$ or Zn, under standard Suzuki conditions (e.g., in the presence of a palladium catalyst, such as tetrakis(triphenylphosphine)palladium(O) or [1,1'-bis(diphenylphosphino)ferrocene]dichloropalladium (II), complex with dichloromethane and a base (e.g., a carbonate base)) or standard Stille conditions (e.g., in the presence of a palladium(O) catalyst, such as tetrakis(triphenylphosphine)palladium(O)) or standard Negishi conditions (e.g., in the presence of a palladium catalyst, such as tetrakis(triphenylphosphine)palladium(O) or [1,1'-bis(diphenylphosphino)ferrocene]dichloropalladium (II)), to give compound 1-3. After coupling, optionally chosen protecting groups can be removed under conditions suitable for their removal that are also compatible with the functionality present in 1-3 (e.g., exposure to aqueous HCl) to afford the resulting compounds of Formula (I).

Alternatively, the $Y^1$ group can be converted to an appropriate substituted metal 1-4 (e.g., $M^2$ is $B(OH)_2$, Bpin, $BF_3K$, $Sn(Bu)_3$, or Zn) and then coupled to 1-5 where $Y^2$ is halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(O) or [1,1'-bis(diphenylphosphino)ferrocene]dichloropalladium (II), complex with dichloromethane and a base (e.g., a carbonate base)) or standard Stille conditions (e.g., in the presence of a palladium(O) catalyst, such as tetrakis(triphenylphosphine)palladium(O)) or standard Negishi conditions (e.g., in the presence of a palladium (O) catalyst, such as tetrakis(triphenylphosphine)palladium (O) or [1,1'-bis(diphenylphosphino)ferrocene] dichloropalladium (II)) to give to give compound 1-3. After coupling, optionally chosen protecting groups can be removed under conditions suitable for their removal that are also compatible with the functionality present in 1-3 (e.g., exposure to aqueous HCl) to afford the resulting compounds of Formula (I).

Scheme I

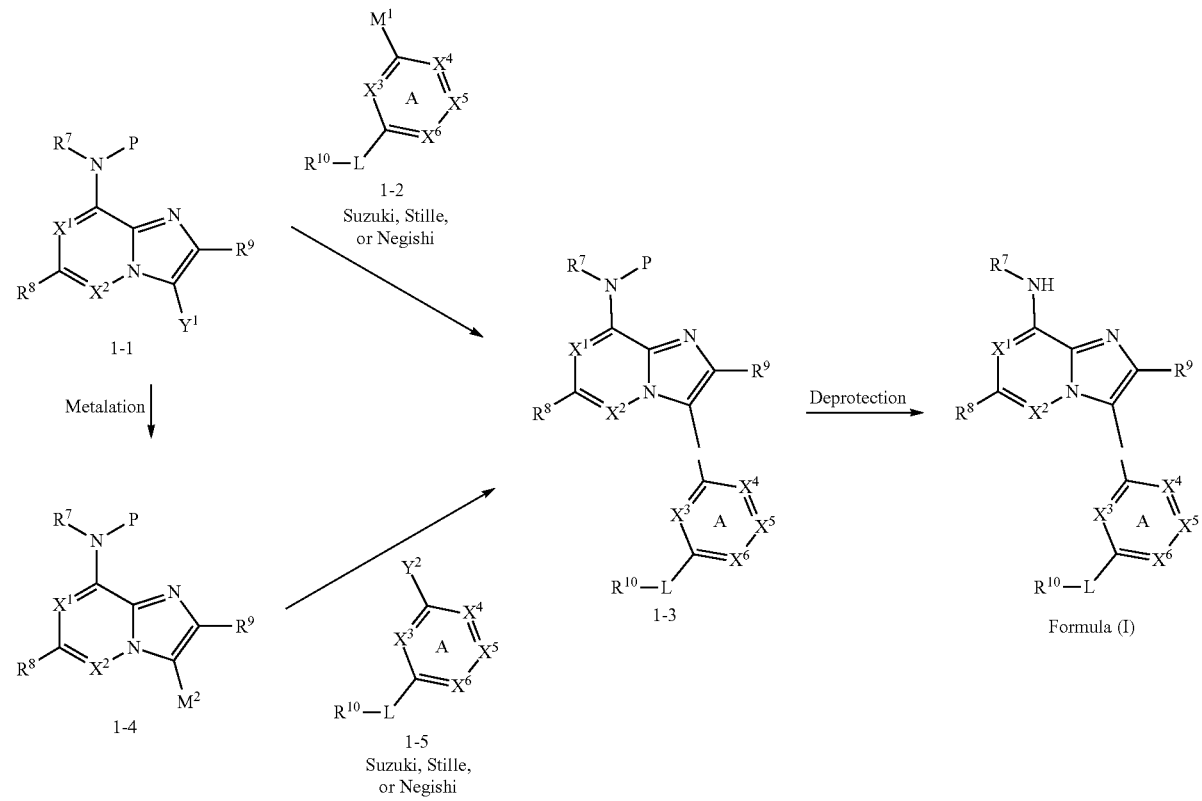

Intermediates for making compounds of the invention can be prepared as shown in Scheme II. For example, sulfonyl halide 2-1, where $Y^3$ is a halogen (e.g., Cl or F), can be coupled with an amine 2-2 by various methods (e.g. treatment with an appropriate base such as pyridine or trimethylamine and optionally with a catalyst such as 4-dimethylaminopyridine). The $Y^2$ halo (e.g., Cl, Br, or I) or pseudohalo group (e.g., OTf or OMs) of sulfonamide 2-3 can be converted to an appropriate substituted metal 2-4 (e.g., $M^2$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds of the invention can be synthesized from intermediates 2-4 using the methods described in Scheme I.

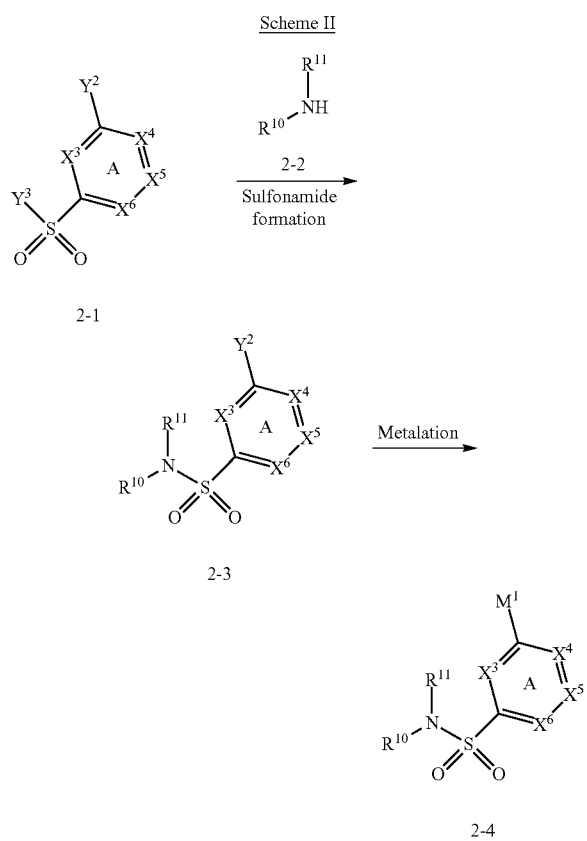

Intermediates for making compounds of the invention can be prepared as shown in Scheme III. For example, an amine 3-1 can be coupled with a sulfonyl halide 3-2, where $Y^4$ is a halogen (e.g., Cl or F), by various methods (e.g. treatment with an appropriate base such as pyridine). The $Y^2$ halo (e.g., Cl, Br, or I) or pseudohalo group (e.g., OTf or OMs) of sulfonamide 3-3 can be converted to an appropriate substituted metal 3-4 (e.g., $M^2$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds of the invention can be synthesized from intermediates 3-4 using the methods described in Scheme I.

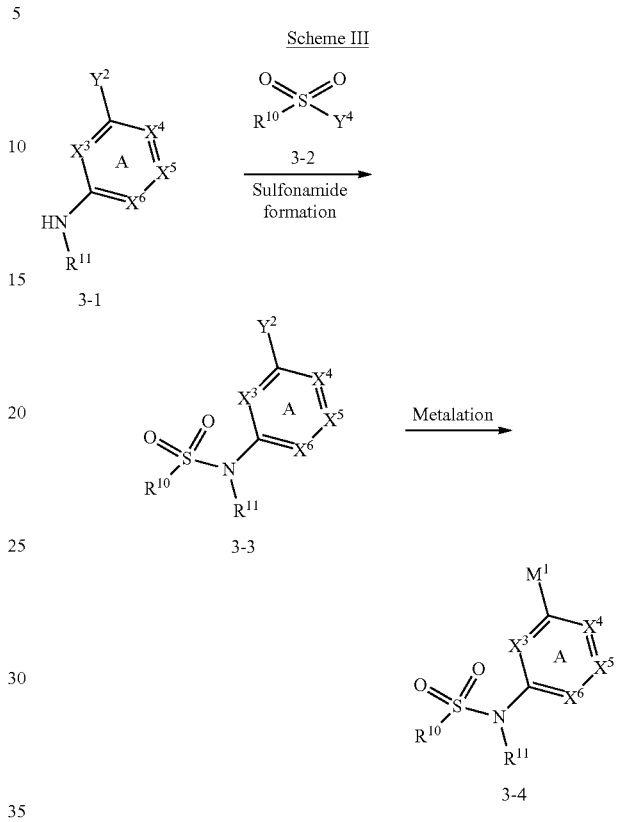

Intermediates for making compounds of the invention can be prepared as shown in Scheme IV. For example, an aryl halide 4-1 can be converted to organometallic reagent 4-2 where $M^3$ is a metal (e.g., $MgY^a$ where $Y^a$ is a halide) under standard conditions (e.g., in the presence of magnesium and optionally an additive such as 1,2-dibromoethane or lithium chloride). The resulting organometallic reagent 4-2 can be converted to the sulfinate 4-3 under standard conditions (e.g., quenching with sulfur dioxide or 1,4-diazabicyclo[2.2.2]octane bis(sulfur dioxide) adduct) and then alkylated with reagent 4-4 where $Y^9$ is a halo group (e.g., Cl, Br, or I) or other leaving group (e.g., OMs or OTs) to give the sulfone 4-5. Halogenation with suitable reagents, such as N-chlorosuccinimide, N-bromosuccinimide, $Br_2$, or N-iodosuccinimide can give halide 4-6 where $Y^2$ is a halo group (e.g., Cl, Br, or I). The $Y^2$ halo can be converted to an appropriate substituted metal (e.g., $M^2$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate) to give 4-7.

Alternatively, an aryl halide 4-1 can be directly converted to the sulfonate 4-3 under standard metal-catalyzed conditions (e.g., in the presence of a sulfur dioxide donor, such as potassium metabisulfite, a palladium catalyst such as palladium acetate, ligands such as triphenylphosphine and 1,10-phenathroline, and a base (e.g., sodium formate)) and then alkylated with reagent 4-4 where $Y^9$ is a halo group (e.g., Cl, Br, or I) or other leaving group (e.g., OMs or OTs) to give the sulfone 4-5. The sulfone 4-5 can be halogenated and then metalated to give 4-7. Compounds of the invention can be synthesized from intermediates 4-4 using the methods described in Scheme I.

appropriately substituted metal, such as $Sn(Bu)_3$ or Zn, under standard Suzuki conditions (e.g., in the presence of a palladium catalyst, such as bis(diphenylphosphino)ferrocene]dichloropalladium(II), complex with dichloromethane

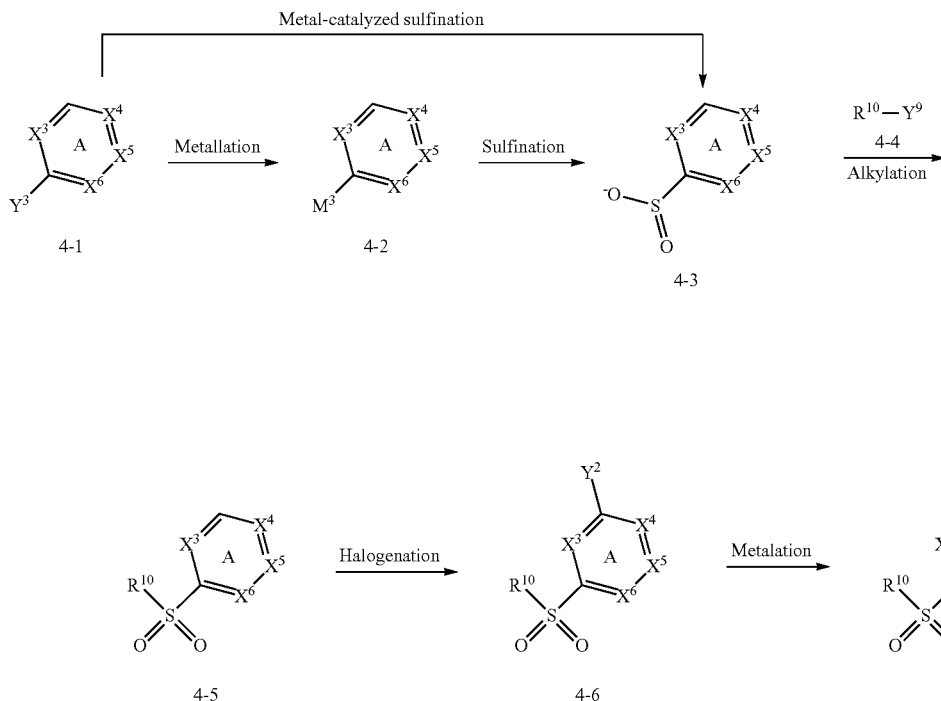

Compounds of Formula (I) can also be prepared as shown in Scheme V. For example, heteroaromatic amine 5-1, where $Y^4$ is a halogen (e.g., Cl, Br, or I), can be reacted with alpha-halo carbonyl derivative 5-2 where $Y^5$ is a halogen (e.g., Cl or Br), to give heterocycle 5-3. The amino group of 5-3 can be optionally protected with a suitable protecting group P, (e.g., acetyl), under standard conditions (e.g., in the presence of acetyl chloride or acetic anhydride, a base (e.g., triethylamine), and optionally a catalyst (e.g., 4-dimethylaminopyridine)) to give the protected amine 5-4. Compound 5-4 can be halogenated with suitable reagents, such as N-chlorosuccinimide, N-bromosuccinimide, or N-iodosuccinimide, to give halide 5-5 where $Y^1$ is a halo group (e.g., Cl, Br, or I). Halide 5-5 can be selectively coupled with 1-2, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(O) and a base (e.g., a carbonate base)) or standard Stille conditions (e.g., in the presence of a palladium(O) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 5-6. Compound 5-6 can be coupled with 5-7, where $M^4$ is a boronic acid, boronate ester, potassium trifluoroborate, or an or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 5-8. The optionally chosen protecting group can be removed according to Scheme I to afford the resulting compounds of Formula (I).

Alternatively, halide 5-5 can be selectively coupled with 5-7, where $M^4$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 5-9, which can be elaborated according to Scheme I to afford the resulting compounds of Formula (I).

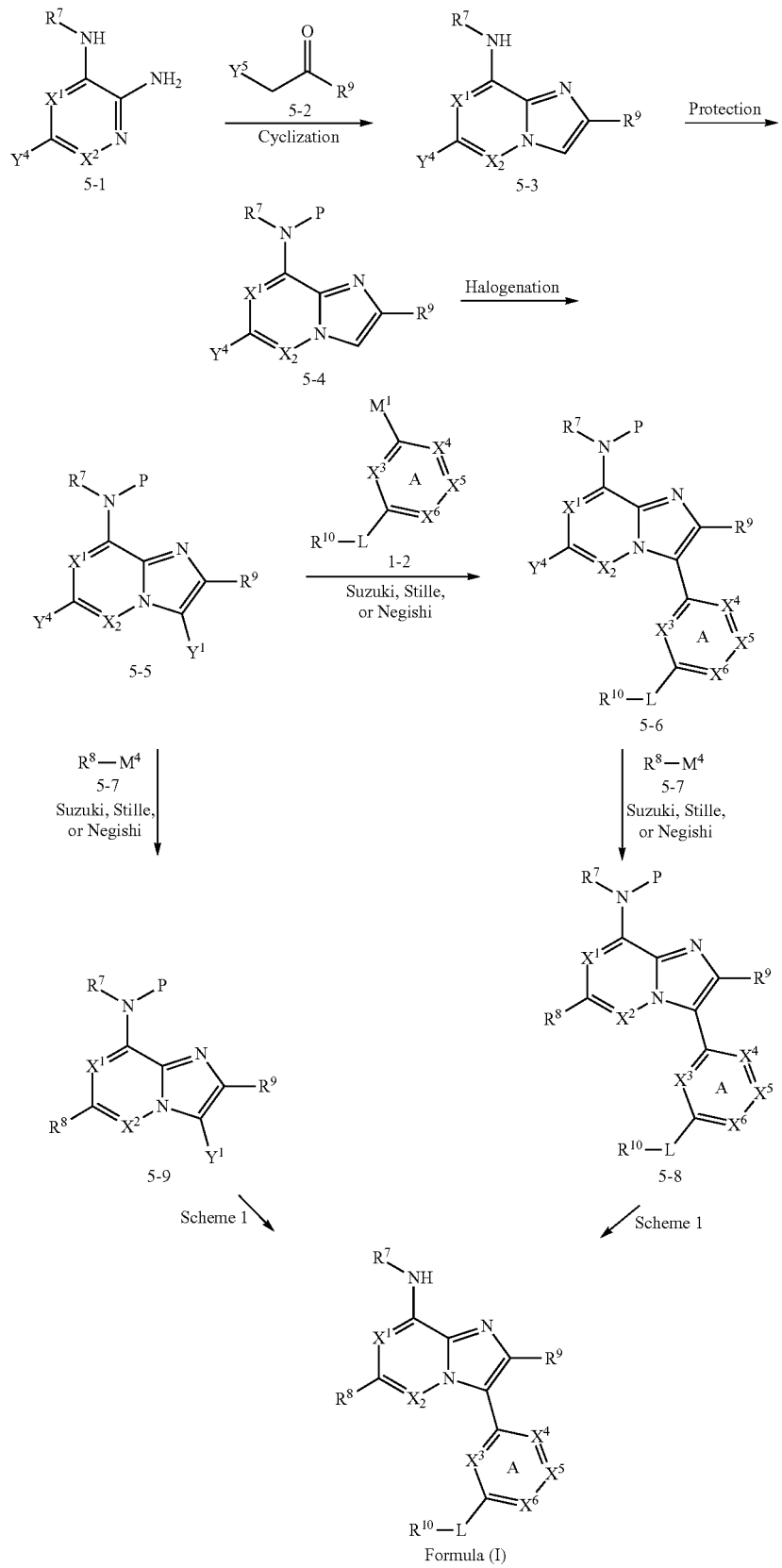

Compounds of Formula (I) can also be prepared as shown in Scheme VI. For example, hetereoaromatic amine 6-1, where $Y^4$ and $Y^6$ are halo groups, can be reacted with alpha-halo carbonyl derivatives 5-2 where $Y^5$ is a halogen (e.g., Cl or Br), to give heterocycle 6-2. Halogenation of heterocycle 6-2 with suitable reagents, such as N-chlorosuccinimide, N-bromosuccinimide, or N-iodosuccinimide can give halide 6-3 where $Y^1$ is a halo group (e.g., Cl, Br, or I). Nucleophilic aromatic substitution of the halide of 6-3 with amine 6-4 can provide halide 6-5. Halide 6-5 can be selectively coupled with 1-2, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene] dichloropalladium (II)), to give compound 6-6. Coupling of compound 6-6 with 6-7, where $M^4$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), can afford the resulting compounds of Formula (I).

Alternatively, selective coupling of halide 6-5 with 6-7, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene] dichloropalladium (II)), can afford compound 6-8, which can be further reacted according to Scheme I to afford the resulting compounds of Formula (I).

Scheme VI

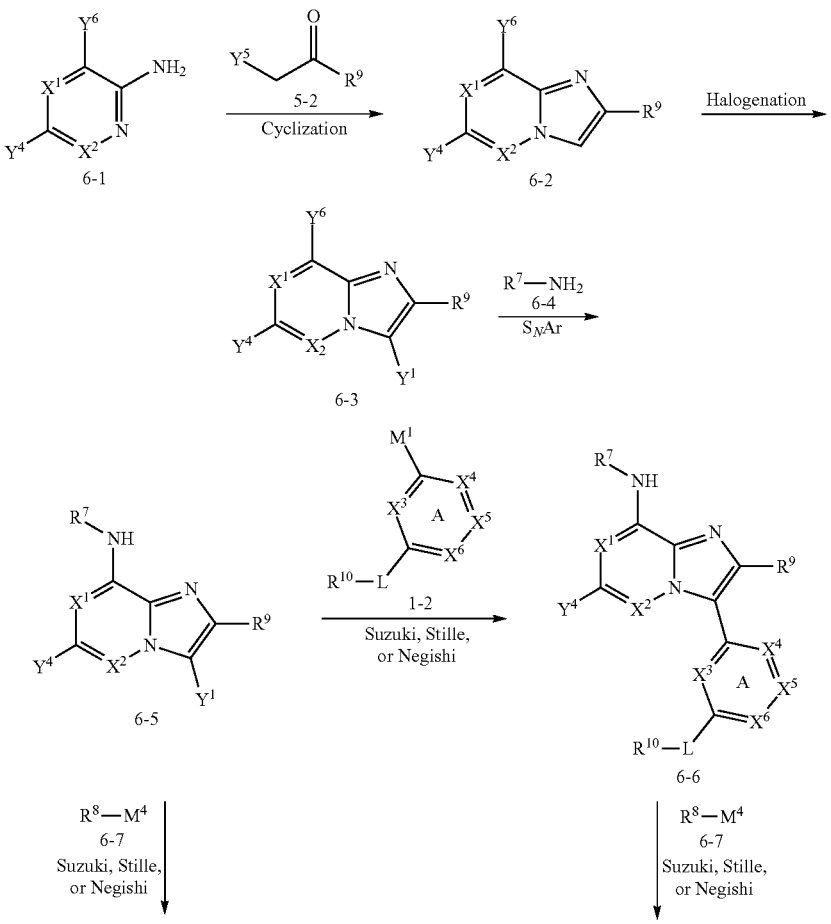

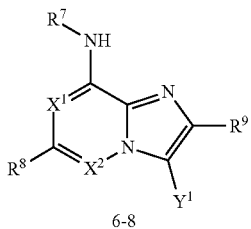

6-8

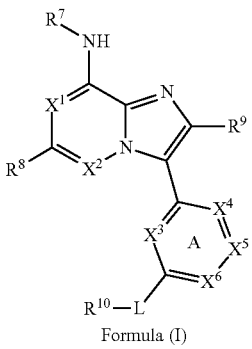

Scheme 1

Formula (I)

Compounds of Formula (I) can also be prepared as shown in Scheme VII. For example, hetereoaromatic amine 7-1, where $Y^6$ is a halogen group, can be reacted with alpha-halo carbonyl derivatives 5-2 where $Y^5$ is a halogen (e.g., Cl or Br), to give heterocycle 7-2. Halogenation of heterocycle 7-2 with suitable reagents, such as N-chlorosuccinimide, N-bromosuccinimide, or N-iodosuccinimide, can give halide 7-3 where $Y^1$ is a halo group (e.g., Cl, Br, or I). Nucleophilic aromatic substitution of the halide 7-3 with amine 7-4 can provide halide 7-5. Halide 7-5 can be further reacted according to Scheme I to afford the resulting compounds of Formula (I).

Scheme VII

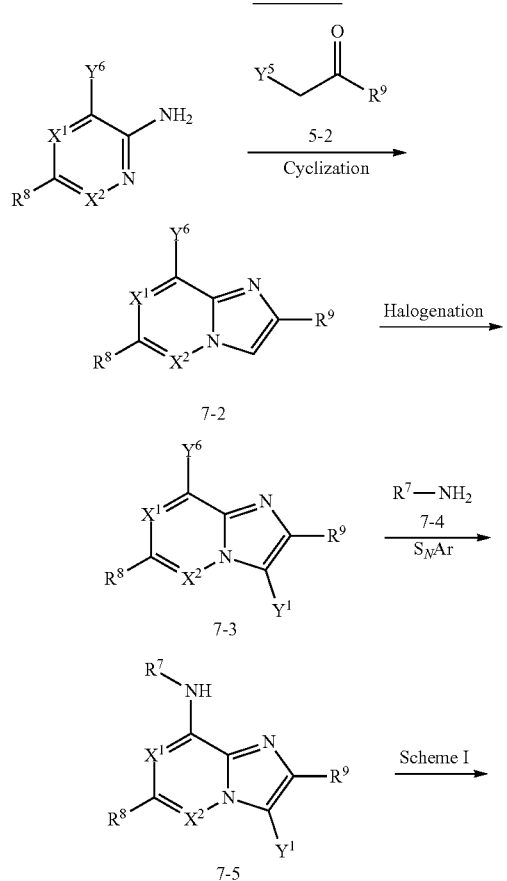

-continued

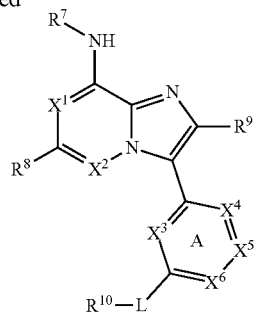

Formula (I)

Compounds of Formula (I) can also be prepared as shown in Scheme VIII. For example, hetereoaromatic amine 8-1, where $Y^7$ is a halogen group, can be reacted with alpha-halo carbonyl derivatives 5-2 where $Y^5$ is a halogen (e.g., Cl or Br), to give heterocycle 8-3. The amino group of 8-3 can be optionally protected with a suitable protecting group P (e.g., acetyl), under standard conditions (e.g., in the presence of acetyl chloride or acetic anhydride, a base (e.g., triethylamine), and optionally a catalyst (e.g., 4-dimethylaminopyridine)) to give protected amine 8-4. Compound 8-4 can be halogenated with suitable reagents, such as N-chlorosuccinimide, N-bromosuccinimide, or N-iodosuccinimide, to give a halide 8-5 where $Y^1$ is a halo group (e.g., Cl, Br, or I). Halide 8-5 can be selectively coupled with 1-2, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as bis(diphenylphosphino)ferrocene]dichloropalladium(II), complex with dichloromethane) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 8-6. Coupling of compound 8-6 with 8-7, where $M^5$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as bis(di-tert-butyl(4-dimethylaminophenyl)phosphine)dichloropalladium(II) and a base (e.g., cesium fluoride)) or standard Stille conditions (e.g., in the presence of a palladium(0) catalyst, such as tetrakis(triphenylphosphine)palladium(0))

or standard Negishi conditions (e.g., in the presence of a palladium catalyst, such as tetrakis(triphenylphosphine)palladium(0) or [1,1'-bis(diphenylphosphino)ferrocene] dichloropalladium (II)), can give compound 8-8. The optionally chosen protecting group can be removed according to Scheme I to afford the resulting compounds of Formula (I).

Alternatively, halide 8-5 can be selectively coupled with 8-7, where $M^4$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as bis(di-tert-butyl (4-dimethylaminophenyl)phosphine)dichloropalladium(II) and a base (e.g cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 8-9, which can be further reacted according to Scheme I to afford the resulting compounds of Formula (I).

Scheme VIII

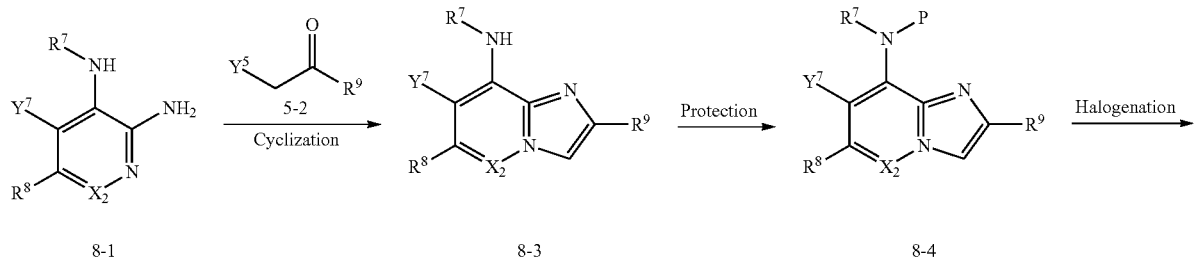

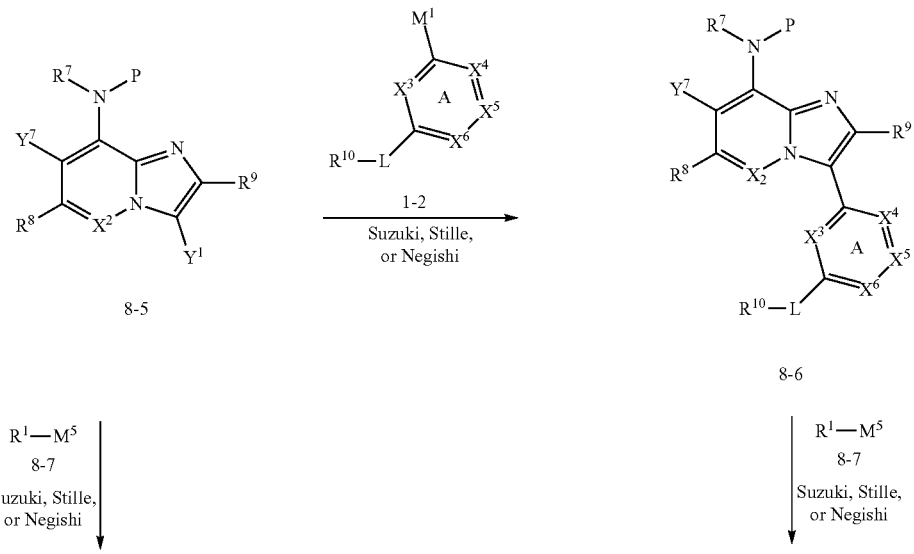

-continued

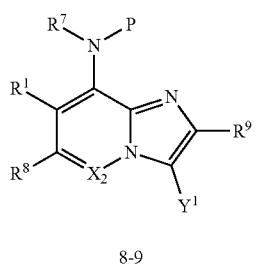

8-9

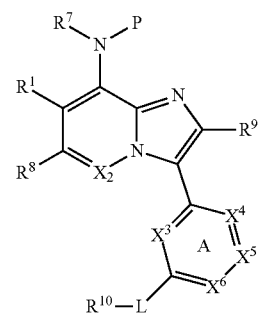

8-8

Scheme I

Scheme I

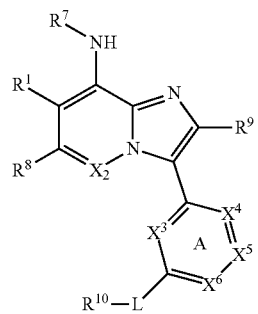

Formula (I)

Compounds of Formula (I) can also be prepared as shown in Scheme IX. Preparation of intermediate 9-7 from imidazole 9-1 can be achieved by methods analogous to those described in International App. No. WO 2014/011974, the disclosure of which is incorporated herein by reference in its entirety. Amination under standard conditions (e.g., in the presence of an $NH_2$-transfer agent such as chloramine, O-(diphenylphosphinyl)hydroxylamine, or O-(4-nitrobenzoyl)hydroxylamine and a base such as sodium hydride, lithium hexamethyldisilazane, or potassium tert-butoxide) and then condensation with an alkyl chloroformate $ClCO_2R^{13}$, where $R^{13}$ is an alkyl group, under standard conditions (e.g. treatment with an appropriate base such as pyridine) can give compound 9-2. Cyclization of 9-2 in the presence of ammonia can provide bicycle 9-3. The bicycle 9-3 can be halogenated with suitable reagents, such as N-chlorosuccinimide, N-bromosuccinimide, or N-iodosuccinimide, to give a halide 9-4 where $Y^1$ is a halo group (e.g., Cl, Br, or I). Dehydrative halogenation (e.g., by treating with a reagent such as $POCl_3$ or $POBr_3$) can afford compound 9-5, where $Y^4$ and $Y^6$ are each halogens (e.g., Cl or Br). Nucleophilic aromatic substitution of the halide of 9-5 with amine 9-6 can provide intermediate 9-7.

Intermediate 9-7 can be selectively coupled with 1-2, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(O) and a base (e.g., a carbonate base)) or standard Stille conditions (e.g., in the presence of a palladium(O) catalyst, such as tetrakis(triphenylphosphine)palladium(O)) or standard Negishi conditions (e.g., in the presence of a palladium catalyst, such as tetrakis(triphenylphosphine)palladium(O) or [1,1'-bis(diphenylphosphino)ferrocene] dichloropalladium (II)), to give compound 9-8. Coupling of compound 9-8 with 9-9, where $M^4$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as bis(diphenylphosphino)ferrocene] dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(O) catalyst, such as tetrakis(triphenylphosphine)palladium(O)) or standard Negishi conditions (e.g., in the presence of a palladium catalyst, such as tetrakis(triphenylphosphine)palladium(O) or [1,1'-bis(diphenylphosphino)ferrocene]dichloropalladium (II)), can afford the resulting compounds of Formula (I).

Scheme IX

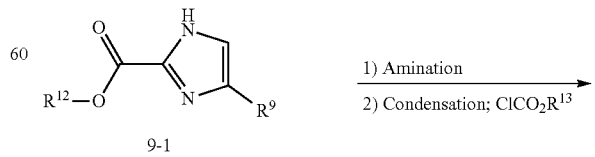

9-1

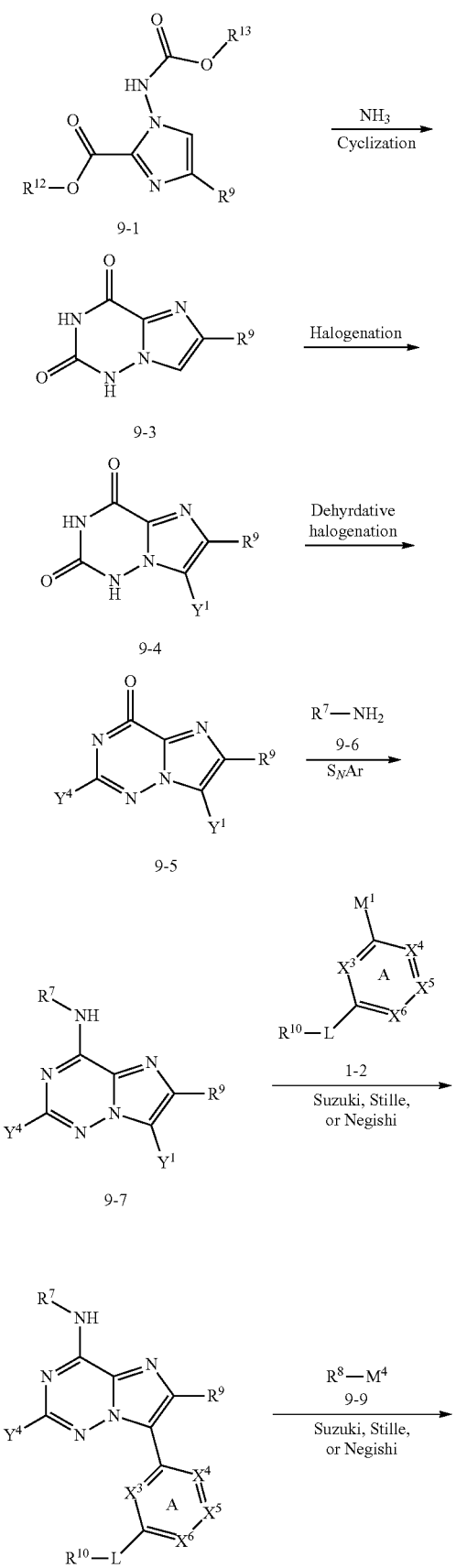

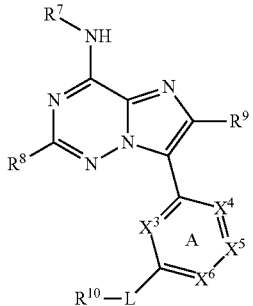

Formula (I)

Intermediates for making compounds of the invention can be prepared as shown in Scheme X. Bis-halogenation of heteroaromatic amine 10-1 with suitable reagents, such as N-chlorosuccinimide, N-bromosuccinimide, $Br_2$, or N-iodosuccinimide can give halide 10-2 where $Y^4$ and $Y^6$ are each halogens (e.g., Cl, Br, or I). Nucleophilic aromatic substitution of halide 10-2 with amine 10-3 can provide compound 10-4. Compounds of the invention can be synthesized from intermediates 10-2 and 10-4 using the methods described in Scheme VI and Scheme V, respectively.

Scheme X

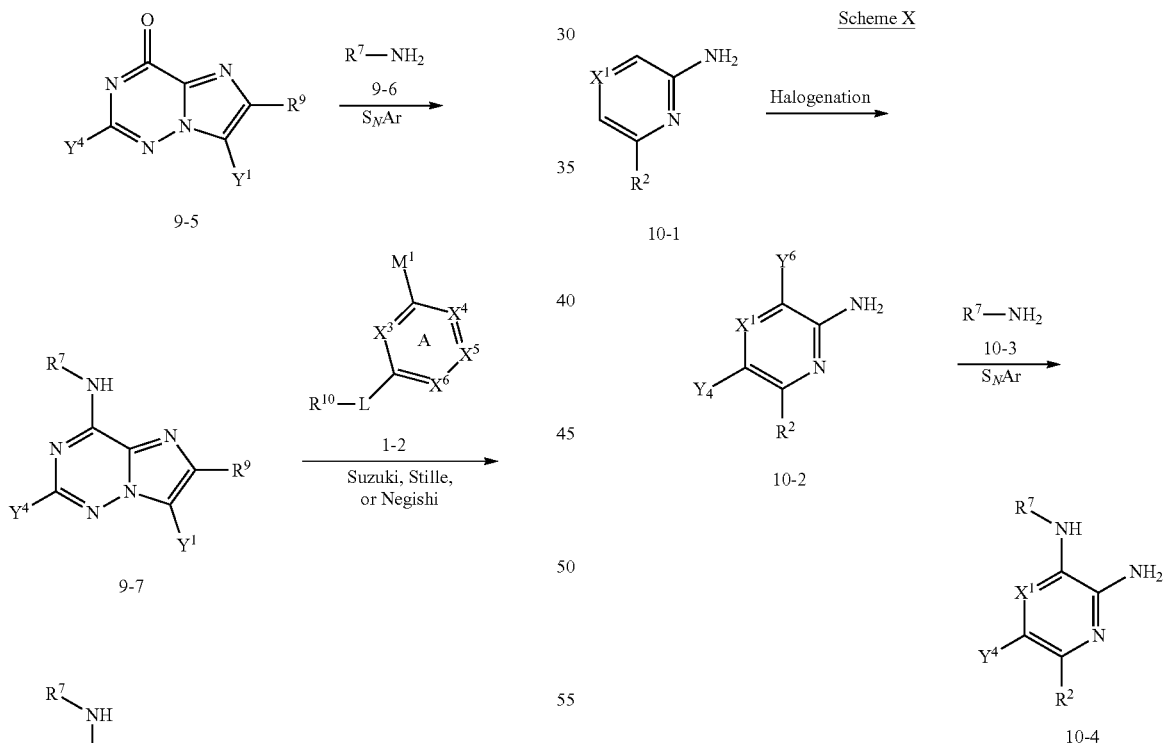

Intermediates for making compounds of the invention can be prepared as shown in Scheme XI. Nucleophilic aromatic substitution of halide 11-1, where $Y^4$ and $Y^8$ are each halogens (e.g., Cl or Br), with ammonia can provide heteroaromatic amine 11-2. Halogenation of heteroaromatic amine 11-2 with suitable reagents, such as N-chlorosuccinimide, N-bromosuccinimide, $Br_2$, or N-iodosuccinimide, optionally in the presence of a base, such sodium bicarbonate or sodium carbonate, can give compound 11-3 where $Y^6$ is a halo group (e.g., Cl, Br, or I). Nucleophilic aromatic substitution of compound 11-3 with amine 11-4 can provide compound 11-5. Compounds of the invention can be synthesized from intermediates 11-3 and 11-5 using the methods described in Scheme VI and Scheme V, respectively.

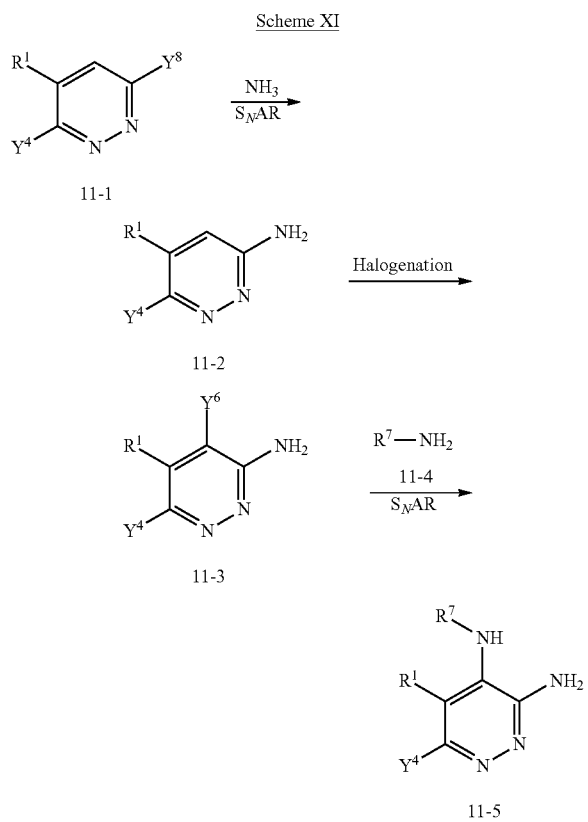

Intermediates for making compounds of the invention can be prepared as shown in Scheme XII. Nucleophilic aromatic substitution of halide 12-1, where $Y^8$ is a halogen (e.g., Cl or Br), with ammonia can provide heteroaromatic amine 12-2. Halogenation of heteroaromatic amine 12-2 with suitable reagents, such as N-chlorosuccinimide, N-bromosuccinimide, $Br_2$, or N-iodosuccinimide, optionally in the presence of a base, such sodium bicarbonate or sodium carbonate, can give compound 12-3, where $Y^6$ is a halo group (e.g., Cl, Br, or I). Nucleophilic aromatic substitution of compound 12-3 with amine 12-4 can provide compound 12-5. Compounds of the invention can be synthesized from intermediates 12-3 and 12-5 using the methods described in Scheme VI and Scheme V, respectively.

Scheme XII

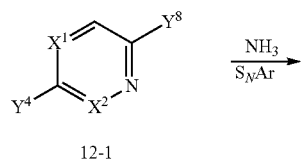

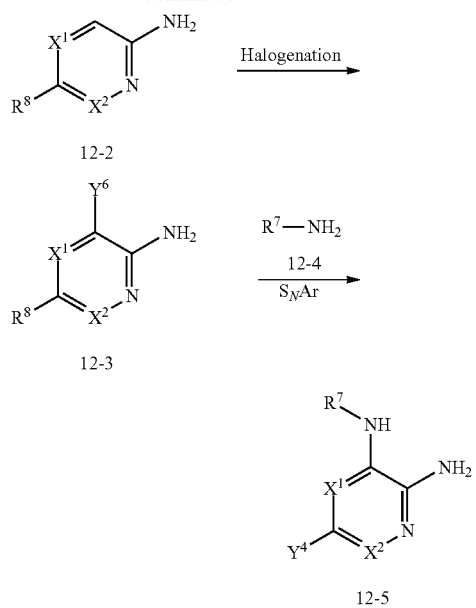

In addition to the synthetic route outlined in Scheme I (hereinafter referred to as Method A), which uses intermediates 2-4 formed as shown in Scheme II, compounds of Formula (I) can also be prepared as shown in Scheme X (Method B). In Method B, halide X-1 where Yi is a halogen (e.g., Cl, Br or I) can be coupled with X-2 where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound X-3. Intermediate X-3 can be treated with chlorosulfonic acid in a suitable solvent at a temperature ranging from 0° C. to 50° C. to afford sulfonyl chloride X-4. Sulfonyl chloride can be reacted with an amine X-5 in the presence of base (such as triethylamine or Hunig's base) to afford compounds of Formula (I).

Scheme X (Method B).

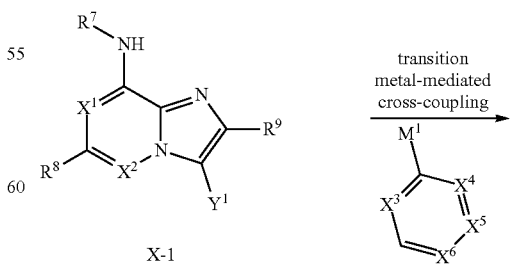

-continued

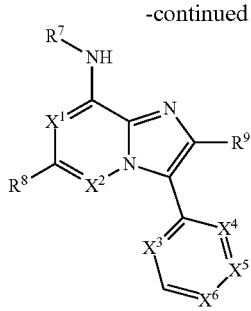

X-3

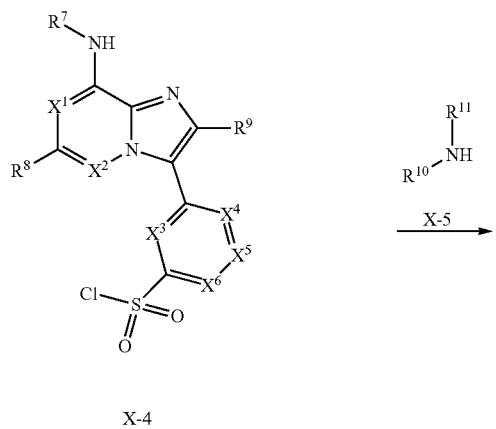

X-4

-continued

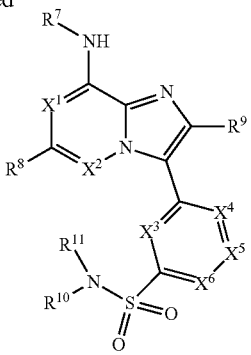

Formula (I)

Intermediates 1-1 (Scheme I) useful for preparing compounds of Formula (I) wherein $X^2$ is N and of varying substitution at $R^b$ can be prepared via the method shown in Scheme Y. Condensation of Y-1 with an amidine at elevated temperature (e.g., 80 to 95° C.) in a suitable solvent (e.g., EtOH) affords bicyclic intermediate Y-2. Alternatively, Y-1 can be treated with a nitrile and acid (e.g., HCl) in a suitable solvent (e.g., dioxane) at elevated temperature (e.g., 100 to 110° C.) to afford Y-2. In some cases of cyclization the use of nitriles requires that the reaction mixture is made basic in the second step to facilitate cyclization. Intermediate Y-2 can be halogenated with suitable reagents, such as N-chlorosuccinimide, N-bromosuccinimide, $Br_2$ or N-iodosuccinimide to afford halide Y-3 where Yi is a halo group (e.g., Cl, Br, or I). Dehydrative halogenation (e.g., by treating with a reagent such as $POCl_3$ or $POBr_3$) can afford compound Y-4 where $Y^6$ is a halogen (e.g., Cl or Br). Nucleophilic aromatic substitution of the halide of Y-4 with ammonia (e.g., using aq. $NH_4OH$ solution) can provide intermediates Y-5, useful for preparing compounds of Formula (I). Alternatively, intermediate Y-3 can be condensed with an amine $R^7NH_2$ (e.g., p-methoxybenzylamine) with a coupling reagent (e.g., BOP) to give intermediate Y-6. Deprotection of Y-6 (e.g., using TFA) can give Y-5.

Scheme Y.

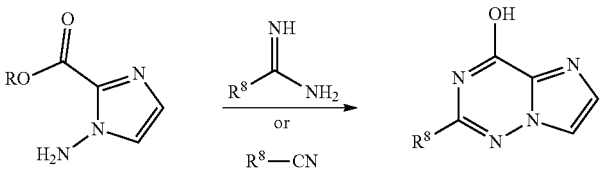

halogenation

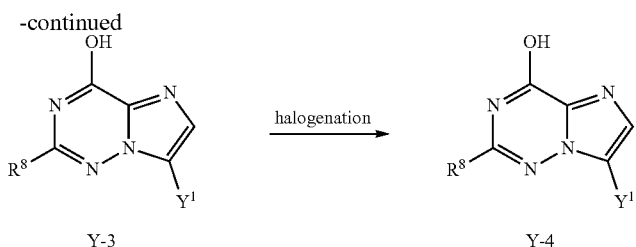

Y-3 → Y-4

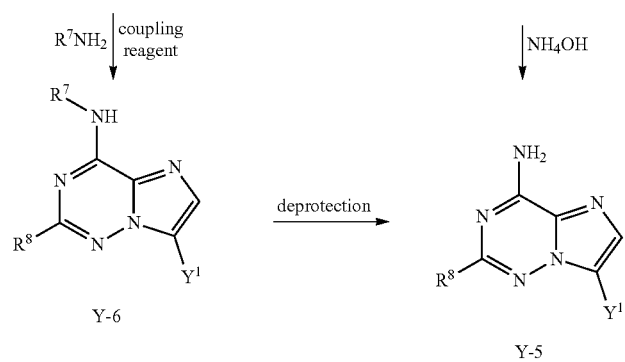

Y-6 → Y-5

Alternatively, intermediates 1-1 (Scheme I) useful for preparing compounds of Formula (I) wherein $X^2$ is N and of varying substitution at $R^b$ can be prepared via the method shown in Scheme Y-B. Condensation of Y-7 with an amidine at elevated temperature (e.g., 80 to 95° C.) in a suitable solvent (e.g., EtOH) affords bicyclic intermediate Y-8. Alternatively, Y-7 can be treated with a nitrile and acid (e.g., HCl) in a suitable solvent (e.g., dioxane) at elevated temperature (e.g., 100 to 110° C.) to afford Y-8. In some cases of cyclization the use of nitriles requires that the reaction mixture is made basic in the second step to facilitate cyclization. Intermediate Y-8 can be halogenated with suitable reagents, such as N-chlorosuccinimide, N-bromosuccinimide, $Br_2$ or N-iodosuccinimide to afford intermediates Y-5, useful for preparing compounds of Formula (I).

Scheme Y-B.

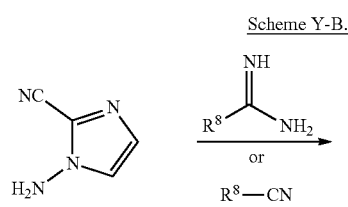

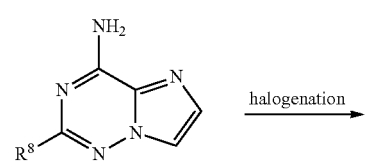

-continued

Y-5

Substituents at $R^g$ may be introduced following the procedure shown in Scheme Z. Intermediate Z-1 can be halogenated with suitable reagents, such as N-chlorosuccinimide, N-bromosuccinimide, $Br_2$ or N-iodosuccinimide to afford halide Z-2 where $Y^9$ is a halo group (e.g., Cl, Br, or I). The $Y^9$ halo group of Z-2 can be coupled to $R^9$-M (Z-3) (e.g., M is $B(OH)_2$, Bpin, $BF_3K$, $Sn(Bu)_3$, Zn or Al) under standard conditions for Suzuki, Stille, Negishi and the like, in the presence of a palladium catalyst, and where appropriate, a base, to afford compounds of Formula (I).

Scheme Z.

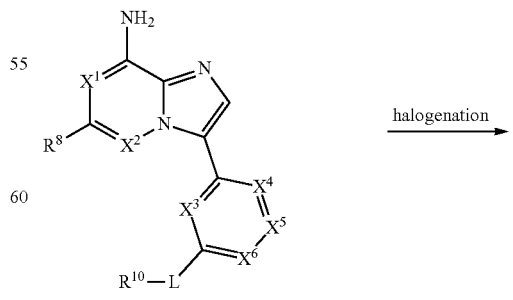

Z-1

-continued

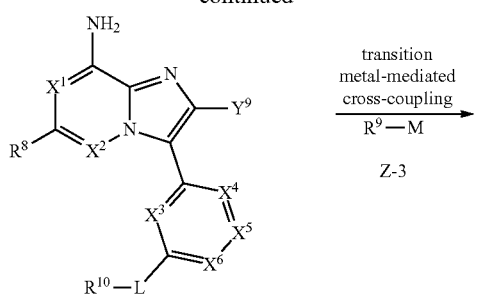

Z-2

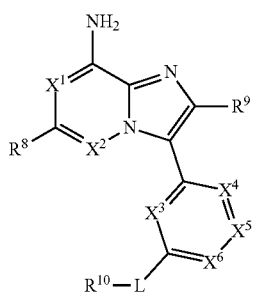

Formula (I)

Substituents at R⁴ may be introduced following the procedure outlined in Scheme Q. Intermediate Q-1 can be selectively coupled with Q-2 bearing a halogen substituent $Y^4$ (e.g., Cl) to afford intermediate Q-3. The $Y^4$ halo group of Q-3 can be coupled to $R^4$-M (Q-4) (e.g., M is B(OH)₂, Bpin, BF₃K, Sn(Bu)₃, Zn or Al) under standard conditions for Suzuki, Stille, Negishi and the like, in the presence of a palladium catalyst and where appropriate, a base, to afford compounds of Formula (I).

Scheme Q.

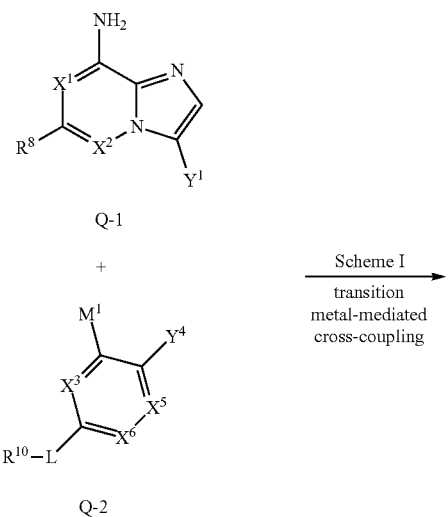

-continued

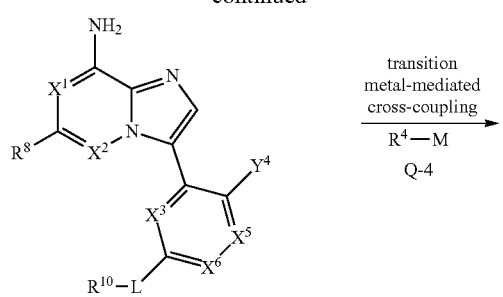

Q-3

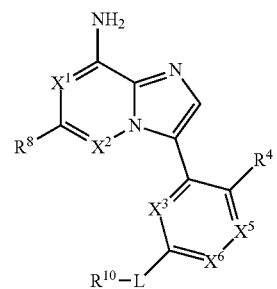

Formula (I)

Where not commercially available, optionally protected ("PHN") amines, such as YY-1 wherein $X^7$ can be N, O, or C and optionally substituted with 0, 1 or 2 $R^b$ groups; and m, n, p can independently be 0, 1, 2, 3 or 4, required to prepare compounds of Formula (I) can be prepared following the steps outlined in Scheme YY. Carboxylic acid YY-1 can be converted to a primary amide YY-2 by activation using an alkyl chloroformate (e.g., ethyl chloroformate) in the presence of a base (e.g., Hunig's base ortriethylamine) followed by reaction with an ammonia source (e.g., aq. NH₄OH solution) to afford primary amide intermediate YY-2. Alternative activating agents can be used in this transformation (e.g., thionyl chloride, oxalyl chloride or peptide coupling reagents such as DCC, or HATU). Primary amide YY-2 can be converted to nitrile YY-3 using reagents for dehydration (e.g., trichloroacetyl chloride, thionyl chloride, trifluoroacetic anhydride) in the presence of base (e.g., Hunig's base or triethylamine).

Scheme YY.

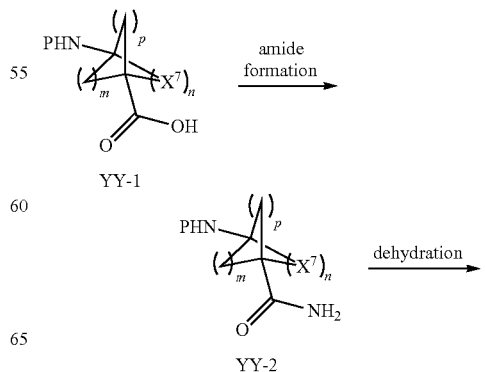

-continued

YY-3

Where not commercially available, optionally protected (P) amines, such as XX-1 wherein $X^7$ can be N, O, or C and optionally substituted with 0, 1 or 2 $R^b$ groups; m, n, p can independently be 0, 1, 2, 3 or 4, and $R^b$ can be alkyl (e.g., methyl, ethyl ester) or a leaving group formed by activation with reagents (e.g., chloroformate), required to prepare compounds of Formula (I) can also be prepared following the steps outlined in Scheme XX. Ester XX-1 can be reacted with a nucleophile (e.g., a Grignard reagent or alkyllithium reagent) to afford alcohol XX-2 or reduced to afford XX-6. The carboxylic acid XX-3 can be converted to heterocycles XX-4 by methods known to one skilled in the art. Alternatively, the carboxylic acid of XX-3 can be converted into carboxylic amides, XX-5, by treatment with an amine in the presence of a coupling reagent and base. The carboxylic acid can also give rise to alcohol XX-6 via reduction. Alcohol XX-6 can be used to afford fluorinated products such as XX-7 by deoxofluorination or oxidation to XX-8, followed by deoxofluorination to afford XX-9. Derivatives such as XX-10 and XX-11 can be prepared by activation of the alcohol to displacement by conversion to a leaving group (e.g., Cl, Br, I, OMs or OTs) and carrying out the displacement with cyanide, amines or heterocycles. Alternatively, optionally protected amines XX-11 can be prepared by reductive amination of aldehyde XX-8. Amines such as XX-12 can be functionalized via reductive amination, acylation and other reactions known to one skilled in the art, to afford intermediates of type XX-13 which are useful for preparing compounds of Formula (I). Depending on which compound of Formula (I) being prepared the $R^b$ groups pending from XX-1 to XX-13 can be any selected from any of the appropriate $R^b$ groups as described in this disclosure.

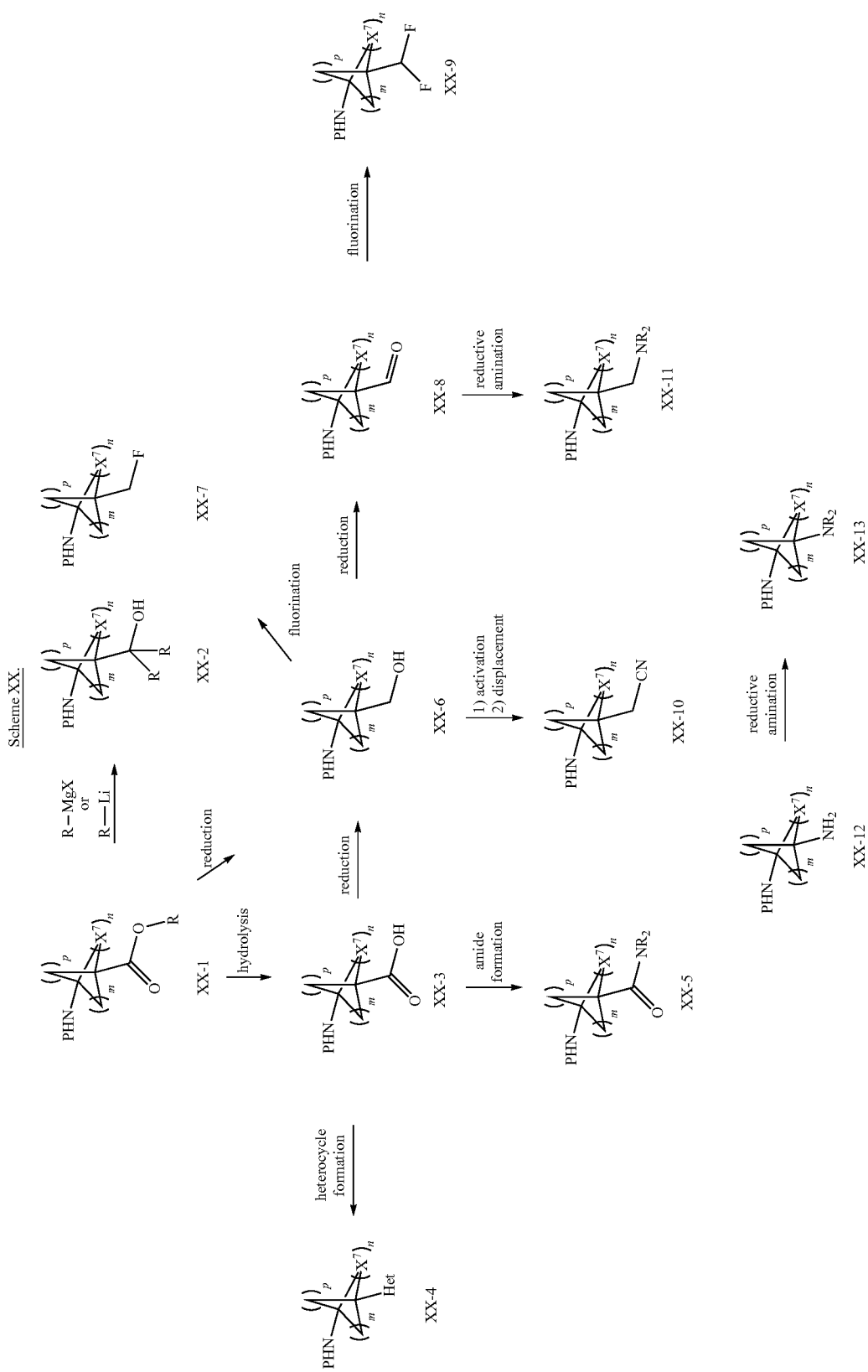

Where desired, any of the amines from Scheme YY or Scheme XX can be used to prepare secondary amines by alkylation before removal of the protecting group as shown in Scheme XX-B. Suitably protected amines XX-B-1 can be treated with base (e.g., NaH, $K_2CO_3$) and an alkylating agent R'-LG wherein LG is a leaving group (e.g., Cl, Br, I, OMs or OTs), to afford intermediate XX-B-2. Deprotection furnishes secondary amines XX-B-3 which are useful for preparing compounds of Formula (I).

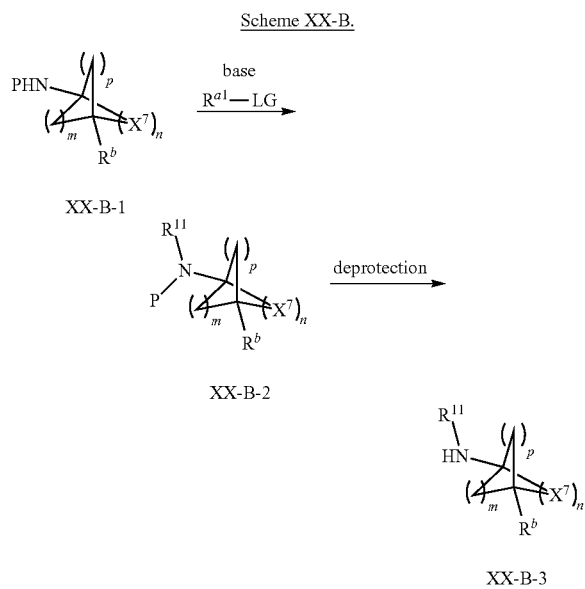

Scheme XX-B.

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual/patient in need of the inhibition by administering an effective amount of a compound or salt of described herein. In some embodiments, modulating is inhibiting. In some embodiments, the contacting is in vivo. In some embodiments, the contacting is ex vivo. Advantageously, the compounds as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the invention are selective inhibitors of PI3Kγ over PI3Kδ, PI3Kα, and PI3Kδ. In some embodiments, the compounds of the invention are selective inhibitors of PI3Kγ over PI3Kα and PI3KO. In some embodiments, selectivity can be at least about 2-fold, 3-fold, 5-fold, 10-fold, at or 20-fold over PI3Kδ as measured by the assays described herein. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase PI3Kγ-associated disease or disorder in an individual (e.g., patient) by administering to the individual in need of such treatment a therapeutically effective amount or dose of one or more compounds of the present invention or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is acute myeloid leukemia (e.g., acute monocytic leukemia), small lymphocytic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the non-Hodgkin's lymphoma (NHL) is relapsed NHL, refractory NHL, recucurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma.

In some embodiments, the Burkitt's lymphoma is endemic Burkitt's lymphoma, sporadic Burkitt's lymphoma, or Burkitt's-like lymphoma In some embodiments, the disease or disorder is rheumatoid arthritis, multiple sclerosis, systemic lupus erythematous, asthma, allergy (e.g, allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertropy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), autoimmune hemolytic anemia, vasculitis, lupus nephritis, pemphigus, or membranous nephropathy.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schonlein purpura (HSP), hypersensitivity vasculitis, microscopic polyangiitis, Wegener's granulomatosis, or anti-neutrophil cytoplasm antibody associated (ANCA) systemic vasculitis (AASV).

The present invention further provides a compound described herein, or a pharmaceutically acceptable salt thereof, for use in any of the methods described herein.

The present invention further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as Bcr-Abl, Flt-3, EGFR, HER2, JAK, c-MET, VEGFR, PDGFR, c-Kit, IGF-1R, RAF and FAK kinase inhibitors such as, for example, those described in WO 2006/056399. Other agents such as therapeutic antibodies can be used in combination with the compounds of the present invention for treatment of PI3K-associated diseases, disorders or conditions. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSF1R, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Ax1, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™ intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™ Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, and may improve the treatment response as compared to the response to the chemotherapeutic agent alone, without exacerbation of its toxic effects. In some embodiments, the compounds of the invention can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present invention with an additional agent.

In some embodiments, PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds of the invention provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the invention can be used in combination with one or more metabolic enzyme inhibitors. In some embodiments, the metabolic enzyme inhibitor is an inhibitor of IDO1, TDO, or arginase. Examples of IDO1 inhibitors include epacadostat and NGL919.

In some embodiments, the compounds of the invention can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the invention where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the invention with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, *Herpes, Giardia, Malaria, Leishmania, Staphylococcus aureus, Pseudomonas Aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (albicans, krusei, glabrata, tropicalis, etc.), *Cryptococcus neoformans, Aspergillus* (fumigatus, niger, etc.), Genus Mucorales (mucor, absidia, rhizophus), *Sporothrix schenkii, Blastomyces dermatitidis, Paracoccidioides brasiliensis, Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). The radionuclide that is incorporated in the instant radio-labeled compounds will depend on the specific application of that radio-labeled compound. For example, for in vitro PI3K labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J Combi. Chem.*, 5, 670 (2003); and "Preparative LC-MS Purification: Improved Compound Specific Method Optimization", K. Blom, B. Glass, R. Sparks, A. Combs, J. Combi. Chem., 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, J Comb. Chem., 6, 874-883 (2004)). Typically, the flow rate used with the 30×100 mm column was 60 mL/minute.

pH=10 purifications: Waters XBridge $C_{18}$ 5 µm, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with 30×100 mm column was 60 mL/minute.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. 3-(8-Aminoimidazo[1,2-a]pyridin-3-yl)-N-(trans-4-hydroxycyclohexyl)-4-methylbenzenesulfonamide Trifluoroacetate

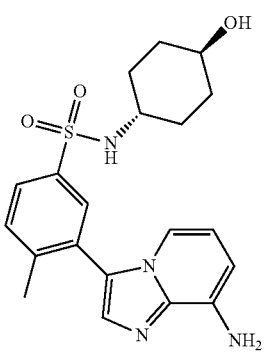

Step 1. 3-Bromo-N-(trans-4-hydroxycyclohexyl)-4-methylbenzenesulfonamide

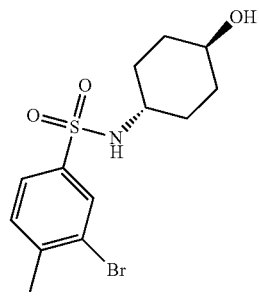

To a mixture of trans-4-aminocyclohexanol (0.47 g, 4.1 mmol), 4-dimethylaminopyridine (9 mg, 0.07 mmol), and triethylamine (1.0 mL, 7.4 mmol) in DCM (20 mL) at 0° C. was added 3-bromo-4-methylbenzenesulfonyl chloride (1.0 g, 3.7 mmol) (Combi-Blocks, WZ-9240) in a single portion. The reaction mixture was stirred overnight while coming to room temperature. The reaction was then quenched with sat. NaHCO$_3$. The organic layer was removed, and the aqueous layer was extracted with DCM (2×). The combined organic layers were dried over Na$_2$SO$_4$, filtered, and concentrated. Purification via silica gel chromatography (20-75% EtOAc in DCM (1% MeOH)) afforded the title compound as a white solid (0.94 g, 73%). LCMS for C$_{13}$H$_{18}$BrNO$_3$SNa (M+Na)$^+$: calculated m/z=370.0, 372.0; found 370.0, 372.0.

Step 2. N-(trans-4-Hydroxycyclohexyl)-4-methyl-3-(4,4,5,5-tetramethyl-1,3,2-dioxaborolan-2-yl)benzenesulfonamide

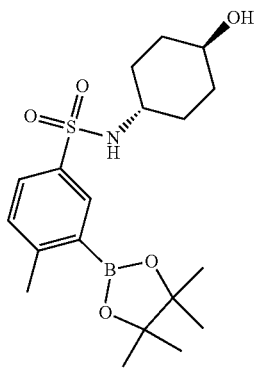

Two microwave vials were each charged with a mixture of 3-bromo-N-(trans-4-hydroxycyclohexyl)-4-methylbenzenesulfonamide (0.47 g, 1.4 mmol), bis(pinacolato)diboron (0.43 g, 1.7 mmol), KOAc (0.43 g, 4.4 mmol), and dichloro[bis(triphenylphosphoranyl)]palladium (38 mg, 0.055 mmol). THF (25 mL) was added to each vial, and the reaction mixtures were degassed with N$_2$ for 5 min. The reaction mixtures were then heated at 140° C. in a microwave for 20 min. The reaction mixtures were diluted with EtOAc, combined, and filtered through Celite. The Celite was then rinsed with EtOAc. The filtrate was washed with water and then brine, dried over Na$_2$SO$_4$, filtered, and concentrated. Purification via silica gel chromatography (1-7% MeOH in DCM) afforded the title compound a white solid (1.3 g, >99%). LCMS for C$_{19}$H$_{31}$BNO$_5$S (M+H)$^+$: calculated m/z=396.2; found 396.2.

Step 3. 3-(8-Aminoimidazo[1,2-a]pyridin-3-yl)-N-(trans-4-hydroxycyclohexyl)-4-methylbenzenesulfonamide Trifluoroacetate A 1-dram vial was charged with 3-bromoimidazo[1,2-a]pyridin-8-amine (2 mg, 0.009 mmol) (Synthonix, B0590), N-(trans-4-hydroxycyclohexyl)-4-methyl-3-(4,4,5,5-tetramethyl-1,3,2-dioxaborolan-2-yl)benzenesulfonamide (3.5 mg, 0.0088 mmol), and [1,1'-bis(diphenylphosphino)ferrocene]dichloropalladium(II), complex with dichloromethane (1 mg, 0.002 mmol). THF (0.12 mL) and then 1.0 M K$_2$CO$_3$ in water (22 µL, 0.022 mmol) were added. The reaction mixture was degassed with N$_2$ briefly and subsequently heated at 80° C. overnight. The reaction mixture was diluted with MeOH and filtered through Celite. Purification via preparative HPLC on a C-18 column (pH 2, 12-32% MeCN/0.1% TFA (aq) over 5 min, 60 mL/min) afforded the title compound as an off-white solid (1.8 mg, 40%). LCMS for C$_{20}$H$_{25}$N$_4$O$_3$S (M+H)$^+$: calculated m/z=401.2; found 401.1.

Example 2. N-[5-(8-Aminoimidazo[1,2-a]pyridin-3-yl)-2-fluoropyridin-3-yl]ethanesulfonamide Bis(Trifluoroacetate)

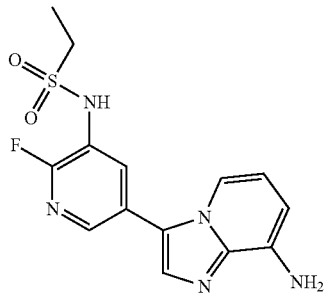 [SMILES: CCS(=O)(=O)Nc1cc(-c2cnc3c(N)cccn23)cnc1F]

Step 1.
N-(5-bromo-2-fluoropyridin-3-yl)ethanesulfonamide

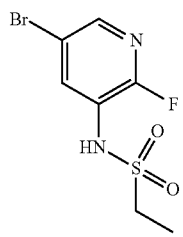

To a solution of 5-bromo-2-fluoropyridin-3-amine (3 g, 20 mmol) in pyridine (10 mL) and DCM (20 mL) at room temperature was added ethanesulfonyl chloride (2.2 mL, 24 mmol). After stirring for 30 min, the solvent was evaporated. The resulting residue was diluted with MeOH (4 mL) and partitioned between EtOAc and brine. The organic layer was separated, and the aq. layer was extracted with EtOAc. The combined organic layers were dried over $Na_2SO_4$, filtered, and concentrated. Purification via silica gel chromatography afforded the title compound (2 g, 40%). LCMS for $C_7H_9BrFN_2O_2S$ (M+H)$^+$: calculated m/z=283.0, 285.0; found 283.0, 284.9.

Step 2. N-[2-fluoro-5-(4,4,5,5-tetramethyl-1,3,2-dioxaborolan-2-yl)pyridin-3-yl]ethanesulfonamide

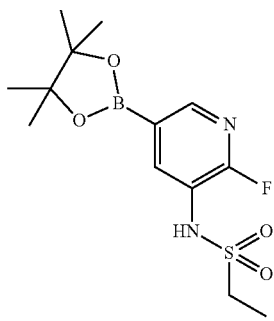 [SMILES: CCS(=O)(=O)Nc1cc(B2OC(C)(C)C(C)(C)O2)cnc1F]

A mixture of bis(pinacolato)diboron (0.77 g, 3.0 mmol), N-(5-bromo-2-fluoropyridin-3-yl)ethanesulfonamide (1.0 g, 0.32 mmol), and KOAc (1.3 g, 13 mmol) in 1,4-dioxane (50 mL,) was degassed by $N_2$ for 5 min. Then [1,1'-bis(diphenylphosphino)ferrocene]dichloropalladium(II), complex with dichloromethane (260 mg, 0.32 mmol) was added, and the resultant mixture was heated for 1 h at 120° C. The crude mixture was filtered through Celite to afford the title compound as a solution in 1,4-dioxane. LCMS for $C_{13}H_{21}BFN_2O_4S$ (M+H)$^+$: calculated m/z=331.1; found 331.0.

Step 3. N-[5-(8-Aminoimidazo[1,2-a]pyridin-3-yl)-2-fluoropyridin-3-yl]ethanesulfonamide Bis(Trifluoroacetate)

The title compound was synthesized according to an experimental procedure analogous to the synthesis of Example 1, Step 3 substituting a solution of N-[2-fluoro-5-(4,4,5,5-tetramethyl-1,3,2-dioxaborolan-2-yl)pyridin-3-yl]ethanesulfonamide in 1,4-dioxane for N-(trans-4-hydroxycyclohexyl)-4-methyl-3-(4,4,5,5-tetramethyl-1,3,2-dioxaborolan-2-yl)benzenesulfonamide. LCMS for $C_{14}H_{15}FN_5O_2S$ (M+H)$^+$: calculated m/z=336.1; found 336.1.

Example 3. 3-(8-Aminoimidazo[1,2-a]pyridin-3-yl)-4-methyl-N-[(3-methyloxetan-3-yl)methyl]benzenesulfonamide Trifluoroacetate

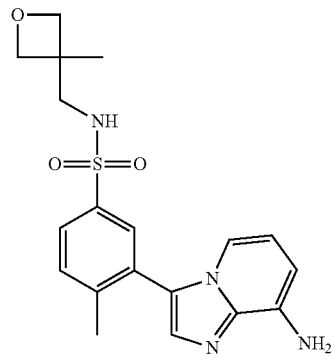 [SMILES: Cc1ccc(S(=O)(=O)NCC2(C)COC2)cc1-c1cnc2c(N)cccn12]

Step 1. 3-Bromo-4-methyl-N-[(3-methyloxetan-3-yl)methyl]benzenesulfonamide

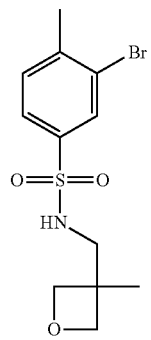

To a solution of 3-bromo-4-methylbenzenesulfonyl chloride (500.0 mg, 1.855 mmol) (Combi-Blocks, WZ-9240) in THF (10.0 mL) and pyridine (0.300 mL, 3.71 mmol) was added 1-(3-methyloxetan-3-yl)methanamine (225 mg, 2.22 mmol) (Combi-Blocks, SS-0093). The resulting mixture was stirred at room temperature overnight. The reaction mixture was then concentrated in vacuo. The resulting residue was added to 1.0 N HCl (100 mL) and extracted with EtOAc (2×100 mL). The combined organic layers were washed with sat. Na$_2$CO$_3$ solution (100 mL) and brine, dried over MgSO$_4$, filtered, and concentrated. Purification via on silica gel chromatography (10-80% EtOAc/hexanes) afforded the title compound (296.0 mg, 48%). LCMS for C$_{12}$H$_{17}$BrNO$_3$S (M+H)$^+$: calculated m/z=334.0, 336.0; found 333.9, 335.9.

Step 2. 4-Methyl-N-[(3-methyloxetan-3-yl)methyl]-3-(4,4,5,5-tetramethyl-1,3,2-dioxaborolan-2-yl)benzenesulfonamide

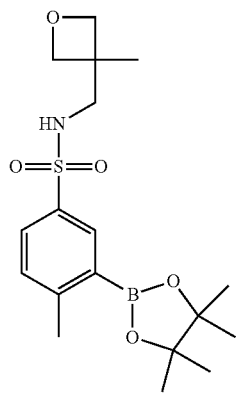 [SMILES: Cc1ccc(S(=O)(=O)NCC2(C)COC2)cc1B1OC(C)(C)C(C)(C)O1]

To a vial was added 3-bromo-4-methyl-N-[(3-methyloxetan-3-yl)methyl]benzenesulfonamide (296 mg, 0.886 mmol), KOAc (156 mg, 1.59 mmol), [1,1'-bis(diphenylphosphino)ferrocene]dichloropalladium(II), complex with dichloromethane (36.2 mg, 0.0443 mmol), bis(pinicolato)diboron (337 mg, 1.33 mmol), and 1,2-dimethoxyethane (4.43 mL, 42.6 mmol). The mixture was degassed by bubbling N$_2$ for 10 minutes. The vial was then sealed, and the reaction mixture was heated at 90° C. for 2 h. The reaction mixture was then poured into water and extracted with EtOAc. The organic layer was washed with brine, dried over MgSO$_4$, filtered, and concentrated. Purification via silica gel chromatography (10-40% EtOAc [5% MeOH]/hexanes) afforded the title compound (96.0 mg, 31%). LCMS for C$_{18}$H$_{29}$BNO$_5$S (M+H)$^+$: calculated m/z=382.2; found 382.2.

Step 3. 3-(8-Aminoimidazo[1,2-a]pyridin-3-yl)-4-methyl-N-[(3-methyloxetan-3-yl)methyl]benzenesulfonamide Trifluoroacetate The title compound was synthesized according to an experimental procedure analogous to the synthesis of Example 1, Step 3 substituting 4-methyl-N-[(3-methyloxetan-3-yl)methyl]-3-(4,4,5,5-tetramethyl-1,3,2-dioxaborolan-2-yl)benzenesulfonamide for N-(trans-4-hydroxycyclohexyl)-4-methyl-3-(4,4,5,5-tetramethyl-1,3,2-dioxaborolan-2-yl)benzenesulfonamide. $^1$H NMR (400 MHz, d$_6$-DMSO) δ 8.22 (s, 1H), 8.06-7.80 (m, 3H), 7.73 (dd, J=8.3, 4.7 Hz, 1H), 7.47 (d, J=6.7 Hz, 1H), 7.12 (t, J=7.0 Hz, 1H), 6.89 (d, J=7.4 Hz, 1H), 6.26 (s, 2H), 4.30 (d, J=5.9 Hz, 2H), 4.17 (d, J=5.9 Hz, 2H), 2.97 (d, J=6.5 Hz, 2H), 2.25 (s, 3H), 1.19 (s, 3H). LCMS for C$_{19}$H$_{23}$N$_4$O$_3$S (M+H)$^+$: calculated m/z=387.1; found 387.1.

Example 4. 3-(8-Amino-6-chloroimidazo[1,2-a]pyridin-3-yl)-N-(trans-4-hydroxycyclohexyl)-4-methylbenzenesulfonamide Trifluoroacetate

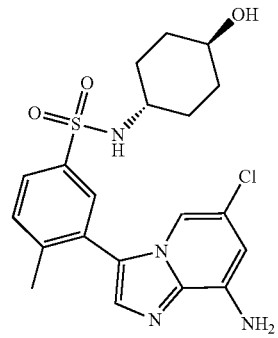

Step 1. 6-Chloroimidazo[1,2-a]pyridin-8-amine

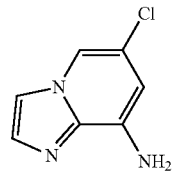

To a solution of 5-chloro-2,3-diaminopyridine (1 g, 7 mmol) in ethanol (50 mL) was slowly added chloroacetaldehyde (3.5 mL, 27 mmol, 50% in H$_2$O). The reaction mixture was refluxed for 6 h. Heating was discontinued, and the reaction mixture was stirred overnight. The reaction mixture was concentrated. Et$_2$O was added to the resulting residue, and the solvent was removed in vacuo. The resulting oil was dissolved in water, and the aqueous layer was basified by addition of 1 M NaOH (aq). The aqueous layer was then extracted with DCM (3×). The combined organic layers were dried over MgSO$_4$, filtered, and concentrated. Purification via silica gel chromatography (1-10% MeOH in DCM) afforded the title compound as a light brown solid (0.9 g, 80%). $^1$H NMR (600 MHz, d$_6$-DMSO) δ 7.99 (d, J=1.9 Hz, 1H), 7.79 (d, J=1.1 Hz, 1H), 7.45 (d, J=1.1 Hz, 1H), 6.21 (d, J=1.9 Hz, 1H), 6.01 (s, 2H). LCMS for C$_7$H$_7$ClN$_3$ (M+H)$^+$: calculated m/z=168.0; found 168.1.

Step 2. N-(6-Chloroimidazo[1,2-a]pyridin-8-yl)acetamide

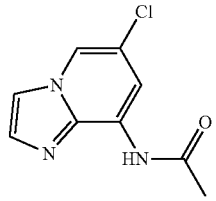

To a solution of 6-chloroimidazo[1,2-a]pyridin-8-amine (0.25 g, 1.5 mmol) and 4-dimethylaminopyridine (5 mg, 0.04 mmol) in DCM (10 mL) at 0° C. was added triethylamine (0.63 mL, 4.5 mmol) and then acetic anhydride (0.21 mL, 2.2 mmol). After coming to room temperature, the reaction mixture was stirred overnight. The reaction mixture was again cooled to 0° C. Additional portions of 4-dimethylaminopyridine (7 mg, 0.06 mmol), triethylamine (0.63 mL, 4.5 mmol), and acetic anhydride (0.21 mL, 2.2 mmol) were added. After coming to room temperature, the reaction mixture was stirred overnight. The reaction mixture was diluted with DCM and washed with sat. NaHCO₃ (aq), water, and then brine. The organic layer was dried over Na₂SO₄, filtered, and concentrated. Purification via silica gel chromatography (17-100% EtOAc in hexanes, then 1-10% MeOH in EtOAc) afforded the title compound as a brown solid (0.12 g, 38%). LCMS for C₉H₉ClN₃O (M+H)⁺: calculated m/z=210.0; found 210.0.

Step 3. N-(3-Bromo-6-chloroimidazo[1,2-a]pyridin-8-yl)acetamide

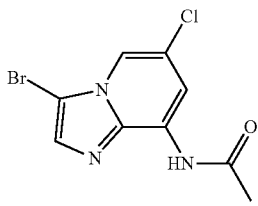

To a solution of N-(6-chloroimidazo[1,2-a]pyridin-8-yl acetamide (50. mg, 0.24 mmol) in DCM (6 mL) was added N-bromosuccinimide (43 mg, 0.24 mmol). The reaction mixture was stirred at room temperature for 30 min. The mixture was then washed with Na₂CO₃ (10% aq), dried over Na₂SO₄, filtered, and concentrated. Purification via silica gel chromatography (1-10% MeOH in DCM) afforded the title compound as a tan solid (56 mg, 81%). ¹H NMR (600 MHz, CDCl₃) δ 8.49 (s, 1H), 8.27 (d, J=1.6 Hz, 1H), 7.89 (d, J=1.7 Hz, 1H), 7.51 (s, 1H), 2.30 (s, 3H). LCMS for C₉H₈BrClN₃O (M+H)⁺: calculated m/z=288.0, 289.9; found 288.0, 290.0.

Step 4. 3-(8-Amino-6-chloroimidazo[1,2-a]pyridin-3-yl)-N-(trans-4-hydroxycyclohexyl)-4-methylbenzenesulfonamide Trifluoroacetate A 1-dram vial was charged with N-(3-bromo-6-chloroimidazo[1,2-a]pyridin-8-yl)acetamide (10. mg, 0.035 mmol), N-(trans-4-hydroxycyclohexyl)-4-methyl-3-(4,4,5,5-tetramethyl-1,3,2-dioxaborolan-2-yl)benzenesulfonamide (Example 1, Step 2, 17 mg, 0.043 mmol), and [1,1'-bis(diphenylphosphino)ferrocene]dichloropalladium(II), complex with dichloromethane (6 mg, 0.007 mmol). THF (0.50 mL) and then 1.0 M K₂CO₃ in water (87 μL, 0.087 mmol) were added. The reaction mixture was degassed with N₂ for 5 min and subsequently heated at 80° C. overnight. The reaction mixture was then diluted with MeOH and filtered through a plug of Na₂SO₄ and Celite, rinsing with MeOH. The filtrate was concentrated.

The resulting residue was dissolved in 10:1 EtOH/conc. HCl (1.0 mL), and the reaction mixture was heated at 80° C. for 2 h. The reaction mixture was diluted with MeOH and filtered via syringe filter. Purification via preparative HPLC on a C-18 column (pH 2, 15-35% MeCN/0.1% TFA (aq) over 5 min, 60 mL/min) afforded the title compound as a white solid (9.5 mg, 50%). LCMS for C₂₀H₂₄ClN₄O₃S (M+H)⁺: calculated m/z=435.1; found 435.2.

Example 5. N-[6-chloro-3-(5-{[(trans-4-hydroxycyclohexyl)amino]sulfonyl}-2-methylphenyl)imidazo[12-a]pyridin-8-yl]acetamide

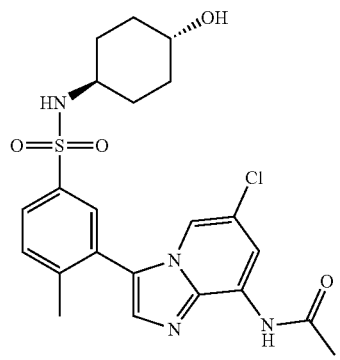

The title compound was synthesized according to experimental procedures analogous to the synthesis of Example 1, Step 3 substituting N-(3-bromo-6-chloroimidazo[1,2-a]pyridin-8-yl)acetamide for 3-bromoimidazo[1,2-a]pyridin-8-amine. Purification via preparative HPLC on a C-18 column (pH 10, 26-46% MeCN/0.1% NH₄OH (aq) over 5 min, 60 mL/min) afforded the title compound as a white residue (3.4 mg). LCMS for C₂₂H₂₆ClN₄O₄S (M+H)⁺: calculated m/z=477.1; found 477.1.

Example 6. N-[5-(8-Amino-6-chloroimidazo[1,2-a]pyridin-3-yl)-2-oxo-1,2-dihydropyridin-3-yl]ethanesulfonamide Trifluoroacetate; and Example 7. N-[5-(8-Amino-6-chloroimidazo[1,2-a]pyridin-3-yl)-2-ethoxypyridin-3-yl]ethanesulfonamide Bis(Trifluoroacetate)

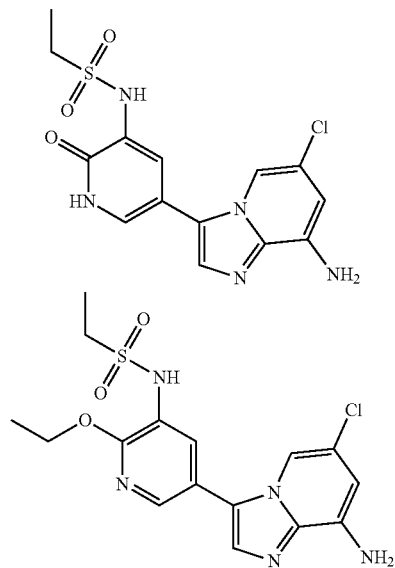

The title compound was synthesized according to experimental procedures analogous to the synthesis of Example 4, Step 4 substituting a solution of N-[2-fluoro-5-(4,4,5,5-tetramethyl-1,3,2-dioxaborolan-2-yl)pyridin-3-yl]ethanesulfonamide in 1,4-dioxane (Example 2, Step 2) for N-(trans-4-hydroxycyclohexyl)-4-methyl-3-(4,4,5,5-tetramethyl-1,3,2-dioxaborolan-2-yl)benzenesulfonamide. Purification via preparative HPLC on a C-18 column (pH 2, 15-41% MeCN/0.1% TFA (aq) over 5 min, 60 mL/min) afforded Example 6 as a white solid (4.7 mg, first to elute, $t_R$=3.2 min) and Example 7 as an off-white solid (2.8 mg, second to elute, $t_R$=5.1 min). Example 6: LCMS for $C_{14}H_{15}ClN_5O_3S$ (M+H)$^+$: calculated m/z=368.1; found 368.1. Example 7: LCMS for $C_{16}H_{19}ClN_5O_3S$ (M+H)$^+$: calculated m/z=396.1; found 396.1.

Example 8. 3-[8-Amino-6-(1-methyl-1H-pyrazol-4-yl)imidazo[1,2-a]pyridin-3-yl]-N-(trans-4-hydroxycyclohexyl)-4-methylbenzenesulfonamide Bis(Trifluoroacetate)

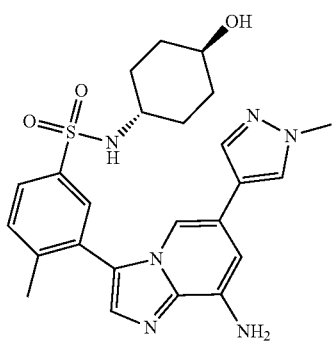

A 1-dram vial was charged with N-(3-bromo-6-chloroimidazo[1,2-a]pyridin-8-yl)acetamide (Example 4, Step 3, 30.7 mg, 0.106 mmol), N-(trans-4-hydroxycyclohexyl)-4-methyl-3-(4,4,5,5-tetramethyl-1,3,2-dioxaborolan-2-yl)benzenesulfonamide (Example 1, Step 2, 52 mg, 0.13 mmol), and [1,1'-bis(diphenylphosphino)ferrocene]dichloropalladium(II), complex with dichloromethane (18 mg, 0.022 mmol). THF (1.6 mL) and then 1.0 M $K_2CO_3$ in water (0.27 mL, 0.27 mmol) were added. The reaction mixture was degassed with $N_2$ for 5 min and subsequently heated at 80° C. for 4 h. An additional portion of N-(trans-4-hydroxycyclohexyl)-4-methyl-3-(4,4,5,5-tetramethyl-1,3,2-dioxaborolan-2-yl)benzenesulfonamide (15 mg, 0.038 mmol) was added, and the reaction mixture was subsequently heated at 80° C. for 3 h. The reaction mixture was diluted with MeOH and filtered through a plug of $Na_2SO_4$ and Celite, rinsing with MeOH. The filtrate was concentrated to afford the crude intermediate.

To 1-dram vial was added a portion of the crude intermediate (10 mg), 1-methyl-4-(4,4,5,5-tetramethyl-1,3,2-dioxaborolan-2-yl)-1H-pyrazole (9.3 mg, 0.045 mmol), bis(di-tert-butyl(4-dimethylaminophenyl)phosphine) dichloropalladium(II) (1 mg, 0.001 mmol), 1-butanol (0.2 mL), CsF (11 mg, 0.072 mmol), and water (42 µL). The mixture degassed with $N_2$ for 5 min. The vial was capped, and the reaction mixture was heated at 100° C. for 1.5 h. Heating was discontinued, and the reaction mixture was stirred overnight. The reaction mixture was diluted with MeOH and filtered through a plug of $Na_2SO_4$ and Celite, rinsing with MeOH.

The resulting residue was dissolved in 10:1 EtOH/conc. HCl (0.61 mL), and the reaction mixture was heated at 80° C. for 1 h. The reaction mixture was diluted with MeOH and filtered via syringe filter. Purification via preparative HPLC on a C-18 column (pH 2, 14-34% MeCN/0.1% TFA (aq) over 5 min, 60 mL/min) afforded the title compound as a white solid (3.6 mg). LCMS for $C_{24}H_{29}N_6O_3S$ (M+H)$^+$: calculated m/z=481.2; found 481.2.

Example 9 and Example 10

Examples 9 and 10 were synthesized according to procedures analogous to the synthesis of Example 8, and the data are listed in Table 1.

TABLE 1

![structure]

| Ex. No. | Name | R$^8$ | LCMS [M + H]$^+$ |
|---|---|---|---|
| 9 | 3-(8-Amino-6-pyrimidin-5-ylimidazo[1,2-a]pyridin-3-yl)-N-(trans-4-hydroxycyclohexyl)-4-methylbenzenesulfonamide | pyrimidin-5-yl | 479.1 |
| 10 | 3-[8-Amino-6-(1-methyl-1H-pyrazol-5-yl)imidazo[1,2-a]pyridin-3-yl]-N-(trans-4-hydroxycyclohexyl)-4-methylbenzenesulfonamide bis(trifluoroacetate) | 1-methyl-1H-pyrazol-5-yl | 481.2 |

Example 11. 3-(8-Amino-7-chloroimidazo[1,2-a]pyridin-3-yl)-N-(trans-4-hydroxycyclohexyl)-4-methylbenzenesulfonamide Trifluoroacetate

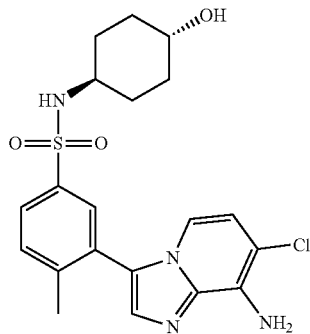 [SMILES: Cc1ccc(S(=O)(=O)N[C@H]2CC[C@H](O)CC2)cc1-c1cnc2c(N)c(Cl)ccn12]

Step 1. 7-Chloroimidazo[1,2-a]pyridin-8-amine

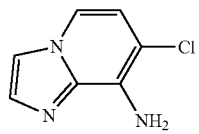

The title compound was synthesized according to an experimental procedure analogous to the synthesis of Example 4, Step 1, substituting 4-chloro-2,3-diaminopyridine (Synthonix, D0349) for 5-chloro-2,3-diaminopyridine. LCMS for $C_7H_7ClN_3$ (M+H)$^+$: calculated m/z=168.0; found 168.0.

Step 2. N-Acetyl-N-(7-chloroimidazo[1,2-a]pyridin-8-yl)acetamide

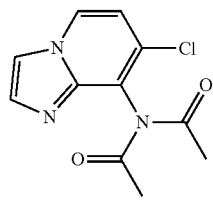 [SMILES: CC(=O)N(C(C)=O)c1c(Cl)ccn2ccnc12]

To a solution of 7-chloroimidazo[1,2-a]pyridin-8-amine (0.50 g, 3.0 mmol) and 4-dimethylaminopyridine (37 mg, 0.30 mmol) in DCM (20 mL) at 0° C. was added triethylamine (2.5 mL, 18 mmol) and then acetic anhydride (0.84 mL, 9.0 mmol). After coming to room temperature, the reaction mixture was stirred overnight at room temperature. The reaction mixture was then cooled to 0° C., and acetyl chloride (0.42 mL, 6.0 mmol) was added dropwise. The reaction mixture was warmed to room temperature, stirred for 3 h, and then heated at reflux for 4 h. The reaction mixture was diluted with DCM and washed successively with sat. NaHCO$_3$, water, and brine. The organic layer was dried over Na$_2$SO$_4$, filtered, and concentrated. Purification via silica gel chromatography (1-10% MeOH in DCM) afforded the title compound as a brown solid (0.68 g, 90%). LCMS for $C_{11}H_{11}ClN_3O_2$ (M+H)$^+$: calculated m/z=252.1; found 252.0.

Step 3. N-Acetyl-N-(3-bromo-7-chloroimidazo[1,2-a]pyridin-8-yl)acetamide

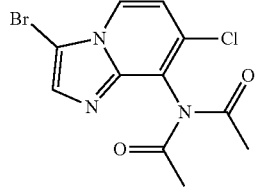 [SMILES: CC(=O)N(C(C)=O)c1c(Cl)ccn2c(Br)cnc12]

The title compound was synthesized according to an experimental procedure analogous to the synthesis of Example 4, Step 3, substituting N-acetyl-N-(7-chloroimidazo[1,2-a]pyridin-8-yl)acetamide for N-(6-chloroimidazo[1,2-a]pyridin-8-yl)acetamide. LCMS for $C_{11}H_9BrClN_3NaO_2$ (M+Na)$^+$: calculated m/z=352.0, 353.9; found 351.8, 353.8.

Step 4. 3-(8-Amino-7-chloroimidazo[1,2-a]pyridin-3-yl)-N-(trans-4-hydroxycyclohexyl)-4-methylbenzenesulfonamide Trifluoroacetate The title compound was synthesized according to an experimental procedure analogous to the synthesis of Example 4, Step 4, substituting N-acetyl-N-(3-bromo-7-chloroimidazo[1,2-a]pyridin-8-yl)acetamide for N-(3-bromo-6-chloroimidazo[1,2-a]pyridin-8-yl)acetamide. $^1$H NMR (600 MHz, CD$_3$OD) δ 8.13 (s, 1H), 8.01 (dd, J=8.2, 2.0 Hz, 1H), 7.96 (d, J=2.0 Hz, 1H), 7.70 (d, J=8.2 Hz, 1H), 7.49 (d, J=7.1 Hz, 1H), 7.35 (d, J=7.1 Hz, 1H), 3.52-3.39 (m, 1H), 3.10-3.01 (m, 1H), 2.29 (s, 3H), 1.86 (apparent d, J=12.0 Hz 2H), 1.77 (apparent d, J=11.9 Hz, 2H), 1.33-1.17 (m, 4H). LCMS for $C_{20}H_{24}ClN_4O_3S$ (M+H)$^+$: calculated m/z=435.1; found 435.1.

Example 12. 3-[8-Amino-7-(1-methyl-1H-pyrazol-4-yl)imidazo[1,2-a]pyridin-3-yl]-N-(trans-4-hydroxycyclohexyl)-4-methylbenzenesulfonamide

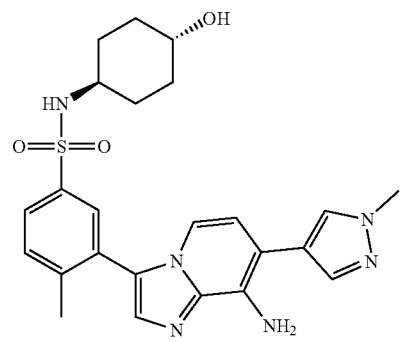 [SMILES: Cc1ccc(S(=O)(=O)N[C@H]2CC[C@H](O)CC2)cc1-c1cnc2c(N)c(-c3cnn(C)c3)ccn12]

Step 1. N-[7-Chloro-3-(5-{[(trans-4-hydroxycyclohexyl)amino]sulfonyl}-2-methylphenyl)imidazo[1,2-a]pyridin-8-yl]acetamide

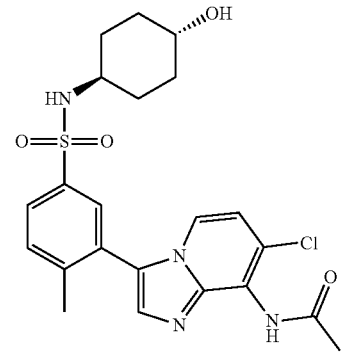

A 1-dram vial was charged with N-acetyl-N-(3-bromo-7-chloroimidazo[1,2-a]pyridin-8-yl)acetamide (Example 11, Step 3, 18 mg, 0.054 mmol), N-(trans-4-hydroxycyclohexyl)-4-methyl-3-(4,4,5,5-tetramethyl-1,3,2-dioxaborolan- 2-yl)benzenesulfonamide (Example 1, Step 2, 27 mg, 0.068 mmol), and [1,1'-bis(diphenylphosphino)ferrocene]dichloropalladium(II), complex with dichloromethane (9 mg, 0.01 mmol). THF (0.81 mL) and then 1.0 M $K_2CO_3$ in water (0.14 mL, 0.14 mmol) were added. The reaction mixture was degassed with $N_2$ for 5 min and subsequently heated at 80° C. overnight. Additional portions of N-(trans-4-hydroxycyclohexyl)-4-methyl-3-(4,4,5,5-tetramethyl-1,3,2-dioxaborolan-2-yl)benzenesulfonamide (28 mg, 0.071 mmol) and [1,1'-bis(diphenylphosphino)ferrocene]dichloropalladium (II), complex with dichloromethane (9 mg, 0.01 mmol) were added. The reaction mixture was degassed briefly and subsequently heated at 80° C. for 5 h. The reaction mixture was diluted with DCM and washed successively with water and brine. The organic layer was filtered through a plug of $Na_2SO_4$ and concentrated. Purification via silica gel chromatography (5-20% MeOH in DCM) afforded the title compound as a brown solid (27 mg). LCMS for $C_{22}H_{26}ClN_4O_4S$ $(M+H)^+$: calculated m/z=477.1; found 477.1.

Step 2. 3-[8-Amino-7-(1-methyl-1H-pyrazol-4-yl) imidazo[1,2-a]pyridin-3-yl]-N-(trans-4-hydroxycyclohexyl)-4-methylbenzenesulfonamide To 1-dram vial was added N-[7-chloro-3-(5-{[(trans-4-hydroxycyclohexyl)amino]sulfonyl}-2-methylphenyl)imidazo[1,2-a]pyridin-8-yl]acetamide (8.7 mg, 0.018 mmol), 1-methyl-4-(4,4,5,5-tetramethyl-1,3,2-dioxaborolan-2-yl)-1H-pyrazole (9 mg, 0.04 mmol), bis(di-tert-butyl(4-dimethylaminophenyl)phosphine)dichloropalladium(II) (1 mg, 0.001 mmol), 1-butanol (0.2 mL), CsF (11 mg, 0.072 mmol), and water (36 μL, 2.0 mmol). The solvent degassed with $N_2$ for 5 min. The vial was capped, and the mixture was heated at 100° C. for 1.5 h. The reaction mixture was diluted with MeOH and filtered through a plug of $Na_2SO_4$ and Celite. The filtrate was concentrated.

The resulting residue was dissolved in 10:1 EtOH/conc. HCl (0.53 mL), and the reaction mixture was heated at 80° C. for 8 h. The reaction mixture was diluted with MeCN and filtered via syringe filter. Purification via preparative HPLC on a C-18 column (pH 2, 15-35% MeCN/0.1% TFA (aq) over 5 min, 60 mL/min) afforded a yellow residue (3.3 mg). This residue was partitioned between DCM and 1 M NaOH (aq). The organic layer was removed, and the aqueous layer extracted with DCM (2×). The organic layers were filtered through a plug of $Na_2SO_4$ and concentrated to afford the title compound as a white residue (0.9 mg). LCMS for $C_{24}H_{29}N_6O_3S$ $(M+H)^+$: calculated m/z=481.2; found 481.1.

Example 13. 3-(8-Aminoimidazo[1,2-a]pyrazin-3-yl)-N-(trans-4-hydroxycyclohexyl)-4-methylbenzenesulfonamide

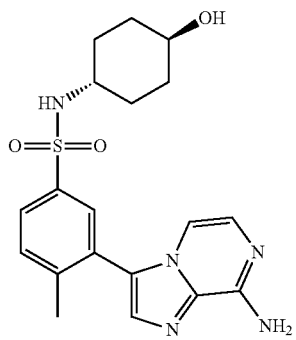

A microwave vial was charged with 3-bromoimidazo[1,2-a]pyrazin-8-amine (50. mg, 0.23 mmol), N-(trans-4-hydroxycyclohexyl)-4-methyl-3-(4,4,5,5-tetramethyl-1,3,2-dioxaborolan-2-yl)benzenesulfonamide (Example 1, Step 2, 110 mg, 0.28 mmol), and [1,1'-bis(diphenylphosphino)ferrocene]dichloropalladium(II), complex with dichloromethane (38 mg, 0.047 mmol). THF (3.5 mL) and then 1.0 M $K_2CO_3$ in water (0.58 mL, 0.58 mmol) were added. The reaction mixture was degassed with $N_2$ for 5 min and subsequently heated at 80° C. overnight. The reaction mixture was poured into 50% sat. NaCl (10 mL) and extracted with DCM (3×10 mL). The combined organic layers were dried over $Na_2SO_4$, filtered, and concentrated. Purification via preparative HPLC on a C-18 column (pH 10, 20-33% MeCN/0.1% $NH_4OH$ (aq) over 5 min, 60 mL/min) afforded a white solid (41 mg, 44%). $^1H$ NMR (600 MHz, $d_6$-DMSO) δ 7.83 (dd, J=8.1, 2.0 Hz, 1H), 7.76 (d, J=2.0 Hz, 1H), 7.68 (s, 1H), 7.65 (d, J=8.2 Hz, 1H), 7.63 (br s, 1H), 7.25 (d, J=4.7 Hz, 1H), 7.18 (d, J=4.7 Hz, 1H), 7.03 (s, 2H), 4.47 (d, J=4.2 Hz, 1H), 3.34-3.24 (m, 1H), 2.98-2.89 (m, 1H), 2.25 (s, 3H), 1.74-1.68 (m, 2H), 1.64-1.57 (m, 2H), 1.22-1.12 (m, 2H), 1.12-1.02 (m, 2H). LCMS for $C_{19}H_{24}N_5O_3S$ $(M+H)^+$: calculated m/z=402.2; found 402.2.

Example 14. N-[5-(8-Aminoimidazo[1,2-a]pyrazin-3-yl)-2-fluoropyridin-3-yl]ethanesulfonamide Bis (Trifluoroacetate)

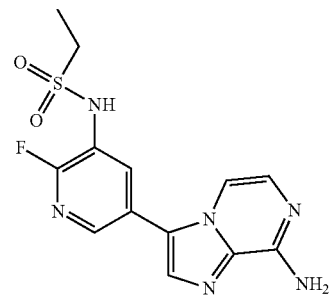 [SMILES: CCS(=O)(=O)Nc1cc(-c2cnc3c(N)nccn23)cnc1F]

To a 1-dram vial was added 3-bromoimidazo[1,2-a]pyrazin-8-amine (10. mg, 0.047 mmol) (Synthonix, A11597), a solution of N-[2-fluoro-5-(4,4,5,5-tetramethyl-1,3,2-dioxaborolan-2-yl)pyridin-3-yl]ethanesulfonamide (Example 2, Step 2, 31 mg, 0.094 mmol) in 1,4-dioxane (1.2 mL, 15 mmol), and [1,1'-bis(diphenylphosphino)ferrocene]dichloropalladium(II), complex with dichloromethane (8 mg, 0.009 mmol). THF (0.70 mL, 8.6 mmol) and then 1.0 M $K_2CO_3$ in water (0.12 mL, 0.12 mmol) were added. The reaction mixture was degassed with $N_2$ for 5 min and subsequently heated at 80° C. overnight. The reaction mixture was diluted with MeOH and filtered through Celite. Purification via preparative HPLC on a C-18 column (pH 2, 15-35% MeCN/0.1% TFA (aq) over 5 min, 60 mL/min) afforded the title compound as a white solid (9.5 mg, 36%). $^1H$ NMR (600 MHz, $d_6$-DMSO) δ 10.24 (br s, 1H), 8.86 (br s, 2H), 8.31 (dd, J=2.0, 1.1 Hz, 1H), 8.14 (dd, J=9.3, 2.2 Hz, 1H), 8.04 (s, 1H), 7.81 (d, J=5.5 Hz, 1H), 7.35 (d, J=5.5 Hz, 1H), 3.28 (q, J=7.3 Hz, 2H), 1.28 (t, J=7.3 Hz, 3H). LCMS for $C_{13}H_{14}FN_6O_2S$ $(M+H)^+$: calculated m/z=337.1; found 337.1.

Example 15. 3-(8-Aminoimidazo[1,2-a]pyrazin-3-yl)-4-methyl-N-[(3-methyloxetan-3-yl)methyl]benzenesulfonamide Trifluoroacetate

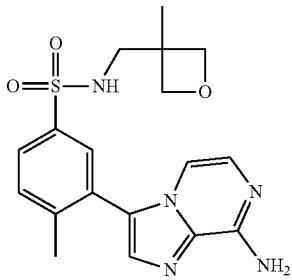 [SMILES: Cc1ccc(S(=O)(=O)NCC2(C)COC2)cc1-c1cnc2c(N)nccn12]

The title compound was synthesized according to an experimental procedure analogous to the synthesis of Example 14, substituting 4-methyl-N-[(3-methyloxetan-3-yl)methyl]-3-(4,4,5,5-tetramethyl-1,3,2-dioxaborolan-2-yl)benzenesulfonamide for a solution of N-[2-fluoro-5-(4,4,5,5-tetramethyl-1,3,2-dioxaborolan-2-yl)pyridin-3-yl]ethanesulfonamide in 1,4-dioxane. LCMS for $C_{18}H_{22}N_5O_3S$ $(M+H)^+$: calculated m/z=388.1; found 388.1.

Example 16. 3-(8-Amino-6-bromoimidazo[1,2-a]pyrazin-3-yl)-N-(trans-4-hydroxycyclohexyl)-4-methylbenzenesulfonamide

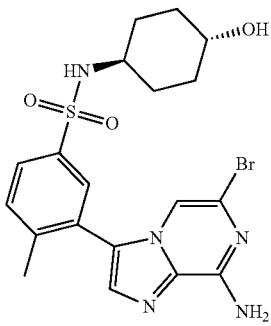 [SMILES: Cc1ccc(S(=O)(=O)N[C@H]2CC[C@H](O)CC2)cc1-c1cnc2c(N)nc(Br)cn12]

Step 1. 6,8-Dibromo-3-iodoimidazo[1,2-a]pyrazine

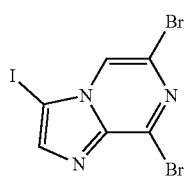

To a solution of 6,8-dibromoimidazo[1,2-a]pyrazine (0.50 g, 1.8 mmol) (Combi-Blocks, OR-7964) in DMF (12 mL) was added N-iodosuccinimide (0.45 g, 2.0 mmol). The reaction mixture was then heated at 60° C. for 15.5 h. The reaction mixture was concentrated in vacuo. The resulting solid was taken up into DCM. The organic layer was washed sequentially with water and sat. $Na_2S_2O_3$ (aq). The organic layer was then dried over $Na_2SO_4$, filtered, and concentrated to afford the title compound as a light yellow solid (0.64 g, 88%). LCMS for $C_6H_3Br_2IN_3$ $(M+H)^+$: calculated m/z=401.8, 403.8, 405.8; found 401.8, 403.7, 405.6.

Step 2. 6-Bromo-3-iodoimidazo[1,2-a]pyrazin-8-amine

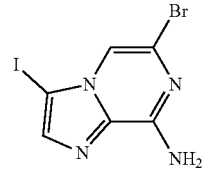

A suspension of 6,8-dibromo-3-iodoimidazo[1,2-a]pyrazine (539 mg, 1.34 mmol) in conc. $NH_4OH$ (aq) (10 mL) was heated at 150° C. for 15 min in a microwave. After cooling to 0° C., the reaction mixture was diluted with cold water and filtered. The collected solid was then washed with cold water to afford the title compound as an off-white solid (356 mg, 79%). LCMS for $C_6H_5BrIN_4$ $(M+H)^+$: calculated m/z=338.9, 340.9; found 338.8, 340.9.

Step 3. 3-(8-Amino-6-bromoimidazo[1,2-a]pyrazin-3-yl)-N-(trans-4-hydroxycyclohexyl)-4-methylbenzenesulfonamide A mixture of 6-bromo-3-iodoimidazo[1,2-a]pyrazin-8-amine (Example 16, Step 2, 0.20 g, 0.59 mmol), N-(trans-4-hydroxycyclohexyl)-4-methyl-3-(4,4,5,5-tetramethyl-1,3,2-dioxaborolan-2-yl)benzenesulfonamide (Example 1, Step 2, 0.26 g, 0.65 mmol), tetrakis(triphenylphosphine)palladium(0) (45 mg, 0.039 mmol), ethanol (8 mL, 100 mmol), and 2.0 M $Na_2CO_3$ in water (0.59 mL, 1.2 mmol) was degassed for 5 min with $N_2$. The reaction mixture was then heated at 130° C. for 20 min in a microwave. The reaction mixture was diluted with DCM and water. The biphasic mixture was filtered through a plug of Celite. The organic layer was removed from the filtrate, and the aqueous layer was extracted with DCM (2×). The combined organic layers were washed with brine, dried over $MgSO_4$, filtered, and concentrated. Purification via silica gel chromatography (1-20% MeOH in DCM) afforded a white solid (0.12 g, 42%). LCMS for $C_{19}H_{22}BrN_5O_3S$ $(M+H)^+$: calculated m/z=480.1, 482.1; found 480.0, 482.0.

Example 17. 3-[8-Amino-6-(2-methylphenyl)imidazo[1,2-a]pyrazin-3-yl]-N-(trans-4-hydroxycyclohexyl)-4-methylbenzenesulfonamide

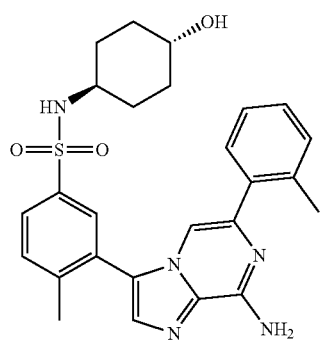 [SMILES: Cc1ccccc1-c1cn2c(-c3cc(S(=O)(=O)N[C@H]4CC[C@H](O)CC4)ccc3C)cnc2c(N)n1]

A 1-dram vial was charged with 3-(8-amino-6-bromoimidazo[1,2-a]pyrazin-3-yl)-N-(trans-4-hydroxycyclohexyl)-4-methylbenzenesulfonamide (Example 16, 6 mg, 0.01 mmol), (2-methylphenyl)boronic acid (3 mg, 0.02 mmol), and [1,1'-bis(diphenylphosphino)ferrocene]dichloropalladium(II), complex with dichloromethane (2 mg, 0.002 mmol). THF (0.2 mL) and then 1.0 M $K_2CO_3$ in water (31 μL, 0.031 mmol) were added. The reaction mixture was degassed with $N_2$ briefly and then heated at 80° C. for 16 h. Heating was discontinued, and the reaction mixture was stirred for 2 days. The reaction mixture was diluted with MeOH and filtered through Celite. The filtrate was concentrated. Purification via preparative HPLC on a C-18 column (pH 10, 28-48% MeCN/0.1% $NH_4OH$ (aq) over 5 min, 60 mL/min) afforded the title compound as a white solid (3 mg, 50%). $^1$H NMR (600 MHz, $d_6$-DMSO) δ 7.84-7.79 (m, 2H), 7.73 (s, 1H), 7.63 (d, J=8.7 Hz, 1H), 7.34 (d, J=7.2 Hz, 1H), 7.28-7.22 (m, 2H), 7.19 (td, J=7.1, 1.9 Hz, 1H), 7.15 (s, 1H), 7.14 (br s, 2H), 4.43 (d, J=4.2 Hz, 1H), 3.28-3.16 (m, 1H), 2.98-2.85 (m, 1H), 2.34 (s, 3H), 2.29 (s, 3H), 1.70-1.61 (m, 2H), 1.61-1.51 (m, 2H), 1.22-1.07 (m, 2H), 1.07-0.93 (m, 2H). LCMS for $C_{26}H_{30}N_5O_3S$ $(M+H)^+$: calculated m/z=492.2; found 492.2.

Examples listed in Table 2 were synthesized according to procedures analogous to the synthesis of Example 17.

TABLE 2

| Ex. No. | Name | R⁸ | LCMS [M + H]⁺ |
|---|---|---|---|
| | $^1$H NMR Spectrum | | |
| 18 | 3-[8-Amino-6-(4-methylphenyl)imidazo[1,2-a]pyrazin-3-yl]-N-(trans-4-hydroxycyclohexyl)-4-methylbenzenesulfonamide | 4-methylphenyl | 492.2 |
| 19 | 3-[8-Amino-6-(3-methylphenyl)imidazo[1,2-a]pyrazin-3-yl]-N-(trans-4-hydroxycyclohexyl)-4-methylbenzenesulfonamide | 3-methylphenyl | 492.2 |
| 20 | 3-[8-Amino-6-(4-fluorophenyl)imidazo[1,2-a]pyrazin-3-yl]-N-(trans-4-hydroxycyclohexyl)-4-methylbenzenesulfonamide | 4-fluorophenyl | 496.1 |

$^1$H NMR (400 MHz, $d_6$-DMSO) δ 7.96-7.89 (m, 2H), 7.88-7.80 (m, 2H), 7.70-7.61 (m, 3H), 7.26-7.15 (m, 3H), 4.48 (d, J = 4.1 Hz, 1H), 3.39-3.20 (m, 1H), 2.94 (br s, 1H), 2.28 (s, 3H), 1.81-1.54 (m, 4H), 1.28-0.91 (m, 4H).

TABLE 2-continued

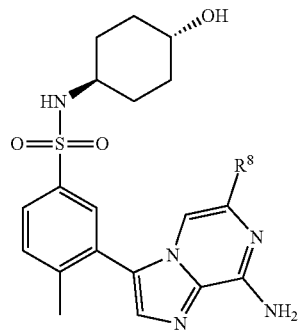

| Ex. No. | Name<br>¹H NMR Spectrum | R⁸ | LCMS [M + H]⁺ |
|---|---|---|---|
| 21 | 3-[8-Amino-6-(3-fluorophenyl)imidazo[1,2-a]pyrazin-3-yl]-N-(trans-4-hydroxycyclohexyl)-4-methylbenzenesulfonamide | 3-fluorophenyl | 496.1 |

¹H NMR (400 MHz, d₆-DMSO) δ 7.89-7.80 (m, 2H), 7.78-7.63 (m, 6H), 7.47-7.38 (m, 1H), 7.25 (s, 2H), 7.16 (t, J = 8.3 Hz, 1H), 4.46 (d, J = 3.6 Hz, 1H), 3.40-3.20 (m, 1H), 2.95 (br s, 1H), 2.28 (s, 3H), 1.65 (m, 4H), 1.27-0.97 (m, 4H).

| 22 | 3-[8-Amino-6-(2-fluorophenyl)imidazo[1,2-a]pyrazin-2-yl]-N-(trans-4-hydroxycyclohexyl)-4-methylbenzenesulfonamide | 2-fluorophenyl | 496.1 |

¹H NMR (400 MHz, d₆-DMSO) δ 8.07 (td, J = 8.0, 1.7 Hz, 1H), 7.87-7.79 (m, 2H), 7.74 (s, 1H), 7.71-7.60 (m, 3H), 7.38 (s, 1H), 7.33-7.17 (m, 4H), 4.46 (d, J = 4.1 Hz, 1H), 3.39-3.19 (m, 1H), 2.92 (br s, 1H), 2.29 (s, 3H), 1.75-1.63 (m, 2H), 1.63-1.51 (m, 2H), 1.25-0.97 (m, 4H).

| 23 | 3-[8-Amino-6-phenylimidazo[1,2-a]pyrazin-3-yl]-N-(trans-4-hydroxycyclohexyl)-4-methylbenzenesulfonamide | phenyl | 478.2 |

¹H NMR (400 MHz, d₆-DMSO) δ 7.90-7.82 (m, 4H), 7.72-7.58 (m, 4H), 7.40 (t, J = 7.3 Hz, 2H), 7.33 (t, J = 7.3 Hz, 1H), 7.20 (s, 2H), 4.47 (d, J = 4.4 Hz, 1H), 3.37-3.21 (m, 1H) 2.95 (s, 1H), 2.29 (s, 3H) 1.65 (m, 4H), 1.26-0.96 (m, 4H).

| 24 | 3-[8-Amino-6-(4-cyanophenyl)imidazo[1,2-a]pyrazin-2-yl]-N-(trans-4-hydroxycyclohexyl)-4-methylbenzenesulfonamide | 4-cyanophenyl | 503.2 |
| 25 | 3-(8-Amino-6-pyridin-4-ylimidazo[1,2-a]pyrazin-3-yl)-N-(trans-4-hydroxycyclohexyl)-4-methylbenzenesulfonamide | pyridin-4-yl | 479.2 |

TABLE 2-continued

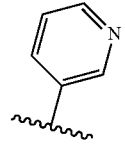 [SMILES: *c1cccnc1]

| Ex. No. | Name<br>¹H NMR Spectrum | R⁸ | LCMS [M + H]⁺ |
|---|---|---|---|
| 26 | 3-(8-Amino-6-pyridin-3-ylimidazo[1,2-a]pyrazin-3-yl)-N-(trans-4-hydroxycyclohexyl)-4-methylbenzenesulfonamide | 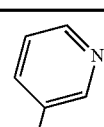 | 479.1 |
| | ¹H NMR (400 MHz, d₆-DMSO) δ 9.08 (d, J = 2.3 Hz, 1H), 8.52 (dd, J = 4.7, 1.6 Hz, 1H), 8.23 (dt, J = 8.0, 1.9 Hz, 1H), 7.88-7.81 (m, 2H), 7.78 (s, 1H), 7.70 (s, 1H), 7.66 (d, J = 8.0 Hz, 1H), 7.42 (dd, J = 8.0, 4.8 Hz, 1H), 7.29 (s, 2H), 4.46 (d, J = 3.1 Hz, 1H), 3.43-3.19 (m, 1H), 2.95 (s, 1H), 2.28 (s, 3H), 1.62 (s, 4H), 1.24-0.95 (m, 4H). | | |
| 27 | 3-[8-Amino-6-(2-thienyl)imidazo[1,2-a]pyrazin-3-yl]-N-(trans-4-hydroxycyclohexyl)-4-methylbenzenesulfonamide | 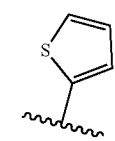 [SMILES: *c1cccs1] | 484.1 |
| 28 | 3-[8-Amino-6-(1-methyl-1H-pyrazol-5-yl)imidazo[1,2-a]pyrazin-3-yl]-N-(trans-4-hydroxycyclohexyl)-4-methylbenzenesulfonamide | 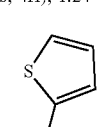 | 482.2 |
| 29 | 3-[8-Amino-6-(1-methyl-1H-pyrazol-4-yl)imidazo[1,2-a]pyrazin-3-yl]-N-(trans-4-hydroxycyclohexyl)-4-methylbenzenesulfonamide | 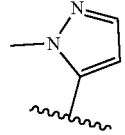 [SMILES: *c1ccnn1C] | 482.2 |
| 30 | 3-[8-Amino-6-(2-fluoro-3-methoxyphenyl)imidazo[1,2-a]pyrazin-3-yl]-N-(trans-4-hydroxycyclohexyl)-4-methylbenzenesulfonamide | 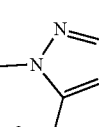 | 526.2 |
| 31 | 3-[8-Amino-3-(5-{[(trans-4-hydroxycyclohexyl)amino]sulfonyl}-2-methylphenyl)imidazo[1,2-a]pyrazin-6-yl]-4-fluoro-N-methylbenzamide | 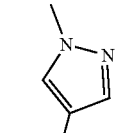 | 553.2 |

TABLE 2-continued

| Ex. No. | Name ¹H NMR Spectrum | R⁸ | LCMS [M + H]⁺ |
|---|---|---|---|
| 32 | 3-{8-Amino-6-[2-fluoro-4-(hydroxymethyl)phenyl]imidazo[1,2-a]pyrazin-3-yl}-N-(trans-4-hydroxycyclohexyl)-4-methylbenzenesulfonamide | 2-fluoro-4-(hydroxymethyl)phenyl | 526.2 |
| 33 | 3-{8-Amino-6-[3-(methylsulfonyl)phenyl]imidazo[1,2-a]pyrazin-3-yl}-N-(trans-4-hydroxycyclohexyl)-4-methylbenzenesulfonamide | 3-(methylsulfonyl)phenyl | 526.2 |
| 34 | 3-[8-Amino-6-(2-fluoro-6-methoxyphenyl)imidazo[1,2-a]pyrazin-3-yl]-N-(trans-4-hydroxycyclohexyl)-4-methylbenzenesulfonamide | 2-fluoro-6-methoxyphenyl | 556.2 |
| 35 | 3-[8-Amino-6-(2-methylthiazol-5-yl)imidazo[1,2-a]pyrazin-3-yl]-N-(trans-4-hydroxycyclohexyl)-4-methylbenzenesulfonamide | 2-methylthiazol-5-yl | 499.2 |

¹H NMR (400 MHz, d₆-DMSO) δ 7.99 (s, 1H), 7.84 (d, J = 8.0 Hz, 1H), 7.79 (s, 1H) 7.70-7.59 (m, 3H), 7.29 (s, 2H), 4.68-4.21 (m, 1H), 3.05-2.83 (m, 1H), 2.62 (s, 3H), 2.25 (s, 3H), 1.85-1.53 (m, 4H), 1.33-0.93 (m, 4H).

| 75 | 3-[8-amino-6-(3-methylisoxazol-5-yl)imidazo[1,2-a]pyrazin-3-yl]-N-(trans-4-hydroxycyclohexyl)-4-methylbenzenesulfonamide | 3-methylisoxazol-5-yl | 483.2 |

¹H NMR (600 MHz, DMSO-d₆) δ 7.86 (dd, J = 8.1, 1.9 Hz, 1H), 7.81 (d, J = 1.7 Hz, 1H), 7.75 (s, 1H), 7.66 (d, J = 8.1 Hz, 1H), 7.63 (s, 1H), 7.40 (s, 2H), 6.65 (s, 1H), 4.50-4.36 (m, 1H), 3.40-3.32 (m, 1H), 3.02-2.89 (m, 1H), 2.26 (s, 3H), 2.25 (s, 3H), 1.75-1.66 (m, 2H), 1.66-1.57 (m, 2H), 1.28-1.12 (m, 2H), 1.12-1.00 (m, 2H).

TABLE 2-continued

| Ex. No. | Name ¹H NMR Spectrum | R⁸ | LCMS [M + H]⁺ |
|---|---|---|---|
| 76 | 3-{8-amino-6-[1-(2,2,2-trifluoroethyl)-1H-pyrazol-4-yl]imidazo[1,2-a]pyrazin-3-yl}-N-(trans-4-hydroxycyclohexyl)-4-methylbenzenesulfonamide | pyrazole with CH₂CF₃ | 550.4 |

¹H NMR (400 MHz, DMSO-d₆) δ 8.16 (s, 1H), 7.93 (s, 1H), 7.84 (d, J = 8.1 Hz, 1H), 7.77 (s, 1H), 7.64 (d, J = 8.1 Hz, 1H), 7.61 (s, 1H), 7.52 (s, 1H), 7.11 (s, 2H), 5.13 (q, J = 9.0 Hz, 2H), 4.55-4.35 (m, 1H), 3.03-2.83 (m, 1H), 2.24 (s, 3H), 1.80-1.53 (m, 4H), 1.28-0.97 (m, 4H).

| 77 | 3-[8-amino-6-(3,5-dimethylisoxazol-4-yl)imidazo[1,2-a]pyrazin-3-yl]-N-(trans-4-hydroxycyclohexyl)-4-methylbenzenesulfonamide | 3,5-dimethylisoxazol-4-yl | 497.2 |

¹H NMR (400 MHz, DMSO-d₆) δ 7.84-7.78 (m, 2H), 7.71 (s, 1H), 7.66-7.56 (m, 2H), 7.27 (s, 1H), 7.19 (br s, 2H), 4.45 (d, J = 4.2 Hz, 1H), 3.28-3.20 (m, 1H), 3.01-2.78 (m, 1H), 2.46 (s, 3H), 2.28 (d, J = 12.4 Hz, 6H), 1.74-1.63 (m, 2H), 1.62-1.49 (m, 2H), 1.21-0.95 (m, 4H).

| 78 | 3-{8-amino-6-[1-(1-cyano-1-methylethyl)-1H-pyrazol-4-yl]imidazo[1,2-a]pyrazin-3-yl}-N-(trans-4-hydroxycyclohexyl)-4-methylbenzenesulfonamide | pyrazole with C(CH₃)₂CN | 535.2 |

¹H NMR (400 MHz, DMSO-d₆) δ 8.32 (s, 1H), 7.99 (s, 1H), 7.85 (d, J = 8.0 Hz, 1H), 7.77 (s, 1H), 7.65 (d, J = 8.0 Hz, 1H), 7.61 (s, 1H), 7.55 (s, 1H), 7.13 (s, 2H), 4.47 (br s, 1H), 3.28-3.22 (m, 1 H), 3.03-2.84 (m, 1H), 2.24 (s, 3H), 1.96 (s, 6H), 1.73-1.57 (m, 4H), 1.12 (dq, J = 35.0, 11.7, 9.9 Hz, 4H).

| 79 | 4-[8-Amino-3-(5-{[(trans-4-hydroxycyclohexyl)amino]sulfonyl}-2-methylphenyl)imidazo[1,2-a]pyrazin-6-yl]-3-fluoro-N,N-dimethylbenzamide trifluoroacetate | 3-fluoro-4-(N,N-dimethylcarbamoyl)phenyl | 567.2 |

TABLE 2-continued

| Ex. No. | Name | R⁸ ¹H NMR Spectrum | LCMS [M + H]⁺ |
|---|---|---|---|
| 80 | 3-{8-Amino-6-[1-methyl-3-(trifluoromethyl)-1H-pyrazol-5-yl]imidazo[1,2-a]pyrazin-3-yl}-N-(trans-4-hydroxycyclohexyl)-4-methylbenzenesulfonamide | (1-methyl-3-trifluoromethylpyrazol-5-yl) | 550.2 |
| 81 | 3-[8-Amino-6-(3-fluoropyridin-4-yl)imidazo[1,2-a]pyrazin-3-yl]-N-(trans-4-hydroxycyclohexyl)-4-methylbenzenesulfonamide | (3-fluoropyridin-4-yl) | 497.1 |
| 82 | 3-(8-Amino-6-(2-fluoro-4-(1-hydroxyethyl)phenyl)imidazo[1,2-a]pyrazin-3-yl)-N-(trans-4-hydroxycyclohexyl)-4-methylbenzenesulfonamide | (2-fluoro-4-(1-hydroxyethyl)phenyl) | 540.1 |

Example 36. 3-[6-(2-Fluorophenyl)-8-(methylamino)imidazo[1,2-a]pyrazin-3-yl]-N-(trans-4-hydroxycyclohexyl)-4-methylbenzenesulfonamide Trifluoroacetate

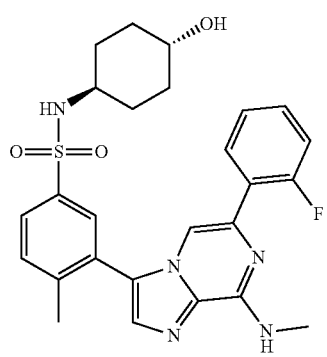

Step 1. 6-Bromo-3-iodo-N-methylimidazo[1,2-a]pyrazin-8-amine

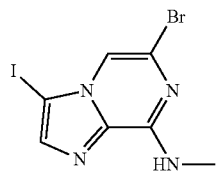

The title compound was synthesized according to an experimental procedure analogous to the synthesis of Example 16, Step 2 substituting methylamine (40% w/w in water) for conc. NH₄OH (aq). LCMS for $C_7H_7BrIN_4$ (M+H)⁺: calculated m/z=352.9, 354.9; found 352.9, 354.9.

Step 2. 3-[6-(2-Fluorophenyl)-8-(methylamino)imidazo[1,2-a]pyrazin-3-yl]-N-(trans-4-hydroxycyclohexyl)-4-methylbenzenesulfonamide Trifluoroacetate A mixture of 6-bromo-3-iodo-N-methylimidazo[1,2-a]pyrazin-8-amine (7.6 mg, 0.022 mmol), N-(trans-4-hydroxycyclohexyl)-4-methyl-3-(4,4,5,5-tetramethyl-1,3,2-dioxaborolan-2-yl)benzenesulfonamide (Example 1, Step 2, 10 mg, 0.02 mmol), tetrakis(triphenylphosphine)palladium (0) (2 mg, 0.002 mmol), ethanol (0.5 mL), and 2.0 M Na$_2$CO$_3$ in water (22 μL, 0.043 mmol) was degassed for 5 min with N$_2$. The reaction mixture was then heated in a microwave reactor at 130° C. for 30 min. The reaction mixture was diluted with MeOH and filtered through a plug of Celite. The filtrate was concentrated to afford the crude intermediate.

A 1-dram vial was charged with the crude intermediate, (2-fluorophenyl)boronic acid (9 mg, 0.06 mmol), and [1,1'-bis(diphenylphosphino)ferrocene]dichloropalladium(II), complex with dichloromethane (4 mg, 0.004 mmol). THF (0.4 mL) and 1.0 M K$_2$CO$_3$ in water (56 μL, 0.056 mmol) were added. The reaction mixture was degassed with N$_2$ briefly and then heated at 80° C. overnight. The reaction mixture was diluted with MeOH and filtered through a plug of Na$_2$SO$_4$ and Celite. Purification via preparative HPLC on a C-18 column (pH 10, 36-56% MeCN/0.1% NH$_4$OH (aq) over 5 min, 60 mL/min) and then subsequent purification via preparative HPLC on a C-18 column (pH 2, 31-42% MeCN/0.1% TFA (aq) over 5 min, 60 mL/min) afforded the title compound as a white solid (4.2 mg, 30%). $^1$H NMR (400 MHz, d$_6$-DMSO) δ 8.20 (t, J=7.3 Hz, 1H), 7.93-7.83 (br m, 2H), 7.82 (s, 1H), 7.73 (s, 1H), 7.70-7.62 (m, 2H), 7.60 (s, 1H), 7.44-7.36 (m, 1H), 7.32 (t, J=7.5 Hz, 1H), 7.23 (dd, J=12.0, 8.2 Hz, 1H), 3.34-3.20 (m, 1H), 3.08 (d, J=2.2 Hz, 3H), 3.00-2.87 (m, 1H), 1.68 (apparent d, J=10.8 Hz, 2H), 1.59 (apparent d, J=11.6 Hz, 2H), 1.31-0.93 (m, 4H). LCMS for C$_{26}$H$_{29}$FN$_5$O$_3$S (M+H)$^+$: calculated m/z=510.2; found 510.1.

Example 37. 3-(8-Amino-6-methylimidazo[1,2-a]pyrazin-3-yl)-N-(trans-4-hydroxycyclohexyl)-4-methylbenzenesulfonamide

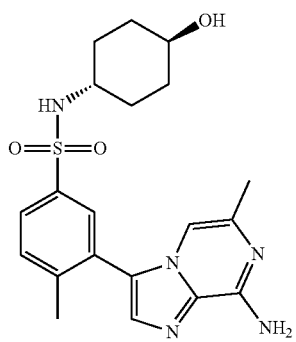 [SMILES: Cc1cn2c(-c3cc(S(=O)(=O)N[C@H]4CC[C@H](O)CC4)ccc3C)cnc2c(N)n1]

The title compound was synthesized according to experimental procedures analogous to the synthesis of Example 16, substituting 8-bromo-6-methylimidazo[1,2-a]pyrazine (Frontier, B12886) for 6,8-dibromoimidazo[1,2-a]pyrazine. $^1$H NMR (600 MHz, d$_6$-DMSO) δ 7.83 (dd, J=8.0, 2.0 Hz, 1H), 7.74 (d, J=2.0 Hz, 1H), 7.64 (d, J=8.1 Hz, 2H), 7.60 (s, 1H), 7.00 (d, J=1.0 Hz, 1H), 6.98 (br s, 2H), 4.47 (d, J=4.2 Hz, 1H), 3.36-3.22 (m, 1H), 3.00-2.87 (m, 1H), 2.23 (s, 3H), 2.15 (d, J=0.8 Hz, 3H), 1.75-1.68 (m, 2H), 1.65-1.57 (m, 2H), 1.22-1.13 (m, 2H), 1.13-1.04 (m, 2H). LCMS for C$_{20}$H$_{26}$N$_5$O$_3$S (M+H)$^+$: calculated m/z=416.2; found 416.2.

Example 38. 3-(8-Amino-6-ethylimidazo[1,2-a]pyrazin-3-yl)-N-(trans-4-hydroxycyclohexyl)-4-methylbenzenesulfonamide

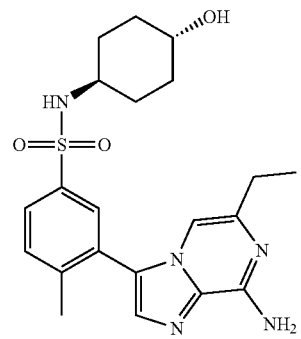 [SMILES: CCc1cn2c(-c3cc(S(=O)(=O)N[C@H]4CC[C@H](O)CC4)ccc3C)cnc2c(N)n1]

Step 1. 3-(8-Amino-6-vinylimidazo[1,2-a]pyrazin-3-yl)-N-(trans-4-hydroxycyclohexyl)-4-methylbenzenesulfonamide

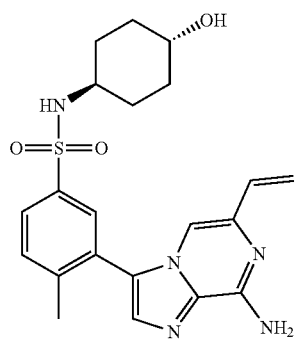 [SMILES: C=Cc1cn2c(-c3cc(S(=O)(=O)N[C@H]4CC[C@H](O)CC4)ccc3C)cnc2c(N)n1]

A microwave vial was charged with 3-(8-amino-6-bromoimidazo[1,2-a]pyrazin-3-yl)-N-(trans-4-hydroxycyclohexyl)-4-methylbenzenesulfonamide (Example 16, 21 mg, 0.044 mmol), potassium vinyltrifluoroborate (17 mg, 0.12 mmol), and [1,1'-bis(diphenylphosphino)ferrocene]dichloropalladium(II), complex with dichloromethane (6 mg, 0.007 mmol). THF (0.57 mL) and 1.0 M K$_2$CO$_3$ in water (0.12 mL, 0.12 mmol) were added. The reaction mixture was degassed with N$_2$ for 5 min and subsequently heated to 80° C. for 4 h. The reaction mixture was diluted with MeOH and filtered through a plug of Na$_2$SO$_4$ and Celite. The filtrate was concentrated. Purification via silica gel chromatography (1-10% MeOH in DCM) afforded the title compound as a light brown solid (17 mg, 91%). LCMS for C$_{21}$H$_{26}$N$_5$O$_3$S (M+H)$^+$: calculated m/z=428.2; found 428.3.

Step 2. 3-(8-Amino-6-ethylimidazo[1,2-a]pyrazin-3-yl)-N-(trans-4-hydroxycyclohexyl)-4-methylbenzenesulfonamide To a solution of 3-(8-amino-6-vinylimidazo[1,2-a]pyrazin-3-yl)-N-(trans-4-hydroxycyclohexyl)-4-methylbenzenesulfonamide (8 mg, 0.02 mmol) in ethanol (4 mL) under N$_2$ was added wet 10% Pd/C (8 mg, ~50% H$_2$O) [Sigma-Aldrich, 330108]. The reaction mixture was then placed under an atm of H$_2$ and stirred for 1 h. The reaction mixture was filtered through Celite, the Celite plug was rinsed with MeOH, and the filtrate was concentrated. Purification via preparative HPLC on a C-18 column (pH 10, 23-40% MeCN/0.1% NH$_4$OH (aq) over 5 min, 60 mL/min) afforded the title compound as a white solid (5 mg, 60%). $^1$H NMR (600 MHz, d$_6$-DMSO) δ 7.83 (dd, J=8.0, 2.0 Hz, 1H), 7.75 (d, J=2.0 Hz, 1H), 7.64 (d, J=8.1 Hz, 1H), 7.61 (s, 1H), 6.98 (s, 2H), 6.97 (s, 1H), 4.47 (s, 1H), 3.38-3.24 (m, 1H), 2.99-2.87 (m, 1H), 2.45 (q, J=7.4 Hz, 2H), 2.23 (s, 3H), 1.75-1.66 (m, 2H), 1.65-1.57 (m, 2H), 1.23-1.03 (m, 7H). LCMS for C$_{21}$H$_{28}$N$_5$O$_3$S (M+H)$^+$: calculated m/z=430.2; found 430.2.

Example 39. 3-(4-Aminoimidazo[2,1-f][1,2,4]triazin-7-yl)-N-(trans-4-hydroxycyclohexyl)-4-methylbenzenesulfonamide

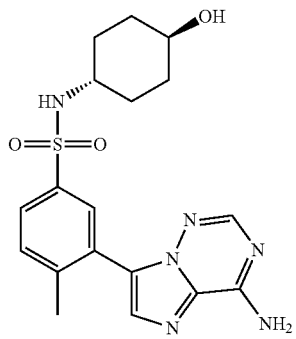 [SMILES: Cc1ccc(S(=O)(=O)N[C@H]2CC[C@H](O)CC2)cc1-c1cnc2c(N)ncnn12]

The title compound was synthesized according to experimental procedures analogous to the synthesis of Example 13, substituting 7-bromoimidazo[2,1-f][1,2,4]triazin-4-amine (Synthonix, A8092) for 3-bromoimidazo[1,2-a]pyrazin-8-amine. $^1$H NMR (600 MHz, d$_6$-DMSO) δ 8.28 (apparent d, J=48.1 Hz, 2H), 8.06 (s, 1H), 7.91 (d, J=2.0 Hz, 1H), 7.79 (s, 1H), 7.78 (dd, J=8.0, 2.0 Hz, 1H), 7.59 (d, J=8.2 Hz, 1H), 4.47 (s, 1H), 3.39-3.23 (m, 1H), 3.01-2.85 (m, 1H), 2.33 (s, 3H), 1.75-1.67 (m, 2H), 1.67-1.59 (m, 2H), 1.22-1.12 (m, 2H), 1.12-1.02 (m, 2H). LCMS for C$_{18}$H$_{23}$N$_6$O$_3$S (M+H)$^+$: calculated m/z=403.2; found 403.2.

Example 40. 6-(2-Fluorophenyl)-3-[2-methyl-5-(methylsulfonyl)phenyl]imidazo[1,2-a]pyrazin-8-amine Trifluoroacetate

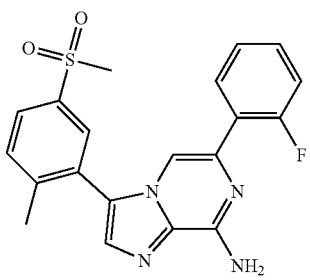 [SMILES: Cc1ccc(S(C)(=O)=O)cc1-c1cnc2c(N)nc(-c3ccccc3F)cn12]

Step 1. 4,4,5,5-Tetramethyl-2-[2-methyl-5-(methylsulfonyl)phenyl]-1,3,2-dioxaborolane

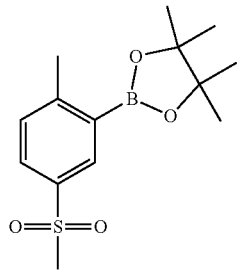 [SMILES: Cc1ccc(S(C)(=O)=O)cc1B1OC(C)(C)C(C)(C)O1]

The title compound was synthesized according to an experimental procedure analogous to the synthesis of Example 1, Step 2 substituting 2-bromo-1-methyl-4-(methylsulfonyl)benzene (Combi-Blocks, OT-1007) for 3-bromo-N-(trans-4-hydroxycyclohexyl)-4-methylbenzenesulfonamide. $^1$H NMR (400 MHz, CDCl$_3$) δ 8.31 (d, J=2.0 Hz, 1H), 7.86 (dd, J=8.1, 2.2 Hz, 1H), 7.34 (d, J=8.1 Hz, 1H), 3.04 (s, 3H), 2.62 (s, 3H), 1.35 (s, 12H). LCMS for C$_{14}$H$_{22}$BO$_4$S (M+H)$^+$: calculated m/z=297.1; found 297.1.

Step 2. 6-(2-Fluorophenyl)-3-[2-methyl-5-(methylsulfonyl)phenyl]imidazo[1,2-a]pyrazin-8-amine trifluoroacetate A mixture of 6-bromo-3-iodoimidazo[1,2-a]pyrazin-8-amine (Example 16, Step 2, 10. mg, 0.030 mmol), 4,4,5,5-tetramethyl-2-[2-methyl-5-(methylsulfonyl)phenyl]-1,3,2-dioxaborolane (10. mg, 0.035 mmol), tetrakis(triphenylphosphine)palladium(0) (2 mg, 0.002 mmol), ethanol (0.52 mL), and 2.0 M Na$_2$CO$_3$ in water (30 μL, 0.059 mmol) was degassed for 5 min with N$_2$. The reaction mixture was then heated in a microwave reactor at 130° C. for 30 min. The reaction mixture was diluted with MeOH and filtered through a plug of Na$_2$SO$_4$ and Celite. The filtrate was concentrated to afford the crude intermediate.

A 1-dram vial was charged with the crude intermediate, (2-fluorophenyl)boronic acid (12 mg, 0.090 mmol), and [1,1'-bis(diphenylphosphino)ferrocene]dichloropalladium (II), complex with dichloromethane (5 mg, 0.006 mmol). THF (0.5 mL) and then 1.0 M K$_2$CO$_3$ in water (75 L, 0.075 mmol) were added. The reaction mixture was degassed with N$_2$ for 15 min and then heated at 80° C. for 16 h. Heating was discontinued, and the reaction mixture was stirred for 3 days. The reaction mixture was diluted with MeOH and filtered through a plug of Na$_2$SO$_4$ and Celite. Purification via preparative HPLC on a C-18 column (pH 10, 29-52% MeCN/0.1% NH$_4$OH (aq) over 5 min, 60 mL/min) and then subsequent purification via preparative HPLC on a C-18 column (pH 2, 24-39% MeCN/0.1% TFA (aq) over 5 min, 60 mL/min) afforded the title compound as a white solid (3.3 mg, 22%). $^1$H NMR (400 MHz, d$_6$-DMSO) δ 8.06-7.91 (m, 3H), 7.81 (s, 1H), 7.75 (d, J=8.0 Hz, 1H), 7.65 (s, 1H), 7.45-7.37 (m, 1H), 7.35-7.20 (m, 2H), 3.26 (s, 3H), 2.31 (s, 3H). LCMS for C$_{20}$H$_{18}$FN$_4$O$_2$S (M+H)$^+$: calculated m/z=397.1; found 397.2.

Examples listed in Table 3 were synthesized according to procedures analogous to the synthesis of Example 1, Steps 1 and 2, and Example 13.

TABLE 3

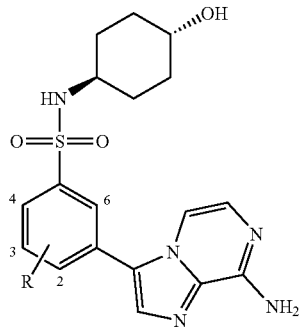

| Ex. No. | Name<br>¹H NMR Spectrum | R = | LCMS [M + H]⁺ |
|---|---|---|---|
| 41 | 5-(8-Aminoimidazo[1,2-a]pymzin-3-yl)-N-(trans-4-hydroxycyclohexyl)-2-methylbenzenesulfonamide<br>¹H NMR (400 MHz, d₆-DMSO) δ 8.02 (d, J = 1.7 Hz, 1H), 7.83-7.73 (m, 3H), 7.68 (d, J = 4.7 Hz, 1H), 7.56 (d, J = 8.0 Hz, 1H), 7.30 (d, J = 4.7 Hz, 1H), 7.01 (s, 2H), 4.45 (d, J = 4.3 Hz, 1H), 3.28-3.19 (m, 1H), 3.04-2.86 (m, 1H), 2.63 (s, 3H), 1.82-1.53 (m, 4H), 1.38-0.94 (m, 4H) | 4-Me | 402.2 |
| 42 | 3-(8-Aminoimidazo[1,2-a]pymzin-3-yl)-4-fluoro-N-(trans-4-hydroxycyclohexyl)benzenesulfonamide<br>¹H NMR (400 MHz, d₆-DMSO) δ 8.05-7.99 (m, 1H), 7.99-7.91 (m, 1H), 7.78 (s, 1H), 7.74 (s, 1H), 7.70-7.61 (m, 1H), 7.53-7.44 (m, 1H), 7.30 (d, J = 4.7 Hz, 1H), 7.05 (s, 2H), 4.46 (d, J = 4.2 Hz, 1H), 3.38-3.19 (m, 1H), 3.05-2.88 (m, 1H), 1.81-1.51 (m, 4H), 1.28-0.95 (m, 4H) | 2-F | 406.1 |
| 43 | 5-(8-Aminoimidazo[1,2-a]pymzin-3-yl)-N-(trans-4-hydroxycyclohexyl)-2-methoxybenzenesulfonamide<br>¹H NMR (400 MHz, d₆-DMSO) δ 7.90 (d, J = 2.2 Hz, 1H), 7.88-7.82 (m, 1H), 7.71 (s, 1H), 7.62 (d, J = 4.7 Hz, 1H), 7.38 (d, J = 8.6 Hz, 1H), 7.34 (br s, 1H), 7.28 (d, J = 4.7 Hz, 1H), 6.97 (s, 2H), 4.45 (d, J = 4.1 Hz, 1H), 3.96 (s, 3H), 3.29-3.20 (m, 1H), 3.09-2.94 (m, 1H), 1.78-1.51 (m, 4H), 1.34-0.96 (m, 4H) | 4-OMe | 418.1 |
| 44 | 3-(8-Aminoimidazo[1,2-a]pymzin-3-yl)-N-(trans-4-hydroxycyclohexyl)-5-methylbenzenesulfonamide<br>¹H NMR (400 MHz, d₆-DMSO) δ 7.82 (s, 1H), 7.79 (s, 1H), 7.77-7.71 (m, 2H), 7.71-7.64 (m, 2H), 7.32 (d, J = 4.7 Hz, 1H), 7.01 (s, 2H), 4.45 (d, J = 4.3 Hz, 1H), 3.28-3.20 (m, 1H), 3.05-2.84 (m, 1H), 2.48 (s, 3H), 1.83-1.47 (m, 4H), 1.33-0.95 (m, 4H) | 3-Me | 402.2 |
| 45 | 5-(8-Aminoimidazo[1,2-a]pyrazin-3-yl)-2-fluoro-N-(trans-4-hydroxycyclohexyl)benzenesulfonamide<br>¹H NMR (400 MHz, d₆-DMSO) δ 8.03 (s, 1H), 7.99-7.90 (m, 2H), 7.79 (s, 1H), 7.68 (d, J = 4.7 Hz, 1H), 7.66-7.56 (m, 1H), 7.30 (d, J = 4.7 Hz, 1H), 7.01 (s, 2H), 4.47 (d, J = 4.2 Hz, H), 3.29-3.20 (m, 1H), 3.16-3.01 (m, 1H), 1.82-1.54 (m, 4H), 1.40-1.18 (m, 2H), 1.18-0.96 (m, 2H) | 4-F | 406.1 |

TABLE 3-continued

| Ex. No. | Name<br>¹H NMR Spectrum | R = | LCMS [M + H]⁺ |
|---|---|---|---|
| 46 | 5-(8-Aminoimidazo[1,2-a]pyrazin-3-yl)-2-chloro-N-(trans-4-hydroxycyclohexyl)benzenesulfonamide<br>¹H NMR (400 MHz, d₆-DMSO) δ 8.15 (d, J = 2.1 Hz, 1H), 7.94 (s, 1H), 7.89 (dd, J = 8.3, 2.1 Hz, 1H), 7.85 (s, 1H), 7.79 (d, J = 8.3 Hz, 1H), 7.73 (d, J = 4.7 Hz, 1H), 7.32 (d, J = 4.7 Hz, 1H), 7.03 (s, 2H), 4.46 (d, J = 4.0 Hz, 1H), 3.33-3.21 (m, 1H), 3.14-2.96 (m, 1H), 1.84-1.53 (m, 4H), 1.42-0.98 (m, 4H) | 4-Cl | 422.1 |
| 83 | 5-(8-aminoimidazo[1,2-a]pyrazin-3-yl)-N-(trans-4-hydroxycyclohexyl)-2-methoxy-4-methylbenzenesulfonamide<br>¹H NMR (400 MHz, DMSO-d₆) δ 7.62 (s, 1H), 7.59 (s, 1H), 7.36-7.18 (m, 3H), 7.13 (d, J = 4.6 Hz, 1H), 6.96 (s, 2H), 4.45 (d, J = 4.2 Hz, 1H), 3.96 (s, 3H), 3.07-2.87 (m, 1H), 2.19 (s, 3H), 1.78-1.65 (m, 2H), 1.65-1.48 (m, 2H), 1.33-1.15 (m, 2H), 1.15-0.93 (m, 2H). | 2-Me, 4-OMe | 432.1 |

Compounds in the following tables were prepared by Method A (default method) or Method B as indicated (See footnote or separate column). Method A: Sulfonamide formation precedes Suzuki coupling (e.g., Example 1, Steps 1 and 2; Example 13); Method B: Sulfonamide formation subsequent to Suzuki coupling (e.g., Example 250). The sulfonamide formation can be executed via Schotten-Baumann conditions (e.g., Example 251, Step 4) and/or using base (e.g. triethylamine or Hunig's base) in polar aprotic solvent (e.g. DMF or DMA) (as in Example 250, Step 5). For instance, Examples listed in Table 4 were synthesized according to procedures analogous to the synthesis of Example 1, Step 1 and 2, and Example 13. The data are listed in Table 4.

TABLE 4

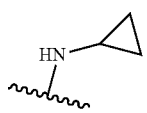

| Ex. No. | Name <br> ¹H NMR Spectrum | —N(R)₂ | LCMS [M + H]⁺ |
|---|---|---|---|
| 47 | 3-(8-Aminoimidazo[1,2-a]pyrazin-3-yl)-N-cyclopropyl-4-methylbenzenesulfonamide | 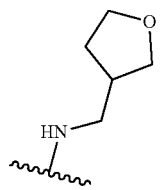 [SMILES: *NCC1CCOC1] | 344.1 |

¹H NMR (d₆-DMSO) δ: 7.99 (s, 1H), 7.96 (d, J = 2.7 Hz, 1H) 7.89 (dd, J = 8.1, 2.0 Hz, 1H), 7.77 (d, J = 2.0 Hz, 1H), 7.71 (d, J = 8.2 Hz, 1H), 7.41 (d, J = 5.7 Hz, 1H), 7.27 (d, J = 5.7 Hz, 1H), 2.26 (s, 3H), 2.19-2.13 (m, 1H), 0.53-0.45 (m, 2H), 0.43-0.37 (m, 2H)

| 48 | 3-(8-Aminoimidazo[1,2-a]pyrazin-3-yl)-4-methyl-N-(tetrahydrofuran-3-ylmethyl)benzenesulfonamide | 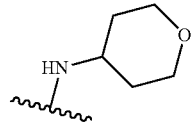 | 388.1 |

¹H NMR (d₆-DMSO) δ: 7.94 (s, 1H), 7.90 (dd, J = 8.1, 2.0 Hz, 1H), 7.85 (d, J = 7.2 Hz, 1H), 7.79 (d, J = 2.0 Hz, 1H), 7.68 (d, J = 8.2 Hz, 1H), 7.35 (d, J = 5.5 Hz, 1H), 7.28 (d, J = 5.5 Hz, 1H), 3.75-3.68 (m, 2H), 3.26-3.18 (m, 4H), 2.25 (s, 3H), 1.56-1.50 (m, 1H), 1.41-1.31 (m, 2H)

| 49 | 3-(8-Aminoimidazo[1,2-a]pyrazin-3-yl)-4-methyl-N-(tetrahydro-2H-pyran-4-yl)benzenesulfonamide | 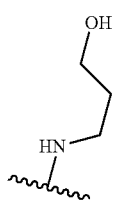 [SMILES: *NCCCO] | 388.1 |
| 50 | 3-(8-Aminoimidazo[1,2-a]pyrazin-3-yl)-N-(3-hydroxypropyl)-4-methylbenzenesulfonamide | 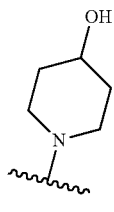 [SMILES: *N1CCC(O)CC1] | 362.1 |
| 51 | 1-{[3-(8-Aminoimidazo[1,2-a]pyrazin-3-yl)-4-methylphenyl]sulfonyl}piperidin-4-ol | | 388.1 |

¹H NMR (d₆-DMSO) δ: 7.76 (dd, J = 8.1, 2.0 Hz, 1H), 7.70 (d, J = 8.1 Hz, 1H), 7.68 (s, 1H), 7.65 (d, J = 2.0 Hz, 1H), 7.24 (d, J = 4.7 Hz, 1H), 7.21 (d, J = 4.7 Hz, 1H), 7.00 (s, 2H), 4.68 (s, 1H), 3.59-3.49 (m, 1H), 3.23-3.11 (m, 2H), 2.80-2.67 (m, 2H), 2.25 (s, 3H), 1.78-1.68 (m, 2H), 1.48-1.35 (m, 2H)

TABLE 4-continued

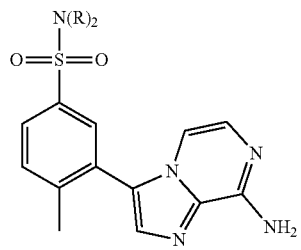

| Ex. No. | Name<br>¹H NMR Spectrum | —N(R)₂ | LCMS [M + H]⁺ |
|---|---|---|---|
| 52 | 3-(8-Aminoimidazo[1,2-a]pyrazin-3-yl)-N-(trans-4-hydroxycyclohexyl)-N,4-dimethylbenzenesulfonamide | (N-methyl, trans-4-hydroxycyclohexyl) | 416.1 |
| | ¹H NMR (d₆-DMSO) δ: 7.82 (dd, J = 8.1, 2.0 Hz, 1H), 7.71 (d, J = 2.0 Hz, 1H), 7.66 (d, J = 8.2 Hz, 1H), 7.65 (s, 1H), 7.23 (d, J = 4.7 Hz, 1H), 7.13 (d, J = 4.7 Hz, 1H), 7.01 (s, 2H), 4.50 (m, 1H), 3.70-3.58 (m, 1H), 3.28-3.22 (m, 1H), 2.66 (s, 3H), 2.22 (s, 3H), 1.81-1.70 (m, 2H), 1.49-1.37 (m, 2H), 1.27 (d, J = 11.9 Hz, 2H), 1.22-1.10 (m, 2H) | | |
| 53 | 3-(8-Aminoimidazo[1,2-a]pyrazin-3-yl)-N-(trans-4-methoxycyclohexyl)-4-methylbenzenesulfonamide | (HN, trans-4-methoxycyclohexyl) | 416.1 |
| 54 | 3-(8-Aminoimidazo[1,2-a]pyrazin-3-yl)-N-(trans-3-hydroxycyclobutyl)-4-methylbenzenesulfonamide | (HN, trans-3-hydroxycyclobutyl) | 374.1 |
| 55 | tert-Butyl [trans-4-({[3-(8-aminoimidazo[1,2-a]pyrazin-3-yl)-4-methylphenyl]sulfonyl}amino)cyclohexyl]carbamate | (HN, trans-4-NHBoc cyclohexyl) | 501.1 |
| 56 | 3-(8-Aminoimidazo[1,2-a]pyrazin-3-yl)-N-[trans-3-(hydroxymethyl)cyclobutyl]-4-methylbenzenesulfonamide | (HN, trans-3-(hydroxymethyl)cyclobutyl) | 388.1 |
| 57 | 3-(8-Aminoimidazo[1,2-a]pyrazin-3-yl)-N-[(3S,6R)-6-(hydroxymethyl)tetrahydro-2H-pyran-3-yl]-4-methylbenzenesulfonamide | (HN, (3S,6R)-6-(hydroxymethyl)tetrahydro-2H-pyran-3-yl) | 418.1 |
| 84 | 3-(8-aminoimidazo[1,2-a]pyrazin-3-yl)-N-(4,4-difluorocyclohexyl)-4-methylbenzenesulfonamide | (HN, 4,4-difluorocyclohexyl) | 422.1 |
| 85 | 3-(8-aminoimidazo[1,2-a]pyrazin-3-yl)-N-(trans-4-hydroxy-4-methylcyclohexyl)-4-methylbenzenesulfonamide | (HN, trans-4-hydroxy-4-methylcyclohexyl) | 416.1 |

TABLE 4-continued

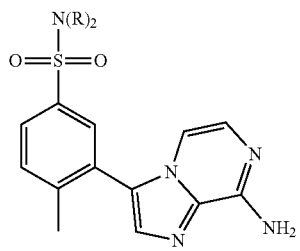

| Ex. No. | Name | ¹H NMR Spectrum | —N(R)₂ | LCMS [M + H]⁺ |
|---|---|---|---|---|
| 86 | 3-(8-aminoimidazo[1,2-a]pyrazin-3-yl)-N-((1-(cyclopropanecarbonyl)piperidin-4-yl)methyl)-4-methylbenzenesulfonamide | | 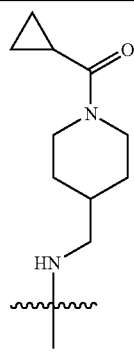 | 469.1 |

‡ or ᴮ denotes that the compound named was prepared using Method B (Scheme X).

Example 58. N-(trans-4-Aminocyclohexyl)-3-(8-aminoimidazo[1,2-a]pyrazin-3-yl)-4-methylbenzenesulfonamide

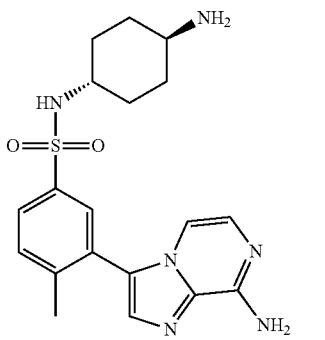 [SMILES: Cc1ccc(S(=O)(=O)N[C@H]2CC[C@H](N)CC2)cc1-c1cnc2c(N)nccn12]

tert-Butyl [trans-4-({[3-(8-aminoimidazo[1,2-a]pyrazin-3-yl)-4-methylphenyl]sulfonyl}amino)cyclohexyl]carbamate (Example 55) was treated with TFA/DCM for 15 min. The reaction mixture was concentrated. Purification via preparative HPLC on a C-18 column (pH 10, 15-33% 0.1% MeCN/NH₄OH (aq) over 5 min, 60 mL/min) afforded the title compound (1.2 mg). LCMS for $C_{19}H_{25}N_6O_2S$ (M+H)⁺: calculated m/z=401.2; found 401.3.

Example 59. N-[trans-4-({[3-(8-Aminoimidazo[1,2-a]pyrazin-3-yl)-4-methylphenyl]sulfonyl}amino)cyclohexyl]acetamide

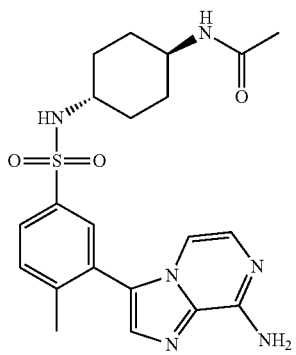

Step 1. N-(trans-4-Aminocyclohexyl)-3-(8-aminoimidazo[1,2-a]pyrazin-3-yl)-4-methylbenzenesulfonamide Hydrochloride

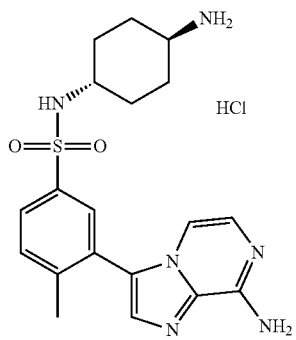 [SMILES: Cc1ccc(S(=O)(=O)N[C@H]2CC[C@H](N)CC2)cc1-c1cnc2c(N)nccn12 ; Cl]

tert-Butyl [trans-4-({[3-(8-aminoimidazo[1,2-a]pyrazin-3-yl)-4-methylphenyl]sulfonyl}amino)cyclohexyl]carbamate (18.9 mg, 0.037 mmol) was stirred with 4.0 M hydrogen chloride in 1,4-dioxane (1.0 mL, 4.0 mmol) at room temperature for 15 min. Evaporation gave the title compound (17.0 mg). LCMS for $C_{19}H_{25}N_6O_2S$ (M+H)$^+$: calculated m/z=401.2; found 401.1.

Step 2. N-[trans-4-({[3-(8-Aminoimidazo[1,2-a]pyrazin-3-yl)-4-methylphenyl]sulfonyl}amino)cyclohexyl]acetamide To a solution of N-(trans-4-aminocyclohexyl)-3-(8-aminoimidazo[1,2-a]pyrazin-3-yl)-4-methylbenzenesulfonamide hydrochloride (8.5 mg, 0.019 mmol) in methylene chloride (0.64 mL) was added triethylamine (16.3 μL, 0.117 mmol) and acetyl chloride (2.1 μL, 0.029 mmol). The reaction mixture was stirred for 2 min and diluted with MeOH. Purification via preparative HPLC on a C-18 column (pH 10, 17-37% 0.1% MeCN/NH$_4$OH (aq) over 5 min, 60 mL/min) afforded the title compound as a white residue (3.4 mg). LCMS for $C_{21}H_{27}N_6O_3S$ (M+H)$^+$: calculated m/z=443.2; found 443.1.

Examples 60 to 72 were synthesized according to procedures analogous to the synthesis of Example 1, Steps 1 and 2, and Example 39. The data are listed in Table 5. Examples 215 to 248 were made from the coupling of the corresponding amine and 3-(4-aminoimidazo[1,2-f][1,2,4]triazin-7-yl)-4-methylbenzene-1-sulfonyl chloride (i.e., Method B). Example 174 was prepared using Method B with tert-butyl (S)-2-(hydroxymethyl)piperazine-1-carboxylate. The BOC intermediate (S)-tert-butyl 4-(3-(4-aminoimidazo[1,2-f][1,2,4]triazin-7-yl)-4-methylphenylsulfonyl)-2-(hydroxymethyl)piperazine-1-carboxylate was then stirred at room temperature for 24 h with 2.0 M phosgene in toluene to prepare Example 174.

TABLE 5

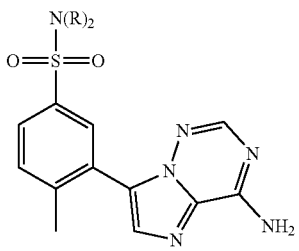

| Ex. No. | Name / $^1$H NMR | N(R)$_2$ | LCMS [M + H]$^+$ |
|---|---|---|---|
| 60 | 3-(4-Aminoimidazo[2,1-f][1,2,4]triazin-7-yl)-N-[trans-3-(hydroxymethyl)cyclobutyl]-4-methylbenzenesulfonamide<br><br>$^1$H NMR (400 MHz, CD$_3$OD) δ 8.08 (s, 1H), 7.95 (d, J = 1.7 Hz, 1H), 7.89-7.81 (m, 1H), 7.73 (s, 1H), 7.58 (d, J = 8.1 Hz, 1H), 3.88 (m, 1H), 3.51 (d, J = 6.9 Hz, 2H), 2.37 (s, 3H), 2.23 (s, 1H), 2.04-1.93 (m, 4H). | 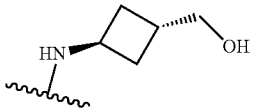 [SMILES: *N[C@H]1C[C@H](CO)C1] | 389.1 |
| 61 | 3-(4-Aminoimidazo[2,1-f][1,2,4]triazin-7-yl)-N-[cis-3-(hydroxymethyl)cyclobutyl]-4-methylbenzenesulfonamide<br><br>$^1$H NMR (400 MHz, CD$_3$OD) δ 8.07 (s, 1H), 7.96 (d, J = 1.9 Hz, 1H), 7.89-7.83 (m, 1H), 7.73 (s, 1H), 7.58 (d, J = 8.1 Hz, 1H), 3.76-3.61 (m, 1H), 3.42 (d, J = 6.0 Hz, 2H), 2.37 (s, 3H), 2.19 (m, 2H), 2.00 (m, 1H), 1.64-1.51 (m, 2H). | 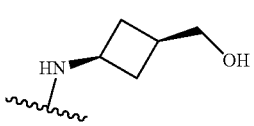 [SMILES: *N[C@H]1C[C@@H](CO)C1] | 389.0 |

TABLE 5-continued

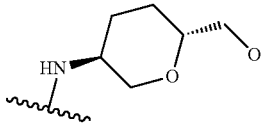

| Ex. No. | Name <br> ¹H NMR | N(R)₂ | LCMS [M + H]⁺ |
|---|---|---|---|
| 62 | 3-(4-Aminoimidazo[2,1-f][1,2,4]triazin-7-yl)-N-[(3S,6R)-6-(hydroxymethyl)tetrahydro-2H-pyran-3-yl]-4-methylbenzenesulfonamide | 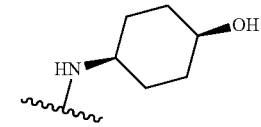 [SMILES: *N[C@H]1CC[C@@H](O)CC1] | 419.1 |
| | ¹H NMR (400 MHz, CD₃OD) δ 8.08 (s, 1H), 8.01 (d, J = 1.9 Hz, 1H), 7.89 (dd, J = 8.1, 1.9 Hz, 1H), 7.75 (s, 1H), 7.60 (d, J = 8.2 Hz, 1H), 3.92 (d, J = 10.6 Hz, 1H), 3.46 (d, J = 4.9 Hz, 2H), 3.23-3.04 (m, 3H), 2.39 (s, 3H), 1.86 (s, 1H), 1.64 (d, J = 12.6 Hz, 1H), 1.48-1.23 (m, 2H). | | |
| 63 | 3-(4-Aminoimidazo[2,1-f][1,2,4]triazin-7-yl)-N-(cis-4-hydroxycyclohexyl)-4-methylbenzenesulfonamide | 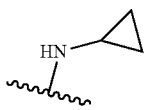 | 403.1 |
| | ¹H NMR (400 MHz, CD₃OD) δ 8.06 (s, 1H), 8.00 (d, J = 1.8 Hz, 1H), 7.89 (dd, J = 8.1, 1.9 Hz, 1H), 7.73 (s, 1H), 7.59 (d, J = 8.1 Hz, 1H), 3.75 (m, 1H), 3.22-3.13 (m, 1H), 2.38 (s, 3H), 1.74-1.60 (m, 4H), 1.60-1.44 (m, 4H). | | |
| 64 | 3-(4-Aminoimidazo[2,1-f][1,2,4]triazin-7-yl)-N-cyclopropyl-4-methylbenzenesulfonamide | 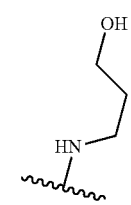 | 345.1 |
| 65 | 3-(4-Aminoimidazo[2,1-f][1,2,4]triazin-7-yl)-N-(3-hydroxypropyl)-4-methylbenzenesulfonamide | 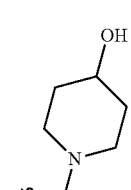 | 363.1 |
| 66 | 1-{[3-(4-Aminoimidazo[2,1-f][1,2,4]triazin-7-yl)-4-methylphenyl]sulfonyl}piperidin-4-ol | 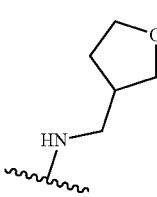 | 389.1 |
| 67 | 3-(4-Aminoimidazo[2,1-f][1,2,4]triazin-7-yl)-4-methyl-N-(tetrahydrofuran-3-ylmethyl)benzenesulfonamide | | 389.1 |

TABLE 5-continued

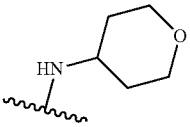

| Ex. No. | Name | N(R)₂ | LCMS [M + H]⁺ |
|---|---|---|---|
| 68 | 3-(4-Aminoimidazo[2,1-f][1,2,4]triazin-7-yl)-4-methyl-N-(tetrahydro-2H-pyran-4-yl)benzenesulfonamide | 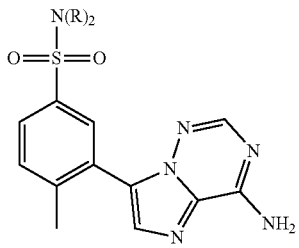 | 389.1 |
| | ¹H NMR (d₆-DMSO) δ 8.05 (s, 1H), 7.88 (d, J = 2.0 Hz, 1H), 7.78 (s, 1H), 7.76 (dd, J = 8.0, 2.0 Hz, 1H), 7.59 (d, J = 8.1 Hz, 1H), 3.68-3.60 (m, 2H), 3.57-3.50 (m, 1H), 3.40-3.35 (m, 1H), 2.76-2.70 (m, 2H), 2.31 (s, 3H), 2.30-2.25 (m, 1H), 1.90-1.81 (m, 1H), 1.51-1.41 (m, 1H) | | |
| 69 | 3-(4-Aminoimidazo[2,1-f][1,2,4]triazin-7-yl)-N-(trans-4-hydroxycyclohexyl)-N,4-dimethylbenzenesulfonamide | 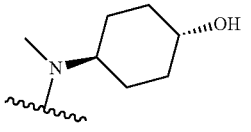 [SMILES: *N(C)[C@H]1CC[C@H](O)CC1] | 417.1 |
| 70 | 3-(4-Aminoimidazo[2,1-f][1,2,4]triazin-7-yl)-N-(trans-4-methoxycyclohexyl)-4-methylbenzenesulfonamide | 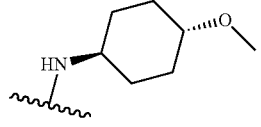 [SMILES: *N[C@H]1CC[C@H](OC)CC1] | 417.1 |
| 71 | 3-(4-Aminoimidazo[2,1-f][1,2,4]triazin-7-yl)-N-(trans-3-hydroxycyclobutyl)-4-methylbenzenesulfonamide | 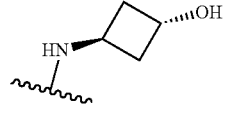 [SMILES: *N[C@H]1C[C@H](O)C1] | 375.1 |
| 72 | tert-Butyl [trans-4-({[3-(4-aminoimidazo[2,1-f][1,2,4]triazin-7-yl)-4-methylphenyl]sulfonyl}amino)cyclohexyl]carbamate | 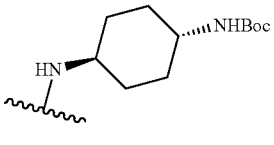 [SMILES: *N[C@H]1CC[C@H](NC(=O)OC(C)(C)C)CC1] | 502.1 |
| 87 | 3-(4-Aminoimidazo[1,2-f][1,2,4]triazin-7-yl)-N-((1r,3r)-3-cyano-3-methylcyclobutyl)-4-methylbenzenesulfonamide trifluoroacetate salt |  | 398.0 |
| | ¹H NMR (400 MHz, DMSO-d₆) δ 8.35 (s, 1H), 8.26 (s, 1H), 8.14-8.06 (m, 2H), 7.93 (d, J = 1.3 Hz, 1H), 7.83 (s, 1H), 7.78 (dd, J = 8.1, 1.5 Hz, 1H), 7.62 (d, J = 8.2 Hz, 1H), 3.88-3.77 (m, 1H), 2.66-2.55 (m, 2H), 2.36 (s, 3H), 1.98-1.86 (m, 2H), 1.37 (s, 3H) | | |
| 88‡ | Methyl 3-(3-(4-aminoimidazo[1,2-f][1,2,4]triazin-7-yl)-4-methylphenylsulfonamido)bicyclo[1.1.1]pentane-1-carboxylate trifluoroacetate salt | 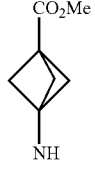 | 429.1 |
| | ¹H NMR (400 MHz, CD₃OD) δ 8.13 (s, 1H), 8.01 (d, J = 1.9 Hz, 1H), 7.88 (dd, J = 8.1, 1.9 Hz, 1H), 7.81 (s, 1H), 7.62 (d, J = 8.1 Hz, 1H), 3.66 (s, 3H), 2.42 (s, 3H), 2.12 (s, 6H) | | |

TABLE 5-continued

| Ex. No. | Name<br>¹H NMR | N(R)₂ | LCMS [M + H]⁺ |
|---|---|---|---|
| 89 | 3-(4-Aminoimidazo[1,2-f][1,2,4]triazin-7-yl)-N-((1r,3r)-3-cyanocyclobutyl)-4-methylbenzenesulfonamide trifluoroacetate salt | 3-cyanocyclobutyl-NH | 384.1 |
|   | ¹H NMR (500 MHz, DMSO-d₆) δ 8.45 (s, 1H), 8.34 (s, 1H), 8.18 (d, J = 8.1 Hz, 1H), 8.12 (s, 1H), 7.92 (d, J = 2.0 Hz, 1H), 7.84 (s, 1H), 7.78 (dd, J = 8.1, 2.0 Hz, 1H), 7.62 (d, J = 8.2 Hz, 1H), 4.01-3.91 (m, 1H), 3.22-3.10 (m, 1H), 2.43-2.35 (m, 2H), 2.35 (s, 3H), 2.25-2.15 (m, 2H). | | |
| 90‡ | 3-(4-Aminoimidazo[1,2-f][1,2,4]triazin-7-yl)-N-(4-cyanobicyclo[2.2.1]heptan-1-yl)-4-methylbenzenesulfonamide trifluoroacetate salt | 4-cyanobicyclo[2.2.1]heptan-1-yl-NH | 424.1 |
|   | ¹H NMR (400 MHz, DMSO-d₆) δ 8.38 (s, 1H), 8.29 (s, 1H), 8.24 (s, 1H), 8.09 (s, 1H), 7.97 (d, J = 1.9 Hz, 1H), 7.83 (s, 1H), 7.81 (dd, J = 8.1, 2.0 Hz, 1H), 7.61 (d, J = 8.1 Hz, 1H), 2.36 (s, 3H), 1.98-1.85 (m, 2H), 1.82 (s, 2H), 1.80-1.64 (m, 4H), 1.56-1.44 (m, 2H) | | |
| 91‡ | 3-(4-Aminoimidazo[1,2-f][1,2,4]triazin-7-yl)-N-(3-(cyanomethyl)bicyclo[1.1.1]pentan-1-yl)-4-methylbenzenesulfonamide trifluoroacetate salt | 3-(cyanomethyl)bicyclo[1.1.1]pentan-1-yl-NH | 410.1 |
|   | ¹H NMR (400 MHz, DMSO-d₆) δ 8.65 (s, 1H), 8.38 (s, 1H), 8.28 (s, 1H), 8.10 (s, 1H), 7.92 (d, J = 1.7 Hz, 1H), 7.82 (s, 1H), 7.79 (dd, J = 8.1, 1.8 Hz, 1H), 7.62 (d, J = 8.1 Hz, 1H), 2.81 (s, 2H), 2.35 (s, 3H), 1.74 (s, 6H) | | |
| 92‡ | N-(3-((1H-pyrazol-1-yl)methyl)bicyclo[1.1.1]pentan-1-yl)-3-(4-aminoimidazo[1,2-f][1,2,4]triazin-7-yl)-4-methylbenzenesulfonamide trifluoroacetate salt | 3-((1H-pyrazol-1-yl)methyl)bicyclo[1.1.1]pentan-1-yl-NH | 451.3 |
|   | ¹H NMR (400 MHz, DMSO-d₆) δ 8.56 (s, 1H), 8.45 (s, 1H), 8.34 (s, 1H), 8.07 (s, 1H), 7.88 (d, J = 1.9 Hz, 1H), 7.80 (s, 1H), 7.75 (dd, J = 8.1, 1.9 Hz, 1H), 7.60 (d, J = 8.3 Hz, 1H), 7.58 (d, J = 2.2 Hz, 1H), 7.38 (d, J = 1.7 Hz, 1H), 6.19 (t, J = 2.0 Hz, 1H), 4.21 (s, 2H), 2.34 (s, 3H), 1.61 (s, 6H) | | |

TABLE 5-continued

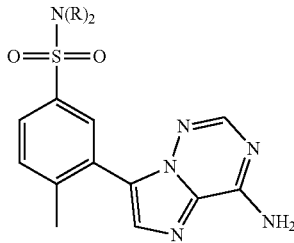

| Ex. No. | Name <br> ¹H NMR | N(R)₂ | LCMS [M + H]⁺ |
|---|---|---|---|
| 93‡ | 3-(4-Aminoimidazo[1,2-f][1,2,4]triazin-7-yl)-N-(3-(2-hydroxypropan-2-yl)bicyclo[1.1.1]pentan-1-yl)-4-methylbenzenesulfonamide trifluoroacetate salt | 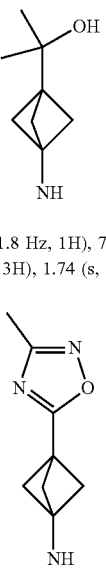 | 429.1 |
| | ¹H NMR (400 MHz, CD₃OD) δ 8.13 (s, 1H), 7.99 (d, J = 1.8 Hz, 1H), 7.88 (dd, J = 8.1, 1.9 Hz, 1H), 7.80 (s, 1H), 7.61 (d, J = 8.1 Hz, 1H), 2.39 (s, 3H), 1.74 (s, 6H), 1.10 (s, 6H) | | |
| 94‡ | 3-(4-Aminoimidazo[1,2-f][1,2,4]triazin-7-yl)-4-methyl-N-(3-(3-methyl-1,2,4-oxadiazol-5-yl)bicyclo[1.1.1]pentan-1-yl)benzenesulfonamide trifluoroacetate salt | | 453.1 |
| | ¹H NMR (400 MHz, CD₃OD) δ 8.12 (s, 1H), 8.05 (d, J = 1.6 Hz, 1H), 7.90 (dd, J = 8.1, 1.6 Hz, 1H), 7.81 (s, 1H), 7.64 (d, J = 8.1 Hz, 1H), 2.42 (s, 3H), 2.36 (s, 6H), 2.33 (s, 3H) | | |
| 95‡ | N-(3-Acetylbicyclo[1.1.1]pentan-1-yl)-3-(4-aminoimidazo[1,2-f][1,2,4]triazin-7-yl)-4-methylbenzenesulfonamide trifluoroacetate salt | 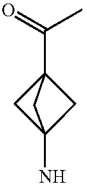 | 413.2 |
| | ¹H NMR (500 MHz, CD₃OD) δ 8.08 (s, 1H), 8.01 (d, J = 2.0 Hz, 1H), 7.88 (dd, J = 8.1, 2.0 Hz, 1H), 7.76 (s, 1H), 7.61 (d, J = 8.1 Hz, 1H), 2.40 (s, 3H), 2.11 (s, 6H), 2.10 (s, 3H) | | |
| 96‡ | 3-(3-(4-Aminoimidazo[1,2-f][1,2,4]triazin-7-yl)-4-methylphenylsulfonamido)-N,N-dimethylbicyclo[1.1.1]pentane-1-carboxamide trifluoroacetate salt | 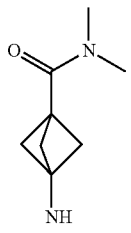 | 442.2 |
| | ¹H NMR (400 MHz, DMSO-d₆) δ 8.69 (s, 1H), 8.42 (s, 1H), 8.31 (s, 1H), 8.09 (s, 1H), 7.94 (d, J = 1.8 Hz, 1H), 7.83 (s, 1H), 7.80 (dd, J = 8.1, 1.9 Hz, 1H), 7.63 (d, J = 8.2 Hz, 1H), 2.92 (s, 3H), 2.75 (s, 3H), 2.35 (s, 3H), 2.04 (s, 6H) | | |

TABLE 5-continued

| Ex. No. | Name / ¹H NMR | N(R)₂ | LCMS [M + H]⁺ |
|---|---|---|---|
| 97‡ | 3-(4-Aminoimidazo[1,2-f][1,2,4]triazin-7-yl)-4-methyl-N-(3-(trifluoromethyl)bicyclo[1.1.1]pentan-1-yl)benzenesulfonamide trifluoroacetate salt<br><br>¹H NMR (400 MHz, DMSO-d₆) δ 8.91 (s, 1H), 8.41 (s, 1H), 8.30 (s, 1H), 8.03 (s, 1H), 7.96 (d, J = 1.9 Hz, 1H), 7.84 (s, 1H), 7.81 (dd, J = 8.1, 2.0 Hz, 1H), 7.64 (d, J = 8.2 Hz, 1H), 2.37 (s, 3H), 2.03 (s, 6H) | 3-(trifluoromethyl)bicyclo[1.1.1]pentan-1-yl-NH– | 439.2 |
| 98‡ | 3-(4-Aminoimidazo[1,2-f][1,2,4]triazin-7-yl)-N-(3-fluorobicyclo[1.1.1]pentan-1-yl)-4-methylbenzenesulfonamide trifluoroacetate salt<br><br>¹H NMR (400 MHz, CD₃OD) δ 8.10 (s, 1H), 7.99 (d, J = 1.8 Hz, 1H), 7.87 (dd, J = 8.1, 1.8 Hz, 1H), 7.79 (s, 1H), 7.62 (d, J = 8.2 Hz, 1H), 2.40 (s, 3H), 2.14 (d, J = 2.0 Hz, 6H) | 3-fluorobicyclo[1.1.1]pentan-1-yl-NH– | 389.1 |
| 99‡ | N-(3-(1H-tetrazol-5-yl)bicyclo[1.1.1]pentan-1-yl)-3-(4-aminoimidazo[1,2-f][1,2,4]triazin-7-yl)-4-methylbenzenesulfonamide trifluoroacetate salt<br><br>¹H NMR (400 MHz, CD₃OD) δ 8.10 (s, 1H), 8.04 (d, J = 1.6 Hz, 1H), 7.92 (dd, J = 8.1, 1.7 Hz, 1H), 7.80 (s, 1H), 7.64 (d, J = 8.2 Hz, 1H), 2.41 (s, 3H), 2.36 (s, 6H) | 3-(1H-tetrazol-5-yl)bicyclo[1.1.1]pentan-1-yl-NH– | 439.1 |
| 100 | 3-(4-Aminoimidazo[1,2-f][1,2,4]triazin-7-yl)-4-methyl-N-(2-methyltetrahydrofuran-3-yl)benzenesulfonamide trifluoroacetate salt (mixture of diastereomers prepared) | 2-methyltetrahydrofuran-3-yl-NH– | 389.1 |
| 101 | 3-(4-Aminoimidazo[1,2-f][1,2,4]triazin-7-yl)-N-((1-cyanocyclopropyl)methyl)-4-methylbenzenesulfonamide trifluoroacetate salt<br><br>¹H NMR (400 MHz, DMSO-d₆) δ 8.42 (s, 1H), 8.32 (s, 1H), 8.24 (t, J = 6.4 Hz, 1H), 8.10 (s, 1H), 7.91 (d, J = 1.7 Hz, 1H), 7.85-7.69 (m, 2H), 7.61 (d, J = 8.2 Hz, 1H), 2.95 (d, J = 6.4 Hz, 2H), 2.32 (s, 3H), 1.22-1.09 (m, 2H), 1.06-0.91 (m, 2H) | (1-cyanocyclopropyl)methyl-NH– | 384.2 |

TABLE 5-continued

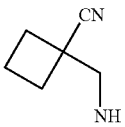

| Ex. No. | Name | N(R)₂ | LCMS [M + H]⁺ |
|---|---|---|---|
| | | ¹H NMR | |
| 102 | 3-(4-Aminoimidazo[1,2-f][1,2,4]triazin-7-yl)-N-((1-cyanocyclobutyl)methyl)-4-methylbenzenesulfonamide trifluoroacetate salt | 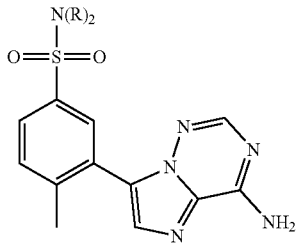 | 398.1 |
| | ¹H NMR (400 MHz, DMSO-d₆) δ 8.42 (s, 1H), 8.32 (s, 1H), 8.22 (t, J = 6.7 Hz, 1H), 8.10 (s, 1H), 7.95 (d, J = 1.9 Hz, 1H), 7.86-7.80 (m, 2H), 7.63 (d, J = 8.1 Hz, 1H), 3.14 (d, J = 6.7 Hz, 2H), 2.38-2.27 (m, 2H), 2.34 (s, 3H), 2.24-2.10 (m, 2H), 2.07-1.84 (m, 2H) | | |
| 103 | N-(1-Acetylazetidin-3-yl)-3-(4-aminoimidazo[1,2-f][1,2,4]triazin-7-yl)-methylbenzenesulfonamide trifluoroacetate salt | 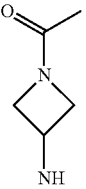 | 402.1 |
| 104 | 3-(4-Aminoimidazo[1,2-f][1,2,4]triazin-7-yl)-4-methyl-N-(oxetan-3-yl)benzenesulfonamide | 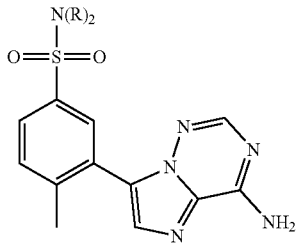 | 361.1 |
| | ¹H NMR (400 MHz, DMSO-d₆) δ 8.54 (d, J = 8.1 Hz, 1H), 8.38 (s, 1H), 8.28 (s, 1H), 8.10 (s, 1H), 7.88 (d, J = 1.8 Hz, 1H), 7.82 (s, 1H), 7.77 (dd, J = 8.1, 1.9 Hz, 1H), 7.61 (d, J = 8.1 Hz, 1H), 4.54 (t, J = 6.7 Hz, 2H), 4.41 (dq, J = 14.4, 7.6, 7.1 Hz, 1H), 4.28 (t, J = 6.3 Hz, 2H), 2.33 (s, 3H) | | |
| 105‡ | 3-(4-Aminoimidazo[1,2-f][1,2,4]triazin-7-yl)-N-(3-(hydroxymethyl)bicyclo[1.1.1]pentan-1-yl)-4-methylbenzenesulfonamide trifluoroacetate salt | 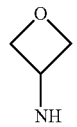 | 401.2 |
| | ¹H NMR (400 MHz, DMSO-d₆) δ 8.51 (s, 1H), 8.39 (s, 1H), 8.29 (s, 1H), 8.09 (s, 1H), 7.91 (d, J = 1.8 Hz, 1H), 7.80 (s, 1H), 7.78 (dd, J = 8.1, 1.9 Hz, 1H), 7.61 (d, J = 8.2 Hz, 1H), 3.35 (s, 2H), 2.34 (s, 3H), 1.60 (s, 6H) | | |
| 106‡ | 3-(4-Aminoimidazo[1,2-f][1,2,4]triazin-7-yl)-N-(bicyclo[1.1.1]pentan-1-yl)-4-methylbenzenesulfonamide trifluoroacetate salt | 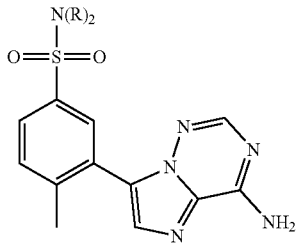 | 371.1 |
| | ¹H NMR (400 MHz, CD₃OD) δ 8.11 (s, 1H), 7.98 (d, J = 1.9 Hz, 1H), 7.88 (dd, J = 8.1, 2.0 Hz, 1H), 7.79 (s, 1H), 7.60 (d, J = 8.1 Hz, 1H), 2.39 (s, 3H), 2.31 (s, 1H), 1.86 (s, 6H). | | |

TABLE 5-continued

| Ex. No. | Name | ¹H NMR | N(R)₂ | LCMS [M + H]⁺ |
|---|---|---|---|---|
| 107‡ | 3-(4-Aminoimidazo[1,2-f][1,2,4]triazin-7-yl)-N-(4-(hydroxymethyl)bicyclo[2.1.1]hexan-1-yl)-4-methylbenzenesulfonamide trifluoroacetate salt | ¹H NMR (400 MHz, CD₃OD) δ 8.11 (s, 1H), 8.00 (d, J = 1.5 Hz, 1H), 7.90 (d, J = 8.2, 1.6 Hz, 1H), 7.78 (s, 1H), 7.59 (d, J = 8.1 Hz, 1H), 3.54 (s, 2H), 2.38 (s, 3H), 1.86-1.72 (m, 2H), 1.64-1.53 (m, 2H), 1.53-1.43 (m, 2H), 1.27-1.18 (m, 2H) | HO–CH₂–bicyclo[2.1.1]hexane–NH | 415.2 |
| 108‡ | 3-(4-Aminoimidazo[1,2-f][1,2,4]triazin-7-yl)-N-(4-(cyanomethyl)bicyclo[2.1.1]hexan-1-yl)-4-methylbenzenesulfonamide trifluoroacetate salt | ¹H NMR (400 MHz, CD₃OD) δ 8.13 (s, 1H), 8.01 (d, J = 1.8 Hz, 1H), 7.90 (dd, J = 8.1, 1.9 Hz, 1H), 7.80 (s, 1H), 7.61 (d, J = 8.1 Hz, 1H), 2.66 (s, 2H), 2.39 (s, 3H), 1.89-1.80 (m, 2H), 1.67-1.61 (m, 2H), 1.61-1.53 (m, 2H), 1.43-1.31 (m, 2H) | NC–CH₂–bicyclo[2.1.1]hexane–NH | 424.1 |
| 109‡ | 4-(3-(4-Aminoimidazo[1,2-f][1,2,4]triazin-7-yl)-N-(4-methylphenylsulfonamido)bicyclo[2.1.1]hexane-1-carboxylic acid | ¹H NMR (400 MHz, DMSO-d₆) δ 8.49 (s, 1H), 8.36 (s, 1H), 8.26 (s, 1H), 8.07 (s, 1H), 7.96 (d, J = 1.8 Hz, 1H), 7.83-7.77 (m, 2H), 7.61 (d, J = 8.2 Hz, 1H), 2.35 (s, 3H), 1.81-1.62 (m, 6H), 1.43-1.30 (m, 2H) | HO₂C–bicyclo[2.1.1]hexane–NH | 429.2 |
| 110‡ | 4-(3-(4-Aminoimidazo[1,2-f][1,2,4]triazin-7-yl)-N-(4-methylphenylsulfonamido)bicyclo[2.1.1]hexane-1-carboxamide trifluoroacetate salt | ¹H NMR (400 MHz, DMSO-d₆) δ 8.42 (s, 1H), 8.40 (s, 1H), 8.30 (s, 1H), 8.09 (s, 1H), 7.95 (d, J =1.8 Hz, 1H), 7.83-7.78 (m, 2H), 7.60 (d, J = 8.2 Hz, 1H), 7.06 (s, 1H), 6.84 (s, 1H), 2.35 (s, 3H), 1.74-1.57 (m, 6H), 1.39-1.29 (m, 2H) | H₂N–C(=O)–bicyclo[2.1.1]hexane–NH | 428.2 |
| 111‡ | 3-(4-Aminoimidazo[1,2-f][1,2,4]triazin-7-yl)-4-methyl-N-(3-(oxazol-5-yl)bicyclo[1.1.1]pentan-1-yl)benzenesulfonamide trifluoroacetate salt | ¹H NMR (400 MHz, CD₃OD) δ 8.08 (s, 1H), 8.05 (s, 1H), 8.03 (d, J = 2.0 Hz, 1H), 7.90 (dd, J = 8.1, 1.9 Hz, 1H), 7.76 (s, 1H), 7.62 (d, J = 8.1 Hz, 1H), 6.88 (s, 1H), 2.41 (s, 3H), 2.20 (s, 6H) | oxazol-5-yl–bicyclo[1.1.1]pentane–NH | 438.1 |

TABLE 5-continued

| Ex. No. | Name | ¹H NMR | N(R)₂ | LCMS [M + H]⁺ |
|---|---|---|---|---|
| 112‡ | N-(3-((1H-Imidazol-1-yl)methyl)bicyclo[1.1.1]pentan-1-yl)-3-(4-aminoimidazo[1,2-f][1,2,4]triazin-7-yl)-4-methylbenzenesulfonamide trifluoroacetate salt | ¹H NMR (400 MHz, DMSO-d₆) δ 9.07-8.98 (m, 1H), 8.68 (s, 1H), 8.38 (s, 1H), 8.29 (s, 1H), 8.08 (s, 1H), 7.91 (d, J = 1.9 Hz, 1H), 7.80 (s, 1H), 7.76 (dd, J = 8.1, 2.0 Hz, 1H), 7.68-7.65 (m, 1H), 7.65-7.63 (m, 1H), 7.61 (d, J = 8.2 Hz, 1H), 4.35 (s, 2H), 2.34 (s, 3H), 1.68 (s, 6H) | (imidazol-1-yl-methyl-bicyclo[1.1.1]pentyl-NH) | 451.1 |
| 113‡ | N-(3-((1H-1,2,4-triazol-1-yl)methyl)bicyclo[1.1.1]pentan-1-yl)-3-(4-aminoimidazo[1,2-f][1,2,4]triazin-7-yl)-4-methylbenzenesulfonamide trifluoroacetate salt | ¹H NMR (400 MHz, DMSO-d₆) δ 8.60 (s, 1H), 8.43 (s, 1H), 8.40 (s, 1H), 8.30 (s, 1H), 8.07 (s, 1H), 7.93 (s, 1H), 7.89 (d, J = 1.8 Hz, 1H), 7.79 (s, 1H), 7.75 (dd, J = 8.1, 1.9 Hz, 1H), 7.60 (d, J = 8.2 Hz, 1H), 4.31 (s, 2H), 2.34 (s, 3H), 1.64 (s, 6H) | (1,2,4-triazol-1-yl-methyl-bicyclo[1.1.1]pentyl-NH) | 452.2 |
| 114‡ | 3-(4-Aminoimidazol[1,2-f][1,2,4]triazin-7-yl)-4-methyl-N-(3-(thiazol-2-yl)bicyclo[1.1.1]pentan-1-yl)benzenesulfonamide trifluoroacetate salt | ¹H NMR (400 MHz, CD₃OD) δ 8.12 (s, 1H), 8.05 (d, J = 1.9 Hz, 1H), 7.92 (dd, J = 8.1, 2.0 Hz, 1H), 7.83 (s, 1H), 7.71 (d, J = 3.3 Hz, 1H), 7.64 (d, J = 8.1 Hz, 1H), 7.51 (d, J = 3.3 Hz, 1H), 2.41 (s, 3H), 2.30 (s, 6H) | (thiazol-2-yl-bicyclo[1.1.1]pentyl-NH) | 454.1 |
| 115‡ | Methyl 3-(3-(4-aminoimidazol[1,2-f][1,2,4]triazin-7-yl)-4-methylphenylsulfonamido)bicyclo[1.1.1]pentan-1-ylcarbamate trifluoroacetate salt | ¹H NMR (400 MHz, DMSO-d₆) δ 8.61 (s, 1H), 8.41 (s, 1H), 8.31 (s, 1H), 8.11 (s, 1H), 7.92 (d, J = 1.8 Hz, 1H), 7.82 (s, 1H), 7.78 (dd, J = 8.0, 1.9 Hz, 1H), 7.62 (d, J = 8.2 Hz, 1H), 3.47 (s, 3H), 2.35 (s, 3H), 1.90 (s, 6H) | (OMe-OC(=O)-NH-bicyclo[1.1.1]pentyl-NH) | 444.2 |

TABLE 5-continued

| Ex. No. | Name | N(R)₂ | LCMS [M + H]⁺ |
|---|---|---|---|
| 116‡ | 3-(4-Aminoimidazol[1,2-f][1,2,4]triazin-7-yl)-4-methyl-N-(3-morpholinobicyclo[1.1.1]pentan-1-yl)benzenesulfonamide trifluoroacetate salt | (morpholine-bicyclopentane-NH) | 456.2 |

¹H NMR (400 MHz, CD₃OD) δ 8.09 (s, 1H), 8.01 (d, J = 2.0 Hz, 1H), 7.89 (dd, J = 8.1, 2.0 Hz, 1H), 7.76 (s, 1H), 7.63 (d, J = 8.1 Hz, 1H), 3.97-3.71 (m, 4H), 3.23-2.94 (m, 4H), 2.40 (s, 3H), 2.19 (s, 6H)

| | | | |
|---|---|---|---|
| 117‡ | 3-(4-Aminoimidazol[1,2-f][1,2,4]triazin-7-yl)-4-methyl-N-(3-methylbicyclo[1.1.1]pentan-1-yl)benzenesulfonamide | (methyl-bicyclopentane-NH) | 385.2 |

¹H NMR (400 MHz, DMSO-d₆) δ 7.25 (s, 1H), 7.15 (s, 1H), 7.05 (d, J = 7.8 Hz, 1H), 6.92 (s, 1H), 6.78 (d, J = 8.0 Hz, 1H), 1.57 (s, 3H), 0.89 (s, 6H), 0.34 (s, 3H)

| | | | |
|---|---|---|---|
| 118‡ | N-(3-aminobicyclo[1.1.1]pentan-1-yl)-3-(4-aminoimidazo[1,2-f][1,2,4]triazin-7-yl)-N,4-dimethylbenzenesulfonamide trifluoroacetate salt | (NH₂-bicyclopentane-NMe) | 400.1 |

¹H NMR (600 MHz, CD₃OD) δ 8.09 (s, 1H), 8.00 (d, J = 2.0 Hz, 1H), 7.85 (dd, J = 8.1, 2.1 Hz, 1H), 7.78 (s, 1H), 7.66 (d, J = 8.2 Hz, 1H), 2.93 (s, 3H), 2.43 (s, 3H), 2.29 (s, 6H)

| | | | |
|---|---|---|---|
| 119 | 5-{[3-(4-aminoimidazo[2,1-f][1,2,4]triazin-7-yl)-4-methylphenyl]sulfonyl}-5-azaspiro[2.5]octan-8-ol | (OH-azaspiro[2.5]octane) | 415.2 |
| 120 | 8-{[3-(4-aminoimidazo[2,1-f][1,2,4]triazin-7-yl)-4-methylphenyl]sulfonyl}-8-azabicyclo[3.2.1]octan-3-ol | (OH-azabicyclo[3.2.1]octane) | 415.2 |

TABLE 5-continued

| Ex. No. | Name ¹H NMR | N(R)₂ | LCMS [M + H]⁺ |
|---|---|---|---|
| 121 | 3-(4-aminoimidazo[2,1-f][1,2,4]triazin-7-yl)-N-{[4-(hydroxymethyl)tetrahydro-2H-pyran-4-yl]methyl}-4-methylbenzenesulfonamide | | 433.3 |
| 122 | 3-(4-aminoimidazo[2,1-f][1,2,4]triazin-7-yl)-N-(4,4-difluorocyclohexyl)-4-methylbenzenesulfonamide | | 423.1 |
| 123 | 3-(4-aminoimidazo[2,1-f][1,2,4]triazin-7-yl)-N-[(3S,4R)-4-hydroxytetrahydrofuran-3-yl]-4-methylbenzenesulfonamide | | 391.1 |
| 124 | 3-(4-aminoimidazo[2,1-f][1,2,4]triazin-7-yl)-N-[cis-4-hydroxy-4-(trifluoromethyl)cyclohexyl]-4-methylbenzenesulfonamide | | 471.1 |
| 125 | 3-(4-aminoimidazo[2,1-f][1,2,4]triazin-7-yl)-N-[trans-4-(1-hydroxy-1-methylethyl)cyclohexyl]-4-methylbenzenesulfonamide | | 445.2 |
| 126 | 3-(4-aminoimidazo[2,1-f][1,2,4]triazin-7-yl)-N-[3,3-bis(hydroxymethyl)cyclobutyl]-4-methylbenzenesulfonamide | | 419.1 |
| 127 | 3-(4-aminoimidazo[2,1-f][1,2,4]triazin-7-yl)-N-(trans-4-hydroxy-1-methylcyclohexyl)-4-methylbenzenesulfonamide | | 417.1 |

TABLE 5-continued

| Ex. No. | Name | ¹H NMR | N(R)₂ | LCMS [M + H]⁺ |
|---|---|---|---|---|
| 128 | (1-((3-(4-aminoimidazo[2,1-f][1,2,4]triazin-7-yl)-4-methylphenyl)sulfonyl)azetidin-3-yl)methanol | | | 375.1 |
| 129 | 3-(4-aminoimidazo[2,1-f][1,2,4]triazin-7-yl)-N-(2-(1,1-dioxidothiomorpholino)ethyl)-4-methylbenzenesulfonamide | | | 466.1 |
| 130 | 3-(4-aminoimidazo[2,1-f][1,2,4]triazin-7-yl)-N-((4,4-difluorocyclohexyl)methyl)-4-methylbenzenesulfonamide | | | 437.1 |
| 131 | 7-(5-((3-fluoroazetidin-1-yl)sulfonyl)-2-methylphenyl)imidazo[2,1-f][1,2,4]triazin-4-amine | | | 363.1 |
| 132 | 3-(4-aminoimidazo[2,1-f][1,2,4]triazin-7-yl)-N-(3,3-difluorocyclobutyl)-4-methylbenzenesulfonamide | | | 395.0 |
| 133 | 3-(4-aminoimidazo[2,1-f][1,2,4]triazin-7-yl)-N-((1S,4S)-4-hydroxy-4-methylcyclohexyl)-4-methylbenzenesulfonamide | | | 417.2 |
| 134 | 3-(4-aminoimidazo[2,1-f][1,2,4]triazin-7-yl)-N-((4-fluorotetrahydro-2H-pyran-4-yl)methyl)-4-methylbenzenesulfonamide | | | 421.2 |

TABLE 5-continued

| Ex. No. | Name / ¹H NMR | N(R)₂ | LCMS [M + H]⁺ |
|---|---|---|---|
| 135 | 3-(4-aminoimidazo[2,1-f][1,2,4]triazin-7-yl)-N-((1,1-dioxidotetrahydrothiophen-3-yl)methyl)-4-methylbenzenesulfonamide | | 437.2 |
| 136 | 3-(8-aminoimidazo[1,2-a]pyrazin-3-yl)-N-((1-(cyclopropanecarbonyl)piperidin-4-yl)methyl)-4-methylbenzenesulfonamide | | 469.1 |
| 137 | 3-(4-aminoimidazo[2,1-f][1,2,4]triazin-7-yl)-N-(2-hydrocyclohexyl)-4-methylbenzenesulfonamide | | 403.2 |
| 138 | 3-(4-aminoimidazo[2,1-f][1,2,4]triazin-7-yl)-4-methyl-N-(2-(2-oxopyrrolidin-1-yl)ethyl)benzenesulfonamide | | 416.2 |
| 139 | 3-(4-aminoimidazo[2,1-f][1,2,4]triazin-7-yl)-4-methylbenzenesulfonamide | | 305.1 |

TABLE 5-continued

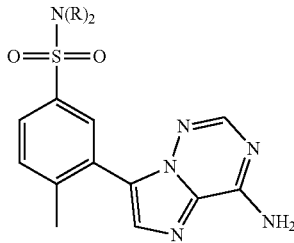

| Ex. No. | Name / ¹H NMR | N(R)₂ | LCMS [M + H]⁺ |
|---|---|---|---|
| 140[B] | 3-(4-aminoimidazo[2,1-f][1,2,4]triazin-7-yl)-N-((1S,3S)-3-hydroxy-3-(trifluoromethyl)cyclobutyl)-4-methylbenzenesulfonamide | 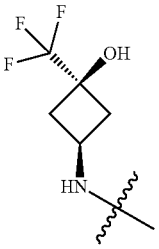 [SMILES: *N[C@H]1C[C@](O)(C(F)(F)F)C1] | 443.2 |
| 141[B] | 2-((3-(4-aminoimidazo[2,1-f][1,2,4]triazin-7-yl)-4-methylphenyl)sulfonyl)-6-(trifluoromethyl)-2-azaspiro[3.3]heptan-6-ol | 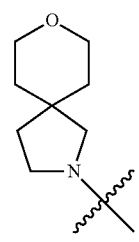 [SMILES: *N1CCC2(CCOCC2)C1] | 469.2 |
| 142[B] | 7-(5-((8-oxa-2-azaspiro[4.5]decan-2-yl)sulfonyl)-2-methylphenyl)imidazo[2,1-f][1,2,4]triazin-4-amine | 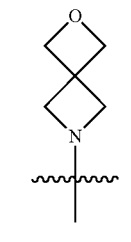 [SMILES: *N1CC2(COC2)C1] | 429.2 |
| 143[B] | 7-(5-((2-oxa-6-azaspiro[3.3]heptan-6-yl)sulfonyl)-2-methylphenyl)imidazo[2,1-f][1,2,4]triazin-4-amine | | 387.2 |
| 144[B] | 1-((3-(4-aminoimidazo[2,1-f][1,2,4]triazin-7-yl)-4-methylphenyl)sulfonyl)-3-cyclopropylazetidin-3-ol, TFA | 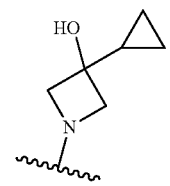 [SMILES: *N1CC(O)(C2CC2)C1] | 401.1 |

TABLE 5-continued

| Ex. No. | Name / ¹H NMR | N(R)₂ | LCMS [M + H]⁺ |
|---|---|---|---|
| 145[B] | 2-((3-(4-aminoimidazo[2,1-f][1,2,4]triazin-7-yl)-4-methylphenyl)sulfonyl)-2-azaspiro[3.3]heptan-6-ol, TFA | | 401.1 |
| 146[B] | 7-(2-methyl-5-((3-morpholinoazetidin-1-yl)sulfonyl)phenyl)imidazo[2,1-f][1,2,4]triazin-4-amine, 2TFA | | 430.1 |
| 147[B] | (S)-7-(5-((2-(methoxymethyl)pyrrolidin-1-yl)sulfonyl)-2-methylphenyl)imidazo[2,1-f][1,2,4]triazin-4-amine | | 403.2 |
| 148[B] | 3-(4-aminoimidazo[2,1-f][1,2,4]triazin-7-yl)-N-cyclopropyl-N,4-dimethylbenzenesulfonamide | | 359.2 |
| 149[B] | 7-(5-((4-azaspiro[2.5]octan-4-yl)sulfonyl)-2-methylphenyl)imidazo[2,1-f][1,2,4]triazin-4-amine | | 399.2 |
| 150[B] | (R)-1-((3-(4-aminoimidazo[2,1-f][1,2,4]triazin-7-yl)-4-methylphenyl)sulfonyl)pyrrolidine-3-carbonitrile | | 384.2 |

TABLE 5-continued

| Ex. No. | Name | ¹H NMR | N(R)₂ | LCMS [M + H]⁺ |
|---|---|---|---|---|
| 151[B] | 7-(5-(((3R,4R)-3-fluoro-4-methoxypyrrolidin-1-yl)sulfonyl)-2-methylphenyl)imidazo[2,1-f][1,2,4]triazin-4-amine | | | 407.2 |
| 152[B] | (R)-(1-((3-(4-aminoimidazo[2,1-f][1,2,4]triazin-7-yl)-4-methylphenyl)sulfonyl)pyrrolidin-2-yl)methanol | | | 389.2 |
| 153[B] | 7-(2-methyl-5-((3-(oxetan-3-yl)azetidin-1-yl)sulfonyl)phenyl)imidazo[2,1-f][1,2,4]triazin-4-amine | | | 401.2 |
| 154[B] | 3-(4-aminoimidazo[2,1-f][1,2,4]triazin-7-yl)-N-(2-cyanoethyl)-N,4-dimethylbenzenesulfonamide | | | 372.2 |
| 155[B] | 7-(5-(((3,5-dimethylmorpholino)sulfonyl)-2-methylphenyl)imidazo[2,1-f][1,2,4]triazin-4-amine | | | 403.2 |
| 156[B] | 7-(5-(((3,3-dimethylmorpholino)sulfonyl)-2-methylphenyl)imidazo[2,1-f][1,2,4]triazin-4-amine | | | 403.2 |

TABLE 5-continued

| Ex. No. | Name ¹H NMR | N(R)₂ | LCMS [M + H]⁺ |
|---|---|---|---|
| 157[B] | (1-((3-(4-aminoimidazo[2,1-f][1,2,4]triazin-7-yl)-4-methylphenyl)sulfonyl)-6-methylpiperidin-2-yl)methanol | 6-methyl-2-(hydroxymethyl)piperidinyl | 417.2 |
| 158[B] | 7-(2-methyl-5-((2,5,5-trimethylmorpholino)sulfonyl)phenyl)imidazo[2,1-f][1,2,4]triazin-4-amine | 2,5,5-trimethylmorpholinyl | 417.2 |
| 159[B] | 3-(4-aminoimidazo[2,1-f][1,2,4]triazin-7-yl)-N-((1R,3R)-3-hydroxycyclobutyl)-N,4-dimethylbenzenesulfonamide | N-methyl-N-(3-hydroxycyclobutyl)amino | 389.2 |
| 160[B] | 3-(4-aminoimidazo[2,1-f][1,2,4]triazin-7-yl)-N-((1-(hydroxymethyl)cyclopropyl)methyl)-N,4-dimethylbenzenesulfonamide | N-methyl-N-((1-(hydroxymethyl)cyclopropyl)methyl)amino | 403.2 |
| 161[B] | 4-((3-(4-aminoimidazo[2,1-f][1,2,4]triazin-7-yl)-4-methylphenyl)sulfonyl)thiomorpholine 1,1-dioxide | thiomorpholine 1,1-dioxide | 423.2 |

TABLE 5-continued

| Ex. No. | Name  ¹H NMR | N(R)₂ | LCMS [M + H]⁺ |
|---|---|---|---|
| 162[B] | 4-((3-(4-aminoimidazo[2,1-f][1,2,4]triazin-7-yl)-4-methylphenyl)sulfonyl)-3-methylthiomorpholine 1,1-dioxide | | 437.2 |
| 163[B] | 3-(4-aminoimidazo[2,1-f][1,2,4]triazin-7-yl)-N,4-dimethyl-N-(2,2,2-trifluoroethyl)benzenesulfonamide | | 401.2 |
| 164[B] | 3-(4-aminoimidazo[2,1-f][1,2,4]triazin-7-yl)-N-(cyclopropylmethyl)-4-methyl-N-propylbenzenesulfonamide | | 401.2 |
| 165[B] | 3-(4-aminoimidazo[2,1-f][1,2,4]triazin-7-yl)-N-(2-cyanoethyl)-N-cyclopentyl-4-methylbenzenesulfonamide | | 426.2 |
| 166[B] | (R)-(1-((3-(4-aminoimidazo[2,1-f][1,2,4]triazin-7-yl)-4-methylphenyl)sulfonyl)piperazin-2-yl)methanol | | 404.0 |

TABLE 5-continued

| Ex. No. | Name | ¹H NMR | N(R)₂ | LCMS [M + H]⁺ |
|---|---|---|---|---|
| 167[B] | (3S,4S)-1-((3-(4-aminoimidazo[2,1-f][1,2,4]triazin-7-yl)-4-methylphenyl)sulfonyl)-4-(4-methylpiperazin-1-yl)pyrrolidin-3-ol | | | 473.2 |
| 168[B] | 7-(5-((2-(3,5-dimethylisoxazol-4-yl)pyrrolidin-1-yl)sulfonyl)-2-methylphenyl)imidazo[2,1-f][1,2,4]triazin-4-amine | | | 454.2 |
| 169[B] | 7-(2-methyl-5-((3-morpholino-8-azabicyclo[3.2.1]octan-8-yl)sulfonyl)phenyl)imidazo[2,1-f][1,2,4]triazin-4-amine | | | 484.2 |
| 170[B] | 7-(2-methyl-5-(((1R,5S)-3-methyl-3,8-diazabicyclo[3.2.1]octan-8-yl)sulfonyl)phenyl)imidazo[2,1-f][1,2,4]triazin-4-amine | | | 414.2 |
| 171[B] | 4-((3-(4-aminoimidazo[2,1-f][1,2,4]triazin-7-yl)-4-methylphenyl)sulfonyl)-1-cyclopropylpiperazin-2-one | | | 428.2 |

TABLE 5-continued

| Ex. No. | Name<br>¹H NMR | N(R)₂ | LCMS [M + H]⁺ |
|---|---|---|---|
| 172[B] | (R)-2-((3-(4-aminoimidazo[2,1-f][1,2,4]triazin-7-yl)-4-methylphenyl)sulfonyl)octahydro-4H-pyrido[1,2-a]pyrazin-4-one | | 442.2 |
| 173[B] | 3-(4-aminoimidazo[2,1-f][1,2,4]triazin-7-yl)-N-(2-cyanoethyl)-N-cyclohexyl-4-methylbenzenesulfonamide | | 440.2 |
| 174[B] | (R)-7-((3-(4-aminoimidazo[2,1-f][1,2,4]triazin-7-yl)-4-methylphenyl)sulfonyl)hexahydro-3H-oxazolo[3,4-a]pyrazin-3-one | | 430.1 |

¹H NMR (400 MHz, DMSO-d₆) δ 8.35 (s, 1H), 8.26 (s, 1H), 8.08 (s, 1H), 7.87 (m, 2H), 7.71 (m, 2H), 4.34 (s, 1H), 3.95 (m, 2H), 3.84 (m, 1 H), 3.67 (m, 2H), 3.09 (m, 1H), 2.39 (s, 3H), 2.37 (m, 2H).

| 175[B] | 3-(4-aminoimidazo[2,1-f][1,2,4]triazin-7-yl)-N-(2-cyanoethyl)-N-(3-hydroxypropyl)-4-methylbenzenesulfonamide | | 416.2 |

TABLE 5-continued

| Ex. No. | Name | N(R)₂ | LCMS [M + H]⁺ |
|---|---|---|---|
| 176[B] | 3-(4-aminoimidazo[2,1-f][1,2,4]triazin-7-yl)-N,4-dimethyl-N-((3-methyloxetan-3-yl)methyl)benzenesulfonamide | | 403.2 |
| 177[B] | 3-(4-aminoimidazo[2,1-f][1,2,4]triazin-7-yl)-N-(1-(methoxymethyl)cyclopropyl)-N,4-dimethylbenzenesulfonamide | | 403.2 |
| 178[B] | 3-(4-aminoimidazo[2,1-f][1,2,4]triazin-7-yl)-N-((1-(hydroxymethyl)cyclobutyl)methyl)-N,4-dimethylbenzenesulfonamide | | 417.2 |
| 179[B] | 3-(4-aminoimidazo[2,1-f][1,2,4]triazin-7-yl)-N-ethyl-4-methyl-N-((tetrahydrofuran-2-yl)methyl)benzenesulfonamide | | 417.2 |
| 180 | 3-(4-aminoimidazo[1,2-f][1,2,4]triazin-7-yl)-N-(bicyclo[2.2.1]heptan-1-yl)-4-methylbenzenesulfonamide trifluoroacetate salt | | 399.1 |
| 181 | 3-(4-aminoimidazo[1,2-f][1,2,4]triazin-7-yl)-N-(bicyclo[2.2.2]octan-1-yl)-4-methylbenzenesulfonamide trifluoroacetate salt | | 413.1 |

TABLE 5-continued

| Ex. No. | Name / ¹H NMR | N(R)₂ | LCMS [M + H]⁺ |
|---|---|---|---|
| 182 | 3-(4-aminoimidazo[1,2-f][1,2,4]triazin-7-yl)-4-methyl-N-(quinuclidin-4-yl)benzenesulfonamide trifluoroacetate salt | quinuclidin-4-yl | 414.1 |
| 183 | 3-(4-aminoimidazo[2,1-f][1,2,4]triazin-7-yl)-N-((3S,6R)-6-(cyanomethyl)tetrahydro-2H-pyran-3-yl)-4-methylbenzenesulfonamide<br><br>¹H NMR (400 MHz, DMSO-d₆) δ 8.31 (br s, 1H), 8.23 (br s, 1H), 8.06 (s, 1H), 7.94 (s, 1H), 7.87-7.74 (m, 3H), 7.60 (d, J = 7.5 Hz, 1H), 3.72 (d, J = 7.5 Hz, 1H), 3.51-3.38 (m, 1H), 3.13-2.91 (m, 2H), 2.76-2.54 (m, 2H), 2.34 (s, 3H), 1.83-1.55 (m, 2H), 1.47-1.17 (m, 2H). | (3S,6R)-6-(cyanomethyl)tetrahydro-2H-pyran-3-ylamino | 428.1 |
| 184‡ | 3-(4-aminoimidazo[2,1-f][1,2,4]triazin-7-yl)-N-(trans-4-(cyanomethyl)cyclohexyl)-4-methylbenzenesulfonamide trifluoroacetate<br><br>¹H NMR (400 MHz, DMSO-d₆) δ 8.34 (br s, 1H), 8.25 (br s, 2H), 8.06 (s, 1H), 7.91 (d, J = 1.9 Hz, 1H), 7.85-7.74 (m, 2H), 7.65 (d, J = 7.2 Hz, 1H), 7.58 (d, J = 8.2 Hz, 1H), 2.98-2.80 (m, 1H), 2.37 (d, J = 6.5 Hz, 2H), 2.32 (s, 3H), 1.78-1.60 (m, 3H), 1.60-1.36 (m, 1H), 1.28-1.10 (m, 2H), 1.08-0.88 (m, 2H). | trans-4-(cyanomethyl)cyclohexylamino | 426.3 |
| 185‡ | 3-(4-aminoimidazo[2,1-f][1,2,4]triazin-7-yl)-N-(4-hydroxybicyclo[2.2.2]octan-1-yl)-4-methylbenzenesulfonamide<br><br>¹H NMR (400 MHz, DMSO-d₆) δ 8.31 (br s, 1H), 8.23 (br s, 1H), 8.05 (s, 1H), 7.90 (s, 1H), 7.83-7.73 (m, 2H), 7.55 (d, J = 8.1 Hz, 1H), 7.46 (s, 1H), 4.23 (s, 1H), 4.23 (s, 1H), 2.32 (s, 3H), 1.81-1.58 (m, 6H), 1.57-1.33 (m, 6H). | 4-hydroxybicyclo[2.2.2]octan-1-ylamino | 429.1 |
| 186‡ | 3-(4-aminoimidazo[2,1-f][1,2,4]triazin-7-yl)-N-(4-(hydroxymethyl)bicyclo[2.2.2]octan-1-yl)-4-methylbenzenesulfonamide<br><br>¹H NMR (400 MHz, DMSO-d₆) δ 8.31 (br s, 1H), 8.23 (br s, 1H), 8.05 (s, 1H), 7.91 (s, 1H), 7.86-7.68 (m, 2H), 7.55 (d, J = 7.8 Hz, 1H), 7.44 (s, 1H), 4.41-4.15 (m, 1H), 2.93 (d, J = 4.9 Hz, 2H), 2.32 (s, 3H), 1.74-1.46 (m, 6H), 1.40-1.08 (m, 6H). | 4-(hydroxymethyl)bicyclo[2.2.2]octan-1-ylamino | 443.2 |
| 187‡ | 3-(4-aminoimidazo[2,1-f][1,2,4]triazin-7-yl)-N-(4-cyanobicyclo[2.2.2]octan-1-yl)-4-methylbenzenesulfonamide<br><br>¹H NMR (400 MHz, DMSO-d₆) δ 8.43-8.13 (m, 2H) 8.08 (s, 1H), 7.92 (s, 1H), 7.86-7.71 (m, 2H), 7.71-7.62 (m, 1H), 7.61-7.47 (m, 1H), 2.33 (s, 3H), 1.96-1.76 (m, 6H), 1.76-1.51 (m, 6H). | 4-cyanobicyclo[2.2.2]octan-1-ylamino | 438.2 |

TABLE 5-continued

| Ex. No. | Name | N(R)₂ | LCMS [M + H]⁺ |
|---|---|---|---|
| | ¹H NMR | | |
| 188‡ | 3-(4-aminoimidazo[2,1-f][1,2,4]triazin-7-yl)-N-(4-fluorobicyclo[2.2.2]octan-1-yl)-4-methylbenzenesulfonamide | | 431.1 |
| | ¹H NMR (400 MHz, DMSO-d₆) δ 8.44-8.11 (m, 2H), 8.06 (s, 1H), 7.92 (d, J = 1.7 Hz, 1H), 7.84-7.72 (m, 2H), 7.56 (d, J = 8.2 Hz, 1H), 2.32 (s, 3H), 1.89-1.77 (m, 6H), 1.77-1.63 (m, 6H). | | |
| 189‡ | 3-(4-aminoimidazo[2,1-f][1,2,4]triazin-7-yl)-N-(1-cyanocyclopropyl)-4-methylbenzenesulfonamide | | 370.1 |
| | ¹H NMR (400 MHz, DMSO-d₆) δ 9.08 (s, 1H), 8.36 (br s, 1H), 8.26 (br s, 1H), 8.09 (s, 1H), 7.95 (s, 1H), 7.85-7.74 (m, 2H), 7.64 (d, J = 8.1 Hz, 1H), 2.34 (s, 3H), 1.50-1.35 (m, 2H), 1.32-1.15 (m, 2H). | | |
| 190‡ | 2-((3-(4-aminoimidazo[2,1-f][1,2,4]triazin-7-yl)-4-methylphenyl)sulfonamido)-2-methylpropanamide trifluoroacetate | | 390.3 |
| | ¹H NMR (400 MHz, DMSO-d₆) δ 8.38 (br s, 1H), 8.28 (br s, 1H), 8.07 (s, 1H), 7.93 (d, J = 1.8 Hz, 1H), 7.86-7.77 (m, 2H), 7.75 (s, 1H), 7.56 (d, J = 8.2 Hz, 1H), 7.05 (d, J = 18.3 Hz, 2H), 2.31 (s, 3H), 1.23 (s, 6H). | | |
| 191‡ | 3-(4-aminoimidazo[2,1-f][1,2,4]triazin-7-yl)-N-((1s,3s)-3-hydroxy-1-methylcyclobutyl)-4-methylbenzenesulfonamide | | 389.1 |
| | ¹H NMR (400 MHz, DMSO-d₆) δ 8.31 (br s, 1H), 8.22 (br s, 1H), 8.06 (s, 1H), 7.90 (d, J = 1.9 Hz, 1H), 7.82 (s, 1H), 7.80-7.72 (m, 2H), 7.57 (d, J = 8.1 Hz, 1H), 4.95 (d, J = 5.7 Hz, 1H), 3.84 (M, 1H), 2.31 (s, 3H), 2.06 (M, 2H), 1.94 (M, 2H), 1.17 (s, 3H). | | |
| 192‡ | 3-(4-aminoimidazo[2,1-f][1,2,4]triazin-7-yl)-N-(1-cyanocyclobutyl)-4-methylbenzenesulfonamide trifluoroacetate | | 384.1 |
| | ¹H NMR (400 MHz, DMSO-d₆) δ 8.86 (s, 1H), 8.39 (br s, 1H), 8.28 (br s, 1H), 8.08 (s, 1H), 7.94 (d, J = 2.0 Hz, 1H), 7.85-7.74 (m, 2H), 7.62 (d, J = 8.2 Hz, 1H), 2.47-2.38 (m, 2H), 2.38-2.26 (m, 5H), 2.03-1.80 (m, 2H). | | |

TABLE 5-continued

| Ex. No. | Name | N(R)₂ | LCMS [M + H]⁺ |
|---|---|---|---|
| 193‡ | 8-((3-(4-Aminoimidazo[2,1-f][1,2,4]triazin-7-yl)-4-methylphenyl)sulfonyl)-3-oxa-1,8-diazaspiro[4.5]decan-2-one | | 444.1 |
| 194‡ | 7-(5-((1-Oxa-8-azaspiro[4.5]decan-8-yl)sulfonyl)-2-methylphenyl)imidazo[2,1-f][1,2,4]triazin-4-amine | | 429.2 |
| 195‡ | 2-((3-(4-Aminoimidazo[2,1-f][1,2,4]triazin-7-yl)-4-methylphenyl)sulfonyl)-6-methyl-2,6-diazaspiro[3.4]octan-5-one | | 428.2 |
| 196‡ | 1-((3-(4-Aminoimidazo[2,1-f][1,2,4]triazin-7-yl)-4-methylphenyl)sulfonyl)-4,4-difluoropiperidin-3-ol | | 425.2 |

¹H NMR (500 MHz, DMSO-d₆) δ 8.33 (br s, 1H), 8.24 (br s, 1H), 8.07 (s, 1H), 7.90 (d, J = 2.0 Hz, 1H), 7.85 (s, 1H), 7.76 (dd, J = 8.1, 2.0 Hz, 1H), 7.66 (d, J = 8.2 Hz, 1H), 5.93 (d, J = 5.7 Hz, 1H), 3.81 (br s, 1H), 3.26-3.13 (m, 2H), 3.04-2.97 (m, 1H), 2.96-2.88 (m, 1H), 2.38 (s, 3H), 2.30-2.10 (m, 1H), 2.09-1.89 (m, 1H).

| 197‡ | (S)-1-((3-(4-Aminoimidazo[2,1-f][1,2,4]triazin-7-yl)-4-methylphenyl)sulfonyl)pyrrolidin-3-ol | | 375.2 |

TABLE 5-continued

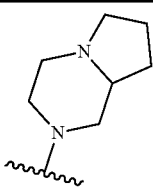

| Ex. No. | Name | ¹H NMR | N(R)₂ | LCMS [M + H]⁺ |
|---|---|---|---|---|
| 198‡ | 7-(5-((Hexahydropyrrolo[1,2-a]pyrazin-2(1H)-yl)sulfonyl)-2-methylphenyl)imidazo[2,1-f][1,2,4]triazin-4-amine | | 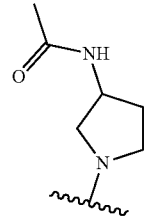 [SMILES: *N1CCC(NC(C)=O)C1] | 414.2 |
| 199‡ | N-(1-((3-(4-Aminoimidazo[2,1-f][1,2,4]triazin-7-yl)-4-methylphenyl)sulfonyl)pyrrolidin-3-yl)acetamide | | 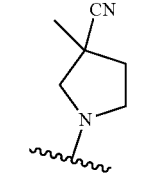 [SMILES: *N1CCC(C)(C#N)C1] | 416.2 |
| 200‡ | 1-((3-(4-Aminoimidazo[2,1-f][1,2,4]triazin-7-yl)-4-methylphenyl)sulfonyl)-3-methylpyrrolidine-3-carbonitrile | | 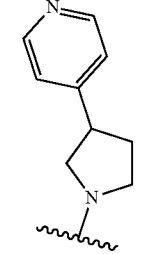 [SMILES: *N1CCC(c2ccncc2)C1] | 398.2 |
| 201‡ | 7-(2-Methyl-5-((3-(pyridin-4-yl)pyrrolidin-1-yl)sulfonyl)phenyl)imidazo[2,1-f][1,2,4]triazin-4-amine | | 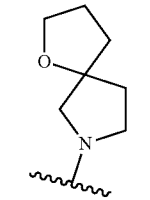 [SMILES: *N1CCC2(CCCO2)C1] | 436.2 |
| 202‡ | 7-(5-((1-Oxa-7-azaspiro[4.4]nonan-7-yl)sulfonyl)-2-methylphenyl)imidazo[2,1-f][1,2,4]triazin-4-amine | | 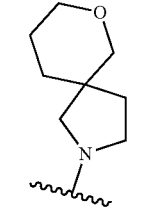 [SMILES: *N1CCC2(CCCOC2)C1] | 415.1 |
| 203‡ | 7-(5-((7-Oxa-2-azaspiro[4.5]decan-2-yl)sulfonyl)-2-methylphenyl)imidazo[2,1-f][1,2,4]triazin-4-amine | |  | 429.1 |

TABLE 5-continued

| Ex. No. | Name ¹H NMR | N(R)₂ | LCMS [M + H]⁺ |
|---|---|---|---|
| 204‡ | 7-(5-((3-(Dimethylamino)pyrrolidin-1-yl)sulfonyl)-2-methylphenyl)imidazo[2,1-f][1,2,4]triazin-4-amine | | 402.1 |
| 205‡ | 7-(5-((1-Oxa-6-azaspiro[3.4]octan-6-yl)sulfonyl)-2-methylphenyl)imidazo[2,1-f][1,2,4]triazin-4-amine | | 401.1 |
| 206‡ | 7-(2-Methyl-5-((1-methyl-8-oxa-2-azaspiro[4.5]decan-2-yl)sulfonyl)phenyl)imidazo[2,1-f][1,2,4]triazin-4-amine | | 443.1 |
| 207‡ | 7-(5-((8,8-Difluoro-2-azaspiro[4.5]decan-2-yl)sulfonyl)-2-methylphenyl)imidazo[2,1-f][1,2,4]triazin-4-amine | | 463.1 |
| 208‡ | 7-(5-((7-Oxa-1-azaspiro[4.4]nonan-1-yl)sulfonyl)-2-methylphenyl)imidazo[2,1-f][1,2,4]triazin-4-amine | | 415.1 |
| 209‡ | 7-(5-((8-Oxa-1-azaspiro[4.5]decan-1-yl)sulfonyl)-2-methylphenyl)imidazo[2,1-f][1,2,4]triazin-4-amine | | 429.1 |

TABLE 5-continued

| Ex. No. | Name / ¹H NMR | N(R)₂ | LCMS [M + H]⁺ |
|---|---|---|---|
| 210‡ | 7-(5-((Hexahydropyrano[3,4-c]pyrrol-2(3H)-yl)sulfonyl)-2-methylphenyl)imidazo[2,1-f][1,2,4]triazin-4-amine | | 415.1 |
| 211‡ | 7-(5-((cis-Hexahydro-5H-furo[2,3-c]pyrrol-5-yl)sulfonyl)-2-methylphenyl)imidazo[2,1-f][1,2,4]triazin-4-amine | | 401.1 |
| 212‡ | (S)-(1-((3-(4-Aminoimidazo[2,1-f][1,2,4]triazin-7-yl)-4-methylphenyl)sulfonyl)-4,4-difluoropyrrolidin-2-yl)methanol | | 425.1 |
| 213‡ | (S)-2-(1-((3-(4-Aminoimidazo[2,1-f][1,2,4]triazin-7-yl)-4-methylphenyl)sulfonyl)pyrrolidin-2-yl)propan-2-ol | | 417.2 |
| 214 | 3-(4-aminoimidazo[2,1-f][1,2,4]triazin-7-yl)-4-methyl-N-(1,3,5-trimethyl-1H-pyrazol-4-yl)benzenesulfonamide | | 413.2 |
| 215ᴮ | 7-(5-((6,7-dihydropyrazolo[1,5-a]pyrimidin-4(5H)-yl)sulfonyl)-2-methylphenyl)imidazo[2,1-f][1,2,4]triazin-4-amine | | 411.2 |

TABLE 5-continued

| Ex. No. | Name | ¹H NMR | N(R)₂ | LCMS [M + H]⁺ |
|---|---|---|---|---|
| 216[B] | 7-(2-methyl-5-((4-(pyridin-2-yl)piperidin-1-yl)sulfonyl)phenyl)imidazo[2,1-f][1,2,4]triazin-4-amine | | | 450.2 |
| 217[B] | 1-((3-(4-aminoimidazo[2,1-f][1,2,4]triazin-7-yl)-4-methylphenyl)sulfonyl)piperdine-4-carbonitrile | | | 398.2 |
| 218[B] | 7-(2-methyl-5-((3-(trifluoromethyl)piperidin-1-yl)sulfonyl)phenyl)imidazo[2,1-f][1,2,4]triazin-4-amine | | | 441.2 |
| 219[B] | 7-(2-methyl-5-((3-(tetrahydrofuran-3-yl)azetidin-1-yl)sulfonyl)phenyl)imidazo[2,1-f][1,2,4]triazin-4-amine | | | 415.1 |
| 220[B] | 7-(5-((6-oxa-2-azaspiro[3.4]octan-2-yl)sulfonyl)-2-methylphenyl)imidazo[2,1-f][1,2,4]triazin-4-amine | | | 401.1 |
| 221[B] | 7-(5-((-2-oxa-6-azaadamantan-6-yl)sulfonyl)-2-methylphenyl)imidazo[2,1-f][1,2,4]triazin-4-amine | | | 427.1 |

TABLE 5-continued

| Ex. No. | Name / $^1$H NMR | N(R)$_2$ | LCMS [M + H]$^+$ |
|---|---|---|---|
| 222$^B$ | 7-(2-methyl-5-((8-methyl-5,6-dihydro-[1,2,4]triazolo[4,3-a]pyrazin-7(8H)-yl)sulfonyl)phenyl)imidazo[2,1-f][1,2,4]triazin-4-amine | | 426.2 |
| 223$^B$ | 7-(5-((5,6-dihydroimidazo[1,2-a]pyrazin-7(8H)-yl)sulfonyl)-2-methylphenyl)imidazo[2,1-f][1,2,4]triazin-4-amine | | 411.1 |
| 224$^B$ | 7-(2-methyl-5-((3,4,6,7-tetrahydro-5H-imidazo[4,5-c]pyridin-5-yl)sulfonyl)phenyl)imidazo[2,1-f][1,2,4]triazin-4-amine | | 411.2 |
| 225$^B$ | 7-(2-methyl-5-((2-methyl-2,4,6,7-tetrahydro-5H-pyrazolo[4,3-c]pyridin-5-yl)sulfonyl)phenyl)imidazo[2,1-f][1,2,4]triazin-4-amine | | 425.3 |
| 226$^B$ | N-(1-((3-(4-aminoimidazo[2,1-f][1,2,4]triazin-7-yl)-4-methylphenyl)sulfonyl)piperidin-4-yl)acetamide | | 430.2 |

TABLE 5-continued

| Ex. No. | Name<br>¹H NMR | N(R)₂ | LCMS [M + H]⁺ |
|---|---|---|---|
| 227[B] | 1-((3-(4-aminoimidazo[2,1-f][1,2,4]triazin-7-yl)-4-methylphenyl)sulfonyl)-N-methylpiperidine-4-carboxamide | | 430.2 |
| 228[B] | 4-((3-(4-aminoimidazo[2,1-f][1,2,4]triazin-7-yl)-4-methylphenyl)sulfonyl)-1-methylpiperazin-2-one | | 402.2 |
| 229[B] | 1-(4-((3-(4-aminoimidazo[2,1-f][1,2,4]triazin-7-yl)-4-methylphenyl)sulfonyl)piperazin-1-yl)ethan-1-one | | 416.3 |
| 230[B] | 7-(2-methyl-5-((4-(pyrimidin-2-yl)piperazin-1-yl)sulfonyl)phenyl)imidazo[2,1-f][1,2,4]triazin-4-amine | | 452.1 |
| 231[B] | 3-(4-((3-(4-aminoimidazo[2,1-f][1,2,4]triazin-7-yl)-4-methylphenyl)sulfonyl)piperazin-1-yl)pyrazine-2-carbonitrile | | 477.2 |

TABLE 5-continued

| Ex. No. | Name ¹H NMR | N(R)₂ | LCMS [M + H]⁺ |
|---|---|---|---|
| 232[B] | 6-(4-((3-(4-aminoimidazo[2,1-f][1,2,4]triazin-7-yl)-4-methylphenyl)sulfonyl)piperazin-1-yl)nicotinonitrile | | 476.2 |
| 233[B] | 3-(4-aminoimidazo[2,1-f][1,2,4]triazin-7-yl)-4-methyl-N-(pyrazin-2-ylmethyl)benzenesulfonamide | | 397.1 |
| 234[B] | 3-(4-aminoimidazo[2,1-f][1,2,4]triazin-7-yl)-4-methyl-N-(2,2,2-trifluoro-1-(pyridin-2-yl)ethyl)benzenesulfonamide | | 464.1 |
| 235[B] | 3-(4-aminoimidazo[2,1-f][1,2,4]triazin-7-yl)-4-methyl-N-((6-(trifluoromethyl)pyridin-2-yl)methyl)benzenesulfonamide | | 464.1 |
| 236[B] | 3-(4-aminoimidazo[2,1-f][1,2,4]triazin-7-yl)-4-methyl-N-((1-methyl-1H-pyrazol-5-yl)methyl)benzenesulfonamide | | 399.1 |

TABLE 5-continued

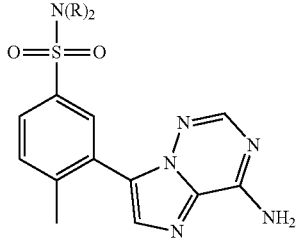

| Ex. No. | Name / ¹H NMR | N(R)₂ | LCMS [M + H]⁺ |
|---|---|---|---|
| 237[B] | 3-(4-aminoimidazo[2,1-f][1,2,4]triazin-7-yl)-4-methyl-N-((5-methyl-1,2,4-oxadiazol-3-yl)methyl)benzenesulfonamide | 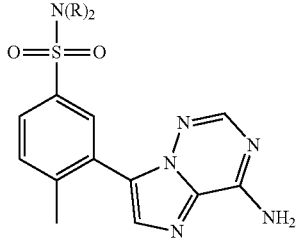 | 401.1 |
| 238[B] | N-(2-amino-1-cyclopropylethyl)-3-(4-aminoimidazo[2,1-f][1,2,4]triazin-7-yl)-4-methylbenzenesulfonamide | 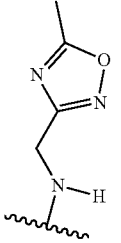 [SMILES: *NCc1noc(C)n1] | 388.3 |
| 239[B] | 3-(4-aminoimidazo[2,1-f][1,2,4]triazin-7-yl)-4-methyl-N-(2-methyl-1-(pyrrolidin-1-yl)propan-2-yl)benzenesulfonamide | 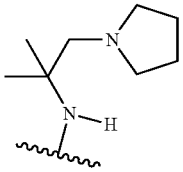 [SMILES: *NC(C)(C)CN1CCCC1] | 430.2 |
| 240[B] | 5-((3-(4-aminoimidazo[2,1-f][1,2,4]triazin-7-yl)-4-methylphenyl)sulfonyl)-4,5,6,7-tetrahydropyrazolo[1,5-a]pyrazine-3-carbonitrile | 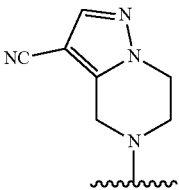 | 436.2 |
| 241[B] | 7-((3-(4-aminoimidazo[2,1-f][1,2,4]triazin-7-yl)-4-methylphenyl)sulfonyl)-N-(2,2,2-trifluoroethyl)-5,6,7,8-tetrahydroimidazo[1,5-a]pyrazine-1-carboxamide | 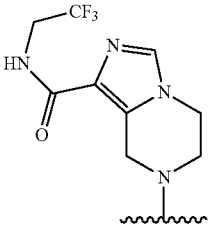 | 536.2 |

TABLE 5-continued

| Ex. No. | Name | N(R)₂ | LCMS [M + H]⁺ |
|---|---|---|---|
| | | ¹H NMR | |
| 242[B] | 3-(4-aminoimidazo[2,1-f][1,2,4]triazin-7-yl)-N-(6-(3-hydroxyazetidine-1-carbonyl)pyridin-3-yl)-4-methylbenzenesulfonamide | | 481.2 |
| 243[B] | 3-(4-aminoimidazo[2,1-f][1,2,4]triazin-7-yl)-4-methyl-N-(1H-pyrazolo[3,4-c]pyridin-5-yl)benzenesulfonamide | | 422.1 |
| 244[B] | N-(5-((3-(4-aminoimidazo[2,1-f][1,2,4]triazin-7-yl)-4-methylphenyl)sulfonamido)pyridin-2-yl)acetamide | | 439.2 |
| 245[B] | 3-(4-aminoimidazo[2,1-f][1,2,4]triazin-7-yl)-4-methyl-N-(4-methylpyridin-3-yl)benzenesulfonamide | | 396.1 |

TABLE 5-continued

| Ex. No. | Name | $^1$H NMR | N(R)$_2$ | LCMS [M + H]$^+$ |
|---|---|---|---|---|
| 246$^B$ | 3-(4-aminoimidazo[2,1-f][1,2,4]triazin-7-yl)-N-(6-methoxy-2-methylpyridin-3-yl)-4-methylbenzenesulfonamide | | | 426.1 |
| 247$^B$ | 3-(4-aminoimidazo[2,1-f][1,2,4]triazin-7-yl)-N,4-dimethyl-N-(pyridin-4-yl)benzenesulfonamide | | | 396.2 |
| 248$^B$ | 3-(4-aminoimidazo[2,1-f][1,2,4]triazin-7-yl)-N-(2-cyanopyridin-4-yl)-4-methylbenzenesulfonamide | | | 407.2 |

$^‡$ or $^B$ denotes that the compound named was prepared using Method B (Scheme X).

Example 73. N-(trans-4-Aminocyclohexyl)-3-(8-aminoimidazo[1,2-a]pyrazin-3-yl)-4-methylbenzenesulfonamide Bis-Hydrochloride

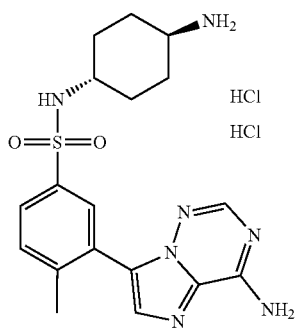 [SMILES: Cc1ccc(S(=O)(=O)N[C@H]2CC[C@H](N)CC2)cc1-c1cnc2c(N)ncnn12 ; Cl ; Cl]

The title compound was synthesized according to experimental procedures analogous to the synthesis of Example 59, Step 1 substituting tert-butyl [trans-4-({[3-(4-aminoimidazo[2,1-f][1,2,4]triazin-7-yl)-4-methylphenyl]sulfonyl}amino)cyclohexyl]carbamate (Example 72) for tert-butyl [trans-4-({[3-(8-aminoimidazo[1,2-a]pyrazin-3-yl)-4-methylphenyl]sulfonyl}amino)cyclohexyl]carbamate. LCMS for $C_{18}H_{24}N_7O_2S$ (M+H)$^+$: calculated m/z=402.2; found 402.1.

Example 74. N-[trans-4-({[3-(4-Aminoimidazo[2,1-f][1,2,4]triazin-7-yl)-4-methylphenyl]sulfonyl}amino)cyclohexyl]acetamide

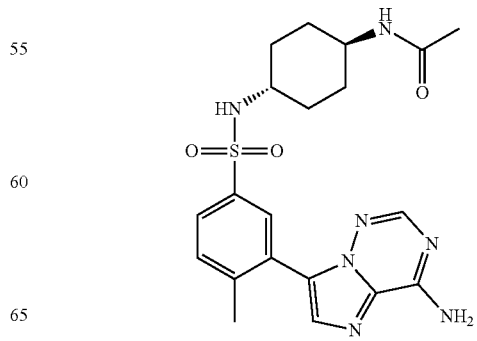

The title compound was synthesized according to experimental procedures analogous to the synthesis of Example 59, Step 2 substituting N-(trans-4-aminocyclohexyl)-3-(8-aminoimidazo[1,2-a]pyrazin-3-yl)-4-methylbenzenesulfonamide bis-hydrochloride (Example 73) for N-(trans-4-aminocyclohexyl)-3-(8-aminoimidazo[1,2-a]pyrazin-3-yl)-4-methylbenzenesulfonamide hydrochloride (Example 59). $^1$H NMR (d$_6$-DMSO) δ: 8.06 (s, 1H), 7.91 (d, J=2.0 Hz, 1H), 7.78 (s, 1H), 7.78-7.77 (m, 1H), 7.76 (d, J=2.0 Hz, 1H), 7.63 (d, J=7.7 Hz, 1H), 7.58 (d, J=8.2 Hz, 1H), 3.38-3.33 (m, 2H), 2.98-2.88 (m, 2H), 2.32 (s, 3H), 1.72 (s, 3H), 1.67 (d, J=10.0 Hz, 2H), 1.25-1.14 (m, 2H), 1.12-1.01 (m, 2H). LCMS for C$_{20}$H$_{26}$N$_7$O$_3$S (M+H)$^+$: calculated m/z=444.2; found 444.1.

Example 249. (S)-3-(4-Amino-2-(trifluoromethyl)imidazo[2,1-f][1,2,4]triazin-7-yl)-N-(1-hydroxypropan-2-yl)-4-methylbenzenesulfonamide

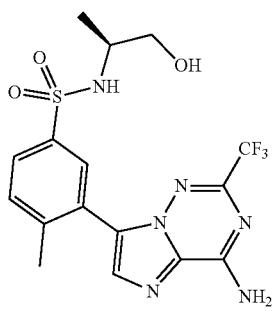 [SMILES: Cc1ccc(S(=O)(=O)N[C@@H](C)CO)cc1-c1cnc2c(N)nc(C(F)(F)F)nn12]

Step 1. (S)-3-Bromo-N-(1-hydroxypropan-2-yl)-4-methylbenzenesulfonamide

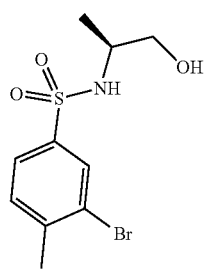 [SMILES: Cc1ccc(S(=O)(=O)N[C@@H](C)CO)cc1Br]

To a mixture of (S)-2-aminopropan-1-ol (55.7 mg, 0.742 mmol, Aldrich) and triethylamine (0.16 mL, 1.1 mmol) in DCM (4.0 mL) at 0° C. was added dropwise a solution of 3-bromo-4-methylbenzenesulfonyl chloride (100.0 mg, 0.371 mmol, Enamine) in DCM (2.0 mL). The reaction mixture was stirred for one hr at 0° C. Solvent was removed in vacuo and the product was purified by flash chromatography, eluting with a gradient from 0-17% EtOAc in hexanes to afford a colorless oil (0.096 g, 84%). LCMS for C$_{10}$H$_{15}$BrNO$_3$S (M+H)$^+$: calculated m/z=308.0; found 307.9.

Step 2. (S)-N-(1-hydroxypropan-2-yl)-4-methyl-3-(4,4,5,5-tetramethyl-1,3,2-dioxaborolan-2-yl)benzenesulfonamide

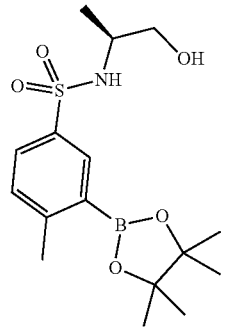 [SMILES: Cc1ccc(S(=O)(=O)N[C@@H](C)CO)cc1B1OC(C)(C)C(C)(C)O1]

A degassed mixture of (S)-3-bromo-N-(1-hydroxypropan-2-yl)-4-methylbenzenesulfonamide (96 mg, 0.31 mmol), 4,4,4',4',5,5,5',5'-octamethyl-2,2'-bi(1,3,2-dioxaborolane) (103 mg, 0.405 mmol), potassium acetate (101 mg, 1.03 mmol) and dichlorobis(triphenylphosphine)-palladium(II) (8.8 mg, 0.012 mmol) in THF (1.5 mL) was heated in a microwave at 140° C. for 20 minutes. The reaction mixture was cooled to room temperature, diluted with EtOAc and filtered through Celite™, rinsing with EtOAc. The filtrate was washed with water and then brine, dried over Na$_2$SO$_4$, filtered, and concentrated. Purification via flash chromatography, eluting with a gradient of 0-50% EtOAc in hexanes afforded product as a clear oil (0.136 g, theoretical yield assumed). LCMS for C$_{1-6}$H$_{27}$BNO$_5$S (M+H)$^+$: calculated m/z=356.2; found 356.2.

Step 3. 2-(Trifluoromethyl)imidazo[1,2-f][1,2,4]triazin-4-ol

Ethyl 1-amino-1H-imidazole-2-carboxylate (3.22 g, 20.8 mmol, prepared as in US2015/0274767) and trifluoroacetamidine (9.36 mL, 125 mmol, Oakwood) in EtOH (86 mL) were stirred in an oil bath held at 95° C. for 96 hours. The reaction mixture was allowed to cool to room temperature and the white solid product was isolated by filtration (1.42 g, 34%). LCMS for C$_6$H$_4$F$_3$N$_4$O (M+H)$^+$: calculated m/z=205.0; found 205.1. $^1$H NMR (400 MHz, CD$_3$OD) δ 7.77 (s, 1H), 7.49 (s, 1H).

Step 4. 7-Bromo-2-(trifluoromethyl)imidazo[1,2-f][1,2,4]triazin-4-ol

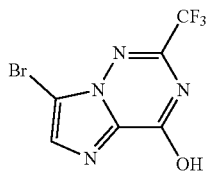

A solution of 2-(trifluoromethyl)imidazo[2,1-f][1,2,4]triazin-4-ol (1.46 g, 7.19 mmol) in DMF (25 mL) was treated with NBS (1.41 g, 7.91 mmol) for 1 h. The reaction mixture was diluted with water (100 mL), acidified to pH 2 using 1 N HCl, and was extracted with EtOAc twice. The combined organic extracts were washed with water (3×100 mL) and brine (100 mL), dried over $Na_2SO_4$, filtered and concentrated to afford a white solid (1.92 g, 95%). LCMS for $C_6H_3BrF_3N_4O$ (M+H)$^+$: calculated m/z=282.9, 284.9; found 283.0, 285.0. $^1$H NMR (400 MHz, CD$_3$OD) δ 7.67 (s, 1H).

Step 5. 7-Bromo-4-chloro-2-(trifluoromethyl)imidazo[1,2-f][1,2,4]triazine

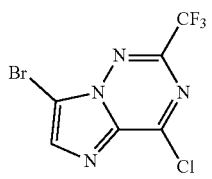

7-Bromo-2-(trifluoromethyl)imidazo[2,1-f][1,2,4]triazin-4-ol (1.92 g, 6.80 mmol) was heated to 110° C. in POCl$_3$ (20.0 mL, 215 mmol) for 30 minutes. Upon cooling to room temperature, POCl$_3$ was removed in vacuo. The residue was poured into a mixture of ice water. The aqueous mixture was made basic by the addition of sat'd NaHCO$_3$ solution, and the mixture was extracted with EtOAc (3×). The combined organic extracts were dried over sodium sulfate, filtered and concentrated. The product was used without further purification in the next step (2.0 g, 98%). LCMS for $C_6H_2BrClF_3N_4$(M+H)$^+$: calculated m/z=300.9, 302.9; found 301.0, 303.0.

Step 6. 7-Bromo-2-(trifluoromethyl)imidazo[1,2-f][1,2,4]triazin-4-amine

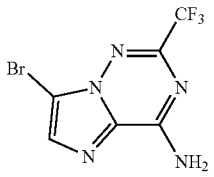

A suspension of 7-bromo-4-chloro-2-(trifluoromethyl)imidazo[2,1-f][1,2,4]triazine (2.0 g, 6.6 mmol) in ammonium hydroxide (23 mL, 330 mmol, 14.8 M NH$_4$OH) was heated to 80° C. in oil bath for 45 minutes. Upon cooling to room temperature, water was added and the mixture was extracted with EtOAc (3×). The combined organic extracts were dried over Na$_2$SO$_4$, filtered and concentrated to afford an off-white solid (1.7 g, 92%). LCMS for $C_6H_4BrF_3N_5$(M+H)$^+$: calculated m/z=282.0, 284.0; found 282.0, 284.0. $^1$H NMR (400 MHz, CDCl$_3$) δ 7.72 (s, 1H), 6.75 (br s, 1H), 6.46 (br s, 1H).

Step 7. (S)-3-(4-Amino-2-(trifluoromethyl)imidazo[2,1-f][1,2,4]triazin-7-yl)-N-(1-hydroxypropan-2-yl)-4-methylbenzenesulfonamide A microwave vial was charged with (S)-N-(1-hydroxypropan-2-yl)-4-methyl-3-(4,4,5,5-tetramethyl-1,3,2-dioxaborolan-2-yl)benzenesulfonamide (80.0 mg, 0.18 mmol, from Step 2), 7-bromo-2-(trifluoromethyl)imidazo[2,1-f][1,2,4]triazin-4-amine (51 mg, 0.18 mmol), dichloro[1,1'-bis(diphenylphosphino)ferrocene]palladium (II) dichloromethane adduct (29.0 mg, 0.036 mmol) and THF (14.0 mL) was added followed by the addition of 1 M potassium carbonate solution (0.72 mL, 0.72 mmol). The reaction mixture was degassed with N$_2$ and then heated in a microwave at 140° C. for 30 minutes. The reaction mixture was diluted with MeOH and filtered through a plug of Na$_2$SO$_4$ and Celite™. The filtrate was concentrated. The product was purified by preparative HPLC-MS (pH 2) to afford 49 mg white solid which suffered some formation of trifluoroacetate ester. The product was then treated with aq. NH$_4$OH in MeCN, and was repurified by preparative HPLC-MS (pH 10) to afford product as the free base (24 mg, 31%). LCMS for $C_{16}H_{18}F_3N_6O_3S$ (M+H)$^+$: calculated m/z=431.1; found 431.2. $^1$H NMR (500 MHz, DMSO-d$_6$) δ 8.51 (br s, 2H), 7.96-7.87 (m, 2H), 7.83 (dd, J=8.1, 2.0 Hz, 1H), 7.62 (d, J=8.2 Hz, 1H), 4.67 (br s, 1H), 3.36-3.28 (m, 1H), 3.20-3.10 (m, 2H), 2.33 (s, 3H), 0.92 (d, 3H).

Example 250. 3-(4-Aminoimidazo[2,1-f][1,2,4]triazin-7-yl)-N-(3-cyanobicyclo[1.1.1]pentan-1-yl)-4-methylbenzenesulfonamide

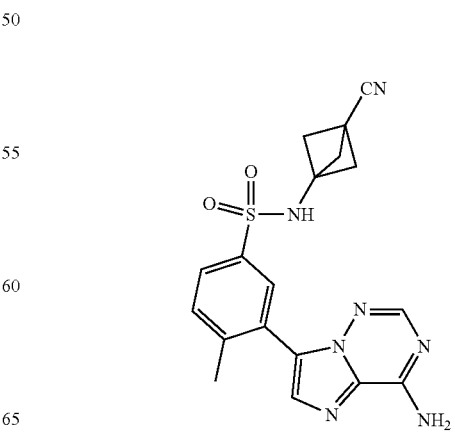

Step 1. 3-((tert-Butoxycarbonyl)amino)bicyclo[1.1.1]pentane-1-carboxylic Acid

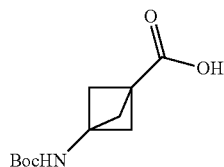 [SMILES: CC(C)(C)OC(=O)NC12CC(C(=O)O)(C1)C2]

A mixture of 3-aminobicyclo[1.1.1]pentane-1-carboxylic acid, HCl (500.0 mg, 3.06 mmol, PharmaBlock) and N,N-diisopropylethylamine (1.0 mL, 6.1 mmol) in THF (10 mL) and water (10 mL) was treated with di-tert-butyl dicarbonate (667 mg, 3.06 mmol). After stirring overnight, the reaction was treated with 1 N HCl to achieve pH 2 and was extracted with EtOAc. The combined organic extracts were washed with water, brine, dried over $Na_2SO_4$, filtered and concentrated to afford a white solid (665 mg, 96%). LCMS for $C_{11}H_{17}NO_4Na$ $(M+Na)^+$: calculated m/z=250.1; found 250.1.

Step 2. tert-Butyl 3-carbamoylbicyclo[1.1.1]pentan-1-ylcarbamate

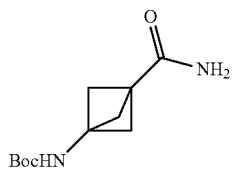 [SMILES: CC(C)(C)OC(=O)NC12CC(C(N)=O)(C1)C2]

A solution of 3-((tert-butoxycarbonyl)amino)bicyclo[1.1.1]pentane-1-carboxylic acid (660 mg, 2.90 mmol) in THF (15 mL) was treated with triethylamine (0.49 mL, 3.5 mmol). The resulting mixture was cooled to −15° C. and ethyl chloroformate (0.31 mL, 3.2 mmol) was added and the mixture was stirred for 1 h. To the mixture was added ammonium hydroxide (19.5 mL, 145 mmol) solution. After stirring for 3 hours, THF was evaporated and to the white crude solid was added water. The aqueous suspension was extracted with EtOAc (3×). The combined organic extracts (fine suspension) were dried over $Na_2SO_4$, and decanted (rather than filtered). The liquid decanted was concentrated to afford a white solid (0.65 g, 100%). LCMS for $C_{11}H_{18}N_2O_3Na$ $(M+Na)^+$: calculated m/z=249.1, found 249.2. $^1$H NMR (400 MHz, DMSO-$d_6$) δ 7.50 (br s, 1H), 7.21 (s, 1H), 6.91 (s, 1H), 2.02 (s, 6H), 1.38 (s, 9H).

Step 3. Tert-Butyl 3-cyanobicyclo[1.1.1]pentan-1-ylcarbamate

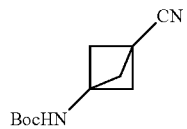

tert-Butyl (3-carbamoylbicyclo[1.1.1]pentan-1-yl)carbamate (200.0 mg, 0.884 mmol) in DCM and triethylamine (0.370 mL, 2.65 mmol) at 0° C. was treated with trichloroacetyl chloride (0.15 mL, 1.3 mmol). After 30 minutes, additional triethylamine (0.37 mL, 3.0 eq) and trichloroacetyl chloride (0.15 mL, 1.5 eq) were added. After 30 minutes, the reaction was quenched by the addition of sat'd. $NaHCO_3$ solution and the aqueous mixture was extracted with EtOAc. The combined organic extracts were dried over $Na_2SO_4$, filtered and concentrated. The residue was purified by flash chromatography, eluting with a gradient from 0-100% EtOAc in hexanes and ELSD was used to detect the product which was isolated as a white solid (107 mg, 58%). $^1$H NMR (400 MHz, CDCl$_3$) δ 5.08 (s, 1H), 2.49 (s, 6H), 1.46 (s, 9H).

Step 4. 3-Aminobicyclo[1.1.1]pentane-1-carbonitrile, Hydrochloric Acid Salt

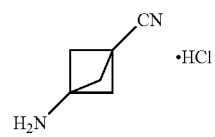

tert-Butyl (3-cyanobicyclo[1.1.1]pentan-1-yl)carbamate (0.050 g, 0.24 mmol) was stirred for 2 hours in 4 M HCl in dioxane (3.0 mL, 12.0 mmol). Volatiles were removed in vacuo to afford product (32 mg, 92%). $^1$H NMR (400 MHz, CD$_3$OD) δ 2.61 (s, 6H).

Step 5. 3-(4-Aminoimidazo[2,1-f][1,2,4]triazin-7-yl)-N-(3-cyanobicyclo[1.1.1]pentan-1-yl)-4-methyl-benzenesulfonamide To 3-aminobicyclo[1.1.1]pentane-1-carbonitrile, HCl salt (0.160 g, 1.11 mmol, prepared as in Step 4) and triethylamine (0.46 mL, 3.3 mmol) in DMA (15 mL) at 0° C. was added 3-(4-aminoimidazo[2,1-f][1,2,4]triazin-7-yl)-4-methylbenzenesulfonyl chloride (0.358 g, 1.11 mmol, Prepared as in Example 424, Step 7). The reaction was stirred for 2 hours at 0° C. The reaction mixture was poured into pH 7 buffer and EtOAc. The layers were separated and the aqueous layer was extracted with two further portions of EtOAc. The combined organic extracts were washed with water (3×), followed by brine, dried over sodium sulfate, filtered and concentrated. The product was purified by preparative HPLC-MS (pH 2) then repurified at (pH 10) (163 mg, 37%). LCMS for $C_{18}H_{18}N_7O_2S$ $(M+H)^+$: calculated m/z=396.1; found 396.1. $^1$H NMR (600 MHz, DMSO-$d_6$) δ 8.36 (s, 1H), 8.26 (s, 1H), 8.07 (s, 1H), 7.93 (d, J=2.0 Hz, 1H), 7.83 (s, 1H), 7.79 (dd, J=8.1, 2.0 Hz, 1H), 7.63 (d, J=8.2 Hz, 1H), 2.36 (s, 3H), 2.27 (s, 6H).

Example 251. 3-(4-Aminoimidazo[2,1-f][1,2,4]triazin-7-yl)-N-(4-cyanobicyclo[2.1.1]hexan-1-yl)-4-methylbenzenesulfonamide Trifluoroacetate Salt

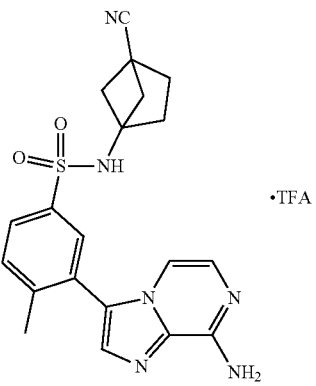 [SMILES: Cc1ccc(S(=O)(=O)NC23CCC(C#N)(C2)C3)cc1-c1cnc2c(N)nccn12]

Step 1. 3-((tert-butoxycarbonyl)amino)bicyclo[1.1.1]pentane-1-carboxylic Acid

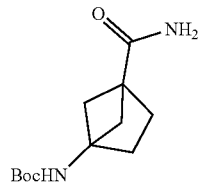 [SMILES: CC(C)(C)OC(=O)NC12CCC(C(N)=O)(C1)C2]

A solution of 4-((tert-butoxycarbonyl)amino)bicyclo[2.1.1]hexane-1-carboxylic acid (250 mg, 1.04 mmol) (Spirochem catalog #SPC-a643) and triethylamine (0.17 mL, 1.2 mmol) in THF (5 mL) at −15° C. was treated with ethyl chloroformate (0.109 mL, 1.14 mmol) and the reaction was stirred for 1 hour. To the mixture was added ammonium hydroxide (14.8 M, 7.0 mL, 52 mmol) in one portion. The reaction mixture was stirred at room temperature overnight. THF was evaporated, and to the white crude solid was added water. The aqueous suspension was extracted with EtOAc (3×). The combined organic extracts were dried over Na$_2$SO$_4$, filtered and concentrated to afford product as a white solid (219 mg, 88%). LCMS for C$_{12}$H$_{21}$N$_2$O$_3$ (M+H)$^+$: calculated m/z=241.2, found 241.3. $^1$H NMR (400 MHz, DMSO-d$_6$) δ 7.30 (br s, 1H), 7.07 (s, 1H), 6.83 (s, 1H), 1.93 (br, 2H), 1.70 (s, 4H), 1.49 (s, 2H), 1.38 (s, 9H).

Step 2. tert-Butyl (4-cyanobicyclo[2.1.1]hexan-1-yl)carbamate

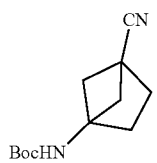 [SMILES: CC(C)(C)OC(=O)NC12CCC(C#N)(C1)C2]

tert-Butyl (4-carbamoylbicyclo[2.1.1]hexan-1-yl)carbamate (290 mg, 1.21 mmol) in DCM (20 mL) containing triethylamine (1.35 mL, 9.65 mmol) at 0° C. was treated with trichloroacetyl chloride (0.54 mL, 4.8 mmol). After 40 minutes, the reaction was quenched with saturated NaHCO$_3$ at 0° C. and the aqueous mixture was extracted with DCM. The organic extract was dried over MgSO$_4$, filtered and concentrated, and the residue was purified by flash chromatography (eluting with a gradient from 0-20% EtOAc/hexanes) to afford product as a white solid (230 mg, 86%). LCMS for C$_{12}$H$_{19}$N$_2$O$_2$ (M+H)$^+$: calculated m/z=223.1, found 223.1. $^1$H NMR (400 MHz, CD$_3$OD) δ 2.35 (br, 2H), 2.06-1.98 (m, 2H), 1.90-1.82 (m, 2H), 1.82-1.78 (m, 2H), 1.45 (s, 9H).

Step 3. 4-Aminobicyclo[2.1.1]hexane-1-carbonitrile, Hydrochloric Acid Salt

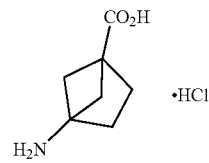

tert-Butyl (4-cyanobicyclo[2.1.1]hexan-1-yl)carbamate (0.99 g, 4.45 mmol, prepared as in Step 2) was dissolved in DCM (50 mL) and 4 N HCl in dioxane (11.1 mL, 44 mmol) was added. The mixture was stirred overnight and volatiles were removed in vacuo to afford product as a white solid (0.7 g, 100%). LCMS for C$_7$H$_{11}$N$_2$(M+H)$^+$: calculated m/z=123.1, found 123.2. $^1$H NMR (500 MHz, DMSO-d$_6$) δ 9.03 (s, 3H), 2.26-2.20 (m, 2H), 2.11-2.06 (m, 2H), 1.89-1.82 (m, 4H).

Step 4. 3-(4-Aminoimidazo[2,1-f][1,2,4]triazin-7-yl)-N-(4-cyanobicyclo[2.1.1]hexan-1-yl)-4-methylbenzenesulfonamide, Trifluoroacetate Salt 1 M Sodium carbonate (0.43 mL, 0.43 mmol) was added to a mixture of 4-aminobicyclo[2.1.1]hexane-1-carbonitrile, HCl salt (20.6 mg, 0.130 mmol) in DCM (0.6 mL) and acetonitrile (0.3 mL). The mixture was stirred for 5 minutes, then 3-(4-aminoimidazo[2,1-f][1,2,4]triazin-7-yl)-4-methylbenzenesulfonyl chloride (35 mg, 0.11 mmol, prepared as in Example 424, Step 7) was added and the reaction was stirred overnight. Purification via preparative HPLC-MS (pH 2) afforded product as the 1.4×TFA salt (44 mg, 71%). LCMS for C$_{19}$H$_{20}$N$_7$O$_2$S (M+H)$^+$: calculated m/z=410.1, found 410.1. $^1$H NMR (600 MHz, DMSO-d$_6$) δ 8.69 (s, 1H), 8.45 (s, 1H), 8.34 (s, 1H), 8.10 (s, 1H), 7.96 (d, J=2.1 Hz, 1H), 7.85 (s, 1H), 7.81 (dd, J=8.1, 2.1 Hz, 1H), 7.62 (d, J=8.2 Hz, 1H), 2.36 (s, 3H), 2.01-1.93 (m, 2H), 1.92-1.85 (m, 2H), 1.74-1.66 (m, 2H), 1.63-1.55 (m, 2H).

Example 252. 3-(8-Amino-6-(trifluoromethyl)imidazo[1,2-a]pyrazin-3-yl)-N-(4-hydroxybicyclo[2.1.1]hexan-1-yl)-4-(methyl-d₃)benzenesulfonamide

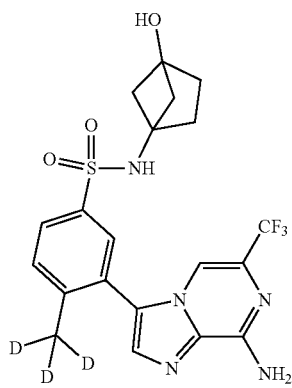 [SMILES: [2H]C([2H])([2H])c1ccc(S(=O)(=O)NC23CCC(O)(C2)C3)cc1-c1cnc2c(N)nc(C(F)(F)F)cn12]

Step 1. 4-Aminobicyclo[2.1.1]hexane-1-carboxylic Acid

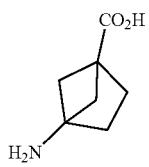

To 4-((tert-Butoxycarbonyl)amino)bicyclo[2.1.1]hexane-1-carboxylic acid (200.0 mg, 0.829 mmol, Spirochem) was added 4 N HCl in dioxane (1.0 mL, 4.0 mmol) and the reaction was stirred for 3 hours. Volatiles were removed in vacuo and the product was used crude in the next step (117 mg, 100%).

Step 2. 4-Hydroxybicyclo[2.1.1]hexane-1-carboxylic Acid

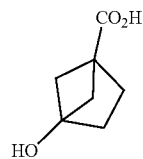

Sodium nitrite (182 mg, 2.63 mmol) in water (0.2 mL) was added dropwise to a 10° C. mixture of 4-aminobicyclo[2.1.1]hexane-1-carboxylic acid (117 mg, 0.829 mmol) and 10% acetic acid in water (1.2 mL). The mixture was then heated to 65° C. and stirred at this temperature overnight. The reaction mixture was then cooled to 5° C. and potassium hydroxide (370 mg, 6.6 mmol) in MeOH (0.8 mL) was added dropwise. The reaction was again heated to 65° C. for 3 hours. The reaction mixture was cooled to room temperature and water was added. The aqueous mixture was washed with EtOAc (2×). The aqueous layer was cooled to 0° C. and acidified by the addition of 1 N HCl to pH 3. This acidic aqueous mixture was extracted with EtOAc (4×). The organic extracts of the acidic aqueous layer were dried over MgSO₄, filtered and concentrated to afford product which was used without further purification (80.0 mg, 68%).

Step 3. Benzyl (4-hydroxybicyclo[2.1.1]hexan-1-yl) carbamate

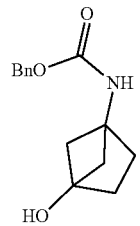 [SMILES: O=C(NC12CCC(O)(C1)C2)OCc1ccccc1]

4-Hydroxybicyclo[2.1.1]hexane-1-carboxylic acid (70.0 mg, 0.49 mmol) in toluene (1 mL) was cooled to 10° C. and was treated with benzyl alcohol (230 µL, 2.2 mmol). The reaction mixture was then treated with DIEA (150 µL, 0.86 mmol) and diphenylphosphoryl azide (115 µL, 0.54 mmol). The reaction mixture was then slowly heated to 110° C. overnight. The reaction mixture was concentrated to remove solvent and was partitioned between EtOAc and brine. The organic layer was dried over MgSO₄, filtered and concentrated. The residue was slurried in DCM and filtered to remove reagent byproducts and the filtrate was purified by flash chromatography, eluting with a gradient of 0-100% EtOAc in hexanes (50.0 mg, 41%). $^1$H NMR (400 MHz, CD₃OD) δ 7.47-7.15 (m, 5H), 5.14-5.01 (m, 2H), 1.88-1.77 (m, 4H), 1.76-1.72 (m, 2H), 1.72-1.63 (m, 2H).

Step 4. 4-Aminobicyclo[2.1.1]hexan-1-ol, Hydrochloric Acid Salt

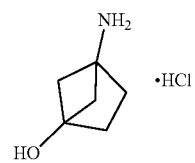

To a solution of benzyl (4-hydroxybicyclo[2.1.1]hexan-1-yl)carbamate (25 mg, 0.10 mmol) in MeOH (2 mL) and water (1 mL) was added palladium (10 mg of 10% on carbon) and the reaction mixture was shaken under H₂ at 30 psi for 3 hours. The reaction mixture was filtered and MeOH was removed in vacuo. The resulting aqueous mixture was adjusted to pH 3 by the addition of 1 N HCl and was washed with EtOAc to remove impurities. The aqueous mixture was then lyophilized to afford product as the HCl salt (7.0 mg, 47%).

Step 5. 3-(8-Amino-6-(trifluoromethyl)imidazo[1,2-a]pyrazin-3-yl)-N-(4-hydroxybicyclo[2.1.1]hexan-1-yl)-4-(methyl-d₃)benzenesulfonamide 4-Aminobicyclo[2.1.1]hexan-1-ol HCl salt (7 mg, 0.047 mmol) and DIPEA (8.17 µL, 0.047 mmol) were combined in DCM (0.6 mL) and cooled to 0° C. After stirring for 5 minutes, 3-(8-amino-6-(trifluoromethyl)imidazo[1,2-a]

pyrazin-3-yl)-4-(methyl-d₃)benzenesulfonyl chloride (14.7 mg, 0.037 mmol, prepared as in Example 253, Steps 1 through 3, using 3-bromo-6-(trifluoromethyl)imidazo[1,2-a]pyrazin-8-amine in Step 1) in 0.5 mL DMA was added. The reaction was allowed to warm to room temperature and the mixture was purified by preparative HPLC-MS (pH 10) to afford product as the free base (5.0 mg, 23%). LCMS for $C_{20}H_{18}D_3F_3N_5O_3S$ (M+H)⁺: calculated m/z=471.1, found 471.2. ¹H NMR (400 MHz, DMSO-d₆) δ 8.30 (br s, 1H), 7.86 (dd, J=8.1, 2.0 Hz, 1H), 7.83-7.80 (m, 2H), 7.71 (br s, 2H), 7.67 (d, J=8.1 Hz, 1H), 7.58 (s, 1H), 5.59 (br s, 1H), 1.65-1.57 (m, 2H), 1.48-1.40 (m, 4H), 1.37-1.31 (m, 2H).

Example 253. 3-(4-Aminoimidazo[2,1-f][1,2,4]triazin-7-yl)-N-(4-cyanobicyclo[2.1.1]hexan-1-yl)-4-(methyl-d₃)benzenesulfonamide (Crystalline Free Base)

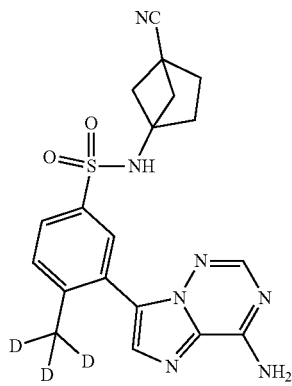 [SMILES: [2H]C([2H])([2H])c1ccc(S(=O)(=O)NC23CCC(C#N)(C2)C3)cc1-c1cnc2c(N)ncnn12]

Step 1. 4,4,5,5-Tetramethyl-2-(2-(methyl-d₃)phenyl)-1,3,2-dioxaborolane

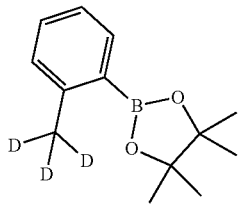 [SMILES: [2H]C([2H])([2H])c1ccccc1B1OC(C)(C)C(C)(C)O1]

A degassed mixture of 1-bromo-2-(methyl-d₃)benzene (0.57 g, 3.3 mmol, Combiphos catalog #032D), 4,4,4',4',5,5,5',5'-octamethyl-2,2'-bi(1,3,2-dioxaborolane) (1.25 g, 4.91 mmol, Aldrich), potassium acetate (1.06 g, 10.8 mmol) and 1,1'-bis(diphenylphosphino)ferrocene-palladium(II)dichloride dichloromethane complex (0.214 g, 0.262 mmol, Aldrich) in dioxane (16.4 mL) was heated to 110° C. for 3 hours. The reaction mixture was cooled to room temperature, diluted with DCM and filtered through Celite®, and the filtrate was concentrated. Purification via flash chromatography, eluting with a gradient of 0-10% EtOAc in hexanes afforded product (647 mg, 89%). LCMS for $C_{13}H_{17}D_3BO_2$ (M+H)⁺: calculated m/z=222.2, found 222.2.

Step 2. 7-(2-(methyl-d₃)phenyl)imidazo[2,1-f][1,2,4]triazin-4-amine

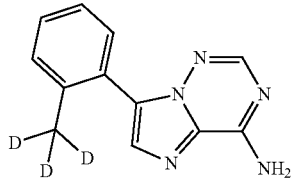

A microwave vial was charged with 4,4,5,5-tetramethyl-2-(2-(methyl-d₃)phenyl)-1,3,2-dioxaborolane (0.34 g, 1.5 mmol), 7-bromoimidazo[2,1-f][1,2,4]triazin-4-amine (0.395 g, 1.85 mmol, Synthonix), dichloro[1,1'-bis(diphenylphosphino)ferrocene]palladium (II) dichloromethane adduct (0.251 g, 0.308 mmol, Aldrich) and THF (10 mL) was added followed by the addition of 1 M aq. K₂CO₃ (4.6 mL, 4.6 mmol). The reaction mixture was degassed with N₂ and heated in an oil bath at 90° C. for 4 hours, then continued overnight at 80° C. Upon cooling to room temperature, the mixture was filtered and the solid white product (160 mg) was washed with DCM. Further product was isolated by removing solvent from the filtrate and isolation of the solid by filtration, washing with water and DCM (total: 217 mg, 62%). LCMS for $C_{12}H_9D_3N_5$(M+H)⁺: calculated m/z=229.1, found 229.1. ¹H NMR (400 MHz, DMSO-d₆) δ 8.20 (s, 2H), 8.04 (s, 1H), 7.68 (s, 1H), 7.52-7.23 (m, 4H).

Step 3. 3-(4-Aminoimidazo[2,1-f][1,2,4]triazin-7-yl)-4-(methyl-d₃)benzenesulfonyl Chloride

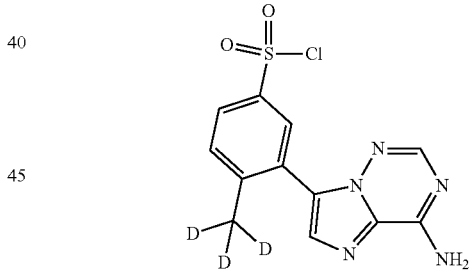

7-(2-(methyl-d₃)phenyl)imidazo[2,1-f][1,2,4]triazin-4-amine (214 mg, 0.937 mmol) in DCM (2 mL) was stirred at 0° C. for 10 minutes. Chlorosulfonic acid (0.44 mL, 6.6 mmol) was added dropwise. The ice bath was removed, and the reaction mixture was allowed to warm to room temperature. After 2.5 hours at room temperature, the mixture was heated for 2 hours in an 50° C. oil bath. Upon cooling, the reaction mixture was diluted with DCM (5 mL) and added to a stirring mixture of ice (10 g) and DCM (10 mL) kept in an ice-bath. The precipitated product was isolated by filtration and rinsed with DCM. The biphasic filtrate was extracted with DCM (2×), and the combined organic extracts were dried over Na₂SO₄, filtered, and concentrated and the solid so obtained was combined with the initial solid product isolated by filtration (total: 253 mg light yellow solid powder, 83%). LCMS for $C_{12}H_8D_3ClN_5O_2S$ (M+H)⁺: calculated m/z=327.0, found 327.1.

Figure 2:
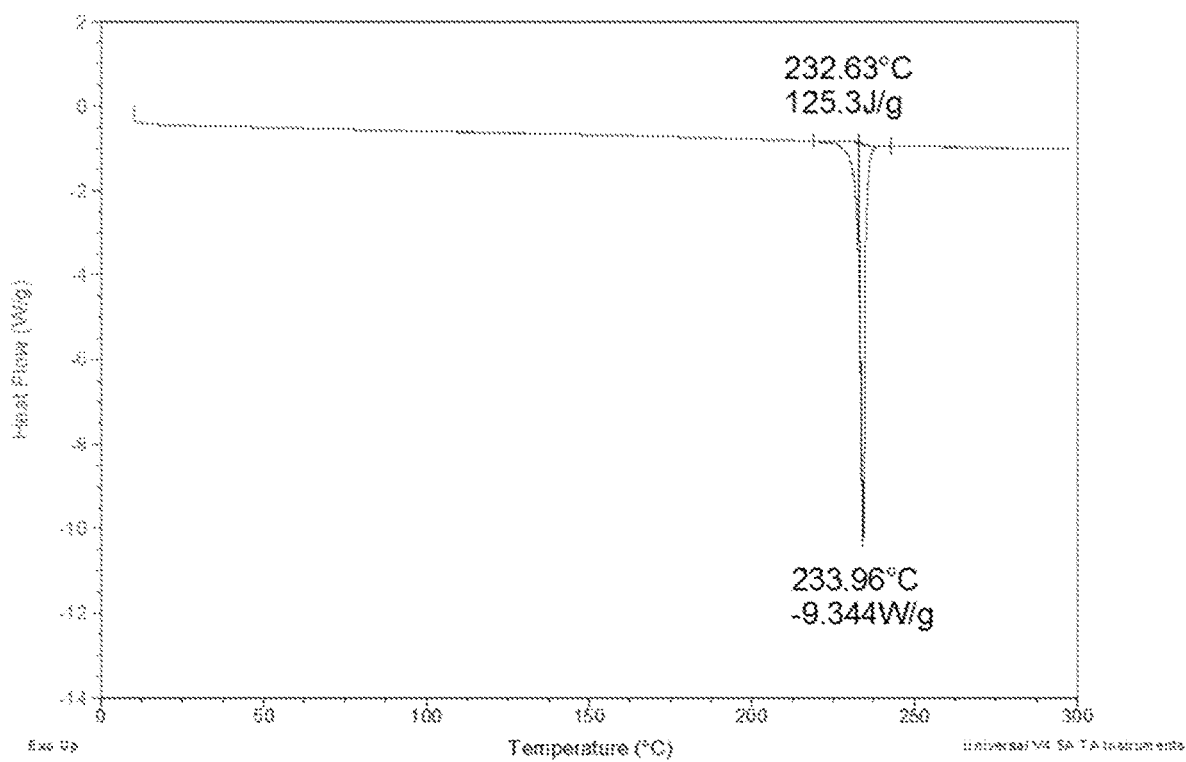
FIG. 2 shows a Differential Scanning Calorimetry (DSC) thermogram characteristic of the crystalline compound of Example 253.

Step 4. 3-(4-Aminoimidazo[2,1-f][1,2,4]triazin-7-yl)-N-(4-cyanobicyclo[2.1.1]hexan-1-yl)-4-(methyl-d₃)benzenesulfonamide To 4-aminobicyclo[2.1.1]hexane-1-carbonitrile, HCl (2.60 g, 16.4 mmol, prepared as in Example 251, Step 3) in a mixture of DCM (82 mL) and acetonitrile (82 mL) was added 1 M aq. Na₂CO₃ (65 mL, 65 mmol). After stirring for 5 minutes, 3-(4-aminoimidazo[2,1-f][1,2,4]triazin-7-yl)-4-(methyl-d₃)benzenesulfonyl chloride (5.62 g, 17.2 mmol, prepared as in Step 3) was added. The suspension was stirred overnight. EtOAc (300 mL) and brine (150 mL) were added. The layers were separated and the aqueous layer was extracted with EtOAc (4×300 mL). The combined EtOAc extracts were dried over Na₂SO₄, filtered and concentrated to give crude product as an off-white solid (5.8 g). The product was purified by flash chromatography in batches, eluting with a slow gradient of 0-5% MeOH in DCM to give a white solid (5.1 g). The purified product was then slurried in acetone (51 mL) overnight. The product as the crystalline free base was isolated by filtration and air dried to afford the desired product as a white powder (4.5 g, 66%). Crystalline free base was characterized by XRPD. The X-Ray Powder Diffraction (XRPD) was obtained from Bruker D2 PHASER X-ray Powder Diffractometer (XRPD) instrument. The general experimental procedures for XRPD were: (1) X-ray radiation from copper at 1.054056 Å with $K_\beta$ filter and LYNXEYE™ detector; (2) X-ray power at 30 kV, 10 mA; and (3) the sample powder was dispersed on a zero-background sample holder. The general measurement conditions for XRPD were: Start Angle 5 degrees; Stop Angle 30 degrees; Sampling 0.015 degrees; and Scan speed 2 degree/min. The XRPD pattern is shown in FIG. 1 and the XRPD data are provided in Table 6. LCMS for $C_{19}H_{17}D_3N_7O_2S$ (M+H)⁺: calculated m/z=413.2, found 413.2. ¹H NMR (400 MHz, DMSO-d₆) δ 8.68 (s, 1H), 8.34 (s, 1H), 8.25 (s, 1H), 8.08 (s, 1H), 7.97 (d, J=2.0 Hz, 1H), 7.83 (s, 1H), 7.81 (dd, J=8.1, 2.1 Hz, 1H), 7.62 (d, J=8.1 Hz, 1H), 2.03-1.93 (m, 2H), 1.93-1.81 (m, 2H), 1.78-1.67 (m, 2H), 1.67-1.55 (m, 2H). Crystalline free base was characterized by DSC. The DSC was obtained from TA Instruments Differential Scanning Calorimetry, Model Q2000 with autosampler. The DSC instrument conditions were as follows: 10-300° C. at 10° C./min; Tzero aluminum sample pan and lid; and nitrogen gas flow at 50 mL/min. The DSC thermogram is shown in FIG. 2. The DSC thermogram revealed one endothermal event at an onset temperature of 232.6° C. with a peak temperature of 234.0° C. which is believed to be the melting/decomposition of the compound. Crystalline free base was characterized by TGA. The TGA was obtained from PerkinElmer Thermogravimetric Analyzer, Model Pyris 1. The general experimental conditions for TGA were: ramp from 20° C. to 300° C. at 10° C./min; nitrogen purge gas flow at 60 mL/min; ceramic crucible sample holder. The TGA thermogram is shown in FIG. 3. A weight loss of about 0.4% between 150° C. and 250° C. which is believed to be the decomposition. The compound further decomposes above 250° C.

TABLE 6

| 2-Theta (°) | Net Intensity | Relative Intensity (%) |
|---|---|---|
| 7.9 | 1446 | 6.4 |
| 8.4 | 2441 | 10.9 |
| 9.3 | 770 | 3.4 |
| 10.5 | 1655 | 7.4 |

TABLE 6-continued

| 2-Theta (°) | Net Intensity | Relative Intensity (%) |
|---|---|---|
| 12.0 | 2110 | 9.4 |
| 12.3 | 1167 | 5.2 |
| 12.5 | 828 | 3.7 |
| 12.7 | 275 | 1.2 |
| 13.0 | 143 | 0.6 |
| 13.5 | 1778 | 7.9 |
| 14.4 | 329 | 1.5 |
| 15.3 | 2464 | 11.0 |
| 15.7 | 283 | 1.3 |
| 16.5 | 858 | 3.8 |
| 16.9 | 22415 | 100 |
| 17.3 | 2564 | 11.4 |
| 17.6 | 6542 | 29.2 |
| 17.4 | 2272 | 10.1 |
| 18.6 | 873 | 3.9 |
| 18.8 | 340 | 1.5 |
| 19.4 | 2394 | 10.7 |
| 19.9 | 1960 | 8.7 |
| 20.6 | 3902 | 17.4 |
| 21.0 | 616 | 2.7 |
| 21.1 | 561 | 2.5 |
| 21.3 | 324 | 1.4 |
| 21.9 | 700 | 3.1 |
| 22.2 | 548 | 2.4 |
| 22.6 | 169 | 0.8 |
| 23.2 | 1528 | 6.8 |
| 23.6 | 278 | 1.2 |
| 23.9 | 1350 | 6.0 |
| 24.1 | 1139 | 5.1 |
| 24.4 | 1049 | 4.7 |
| 24.9 | 8538 | 38.1 |
| 25.5 | 1651 | 7.4 |
| 26.1 | 291 | 1.3 |
| 26.2 | 469 | 2.1 |
| 26.5 | 3588 | 16.0 |
| 27.1 | 1837 | 8.2 |
| 27.6 | 169 | 0.8 |
| 28.1 | 168 | 0.7 |
| 28.6 | 900 | 4.0 |
| 29.3 | 180 | 0.8 |

Example 254. 3-(4-Aminoimidazo[2,1-f][1,2,4]triazin-7-yl)-N-(4-cyanobicyclo[2.1.1]hexan-1-yl)-4-(methyl-d₃)benzenesulfonamide Crystalline Hydrochloric Acid Salt

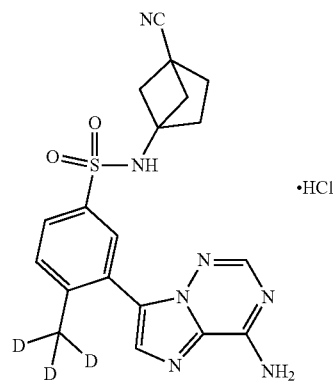 [SMILES: [2H]C([2H])([2H])c1ccc(S(=O)(=O)NC23CCC(C#N)(C2)C3)cc1-c1cnc2c(N)ncnn12 ; Cl]

Figure 5:
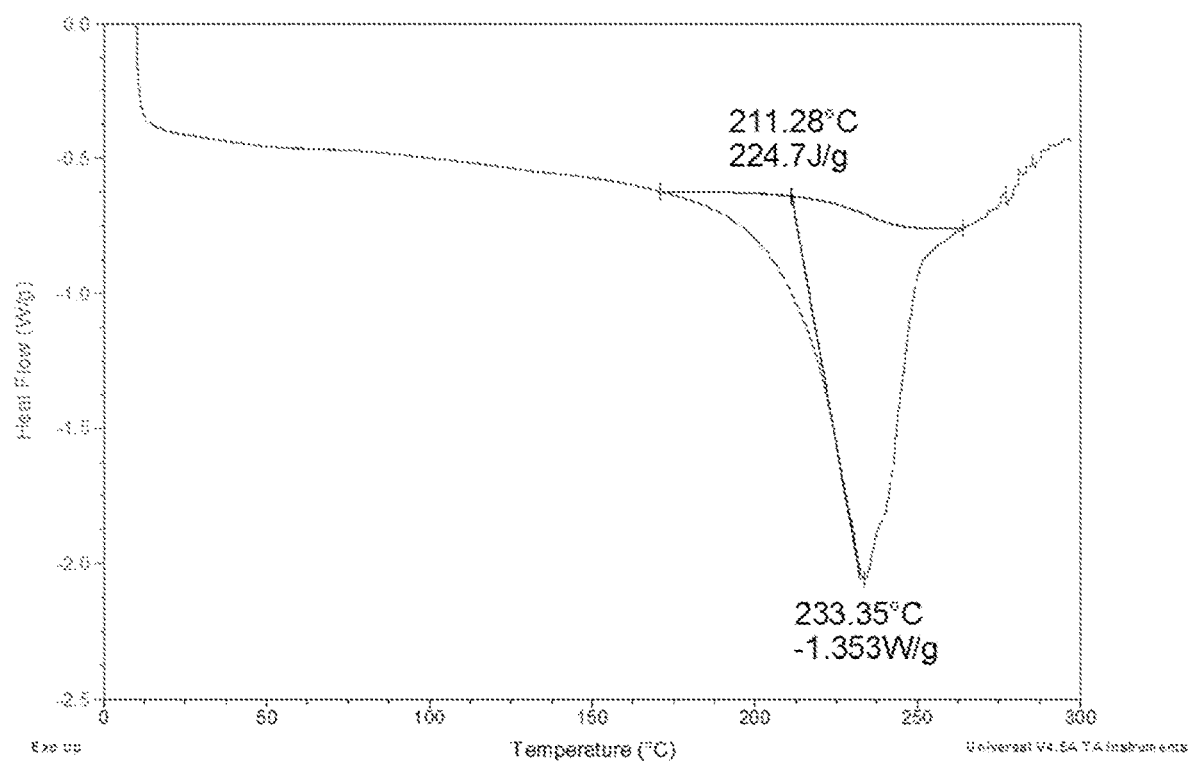
FIG. 5 shows a Differential Scanning Calorimetry (DSC) thermogram characteristic of the crystalline hydrochloric acid salt of Example 254.

Hydrochloric acid (1.07 mL, 2.67 mmol) (2.5 M solution in EtOH) was added to a suspension of 3-(4-aminoimidazo[2,1-f][1,2,4]triazin-7-yl)-N-(4-cyanobicyclo[2.1.1]hexan-1-yl)-4-(methyl-d₃)benzenesulfonamide (1.0 g, 2.4 mmol, from Example 253) in acetone (40.0 mL). The solvent was removed from the solution in vacuo to afford a solid. Ethyl acetate (9.9 mL, 100 mmol) was added and the mixture was stirred at room temperature for 2.5 hours. The solid was isolated by filtration and dried on funnel under house vacuum for 2 hours, followed by overnight under vacuum/ $N_2$ stream. (1.02 g, 94%). The hydrochloric acid salt was shown to be a 1:1 salt by chloride titration and was characterized by XRPD. Experimental parameters for acquiring the XRPD data are as described in Example 253. The XRPD pattern is shown in FIG. 4 and the XRPD data are provided in Table 7. LCMS for $C_{19}H_{17}D_3N_7O_2S$ (M+H)$^+$: calculated m/z=413.2, found 413.0. $^1$H NMR (500 MHz, DMSO-d$_6$) δ 8.91 (s, 1H), 8.75 (s, 1H), 8.74 (s, 1H), 8.20 (s, 1H), 7.99 (s, 1H), 7.96 (d, J=2.0 Hz, 1H), 7.84 (dd, J=8.1, 2.1 Hz, 1H), 7.64 (d, J=8.1 Hz, 1H), 2.02-1.93 (m, 2H), 1.92-1.84 (m, 2H), 1.74-1.66 (m, 2H), 1.63-1.56 (m, 2H). Crystalline hydrochloric acid salt was characterized by DSC. Experimental parameters for acquiring the DSC data are as described in Example 253. The DSC thermogram is shown in FIG. 5. The DSC thermogram revealed one major endothermal event at an onset temperature of 211.3° C. with a peak temperature of 233.4° C. which is believed to be the melting/decomposition of the compound. Crystalline hydrochloric acid salt was characterized by TGA. Experimental parameters for acquiring the TGA data are as described in Example 253. The TGA thermogram is shown in FIG. 6. A weight loss of about 6.8% below 220° C. in the first step and a weight loss of about 2.7% between 220° C. and 300° C. in the second step were observed and believed to be associated with the decomposition of the compound.

TABLE 7

| 2-Theta (°) | Net Intensity | Relative Intensity (%) |
|---|---|---|
| 7.1 | 228 | 3.8 |
| 9.7 | 563 | 9.4 |
| 9.9 | 1507 | 25.2 |
| 11.3 | 57 | 0.9 |
| 12.5 | 205 | 3.4 |
| 13.4 | 4704 | 78.6 |
| 14.1 | 1625 | 27.1 |
| 15.1 | 445 | 7.4 |
| 15.6 | 348 | 5.8 |
| 15.8 | 1475 | 24.6 |
| 16.1 | 3276 | 54.7 |
| 16.2 | 1874 | 31.3 |
| 16.5 | 1138 | 19.0 |
| 17.4 | 5988 | 100 |
| 18.0 | 4434 | 74.0 |
| 19.3 | 746 | 12.5 |
| 19.9 | 378 | 6.3 |
| 20.9 | 384 | 6.4 |
| 21.3 | 711 | 11.9 |
| 21.7 | 1938 | 32.4 |
| 22.0 | 3390 | 56.6 |
| 22.4 | 1107 | 18.5 |
| 23.4 | 776 | 13.0 |
| 23.9 | 83 | 1.4 |
| 24.5 | 1039 | 17.4 |
| 25.3 | 804 | 13.4 |
| 26.4 | 805 | 13.4 |
| 26.8 | 1201 | 20.1 |
| 27.9 | 1298 | 21.7 |
| 29.2 | 598 | 10.0 |

Example 255. 3-(4-Aminoimidazo[2,1-f][1,2,4]triazin-7-yl)-N-(4-cyanobicyclo[2.1.1]hexan-1-yl)-4-(methyl-d$_3$)benzenesulfonamide Crystalline Benzenesulfonic Acid Salt

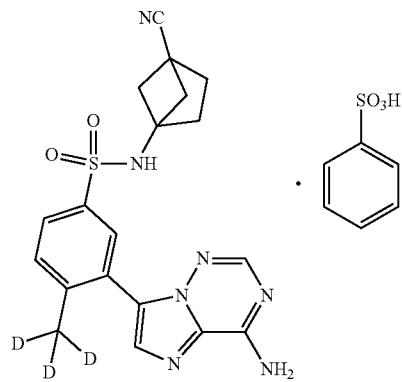

Figure 8:
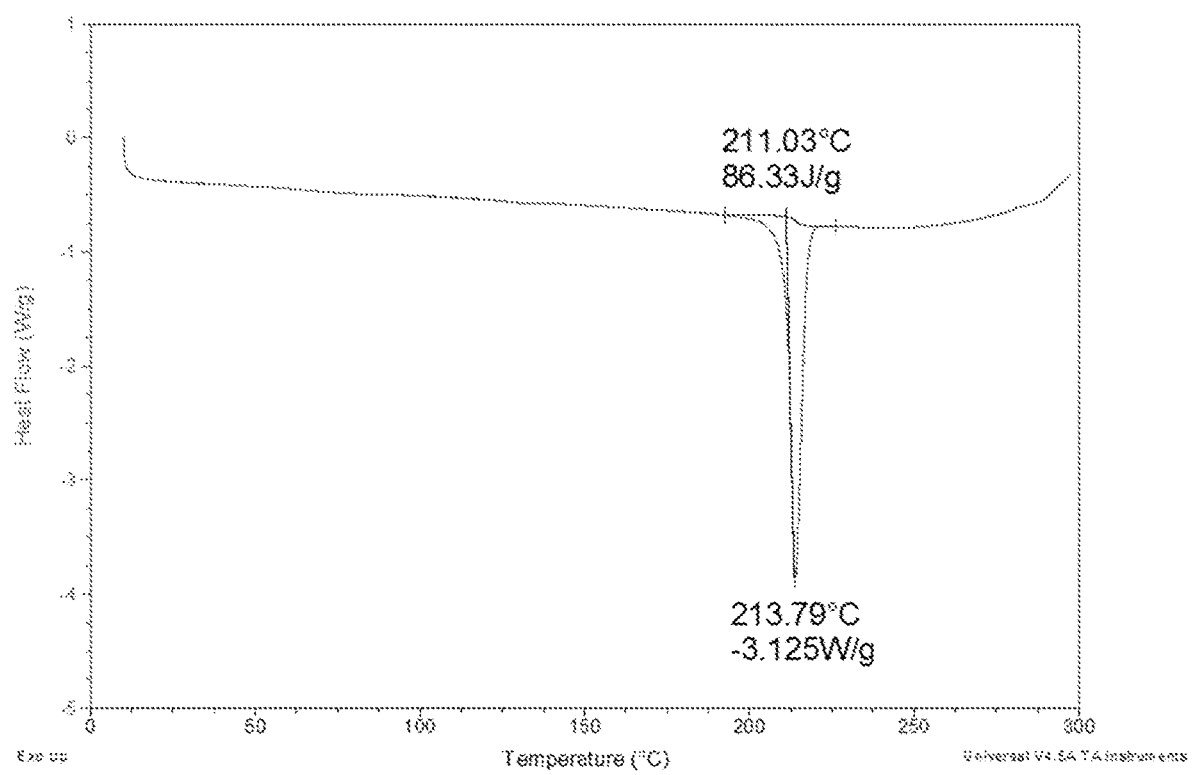
FIG. 8 shows a Differential Scanning Calorimetry (DSC) thermogram characteristic of the crystalline benzenesulfonic acid salt of Example 255.

To 3-(4-aminoimidazo[2,1-f][1,2,4]triazin-7-yl)-N-(4-cyanobicyclo[2.1.1]hexan-1-yl)-4-(methyl-d$_3$)benzenesulfonamide (1.00 g, 2.424 mmol, from Example 253) in acetone (40.0 mL) was added benzenesulfonic acid in THF (1 M, 2.67 mL, 2.67 mmol) to obtain a solution. The acetone was removed in vacuo and the solid was slurried in ethyl acetate (10 mL) and was stirred for 1.5 hours. The solid was isolated by filtration, washed with a small amount of EtOAc and hexanes. The solid product was air dried for 2 hours and under vacuum/N$_2$ stream overnight at 50° C. (1.3 g, 94%). The benzenesulfonic acid salt was shown to be a 1:1 salt by $^1$H NMR and was characterized by XRPD. Experimental parameters for acquiring the XRPD data are as described in Example 253. The XRPD pattern is shown in FIG. 7 and the XRPD data are provided in Table 8. LCMS for $C_{19}H_{17}D_3N_7O_2S$ (M+H)$^+$: calculated m/z=413.2, found 413.1. $^1$H NMR (400 MHz, CD$_3$OD) δ 8.30 (s, 1H), 8.04 (d, J=2.0 Hz, 1H), 8.01 (s, 1H), 7.93 (dd, J=8.2, 2.1 Hz, 1H), 7.88-7.82 (m, 2H), 7.65 (d, J=8.2 Hz, 1H), 7.48-7.40 (m, 3H), 2.15-2.05 (m, 2H), 1.99-1.91 (m, 2H), 1.86-1.79 (m, 2H), 1.69-1.60 (m, 2H). Crystalline besylate salt was characterized by DSC. Experimental parameters for acquiring the DSC data are as described in Example 253. The DSC thermogram is shown in FIG. 8. The DSC thermogram revealed one endothermal event at an onset temperature of 211.0° C. with a peak temperature of 213.8° C. which is believed to be the melting/decomposition of the compound. Crystalline besylate salt was characterized by TGA. Experimental parameters for acquiring the TGA data are as described in Example 253. The TGA thermogram is shown in FIG. 9. A weight loss of about 0.4% between 150° C. and 230° C. was observed in the first step and followed by a significant weight loss above 230° C. which is believed to be associated with the decomposition of the compound.

TABLE 8

| 2-Theta (°) | Net Intensity | Relative Intensity (%) |
|---|---|---|
| 6.5 | 1795 | 26.7 |
| 8.0 | 374 | 5.6 |
| 8.9 | 83 | 1.2 |
| 9.9 | 5204 | 77.5 |
| 10.5 | 5702 | 84.9 |
| 11.2 | 809 | 12.0 |

TABLE 8-continued

| 2-Theta (°) | Net Intensity | Relative Intensity (%) |
|---|---|---|
| 12.2 | 477 | 7.1 |
| 13.1 | 621 | 9.3 |
| 14.3 | 808 | 12.0 |
| 14.8 | 3627 | 54.0 |
| 15.8 | 3818 | 56.9 |
| 16.5 | 4198 | 62.5 |
| 16.7 | 6714 | 100 |
| 17.1 | 4294 | 64.0 |
| 17.3 | 1001 | 14.9 |
| 17.9 | 591 | 8.8 |
| 18.6 | 2402 | 35.8 |
| 18.9 | 4034 | 60.1 |
| 19.2 | 2278 | 33.9 |
| 19.8 | 2131 | 31.7 |
| 20.3 | 1593 | 23.7 |
| 21.0 | 694 | 10.3 |
| 21.2 | 1626 | 24.2 |
| 21.8 | 918 | 13.7 |
| 22.2 | 2303 | 34.3 |
| 22.8 | 3238 | 48.2 |
| 23.6 | 2104 | 31.3 |
| 23.9 | 729 | 10.9 |
| 24.5 | 2109 | 31.4 |
| 24.9 | 2275 | 33.9 |
| 26.0 | 726 | 10.8 |
| 25.9 | 1789 | 26.6 |
| 26.3 | 986 | 14.7 |
| 26.8 | 353 | 5.3 |
| 27.1 | 197 | 2.9 |
| 27.7 | 562 | 8.4 |
| 28.5 | 1018 | 15.2 |
| 28.7 | 572 | 8.5 |
| 29.2 | 482 | 7.2 |
| 29.7 | 569 | 8.5 |

Example 256. 5-(4-Aminoimidazo[2,1-f][1,2,4]triazin-7-yl)-N-(4-cyanobicyclo[2.1.1]hexan-1-yl)-6-methylpyridine-3-sulfonamide Trifluoroacetate Salt

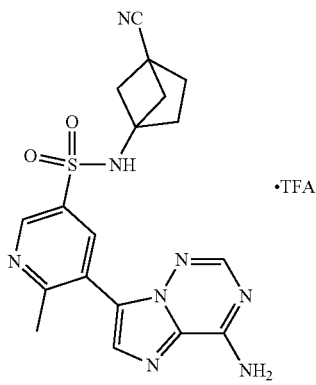 [SMILES: Cc1ncc(S(=O)(=O)NC23CCC(C#N)(C2)C3)cc1-c1cnc2c(N)ncnn12 ; "·TFA"]

Step 1. 5-Bromo-6-methylpyridine-3-sulfonyl Chloride

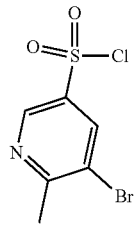

A round-bottom flask was charged with water (7.5 mL, 41 mmol) and cooled in an ice bath. To this was added thionyl chloride (1.23 mL, 16.9 mmol) over 15 minutes. The reaction mixture was then warmed to room temperature using a warm water bath, and copper(I) chloride (0.018 g, 0.18 mmol) was added. The reaction mixture was placed in a brine-ice bath.

Concurrently in a separate round-bottom flask, 5-bromo-6-methylpyridin-3-amine (0.686 g, 3.67 mmol, Combi-Blocks) was dissolved in 12 N HCl (7.3 mL, 88 mmol). After a few minutes, white solids were observed. This mixture was also placed in a brine-ice bath. A solution of sodium nitrite (0.278 g, 4.03 mmol) in water (0.99 mL, 55 mmol) was added over 1-2 minutes, giving dissolution of solids. After stirring for 5 minutes, this mixture was slowly added (over 5 minutes) to the thionyl chloride solution generated above. After 2 hours, the reaction mixture was warmed to room temperature and stirred for 1 hour. DCM (15 mL) and DI water (25 mL) were added to the reaction mixture. Solid sodium bicarbonate (11.1 g, 132 mmol) was added in portions until pH 7. Water and ethyl acetate were added and the layers were separated. The aqueous layer was extracted with EtOAc (2×). The combined organic extracts were washed with brine, dried with magnesium sulfate, filtered, and concentrated to give a brown oil, which was used without further purification (440 mg, 44%).

Step 2. 5-Bromo-N-(4-cyanobicyclo[2.1.1]hexan-1-yl)-6-methylpyridine-3-sulfonamide

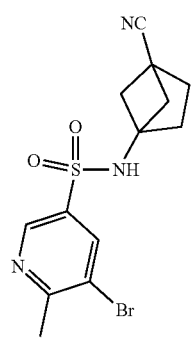 [SMILES: Cc1ncc(S(=O)(=O)NC23CCC(C#N)(C2)C3)cc1Br]

4-Aminobicyclo[2.1.1]hexane-1-carbonitrile, HCl salt (36 mg, 0.23 mmol) in DCM (2 mL) containing DIPEA (0.097 mL, 0.55 mmol) was cooled to 0° C. and stirred for 5 minutes, at which time 5-bromo-6-methylpyridine-3-sulfonyl chloride (50.0 mg, 0.185 mmol, from Step 1) in DCM (0.5 mL) was added. After 1 hour, water was added and the layers were separated. The aqueous layer was extracted with EtOAc (3×). The combined organic extracts were washed with brine, dried over MgSO$_4$, filtered and concentrated. The product was purified by flash chromatography, eluting with a gradient from 0-100% EtOAc in hexanes to provide desired product as a clear oil (50.0 mg, 62%). LCMS for C$_{13}$H$_{15}$BrN$_3$O$_2$S (M+H)$^+$: calculated m/z=356.0, found 356.1. $^1$H NMR (400 MHz, CD$_3$OD) δ 8.84 (d, J=2.0 Hz, 1H), 8.37 (d, J=2.0 Hz, 1H), 2.75 (s, 3H), 2.19-2.07 (m, 2H), 2.01-1.94 (m, 2H), 1.85-1.74 (m, 2H), 1.74-1.62 (m, 2H).

Step 3. N-(4-Cyanobicyclo[2.1.1]hexan-1-yl)-6-methyl-5-(4,4,5,5-tetramethyl-1,3,2-dioxaborolan-2-yl)pyridine-3-sulfonamide

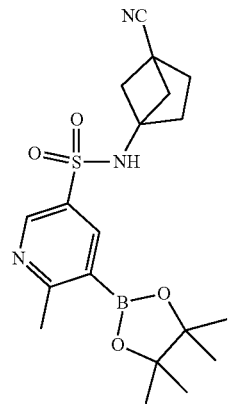 [SMILES: Cc1ncc(S(=O)(=O)NC23CCC(C#N)(C2)C3)cc1B1OC(C)(C)C(C)(C)O1]

A microwave vial was charged with bis(pinacolato)diboron (0.036 g, 0.14 mmol, Aldrich), potassium acetate (0.045 g, 0.46 mmol) and 5-bromo-N-(4-cyanobicyclo[2.1.1]hexan-1-yl)-6-methylpyridine-3-sulfonamide (0.050 g, 0.14 mmol) as a solution in THF (2 mL). The reaction mixture was sparged with nitrogen for 5 minutes. To this mixture was added bis(triphenylphosphine)palladium(II)chloride (0.099 g, 0.14 mmol), and the mixture was sealed and heated to 80° C. overnight. Upon cooling to room temperature, the reaction mixture was diluted with EtOAc and washed with water. The organic layer was washed with brine, dried over MgSO$_4$, filtered and concentrated to afford product, which was used without further purification (55 mg, 97%). LCMS for C$_{19}$H$_{27}$BN$_3$O$_4$S (M+H)$^+$: calculated m/z=404.2, found 404.1.

Step 4. 5-(4-Aminoimidazo[2,1-f][1,2,4]triazin-7-yl)-N-(4-cyanobicyclo[2.1.1]hexan-1-yl)-6-methylpyridine-3-sulfonamide, Trifluoroacetate Salt To a degassed mixture of 7-bromoimidazo[2,1-f][1,2,4]triazin-4-amine (6.4 mg, 0.030 mmol), 1,1'-bis(diphenylphosphino)ferrocene-palladium(II)dichloride dichloromethane complex (2.4 mg, 3.0 μmol, Aldrich), and N-(4-cyanobicyclo[2.1.1]hexan-1-yl)-6-methyl-5-(4,4,5,5-tetramethyl-1,3,2-dioxaborolan-2-yl)pyridine-3-sulfonamide (12 mg, 0.030 mmol) in THF (1.0 mL) was added Na$_2$CO$_3$ (7.9 mg, 0.074 mmol) in water (0.2 mL), and the reaction was heated to 80° C. for 3 hours. The reaction mixture was diluted with MeOH, filtered and purified via preparative HPLC-MS (pH 2) to afford product as the TFA salt (6 mg, 40%). LCMS for C$_{18}$H$_{19}$N$_8$O$_2$S (M+H)$^+$: calculated m/z=411.1, found 411.1. $^1$H NMR (400 MHz, CD$_3$OD) δ 8.97 (d, J=2.2 Hz, 1H), 8.47 (d, J=2.3 Hz, 1H), 8.16 (s, 1H), 7.91 (s, 1H), 2.67 (s, 3H), 2.22-2.13 (m, 2H), 2.01-1.92 (m, 2H), 1.92-1.82 (m, 2H), 1.80-1.67 (m, 2H).

Example 257. 5-(8-amino-6-(trifluoromethyl)imidazo[1,2-a]pyrazin-3-yl)-N-(4-cyanobicyclo[2.1.1]hexan-1-yl)-6-methylpyridine-3-sulfonamide

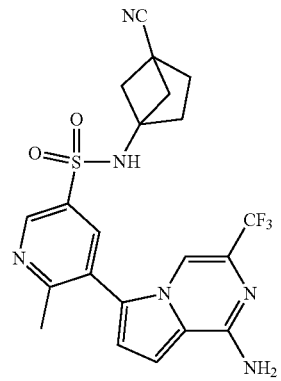 [SMILES: Cc1ncc(S(=O)(=O)NC23CCC(C#N)(C2)C3)cc1-c1ccc2c(N)nc(C(F)(F)F)cn12]

Prepared as in Example 256 using 3-bromo-6-(trifluoromethyl)imidazo[1,2-a]pyrazin-8-amine (Example 472, Step 6) in Step 4 followed by purification via preparative HPLC-MS (pH 10) to afford the title compound (6 mg, 30%). LCMS for C$_{20}$H$_{19}$F$_3$N$_7$O$_2$S (M+H)$^+$: calculated m/z=478.1, found 478.2. $^1$H NMR (400 MHz, CD$_3$OD) δ 9.05 (d, J=2.3 Hz, 1H), 8.27 (d, J=2.3 Hz, 1H), 7.84 (s, 1H), 7.75 (s, 1H), 2.54 (s, 3H), 2.21-2.12 (m, 2H), 2.03-1.90 (m, 2H), 1.90-1.79 (m, 2H), 1.79-1.69 (m, 2H).

Example 258. 3-(4-Amino-6-methylimidazo[2,1-f][1,2,4]triazin-7-yl)-N-(4-cyanobicyclo[2.1.1]hexan-1-yl)benzenesulfonamide Trifluoroacetate Salt

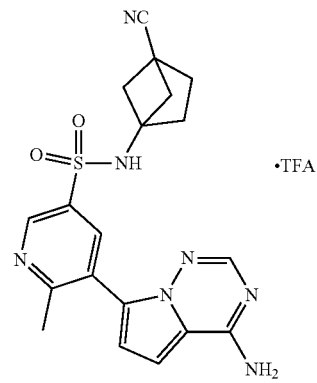 [SMILES: Cc1ncc(S(=O)(=O)NC23CCC(C#N)(C2)C3)cc1-c1ccc2c(N)ncnn12]

Step 1. 3-Bromo-N-(4-cyanobicyclo[2.1.1]hexan-1-yl)benzenesulfonamide

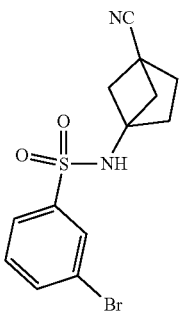 [SMILES: N#CC12CCC(NS(=O)(=O)c3cccc(Br)c3)(C1)C2]

1 M Na$_2$CO$_3$ solution (0.78 mL, 0.78 mmol) was added to 4-aminobicyclo[2.1.1]hexane-1-carbonitrile, HCl salt (37 mg, 0.24 mmol, from 251, Step 3) in DCM (1.0 mL) and acetonitrile (0.5 mL). After 5 minutes, 3-bromobenzenesulfonyl chloride (0.028 mL, 0.196 mmol, Combi-Blocks) was added. The reaction was allowed to warm to room temperature and was stirred overnight. The layers were separated and the aqueous layer was extracted with two portions of DCM. The combined organic extracts were dried over sodium sulfate, filtered and concentrated. Flash chromatography, eluting with a gradient from 0-100% EtOAc in hexanes and using ELSD for detection afforded purified product (64 mg, 96%). LCMS for C$_{13}$H$_{14}$BrN$_2$O$_2$S (M+H)$^+$: calculated m/z=341.0, found 341.0.

Step 2. N-(4-Cyanobicyclo[2.1.1]hexan-1-yl)-3-(4,4,5,5-tetramethyl-1,3,2-dioxaborolan-2-yl)benzenesulfonamide

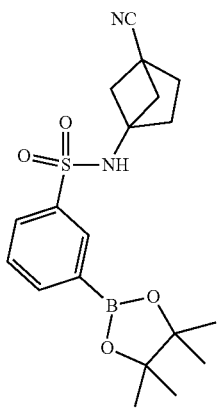 [SMILES: CC1(C)OB(c2cccc(S(=O)(=O)NC34CCC(C#N)(C3)C4)c2)OC1(C)C]

A mixture of 3-bromo-N-(4-cyanobicyclo[2.1.1]hexan-1-yl)benzenesulfonamide (64.0 mg, 0.188 mmol), 4,4,4',4',5,5,5',5'-octamethyl-2,2'-bi(1,3,2-dioxaborolane) (61.9 mg, 0.244 mmol), potassium acetate (61 mg, 0.62 mmol) and dichlorobis(triphenylphosphine)-palladium(II) (5.3 mg, 7.5 µmol) in THF (1.9 mL) was degassed and the mixture was heated in a microwave at 140° C. for 30 minutes. Upon cooling to room temperature, the reaction mixture was diluted with water and EtOAc. The layers were separated and the aqueous portion was extracted with two further portions of EtOAc. The combined organic extracts were washed with brine and dried over sodium sulfate, filtered and concentrated. The product was used without further purification in Step 3. LCMS for C$_{19}$H$_{26}$BN$_2$O$_4$S (M+H)$^+$: calculated m/z=389.2, found 389.2.

Step 3. 3-(4-Aminoimidazo[2,1-f][1,2,4]triazin-7-yl)-N-(4-cyanobicyclo[2.1.1]hexan-1-yl)benzenesulfonamide

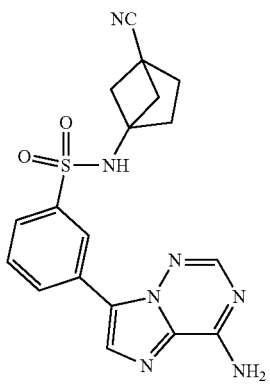 [SMILES: N#CC12CCC(NS(=O)(=O)c3cccc(-c4cnc5c(N)ncnn45)c3)(C1)C2]

A microwave vial was charged with N-(4-cyanobicyclo[2.1.1]hexan-1-yl)-3-(4,4,5,5-tetramethyl-1,3,2-dioxaborolan-2-yl)benzenesulfonamide (70.0 mg, 0.180 mmol), 7-bromoimidazo[2,1-f][1,2,4]triazin-4-amine (46 mg, 0.22 mmol, Synthonix) and THF (1.8 mL), followed by the addition of 1 M aq. K$_2$CO$_3$ (0.54 mL, 0.54 mmol). The reaction mixture was degassed and heated to 90° C. for 3.5 hours. Upon cooling to room temperature, the reaction mixture was partitioned between water and EtOAc. The aqueous layer was extracted with two further portions of EtOAc. The combined organic extracts were dried over sodium sulfate, filtered and concentrated. The product was purified by flash chromatography, eluting with a gradient from 0-100% EtOAc in hexanes to afford a white solid (68 mg, 95%). LCMS for C$_{18}$H$_{18}$N$_7$O$_2$S (M+H)$^+$: calculated m/z=396.1, found 396.1.

Step 4. 3-(4-Amino-6-bromoimidazo[2,1-f][1,2,4]triazin-7-yl)-N-(4-cyanobicyclo[2.1.1]hexan-1-yl)benzenesulfonamide

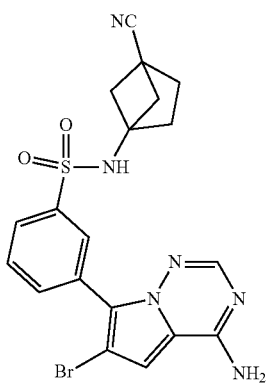 [SMILES: N#CC12CCC(NS(=O)(=O)c3cccc(-c4c(Br)cc5c(N)ncnn45)c3)(C1)C2]

A solution of 3-(4-aminoimidazo[2,1-f][1,2,4]triazin-7-yl)-N-(4-cyanobicyclo[2.1.1]hexan-1-yl)benzenesulfonamide (68 mg, 0.17 mmol) and N-bromosuccinimide (37 mg, 0.21 mmol) in DMF (1.5 mL) was heated to 50° C. for 2 hours. Upon cooling to room temperature, the reaction mixture was diluted with EtOAc, washed with water and brine, dried over Na$_2$SO$_4$, filtered and concentrated. The residue was purified by flash chromatography, eluting with a gradient from 0-100% EtOAc/hexanes to afford product (23 mg, 28%). LCMS for C$_{18}$H$_{17}$BrN$_7$O$_2$S (M+H)$^+$: calculated m/z=474.0, found 474.1.

Step 5. 3-(4-amino-6-methylimidazo[2,1-f][1,2,4]triazin-7-yl)-N-(4-cyanobicyclo[2.1.1]hexan-1-yl)benzenesulfonamide, Trifluoroacetate Salt To a degassed solution of 3-(4-amino-6-bromoimidazo[2,1-f][1,2,4]triazin-7-yl)-N-(4-cyanobicyclo[2.1.1]hexan-1-yl)benzenesulfonamide (0.010 g, 0.021 mmol) in THF (0.5 mL) was added tetrakis(triphenylphosphine)palladium(0) (2.4 mg, 2.1 μmol), followed by 2.0 M trimethylaluminum in hexanes (0.032 mL, 0.063 mmol). The reaction was sealed and heated to 100° C. for 45 minutes. Additional trimethylaluminum (2.0 M in hexanes, 0.032 mL, 0.063 mmol) was introduced, and heating was continued for 2 hours. Upon cooling to room temperature, a few drops of water were added and MeCN was added to make the mixture monophasic. The mixture was stirred until gas evolution subsided and then was filtered, diluted with methanol, and the mixture was purified by preparative HPLC-MS (pH 2) to afford product as the trifluoroacetate salt (7.0 mg, 60%). LCMS for C$_{19}$H$_{20}$N$_7$O$_2$S (M+H)$^+$: calculated m/z=410.1, found 410.2. $^1$H NMR (400 MHz, CD$_3$OD) δ 8.32-8.28 (m, 1H), 8.15 (s, 1H), 7.99-7.94 (m, 2H), 7.77 (t, J=7.9 Hz, 1H), 2.59 (s, 3H), 2.18-2.10 (m, 2H), 2.01-1.92 (m, 2H), 1.89-1.80 (m, 2H), 1.72-1.61 (m, 2H).

Example 259. 3-(4-Amino-2-cyclopropylimidazo[2,1-f][1,2,4]triazin-7-yl)-N-(4-(hydroxymethyl)bicyclo[2.1.1]hexan-1-yl)-4-methylbenzenesulfonamide Trifluoroacetate Salt

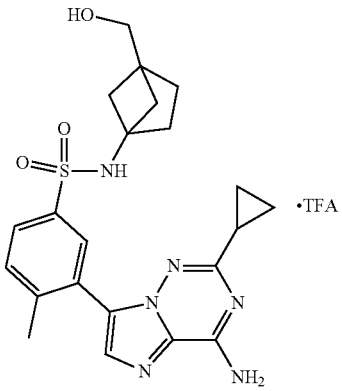 [SMILES: Cc1ccc(S(=O)(=O)NC23CCC(CO)(C2)C3)cc1-c1cnc2c(N)nc(C3CC3)nn12]

Step 1. 2-Cyclopropylimidazo[2,1-f][1,2,4]triazin-4-ol

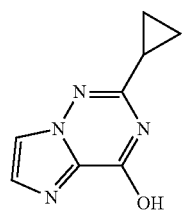 [SMILES: Oc1nc(C2CC2)nn2ccnc12]

Dry HCl gas was bubbled through a solution of ethyl 1-amino-1H-imidazole-2-carboxylate (0.240 g, 1.55 mmol, prepared as in US2015/0274767) and cyclopropanecarbonitrile (0.519 g, 7.73 mmol, Alfa Aesar) in dioxane (2.4 mL) for 2 minutes, during which time the solution became a suspension, then returned to a solution. This solution was heated in a sealed reaction vial to 110° C. for 5.5 hours. Upon cooling to room temperature, solvent was evaporated to afford a sticky solid, which was triturated with EtOAc and stirred overnight and the solid product was filtered off and air dried. LCMS for C$_8$H$_9$N$_4$O (M+H)$^+$: calculated m/z=177.1, found 177.1.

Step 2. 7-Bromo-2-cyclopropylimidazo[2,1-f][1,2,4]triazin-4-ol

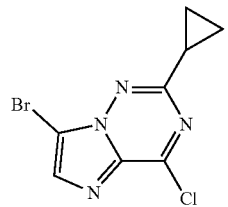 [SMILES: Clc1nc(C2CC2)nn2c(Br)cnc12]

A solution of 2-cyclopropylimidazo[2,1-f][1,2,4]triazin-4-ol (0.330 g, 1.87 mmol, prepared as in Step 1) in DMF (10.0 mL) was treated with NBS (0.367 g, 2.06 mmol) and the mixture was stirred at room temperature for 2 hours. The reaction mixture was diluted with water and sodium thiosulfate solution was added. 1 N HCl was added to achieve pH 3 and the aqueous mixture was extracted with four portions of EtOAc (4×50 mL). The combined organic extracts were dried over sodium sulfate, filtered and concentrated to afford a solid which was azeotroped with heptane on the rotovap to afford an off-white solid. LCMS for C$_8$H$_8$BrN$_4$O (M+H)$^+$: calculated m/z=255.0, found 255.0.

Step 3. 7-Bromo-4-chloro-2-cyclopropylimidazo[2,1-f][1,2,4]triazine

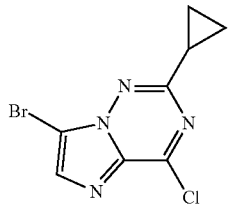 [SMILES: Clc1nc(C2CC2)nn2c(Br)cnc12]

7-Bromo-2-cyclopropylimidazo[2,1-f][1,2,4]triazin-4-ol (0.378 g, 1.48 mmol) was heated in POCl$_3$ (6.9 mL, 74 mmol) to 110° C. overnight and the reaction was less than half complete. N,N-dimethylaniline (0.19 mL, 1.5 mmol) and tetraethylammonium chloride (0.491 g, 2.96 mmol) were added. The reaction mixture was sealed and heating was continued for 2 hours, at which point the reaction was complete. POCl$_3$ was removed on the rotovap and the residue was poured onto crushed ice, then the aqueous mixture was made basic by the addition of solid NaHCO$_3$. The aqueous mixture was extracted with EtOAc (3×). The combined organic extracts were dried over sodium sulfate, filtered and concentrated. The product was used without further purification. LCMS for $C_8H_7BrClN_4$ (M+H)$^+$: calculated m/z=273.0, found 273.0.

Step 4. 7-Bromo-2-cyclopropylimidazo[2,1-f][1,2,4]triazin-4-amine

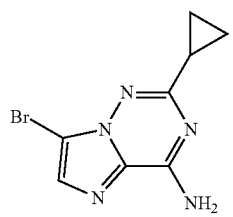 [SMILES: Nc1nc(C2CC2)nn2c(Br)cnc12]

A suspension of 7-bromo-4-chloro-2-cyclopropylimidazo[2,1-f][1,2,4]triazine (0.512 g, 1.87 mmol, prepared as in Step 3) in ammonium hydroxide (14.8 M, 13 mL, 190 mmol) was heated to 80° C. for 30 minutes, then at room temperature overnight. Brine was added and the mixture was extracted with EtOAc (3×). The combined organic extracts were dried over $Na_2SO_4$, filtered and concentrated. The product was purified by flash chromatography, eluting with a gradient from 0-100% EtOAc in hexanes to obtain desired product as white solid (140 mg, 29%). LCMS for $C_8H_9BrN_5$ (M+H)$^+$: calculated m/z=254.0, found 254.0. $^1$H NMR (400 MHz, CDCl$_3$) δ 7.52 (s, 1H), 2.14 (tt, J=8.2, 4.8 Hz, 1H), 1.11 (dt, J=6.1, 3.1 Hz, 2H), 1.01 (dt, J=8.2, 3.1 Hz, 2H).

Step 5. (4-Aminobicyclo[2.1.1]hexan-1-yl)methanol Trifluoroacetate Salt

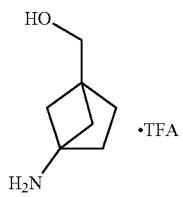

Ethyl chloroformate (0.131 mL, 1.37 mmol) was added dropwise to a solution of 4-((tert-butoxycarbonyl)amino)bicyclo[2.1.1]hexane-1-carboxylic acid (0.300 g, 1.24 mmol, Enamine catalog #EN300-70833) and triethylamine (0.26 mL, 1.9 mmol) in THF (5 mL) at −5° C. The reaction was stirred for 30 minutes at this temperature. The solid formed was filtered and washed with 2 mL THF. The pooled washings and filtrate were cooled to 0° C. and treated with sodium borohydride (141 mg, 3.73 mmol) in one portion followed by MeOH (2 mL), added dropwise. After 30 minutes, the reaction mixture was quenched by the addition of water and 2N HCl. The layers were separated, and the aqueous layer was extracted several times with EtOAc. The combined organic extracts were dried over MgSO$_4$, filtered and concentrated. LCMS for $C_8H_{14}NO_3$ (M-$^t$Bu+H)$^+$: calculated m/z=172.1, found 172.1.

tert-Butyl (4-(hydroxymethyl)bicyclo[2.1.1]hexan-1-yl)carbamate obtained above was dissolved in DCM (1 mL), trifluoroacetic acid (0.96 mL, 12.0 mmol) was added and reaction was stirred for 2 hours. Volatiles were removed in vacuo to afford product as the trifluoroacetate salt (0.15 g, 55%). LCMS for $C_7H_{14}NO$ (M+H)$^+$: calculated m/z=128.1, found 128.1.

Step 6. N-(4-(Hydroxymethyl)bicyclo[2.1.1]hexan-1-yl)-4-methyl-3-(4,4,5,5-tetramethyl-1,3,2-dioxaborolan-2-yl)benzenesulfonamide

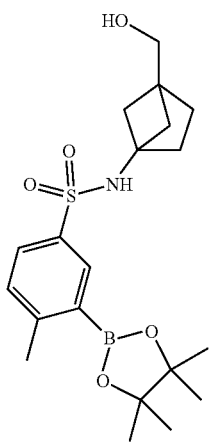 [SMILES: Cc1ccc(S(=O)(=O)NC23CCC(CO)(C2)C3)cc1B1OC(C)(C)C(C)(C)O1]

Prepared from (4-aminobicyclo[2.1.1]hexan-1-yl)methanol Trifluoroacetate Salt analogously to the procedure for Example 249, Steps 1 through 2. LCMS for $C_{20}H_{31}BNO_5S$ (M+H)$^+$: calculated m/z=408.2, found 408.1.

Step 7. 3-(4-Amino-2-cyclopropylimidazo[2,1-f][1,2,4]triazin-7-yl)-N-(4-(hydroxymethyl)bicyclo[2.1.1]hexan-1-yl)-4-methylbenzenesulfonamide, Trifluoroacetate Salt 1,1'-Bis(diphenylphosphino)ferrocene-palladium(II)dichloride dichloromethane complex (1.6 mg, 2.0 μmol) was added to a degassed mixture of 7-bromo-2-cyclopropylimidazo[2,1-f][1,2,4]triazin-4-amine (5.0 mg, 0.020 mmol), N-(4-(hydroxymethyl)bicyclo[2.1.1]hexan-1-yl)-4-methyl-3-(4,4,5,5-tetramethyl-1,3,2-dioxaborolan-2-yl)benzenesulfonamide (8.0 mg, 0.020 mmol, from Step 6), and sodium carbonate (6.2 mg, 0.059 mmol) in dioxane (2 mL) and water (1 mL) and the mixture was heated to 120° C. for 3 hours. The reaction was diluted with MeOH and purified via preparative HPLC-MS (pH 2) to obtain the desired product as a white solid (1.0 mg, 9%). LCMS for $C_{22}H_{27}N_6O_3S$ (M+H)$^+$: calculated m/z=455.2, found 455.1.

Example 260. 3-(4-Aminoimidazo[2,1-f][1,2,4]triazin-7-yl)-4-cyano-N-(4-cyanobicyclo[2.1.1]hexan-1-yl)benzenesulfonamide Trifluoroacetate Salt

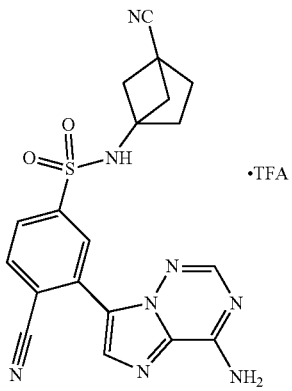 [SMILES: N#Cc1ccc(S(=O)(=O)NC23CCC(C#N)(C2)C3)cc1-c1cnc2c(N)ncnn12]

Step 1. 7-(2-Chlorophenyl)imidazo[2,1-f][1,2,4]triazin-4-amine

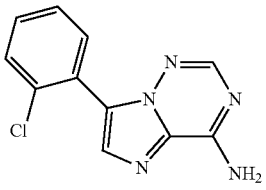 [SMILES: Nc1ncnn2c(-c3ccccc3Cl)cnc12]

A degassed mixture of 7-bromoimidazo[2,1-f][1,2,4]triazin-4-amine (96 mg, 0.45 mmol, Synthonix), (2-chlorophenyl)boronic acid (0.070 g, 0.45 mmol, Aldrich) and 1,1'-bis(diphenylphosphino)ferrocene-palladium(II)dichloride dichloromethane complex (37 mg, 0.045 mmol) in dioxane (2 mL) and sodium carbonate (142 mg, 1.34 mmol) in water (1 mL) was heated to 120° C. for 3 hours. Upon cooling, the reaction mixture was diluted with water and EtOAc and the phases were separated. The product was identified as present in the aqueous layer as a suspension. The aqueous layer was filtered and the off white solid was air dried (0.100 g, 91%). LCMS for $C_{11}H_9ClN_5$ (M+H)$^+$: calculated m/z=246.1, found 246.1.

Step 2. 3-(4-Aminoimidazo[2,1-f][1,2,4]triazin-7-yl)-4-chlorobenzenesulfonyl Chloride

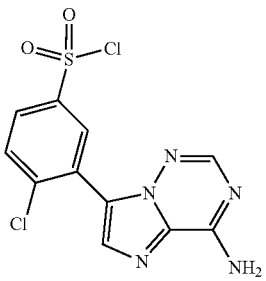 [SMILES: Nc1ncnn2c(-c3cc(S(=O)(=O)Cl)ccc3Cl)cnc12]

7-(2-Chlorophenyl)imidazo[2,1-f][1,2,4]triazin-4-amine (0.030 g, 0.12 mmol) in DCM (10 mL) and under $N_2$ at 0° C. was treated with chlorosulfonic acid (0.081 mL, 1.22 mmol), added dropwise. The ice bath was removed. The mixture was warmed to room temperature and stirred for 1 hour, followed by heating to 50° C. overnight. The reaction mixture was diluted with DCM and added to stirred ice water. After the ice melted, layers were separated and the aqueous layer was extracted with DCM (2×). The combined extracts were dried over $MgSO_4$, filtered and concentrated. The product was purified by flash chromatography, eluting with a gradient from 0-100%, EtOAc in Hexanes, and was isolated as a light yellow oil (0.030 g, 71%). LCMS for $C_{11}H_8Cl_2N_5O_2S$ (M+H)$^+$: calculated m/z=344.0, found 344.0.

Step 3. 3-(4-Aminoimidazo[2,1-f][1,2,4]triazin-7-yl)-4-chloro-N-(4-cyanobicyclo[2.1.1]hexan-1-yl)benzenesulfonamide

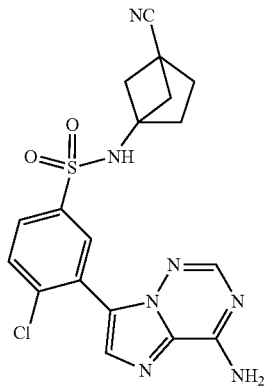 [SMILES: N#CC12CCC(NS(=O)(=O)c3ccc(Cl)c(-c4cnc5c(N)ncnn45)c3)(C1)C2]

To 4-aminobicyclo[2.1.1]hexane-1-carbonitrile, HCl (8.3 mg, 0.052 mmol, from Example 251, Step 3) in DCM (0.6 mL) and acetonitrile (0.3 mL) was added 1 M $Na_2CO_3$ (0.17 mL, 0.17 mmol). The mixture was stirred for 5 minutes, then 3-(4-aminoimidazo[2,1-f][1,2,4]triazin-7-yl)-4-chlorobenzenesulfonyl chloride (15 mg, 0.044 mmol) was added. DMA (1 mL) was added to aid solubility. The reaction was stirred for 2 hours. Purification via flash chromatography, eluting with a gradient from 0-100% EtOAc in hexanes) afforded product as colorless oil. (0.015 g, 80%). LCMS for $C_{18}H_{17}ClN_7O_2S$ (M+H)$^+$: calculated m/z=430.1, found 430.1.

Step 4. 3-(4-Aminoimidazo[2,1-f][1,2,4]triazin-7-yl)-4-cyano-N-(4-cyanobicyclo[2.1.1]hexan-1-yl)benzenesulfonamide, Trifluoroacetate Salt A degassed mixture of 3-(4-aminoimidazo[2,1-f][1,2,4]triazin-7-yl)-4-chloro-N-(4-cyanobicyclo[2.1.1]hexan-1-yl)benzenesulfonamide (15 mg, 0.035 mmol), tris(dibenzylideneacetone)dipalladium(0) (1.6 mg, 1.7 μmol), 2-dicyclohexylphosphino-2',6'-dimethoxybiphenyl (1.4 mg, 3.5 μmol), and zinc cyanide (8.2 mg, 0.070 mmol) in a mixture of DMF (2 mL) and water (20 μL) was heated in microwave at 150° C. for 30 minutes. The crude reaction mixture was filtered and purified via preparative HPLC-MS (pH 2) to afford product as a white solid (5.0 mg, 27%). LCMS for $C_{19}H_{17}N_8O_2S$ (M+H)$^+$: calculated m/z=421.1, found 421.1. $^1$H NMR (600 MHz, DMSO-$d_6$) δ 9.09 (s, 1H), 8.52 (s, 1H), 8.49 (d, J=1.7 Hz, 1H), 8.43 (s, 1H), 8.28 (d, J=8.3 Hz, 1H), 8.19 (s, 1H), 8.14 (s, 1H), 8.02 (dd, J=8.2, 1.9 Hz, 1H), 2.07-1.99 (m, 2H), 1.93-1.87 (m, 2H), 1.76-1.70 (m, 2H), 1.69-1.63 (m, 2H).

Example 261. 3-(4-Aminoimidazo[2,1-f][1,2,4]triazin-7-yl)-N-(4-cyanobicyclo[2.1.1]hexan-1-yl)-N-methyl-4-(methyl-d₃)benzenesulfonamide

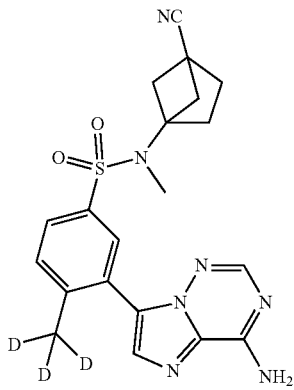 [SMILES: [2H]C([2H])([2H])c1ccc(S(=O)(=O)N(C)C23CCC(C#N)(C2)C3)cc1-c1cnc2c(N)ncnn12]

Step 1. 4-(Methylamino)bicyclo[2.1.1]hexane-1-carbonitrile, Hydrochloric Acid Salt

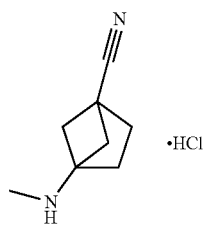

Sodium hydride (60% in mineral oil, 1.2 mg, 0.049 mmol) was added to a mixture of tert-butyl (4-cyanobicyclo[2.1.1]hexan-1-yl)carbamate (0.010 g, 0.045 mmol, prepared as in Example 251, Step 2) in DMF (1 mL) at 0° C. After the reaction mixture was stirred for 5 minutes, it was treated with methyl iodide (3 µL, 0.05 mmol). After stirring for 2 hours at 0° C., water was added and the mixture was extracted with EtOAc. The organic extract was washed with brine, dried over MgSO₄, filtered and concentrated. The crude product was treated with HCl (4M in dioxane) (0.5 mL, 2 mmol) and was stirred for 1 hour. Volatiles were removed in vacuo and the product was used without further purification in Step 2. Theoretical yield was assumed. LCMS for $C_8H_{13}N_2(M+H)^+$: calculated m/z=137.1, found 137.2.

Step 2. 3-(4-Aminoimidazo[2,1-f][1,2,4]triazin-7-yl)-N-(4-cyanobicyclo[2.1.1]hexan-1-yl)-N-methyl-4-(methyl-d₃)benzenesulfonamide To 4-(methylamino)bicyclo[2.1.1]hexane-1-carbonitrile, HCl (5 mg, 0.03 mmol, from Step 1) in DCM (0.6 mL) was added Hunig's base (5 µL, 0.03 mmol) and the mixture was cooled to 0° C. After stirring for 5 minutes, 3-(4-aminoimidazo[2,1-f][1,2,4]triazin-7-yl)-4-(methyl-d₃)benzenesulfonyl chloride (7.6 mg, 0.023 mmol, Example 253, Step 3) in 0.5 mL DMA was added. The mixture was allowed to warm to room temperature over 30 minutes, and the product was purified by preparative HPLC-MS (pH 10) to afford a white solid (4.0 mg, 30%). LCMS for $C_{20}H_{19}D_3N_7O_2S$ $(M+H)^+$: calculated m/z=427.2, found 427.2. ¹H NMR (400 MHz, DMSO-d₆) δ 8.34 (s, 1H), 8.25 (s, 1H), 8.09 (s, 1H), 7.97 (d, J=2.0 Hz, 1H), 7.85 (s, 1H), 7.80 (dd, J=8.1, 2.0 Hz, 1H), 7.64 (d, J=8.1 Hz, 1H), 2.82 (s, 3H), 2.19-2.07 (m, 2H), 2.02-1.85 (m, 4H), 1.71-1.54 (m, 2H).

The following Examples provided in Tables 9-19 were prepared according to Method A or Method B, unless otherwise noted.

TABLE 9

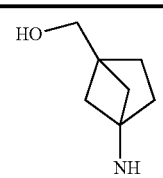

| Ex. No. | Name | -N(R)₂ | LCMS [M + H]⁺ |
|---|---|---|---|
| 262ᴬ | 3-(8-Amino-6-methylimidazo[1,2-a]pyrazin-3-yl)-N-(4-(hydroxymethyl)bicyclo[2.1.1]hexan-1-yl)-4-methylbenzenesulfonamide | | 428.1 |

NMR Spectra

¹H NMR (400 MHz, CD₃OD) δ 7.95 (dd, J = 8.1, 1.8 Hz, 1H), 7.85 (d, J = 1.7 Hz, 1H), 7.64 (d, J = 8.1 Hz, 1H), 7.61 (s, 1H), 7.06 (s, 1H), 3.54 (s, 2H), 2.28 (s, 3H), 2.25 (s, 3H), 1.82-1.71 (m, 2H), 1.59-1.51 (m, 2H), 1.51-1.42 (m, 2H), 1.26-1.13 (m, 2H)

TABLE 9-continued

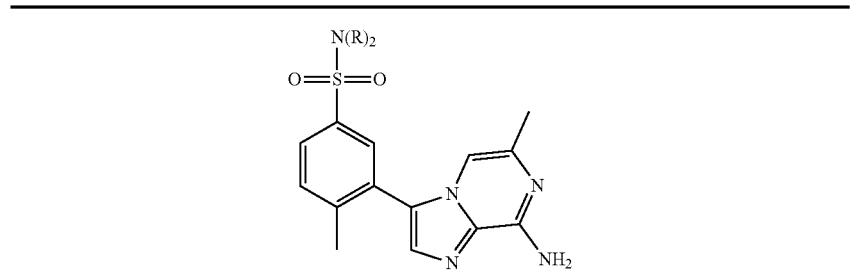

| Ex. No. | Name<br>NMR Spectra | −N(R)₂ | LCMS [M + H]⁺ |
|---|---|---|---|
| 263$^A$ | 3-(8-Amino-6-methylimidazo[1,2-a]pyrazin-3-yl)-N-(4-cyanobicyclo[2.1.1]hexan-1-yl)-4-methylbenzenesulfonamide trifluoroacetate salt | 4-cyanobicyclo[2.1.1]hexan-1-yl-NH | 423.2 |

$^1$H NMR (400 MHz, DMSO-$d_6$) δ 8.77 (s, 1H), 7.94-7.91 (m, 2H), 7.78 (d, J = 1.6 Hz, 1H), 7.71 (d, J = 8.2 Hz, 1H), 7.25 (s, 1H), 2.25 (s, 6H), 2.02-1.93 (m, 2H), 1.93-1.84 (m, 2H), 1.74-1.66 (m, 2H), 1.66-1.53 (m, 2H)

| 264$^B$ | 3-(8-Amino-6-methylimidazo[1,2-a]pyrazin-3-yl)-N-(3-cyanobicyclo[1.1.1]pentan-1-yl)-4-methylbenzenesulfonamide trifluoroacetate salt | 3-cyanobicyclo[1.1.1]pentan-1-yl-NH | 409.1 |

TABLE 10

| Ex. No. | Name<br>NMR Spectra | −N(R)₂ | LCMS [M + H]⁺ |
|---|---|---|---|
| 265$^B$ | 3-(4-Amino-2-methylimidazo[1,2-f][1,2,4]triazin-7-yl)-N-(4-cyanobicyclo[2.1.1]hexan-1-yl)-4-methylbenzenesulfonamide trifluoroacetate salt | 4-cyanobicyclo[2.1.1]hexan-1-yl-NH | 424.1 |

$^1$H NMR (400 MHz, DMSO-$d_6$) δ 8.71 (s, 1H), 8.40 (s, 1H), 8.28 (s, 1H), 7.95 (d, J = 1.9 Hz, 1H), 7.81 (dd, J = 8.1, 2.0 Hz, 1H), 7.79 (s, 1H), 7.62 (d, J = 8.2 Hz, 1H), 2.36 (s, 3H), 2.30 (s, 3H), 2.02-1.93 (m, 2H), 1.93-1.84 (m, 2H), 1.74-1.68 (m, 2H), 1.64-1.56 (m, 2H)

TABLE 10-continued

| Ex. No. | Name NMR Spectra | -N(R)₂ | LCMS [M + H]⁺ |
|---|---|---|---|
| 266[A] | 3-(4-Amino-2-methylimidazo[1,2-f][1,2,4]triazin-7-yl)-4-methyl-N-(3,3,3-trifluoro-2-hydroxypropyl)benzenesulfonamide (single enantiomer isolated) | CF₃ group with CH(OH)CH₂NH | 431.1 |
| | ¹H NMR (600 MHz, DMSO-d₆) δ 8.21 (s, 1H), 8.13 (s, 1H), 7.91 (d, J = 2.0 Hz, 1H), 7.79 (dd, J = 8.1, 2.0 Hz, 1H), 7.73 (s, 1H), 7.62 (d, J = 8.2 Hz, 1H), 6.63 (br s, 1H), 4.10-3.96 (m, 1H), 3.06 (dd, J = 13.6, 4.1 Hz, 1H), 2.90 (dd, J = 13.6, 7.9 Hz, 1H), 2.34 (s, 3H), 2.27 (s, 3H). | | |
| 267[A] | 3-(4-Amino-2-methylimidazo[1,2-f][1,2,4]triazin-7-yl)-4-methyl-N-(3,3,3-trifluoro-2-hydroxypropyl)benzenesulfonamide (single enantiomer isolated) | CF₃ group with CH(OH)CH₂NH | 431.1 |
| | ¹H NMR (400MHz, DMSO-d₆) δ 8.27 (s, 1H), 8.18 (s, 1H), 7.98 (t, J = 6.1 Hz, 1H), 7.91 (d, J = 1.3 Hz, 1H), 7.80 (dd, J = 7.8, 1.2 Hz, 1H), 7.75 (s, 1H), 7.62 (d, J = 8.2 Hz, 1H), 6.60 (br s, 1H), 3.12-2.99 (m, 1H), 2.95-2.86 (m, 1H), 2.34 (s, 3H), 2.28 (s, 3H) | | |
| 268[A] | 3-(4-Amino-2-methylimidazo[1,2-f][1,2,4]triazin-7-yl)-N-(4-(hydroxymethyl)bicyclo[2.1.1]hexan-1-yl)-4-methylbenzenesulfonamide trifluoroacetate salt | HO-CH₂-bicyclo[2.1.1]hexan-NH | 429.2 |
| | ¹H NMR (400 MHz, DMSO-d₆) δ 8.33 (s, 1H), 8.28 (s, 1H), 8.19 (s, 1H), 7.93 (d, J = 1.6 Hz, 1H), 7.79 (dd, J = 8.0, 1.7 Hz, 1H), 7.74 (s, 1H), 7.59 (d, J = 8.1 Hz, 1H), 3.35 (s, 2H), 2.34 (s, 3H), 2.28 (d, J = 4.8 Hz, 3H), 1.76-1.59 (m, 2H), 1.44-1.39 (m, 2H), 1.38-1.28 (m, 2H), 1.12-0.97 (m, 2H) | | |
| 269[A] | 3-(4-Amino-2-methylimidazo[1,2-f][1,2,4]triazin-7-yl)-N-((1-hydroxycyclobutyl)methyl)-4-methylbenzenesulfonamide trifluoroacetate salt | OH-cyclobutyl-CH₂NH | 403.1 |
| | ¹H NMR (600 MHz, DMSO-d₆) δ 8.28 (s, 1H), 8.18 (s, 1H), 7.92 (d, J = 2.0 Hz, 1H), 7.81 (dd, J = 8.0, 2.0 Hz, 1H), 7.74 (s, 1H), 7.60 (d, J = 8.1 Hz, 1H), 7.53 (t, J = 6.4 Hz, 1H), 2.83 (d, J = 6.4 Hz, 2H), 2.32 (s, 3H), 2.29 (s, 3H), 2.04-1.95 (m, 2H), 1.92-1.82 (m, 2H), 1.65-1.55 (m, 1H), 1.45-1.35 (m, 1H). | | |
| 270[B] | 3-(4-Amino-2-methylimidazo[1,2-f][1,2,4]triazin-7-yl)-N-(3-cyanobicyclo[1.1.1]pentan-1-yl)-4-methylbenzenesulfonamide trifluoroacetate salt | CN-bicyclo[1.1.1]pentan-NH | 410.2 |
| | ¹H NMR (400 MHz, DMSO-d₆) δ 8.94 (s, 1H), 8.27 (s, 1H), 8.19 (s, 1H), 7.94-7.89 (m, 1H), 7.81-7.71 (m, 2H), 7.64 (d, , J = 8.0 Hz, 1H), 2.37 (s, 3H), 2.29 (s, 9H) | | |

TABLE 10-continued

| Ex. No. | Name NMR Spectra | -N(R)₂ | LCMS [M + H]⁺ |
|---|---|---|---|
| 271[A] | 3-(4-amino-2-methylimidazo[1,2-f][1,2,4]triazin-7-yl)-N-((1r,4r)-4-hydroxy-4-methylcyclohexyl)-4-methylbenzenesulfonamide trifluoroacetate salt | | 431.1 |
| 272[A] | 3-(4-amino-2-methylimidazo[1,2-f][1,2,4]triazin-7-yl)-N-((1r,3r)-3-cyanocyclobutyl)-4-methylbenzenesulfonamide trifluoroacetate salt | | 398.1 |
| 273[A] | 3-(4-amino-2-methylimidazo[1,2-f][1,2,4]triazin-7-yl)-N-(2-hydroxy-2-methylpropyl)-4-methylbenzenesulfonamide trifluoroacetate salt | | 391.1 |

¹H NMR (600 MHz, DMSO) δ 8.50 (s, 1H), 8.36 (s, 1H), 7.89 (d, J = 2.0 Hz, 1H), 7.79 (dd, J = 8.0, 2.0 Hz, 1H), 7.78 (s, 1H), 7.60 (d, J = 8.2 Hz, 1H), 2.67 (d, J = 6.6 Hz, 2H), 2.33 (s, 3H), 2.30 (s, 3H), 1.07 (s, 6H).

TABLE 11

| Ex. No. | Name NMR Spectra | -N(R)₂ | LCMS [M + H]⁺ |
|---|---|---|---|
| 274[B] | 3-(8-Amino-6-(trifluoromethyl)imidazo[1,2-a]pyrazin-3-yl)-N-(3-(hydroxymethyl)bicyclo[1.1.1]pentan-1-yl)-4-methylbenzenesulfonamide trifluoroacetate salt | | 468.1 |

¹H NMR (400 MHz, CD₃OD) δ 7.96 (dd, J = 8.1, 1.9 Hz, 1H), 7.87 (d, J = 1.8 Hz, 1H), 7.76 (s, 1H), 7.69 (d, J = 8.2 Hz, 1H), 7.59 (s, 1H), 3.54 (s, 2H), 2.30 (s, 3H), 1.75 (s, 6H).

TABLE 11-continued

[Structure: core scaffold with N(R)₂-sulfonyl group, CF₃-substituted imidazo[1,2-a]pyrazin-8-amine, methylbenzene linker]

| Ex. No. | Name / NMR Spectra | -N(R)₂ | LCMS [M + H]⁺ |
|---|---|---|---|
| 275[B] | 3-(8-Amino-6-(trifluoromethyl)imidazo[1,2-a]pyrazin-3-yl)-N-(4-(hydroxymethyl)bicyclo[hexan-1-yl)-4-methylbenzenesulfonamide trifluoroacetate salt | HO-CH₂-bicyclo[2.1.1]hexan-1-yl-NH- | 482.1 |
| | ¹H NMR (400 MHz, CD₃OD) δ 7.98 (dd, J = 8.1, 1.9 Hz, 1H), 7.89 (d, J = 1.8 Hz, 1H), 7.77 (s, 1H), 7.67 (d, J = 8.1 Hz, 1H), 7.58 (s, 1H), 3.54 (s, 2H), 2.30 (s, 3H), 1.83-1.69 (m, 2H), 1.61-1.53 (m, 2H), 1.52-1.42 (m, 2H), 1.28-1.11 (m, 2H) | | |
| 276[B] | 3-(8-Amino-6-(trifluoromethyl)imidazo[1,2-a]pyrazin-3-yl)-N-(3-(cyanomethyl)bicyclo[1.1.1]pentan-1-yl)-4-methylbenzenesulfonamide trifluoroacetate salt | NC-CH₂-bicyclo[1.1.1]pentan-1-yl-NH- | 477.1 |
| | ¹H NMR (400 MHz, DMSO-d₆) δ 8.71 (s, 1H), 7.87 (dd, J = 8.1, 1.9 Hz, 1H), 7.82 (s, 1H), 7.81 (d, J = 1.8 Hz, 1H), 7.70 (br s, 2H), 7.69 (d, J = 8.2 Hz, 1H), 7.59 (s, 1H), 2.79 (s, 2H), 2.28 (s, 3H), 1.73 (s, 6H) | | |
| 277[B] | Methyl 3-(3-(8-amino-6-(trifluoromethyl)imidazo[1,2-a]pyrazin-3-yl)-4-methylphenylsulfonamido)bicyclo[1.1.1]pentane-1-carboxylate trifluoroacetate salt | MeO₂C-bicyclo[1.1.1]pentan-1-yl-NH- | 496.1 |
| 278[B] | 3-(8-Amino-6-(trifluoromethyl)imidazo[1,2-a]pyrazin-3-yl)-N-(3-(difluoromethyl)bicyclo[1.1.1]pentan-1-yl)-4-methylbenzenesulfonamide trifluoroacetate salt | F₂HC-bicyclo[1.1.1]pentan-1-yl-NH- | 488.2 |
| 279[B] | 3-(8-Amino-6-(trifluoromethyl)imidazo[1,2-a]pyrazin-3-yl)-4-methyl-N-(3-(oxazol-5-yl)bicyclo[1.1.1]pentan-1-yl)benzenesulfonamide trifluoroacetate salt | oxazol-5-yl-bicyclo[1.1.1]pentan-1-yl-NH- | 505.2 |
| | ¹H NMR (400 MHz, CD₃OD) δ 8.07 (s, 1H), 7.99 (dd, J = 8.1, 2.0 Hz, 1H), 7.90 (d, J = 1.9 Hz, 1H), 7.78 (s, 1H), 7.71 (d, J = 8.1 Hz, 1H), 7.59 (s, 1H), 6.86 (s, 1H), 5.51 (s, 1H), 2.31 (s, 3H), 2.19 (s, 6H) | | |

TABLE 11-continued

| Ex. No. | Name | -N(R)₂ | LCMS [M + H]⁺ |
|---|---|---|---|
| | NMR Spectra | | |
| 280[B] | N-(3-((1H-1,2,4-triazol-1-yl)methyl)bicyclo[1.1.1]pentan-1-yl)-3-(8-amino-6-(trifluoromethyl)imidazo[1,2-a]pyrazin-3-yl)-4-methylbenzenesulfonamide | | 519.2 |

¹H NMR (400 MHz, DMSO-d₆) δ 8.39 (s, 1H), 7.90 (s, 1H), 7.82 (dd, J = 8.0, 1.9 Hz, 1H), 7.80 (s, 1H), 7.76 (d, J = 1.7 Hz, 1H), 7.71 (s, 2H), 7.65 (d, J = 8.1 Hz, 1H), 7.56 (s, 1H), 4.29 (s, 2H), 2.26 (s, 3H), 1.61 (s, 6H)

| Ex. No. | Name | -N(R)₂ | LCMS [M + H]⁺ |
|---|---|---|---|
| 281[B] | 3-(8-Amino-6-(trifluoromethyl)imidazo[1,2-a]pyrazin-3-yl)-N-(4-cyanobicyclo[2.1.1]hexan-1-yl)-4-methylbenzenesulfonamide trifluoroacetate salt | | 477.2 |
| 282[B] | 3-(8-Amino-6-(trifluoromethyl)imidazo[1,2-a]pyrazin-3-yl)-N-(3-(2-hydroxypropan-2-yl)bicyclo[1.1.1]pentan-1-yl)-4-methylbenzenesulfonamide trifluoroacetate salt | | 496.2 |

¹H NMR (400 MHz, CD₃OD) δ 8.00-7.93 (m, 1H), 7.90-7.83 (m, 1H), 7.77 (s, 1H), 7.69 (d, J = 8.1 Hz, 1H), 7.58 (s, 1H), 2.30 (s, 3H), 1.73 (s, 6H), 1.10 (s, 6H)

| Ex. No. | Name | -N(R)₂ | LCMS [M + H]⁺ |
|---|---|---|---|
| 283[B] | N-(3-((1H-pyrazol-1-yl)methyl)bicyclo[1.1.1]pentan-1-yl)(8-amino-6-(trifluoromethyl)imidazo[1,2-a]pyrazin-3-yl)-4-methylbenzenesulfonamide trifluoroacetate salt | | 518.2 |

¹H NMR (400 MHz, DMSO-d₆) δ 8.62 (s, 1H), 7.83 (dd, J = 8.1, 1.9 Hz, 1H), 7.80 (s, 1H), 7.77 (d, J = 1.8 Hz, 1H), 7.71 (br s, 2H), 7.67 (d, J = 8.1 Hz, 1H), 7.58-7.50 (m, 2H), 7.37 (d, J = 1.4 Hz, 1H), 6.18 (t, J = 2.0 Hz, 1H), 4.19 (s, 2H), 2.26 (s, 3H), 1.59 (s, 6H)

TABLE 11-continued

| Ex. No. | Name<br>NMR Spectra | -N(R)₂ | LCMS [M + H]⁺ |
|---|---|---|---|
| 284[B] | N-(3-((1H-imidazol-1-yl)methyl)bicyclo[1.1.1]pentan-1-yl)-3-(8-amino-6-(trifluoromethyl)imidazo[1,2-a]pyrazin-3-yl)-4-methylbenzenesulfonamide trifluoroacetate salt | | 518.1 |

¹H NMR (400 MHz, DMSO-d₆) δ 9.02 (t, J = 1.4 Hz, 1H), 8.74 (s, 1H), 7.85 (dd, J = 8.0, 1.9 Hz, 1H), 7.81 (s, 1H), 7.79 (d, J = 1.8 Hz, 1H), 7.72 (br s, 2H), 7.69 (d, J = 1.9 Hz, 1H), 7.68-7.65 (m, 2H), 7.63 (t, J = 1.5 Hz, 1H), 7.57 (s, 1H), 7.39 (d, J = 8.0 Hz, 1H), 4.35 (s, 2H), 2.27 (s, 3H), 1.68 (s, 6H)

| 285[B] | 3-(8-Amino-6-(trifluoromethyl)imidazo[1,2-a]pyrazin-3-yl)-N-(3-fluorobicyclo[1.1.1]pentan-1-yl)-4-methylbenzenesulfonamide trifluoroacetate salt | | 456.1 |

¹H NMR (400 MHz, DMSO-d₆) δ 8.84 (s, 1H), 7.87 (dd, J = 8.1, 1.9 Hz, 1H), 7.83 (s, 1H), 7.81 (d, J = 1.7 Hz, 1H), 7.74-7.65 (m, 2H), 7.59 (s, 1H), 2.27 (s, 3H), 2.09 (d, J = 2.0 Hz, 6H)

| 286[B] | 3-(8-Amino-6-(trifluoromethyl)imidazo[1,2-a]pyrazin-3-yl)-N-(3-(fluoromethyl)bicyclo[1.1.1]pentan-1-yl)-4-methylbenzenesulfonamide trifluoroacetate salt | | 470.1 |

¹H NMR (400 MHz, CD₃OD) δ 7.96 (dd, J = 8.1, 2.0 Hz, 1H), 7.87 (d, J = 2.0 Hz, 1H), 7.76 (s, 1H), 7.69 (d, J = 8.2 Hz, 1H), 7.58 (s, 1H), 4.37 (d, J = 47.7 Hz, 1H), 2.31 (s, 3H), 1.84 (s, 6H)

| 287[B] | 3-(8-Amino-6-(trifluoromethyl)imidazo[1,2-a]pyrazin-3-yl)-N-(3-cyanobicyclo[1.1.1]pentan-1-yl)-4-methylbenzenesulfonamide | | 463.2 |

¹H NMR (400 MHz, DMSO-d₆) δ 7.85 (dd, J = 8.1, 1.9 Hz, 1H), 7.83 (s, 1H), 7.79 (d, J = 1.7 Hz, 1H), 7.70 (br s, 2H), 7.68 (d, J = 8.3 Hz, 1H), 7.61 (s, 1H), 2.26 (s, 3H), 2.25 (s, 6H)

TABLE 11-continued

| Ex. No. | Name | -N(R)₂ | LCMS [M + H]⁺ |
|---|---|---|---|
| | NMR Spectra | | |
| 288[B] | 3-(3-(8-Amino-6-(trifluoromethyl)imidazo[1,2-a]pyrazin-3-yl)-4-methylphenylsulfonamido)bicyclo[1.1.1]pentane-1-carboxamide trifluoroacetate salt | | 481.2 |

¹H NMR (400 MHz, DMSO-d₆) δ 8.69 (s, 1H), 7.87 (dd, J = 8.0, 2.0 Hz, 1H), 7.83 (s, 1H), 7.81 (d, J = 1.8 Hz, 1H), 7.70 (br s, 2H), 7.70 (d, J = 8.1 Hz, 1H), 7.60 (s, 1H), 7.17 (s, 1H), 6.91 (s, 1H), 2.27 (s, 3H), 1.88 (s, 6H)

| 289[B] | 3-(8-Amino-6-(trifluoromethyl)imidazo[1,2-a]pyrazin-3-yl)-4-methyl-N-(3-(morpholinomethyl)bicyclo[1.1.1]pentan-1-yl)benzenesulfonamide trifluoroacetate salt | | 537.1 |

¹H NMR (400 MHz, CD₃OD) δ 7.97 (dd, J = 8.1, 1.8 Hz, 1H), 7.87 (d, J = 1.7 Hz, 1H), 7.75 (s, 1H), 7.69 (d, J = 8.2 Hz, 1H), 7.59 (s, 1H), 4.14 - 3.06 (br m, 8H), 3.37 (s, 2H), 2.31 (s, 3H), 2.05 (s, 6H)

| 290[B] | 3-(3-(8-Amino-6-(trifluoromethyl)imidazo[1,2-a]pyrazin-3-yl)-4-methylphenylsulfonamido)bicyclo[1.1.1]pentane-1-carboxylic acid trifluoroacetate salt | | 482.1 |

¹H NMR (400 MHz, CD₃OD) δ 7.97 (dd, J = 8.0, 1.8 Hz, 1H), 7.87 (d, J = 1.5 Hz, 1H), 7.76 (s, 1H), 7.70 (d, J = 8.2 Hz, 1H), 7.59 (s, 1H), 2.31 (s, 3H), 2.09 (s, 6H)

| 291[B] | 4-(3-(8-Amino-6-(trifluoromethyl)imidazo[1,2-a]pyrazin-3-yl)-4-methylphenylsulfonamido)bicyclo[2.1.1]hexane-1-carboxamide trifluoroacetate salt | | 495.1 |

¹H NMR (400 MHz, DMSO-d₆) δ 8.48 (s, 1H), 7.88 (dd, J = 8 1, 1.9 Hz, 1H), 7.85-7.81 (m, 2H), 7.71 (br s, 2H), 7.68 (d, J = 8.2 Hz, 1H), 7.59 (s, 1H), 7.06 (s, 1H), 6.84 (s, 1H), 2.28 (s, 3H), 1.76-1.57 (m, 6H), 1.39-1.25 (m, 2H)

TABLE 11-continued

| Ex. No. | Name | -N(R)₂ | LCMS [M + H]⁺ |
|---|---|---|---|
| | NMR Spectra | | |
| 292[B] | N-(3-(1H-Tetrazol-5-yl)bicyclo[1.1.1]pentan-1-yl)-3-(8-amino-6-(trifluoromethyl)imidazo[l,2-a]pyrazin-3-yl)-4-methylbenzenesulfonamide trifluoroacetate salt | | 506.3 |
| | ¹H NMR (600 MHz, DMSO-d₆) δ 8.75 (br, 1H), 7.91 (dd, J = 8.0, 2.0 Hz, 1H), 7.85 (d, J = 2.0 Hz, 1H), 7.83 (s, 1H), 7.71 (d, J = 8.1 Hz, 1H), 7.70 (br s, 2H), 7.61 (s, 1H), 6.52 (s, 1H), 2.28 (s, 3H), 2.04 (s, 6H) | | |
| 293[B] | 3-(8-Amino-6-(trifluoromethyl)imidazo[1,2-a]pyrazin-3-yl)-4-methyl-N-(3-(3-methyl-1,2,4-oxadiazol-5-yl)bicyclo[1.1.1]pentan-1-yl)benzenesulfonamide trifluoroacetate salt | | 520.0 |
| | ¹H NMR (600 MHz, DMSO-d₆) δ 8.96 (s, 1H), 7.91 (dd, J = 8 1, 2.0 Hz, 1H), 7.85 (d, J = 2.0 Hz, 1H), 7.83 (s, 1H), 7.71 (d, J = 8.2 Hz, 1H), 7.69 (br s, 2H), 7.60 (s, 1H), 2.28 (s, 3H), 2.27 (s, 3H), 2.24 (s, 6H) | | |
| 294[B] | 3-(8-Amino-6-(trifluoromethyl)imidazo[1,2-a]pyrazin-3-yl)-4-methyl-N-(3-(1-methyl-1H-imidazol-2-yl)bicyclo[1.1.1]pentan-1-yl)benzenesulfonamide trifluoroacetate salt | | 518.1 |
| | ¹H NMR (400 MHz, CD₃OD) δ 8.01 (dd, J = 8.1, 1.9 Hz, 1H), 7.91 (d, J = 1.9 Hz, 1H), 7.76 (s, 1H), 7.72 (d, J = 8.2 Hz, 1H), 7.59 (s, 1H), 7.45 (d, J = 1.9 Hz, 1H), 7.42 (d, J = 1.9 Hz, 1H), 3.82 (s, 3H), 2.51 (s, 6H), 2.31 (s, 3H) | | |
| 295[B] | N-(3-(1,2,4-Oxadiazol-5-yl)bicyclo[1.1.1]pentan-1-yl)-3-(8-amino-6-(trifluoromethyl)imidazo[1,2-a]pyrazin-3-yl)-4-methylbenzenesulfonamide trifluoroacetate salt | | 506.0 |

TABLE 11-continued

[Structure: benzenesulfonamide with N(R)₂ group, connected to imidazo[1,2-a]pyrazine core bearing CF₃ and NH₂ substituents, with methyl group on phenyl]

| Ex. No. | Name | -N(R)₂ | LCMS [M + H]⁺ |
|---|---|---|---|
| | NMR Spectra | | |
| 296[B] | 3-(8-Amino-6-(trifluoromethyl)imidazo[1,2-a]pyrazin-3-yl)-4-methyl-N-(3-morpholinobicyclo[1.1.1]pentan-1-yl)benzenesulfonamide trifluoroacetate salt | morpholine-bicyclopentane-NH | 523.1 |
| | ¹H NMR (400 MHz, CD₃OD) δ 7.98 (dd, J = 8.1, 2.0 Hz, 1H), 7.88 (d, J = 2.0 Hz, 1H), 7.76 (s, 1H), 7.71 (d, J = 8.2 Hz, 1H), 7.59 (s, 1H), 3.95-3.80 (m, 4H), 3.03-2.95 (m, 4H), 2.30 (s, 3H), 2.15 (s, 6H) | | |
| 297[B] | 2-((3-(8-amino-6-(trifluoromethyl)imidazo[1,2-a]pyrazin-3-yl)-4-methylphenypsulfonyl)-2-azaspiro[3.3]heptan-6-ol | OH-azaspiro[3.3]heptane | 468.2 |
| 298[B] | 4-((3-(8-amino-6-(trifluoromethyl)imidazo[1,2-a]pyrazin-3-yl)-4-methylphenypsulfonyl)-1-methylpiperazin-2-one | 1-methylpiperazin-2-one | 469.2 |
| 299[B] | 3-(8-amino-6-(trifluoromethyl)imidazo [1,2-a]pyrazin-3-yl)-N-((3S,4S)-4-hydroxy-1-methylpyrrolidin-3-yl)-N,4-dimethylbenzenesulfonamide | (3S,4S)-4-hydroxy-1-methylpyrrolidin-3-yl, N-methyl | 485.2 |
| 300[B] | 3-(5-((2-(3,5-dimethylisoxazol-4-yl)pyrrolidin-1-yl)sulfonyl)-2-methylphenyl)-6-(trifluoromethyl)imidazo [1,2-a]pyrazin-8-amine | 2-(3,5-dimethylisoxazol-4-yl)pyrrolidin-1-yl | 521.1 |

TABLE 11-continued

| Ex. No. | Name | -N(R)₂ | LCMS [M + H]⁺ |
|---|---|---|---|
| | NMR Spectra | | |
| 301[B] | 3-(8-amino-6-(trifluoromethyl)imidazo [1,2-a]pyrazin-3-yl)-N-(2-cyanoethyl)-N-cyclohexyl-4-methylbenzenesulfonamide | | 507.1 |
| 302[B] | 3-((3-(8-amino-6-(trifluoromethyl)imidazo [1,2-a]pyrazin-3-yl)-4-methylphenypsulfonyl)-3-azabicyclo[3.1.0]hexane-1-carbonitrile | | 463.2 |
| 303[B] | 2-((3-(8-amino-6-(trifluoromethyl)imidazo[1,2-a]pyrazin-3-yl)-4-methylphenypsulfonyl)-2,5-diazabicyclo[2.2.1]heptan-7-ol 2HCl | | 469.2 |
| 304[B] | 3-(5-((hexahydropyrrolo [3,4-b][1,4]oxazin-4(4aH)-yl)sulfonyl)-2-methylphenyl)-6-(trifluoromethyl)imidazo [1,2-a]pyrazin-8-amine | | 483.1 |
| 305[Ex.464] | (S)-3-(5-((3-aminopyrrolidin-1-yl)sulfonyl)-2-methylphenyl)-6-(trifluoromethyl)imidazo[1,2-a]pyrazin-8-amine bis(trifluoroacetate) | | 441.1 |

¹H NMR (400 MHz, DMSO-d₆) δ 8.13-7.93 (m, 3H), 7.89-7.78 (m, 3H), 7.76-7.70 (m, 2H), 7.67 (s, 2H), 3.83-3.56 (m, 1H), 3.48-3.36 (m, 1H), 3.32 (dd, J = 10.7, 6.6 Hz, 1H), 3.24-3.08 (m, 2H), 2.29 (s, 3H), 2.17-1.99 (m, 1H), 1.95 1.73 (m, 1H).

TABLE 11-continued

| Ex. No. | Name NMR Spectra | -N(R)₂ | LCMS [M + H]⁺ |
|---|---|---|---|
| 306[Ex.464] | 3-(5-(((3R,5S)-3-amino-5-methylpiperidin-1-yl)sulfonyl)-2-methylphenyl)-6-(trifluoromethyl)imidazo[1,2-a]pyrazin-8-amine<br><br>¹H NMR (400 MHz, DMSO-d₆) δ 8.06-7.43 (m, 7H), 3.66 (d, J = 6.9 Hz, 1H), 3.56 (d, J = 7.9 Hz, 1H), 2.75-2.56 (m, 1H), 2.28 (s, 3H), 1.84-1.69 (m, 3H), 1.69-1.36 (m, 3H), 0.81 (d, J = 6.5 Hz, 3H), 0.58 (dd, J = 11.8 Hz, 1H). | | 469.2 |
| 307[Ex.464] | 3-(5-(((3R,5S)-3-amino-5-(trifluoromethyl)piperidin-1-yl)sulfonyl)-2-methylphenyl)-6-(trifluoromethyl)imidazo[1,2-a]pyrazin-8-amine<br><br>¹H NMR (400 MHz, DMSO-d₆) δ 8.09-7.39 (m, 7H), 3.80 (d, J = 9.8 Hz, 1H), 3.76-3.57 (m, 1H), 2.89-2.60 (m, 2H), 2.40-2.10 (m, 4H), 2.08-1.85 (m, 2H), 1.85-1.41 (m, 2H), 1.17-0.77 (m, 1H). | | 523.1 |
| 308[Ex.464] | 3-(5-(((3S,4R)-3-amino-4-fluoropiperidin-1-yl)sulfonyl)-2-methylphenyl)-6-(trifluoromethyl)imidazo[1,2-a]pyrazin-8-amine<br><br>¹H NMR (400 MHz, DMSO-d₆) δ 8.17-7.21 (m, 7H), 4.64 (d, J = 49.5 Hz, 1H), 3.48-3.33 (m, 2H), 2.98-2.73 (m, 1H), 2.58-2.49 (m, 1H), 2.39-2.30 (m, 1H), 2.28 (s, 3H), 2.08-1.62 (m, 4H). | | 473.1 |
| 309[Ex.464] | (R)-3-(5-((3-(dimethylamino)piperidin-1-yl)sulfonyl)-2-methylphenyl)-6-(trifluoromethyl)imidazo[1,2-a]pyrazin-8-amine<br><br>¹H NMR (400 MHz, DMSO-d₆) δ 8.04-7.33 (m, 7H), 3.55 (d, J = 9.9 Hz, 1H), 3.43 (d, J = 10.9 Hz, 1H), 2.42-2.30 (m, 3H), 2.28 (s, 3H), 2.15 (s, 6H) 1.81-1.63 (m, 2H), 1.54-1.38 (m, 1H), 1.32-1.12 (m, 1H). | | 483.2 |
| 310[A] | 3-(8-Amino-6-(trifluoromethyl)imidazo[1,2-a]pyrazin-3-yl)-N-(trans-4-hydroxycyclohexyl)-4-methylbenzenesulfonamide<br><br>¹H NMR (600 MHz, DMSO-d₆) δ 7.85 (dd, J = 8.0, 2.0 Hz, 1H), 7.81 (d, J = 2.4 Hz, 2H), 7.69 (br s, 2H), 7.67-7.62 (m, 2H), 7.57 (d, J = 0.9 Hz, 1H), 4.48 (d, J = 4.2 Hz, 1H), 3.32-3.23 (m, 1H), 3.00-2.85 (m, 1H), 2.25 (s, 3H), 1.70 (br d, J = 9.7 Hz, 2H), 1.61 (br d, J = 10.6 Hz, 2H), 1.22-1.13 (m, 2H), 1.13-1.02 (m, 2H). | | 470.1 |

TABLE 11-continued

[Core structure: N(R)₂-sulfonyl-methylphenyl-imidazo[1,2-a]pyrazin-8-amine with CF₃]

| Ex. No. | Name / NMR Spectra | -N(R)₂ | LCMS [M + H]⁺ |
|---|---|---|---|
| 311[A] | 3-(8-Amino-6-(trifluoromethyl)imidazo[1,2-a]pyrazin-3-yl)-N-(3S,6R)-6-(hydroxymethyl)tetrahydro-2H-pyran-3-yl)-4-methylbenzenesulfonamide<br><br>$^1$H NMR (600 MHz, DMSO-d₆) δ 7.87 (dd, J = 8.1, 2.1 Hz, 1H), 7.82 (d, J = 2.2 Hz, 1H), 7.82 (s, 1 H) 7.69 (br s, 2H), 7.67 (d, J = 8.2 Hz, 1H), 7.62 (s, 1H), 4.56 (br s, 1H), 3.80-3.60 (m, 1H), 3.37-3.25 (m, 1H), 3.25-3.18 (m, 1H), 3.16-3.07 (m, 1H), 3.05-2.93 (m, 2H), 2.26 (s, 3H), 1.72-1.65 (m, 1H), 1.63-1.52 (m, 1H), 1.40-1.25 (m, 1H), 1.20-1.06 (m, 1H). | tetrahydropyran with HN- and -OH (CH₂OH) substituents | 486.2 |
| 312[B] | (1-((3-(8-Amino-6-(trifluoromethyl)imidazo[1,2-a]pyrazin-3-yl)-4-methylphenyl)sulfonyl)-3-methylpiperidin-3-yl)methanol | 3-methyl-3-(hydroxymethyl)piperidinyl | 484.1 |
| 313[B] | 3-(5((3-Methoxypiperidin-1-yl)sulfonyl)-2-methylphenyl)-6-(trifluoromethyl)imidazo[1,2-a]pyrazin-8-amine | 3-methoxypiperidinyl | 470.1 |
| 314[B] | 1-((3-(8-Amino-6-(trifluoromethyl)imidazo[1,2-a]pyrazin-3-yl)-4-methylphenyl)sulfonyl)piperidine-3-carbonitrile | 3-cyanopiperidinyl | 465.1 |

TABLE 12

[Core structure: N(R)₂-sulfonyl-methylphenyl-imidazo[1,2-f][1,2,4]triazin-4-amine with CF₃]

| Ex. No. | Name / NMR Spectra | -N(R)₂ | LCMS [M + H]⁺ |
|---|---|---|---|
| 315[B] | 3-(4-Amino-2-(trifluoromethyl)imidazo[1,2-f][1,2,4]triazin-7-yl)-N-((3-fluorooxetan-3-yl)methyl)-4-methylbenzenesulfonamide trifluoroacetate salt | (3-fluorooxetan-3-yl)methyl-NH- | 461.1 |

TABLE 12-continued

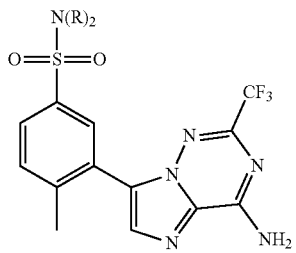

| Ex. No. | Name NMR Spectra | –N(R)₂ | LCMS [M + H]⁺ |
|---|---|---|---|
| | ¹H NMR (400 MHz, DMSO-d₆) δ 8.98 (s, 1H), 8.94 (s, 1H), 8.18 (t, J = 6.5 Hz, 1H), 7.96 (s, 1H), 7.95 (d, J = 1.9 Hz, 1H), 7.85 (dd, J = 8.1, 1.9 Hz, 1H), 7.66 (d, J = 8.2 Hz, 1H), 4.58 (q, J = 8.3 Hz, 2H), 4.53 (q, J = 8.3 Hz, 2H), 3.34 (dd, J = 21.9, 6.5 Hz, 2H), 2.35 (s, 3H) | | |
| 316ᴬ | 3-(4-Amino-2-(trifluoromethyl)imidazo[1,2-f][1,2,4]triazin-7-yl)-N-((3-hydroxyoxetan-3-yl)methyl)-4-methylbenzenesulfonamide trifluoroacetate salt | 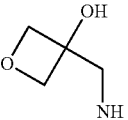 | 459.1 |
| | ¹H NMR (500 MHz, DMSO-d₆) δ 8.97 (s, 1H), 8.93 (s, 1H), 7.95 (s, 1H), 7.94 (d, J = 2.0 Hz, 1H), 7.86 (dd, J = 8.1, 2.0 Hz, 1H), 7.82 (t, J = 6.5 Hz, 1H), 7.65 (d, J = 8.2 Hz, 1H), 4.37 (d, J = 10.3 Hz, 2H), 4.36 (d, J = 10.2 Hz, 2H), 3.03 (d, J = 6.5 Hz, 2H), 2.34 (s, 3H) | | |
| 317ᴬ | 3-(4-Amino-2-(trifluoromethyl)imidazo[1,2-f][1,2,4]triazin-7-yl)-N-(2-hydroxy-2-methylpropyl)-4-methylbenzenesulfonamide trifluoroacetate salt | 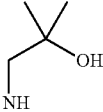 | 445.2 |
| | ¹H NMR (400 MHz, DMSO-d₆) δ 8.97 (s, 1H), 8.93 (s, 1H), 7.94 (s, 1H), 7.91 (d, J = 1.8 Hz, 1H), 7.83 (dd, J = 8.1, 1.9 Hz, 1H), 7.63 (d, J = 8.1 Hz, 1H), 7.50 (t, J = 6.5 Hz, 1H), 2.66 (d, J = 6.6 Hz, 2H), 2.33 (s, 3H), 1.06 (s, 6H) | | |
| 318ᴬ | 3-(4-Amino-2-(trifluoromethyl)imidazo[1,2-f][1,2,4]triazin-7-yl)-4-methyl-N-((3-methyloxetan-3-yl)methyl)benzenesulfonamide trifluoroacetate salt | 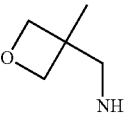 | 457.1 |
| | ¹H NMR (400 MHz, DMSO-d₆) δ 8.98 (s, 1H), 8.93 (s, 1H), 7.96 (s, 1H), 7.94 (d, J = 2.0 Hz, 1H), 7.90-7.81 (m, 2H), 7.66 (d, J = 8.1 Hz, 1H), 4.32 (d, J = 5.8 Hz, 2H), 4.16 (d, J = 5..9 Hz, 2H), 2.97 (d, J = 6.6 Hz, 2H), 2.36 (s, 3H), 1.19 (s, 3H) | | |
| 319ᴮ | 3-(4-Amino-2-(trifluoromethyl)imidazo[1,2-f][1,2,4]triazin-7-yl)-N-(3-(hydroxymethyl)bicyclo[1.1.1]pentan-1-yl)-4-methylbenzenesulfonamide | 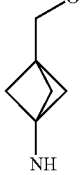 | 469.0 |
| | ¹H NMR (500 MHz, DMSO-d₆) δ 8.96 (s, 1H), 8.92 (s, 1H), 8.53 (s, 1H), 7.92 (s, 1H), 7.90 (d, J = 2.0 Hz, 1H), 7.82 (dd, J = 8.1, 2.0 Hz, 1H), 7.64 (d, J = 8.2 Hz, 1H), 3.33 (s, 2H), 2.34 (s, 3H), 1.59 (s, 6H) | | |
| 320ᴬ | 3-(4-Amino-2-(trifluoromethyl)imidazo[1,2-f][1,2,4]triazin-7-yl)-N-((1S,3R)-3-cyanocyclopentyl)-4-methylbenzenesulfonamide (single enantiomer isolated) | 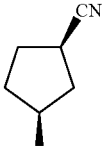 | 466.1 |

TABLE 12-continued

| Ex. No. | Name | NMR Spectra | –N(R)₂ | LCMS [M + H]⁺ |
|---|---|---|---|---|
| 321[A] | 3-(4-Amino-2-(trifluoromethyl)imidazo[1,2-f][1,2,4]triazin-7-yl)-N-((1S,3R)-3-cyanocyclopentyl)-4-methylbenzenesulfonamide (single enantiomer isolated) | | (3-cyanocyclopentyl-NH) | 466.1 |
| 322[A] | 3-(4-Amino-2-(trifluoromethyl)imidazo[1,2-f][1,2,4]triazin-7-yl)-4-methyl-N-(1-methylazetidin-3-yl)benzenesulfonamide  ¹H NMR (500 MHz, DMSO-d₆) δ 8.97 (s, 1H), 8.92 (s, 1H), 8.16 (d, J = 8.3 Hz, 1H), 7.93 (s, 1H), 7.88 (d, J = 2.0 Hz, 1H), 7.80 (dd, J = 8.1, 2.0 Hz, 1H), 7.63 (d, J = 8.2 Hz, 1H), 3.76-3.66 (m, 1H), 3.30-3.27 (m, 2H), 2.64-2.58 (m, 2H), 2.33 (s, 3H), 2.10 (s, 3H). | (1-methylazetidin-3-yl-NH) | 442.1 |
| 323[A] | 3-(4-Amino-2-(trifluoromethyl)imidazo[1,2-f][1,2,4]triazin-7-yl)-N-((1r,3r)-3-(hydroxymethyl)cyclobutyl)-4-methylbenzenesulfonamide trifluoroacetate salt  ¹H NMR (600 MHz, DMSO-d₆) δ 8.97 (s, 1H), 8.93 (s, 1H), 7.96 (d, J = 8.5 Hz, 1H), 7.93 (s, 1H), 7.87 (d, J = 1.7 Hz, 1H), 7.79 (dd, J = 8.0, 1.7 Hz, 1H), 7.62 (d, J = 8.1 Hz, 1H), 3.72 (h, J = 8.0 Hz, 1H), 3.30 (d, J = 6.7 Hz, 2H), 2.32 (s, 3H), 2.08 (dp, J = 12.6, 6.5 Hz, 1H), 1.88-1.76 (m, 4H). ¹⁹F NMR (565 MHz, DMSO-d6) δ −69.03 (s), −74.61 (s). | (3-(hydroxymethyl)cyclobutyl-NH) | 457.2 |
| 324[B] | N-(3-((1H-Imidazol-1-yl)methyl)bicyclo[1.1.1]pentan-1-yl)-3-(4-amino-2-(trifluoromethyl)imidazo[1,2-f][1,2,4]triazin-7-yl)-4-methylbenzenesulfonamide trifluoroacetate salt  ¹H NMR (400 MHz, DMSO-d₆) δ 9.02 (s, 1H), 8.98 (s, 1H), 8.94 (s, 1H), 8.71 (s, 1H), 7.93 (s, 1H), 7.90 (d, J = 1.9 Hz, 1H), 7.80 (dd, J = 8.1, 1.9 Hz, 1H), 7.72-7.56 (m, 3H), 4.34 (s, 2H), 2.34 (s, 3H), 1.68 (s, 6H) | (3-((1H-imidazol-1-yl)methyl)bicyclo[1.1.1]pentan-1-yl-NH) | 519.1 |
| 325[A] | N-((1-Acetyl-3-hydroxyazetidin-3-yl)methyl)-3-(4-amino-2-(trifluoromethyl)imidazo[1,2-f][1,2,4]triazin-7-yl)-4-methylbenzenesulfonamide trifluoroacetate salt | (1-acetyl-3-hydroxyazetidin-3-yl)methyl-NH | 500.1 |

TABLE 12-continued

| Ex. No. | Name | −N(R)₂ | LCMS [M + H]⁺ |
|---|---|---|---|
| | ¹H NMR (400 MHz, DMSO-d₆) δ 8.97 (s, 1H), 8.93 (s, 1H), 7.98-7.80 (m, 4H), 7.65 (d, J = 8.1 Hz, 1H), 5.89 (br s, 1H), 4.03 (d, J = 8.7 Hz, 1H), 3.87-3.78 (m, 2H), 3.55 (d, J = 9.9 Hz, 1H), 2.95 (d, J = 6.3 Hz, 2H), 2.34 (s, 3H), 1.74 (s, 3H) | | |
| 326[B] | 3-(4-Amino-2-(trifluoromethyl)imidazo[1,2-f][1,2,4]triazin-7-yl)-N-(2-hydroxy-2-methylpropyl)-4-methylbenzenesulfonamide trifluoroacetate salt | OMe | 459.1 |
| | ¹H NMR (400 MHz, DMSO-d₆) δ 8.97 (s, 1H), 8.93 (s, 1H), 7.94 (s, 1H), 7.92 (d, J = 1.8 Hz, 1H), 7.84 (dd, J = 8.1, 1.9 Hz, 1H), 7.63 (d, J = 8.2 Hz, 1H), 7.56 (t, J = 6.6 Hz, 1H), 3.02 (s, 3H), 2.77 (d, J = 6.6 Hz, 2H), 2.33 (s, 3H), 1.05 (s, 6H) | | |
| 327[A] | 3-(4-Amino-2-(trifluoromethyl)imidazo[1,2-f][1,2,4]triazin-7-yl)-N-((1r,4r)-4-hydroxy-4-methylcyclohexyl)-4-methylbenzenesulfonamide trifluoroacetate salt | HO | 485.2 |
| | ¹H NMR (400 MHz, DMSO-d₆) δ 8.96 (s, 1H), 8.92 (s, 1H), 7.93 (s, 1H), 7.92 (d, J = 1.9 Hz, 1H), 7.83 (dd, J = 8.1, 2.0 Hz, 1H), 7.62 (d, J = 8.2 Hz, 1H), 7.58 (d, J = 6.9 Hz, 1H), 3.20-2.94 (m, 1H), 2.33 (s, 3H), 1.69-1.54 (m, 2H), 1.55-1.36 (m, 2H), 1.34-1.16 (m, 4H), 1.05 (s, 3H). ¹⁹F NMR (376 MHz, DMSO-d6) δ −69.04 (s), −74.58 (s). | | |
| 328[A] | 3-(4-Amino-2-(trifluoromethyl)imidazo[1,2-f][1,2,4]triazin-7-yl)-N-(4-(hydroxymethyl)bicyclo[2.1.1]hexan-1-yl)-4-methylbenzenesulfonamide trifluoroacetate salt | OH | 483.1 |
| | ¹H NMR (400 MHz, CD₃OD) δ 7.97 (d, J = 1.7 Hz, 1H), 7.92 (dd, J = 8.1, 1.9 Hz, 1H), 7.82 (s, 1H), 7.60 (d, J = 8.1 Hz, 1H), 3.53 (s, 2H), 2.36 (s, 3H), 1.84-1.69 (m, 2H), 1.58 − 1.51 (m, 2H), 1.51-1.38 (m, 2H), 1.26-1.16 (m, 2H) | | |
| 329[A] | 3-(4-Amino-2-(trifluoromethyl)imidazo[1,2-f][1,2,4]triazin-7-yl)-N-(1-(2-hydroxyethyl)azetidin-3-yl)-4-methylbenzenesulfonamide trifluoroacetate salt | OH | 472.1 |

TABLE 12-continued

| Ex. No. | Name | -N(R)₂ | LCMS [M + H]⁺ |
|---|---|---|---|
| 330[B] | 3-(4-Amino-2-(trifluoromethyl)imidazo[1,2-f][1,2,4]triazin-7-yl)-N-(3-cyanobicyclo[1.1.1]pentan-1-yl)-4-methylbenzenesulfonamide trifluoroacetate salt | 3-cyanobicyclo[1.1.1]pentan-1-ylamino | 464.1 |

¹H NMR (400 MHz, CD₃OD) δ 7.98 (d, J = 1.6 Hz, 1H), 7.89 (dd, J = 7.9, 1.6 Hz, 1H), 7.85 (s, 1H), 7.65 (d, J = 8.3 Hz, 1H), 2.41 (s, 3H), 2.31 (s, 6H).

| 331[B] | 3-(4-Amino-2-(trifluoromethyl)imidazo[1,2-f][1,2,4]triazin-7-yl)-N-(3-(fluoromethyl)bicyclo[1.1.1]pentan-1-yl)-4-methylbenzenesulfonamide trifluoroacetate salt | 3-(fluoromethyl)bicyclo[1.1.1]pentan-1-ylamino | 471.1 |

¹H NMR (400 MHz, CD₃OD) δ 7.96 (d, J = 1.9 Hz, 1H), 7.90 (dd, J = 8.1, 2.0 Hz, 1H), 7.83 (s, 1H), 7.62 (d, J = 8.2 Hz, 1H), 4.35 (d, J = 47.7 Hz, 1H), 2.38 (s, 3H), 1.82 (s, 6H)

| 332[B] | N-(3-((1H-pyrazol-1-yl)methyl)bicyclo[1.1.1]pentan-1-yl)-3-(4-amino-2-(trifluoromethyl)imidazo[1,2-f][1,2,4]triazin-7-yl)-4-methylbenzenesulfonamide trifluoroacetate salt | 3-((1H-pyrazol-1-yl)methyl)bicyclo[1.1.1]pentan-1-ylamino | 519.2 |

¹H NMR (400 MHz, DMSO-d₆) δ 8.98 (s, 1H), 8.93 (s, 1H), 8.58 (s, 1H), 7.90 (s, 1H), 7.87 (d, J = 1.8 Hz, 1H), 7.78 (dd, J = 8.1, 1.9 Hz, 1H), 7.62 (d, J = 8.1 Hz, 1H), 7.55 (d, J = 2.0 Hz, 1H), 7.36 (d, J = 1.4 Hz, 1H), 6.18 (t, J = 2.0 Hz, 1H), 4.18 (s, 2H), 2.33 (s, 3H), 1.59 (s, 6H)

| 333[B] | 3-(4-Amino-2-(trifluoromethyl)imidazo[1,2-f][1,2,4]triazin-7-yl)-N-(3-fluorobicyclo[1.1.1]pentan-1-yl)-4-methylbenzenesulfonamide trifluoroacetate salt | 3-fluorobicyclo[1.1.1]pentan-1-ylamino | 457.1 |

¹H NMR (400 MHz, DMSO-d₆) δ 8.97 (s, 1H), 8.92 (s, 1H), 8.80 (s, 1H), 7.95 (s, 1H), 7.92 (d, J = 1.9 Hz, 1H), 7.82 (dd, J = 8.1, 2.0 Hz, 1H), 7.66 (d, J = 8.2 Hz, 1H), 2.36 (s, 3H), 2.08 (d, J = 2.4 Hz, 6H)

| 334[A] | 3-(4-Amino-2-(trifluoromethyl)imidazo[1,2-f][1,2,4]triazin-7-yl)-N-((4-(hydroxymethyl)tetrahydro-2H-pyran-4-yl)methyl)-4-methylbenzenesulfonamide trifluoroacetate salt | (4-(hydroxymethyl)tetrahydro-2H-pyran-4-yl)methylamino | 501.1 |

¹H NMR (400 MHz, DMSO-d₆) δ 8.97 (s, 1H), 8.93 (s, 1H), 7.95 (s, 1H), 7.93-7.88 (m, 1H), 7.87-7.79 (m, 1H), 7.64 (d, J = 8.1 Hz, 1H), 7.45 (t, J = 6.5 Hz, 1H), 3.63-3.37 (m, 4H), 3.29 (s, 2H), 2.79 (d, J = 6.7 Hz, 2H), 2.34 (s, 3H), 1.39-1.26 (m, 4H)

TABLE 12-continued

| Ex. No. | Name<br>NMR Spectra | –N(R)$_2$ | LCMS [M + H]$^+$ |
|---|---|---|---|
| 335$^A$ | 3-(4-Amino-2-(trifluoromethyl)imidazo[1,2-f][1,2,4]triazin-7-yl)-N-((3-hydroxyazetidin-3-yl)methyl)-4-methylbenzenesulfonamide trifluoroacetate salt | 3-hydroxyazetidin-3-yl)methyl-NH | 458.1 |
| | $^1$H NMR (400 MHz, DMSO-d$_6$) δ 8.99 (s, 1H), 8.96 (s, 1H), 8.80 (br s, 1H), 8.66 (br s, 1H), 8.00 (t, J = 6.8 Hz, 1H), 7.95 (s, 1H), 7.93 (d, J = 1.4 Hz, 1H), 7.86 (dd, J = 8.0, 1.8 Hz, 1H), 7.67 (d, J = 8.0 Hz, 1H), 6.26 (s, 1H), 3.99-3.86 (m, 2H), 3.84-3.69 (m, 2H), 3.01 (d, J = 6.5 Hz, 2H), 2.34 (s, 3H) | | |
| 336$^B$ | 3-(4-Amino-2-(trifluoromethyl)imidazo[1,2-f][1,2,4]triazin-7-yl)-4-methylbenzenesulfonamide trifluoroacetate salt | –NH$_2$ | 373.1 |
| | $^1$H NMR (400 MHz, DMSO-d$_6$ containing CD$_3$OD) δ 7.90 (d, J = 1.8 Hz, 1H), 7.86 (dd, J = 7.7, 2.2 Hz, 1H), 7.86 (s, 1H), 7.59 (d, J = 8.1 Hz, 1H), 2.26 (s, 3H) | | |
| 337$^A$ | 3-(4-Amino-2-(trifluoromethyl)imidazo[1,2-f][1,2,4]triazin-7-yl)-4-methyl-N-(1-(oxetan-3-yl)azetidin-3-yl)benzenesulfonamide trifluoroacetate salt | 1-(oxetan-3-yl)azetidin-3-yl-NH | 484.1 |
| 338$^B$ | N-(3-((1H-1,2,4-triazol-1-yl)methyl)bicyclo[1.1.1]pentan-1-yl)-3-(4-amino-2-(trifluoromethyl)imidazo[1,2-f][1,2,4]triazin-7-yl)-4-methylbenzenesulfonamide | triazolylmethyl-bicyclopentyl-NH | 520.2 |
| | $^1$H NMR (400 MHz, DMSO-d$_6$) δ 8.94 (br s, 2H), 8.38 (s, 1H) 7.91 (s, 1H), 7.90 (s, 1H), 7.88 (d, J = 1.9 Hz, 1H), 7.78 (dd, J = 8.1, 1.9 Hz, 1H), 7.62 (d, J = 8.2 Hz, 1H), 4.28 (s, 2H), 2.34 (s, 3H), 1.62 (s, 6H) | | |
| 339$^B$ | 3-(4-Amino-2-(trifluoromethyl)imidazo[1,2-f][1,2,4]triazin-7-yl)-N-(3-(difluoromethyl)bicyclo[1.1.1]pentan-1-yl)-4-methylbenzenesulfonamide trifluoroacetate salt | difluoromethyl-bicyclopentyl-NH | 489.1 |
| | $^1$H NMR (400 MHz, CD$_3$OD) δ 7.97 (d, J = 2.0 Hz, 1H), 7.90 (dd, J = 8.1, 2.0 Hz, 1H), 7.83 (s, 1H), 7.63 (d, J = 8.1 Hz, 1H), 5.81 (t, J = 56.4 Hz, 1H), 2.38 (s, 3H), 1.91 (s, 6H) | | |

TABLE 12-continued

| Ex. No. | Name NMR Spectra | –N(R)₂ | LCMS [M + H]⁺ |
|---|---|---|---|
| 340[B] | 3-(4-Amino-2-(trifluoromethyl)imidazo[1,2-f][1,2,4]triazin-7-yl)-4-methyl-N-(3-morpholinobicyclo[1.1.1]pentan-1-yl)benzenesulfonamide trifluoroacetate salt | morpholino-bicyclo[1.1.1]pentyl-NH | 524.1 |
| 341[B] | 3-(4-Amino-2-(trifluoromethyl)imidazo[1,2-f][1,2,4]triazin-7-yl)-N-(3-aminobicyclo[1.1.1]pentan-1-yl)-4-methylbenzenesulfonamide trifluoroacetate salt<br><br>¹H NMR (400 MHz, CD₃OD) δ 7.97 (d, J = 2.0 Hz, 1H), 7.91 (dd, J = 8.1, 2.0 Hz, 1H), 7.83 (s, 1H), 7.64 (d, J = 8.1 Hz, 1H), 2.38 (s, 3H), 2.15 (s, 6H) | 3-aminobicyclo[1.1.1]pentyl-NH | 454.1 |
| 342[B] | 1-((3-(4-amino-2-(trifluoromethyl)imidazo[2,1-f][1,2,4]triazin-7-yl)-4-methylphenyl)sulfonyl)-3-cyclopropylazetidin-3-ol TFA | 3-cyclopropyl-3-hydroxyazetidinyl | 469.1 |
| 343[B] | 2-((3-(4-amino-2-(trifluoromethyl)imidazo[2,1-f][1,2,4]triazin-7-yl)-4-methylphenyl)sulfonyl)-2-azaspiro[3.3]heptan-6-ol TFA | 6-hydroxy-2-azaspiro[3.3]heptyl | 469.1 |
| 344[B] | 3-(4-amino-2-(trifluoromethyl)imidazo[2,1-f][1,2,4]triazin-7-yl)-N-(2-cyanoethyl)-N,4-dimethylbenzenesulfonamide | N-methyl-N-(2-cyanoethyl)amino | 440.2 |

TABLE 12-continued

| Ex. No. | Name NMR Spectra | –N(R)₂ | LCMS [M + H]⁺ |
|---|---|---|---|
| 345[B] | 3-(4-amino-2-(trifluoromethyl)imidazo[2,1-f][1,2,4]triazin-7-yl)-N-(2-cyanoethyl)-N-cyclopropyl-4-methylbenzenesulfonamide | | 466.2 |
| 346[B] | 3-(4-amino-2-(trifluoromethyl)imidazo[2,1-f][1,2,4]triazin-7-yl)-N-(2-cyanoethyl)-N-cyclopentyl-4-methylbenzenesulfonamide | | 494.2 |
| 347[B] | (S)-(1-((3-(4-amino-2-(trifluoromethyl)imidazo[2,1-f][1,2,4]triazin-7-yl)-4-methylphenyl)sulfonyl)pyrrolidin-2-yl)methanol | | 457.2 |
| 348[B] | 2-((3-(4-amino-2-(trifluoromethyl)imidazo[2,1-f][1,2,4]triazin-7-yl)-4-methylphenyl)sulfonyl)-6-methyl-2,6-diazaspiro[3.4]octan-5-one | | 496.2 |
| 349[B] | 2-((3-(4-amino-2-(trifluoromethyl)imidazo[2,1-f][1,2,4]triazin-7-yl)-4-methylphenyl)sulfonyl)-5-ethyl-2,5-diazabicyclo[2.2.1]heptan-7-ol | | 498.2 |

TABLE 12-continued

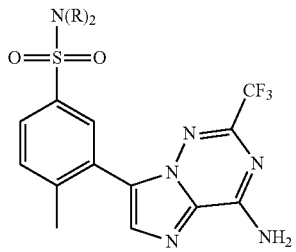

| Ex. No. | Name NMR Spectra | -N(R)₂ | LCMS [M + H]⁺ |
|---|---|---|---|
| 350[B] | 2-((3-(4-amino-2-(trifluoromethyl)imidazo[2,1-f][1,2,4]triazin-7-yl)-4-methylphenyl)sulfonyl)-5-isopropyl-2,5-diazabicyclo[2.2.1]heptan-7-ol | 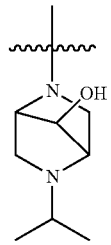 | 512.2 |
| 351[B] | 3-(5-((3-(4-amino-2-(trifluoromethyl)imidazo[2,1-f][1,2,4]triazin-7-yl)-4-methylphenyl)sulfonyl)-7-hydroxy-2,5-diazabicyclo[2.2.1]heptan-2-yl)cyclopentane-1-carbonitrile | 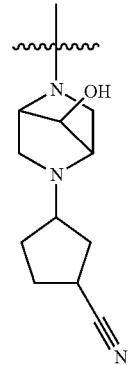 | 563.2 |
| 352[B] | 2-((3-(4-amino-2-(trifluoromethyl)imidazo[2,1-f][1,2,4]triazin-7-yl)-4-methylphenyl)sulfonyl)-5-methyl-2,5-diazabicyclo[2.2.1]heptan-7-ol | 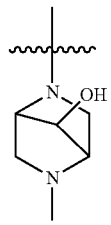 | 484.2 |
| 353[B] | 2-(5-((3-(4-amino-2-(trifluoromethyl)imidazo[2,1-f][1,2,4]triazin-7-yl)-4-methylphenyl)sulfonyl)-7-hydroxy-2,5-diazabicyclo[2.2.1]heptan-2-yl)cyclopentane-1-carbonitrile | 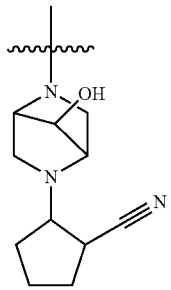 [SMILES: *N1CC2C(O)C1CN2C1CCCC1C#N] | 563.2 |

TABLE 12-continued

| Ex. No. | Name NMR Spectra | -N(R)₂ | LCMS [M + H]⁺ |
|---|---|---|---|
| 354[B] | 3-(5-((3-(4-amino-2-(trifluoromethyl)imidazo[2,1-f][1,2,4]triazin-7-yl)-4-methylphenyl)sulfonyl)-7-hydroxy-2,5-diazabicyclo[2.2.1]heptan-2-yl)cyclobutane-1-carbonitrile | | 549.2 |
| 355[B] | 2-((3-(4-amino-2-(trifluoromethyl)imidazo[2,1-f][1,2,4]triazin-7-yl)-4-methylphenyl)sulfonyl)-2,5-diazabicyclo[2.2.1]heptan-7-ol | | 470.1 |
| 356[A] | 3-(4-amino-2-(trifluoromethyl)imidazo[2,1-f][1,2,4]triazin-7-yl)-N-((3S,6R)-6-(hydroxymethyl)tetrahydro-2H-pyran-3-yl)-4-methylbenzenesulfonamide | | 487.1 |

¹H NMR (400 MHz, DMSO) δ 8.70 (br s, 2H), 7.97-7.85 (m, 2H), 7.82 (dd, J = 8.1, 1.9 Hz, 1H), 7.62 (d, J = 8.2 Hz, 1H), 4.66-4.41 (m, 1H), 3.77-3.55 (m, 1H), 3.28-3.23 (m, 1H), 3.24-3.15 (m, 1H), 3.15-3.06 (m, 1H), 3.03-2.92 (m, 2H), 2.32 (s, 3H), 1.75-1.62 (m, 1H), 1.62-1.47 (m, 1H), 1.40-1.20 (m, 1H), 1.20-1.00 (m, 1H).

| Ex. No. | Name NMR Spectra | -N(R)₂ | LCMS [M + H]⁺ |
|---|---|---|---|
| 357[B] | 3-(4-amino-2-(trifluoromethyl)imidazo[2,1-f][1,2,4]triazin-7-yl)-4-methyl-N-((1-methyl-1H-pyrazol-5-yl)methyl)benzenesulfonamide | | 467.2 |
| 358[B] | 3-(4-amino-2-(trifluoromethyl)imidazo[2,1-f][1,2,4]triazin-7-yl)-4-methyl-N-(pyrazin-2-ylmethyl)benzenesulfonamide | | 465.1 |

TABLE 13

| Ex. No. | Name ¹H NMR | -N(R)₂ | R' = | LCMS [M+H]⁺ |
|---|---|---|---|---|
| 359^A | 5-(8-aminoimidazo[1,2-a]pyrazin-3-yl)-2-fluoro-N-((1r,4r-4-hydroxy-4-methylcyclohexyl)benzenesulfonamide | (1r,4r)-4-hydroxy-4-methylcyclohexylamino | 4-F | 420.2 |
| | ¹H NMR (400 MHz, DMSO-d₆) δ 8.00 (s, 1H), 7.98-7.90 (m, 2H), 7.79 (s, 1H), 7.68 (d, J = 4.6 Hz, 1H), 7.61 (dd, J = 9.5 Hz, 1H), 7.30 (d, J = 4.7 Hz, 1H), 7.01 (s, 2H), 4.13 (s, 1H), 3.27-3.19 (m, 1H), 1.68-1.56 (m, 2H), 1.55-1.43 (m, 2H), 1.38-1.19 (m, 4H), 1.05 (s, 3H). | | | |
| 360^A | 5-(8-aminoimidazo[1,2-a]pyrazin-3-yl)-2-fluoro-N-((4-(hydroxymethyl)tetrahydro-2H-pyran-4-yl)methyl)benzenesulfonamide | (4-(hydroxymethyl)tetrahydro-2H-pyran-4-yl)methylamino | 4-F | 436.1 |
| | ¹H NMR (600 MHz, DMSO-d₆) δ 7.99-7.92 (m, 2H), 7.79 (s, 1H), 7.71 (d, J = 4.7 Hz, 1H), 7.66-7.59 (m, 1H), 7.30 (d, J = 4.7 Hz, 1H), 7.02 (s, 2H), 3.48 (dd, J = 5.5, 5.5 Hz, 4H), 3.29 (s, 2H), 2.95 (s, 2H), 1.42-1.26 (m, 4H). | | | |
| 361^A | 5-(8-aminoimidazo[1,2-a]pyrazin-3-yl)-N-(2-hydroxy-2-methylpropyl)-2,4-dimethylbenzenesulfonamide | 2-hydroxy-2-methylpropylamino | 2,4-diMe | 390.1 |
| | ¹H NMR (400 MHz, DMSO-d₆) δ 7.72 (s, 1H), 7.63 (s 1H), 7.54 (br s, 1H), 7.46 (s, 1H), 7.26-7.17 (m, 2H), 6.99 (s, 2H), 4.36 (s, 1H), 2.71 (s, 2H), 2.62 (s, 3H), 2.18 (s, 3H), 1.02 (s, 6H). | | | |

TABLE 14

| Ex. No. | Name NMR Spectra | —N(R)₂ | R' = | LCMS [M + H]⁺ |
|---|---|---|---|---|
| 362[B] | 3-(4-Aminoimidazo[2,1-f][1,2,4]triazin-7-yl)-N-(4-cyanobicyclo[2.2.1]heptan-1-yl)-4-(methyl-d₃)benzenesulfonamide trifluoroacetate salt | 4-cyanobicyclo[2.2.1]heptan-1-yl (NH) | 2-CD₃ | 427.2 |

¹H NMR (400 MHz, CD₃OD) δ 8.13 (s, 1H), 8.03 (d, J = 2.0 Hz, 1H), 7.90 (dd, J = 8.1, 2.1 Hz, 1H), 7.80 (s, 1H), 7.61 (d, J = 8.1 Hz, 1H), 2.05-1.95 (m, 2H), 1.94 (s, 2H), 1.90-1.76 (m, 4H), 1.70-1.57 (m, 2H)

| Ex. No. | Name NMR Spectra | —N(R)₂ | R' = | LCMS [M + H]⁺ |
|---|---|---|---|---|
| 363[A] | 5-(4-Aminoimidazo[1,2-f][1,2,4]triazin-7-yl)-N-(4-(hydroxymethyl)bicyclo[2.1.1]hexan-1-yl)-2,4-dimethylbenzenesulfonamide | 4-(hydroxymethyl)bicyclo[2.1.1]hexan-1-yl (NH) | 2-CH₃, 4-CH₃ | 429.1 |

¹H NMR (500 MHz, CD₃OD) δ 8.08 (s, 1H), 8.06 (s, 1H), 7.70 (s, 1H), 7.40 (s, 1H) 3.53 (s, 2H), 2.70 (s, 3H), 2.34 (s, 3H), 1.80-1.72 (m, 2H), 1.57-1.51 (m, 2H), 1.51-1.39 (m, 2H), 1.27-1.17 (m, 2H)

| Ex. No. | Name NMR Spectra | —N(R)₂ | R' = | LCMS [M + H]⁺ |
|---|---|---|---|---|
| 364[A] | 3-(4-Aminoimidazo[1,2-f][1,2,4]triazin-7-yl)-N-(4-cyanobicyclo[2.1.1]hexan-1-yl)benzenesulfonamide trifluoroacetate salt | 4-cyanobicyclo[2.1.1]hexan-1-yl (NH) | — | 396.1 |

¹H NMR (400 MHz, DMSO-d₆) δ 8.80 (s, 1H), 8.71-8.64 (m, 1H), 8.38 (s, 1H), 8.37-8.29 (m, 1H), 8.31 (s, 1H), 8.23 (s, 1H), 8.18 (s, 1H), 7.87-7.80 (m, 1H), 7.74 (t, J = 7.8 Hz, 1H), 2.05-1.96 (m, 2H), 1.92-1.84 (m, 2H), 1.77-1.69 (m, 2H), 1.65-1.58 (m, 2H)

| Ex. No. | Name NMR Spectra | —N(R)₂ | R' = | LCMS [M + H]⁺ |
|---|---|---|---|---|
| 365[A] | 5-(4-Aminoimidazo[1,2-f][1,2,4]triazin-7-yl)-N-(4-cyanobicyclo[2.1.1]hexan-1-yl)-2-fluorobenzenesulfonamide trifluoroacetate salt | 4-cyanobicyclo[2.1.1]hexan-1-yl (NH) | 4-F | 414.1 |

¹H NMR (400 MHz, DMSO-d₆) δ 9.11 (s, 1H), 8.68 (dd, J = 7.0, 2.1 Hz, H), 8.40-8.33 (m, 2H), 8.30 (s, 1H), 8.22 (s, 1H), 8.17 (s, 1H), 7.66-7.56 (m, 1H), 2.09-2.01 (m, 2H), 1.93-1.85 (m, 2H), 1.78-1.71 (m, 2H), 1.71-1.64 (m, 2H)

| Ex. No. | Name NMR Spectra | —N(R)₂ | R' = | LCMS [M + H]⁺ |
|---|---|---|---|---|
| 366[A] | 5-(4-Aminoimidazo[1,2-f][1,2,4]triazin-7-yl)-2-fluoro-N-(4-(hydroxymethyl)bicyclo[2.1.1]hexan-1-yl)benzenesulfonamide trifluoroacetate salt | 4-(hydroxymethyl)bicyclo[2.1.1]hexan-1-yl (NH) | 4-F | 419.2 |

¹H NMR (400 MHz, DMSO-d₆) δ 8.72 (s, 1H), 8.66 (dd, J = 6.9, 2.0 Hz, H), 8.41-8.33 (m, 2H), 8.31 (s, 1H), 8.22 (s, 1H), 8.15 (s, 1H), 7.59 (t, J = 9.4 Hz, 1H), 3.33 (s, 2H), 1.74-1.66 (m, 2H), 1.51-1.44 (m, 2H), 1.40-1.31 (m, 2H), 1.12-1.04 (m, 2H)

TABLE 14-continued

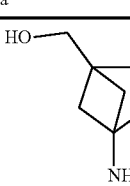

| Ex. No. | Name NMR Spectra | —N(R)₂ | R' = | LCMS [M + H]⁺ |
|---|---|---|---|---|
| 367[A] | 5-(4-Aminoimidazo[1,2-f][1,2,4]triazin-7-yl)-2-chloro-N-(4-(hydroxymethyl)bicyclo[2.1.1]hexan-1-yl)benzenesulfonamide trifluoroacetate salt <br> ¹H NMR (400 MHz, DMSO-d₆) δ 8.87 (d, J = 2.1 Hz, 1H), 8.64 (s, 1H), 8.37 (s, 1H), 8.34-8.27 (m, 2H), 8.22 (s, 1H), 8.19 (s, 1H), 7.78 (d, J = 8.4 Hz, 1H), 3.32 (s, 2H), 1.75-1.67 (m, 2H), 1.50-1.43 (m, 2H), 1.37-1.28 (m, 2H), 1.11-1.02 (m, 2H) | 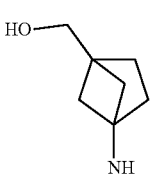 | 4-Cl | 435.1 |
| 368[A] | 3-(4-Aminoimidazo[1,2-f][1,2,4]triazin-7-yl)-N-(4-(hydroxymethyl)bicyclo[2.1.1]hexan-1-yl)benzenesulfonamide trifluoroacetate salt <br> ¹H NMR (400 MHz, CD₃OD) δ 8.75 (s, 1H), 8.32 (d, J = 7.7 Hz, 1H), 8.20 (s, 1H), 8.06 (s, 1H), 7.92 (d, J = 7.7 Hz, 1H), 7.70 (t, J = 7.9 Hz, 1H), 3.52 (s, 2H), 1.86-1.77 (m, 2H), 1.61-1.53 (m, 2H), 1.51-1.43 (m, 2H), 1.27-1.19 (m, 2H) | 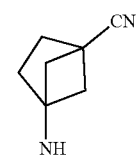 | — | 401.1 |
| 369[B] | 5-(4-Aminoimidazo[1,2-f][1,2,4]triazin-7-yl)-N-(4-cyanobicyclo[2.1.1]hexan-1-yl)-2-methylbenzenesulfonamide trifluoroacetate salt <br> ¹H NMR (600 MHz, DMSO-d₆) δ 8.81 (s, 1H), 8.71 (d, J = 1.7 Hz, 1H), 8.34 (s, 1H), 8.27 (s, 1H), 8.20 (s, 1H), 8.17 (dd, J = 7.9, 1.8 Hz, 1H), 8.12 (s, 1H), 7.55 (d, J = 8.1 Hz, 1H), 2.64 (s, 2H), 2.07-1.98 (m, 2H), 1.91-1.84 (m, 2H), 1.78-1.68 (m, 2H), 1.68-1.60 (m, 2H) |  | 4-CH₃ | 410.1 |
| 370[B] | 3-(4-Aminoimidazo[2,1-f][1,2,4]triazin-7-yl)-N-((1r,3r)-3-cyanocyclobutyl)-4-(methyl-d₃)benzenesulfonamide trifluoroacetate salt <br> ¹H NMR (400 MHz, CD₃OD) δ 8.18 (s, 1H), 8.00 (d, J = 1.9 Hz, 1H), 7.86 (dd, J = 8.1, 2.0 Hz, 1H), 7.81 (s, 1H), 7.62 (d, J = 8.1 Hz, 1H), 4.13 (p, J = 7.7 Hz, 1H), 3.09 (ttd, J = 9.7, 3.7, 1.5 Hz, 1H), 2.54-2.43 (m, 2H), 2.35-2.22 (m, 2H) | | 2-CD₃ | 387.1 |
| 371[B] | 3-(4-Aminoimidazo[2,1-f][1,2,4]triazin-7-yl)-N-(3-(isocyanomethyl)bicyclo[1.1.1]pentan-1-yl)-4-(methyl-d₃)benzenesulfonamide trifluoroacetate salt <br> ¹H NMR (400 MHz, CD₃OD) δ 8.14 (s, 1H), 8.00 (d, J = 2.0 Hz, 1H), 7.88 (dd, J = 8.1, 2.0 Hz, 1H), 7.79 (s, 1H), 7.62 (d, J = 8.1 Hz, 1H), 2.73 (s, 2H), 1.88 (s, 6H) |  | 2-CD₃ | 413.2 |

TABLE 14-continued

| Ex. No. | Name NMR Spectra | —N(R)₂ | R' = | LCMS [M + H]⁺ |
|---|---|---|---|---|
| 372^A | 3-(4-Aminoimidazo[1,2-f][1,2,4]triazin-7-yl)-N-(4-cyanobicyclo[2.1.1]hexan-1-yl)-4-methoxybenzenesulfonamide trifluoroacetate salt | (4-cyanobicyclo[2.1.1]hexan-1-yl)NH– | 2-OMe | 426.1 |

¹H NMR (400 MHz, CD₃OD) δ 8.66 (d, J = 2.4 Hz, 1H), 8.18 (s, 1H), 8.04 (s, 1H), 7.95 (dd, J = 8.9, 2.4 Hz, 1H), 7.37 (d, J = 8.8 Hz, 1H), 4.03 (s, 3H), 2.21-2.09 (m, 2H), 1.99-1.90 (m, 2H), 1.90-1.77 (m, 2H), 1.73-1.58 (m, 2H)

| Ex. No. | Name NMR Spectra | —N(R)₂ | R' = | LCMS [M + H]⁺ |
|---|---|---|---|---|
| 373^A | 3-(4-Aminoimidazo[1,2-f][1,2,4]triazin-7-yl)-N-(4-cyanobicyclo[2.1.1]hexan-1-yl)-4-(trifluoromethoxy)benzenesulfonamide trifluoroacetate salt | (4-cyanobicyclo[2.1.1]hexan-1-yl)NH– | 2-OCF₃ | 480.1 |

¹H NMR (400 MHz, DMSO-d₆) δ 8.93 (s, 1H), 8.54 (d, J = 2.0 Hz, 1H), 8.43 (s, 1H), 8.37 (s, 1H), 8.17 (s, 1H), 8.01 (dd, J = 8.6, 1.8 Hz, 1H), 7.93 (s, 1H), 7.81 (d, J = 8.7 Hz, 1H), 2.09-1.96 (m, 2H), 1.96-1.84 (m, 2H), 1.81-1.69 (m, 2H), 1.69-1.59 (m, 2H)

| Ex. No. | Name NMR Spectra | —N(R)₂ | R' = | LCMS [M + H]⁺ |
|---|---|---|---|---|
| 374^B | 3-(4-Aminoimidazo[2,1-f][1,2,4]triazin-7-yl)-N-(4-hydroxybicyclo[2.1.1]hexan-1-yl)-4-(methyl-d₃)benzenesulfonamide | (4-hydroxybicyclo[2.1.1]hexan-1-yl)NH– | 2-CD₃ | 404.2 |

¹H NMR (400 MHz, CD₃OD) δ 8.08 (s, 1H), 8.00 (d, J = 1.9 Hz, 1H), 7.88 (dd, J = 8.1, 2.1 Hz, 1H), 7.74 (s, 1H), 7.59 (d, J = 8.1 Hz, 1H), 4.59 (s, 1H), 1.81-1.70 (m, 2H), 1.66-1.55 (m, 4H), 1.55-1.49 (m, 2H)

| Ex. No. | Name NMR Spectra | —N(R)₂ | R' = | LCMS [M + H]⁺ |
|---|---|---|---|---|
| 375^A | 3-(4-aminoimidazo[1,2-f][1,2,4]triazin-7-yl)-5-fluoro-N-(1-(hydroxymethyl)-2-oxabicyclo[2.2.2]octan-4-yl)-4-methylbenzenesulfonamide trifluoroacetate salt | (1-(hydroxymethyl)-2-oxabicyclo[2.2.2]octan-4-yl)NH– | 2-CH₃, 3-F | 463.1 |

| Ex. No. | Name NMR Spectra | —N(R)₂ | R' = | LCMS [M + H]⁺ |
|---|---|---|---|---|
| 376^A | 5-(4-aminoimidazo[2,1-f][1,2,4]triazin-7-yl)-2-fluoro-N-((1r,4r)-4-hydroxy-4-methylcyclohexyl)benzenesulfonamide | ((1r,4r)-4-hydroxy-4-methylcyclohexyl)NH– | 4-F | 421.2 |

¹H NMR (400 MHz, DMSO-d₆) δ 8.64 (dd, J = 6.9, 2.1 Hz, 1H), 8.39-8.22 (m, 3H), 8.19 (s, 1H), 8.13 (s, 1H), 7.98 (br s, 1H), 7.57 (dd, J = 9.4, 9.4 Hz, 1H), 4.12 (s, 1H), 3.25-3.12 (m, 1H), 1.68-1.56 (m, 2H), 1.54-1.43 (m, 2H), 1.39-1.18 (m, 4H), 1.04 (s, 3H).

TABLE 14-continued

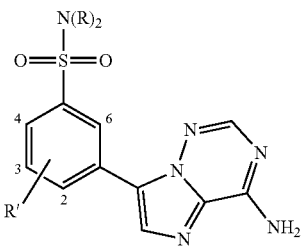

| Ex. No. | Name NMR Spectra | —N(R)₂ | R' = | LCMS [M + H]⁺ |
|---|---|---|---|---|
| 377[A] | 5-(4-aminoimidazo[2,1-f][1,2,4]triazin-7-yl)-2-chloro-N-((1r,4r)-4-hydroxy-4-methylcyclohexyl)benzenesulfonamide | 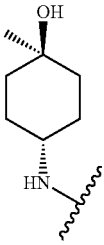 [SMILES: *N[C@H]1CC[C@](C)(O)CC1] | 4-Cl | 437.1 |

¹H NMR (400 MHz, DMSO-d₆) δ 8.85 (d, J = 2.0 Hz, 1H), 8.41-8.24 (m, 3H), 8.19 (d, J = 7.3 Hz, 2H), 7.88 (br s, 1H), 7.77 (d, J = 8.4 Hz, 1H), 4.11 (s, 1H), 3.21-3.06 (m, 1H), 1.66-1.56 (m, 2H), 1.55-1.44 (m, 2H), 1.43-1.29 (m, 2H), 1.29-1.13 (m, 2H), 1.05 (s, 3H).

TABLE 15

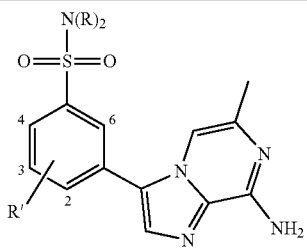

| Ex. No. | Name NMR Spectra | —N(R)₂ | R' = | LCMS [M + H]⁺ |
|---|---|---|---|---|
| 378[B] | 3-(8-Amino-6-methylimidazo[1,2-a]pyrazin-3-yl)-N-(3-(isocyanomethyl)bicyclo[1.1.1]pentan-1-yl)-4-(methyl-d₃)benzenesulfonamide trifluoroacetate salt |  | 2-CD₃ | 426.2 |

¹H NMR (400 MHz, CD₃OD) δ 7.98 (dd, J = 8.1, 2.0 Hz, 1H), 7.86 (d, J = 1.9 Hz, 1H), 7.82 (s, 1H), 7.70 (d, J = 8.1 Hz, 1H), 7.22-7.16 (m, 1H), 2.73 (s, 2H), 2.34 (d, J = 0.9 Hz, 3H), 1.88 (s, 6H)

| 379[B] | 3-(8-Amino-6-methylimidazo[1,2-a]pyrazin-3-yl)-N-(4-cyanobicyclo[2.1.1]hexan-1-yl)-4-(methyl-d₃)benzenesulfonamide trifluoroacetate salt | 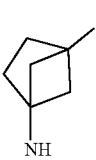 | 2-CD₃ | 426.1 |

¹H NMR (400 MHz, DMSO-d₆) δ 8.76 (s, 1H), 7.91 (dd, J = 8.1, 2.0 Hz, 1H), 7.86 (s, 1H), 7.78 (d, J = 2.0 Hz, 1H), 7.70 (d, J = 8.1 Hz, 1H), 7.21 (s, 1H), 2.23 (s, 3H), 2.02-1.93 (m, 2H), 1.93-1.81 (m, 2H), 1.74-1.65 (m, 2H), 1.65-1.54 (m, 2H)

TABLE 15-continued

| Ex. No. | Name NMR Spectra | —N(R)₂ | R' = | LCMS [M + H]⁺ |
|---|---|---|---|---|
| 380[A] | 5-(8-Amino-6-methylimidazo[1,2-a]pyrazin-3-yl)-N-(4-cyanobicyclo[2.1.1]hexan-1-yl)-2-fluorobenzenesulfonamide trifluoroacetate salt | 4-cyanobicyclo[2.1.1]hexan-1-ylamino | 4-F | 427.1 |
| | ¹H NMR (400 MHz, DMSO-d₆) δ 9.20 (s, 1H), 8.07 (s, 1H), 8.04-7.96 (m, 2H), 7.77-7.65 (m, 2H), 2.29 (s, 3H), 2.08-1.98 (m, 2H), 1.93-1.84 (m, 2H), 1.74-1.68 (m, 2H), 1.68-1.60 (m, 2H) | | | |
| 381[A] | 3-(8-Amino-6-methylimidazo[1,2-a]pyrazin-3-yl)-N-(4-(hydroxymethyl)bicyclo[2.1.1]hexan-1-yl)benzenesulfonamide | 4-(hydroxymethyl)bicyclo[2.1.1]hexan-1-ylamino | — | 414.1 |
| | ¹H NMR (400 MHz, CD₃OD) δ 8.11 (t, J = 1.4 Hz, 1H), 8.03-7.94 (m, 1H), 7.93-7.84 (m, 1H), 7.77 (t, J = 7.8 Hz, 1H), 7.74 (s, 1H), 7.61 (s, 1H), 3.53 (s, 2H), 2.31 (s, 3H), 1.85-1.66 (m, 2H), 1.66-1.53 (m, 2H), 1.53-1.42 (m, 2H), 1.28-1.14 (m, 2H) | | | |
| 382[B] | 5-(8-Amino-6-methylimidazo[1,2-a]pyrazin-3-yl)-N-(3-cyanobicyclo[1.1.1]pentan-1-yl)-2-fluorobenzenesulfonamide trifluoroacetate salt | 3-cyanobicyclo[1.1.1]pentan-1-ylamino | 4-F | 413.1 |
| | ¹H NMR (600 MHz, DMSO-d₆) δ 9.44 (s, 1H), 8.06-7.89 (m, 3H), 7.70 (t, J = 9.3 Hz, 1H), 7.65 (s, 1H), 2.29 (s, 6H), 2.27 (s, 3H) | | | |
| 383[B] | 3-(8-Amino-6-methylimidazo[1,2-a]pyrazin-3-yl)-N-(4-(hydroxymethyl)bicyclo[2.1.1]hexan-1-yl)-4-(methyl-d₃)benzenesulfonamide trifluoroacetate salt | 4-(hydroxymethyl)bicyclo[2.1.1]hexan-1-ylamino | 2-CD₃ | 431.1 |
| | ¹H NMR (400 MHz, DMSO-d₆) δ 9.02 (s, 1H), 8.40 (s, 1H), 7.90 (dd, J = 8.3, 2.1 Hz, 1H), 7.89 (s, 1H), 7.77 (d, J = 1.8 Hz, 1H), 7.68 (d, J = 8.1 Hz, 1H), 7.19 (s, 1H), 3.35 (s, 2H), 2.24 (s, 3H), 1.76-1.58 (m, 2H), 1.45-1.38 (m, 2H), 1.38-1.32 (m, 2H), 1.08-0.99 (m, 2H) | | | |
| 384[B] | 3-(8-Amino-6-methylimidazo[1,2-a]pyrazin-3-yl)-N-(4-hydroxybicyclo[2.1.1]hexan-1-yl)-4-(methyl-d₃)benzenesulfonamide | 4-hydroxybicyclo[2.1.1]hexan-1-ylamino | 2-CD₃ | 417.2 |

TABLE 15-continued

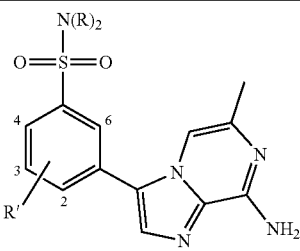

| Ex. No. | Name NMR Spectra | —N(R)₂ | R' = | LCMS [M + H]⁺ |
|---|---|---|---|---|
| 385[A] | 5-(8-amino-6-methylimidazo[1,2-a]pyrazin-3-yl)-2-chloro-N-((1r,4r)-4-hydroxy-4-methylcyclohexyl)benzenesulfonamide | (4-hydroxy-4-methylcyclohexyl)amino | 4-Cl | 450.1 |

¹H NMR (600 MHz, DMSO-d₆) δ 8.12 (d, J = 2.2 Hz, 1H), 7.93 (s, 1H), 7.89 (dd, J = 8.2, 2.2 Hz, 1H), 7.79 (d, J = 8.2 Hz, 1H), 7.78 (s, 1H), 7.58 (d, J = 0.9 Hz, 1H), 7.00 (s, 2H), 4.13 (s, 1H), 3.25-3.14 (m, 1H), 2.20 (s, 3H), 1.66-1.57 (m, 2H), 1.55-1.47 (m, 2H), 1.40-1.30 (m, 2H), 1.29-1.23 (m, 2H), 1.05 (s, 3H).

TABLE 16

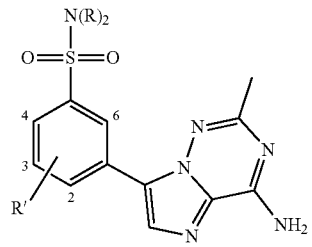

| Ex. No. | Name NMR Spectra | —N(R)₂ | R' = | LCMS [M + H]⁺ |
|---|---|---|---|---|
| 386[B] | 3-(4-Amino-2-methylimidazo[2,1-f][1,2,4]triazin-7-yl)-N-(4-cyanobicyclo[2.1.1]hexan-1-yl)-4-(methyl-d₃)benzenesulfonamide trifluoroacetate salt | (4-cyanobicyclo[2.1.1]hexan-1-yl)amino | 2-CD₃ | 427.3 |

¹H NMR (400 MHz, DMSO-d₆) δ 8.70 (s, 1H), 8.24 (s, 1H), 8.16 (s, 1H), 7.95 (d, J = 1.9 Hz, 1H), 7.80 (dd, J = 8.1, 2.1 Hz, 1H), 7.76 (s, 1H), 7.62 (d, J = 8.1 Hz, 1H), 2.29 (s, 3H), 2.02-1.93 (m, 2H), 1.93-1.84 (m, 2H), 1.77-1.67 (m, 2H), 1.61 (m, 2H)

| 387[A] | 5-(4-Amino-2-methylimidazo[1,2-f][1,2,4]triazin-7-yl)-N-(4-cyanobicyclo[2.1.1]hexan-1-yl)-2-fluorobenzenesulfonamide trifluoroacetate salt | (4-cyanobicyclo[2.1.1]hexan-1-yl)amino | 4-F | 428.1 |

¹H NMR (400 MHz, DMSO-d₆) δ 9.13 (s, 1H), 8.72 (dd, J = 7.1, 2.1 Hz, 1H), 8.35 (ddd, J = 8.1, 4.2, 2.0 Hz, 1H), 8.26 (s, 1H), 8.20 (s, 1H), 8.10 (s, 1H), 7.61 (t, J = 9.4 Hz, 1H), 2.39 (s, 3H), 2.11-1.99 (m, 2H), 1.93-1.79 (m, 2H), 1.79-1.69 (m, 2H), 1.69-1.58 (m, 2H)

TABLE 16-continued

| Ex. No. | Name NMR Spectra | —N(R)₂ | R' = | LCMS [M + H]⁺ |
|---|---|---|---|---|
| 388[B] | 5-(4-Amino-2-methylimidazo[1,2-f][1,2,4]triazin-7-yl)-N-(3-cyanobicyclo[1.1.1]pentan-1-yl)-2-fluorobenzenesulfonamide trifluoroacetate salt | CN-bicyclo[1.1.1]pentyl-NH | 4-F | 414.1 |
| | ¹H NMR (400 MHz, CD₃OD) δ 8.74 (dd, J = 6.9, 2.1 Hz, 1H), 8.32 (ddd, J = 8.2, 4.5, 2.2 Hz, 1H), 7.97 (s, 1H), 7.48 (t, J = 9.3 Hz, 1H), 2.50 (s, 3H), 2.37 (s, 6H) | | | |
| 389[A] | 5-(4-amino-2-methylimidazo[2,1-f][1,2,4]triazin-7-yl)-2-chloro-N-((3S,6R)-6-(cyanomethyl)tetrahydro-2H-pyran-3-yl)-4-methylbenzenesulfonamide | tetrahydropyran-CN | 2-Me, 4-Cl | 476.1 |
| | ¹H NMR (400 MHz, DMSO-d₆) δ 8.29-7.96 (m, 4H), 7.77 (s, 1H), 7.73 (s, 1H), 3.72 (d, J = 8.2 Hz, 1H), 3.49-3.38 (m, 1H), 3.20-3.00 (m, 2H), 2.77-2.63 (m, 1H), 2.57 (dd, J = 17.1, 6.5 Hz, 1H), 2.34 (s, 3H), 2.27 (s, 3H), 1.81-1.71 (m, 1H), 1.71-1.60 (m, 1H), 1.59-1.36 (m, 1H), 1.35-1.14 (m, 1H). | | | |

TABLE 17

| Ex. No. | Name NMR Spectra | —N(R)₂ | R' = | LCMS [M + H]⁺ |
|---|---|---|---|---|
| 390[B] | 3-(8-Amino-6-(trifluoromethyl)imidazo[1,2-a]pyrazin-3-yl)-N-(4-(hydroxymethyl)bicyclo[2.1.1]hexan-1-yl)-4-(methyl-d₃)benzenesulfonamide trifluoroacetate salt | HO-bicyclo[2.1.1]hexyl-NH | 2-CD₃ | 485.1 |
| | ¹H NMR (400 MHz, CD₃OD) δ 7.98 (dd, J = 8.1, 2.0 Hz, 1H), 7.89 (d, J = 2.0 Hz, 1H), 7.77 (s, 1H), 7.67 (d, J = 8.1 Hz, 1H), 7.58 (s, 1H), 3.54 (s, 2H), 1.81-1.71 (m, 2H), 1.61-1.52 (m, 2H), 1.52-1.43 (m, 2H), 1.27-1.15 (m, 2H) | | | |

TABLE 17-continued

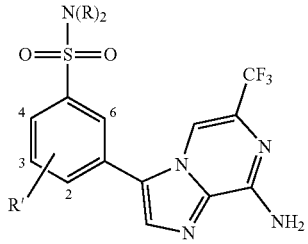

| Ex. No. | Name NMR Spectra | —N(R)₂ | R' = | LCMS [M + H]⁺ |
|---|---|---|---|---|
| 391[B] | 3-(8-Amino-6-(trifluoromethyl)imidazo[1,2-a]pyrazin-3-yl)-N-(3-(hydroxymethyl)bicyclo[1.1.1]pentan-1-yl)-4-(methyl-d₃)benzenesulfonamide trifluoroacetate salt | 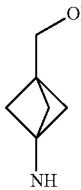 | 2-CD₃ | 471.1 |
| | ¹H NMR (400 MHz, CD₃OD) δ 7.96 (dd, J = 8.1, 2.0 Hz, 1H), 7.87 (d, J = 1.9 Hz, 1H), 7.77 (s, 1H), 7.69 (d, J = 8.1 Hz, 1H), 7.59 (s, 1H), 3.54 (s, 2H), 1.75 (s, 6H) | | | |
| 392[A] | 5-(8-Amino-6-(trifluoromethyl)imidazo[1,2-a]pyrazin-3-yl)-2-chloro-N-(4-cyanobicyclo[2.1.1]hexan-1-yl)benzenesulfonamide trifluoroacetate salt | 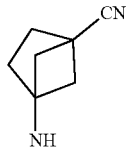 | 4-Cl | 497.1 |
| | ¹H NMR (400 MHz, CD₃OD) δ 8.34 (d, J = 2.0 Hz, 1H), 8.08 (s, 1H), 7.91 (dd, J = 8.2, 2.1 Hz, 1H), 7.89 (s, 1H), 7.84 (d, J = 8.3 Hz, 1H), 2.16-2.06 (m, 2H), 2.01-1.90 (m, 2H), 1.88-1.79 (m, 2H), 1.75-1.67 (m, 2H) | | | |
| 393[B] | 3-(8-Amino-6-(trifluoromethyl)imidazo[1,2-a]pyrazin-3-yl)-4-chloro-N-(4-(hydroxymethyl)bicyclo[2.1.1]hexan-1-yl)benzenesulfonamide | 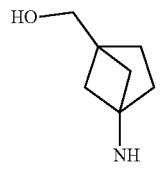 | 2-Cl | 502.1 |
| | ¹H NMR (400 MHz, CD₃OD) δ 8.08-8.01 (m, 2H), 7.89 (d, 1H), 7.82 (s, 1H), 7.69 (s, 1H), 3.55 (s, 2H), 1.85-1.72 (m, 2H), 1.62-1.56 (m, 2H), 1.54-1.48 (m, 2H), 1.29-1.19 (m, 2H) | | | |
| 394[A] | 3-(8-Amino-6-(trifluoromethyl)imidazo[1,2-a]pyrazin-3-yl)-N-(4-(hydroxymethyl)bicyclo[2.1.1]hexan-1-yl)benzenesulfonamide trifluoroacetate salt | 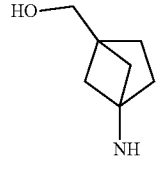 | — | 468.1 |
| 395[A] | 3-(8-Amino-6-(trifluoromethyl)imidazo[1,2-a]pyrazin-3-yl)-N-(4-cyanobicyclo[2.1.1]hexan-1-yl)benzenesulfonamide trifluoroacetate salt | 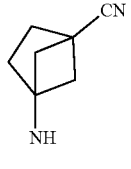 | — | 463.1 |
| | ¹H NMR (400 MHz, DMSO-d₆) δ 8.87 (s, 1H), 8.10-8.06 (m, 1H), 8.04 (s, 1H), 7.99 (d, J = 7.8 Hz, 1H), 7.96-7.91 (m, 2H), 7.81 (t, J = 7.8 Hz, 1H), 7.70 (s, 2H), 2.04-1.94 (m, 2H), 1.92-1.84 (m, 2H), 1.75-1.67 (m, 2H), 1.66-1.56 (m, 2H) | | | |

TABLE 17-continued

| Ex. No. | Name | —N(R)₂ NMR Spectra | R' = | LCMS [M + H]⁺ |
|---|---|---|---|---|
| 396^A | 5-(8-Amino-6-(trifluoromethyl)imidazo[1,2-a]pyrazin-3-yl)-N-(4-cyanobicyclo[2.1.1]hexan-1-yl)-2-fluorobenzenesulfonamide trifluoroacetate salt | | 4-F | 481.1 |

¹H NMR (400 MHz ,CD₃OD) δ 8.14 (dd, J = 6.7, 2.1 Hz, 1H), 8.04 (s, 1H), 8.01-7.92 (m, 1H), 7.85 (s, 1H), 7.58 (t, J = 9.3 Hz, 1H), 2.19-2.10 (m, 2H), 2.02-1.93 (m, 2H), 1.89-1.80 (m, 2H), 1.77-1.70 (m, 2H)

| 397^A | 3-(8-Amino-6-(trifluoromethyl)imidazo[1,2-a]pyrazin-3-yl)-N-(4-cyanobicyclo[2.1.1]hexan-1-yl)-5-fluoro-4-methylbenzenesulfonamide trifluoroacetate salt | | 2-CH₃, 3F | 495.0 |

| 398^A | 5-(8-Amino-6-(trifluoromethyl)imidazo[1,2-a]pyrazin-3-yl)-2-fluoro-N-(4-(hydroxymethyl)bicyclo[2.1.1]hexan-1-yl)benzenesulfonamide trifluoroacetate salt | | 4-F | 486.0 |

¹H NMR (400 MHz, DMSO-d₆) δ 8.78 (s, 1H), 8.05-7.95 (m, 3H), 7.90 (s, 1H), 7.74-7.56 (m, 3H), 3.34 (s, 2H), 1.74-1.63 (m, 2H), 1.49-1.41 (m, 2H), 1.40-1.29 (m, 2H), 1.12-1.03 (m, 2H)

| 399^A | 5-(8-Amino-6-(trifluoromethyl)imidazo[1,2-a]pyrazin-3-yl)-2-chloro-N-(4-(hydroxymethyl)bicyclo[2.1.1]hexan-1-yl)benzenesulfonamide trifluoroacetate salt | | 4-Cl | 502.1 |

¹H NMR (400 MHz, DMSO-d₆) δ 8.70 (s, 1H), 8.20 (d, J = 1.9 Hz, 1H), 8.03 (s, 1H), 7.98-7.92 (m, 2H), 7.85 (d, J = 8.3 Hz, 1H), 7.70 (s, 2H), 3.33 (s, 2H), 1.73-1.63 (m, 2H), 1.48-1.40 (m, 2H), 1.38-1.30 (m, 2H), 1.13-1.03 (m, 2H)

| 400^A | 5-(8-Amino-6-(trifluoromethyl)imidazo[1,2-a]pyrazin-3-yl)-N-(4-(hydroxymethyl)bicyclo[2.1.1]hexan-1-yl)-2,4-dimethylbenzenesulfonamide trifluoroacetate salt | | 2-CH₃, 4-CH₃ | 496.1 |

¹H NMR (400 MHz, CD₃OD) δ 7.93 (s, 1H), 7.73 (s, 1H), 7.57 (s, 1H), 7.50 (s, 1H), 3.53 (s, 2H), 2.74 (s, 3H), 2.25 (s, 3H), 1.81-1.69 (m, 2H), 1.60-1.51 (m, 2H), 1.51-1.42 (m, 2H), 1.28-1.16 (m, 2H)

TABLE 17-continued

| Ex. No. | Name | —N(R)₂ NMR Spectra | R' = | LCMS [M + H]⁺ |
|---|---|---|---|---|
| 401[B,Ex. 260] | 3-(8-Amino-6-(trifluoromethyl)imidazo[1,2-a]pyrazin-3-yl)-4-cyano-N-(4-(hydroxymethyl)bicyclo[2.1.1]hexan-1-yl)benzenesulfonamide trifluoroacetate salt | | 2-CN | 493.1 |
| | ¹H NMR (600 MHz, DMSO-d₆) δ 8.74 (s, 1H), 8.31 (d, J = 8.2 Hz, 1H), 8.17 (d, J = 1.7 Hz, 1H), 8.08 (dd, J = 8.2, 1.8 Hz, 1H), 8.03 (s, 1H), 7.97 (s, 1H), 7.78 (s, 2H), 3.36 (s, 2H), 1.71-1.63 (m, 2H), 1.47-1.40 (m, 2H), 1.40-1.33 (m, 2H), 1.14-1.05 (m, 2H) | | | |
| 402[A] | 5-(4-amino-2-methylimidazo[1,2-f][1,2,4]triazin-7-yl)-2-fluoro-N-((1r,4r)-4-hydroxy-4-methylcyclohexyl)-4-methylbenzenesulfonamide trifluoroacetate salt | | 2-CH₃ 4-F | 449.1 |
| | ¹H NMR (400 MHz, CD₃CN) δ 7.96 (d, J = 7.6 Hz, 1H), 7.62 (s, 1H), 7.34 (d, J = 11.2 Hz, 1H), 5.85 (d, J = 7.6 Hz, 1H), 3.33 (s, 1H), 2.41 (s, 1H), 2.35 (s, 3H), 2.17 (s, 3H), 1.82-1.69 (m, 2H), 1.63-1.51 (m, 2H), 1.48-1.31 (m, 4H), 1.16 (s, 3H). | | | |
| 403[A] | 5-(4-amino-2-methylimidazo[1,2-f][1,2,4]triazin-7-yl)-2-chloro-N-(2-hydroxy-2-methylpropyl)-4-methylbenzenesulfonamide trifluoroacetate salt | | 2-CH₃ 4-Cl | 425.1 |
| 404[A] | 3-(4-amino-2-methylimidazo[1,2-f][1,2,4]triazin-7-yl)-5-fluoro-N-(1-(hydroxymethyl)-2-oxabicyclo[2.2.2]octan-4-yl)-4-methylbenzenesulfonamide trifluoroacetate salt | | 2-CH₃ 3-F | 477.2 |
| 405[A] | 5-(8-amino-6-(trifluoromethyl)imidazo[1,2-a]pyrazin-3-yl)-N-((3S,6R)-6-(cyanomethyl)tetrahydro-2H-pyran-3-yl)-2-fluoro-4-methylbenzenesulfonamide trifluoroacetate salt | | 4-Me 4-F | 513.1 |
| | ¹H NMR (400 MHz, DMSO-d₆) δ 8.15 (d, J = 7.2 Hz, 1H), 7.82-7.74 (m, 2H), 7.70 (s, 1H), 7.65 (br s, 2H), 7.58 (d, J = 11.3 Hz, 1H), 3.82-3.64 (m, 1H), 3.57-3.37 (m,1H), 3.25-3.04 (m, 2H), 2.71 (dd, J = 17.0, 4.4 Hz, 1H), 2.59 (dd, J = 17.0, 6.7 Hz, 1H), 2.20 (s, 3H), 1.82-1.72 (m, 1H), 1.72-1.62 (m, 1H), 1.55-1.37 (m, 1H), 1.36-1.17 (m, 1H). | | | |
| 406[B] | 3-(8-amino-6-(trifluoromethyl)imidazo[1,2-a]pyrazin-3-yl)-N-((3S,6R)-6-(cyanomethyl)tetrahydro-2H-pyran-3-yl)-4-(methyl-d₃)benzenesulfonamide | | 2-CD₃ | 498.2 |
| | ¹H NMR (500 MHz, DMSO-d₆) δ 7.87 (d, J = 7.8 Hz, 1H), 7.84-7.77 (m, 2H), 7.70-7.57 (m, 3H), 3.71 (d, J = 8.9 Hz, 1H), 3.50-3.38 (m, 1H), 3.17-2.94 (m, 2H), 2.70 (dd, J = 17.0, 4.0 Hz, 1H), 2.57 (dd, J = 17.0, 6.6 Hz, 1H), 1.76-1.67 (m, 1H), 1.67-1.58 (m, 1H), 1.46-1.31 (m, 1H), 1.31-1.14 (m, 1H). | | | |

TABLE 17-continued

| Ex. No. | Name NMR Spectra | —N(R)₂ | R' = | LCMS [M + H]⁺ |
|---|---|---|---|---|
| 407[A] | 3-(8-amino-6-(trifluoromethyl)imidazo[1,2-a]pyrazin-3-yl)-N-(2-hydroxy-2-methylpropyl)-4-(trifluoromethyl)benzenesulfonamide | | 2-CF₃ | 498.1 |

¹H NMR (400 MHz, DMSO-d₆) δ 8.27-8.10 (m, 2H), 8.05 (s, 1H), 7.90-7.59 (m, 5H), 4.39 (s, 1H), 2.73 (s, 2H), 1.03 (s, 6H).

| 408[A] | (1-((5-(8-Amino-6-(trifluoromethyl)imidazo[1,2-a]pyrazin-3-yl)-2-fluoro-4-methylphenyl)sulfonyl)piperidin-3-yl)methanol | | 2-Me 4-F | 488.1 |

¹H NMR (400 MHz, DMSO-d₆) δ 7.80 (s, 1H), 7.75 (s, 1H), 7.73 (d, J = 7.1 Hz, 1H), 7.65 (br s, 2H), 7.63 (d, J = 11.4 Hz, 1H), 4.57 (t, J = 5.2 Hz, 1H), 3.71 (d, J = 9.1 Hz, 1H), 3.57 (d, J = 11.4 Hz, 1H), 3.36-3.26 (m, 1H), 3.22-3.10 (m, 1H), 2.61-2.42 (m, 1H), 2.32 (t, J = 10.7 Hz, 1H), 2.25 (s, 3H), 1.78-1.55 (m, 3H), 1.55-1.37 (m, 1H), 0.99 (q, J = 11.6 Hz, 1H). ¹⁹F NMR (376 MHz, DMSO-d₆) δ −66.62, −108.29.

| 409[B] | (1-((3-(8-Amino-6-(trifluoromethyl)imidazo[1,2-a]pyrazin-3-yl)-4-(methyl-d₃)phenyl)sulfonyl)piperidin-3-yl)methanol | | 2-CD₃ | 473.1 |

TABLE 18

| Ex. No. | Name NMR Spectra | —N(R)₂ | R' = | LCMS [M + H]⁺ |
|---|---|---|---|---|
| 410[A] | 5-(4-Amino-2-(trifluoromethyl)imidazo[1,2-f][1,2,4]triazin-7-yl)-2-chloro-N-((1r,4r)-4-hydroxy-4-methylcyclohexyl)-4-methylbenzenesulfonamide trifluoroacetate salt | | 2-CH₃, 4-Cl | 519.1 |

TABLE 18-continued

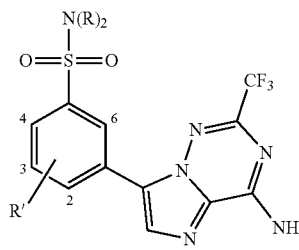

| Ex. No. | Name / NMR Spectra | —N(R)₂ | R' = | LCMS [M + H]⁺ |
|---|---|---|---|---|
| | ¹H NMR (600 MHz, DMSO-d₆) δ 8.97 (s, 1H), 8.93 (s, 1H), 8.14 (s, 1H), 7.99 (s, 1H), 7.82 (d, J = 7.7 Hz, 1H), 7.75 (s, 1H), 3.18-3.08 (m, 1H), 2.37 (s, 3H), 1.64-1.54 (m, 2H), 1.54-1.48 (m, 2H), 1.38-1.29 (m, 2H), 1.29-1.18 (m, 2H), 1.06 (s, 3H). ¹⁹F NMR (376 MHz, DMSO-d₆) δ −69.12 (s), −74.96 (s). | | | |
| 411[A] | 3-(4-Amino-2-(trifluoromethyl)imidazo[1,2-f][1,2,4]triazin-7-yl)-N-(4-(hydroxymethyl)bicyclo[2.1.1]hexan-1-yl)benzenesulfonamide trifluoroacetate salt |  | — | 469.1 |
| | ¹H NMR (400 MHz, CD₃OD) δ 8.68-8.64 (m, 1H), 8.37-8.31 (m, 1H), 8.14 (s, 1H), 7.97-7.90 (m, 1H), 7.72 (t, J = 7.9 Hz, 1H), 3.51 (s, 2H), 1.87-1.72 (m, 2H), 1.59-1.50 (m, 2H), 1.50-1.41 (m, 2H), 1.28-1.15 (m, 2H) | | | |
| 412[A] | 5-(4-Amino-2-(trifluoromethyl)imidazo[1,2-f][1,2,4]triazin-7-yl)-2-fluoro-N-((1r,4r)-4-hydroxy-4-methylcyclohexyl)-4-methylbenzenesulfonamide trifluoroacetate salt | 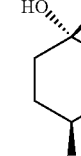 | 2-CH₃, 4-F | 503.0 |
| | ¹H NMR (600 MHz, DMSO-d₆) δ 8.96 (s, 1H), 8.92 (s, 1H), 7.94 (s, 1H), 7.92 (d, J = 7.4 Hz, 1H), 7.91 (d, J = 7.5 Hz, 1H), 7.54 (d, J = 11.2 Hz, 1H), 3.23-3.09 (m, 1H), 2.34 (s, 3H), 1.67-1.56 (m, 2H), 1.56-1.42 (m, 2H), 1.40-1.21 (m, 4H), 1.06 (s, 3H). ¹⁹F NMR (376 MHz, DMSO-d₆) δ −69.09 (s), −75.06 (s), −110.63 (s). | | | |
| 413[A] | 5-(4-Amino-2-(trifluoromethyl)imidazo[1,2-f][1,2,4]triazin-7-yl)-N-((1r,4r)-4-hydroxy-4-methylcyclohexyl)-2,4-dimethylbenzenesulfonamide trifluoroacetate salt | 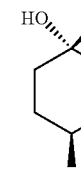 | 2-CH₃, 4-CH₃ | 499.1 |
| | ¹H NMR (600 MHz, DMSO-d₆) δ 8.94 (s, 1H), 8.90 (s, 1H), 7.98 (s, 1H), 7.92 (s, 1H), 7.63 (d, J = 7.7 Hz, 1H), 7.44 (s, 1H), 3.13-3.01 (m, 1H), 2.62 (s, 3H), 2.31 (s, 3H), 1.63-1.53 (m, 2H), 1.53-1.42 (m, 2H), 1.34-1.19 (m, 4H), 1.05 (s, 3H). ¹⁹F NMR (376 MHz, DMSO-d₆) δ −69.06 (s), −74.96 (s). | | | |
| 414[A] | 5-(4-Amino-2-(trifluoromethyl)imidazo[1,2-f][1,2,4]triazin-7-yl)-2-chloro-N-(4-cyanobicyclo[2.1.1]hexan-1-yl)benzenesulfonamide | 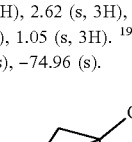 | 4-Cl | 498.0 |
| | ¹H NMR (400 MHz, CD₃OD) δ 8.99 (s, 1H), 8.25 (d, J = 8.1 Hz, 1H), 8.16 (s, 1H), 7.77 (d, J = 8.4 Hz, 1H), 2.17-2.05 (m, 2H), 1.99-1.88 (m, 2H), 1.88-1.77 (m, 2H), 1.74-1.63 (m, 2H) | | | |

TABLE 18-continued

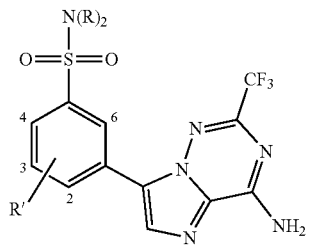

| Ex. No. | Name NMR Spectra | —N(R)₂ | R' = | LCMS [M + H]⁺ |
|---|---|---|---|---|
| 415^A | 3-(4-Amino-2-(trifluoromethyl)imidazo[1,2-f][1,2,4]triazin-7-yl)-N-(4-cyanobicyclo[2.1.1]hexan-1-yl)benzenesulfonamide trifluoroacetate salt | CN-bicyclohexyl-NH | — | 464.1 |

¹H NMR (400 MHz, DMSO-d₆) δ 8.98 (s, 1H), 8.96 (s, 1H), 8.79 (s, 1H), 8.66-8.60 (m, 1H), 8.33-8.26 (m, 2H), 7.91-7.83 (m, 1H), 7.78 (t, J = 7.9 Hz, 1H) 2.03-1.94 (m, 2H), 1.91-1.82 (m, 2H), 1.75-1.67 (m, 2H), 1.66-1.55 (m, 2H)

| 416^A | 3-(4-Amino-2-(trifluoromethyl)imidazo[1,2-f][1,2,4]triazin-7-yl)-N-(4-cyanobicyclo[2.1.1]hexan-1-yl)-5-fluoro-4-methylbenzenesulfonamide trifluoroacetate salt | CN-bicyclohexyl-NH | 2-CH₃, 3-F | 496.1 |
| 417^A | 5-(4-Amino-2-(trifluoromethyl)imidazo[1,2-f][1,2,4]triazin-7-yl)-N-(4-cyanobicyclo[2.1.1]hexan-1-yl)-2-fluorobenzenesulfonamide trifluoroacetate salt | CN-bicyclohexyl-NH | 4-F | 482.1 |

¹H NMR (400 MHz, DMSO-d₆) δ 9.10 (s, 1H), 8.97 (s, 1H), 8.95 (s, 1H), 8.66 (dd, J = 7.0, 2.2 Hz, 1H), 8.33 (ddd, J = 8.5, 4.5, 2.4 Hz, 1H), 8.28 (s, 1H), 7.71-7.61 (m, 1H), 2.07-1.97 (m, 2H), 1.90-1.82 (m, 2H), 1.76-1.68 (m, 2H), 1.68-1.59 (m, 2H)

| 418^A | 5-(4-Amino-2-(trifluoromethyl)imidazo[1,2-f][1,2,4]triazin-7-yl)-2-fluoro-N-(4-(hydroxymethyl)bicyclo[2.1.1]hexan-1-yl)benzenesulfonamide | HO-bicyclohexyl-NH | 4-F | 487.2 |

¹H NMR (400 MHz, DMSO-d₆) δ 8.89 (br s, 3H), 8.61 (dd, J = 6.8, 1.6 Hz, 1H), 8.37-8.27 (m, 1H), 8.25 (s, 1H), 7.63 (t, J = 9.3 Hz, 1H), 4.35 (t, J = 4.9 Hz, 1H), 1.74-1.61 (m, 2H), 1.46-1.37 (m, 2H), 1.37-1.26 (m, 2H), 1.12-0.94 (m, 2H)

| 419^A | 5-(4-Amino-2-(trifluoromethyl)imidazo[1,2-f][1,2,4]triazin-7-yl)-2-chloro-N-(4-(hydroxymethyl)bicyclo[1.1.1]hexan-1-yl)benzenesulfonamide | HO-bicyclohexyl-NH | 4-Cl | 503.1 |
| 420^B | 3-(4-Amino-2-(trifluoromethyl)imidazo[2,1-f][1,2,4]triazin-7-yl)-N-(3-(hydroxymethyl)bicyclo[2.1.1]pentan-1-yl)-4-(methyl-d₃)benzenesulfonamide trifluoroacetate salt | HO-bicyclopentyl-NH | 2-CD₃ | 472.1 |

¹H NMR (400 MHz, CD₃OD) δ 7.96 (d, J = 1.9 Hz, 1H), 7.90 (dd, J = 8.1, 2.0 Hz, 1H), 7.82 (s, 1H), 7.61 (d, J = 8.1 Hz, 1H), 3.53 (s, 2H), 1.75 (s, 6H)

TABLE 19

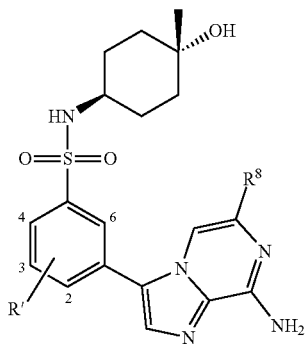

| Ex. No. | Name ¹H NMR | R⁸ | R' = | LCMS [M + H]⁺ |
|---|---|---|---|---|
| 421^{Ex17} | 5-(8-amino-6-(2-fluorophenyl)imidazo[1,2-a]pyrazin-3-yl)-2-fluoro-N-((1r,4r)-4-hydroxy-4-methylcyclohexyl)benzenesulfonamide | 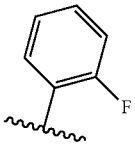 [SMILES: *c1ccccc1F] | 4-F | 514.3 |

¹H NMR (400 MHz, DMSO-d₆) δ 8.12-8.05 (m, 2H), 8.05-7.93 (m, 3H), 7.84 (s, 1H), 7.72-7.59 (m, 1H), 7.44-7.36 (m, 1H), 7.34-7.17 (m, 4H), 4.15 (s, 1H), 3.26-3.15 (m, 1H), 1.67-1.55 (m, 2H), 1.55-1.42 (m, 2H), 1.39-1.16 (m, 4H), 1.05 (s, 3H).

| 422^{Ex17} | 5-(8-amino-6-(3-fluoropyridin-4-yl)imidazo[1,2-a]pyrazin-3-yl)-2-fluoro-N-((1r,4r)-4-hydroxy-4-methylcyclohexyl)benzenesulfonamide | 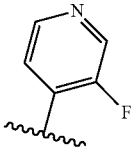 [SMILES: *c1ccncc1F] | 4-F | 515.2 |

¹H NMR (400 MHz, DMSO-d₆) δ 8.62 (d, J = 3.2 Hz, 1H), 8.53 (d, J = 5.0 Hz, 1H), 8.25 (s, 1H), 8.15-8.07 (m, 1H), 8.06-7.92 (m, 3H), 7.87 (s, 1H), 7.65 (dd, J = 9.1, 9.1 Hz, 1H), 7.39 (s, 2H), 4.15 (s, 1H), 3.24-3.12 (m, 1H), 1.66-1.55 (m, 2H), 1.54-1.43 (m, 2H), 1.37-1.18 (m, 4H), 1.05 (s, 3H).

| 423^{Ex17} | 5-(8-amino-6-(2-fluoro-4-(hydroxymethyl)phenyl)imidazo[1,2-a]pyrazin-3-yl)-2-fluoro-N-((1r,4r)-4-hydroxy-4-methylcyclohexyl)benzenesulfonamide | 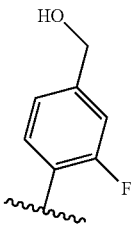 [SMILES: *c1ccc(CO)cc1F] | 4-F | 544.4 |

¹H NMR (600 MHz, DMSO-d₆) δ 8.10-8.03 (m, 2H), 8.03-7.94 (m, 3H), 7.83 (s, 1H), 7.69-7.60 (m, 1H), 7.28-7.16 (m, 4H), 5.34 (br s, 1H), 4.53 (s, 2H), 4.14 (s, 1H), 3.24-3.17 (m, 1H), 1.67-1.56 (m, 2H), 1.55-1.43 (m, 2H), 1.36-1.20 (m, 4H), 1.04 (s, 3H).

Example 424. 3-(4-Aminoimidazo[1,2-f][1,2,4]triazin-7-yl)-4-methyl-N-(1-methyl-2-oxabicyclo[2.1.1]hexan-4-yl)benzenesulfonamide Trifluoroacetate Salt

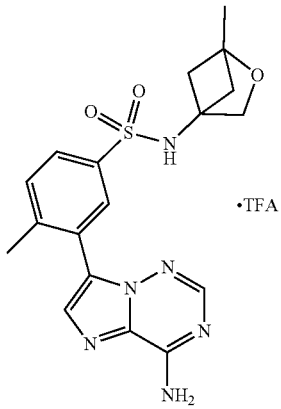

Step 1. (3-Methylenecyclobutane-1,1-diyl)dimethanol

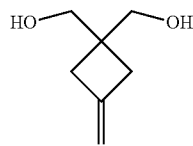

To a suspension of methyltriphenylphosphonium bromide (970 mg, 2.72 mmol) in THF (8 mL) at 0° C. was added potassium tert-butoxide (1.0 M/THF) (2.72 mL, 2.72 mmol). The ice bath was removed and the reaction mixture was stirred at room temperature for 1 h. The resulting yellow solution was cooled to 0° C. and a solution of diisopropyl 3-oxocyclobutane-1,1-dicarboxylate (506 mg, 2.09 mmol, Synthonix) in THF (4 mL) was added dropwise via cannula. The ice bath was removed and the reaction mixture was stirred at room temperature for 1.5 h. The reaction was quenched with saturated NH$_4$Cl and extracted with EtOAc. The organic extracts were washed with brine, dried over MgSO$_4$, filtered, and concentrated. The residue was purified by flash chromatography (0-50% EtOAc/hexanes). The product was not dried under high vacuum due to volatility concerns.

To a solution of diisopropyl 3-methylenecyclobutane-1,1-dicarboxylate (502 mg, 2.09 mmol) in THF (6 mL) at 0° C. was added a solution of lithium aluminum hydride (2.0 M/THF, 3.13 mL, 6.27 mmol) dropwise. The reaction mixture was warmed to room temperature and stirred for 0.5 h. The reaction mixture was diluted with ether and cooled to 0° C. The reaction was quenched by the careful addition of 0.24 mL H$_2$O, followed by 0.24 mL 15% NaOH, and finally 0.72 mL H$_2$O. The resulting mixture was warmed to room temperature and stirred for 15 min. Magnesium sulfate was added and the solids were filtered off. The filter cake was washed with ether and the filtrate was concentrated to afford the product as a colorless oil (180 mg, 67%) that was used without purification.

Step 2. (1-(Iodomethyl)-2-oxabicyclo[2.1.1]hexan-4-yl)methanol (12248-19)

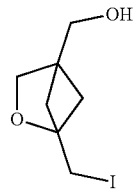

To a solution of (3-methylenecyclobutane-1,1-diyl)dimethanol (1.66 g, 12.95 mmol) in MeCN (50 mL) was added sodium bicarbonate (1.63 g, 19.4 mmol) and N-iodosuccinimide (3.50 g, 15.5 mmol) sequentially. The reaction mixture was stirred at room temperature for 1 h. The reaction was quenched with sat. NaS$_2$O$_3$, partitioned between water and EtOAc, and the layers were separated. The organic layer was washed with brine, dried over MgSO$_4$, filtered and concentrated. The residue was purified by flash chromatography (0-100% EtOAc/hexanes) to afford the product as a yellow semi-solid (1.97 g, 60%) contaminated with succinimide. $^1$H NMR (400 MHz, CDCl$_3$) δ 3.91 (s, 2H), 3.77 (s, 2H), 3.48 (s, 2H), 1.79-1.70 (m, 2H), 1.70-1.61 (m, 2H). LCMS calculated for C$_7$H$_{12}$IO$_2$ (M+H)$^+$: m/z=255.0; found: 255.0.

Step 3. 1-Methyl-2-oxabicyclo[2.1.1]hexane-4-carboxylic Acid

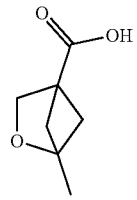

To a solution of (1-(iodomethyl)-2-oxabicyclo[2.1.1]hexan-4-yl)methanol (500 mg, 1.97 mmol) in methanol (6.0 mL) was added Pd—C (10 wt %, 105 mg, 0.098 mmol), followed by triethylamine (0.41 mL, 2.95 mmol). The atmosphere was replaced with hydrogen and the reaction mixture was vigorously stirred under 1 atm of hydrogen for 5 h. The reaction mixture was filtered through a pad of Celite®, concentrated, and the residue was used without further purification.

A solution of (1-methyl-2-oxabicyclo[2.1.1]hexan-4-yl)methanol (250 mg, 1.95 mmol) in CH$_2$C$_2$ (3 mL)/acetonitrile (3.00 mL)/water (3.00 mL) was cooled to 0° C. and stirred rapidly while sodium periodate (1.25 g, 5.9 mmol) and ruthenium(III) chloride hydrate (44.0 mg, 0.20 mmol) were added. The ice bath was removed and the solution was stirred at room temperature for 4 h. The reaction mixture was diluted with EtOAc and stirred while 1 N HCl was added until all solids dissolved. The layers were separated and the aqueous layer was extracted with EtOAc. The combined extracts were washed with 10% NaHSO$_3$ solution, brine, dried over MgSO$_4$, filtered, and concentrated. The residue was purified by flash chromatography (0-20% MeOH/DCM) to afford the title compound (142 mg, 51%).

Step 4. Benzyl 1-methyl-2-oxabicyclo[2.1.1]hexan-4-ylcarbamate

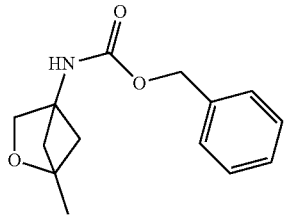 [SMILES: CC12CC(NC(=O)OCc3ccccc3)(CO1)C2]

To a solution of 1-methyl-2-oxabicyclo[2.1.1]hexane-4-carboxylic acid (142 mg, 1.0 mmol) in toluene (3.0 mL) was added triethylamine (0.28 mL, 2.00 mmol), followed by diphenylphosphoryl azide (0.32 mL, 1.50 mmol). The reaction mixture was stirred at room temperature for 1 h, then heated to reflux for 2 h. The reaction mixture was then cooled to room temperature and benzyl alcohol (0.208 mL, 2.0 mmol) was added. The resulting solution was heated to reflux overnight. After cooling to room temperature, the reaction mixture was concentrated in vacuo and purified by flash chromatography (0-50% EtOAc/hexanes) to afford the product as a light yellow solid (contaminated with some benzyl alcohol). $^1$H NMR (400 MHz, CDCl$_3$) δ 7.42-7.35 (m, 5H, overlapped with benzyl alcohol), 5.12 (s, 2H), 3.80 (s, 2H), 2.03-1.87 (m, 3H), 1.75 (m, 1H), 1.46 (s, 3H). LCMS calculated for $C_{14}H_{18}NO_3$ (M+H)$^+$: m/z=248.1; found: 248.1.

Step 5. 1-Methyl-2-oxabicyclo[2.1.1]hexan-4-amine Hydrochloride

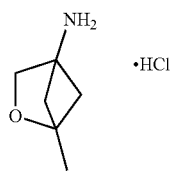

To a solution of benzyl (1-methyl-2-oxabicyclo[2.1.1]hexan-4-yl)carbamate (145 mg, 0.59 mmol) in MeOH (4.0 mL) was added Pd—C (10 wt %, 31.2 mg, 29 μmol). The atmosphere was replaced with hydrogen and the reaction mixture was vigorously stirred under 1 atm of hydrogen for 1 h. The reaction mixture was filtered through a pad of Celite®, treated with 4 M HCl/dioxane (to form the hydrochloride salt), concentrated, and the residue was used without purification. LCMS calculated for $C_6H_{12}NO$ (M+H)$^+$: m/z=114.1; found: 114.1.

Step 6. 7-o-tolylimidazo[1,2-f][1,2,4]triazin-4-amine

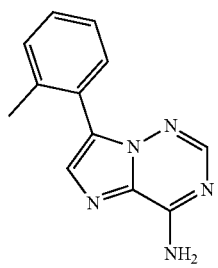 [SMILES: Cc1ccccc1-c1cnc2c(N)ncnn12]

A mixture of 7-bromoimidazo[2,1-j][1,2,4]triazin-4-amine (300 mg, 1.40 mmol), o-tolylboronic acid (210 mg, 1.54 mmol), and Dichloro[1,1'-bis(diphenylphosphino)ferrocene]palladium (II) dichloromethane adduct (57 mg, 0.07 mmol) was taken up in dioxane (8 mL)/water (2 mL) and potassium carbonate (484 mg, 3.50 mmol) was added. The reaction mixture was sparged with N$_2$ and heated to 100° C. for 3 h. Upon cooling to room temperature, the product precipitated. The suspension was cooled in an ice bath and diluted with ether. The solid was filtered, washed with ether, and air dried to yield the title compound as a grey solid (316 mg, 100%). LCMS calculated for $C_{12}H_{12}N_5$(M+H)$^+$: m/z=226.1; found: 226.1.

Step 7. 3-(4-aminoimidazo[1,2-f][1,2,4]triazin-7-yl)-4-methylbenzene-1-sulfonyl chloride

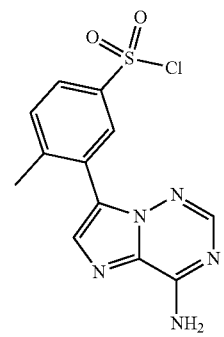 [SMILES: Cc1ccc(S(=O)(=O)Cl)cc1-c1cnc2c(N)ncnn12]

To a suspension of 7-(o-tolyl)imidazo[2,1-f][1,2,4]triazin-4-amine (800 mg, 3.55 mmol) in DCM (10 ml) at 0° C. was added chlorosulfonic acid (8 ml, 119 mmol) dropwise until complete dissolution of the starting material (SM) was observed. The ice bath was removed and the resulting black solution was allowed to warm to room temperature. After stirring for 1 h, thionyl chloride (0.78 ml, 10.7 mmol) was added. The reaction mixture was heated to 50° C. and stirred for 0.5 h. The reaction mixture was cooled to room temperature, diluted with DCM, and carefully added to a rapidly stirring mixture of DCM and ice chips. The precipitated solid was filtered and the filtrate was transferred to a separatory funnel. The layers were separated and the aqueous layer was extracted with DCM. The combined organic layers were dried over anhydrous Na$_2$SO$_4$, filtered and concentrated. The resulting solid was combined with the precipitate to yield the title compound (977 mg, 85%). 1H NMR (400 MHz, DMSO) δ 9.79 (s, 1H), 9.46 (s, 1H), 8.37 (s, 1H), 8.07 (s, 1H), 7.67 (s, 1H), 7.65 (d, J=7.9 Hz, 1H), 7.37 (d, J=7.9 Hz, 1H), 2.22 (s, 3H). LCMS calculated for $C_{12}H_{11}ClN_5O_2S$ (M+H)$^+$: m/z=324.1; found: 324.0.

Step 8. 3-(4-Aminoimidazo[1,2-f][1,2,4]triazin-7-yl)-4-methyl-N-(1-methyl-2-oxabicyclo[2.1.1]hexan-4-yl)benzenesulfonamide Trifluoroacetate Salt To a solution of 1-methyl-2-oxabicyclo[2.1.1]hexan-4-amine hydrochloride (6.93 mg, 0.05 mmol) and DIPEA (16 μL, 0.09 mmol) in DMA (2.0 mL) at 0° C. was added a solution of 3-(4-aminoimidazo[1,2-f][1,2,4]triazin-7-yl)-4-methylbenzene-1-sulfonyl chloride (10.0 mg, 0.03 mmol) in DMA (1 mL) dropwise. The 0° C. bath was removed, and the reaction mixture was stirred at room temp for 1 h. The solution was diluted with MeOH and purified by prep HPLC (pH 2). ¹H NMR (500 MHz, DMSO) δ 8.71 (s, 1H), 8.46 (s, 1H), 8.35 (s, 1H), 8.09 (s, 1H), 7.96 (d, J=2.0 Hz, 1H), 7.83 (s, 1H), 7.82 (dd, J=8 Hz, 2 Hz, 1H), 7.62 (d, J=8.2 Hz, 1H), 3.52 (s, 2H), 2.35 (s, 3H), 1.62 (dd, J=4.4, 1.5 Hz, 2H), 1.45 (dd, J=4.4, 1.6 Hz, 2H), 1.25 (s, 3H). LCMS calculated for C₁₈H₂₁N₆O₃S (M+H)⁺: m/z=401.1; found: 401.1.

Example 425. 3-(8-Amino-6-(trifluoromethyl)imidazo[1,2-a]pyrazin-3-yl)-4-methyl-N-(1-methyl-2-oxabicyclo[2.1.1]hexan-4-yl)benzenesulfonamide Trifluoroacetate Salt

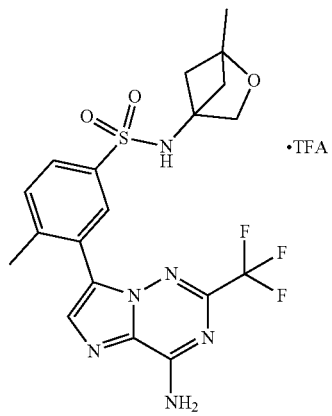 [SMILES: Cc1ccc(S(=O)(=O)NC23COC(C)(C2)C3)cc1-c1cnc2c(N)nc(C(F)(F)F)nn12]

This compound was prepared according to the procedure described for Example 424, Step 8 utilizing 3-(8-amino-6-(trifluoromethyl)imidazo[1,2-a]pyrazin-3-yl)-4-methylbenzene-1-sulfonyl chloride (Example 472, Step 8) instead of 3-(4-aminoimidazo[1,2-f][1,2,4]triazin-7-yl)-4-methylbenzene-1-sulfonyl chloride (Example 424, Step 7). ¹H NMR (500 MHz, DMSO-d₆) δ 8.75 (s, 1H), 7.90 (dd, J=8.1, 2.0 Hz, 1H), 7.84 (d, J=2.0 Hz, 1H), 7.83 (s, 1H), 7.68 (d, J=8.2 Hz, 1H), 7.56 (s, 1H), 3.52 (s, 2H), 2.27 (s, 3H), 1.61 (dd, J=4.4, 1.5 Hz, 2H), 1.45 (dd, J=4.3, 1.6 Hz, 2H), 1.24 (s, 3H). LCMS calculated for C₂₀H₂₁F₃N₅O₃S (M+H): m/z=468.1; found: 468.1.

Example 426. 3-(4-Amino-2-methylimidazo[1,2-f][1,2,4]triazin-7-yl)-4-trideuteromethyl-N-(1-methyl-2-oxabicyclo[2.1.1]hexan-4-yl)benzenesulfonamide Trifluoroacetate Salt

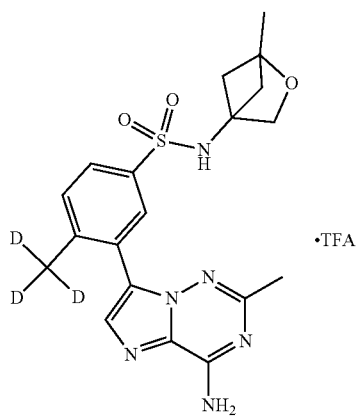 [SMILES: [2H]C([2H])([2H])c1ccc(S(=O)(=O)NC23COC(C)(C2)C3)cc1-c1cnc2c(N)nc(C)nn12]

This compound was prepared according to the procedure described for Example 424, Step 8 utilizing 3-(4-amino-2-methylimidazo[1,2-f][1,2,4]triazin-7-yl)-4-trideuteromethylbenzene-1-sulfonyl chloride (Example 253, Step 3) instead of 3-(4-aminoimidazo[1,2-f][1,2,4]triazin-7-yl)-4-methylbenzene-1-sulfonyl chloride (Example 424, Step 7). LCMS calculated for C₁₉H₂₀D₃N₆O₃S (M+H)f: m/z=418.2; found: 418.2.

Example 427. 3-(4-Amino-2-(trifluoromethyl)imidazo[1,2-f][1,2,4]triazin-7-yl)-N-(1-(hydroxymethyl)-2-oxabicyclo[2.1.1]hexan-4-yl)-4-methylbenzenesulfonamide Trifluoroacetate Salt

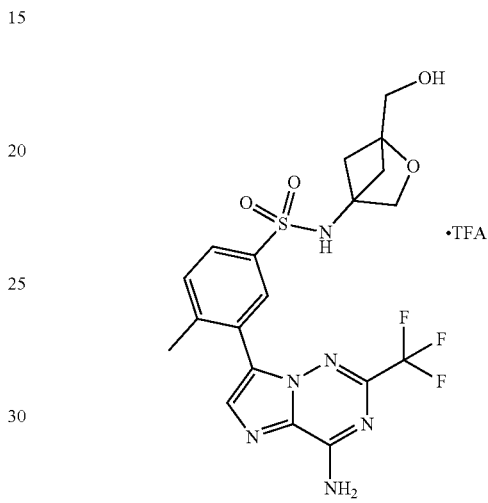

Step 1. (4-(Hydroxymethyl)-2-oxabicyclo[2.1.1]hexan-1-yl)methyl Acetate

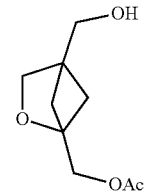 [SMILES: CC(=O)OCC12CC(CO)(CO1)C2]

To a solution of (1-(iodomethyl)-2-oxabicyclo[2.1.1]hexan-4-yl)methanol (874 mg, 3.4 mmol, Example 424, Step 2) in DMF (6.0 mL) was added cesium acetate (990 mg, 5.2 mmol), and the reaction mixture was heated to 100° C. for 2 h. The reaction mixture was partitioned between water and EtOAc and the layers were separated. The organic layer was washed with brine, dried over MgSO₄, filtered and concentrated. The residue was purified by flash chromatography (0-100% EtOAc/hexanes, followed by 15% MeOH/DCM) to afford the title compound (326 mg, 51%). ¹H NMR (400 MHz, CDCl₃) δ 4.34 (s, 2H), 3.90 (s, 2H), 3.75 (s, 2H), 2.10 (s, 3H), 1.74 (dd, J=4.6, 1.3 Hz, 2H), 1.64 (dd, J=4.6, 1.5 Hz, 2H). LCMS calculated for C₉H₁₅O₄(M+H)⁺: m/z=187.1; found: 187.0.

Step 2. 1-(Acetoxymethyl)-2-oxabicyclo[2.1.1]hexane-4-carboxylic Acid

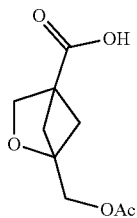 [SMILES: CC(=O)OCC12CC(C(=O)O)(CO1)C2]

A solution of (4-(hydroxymethyl)-2-oxabicyclo[2.1.1]hexan-1-yl)methyl acetate (329 mg, 1.8 mmol) in $CH_2Cl_2$ (3 mL)/acetonitrile (3.00 mL)/water (3.00 mL) at 0° C. was stirred rapidly while sodium periodate (1.13 g, 5.30 mmol) and ruthenium(III) chloride hydrate (40 mg, 0.18 mmol) were added. The ice bath was removed, and the solution was stirred at room temperature for 4 h. The reaction was diluted with EtOAc and stirred while 1M HCl was added until all solids dissolved. The layers were separated and the aqueous layer was extracted with EtOAc. The combined extracts were washed with 10% $NaHSO_3$ solution, brine, dried over $MgSO_4$, filtered, and concentrated. The residue was purified by flash chromatography (0-20% MeOH/DCM) to afford the title compound as a white solid (340 mg, 96%). LCMS calculated for $C_9H_{13}O_5$ $(M+H)^+$: m/z=201.1; found: 201.1.

Step 3. (4-(Benzyloxycarbonylamino)-2-oxabicyclo[2.1.1]hexan-1-yl)methyl Acetate

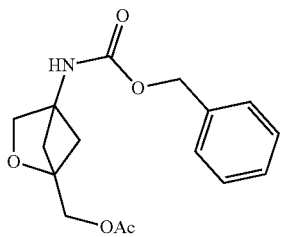 [SMILES: CC(=O)OCC12CC(NC(=O)OCc3ccccc3)(CO1)C2]

To a solution of 1-(acetoxymethyl)-2-oxabicyclo[2.1.1]hexane-4-carboxylic acid (350 mg, 1.75 mmol) in toluene (5.0 mL) was added triethylamine (0.49 mL, 3.50 mmol), followed by diphenylphosphoryl azide (0.56 mL, 2.62 mmol). The reaction mixture was stirred at room temperature for 1 h, then heated to reflux for 2 h. The reaction mixture was then cooled to room temperature and benzyl alcohol (0.36 mL, 3.50 mmol) was added. The resulting solution was heated to reflux overnight. After cooling to room temperature, the reaction mixture was concentrated in vacuo and purified by flash chromatography (0-50% EtOAc/hexanes) to afford the desired product as a colorless oil (391 mg, 73%). LCMS calculated for $C_{16}H_{20}NO_5$ $(M+H)^+$: m/z=306.1; found: 306.1.

Step 4. Benzyl 1-(hydroxymethyl)-2-oxabicyclo[2.1.1]hexan-4-ylcarbamate

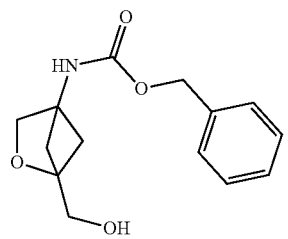 [SMILES: O=C(NC12COC(CO)(C1)C2)OCc1ccccc1]

To a solution of (4-(((benzyloxy)carbonyl)amino)-2-oxabicyclo[2.1.1]hexan-1-yl)methyl acetate (391 mg, 1.28 mmol) in MeOH (6.0 mL) was added potassium carbonate (230 mg, 1.67 mmol) at 0° C. The reaction mixture was warmed to room temperature and stirred for 30 min. The reaction mixture was partitioned between water and EtOAc, and the layers were separated. The aqueous layer was extracted with EtOAc and the combined organic layers were washed with brine, dried over $MgSO_4$, filtered, and concentrated. The resulting white solid was used without purification (316 mg, 94%). LCMS calculated for $C_{14}H_{18}NO_4$ $(M+H)^+$: m/z=264.1; found: 264.2.

Step 5. (4-Amino-2-oxabicyclo[2.1.1]hexan-1-yl)methanol

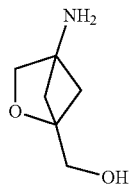

To a solution of benzyl (1-(hydroxymethyl)-2-oxabicyclo[2.1.1]hexan-4-yl)carbamate (40 mg, 0.152 mmol) in MeOH (3 mL) was added palladium hydroxide on carbon (20 wt %, 10.7 mg, 0.02 mmol). The atmosphere was replaced with hydrogen and the reaction mixture was vigorously stirred under 1 atm of hydrogen for 1 h. The reaction mixture was filtered through a pad of Celite®, concentrated in vacuo, and the residue was used without purification. LCMS calculated for $C_6H_{12}NO_2$ $(M+H)^+$: m/z=130.1; found: 130.1.

Step 6. 3-(4-Amino-2-(trifluoromethyl)imidazo[1,2-f][1,2,4]triazin-7-yl)-N-(1-(hydroxymethyl)-2-oxabicyclo[2.1.1]hexan-4-yl)-4-methylbenzenesulfonamide Trifluoroacetate Salt To a solution of (4-amino-2-oxabicyclo[2.1.1]hexan-1-yl)methanol (4.95 mg, 0.038 mmol) and DIPEA (0.013 mL, 0.077 mmol) in DMA (2.0 mL) at 0° C. was added a solution of 3-(4-amino-2-(trifluoromethyl)imidazo[1,2-f][1,2,4]triazin-7-yl)-4-methylbenzene-1-sulfonyl chloride (10 mg, 0.026 mmol, 4N $CF_3$) in DMA (1 mL) dropwise. The 0° C. bath was removed, and the reaction mixture was stirred at room temp for 1 h. The solution was diluted with MeOH and purified by prep HPLC (pH 2). LCMS calculated for $C_{19}H_{20}F_3N_6O_4S$ $(M+H)^+$: m/z=485.1; found: 485.0.

Example 428. 3-(8-amino-6-(trifluoromethyl)imidazo[1,2-a]pyrazin-3-yl)-N-(1-(hydroxymethyl)-2-oxabicyclo[2.1.1]hexan-4-yl)-4-methylbenzenesulfonamide Trifluoroacetate Salt

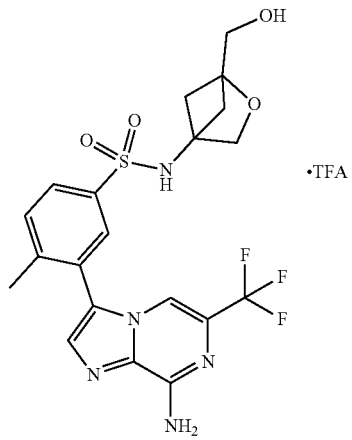 [SMILES: Cc1ccc(S(=O)(=O)NC23COC(CO)(C2)C3)cc1-c1cnc2c(N)nc(C(F)(F)F)cn12]

This compound was prepared according to the procedure described for Example 427, Step 6 utilizing 3-(8-amino-6-(trifluoromethyl)imidazo[1,2-a]pyrazin-3-yl)-4-methylbenzene-1-sulfonyl chloride (Example 472, Step 8) instead of 3-(4-amino-2-(trifluoromethyl)imidazo[1,2-f][1,2,4]triazin-7-yl)-4-methylbenzene-1-sulfonyl chloride (4N CF3). LCMS calculated for $C_{20}H_{21}F_3N_5O_4S$ (M+H)$^+$: m/z=484.1; found: 484.1.

Example 429. 3-(8-Amino-6-(trifluoromethyl)imidazo[1,2-a]pyrazin-3-yl)-N-(1-cyano-2-oxabicyclo[2.1.1]hexan-4-yl)-4-methylbenzenesulfonamide Trifluoroacetate Salt

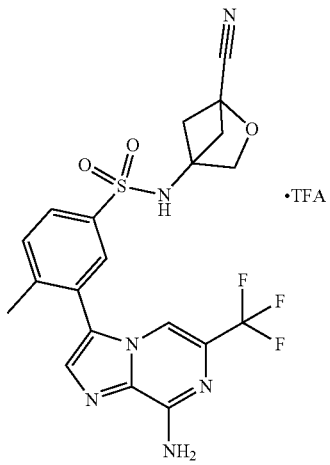 [SMILES: Cc1ccc(S(=O)(=O)NC23COC(C#N)(C2)C3)cc1-c1cnc2c(N)nc(C(F)(F)F)cn12]

Step 1. tert-butyl 1-(hydroxymethyl)-2-oxabicyclo[2.1.1]hexan-4-ylcarbamate

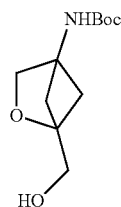

To a solution of (4-amino-2-oxabicyclo[2.1.1]hexan-1-yl)methanol (30 mg, 0.23 mmol, Example 427, Step 5) in THF (3 mL) was added sodium bicarbonate (sat. aq.) (2 mL) followed by di-tert-butyl dicarbonate (76 mg, 0.35 mmol). The reaction mixture was vigorously stirred at room temperature for 4 h. The reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-100% EtOAc/hexanes) to afford the product as a white solid (31.5 mg, 59%). LCMS calculated for $C_{11}H_{19}NO_4Na$ (M+Na)$^+$: m/z=252.1; found: 252.1.

Step 2. tert-butyl 1-formyl-2-oxabicyclo[2.1.1]hexan-4-ylcarbamate

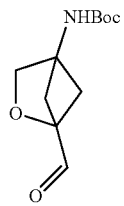

To a solution of tert-butyl (1-(hydroxymethyl)-2-oxabicyclo[2.1.1]hexan-4-yl)carbamate (31.5 mg, 0.14 mmol) in DCM (3.0 mL) was added sodium bicarbonate (23 mg, 0.28 mmol) and Dess-Martin periodinane (87 mg, 0.21 mmol). The reaction mixture was stirred at room temperature for 1 h, at which point TLC indicated complete consumption of SM. The reaction was diluted with DCM, quenched with saturated Na$_2$S$_2$O$_3$ and saturated NaHCO$_3$ (1 mL each), and vigorously stirred until two clear layers were obtained (10 min). The layers were separated and the organic layer was dried over MgSO$_4$, filtered, and concentrated. The residue was used without purification.

Step 3. (E)-tert-butyl 1-((hydroxyimino)methyl)-2-oxabicyclo[2.1.1]hexan-4-ylcarbamate

To a solution of tert-butyl (1-formyl-2-oxabicyclo[2.1.1]hexan-4-yl)carbamate (31.5 mg, 0.14 mmol) in pyridine (3.0 mL) was added hydroxylamine hydrochloride (29 mg, 0.42 mmol) and the reaction mixture was stirred at room temperature for 1 h. The reaction mixture was partitioned between water and EtOAc, and the layers were separated. The organic layer was washed with brine, dried over MgSO$_4$, filtered, and concentrated. The residue was dried under high vac and used without purification. LCMS calculated for $C_{11}H_{18}N_2O_4Na$ (M+Na)$^+$: m/z=265.1; found: 265.1.

Step 4. 4-Amino-2-oxabicyclo[2.1.1]hexane-1-carbonitrile Hydrochloride Salt

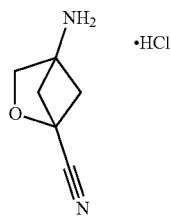

To a solution of tert-butyl (E)-(1-((hydroxyimino)methyl)-2-oxabicyclo[2.1.1]hexan-4-yl)carbamate (33 mg, 0.14 mmol) and triethylamine (76 µL, 0.55 mmol) in DCM (3.0 mL) (gently heated to dissolve, then cooled to 0° C.) was added methanesulfonyl chloride (32 µL, 0.41 mmol). The ice bath was removed and the reaction mixture was allowed to stir at room temperature for 1 h. The reaction was quenched with saturated NaHCO$_3$ and diluted with DCM. The layers were separated and the organic layer was dried over MgSO$_4$, filtered, and concentrated. The residue was stirred in HCl (4 M/dioxane) (2 mL, 65.8 mmol) for 30 min and concentrated to afford the product, which was used without purification. LCMS calculated for C$_6$H$_9$N$_2$O (M+H)$^+$: m/z=125.1; found: 125.1.

Step 5. 3-(8-Amino-6-(trifluoromethyl)imidazo[1,2-a]pyrazin-3-yl)-N-(1-cyano-2-oxabicyclo[2.1.1]hexan-4-yl)-4-methylbenzenesulfonamide Trifluoroacetate Salt Prepared according to the procedure described for Example 428 utilizing 4-amino-2-oxabicyclo[2.1.1]hexane-1-carbonitrile hydrochloride salt instead of (4-amino-2-oxabicyclo[2.1.1]hexan-1-yl)methanol. LCMS calculated for C$_{20}$H$_{18}$F$_3$N$_6$O$_3$S (M+H)$^+$: m/z=479.1; found: 479.1.

Example 430. 3-(4-Aminoimidazo[1,2-f][1,2,4]triazin-7-yl)-N-((1s,4s)-4-(cyanomethyl)bicyclo[2.2.1]heptan-1-yl)-4-methylbenzenesulfonamide Trifluoroacetate Salt

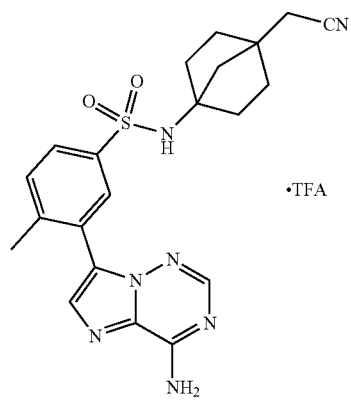 [SMILES: Cc1ccc(S(=O)(=O)NC23CCC(CC#N)(CC2)C3)cc1-c1cnc2c(N)ncnn12]

Step 1. 4-(methoxycarbonyl)bicyclo[2.2.1]heptane-1-carboxylic Acid

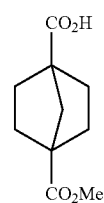

To a solution of dimethyl bicyclo [2.2.1]heptane-1,4-dicarboxylate (1 g, 4.71 mmol, Ark Pharm, AK313189) in THF (32 mL) at 15° C. (ice water bath) was added a solution of sodium hydroxide (188 mg, 4.71 mmol) in methanol (2 mL). After the addition was complete, white solids began to precipitate. The reaction mixture was stirred at room temp overnight. The reaction mixture was concentrated to dryness, slurried in hexanes, filtered, and washed with hexanes. The resulting sodium carboxylate salt was dissolved in water, and slowly treated with 1 N aqueous hydrochloric acid until pH 4. The suspension was diluted with ethyl acetate and transferred to a separatory funnel. The layers were separated and the aqueous layer was further extracted with ethyl acetate. The combined organic layers were washed with brine, dried over MgSO$_4$, and concentrated. The resulting white solid was used without purification. $^1$H NMR (400 MHz, DMSO) δ 3.62 (s, 3H), 1.93 (app d, J=6.6 Hz, 4H), 1.77 (s, 2H), 1.60 (q, J=9.2, 8.7 Hz, 4H).

Step 2. Methyl 4-(benzyloxycarbonylamino)bicyclo[2.2.1]heptane-1-carboxylate

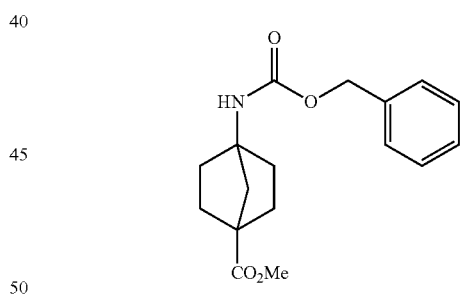

To a solution of 4-(methoxycarbonyl)bicyclo[2.2.1]heptane-1-carboxylic acid (500 mg, 2.52 mmol) in toluene (5.0 mL) was added DIPEA (0.88 mL, 5.04 mmol), followed by diphenylphosphoryl azide (0.65 mL, 3.03 mmol), and the reaction mixture was heated to 60° C. for 0.5 h, then to reflux for 2 h. The reaction mixture was then cooled to 50° C. and benzyl alcohol (0.53 mL, 5.04 mmol) was added. The resulting solution was heated to reflux for 24 h. After cooling to room temperature, the reaction mixture was diluted with EtOAc, washed with water and brine, dried over MgSO$_4$, filtered and concentrated. The residue was purified by flash chromatography (0-50% EtOAc/hexanes) to afford the product as a colorless oil, which was contaminated with a large amount of benzyl alcohol. LCMS calculated for C$_{17}$H$_{22}$NO$_4$ (M+H)$^+$: m/z=304.2; found: 304.1.

Step 3. Benzyl 4-(hydroxymethyl)bicyclo[2.2.1]heptan-1-ylcarbamate

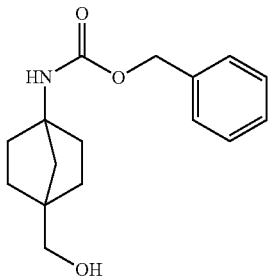

To a solution of methyl 4-(((benzyloxy)carbonyl)amino)bicyclo[2.2.1]heptane-1-carboxylate (500 mg, 1.65 mmol) in THF (5.0 mL) was added lithium borohydride (180 mg, 8.24 mmol) at room temperature and the reaction mixture was stirred overnight. The reaction mixture was cooled to 0° C., and slowly quenched by the dropwise addition of saturated NH$_4$Cl. After warming to room temperature, the reaction mixture was partitioned between water and EtOAc, and the layers were separated. The organic layer was washed with brine, dried over MgSO$_4$, filtered, and concentrated. The residue was purified by flash chromatography (0-50-70% EtOAc/hexanes) to afford the product as a colorless oil (398 mg, 88%). LCMS calculated for $C_{16}H_{22}NO_3$ (M+H)$^+$: m/z=276.2; found: 276.1.

Step 4. (4-(Benzyloxycarbonylamino)bicyclo[2.2.1]heptan-1-yl)methyl Methanesulfonate

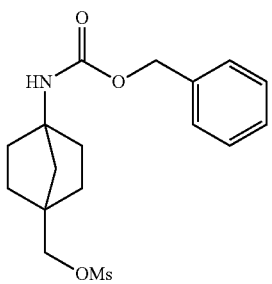 [SMILES: CS(=O)(=O)OCC12CCC(NC(=O)OCc3ccccc3)(CC1)C2]

To a solution of benzyl 4-(hydroxymethyl)bicyclo[2.2.1]heptan-1-yl)carbamate (200 mg, 0.73 mmol) and triethylamine (0.51 mL, 3.63 mmol) in DCM (3.0 mL) at 0° C. was added methanesulfonyl chloride (0.11 mL, 1.45 mmol) dropwise. After stirring at this temperature for min, the reaction mixture was allowed to warm to room temperature and stir for 2 h. The reaction was quenched with saturated NaHCO$_3$ and diluted with DCM. The layers were separated and the organic layer was dried over MgSO$_4$, filtered and concentrated. The residue was purified by flash chromatography (0-50% EtOAc/hexanes) to afford the product as a colorless oil (252 mg, 98%). LCMS calculated for $C_{17}H_{23}NO_5SNa$ (M+Na)$^+$: m/z=376.1; found: 376.1.

Step 5. Benzyl 4-(cyanomethyl)bicyclo[2.2.1]heptan-1-ylcarbamate

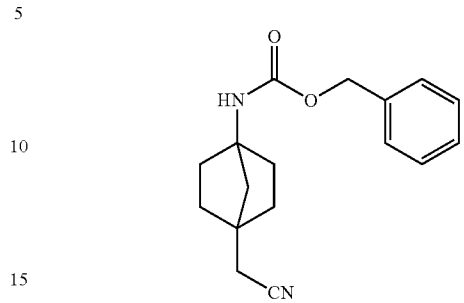

To a solution of 4-(((benzyloxy)carbonyl)amino)bicyclo[2.2.1]heptan-1-yl)methyl methanesulfonate (250 mg, 0.71 mmol) in DMSO (4.0 mL) was added potassium cyanide (461 mg, 7.07 mmol) and the reaction mixture was heated to 100° C. overnight. The reaction mixture was diluted with EtOAc and washed with water and brine. The organic layer was dried over MgSO$_4$, filtered, and concentrated. The residue was purified by flash chromatography (0-50% EtOAc/hexanes) to afford the product as a colorless oil (165 mg, 82%). LCMS calculated for $C_{17}H_{21}N_2O_2$ (M+H)$^+$: m/z=285.2; found: 285.1.

Step 6. 2-(4-Aminobicyclo[2.2.1]heptan-1-yl)acetonitrile

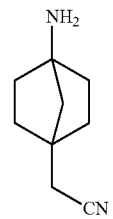

To a solution of benzyl 4-(cyanomethyl)bicyclo[2.2.1]heptan-1-yl)carbamate (165 mg, 0.58 mmol) in MeOH (4 mL) was added palladium on carbon (10 wt %, 30.9 mg, 29 μmol). The vial was purged with hydrogen and the reaction mixture was stirred under 1 atm of hydrogen for 2 h. The reaction mixture was filtered through a pad of Celite*, which was rinsed with additional MeOH. The volatiles were removed in vacuo to afford the product as a colorless oil that was used without purification. LCMS calculated for $C_9H_{15}N_2$(M+H)$^+$: m/z=151.1; found: 151.1.

Step 7. 3-(4-Aminoimidazo[1,2-f][1,2,4]triazin-7-yl)-N-((s,4s)-4-(cyanomethyl)bicyclo[2.2.1]heptan-1-yl)-4-methylbenzenesulfonamide Trifluoroacetate Salt Prepared according to the procedure described for Example 424, Step 8, utilizing 2-(4-aminobicyclo[2.2.1]heptan-1-yl)acetonitrile instead of 1-methyl-2-oxabicyclo[2.1.1]hexan-4-amine hydrochloride. LCMS calculated for $C_{21}H_{24}N_7O_2S$ (M+H)$^+$: m/z=438.2; found: 438.1.

Example 431. 3-(4-Aminoimidazo[1,2-][1,2,4]triazin-7-yl)-N-(4-(2-hydroxypropan-2-yl)bicyclo[2.2.1]heptan-1-yl)-4-methylbenzenesulfonamide Trifluoroacetate Salt

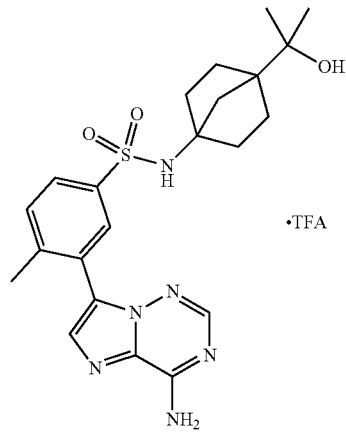 [SMILES: Cc1ccc(S(=O)(=O)NC23CCC(C(C)(C)O)(CC2)C3)cc1-c1cnc2c(N)ncnn12]

·TFA

Step 1. 2-(4-Aminobicyclo[2.2.1]heptan-1-yl)propan-2-ol Hydrochloride

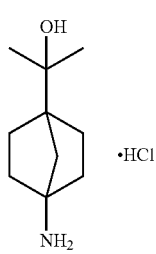

·HCl

To a solution of methyl 4-(((benzyloxy)carbonyl)amino)bicyclo[2.2.1]heptane-1-carboxylate (80 mg, 0.26 mmol, 430, Step 2) in THF (2.0 mL) at 0° C. was added methyllithium (0.99 mL, 1.58 mmol) dropwise. The reaction mixture was allowed to warm to room temperature. After stirring for 2 h, the reaction mixture was heated to 70° C. for 2 h. The reaction mixture was cooled to 0° C. and slowly quenched with 1M HCl. The aqueous layer was washed with EtOAc and concentrated in vacuo. The product was used without purification. LCMS calculated for $C_{10}H_{20}NO$ $(M+H)^+$: m/z=170.2; found: 170.2.

Step 2. 3-(4-Aminoimidazo[1,2-f][1,2,4]triazin-7-yl)-N-((1s,4s)-4-(2-hydroxypropan-2-yl)bicyclo[2.2.1]heptan-1-yl)-4-methylbenzenesulfonamide Trifluoroacetate Salt Prepared according to the procedure described for Example 424, Step 8, utilizing 2-(4-aminobicyclo[2.2.1]heptan-1-yl)propan-2-ol hydrochloride salt instead of 1-methyl-2-oxabicyclo[2.1.1]hexan-4-amine hydrochloride salt. LCMS calculated for $C_{22}H_{29}N_6O_3S$ $(M+H)^+$: m/z=457.2; found: 457.2.

Example 432. 3-(4-Aminoimidazo[1,2-f][1,2,4]triazin-7-yl)-N-(1-(1-hydroxyethyl)-2-oxabicyclo[2.2.2]octan-4-yl)-4-methylbenzenesulfonamide Trifluoroacetate Salt (Racemic)

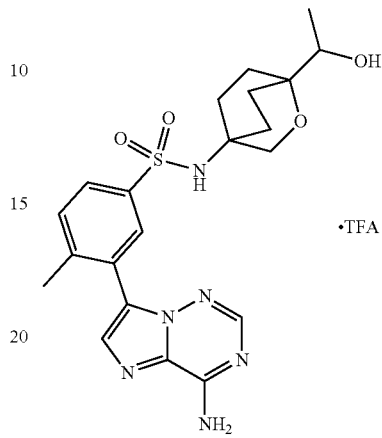

·TFA

Step 1. 1-(4-Amino-2-oxabicyclo[2.2.2]octan-1-yl)ethanol Trifluoroacetate salt

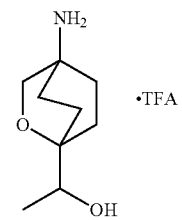

·TFA

To a solution of tert-butyl 1-formyl-2-oxabicyclo[2.2.2]octan-4-ylcarbamate (30 mg, 0.12 mmol, Advanced Chemblocks) in THF (1.0 mL) at 0° C. was added methylmagnesium bromide (0.12 mL, 0.35 mmol) and the reaction mixture was allowed to warm to room temperature. The reaction mixture was quenched with saturated $NH_4Cl$ and partitioned between water and EtOAc. The layers were separated and the organic layer was washed with brine, dried over $MgSO_4$, filtered, and concentrated. The residue was taken up in DCM (2.0 mL) and treated with TFA (0.5 mL, 6.49 mmol). After stirring for 0.5 h, the volatiles were removed in vacuo, the residue was taken up in 1:1 MeCN/$H_2O$, and lyophilized. The residue was used without purification. LCMS calculated for $C_9H_{18}NO_2$ $(M+H)^+$: m/z=172.1; found: 172.1.

Step 2. 3-(4-aminoimidazo[1,2-f][1,2,4]triazin-7-yl)-N-(1-(1-hydroxyethyl)-2-oxabicyclo[2.2.2]octan-4-yl)-4-methylbenzenesulfonamide Trifluoroacetate Salt Prepared according to the procedure described for Example 424, Step 8, utilizing 1-(4-amino-2-oxabicyclo[2.2.2]octan-1-yl)ethanol trifluoroacetate salt instead of 1-methyl-2-oxabicyclo[2.1.1]hexan-4-amine hydrochloride. LCMS calculated for $C_{21}H_{27}N_6O_4S$ $(M+H)^+$: m/z=459.2; found: 459.2.

Example 433. 3-(4-Aminoimidazo[1,2-][1,2,4]triazin-7-yl)-N-(1-(hydroxymethyl)-2-oxabicyclo[2.2.2]octan-4-yl)-4-methylbenzenesulfonamide Trifluoroacetate Salt

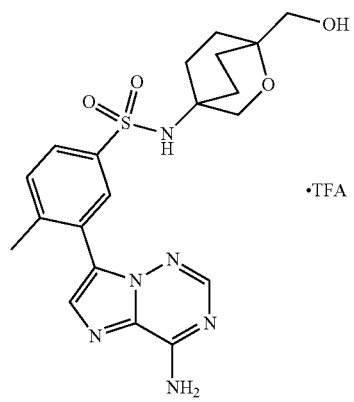 [SMILES: Cc1ccc(S(=O)(=O)NC23CCC(CO)(CC2)OC3)cc1-c1cnc2c(N)ncnn12]

Step 1. (4-Amino-2-oxabicyclo[2.2.2]octan-1-yl)methanol Trifluoroacetate Salt

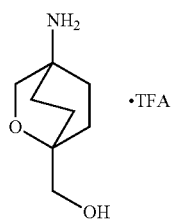 [SMILES: NC12CCC(CO)(CC1)OC2]

To a solution of tert-butyl 1-formyl-2-oxabicyclo[2.2.2]octan-4-ylcarbamate (30 mg, 0.12 mmol, Advanced Chemblocks) in EtOH (1.0 mL) at 0° C. was added sodium borohydride (22 mg, 0.59 mmol). The reaction mixture was warmed to room temperature and stirred for 0.5 h. The reaction mixture was diluted with EtOAc and water, and the layers were separated. The organic layer was washed with brine, dried over MgSO$_4$, filtered, and concentrated. The residue was dissolved in DCM (2.0 mL) and treated with TFA (0.5 mL, 6.49 mmol). After stirring for 0.5 h, the volatiles were removed in vacuo, the residue was dissolved in 1:1 MeCN/H$_2$O, and lyophilized. The product was used without purification. LCMS calculated for C$_8$H$_{16}$NO$_2$ (M+H)$^+$: m/z=158.1; found: 158.2.

Step 2. 3-(4-Aminoimidazo[1,2-f][1,2,4]triazin-7-yl)-N-(1-(hydroxymethyl)-2-oxabicyclo[2.2.2]octan-4-yl)-4-methylbenzenesulfonamide Trifluoracetate Prepared according to the procedure described for Example 424, Step 8, utilizing (4-amino-2-oxabicyclo[2.2.2]octan-1-yl)methanol trifluoroacetate salt instead of 1-methyl-2-oxabicyclo[2.1.1]hexan-4-amine hydrochloride salt. LCMS calculated for C$_{20}$H$_{25}$N$_6$O$_4$S (M+H)$^+$: m/z=445.2; found: 445.2.

Example 434. 3-(4-Aminoimidazo[1,2-][1,2,4]triazin-7-yl)-4-methyl-N-(1-(morpholinomethyl)-2-oxabicyclo[2.2.2]octan-4-yl)benzenesulfonamide Trifluoroacetate Salt

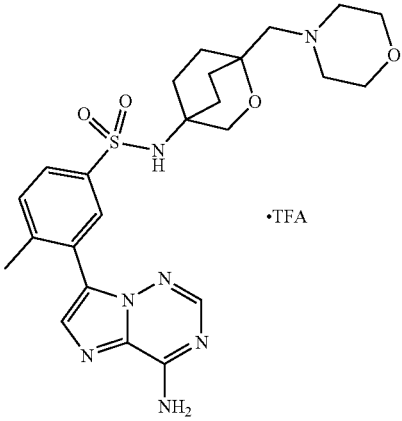 [SMILES: Cc1ccc(S(=O)(=O)NC23CCC(CN4CCOCC4)(CC2)OC3)cc1-c1cnc2c(N)ncnn12]

Step 1. 1-(Morpholinomethyl)-2-oxabicyclo[2.2.2]octan-4-amine Hydrochloride Salt

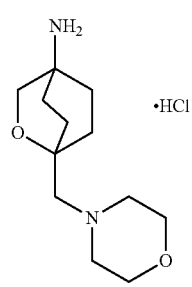 [SMILES: NC12CCC(CN3CCOCC3)(CC1)OC2 ; Cl]

To a solution of tert-butyl 1-formyl-2-oxabicyclo[2.2.2]octan-4-ylcarbamate (20 mg, 0.078 mmol, Advanced Chemblocks) in THF (1.0 mL) was added morpholine (20 μL, 0.24 mmol), sodium triacetoxyborohydride (50 mg, 0.24 mmol), and 1 drop of AcOH. The reaction mixture was stirred at room temperature overnight. The reaction mixture was quenched with saturated NaHCO$_3$ and extracted with EtOAc. The organic layer was washed with brine, dried over MgSO$_4$, filtered and concentrated. The residue was purified by flash chromatography (0-100% EtOAc/hexanes). The product was taken up in HCl (4 M/dioxane) (3 mL) and stirred at room temperature for 1 h. The volatiles were removed in vacuo and the residue was used without purification. LCMS calculated for C$_{12}$H$_{23}$N$_2$O$_2$ (M+H)$^+$: m/z=227.2; found: 227.1.

Step 2. 3-(4-Aminoimidazo[1,2-f][1,2,4]triazin-7-yl)-4-methyl-N-(1-(morpholinomethyl)-2-oxabicyclo[2.2.2]octan-4-yl)benzenesulfonamide Trifluoroacetate Salt Prepared according to the procedure described for Example 424, Step 8, utilizing 1-(morpholinomethyl)-2-oxabicyclo[2.2.2]octan-4-amine hydrochloride salt instead Example 435. 3-(4-Aminoimidazo[1,2-f][1,2,4]tri-
azin-7-yl)-N-(1-((3,3-difluoroazetidin-1-yl)methyl)-
2-oxabicyclo[2.2.2]octan-4-yl)-4-methylbenzene-
sulfonamide Trifluoroacetate Salt

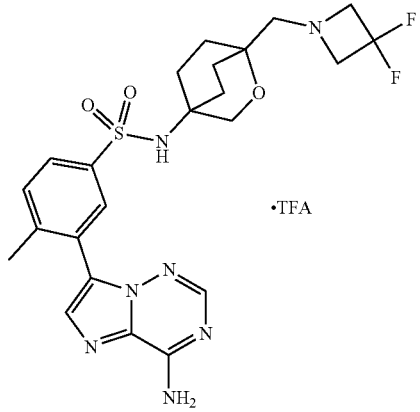 [SMILES: Cc1ccc(S(=O)(=O)NC23CCC(CN4CC(F)(F)C4)(CC2)OC3)cc1-c1cnc2c(N)ncnn12]

Prepared according to the procedure described for Example 434, utilizing 3,3-difluoroazetidine hydrochloride instead of morpholine in Step 1. LCMS calculated for $C_{23}H_{28}F_2N_7O_3S$ (M+H)$^+$: m/z=520.2; found: 520.2.

Example 436. 3-(4-aminoimidazo[1,2-f][1,2,4]tri-
azin-7-yl)-N-(1-(difluoromethyl)-2-oxabicyclo
[2.2.2]octan-4-yl)-4-methylbenzenesulfonamide Tri-
fluoroacetate Salt

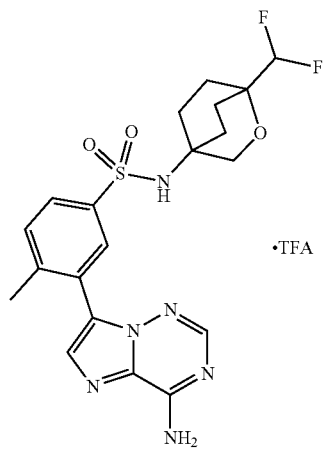 [SMILES: Cc1ccc(S(=O)(=O)NC23CCC(C(F)F)(CC2)OC3)cc1-c1cnc2c(N)ncnn12]

Step 1. 1-(Difluoromethyl)-2-oxabicyclo[2.2.2]oc-
tan-4-amine Hydrochloride

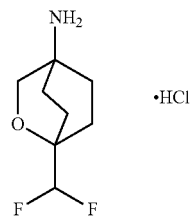 [SMILES: NC12CCC(C(F)F)(CC1)OC2 ; Cl]

To a solution of tert-butyl 1-formyl-2-oxabicyclo[2.2.2] octan-4-ylcarbamate (30 mg, 0.12 mmol, Advanced Chemblocks) in DCM (1.0 mL) was added diethylaminosulfur trifluoride (47 µL, 0.35 mmol). The reaction mixture was stirred at room temperature overnight and was quenched with saturated NaHCO$_3$. The reaction mixture was diluted with DCM and water, and the layers were separated. The organic layer was dried over MgSO$_4$, filtered, and concentrated. The residue was purified by flash chromatography (0-20% EtOAc/hexanes) to afford the desired product as a white solid. This solid was taken up in HCl (4 M/dioxane) (3.0 mL) and stirred at room temperature for 1 h. The volatiles were removed in vacuo to afford the title compound (16 mg, 63%). LCMS calculated for $C_8H_{14}F_2NO$ (M+H)$^+$: m/z=178.1; found: 178.1.

Step 2. 3-(4-Aminoimidazo[1,2-f][1,2,4]triazin-7-
yl)-N-(1-(difluoromethyl)-2-oxabicyclo[2.2.2]octan-
4-yl)-4-methylbenzenesulfonamide Trifluoroacetate
Salt Prepared according to the procedure described for Example 424, Step 8, utilizing 1-(difluoromethyl)-2-oxabicyclo[2.2.2]octan-4-amine hydrochloride instead of 1-methyl-2-oxabicyclo[2.1.1]hexan-4-amine hydrochloride. LCMS calculated for $C_{20}H_{23}F_2N_6O_3S$ (M+H)$^+$: m/z=465.1; found: 465.1.

Example 437. 3-(4-Aminoimidazo[1,2-f][1,2,4]tri-
azin-7-yl)-4-methyl-N-(1-(2,2,2-trifluoro-1-hydroxy-
ethyl)-2-oxabicyclo[2.2.2]octan-4-yl)benzenesulfo-
namide Trifluoroacetate Salt (Racemic)

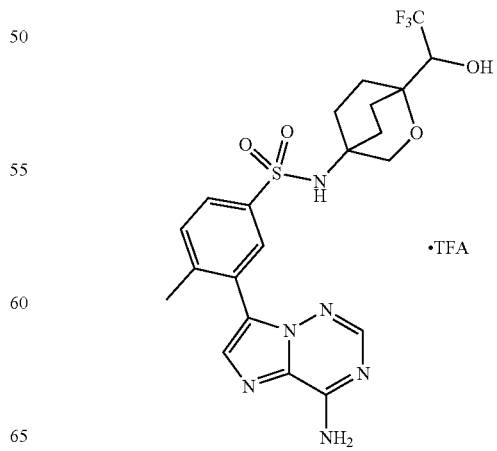

349

Step 1. 1-(4-Amino-2-oxabicyclo[2.2.2]octan-1-yl)-2,2,2-trifluoroethanol Hydrochloride Salt

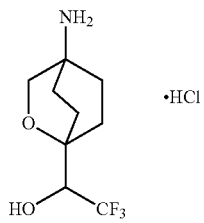

A solution of tert-butyl 1-formyl-2-oxabicyclo[2.2.2]octan-4-ylcarbamate (54 mg, 0.21 mmol, Advanced Chemblocks) and trifluoromethyltrimethylsilane (94 μL, 0.64 mmol) in DMF (2.0 mL) was cooled to 0° C. To this solution was added cesium fluoride (96 mg, 0.64 mmol) and the reaction mixture was stirred overnight at room temperature. The reaction was quenched with saturated NaHCO$_3$ and partitioned between EtOAc and water. The layers were separated and the organic layer was washed with brine, dried over MgSO$_4$, filtered and concentrated. The residue was taken up in HCl (4 M/dioxane) (2 mL) and the solution was stirred at room temperature for 1 h. The volatiles were removed in vacuo and the residue was used without purification. LCMS calculated for C$_9$H$_{15}$F$_3$NO$_2$ (M+H)$^+$: m/z=226.1; found: 226.0.

Step 2. 3-(4-Aminoimidazo[1,2-f][1,2,4]triazin-7-yl)-4-methyl-N-(1-(2,2,2-trifluoro-1-hydroxyethyl)-2-oxabicyclo[2.2.2]octan-4-yl)benzenesulfonamide Trifluoroacetate Salt Prepared according to the procedure described for Example 424, Step 8, utilizing 1-(4-amino-2-oxabicyclo[2.2.2]octan-1-yl)-2,2,2-trifluoroethanol hydrochloride instead of 1-methyl-2-oxabicyclo[2.1.1]hexan-4-amine hydrochloride. LCMS calculated for C$_{21}$H$_{24}$F$_3$N$_6$O$_4$S (M+H)$^+$: m/z=513.2; found: 513.1.

Example 438. 3-(4-Aminoimidazo[1,2-f][1,2,4]triazin-7-yl)-N-(1-(hydroxy(phenyl)methyl)-2-oxabicyclo[2.2.2]octan-4-yl)-4-methylbenzenesulfonamide Trifluoroacetate Salt (Racemic)

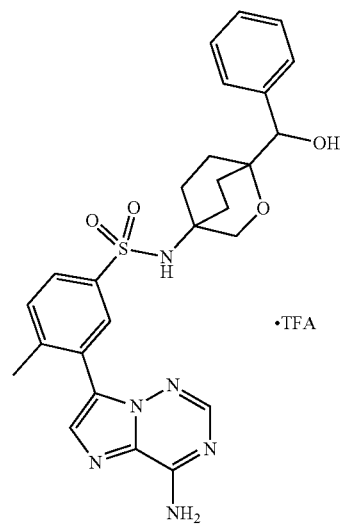 [SMILES: Cc1ccc(S(=O)(=O)NC23CCC(C(O)c4ccccc4)(CC2)OC3)cc1-c1cnc2c(N)ncnn12]

350

Step 1. (4-Amino-2-oxabicyclo[2.2.2]octan-1-yl)(phenyl)methanol Hydrochloride Salt

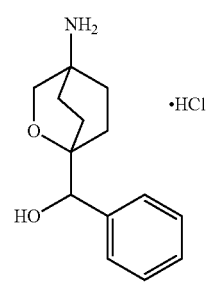

To a solution of tert-butyl 1-formyl-2-oxabicyclo[2.2.2]octan-4-ylcarbamate (25 mg, 98 μmol) in THF (1.0 mL) at 0° C. was added phenylmagnesium bromide (0.33 mL, 0.98 mmol). The reaction mixture was warmed to room temperature and stirred overnight. The reaction was quenched with saturated NH$_4$Cl and extracted with EtOAc. The organic layer was washed with brine, dried over MgSO$_4$, and concentrated. The residue was dissolved in HCl (4M/dioxane) (2 mL, 8.00 mmol) and stirred at room temperature for 1 h. The volatiles were removed in vacuo and the residue was used without purification. LCMS calculated for C$_{14}$H$_{20}$NO$_2$ (M+H)$^+$: m/z=234.1; found: 234.2.

Step 2. 3-(4-Aminoimidazo[1,2-f][1,2,4]triazin-7-yl)-N-(1-(hydroxy(phenyl)methyl)-2-oxabicyclo[2.2.2]octan-4-yl)-4-methylbenzenesulfonamide Trifluoroacetate Salt (Racemic)

Prepared according to the procedure described for Example 424, Step 8, utilizing (4-amino-2-oxabicyclo[2.2.2]octan-1-yl)(phenyl)methanol hydrochloride instead of 1-methyl-2-oxabicyclo[2.1.1]hexan-4-amine hydrochloride. LCMS calculated for C$_{26}$H$_{29}$N$_6$O$_4$S (M+H)$^+$: m/z=521.2; found: 521.1.

Example 439. 3-(4-Aminoimidazo[1,2-f][1,2,4]triazin-7-yl)-4-methyl-N-(1-(1-methyl-1H-imidazol-2-yl)-2-oxabicyclo[2.2.2]octan-4-yl)benzenesulfonamide Trifluoroacetate Salt

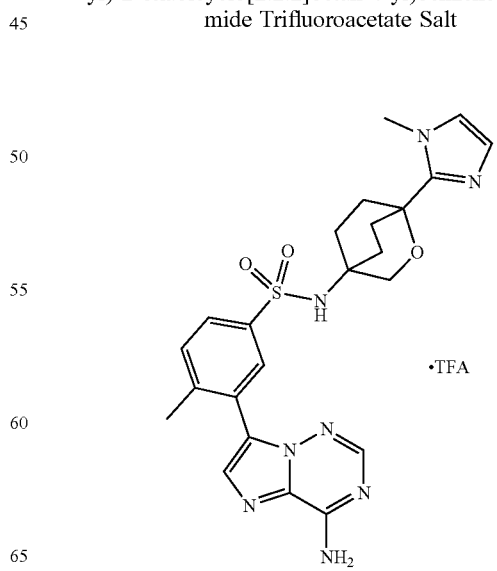

Step 1. tert-butyl 1-(1H-imidazol-2-yl)-2-oxabicyclo[2.2.2]octan-4-ylcarbamate

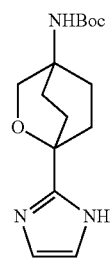 [SMILES: CC(C)(C)OC(=O)NC12CCC(c3ncc[nH]3)(CC1)OC2]

To a solution of tert-butyl 1-formyl-2-oxabicyclo[2.2.2]octan-4-ylcarbamate (50 mg, 0.20 mmol, Advanced Chemblocks) in ammonia (7 N/MeOH) (1 mL, 7.0 mmol) was added glyoxal (67 μL, 0.59 mmol) and the reaction mixture was stirred at room temperature overnight. The volatiles were removed in vacuo and the residue was partitioned between EtOAc and water. The layers were separated and the organic layer was washed with brine, dried over MgSO$_4$, filtered and concentrated. The residue was purified by flash chromatography (0-15% MeOH/DCM) to afford the title compound (24 mg, 42%). LCMS calculated for C$_{15}$H$_{24}$N$_3$O$_3$ (M+H)$^+$: m/z=294.2; found: 294.2.

Step 2. 1-(1-Methyl-1H-imidazol-2-yl)-2-oxabicyclo[2.2.2]octan-4-amine Hydrochloride Salt

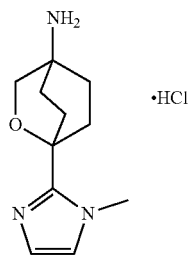

To a solution of tert-butyl 1-(1H-imidazol-2-yl)-2-oxabicyclo[2.2.2]octan-4-ylcarbamate (24 mg, 0.08 mmol) in acetonitrile (3.0 mL) was added potassium carbonate (34 mg, 0.25 mmol), followed by methyl iodide (15 μL, 0.25 mmol), and the reaction mixture was heated to 60° C. overnight. The reaction mixture was cooled to room temperature and partitioned between water and EtOAc. The layers were separated and the organic layer was washed with brine, dried over MgSO$_4$, filtered and concentrated. The residue was taken up in HCl (4M/dioxane, 3.0 mL) and stirred at room temperature for 1 h. The volatiles were removed in vacuo and the product was used without purification. LCMS calculated for C$_{11}$H$_{18}$N$_3$O (M+H)$^+$: m/z=208.1; found: 208.1.

Step 3. 3-(4-aminoimidazo[1,2-f][1,2,4]triazin-7-yl)-4-methyl-N-(1-(1-methyl-H-imidazol-2-yl)-2-oxabicyclo[2.2.2]octan-4-yl)benzenesulfonamide Trifluoroacetate Salt Prepared according to the procedure described for Example 424, Step 8, utilizing 1-(1-methyl-1H-imidazol-2-yl)-2-oxabicyclo[2.2.2]octan-4-amine hydrochloride instead of 1-methyl-2-oxabicyclo[2.1.1]hexan-4-amine hydrochloride. LCMS calculated for C$_{23}$H$_{27}$N$_8$O$_3$S (M+H)$^+$: m/z=495.2; found: 495.3.

Example 440. 3-(4-Aminoimidazo[1,2-f][1,2,4]triazin-7-yl)-4-methyl-N-(1-(oxazol-5-yl)-2-oxabicyclo[2.2.2]octan-4-yl)benzenesulfonamide Trifluoroacetate Salt

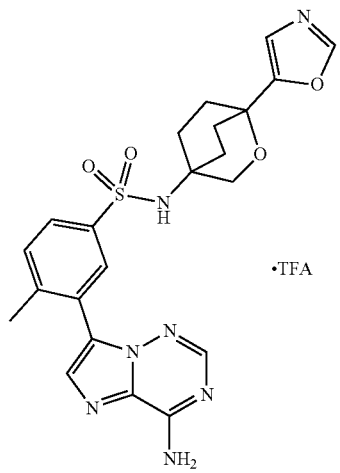 [SMILES: Cc1ccc(S(=O)(=O)NC23CCC(c4cnco4)(CC2)OC3)cc1-c1cnc2c(N)ncnn12]

Step 1. 1-(Oxazol-5-yl)-2-oxabicyclo[2.2.2]octan-4-amine Hydrochloride Salt

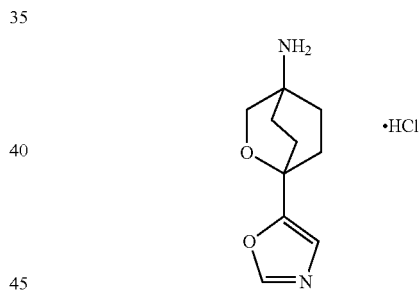

To a solution of tert-butyl 1-formyl-2-oxabicyclo[2.2.2]octan-4-ylcarbamate (30 mg, 0.12 mmol, Advanced Chemblocks) in methanol (1.0 mL) was added potassium carbonate (49 mg, 0.35 mmol), followed by TosMIC (34 mg, 0.18 mmol), and the reaction mixture was heated to reflux overnight. The reaction mixture was partitioned between water and EtOAc, and the layers were separated. The organic layer was washed with brine, dried over MgSO$_4$, filtered and concentrated. The residue was purified by flash chromatography (0-70% EtOAc/hexanes) to afford the desired product as a white solid. This was taken up in HCl (4M/dioxane, 2.0 mL) and stirred at room temperature for 1 h. The volatiles were removed in vacuo to afford the title compound (18 mg, 66%). LCMS calculated for C$_{10}$H$_{15}$N$_2$O$_2$ (M+H)$^+$: m/z=195.1; found: 195.1.

Step 2. 3-(4-Aminoimidazo[1,2-f][1,2,4]triazin-7-yl)-4-methyl-N-(1-(oxazol-5-yl)-2-oxabicyclo[2.2.2]octan-4-yl)benzenesulfonamide Trifluoroacetate Salt Prepared according to the procedure described for Example 424, Step 8, utilizing 1-(oxazol-5-yl)-2-oxabicyclo

[2.2.2]octan-4-amine hydrochloride salt instead of 1-methyl-2-oxabicyclo[2.1.1]hexan-4-amine hydrochloride salt. LCMS calculated for $C_{22}H_{24}N_7O_4S$ (M+H)$^+$: m/z=482.2; found: 482.1.

Example 441. 3-(8-Amino-6-(trifluoromethyl)imidazo[1,2-a]pyrazin-3-yl)-N-(1-(2-hydroxypropan-2-yl)-2-oxabicyclo[2.2.2]octan-4-yl)-4-methylbenzenesulfonamide Trifluoroacetate Salt

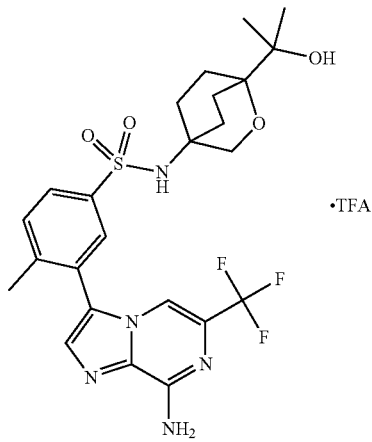 [SMILES: Cc1ccc(S(=O)(=O)NC23CCC(C(C)(C)O)(CC2)OC3)cc1-c1cnc2c(N)nc(C(F)(F)F)cn12]

Step 1. tert-butyl 1-acetyl-2-oxabicyclo[2.2.2]octan-4-ylcarbamate

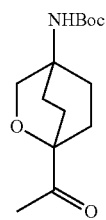

To a solution of tert-butyl 1-(1-hydroxyethyl)-2-oxabicyclo[2.2.2]octan-4-ylcarbamate (213 mg, 0.79 mmol, 432, Step 1) in DCM (5 mL) at 0° C. was added sodium bicarbonate (198 mg, 2.36 mmol), followed by Dess-Martin periodinane (499 mg, 1.18 mmol), and the reaction mixture was allowed to warm to room temperature. After stirring for 1 h, TLC indicated complete consumption of SM. The reaction mixture was diluted with DCM, quenched with saturated $Na_2S_2O_3$ and saturated $NaHCO_3$. The suspension was vigorously stirred until two clear layers were obtained. The layers were separated and the organic layer was dried over $MgSO_4$, filtered and concentrated. The residue was purified by flash chromatography (0-40% EtOAc/hexanes) to afford the product as a white solid (104 mg, 49%).

Step 2. 2-(4-Amino-2-oxabicyclo[2.2.2]octan-1-yl)propan-2-ol hydrochloride Salt

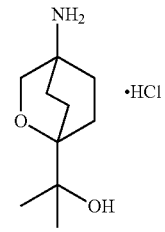

To a solution of tert-butyl 1-acetyl-2-oxabicyclo[2.2.2]octan-4-ylcarbamate (30 mg, 0.11 mmol) in THF (2.0 mL) at 0° C. was added methylmagnesium bromide (0.19 mL, 0.56 mmol). The reaction mixture was allowed to warm to room temperature and stir for 1 h. The reaction was quenched with water and extracted with EtOAc. The organic extracts were washed with brine, dried over $MgSO_4$, filtered, and concentrated. The residue was taken up in HCl (4M/dioxane, 3 mL) and stirred at room temperature for 1 h. The volatiles were removed in vacuo and the residue was used without purification. LCMS calculated for $C_{10}H_{20}NO_2$ (M+H)$^+$: m/z=186.1; found: 186.2.

Step 3. 3-(8-Amino-6-(trifluoromethyl)imidazo[1,2-a]pyrazin-3-yl)-N-(1-(2-hydroxypropan-2-yl)-2-oxabicyclo[2.2.2]octan-4-yl)-4-methylbenzenesulfonamide Trifluoroacetate Salt Prepared according to the procedure described for Example 428, utilizing 2-(4-amino-2-oxabicyclo[2.2.2]octan-1-yl)propan-2-ol hydrochloride salt instead of (4-amino-2-oxabicyclo[2.1.1]hexan-1-yl)methanol. LCMS calculated for $C_{24}H_{29}F_3N_5O_4S$ (M+H)$^+$: m/z=540.2; found: 540.1.

Example 442. 3-(4-Aminoimidazo[1,2-f][1,2,4]triazin-7-yl)-N-((1s,4s)-4-hydroxybicyclo[2.2.1]heptan-1-yl)-4-methylbenzenesulfonamide Trifluoroacetate Salt

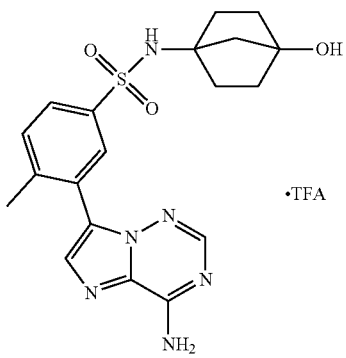 [SMILES: Cc1ccc(S(=O)(=O)NC23CCC(O)(CC2)C3)cc1-c1cnc2c(N)ncnn12]

Step 1. 4-Hydroxybicyclo[2.2.1]heptane-1-carboxylic Acid

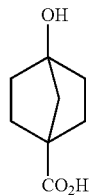 [SMILES: O=C(O)C12CCC(O)(CC1)C2]

To a solution of methyl 4-hydroxybicyclo[2.2.1]heptane-1-carboxylate (487 mg, 2.86 mmol, Advanced Chemblocks, L13452) in MeOH (5 mL) was added sodium hydroxide (572 mg, 14.3 mmol) in water (5.0 mL) and the reaction mixture was stirred at room temperature. After 1 h, the reaction mixture was acidified with 1 M HCl to pH 1 and extracted with three portions of EtOAc. The organic extracts were washed with brine, dried over MgSO$_4$, filtered and concentrated to afford a tan solid (257 mg, 58%) that was used without purification.

Step 2. 4-aminobicyclo[2.2.1]heptan-1-ol hydrochloride Salt

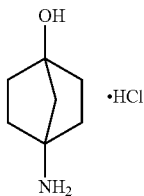

To a solution of 4-hydroxybicyclo[2.2.1]heptane-1-carboxylic acid (257 mg, 1.65 mmol) and triethylamine (0.28 mL, 1.98 mmol) in toluene (6.0 mL) was added diphenylphosphoryl azide (0.43 mL, 1.98 mmol) and the reaction mixture was heated to reflux for 2 h. The reaction mixture was diluted with EtOAc, washed with water and brine, dried over MgSO$_4$ and concentrated. The residue was taken up in a 1:1 mixture of AcOH and 15% HCl (1 mL each) and stirred at room temperature for 1 h. The reaction mixture was washed with EtOAc and the aqueous layer was concentrated to dryness to afford the title compound, which was used without purification.

Step 3. 3-(4-aminoimidazo[1,2-f][1,2,4]triazin-7-yl)-N-((1s,4s)-4-hydroxybicyclo[2.2.1]heptan-1-yl)-4-methylbenzenesulfonamide Trifluoroacetate Salt Prepared according to the procedure described for Example 424, Step 8, utilizing 4-aminobicyclo[2.2.1]heptan-1-ol hydrochloride salt instead of 1-methyl-2-oxabicyclo[2.1.1]hexan-4-amine hydrochloride salt. LCMS calculated for C$_{19}$H$_{23}$N$_6$O$_3$S (M+H)$^+$: m/z=415.1; found: 415.2.

Example 443. 3-(4-Amino-2-methylimidazo[1,2-][1,2,4]triazin-7-yl)-N-(4-hydroxybicyclo[2.2.1]heptan-1-yl)-4-methylbenzenesulfonamide Trifluoroacetate Salt

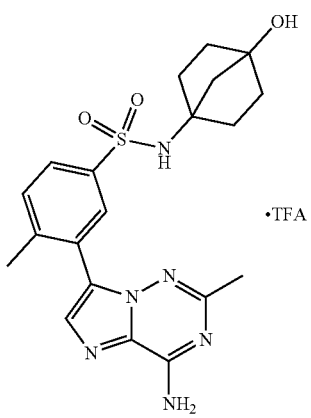 [SMILES: Cc1nc(N)c2ncc(-c3cc(S(=O)(=O)NC45CCC(O)(CC4)C5)ccc3C)n2n1]

Prepared according to the procedure described for Example 442, utilizing 3-(4-amino-2-methylimidazo[1,2-f][1,2,4]triazin-7-yl)-4-methylbenzene-1-sulfonyl chloride (4N Me SO$_2$Cl) instead of 3-(4-aminoimidazo[1,2-f][1,2,4]triazin-7-yl)-4-methylbenzene-1-sulfonyl chloride in Step 3. LCMS calculated for C$_{20}$H$_{25}$N$_6$O$_3$S (M+H)$^+$: m/z=429.2; found: 429.1.

Example 444. 3-(8-Amino-6-(trifluoromethyl)imidazo[1,2-a]pyrazin-3-yl)-N-(4-hydroxybicyclo[2.2.1]heptan-1-yl)-4-methylbenzenesulfonamide Trifluoroacetate Salt

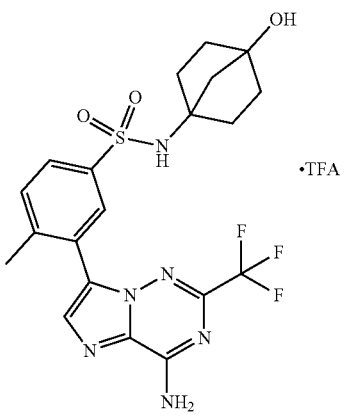 [SMILES: Cc1ccc(S(=O)(=O)NC23CCC(O)(CC2)C3)cc1-c1cnc2c(N)nc(C(F)(F)F)nn12]

Prepared according to the procedure described for Example 442, utilizing 3-(8-amino-6-(trifluoromethyl)imidazo[1,2-a]pyrazin-3-yl)-4-methylbenzene-1-sulfonyl chloride (Example 472, Step 8) instead of 3-(4-aminoimidazo[1,2-f][1,2,4]triazin-7-yl)-4-methylbenzene-1-sulfonyl chloride (Example 424, Step 7) in Step 3. LCMS calculated for C$_{21}$H$_{23}$F$_3$N$_5$O$_3$S (M+H)$^+$: m/z=482.1; found: 482.1.

Example 445. 8-Amino-3-(5-(N-((3,3-difluorocyclobutyl)methyl)sulfamoyl)-2-methylphenyl)-N-methylimidazo[1,2-a]pyrazine-6-carboxamide Trifluoroacetate Salt

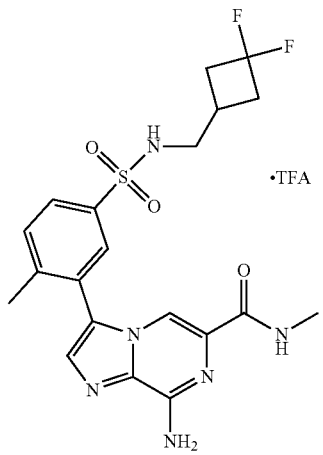

Step 1. N-(3,3-difluorocyclobutyl)-4-methyl-3-(4,4,5,5-tetramethyl-1,3,2-dioxaborolan-2-yl)benzenesulfonamide

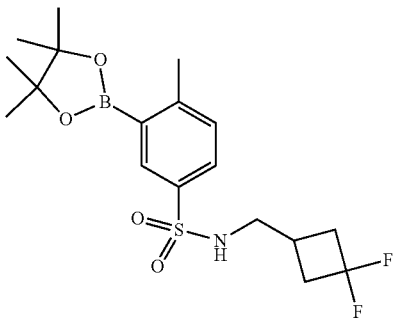 [SMILES: Cc1ccc(S(=O)(=O)NCC2CC(F)(F)C2)cc1B1OC(C)(C)C(C)(C)O1]

To a solution of 3-bromo-4-methylbenzenesulfonyl chloride (300 mg, 1.11 mmol) and i-Pr$_2$NEt (0.58 mL, 3.33 mmol in DCM (11 mL) at 0° C. was added DMAP (6.80 mg, 56 μmol) and (3,3-difluorocyclobutyl)methanamine hydrochloride (193 mg, 1.22 mmol) in one portion. After stirring at 0° C. for 2 h, the reaction was quenched by adding saturated NaHCO$_3$. The layers were separated and the organic layer was dried over MgSO$_4$, filtered, and concentrated. The residue was used without purification.

A mixture of 3-bromo-N-((3,3-difluorocyclobutyl)methyl)-4-methylbenzenesulfonamide (338 mg, 0.95 mmol), 4,4,4',4',5,5,5',5'-octamethyl-2,2'-bi(1,3,2-dioxaborolane) (254 mg, 1.0 mmol), potassium acetate (309 mg, 3.15 mmol), and Dichlorobis(triphenylphosphine)-palladium(II) (27 mg, 38 μmol) in THF (2.7 mL) was degassed with N$_2$ for 5 min. The mixture was heated in a microwave at 140° C. for 20 minutes. The reaction mixture was diluted with EtOAc and filtered through Celite®, rinsing with EtOAc. The filtrate was washed with water and then brine, dried over Na$_2$SO$_4$, filtered, and concentrated. Purification via silica gel chromatography (10-50% EtOAc/DCM) afforded the desired product as a yellow oil. LCMS calculated for C$_{18}$H$_{27}$BF$_2$NO$_4$S (M+H)$^+$: m/z=402.2; found: 402.1.

Step 2. 3-(8-Amino-6-bromoimidazo[1,2-a]pyrazin-3-yl)-N-((3,3-difluorocyclobutyl)methyl)-4-methylbenzenesulfonamide

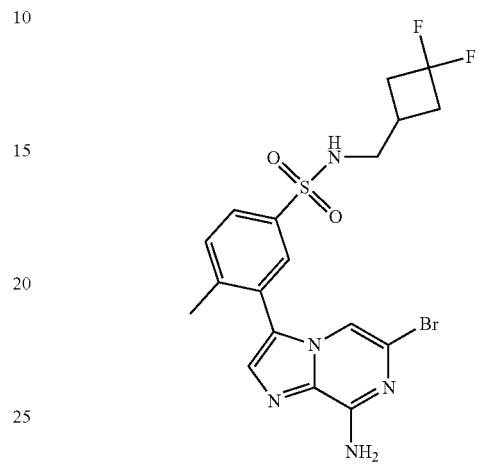

A mixture of 6-bromo-3-iodoimidazo[1,2-a]pyrazin-8-amine (120 mg, 0.35 mmol, 3N Br I), N-((3,3-difluorocyclobutyl)methyl)-4-methyl-3-(4,4,5,5-tetramethyl-1,3,2-dioxaborolan-2-yl)benzenesulfonamide (156 mg, 0.389 mmol), and tetrakis(triphenylphosphine)palladium(0) (24.96 mg, 0.022 mmol) in ethanol (4 mL)/2.0 M sodium carbonate in water (0.35 mL) was degassed for 5 min with N$_2$. The reaction mixture was then heated in a microwave reactor at 130° C. for 20 min. The reaction mixture was diluted with MeOH and filtered through a plug of Celite©. The filtrate was concentrated and the residue was purified by flash chromatography (0-100% EtOAc/hexanes) to afford the title compound (170 mg, 99%). LCMS calculated for C$_{18}$H$_{19}$BrF$_2$N$_5$O$_2$S (M+H)$^+$: m/z=486.0; found: 486.0.

Step 3. Methyl 8-amino-3-(5-(N-((3,3-difluorocyclobutyl)methyl)sulfamoyl)-2-methylphenyl)imidazo[1,2-a]pyrazine-6-carboxylate

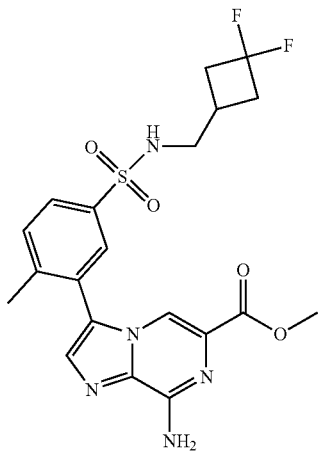

In a 40 mL vial, a solution of 3-(8-amino-6-bromoimidazo[1,2-a]pyrazin-3-yl)-N-((3,3-difluorocyclobutyl)methyl)-4-methylbenzenesulfonamide (200 mg, 0.41 mmol), dichloro[1,1'-bis(diphenylphosphino)ferrocene]palladium (II) dichloromethane adduct (34 mg, 41 µmol), and triethylamine (0.23 mL, 1.65 mmol) in methanol (10 mL) was saturated with CO by bubbling the gas through the solution for 5 min. The vessel was heated to 60° C. under 1 atm of CO for 5 h. Upon standing at room temperature overnight, the product precipitated. The suspension was treated with ether and cooled in an ice bath. The solid was filtered, washed with ether, and air dried to yield the desired product as a tan solid (84 mg, 44%). LCMS calculated for $C_{20}H_{22}F_2N_5O_4S$ (M+H)$^+$: m/z=466.1; found: 466.2.

Step 4. 8-Amino-3-(5-(N-((3,3-difluorocyclobutyl)methyl)sulfamoyl)-2-methylphenyl)-N-methylimidazo[1,2-a]pyrazine-6-carboxamide Trifluoroacetate Salt To a solution of methyl 8-amino-3-(5-(N-((3,3-difluorocyclobutyl)methyl)sulfamoyl)-2-methylphenyl)imidazo[1,2-a]pyrazine-6-carboxylate (15 mg, 0.032 mmol) in THF (2.0 mL) at rt was added methanamine (0.161 mL, 0.322 mmol), and trimethylaluminum (0.081 mL, 0.161 mmol) (2M in toluene). The resultant solution was heated at 80° C. for 3 h. After cooling to rt, MeOH (2 mL) was added. The mixture was stirred at rt for 1 h and filtered through Celite®. The filtrate was concentrated under vacuum. The residue was dissolved in MeOH (5 mL) and purified by pH 2 prep-LCMS to afford the desired product. LCMS calculated for $C_{20}H_{23}F_2N_6O_3S$ (M+H)$^+$: m/z=465.1; found: 465.1.

Example 446 listed in following table was prepared analogously to Example 445 utilizing the appropriate commercially available amine:

Example 447. 8-Amino-3-(5-(N-(3,3-difluorocyclobutyl)sulfamoyl)-2-methylphenyl)-N-methylimidazo[1,2-a]pyrazine-6-carboxamide Trifluoroacetate Salt

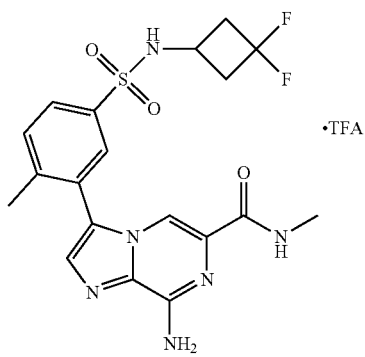

Prepared according to the procedure described for Example 445 utilizing 3,3-difluorocyclobutanamine hydrochloride salt instead of (3,3-difluorocyclobutyl)methanamine hydrochloride salt in Step 1. LCMS calculated for $C_{19}H_{21}F_2N_6O_3S$ (M+H)$^+$: m/z=451.1; found: 451.1.

Example 448 in the following table was prepared analogously to Example 447 utilizing the appropriate commercially available amine:

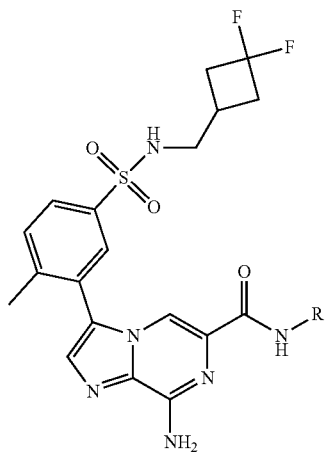

| Ex. No. | Name | R | LCMS |
|---|---|---|---|
| 446 | 8-amino-N-cyclobutyl-3-(5-(N-((3,3-difluorocyclobutypmethyl)sulfamoyl)-2-methylphenypimidazo [1,2-a]pyrazine-6-carboxamide trifluoroacetate salt | | 505.2 |

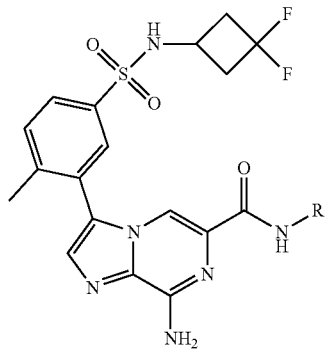

| Ex. No. | Name | R | LCMS |
|---|---|---|---|
| 448 | 8-amino-N-cyclobutyl-3-(5-(N-(3,3-difluorocyclobutyl)sulfamoyl)-2-methylphenyl)imidazo[1,2-a]pyrazine-6-carboxamide trifluoroacetate salt | | 491.1 |

Example 449. 8-Amino-3-(5-(N-((3S,6R)-6-(cyanomethyl)tetrahydro-2H-pyran-3-yl)sulfamoyl)-2-methylphenyl)-N-methylimidazo[1,2-a]pyrazine-6-carboxamide Trifluoroacetate Salt

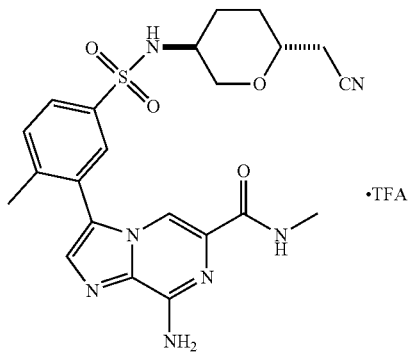

Prepared according to the procedure described for Example 445 utilizing 2-((2R,5S)-5-aminotetrahydro-2H-pyran-2-yl)acetonitrile instead of (3,3-difluorocyclobutyl)methanamine hydrochloride in Step 1. LCMS calculated for $C_{22}H_{26}N_7O_4S$ (M+H)$^+$: m/z=484.2; found: 484.1.

Examples 450 and 451 in the following table were prepared analogously to Example 449 utilizing the appropriate commercially available amine:

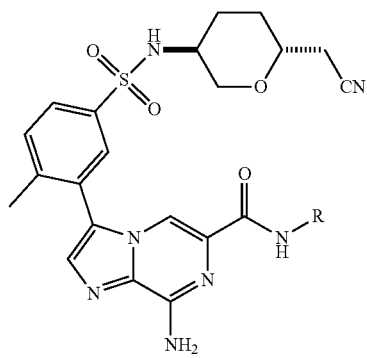

| Ex. No. | Name | R | LCMS |
|---|---|---|---|
| 450 | 8-amino-3-(5-(N-((3S,6R)-6-(cyanomethyl)tetrahydro-2H-pyran-3-yl)sulfamoyl)-2-methylphenyl)-N-cyclobutylimidazo[1,2-a]pyrazine-6-carboxamide trifluoroacetate salt | ![cyclobutyl] | 524.2 |
| 451 | 8-amino-3-(5-(N-((3S,6R)-6-(cyanomethyl)tetrahydro-2H-pyran-3-yl)sulfamoyl)-2-methylphenyl)-N-(3,3-difluorocyclobutyl)imidazo[1,2-a]pyrazine-6-carboxamide trifluoroacetate salt | ![3,3-difluorocyclobutyl] | 560.2 |

Example 452. 8-Amino-N-(4-(diethylamino)butyl)-3-(2-methyl-5-(methylsulfonyl)phenyl)imidazo[1,2-a]pyrazine-6-carboxamide Trifluoroacetate Salt

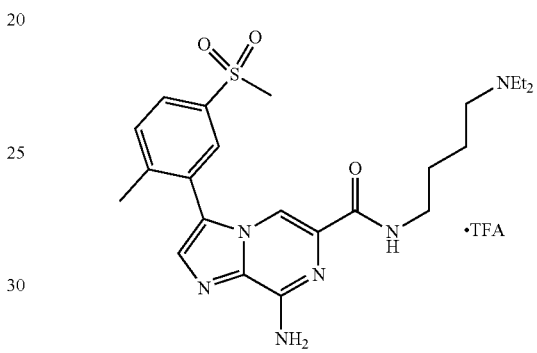

To a solution of methyl 8-amino-3-(2-methyl-5-(methylsulfonyl)phenyl)imidazo[1,2-a]pyrazine-6-carboxylate (15 mg, 42 µmol, Example 458, Step 1) in THF (1.0 mL) at room temperature was added N,N-diethylbutane-1,4-diamine (80 mg, 0.41 mmol), and trimethylaluminum (0.10 mL, 0.21 mmol) (2 M in toluene). The resultant solution was heated at 80° C. for 3 h. After cooling to room temperature, MeOH (2 mL) was added. The mixture was stirred at room temperature for 1 h and filtered through Celite*. The filtrate was concentrated under vacuum. The residue was dissolved in MeOH (5 mL) and purified by pH 2 prep-LCMS to afford the desired product. LCMS calculated for $C_{23}H_{33}N_6O_3S$ (M+H)$^+$: m/z=473.2; found: 473.2.

The compounds listed in the following table were prepared analogously to Example 452 utilizing the appropriate commercially available amine:

| Ex. No. | Name | R | LCMS |
|---|---|---|---|
| 453 | 8-amino-N-(2-(1-methyl-1H-pyrazol-4-yl) ethyl)-3-(2-methyl-5-(methylsulfonyl)phenyl) imidazo[1,2-a]pyrazine-6-carboxamide trifluoroacetate salt | 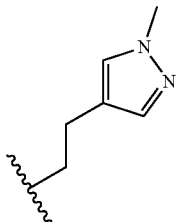 [SMILES: *CCc1cnn(C)c1] | 454.1 |
| 454 | 8-amino-N-(5-(furan-2-yl)-1H-pyrazol-3-yl)-3-(2-methyl-5-(methylsulfonyl)phenyl) imidazo[1,2-a]pyrazine-6-carboxamide trifluoroacetate salt | 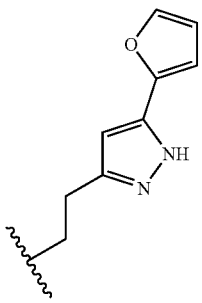 [SMILES: *CCc1cc(-c2ccco2)[nH]n1] | 478.0 |
| 455 | 8-amino-3-(2-methyl-5-(methylsulfonyl) phenyl)-N-(5-(4-methylpiperadzin-1-yl) pyridin-2-yl)imidazo[1,2-a]pyrazine-6-carboxamide trifluoroacetate salt | 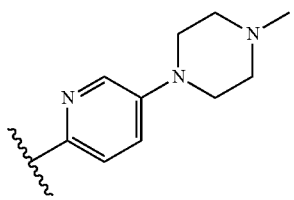 [SMILES: *c1ccc(N2CCN(C)CC2)cn1] | 521.3 |
| 456 | 8-amino-3-(2-methyl-5-(methylsulfonyl) phenyl)-N-((4-(trifluoromethyl)cyclohexyl) methyl)imidazo[1,2-a]pyrazine-6-carboxamide trifluoroacetate salt (1:1 cis/trans isomers) | 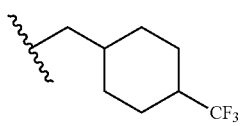 | 510.1 |
| 457 | N-(3-(1H-pyrazol-1-yl)propyl)-8-amino-3-(2-methyl-5-(methylsulfonyl)phenyl)imidazo [1,2-a]pyrazine-6-carboxamide trifluoroacetate salt | 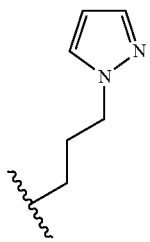 [SMILES: *CCCn1cccn1] | 454.1 |

Example 458. 8-Amino-N-(1-(2-methoxyethyl)piperidin-3-yl)-3-(2-methyl-5-(methylsulfonyl)phenyl)imidazo[1,2-a]pyrazine-6-carboxamide Trifluoroacetate Salt

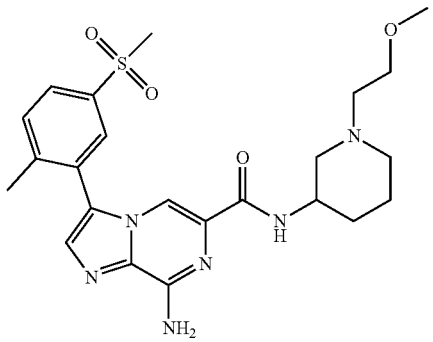

Step 1. Methyl 8-amino-3-(2-methyl-5-(methylsulfonyl)phenyl)imidazo[1,2-a]pyrazine-6-carboxylate

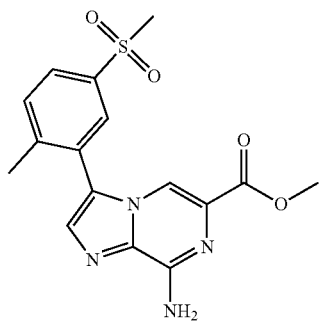

In a 40 mL vial, a solution of 6-bromo-3-(2-methyl-5-(methylsulfonyl)phenyl)imidazo[1,2-a]pyrazin-8-amine (400 mg, 1.05 mmol), Dichloro[1,1'-bis(diphenylphosphino)ferrocene]palladium (II) dichloromethane adduct (86 mg, 0.11 mmol), and triethylamine (0.59 mL, 4.20 mmol) in methanol (8 mL) was saturated with CO by bubbling the gas through the solution for 5 min. The vessel was heated to 60° C. under 1 atm of CO for 5 h. The volatiles were removed in vacuo and the resulting solid was suspended in EtOAc, filtered, washed with additional EtOAc, and air dried to yield the desired product as a light brown solid. LCMS calculated for $C_{16}H_{17}N_4O_4S$ (M+H)$^+$: m/z=361.1; found: 361.1.

Step 2. 8-Amino-3-(2-methyl-5-(methylsulfonyl)phenyl)-N-(piperidin-3-yl)imidazo[1,2-a]pyrazine-6-carboxamide Trifluoroacetate Salt

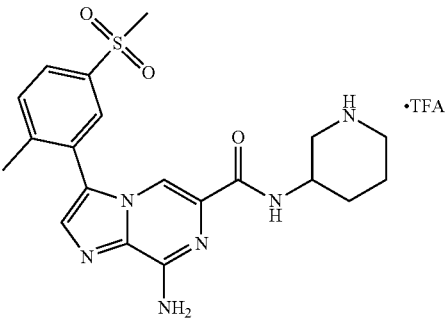 [SMILES: Cc1ccc(S(C)(=O)=O)cc1-c1cnc2c(N)nc(C(=O)NC3CCCNC3)cn12 ; "·TFA"]

To a solution of methyl 8-amino-3-(2-methyl-5-(methylsulfonyl)phenyl)imidazo[1,2-a]pyrazine-6-carboxylate (100 mg, 0.28 mmol) in THF (3.0 mL) at room temperature was added tert-butyl 3-aminopiperidine-1-carboxylate (0.19 mL, 0.83 mmol), and trimethylaluminum (2M/toluene, 0.42 mL, 0.83 mmol). The resultant solution was heated at 80° C. for 3 h. After cooling to room temperature, MeOH (2 mL) was added. The mixture was stirred at room temperature for 1 h and filtered through Celite®. The filtrate was concentrated under vacuum. The residue was dissolved in DCM (3 mL) and trifluoroacetic acid (2 mL) was added. After stirring for 0.5 h, the volatiles were removed in vacuo and the residue was used without purification. LCMS calculated for $C_{20}H_{25}N_6O_3S$ (M+H)$^+$: m/z=429.2; found: 429.1.

Step 3. 8-amino-N-(1-(2-methoxyethyl)piperidin-3-yl)-3-(2-methyl-5-(methylsulfonyl)phenyl)imidazo[1,2-a]pyrazine-6-carboxamide Trifluoroacetate Salt To a solution of 8-Amino-3-(2-methyl-5-(methylsulfonyl)phenyl)-N-(piperidin-3-yl)imidazo[1,2-a]pyrazine-6-carboxamide trifluoroacetate salt (15 mg, 28 µmol) in acetonitrile (1.0 mL) was added potassium carbonate (12 mg, 83 µmol), followed by 2-bromoethyl methyl ether (6 µl, 83 µmol), and the reaction mixture was heated to 60° C. overnight. No conversion was observed so the temperature was increased to 90° C. for a further 24 h. There was still no conversion so several equivalents of cesium carbonate and excess electrophile were added. Heating was continued at 90° C. overnight. Full conversion was observed by LCMS. The reaction mixture was partitioned between water and EtOAc, and the layers were separated. The organic layer was washed with brine, dried over MgSO$_4$, filtered and concentrated. The residue was purified by prep HPLC (pH 2). LCMS calculated for $C_{23}H_{31}N_6O_4S$ (M+H)$^+$: m/z=487.2; found: 487.2.

'Example 459. 8-Amino-N-(1-(cyanomethyl)piperidin-3-yl)-3-(2-methyl-5-(methylsulfonyl)phenyl)imidazo[1,2-a]pyrazine-6-carboxamide Trifluoroacetate Salt

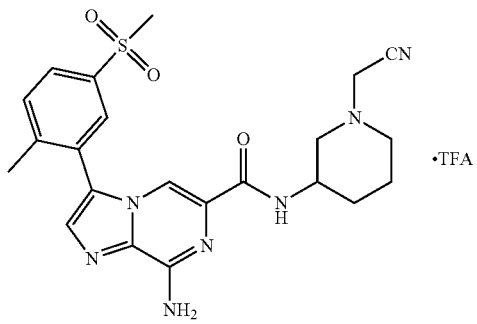 [SMILES: Cc1ccc(S(C)(=O)=O)cc1-c1cnc2c(N)nc(C(=O)NC3CCCN(CC#N)C3)cn12 ; "·TFA"]

Prepared according to the procedure described for Example 458, utilizing bromoacetonitrile instead of 2-bromoethyl methyl ether. LCMS calculated for $C_{22}H_{26}N_7O_3S$ $(M+H)^+$: m/z=468.2; found: 468.1.

Example 460. 8-Amino-N-(1-(2-hydroxyethyl)piperidin-3-yl)-3-(2-methyl-5-(methylsulfonyl)phenyl)imidazo[1,2-a]pyrazine-6-carboxamide Trifluoroacetate Salt (Racemic)

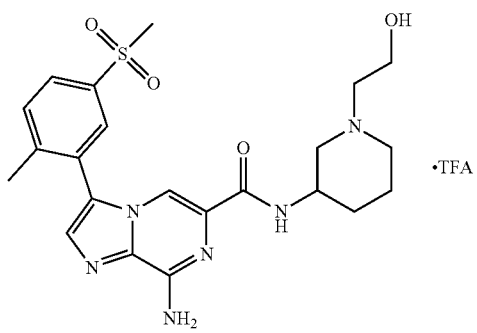 [SMILES: Cc1ccc(S(C)(=O)=O)cc1-c1cnc2c(N)nc(C(=O)NC3CCCN(CCO)C3)cn12 ; "·TFA"]

Prepared according to the procedure described for Example 458, utilizing 2-bromoethanol instead of 2-bromoethyl methyl ether. LCMS calculated for $C_{22}H_{29}N_6O_4S$ $(M+H)^+$: m/z=473.2; found: 473.1.

Example 461. Methyl 3-(8-amino-3-(2-methyl-5-(methylsulfonyl)phenyl)imidazo[1,2-a]pyrazine-6-carboxamido)piperidine-1-carboxylate Trifluoroacetate Salt

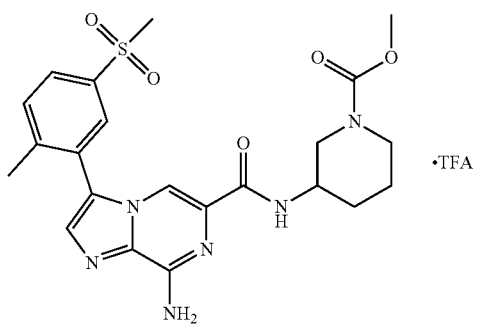

To a solution of 8-amino-3-(2-methyl-5-(methylsulfonyl)phenyl)-N-(piperidin-3-yl)imidazo[1,2-a]pyrazine-6-carboxamide trifluoroacetate salt (12 mg, 22 μmol, Example 458, Step 1) and DIPEA (19 μL, 0.11 mmol) in acetonitrile (1.0 mL) was added methyl chloroformate (9 μL, 0.11 mmol) at 0° C., and the reaction mixture was allowed to warm to room temperature. After stirring for 1 h, the reaction mixture was diluted with MeOH and purified by prep HPLC (pH 2). LCMS calculated for $C_{22}H_{27}N_6O_5S$ $(M+H)^+$: m/z=487.2; found: 487.2.

Example 462. 8-Amino-3-(2-methyl-5-(methylsulfonyl)phenyl)-N-(1-(methylsulfonyl)piperidin-3-yl)imidazo[1,2-a]pyrazine-6-carboxamide Trifluoroacetate Salt

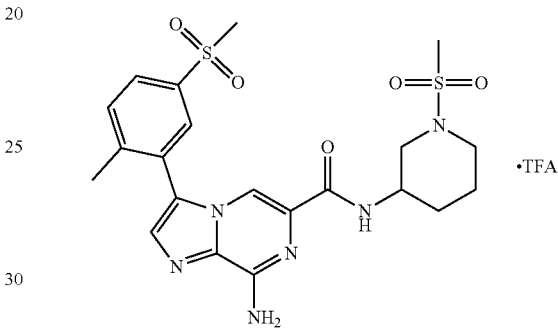

Prepared according to the procedure described for Example 461, utilizing methanesulfonyl chloride instead of methyl chloroformate. LCMS calculated for $C_{21}H_{27}N_6O_5S_2$ $(M+H)^+$: m/z=507.1; found: 507.1.

Example 463. 3-(4-Aminoimidazo[2,1-f][1,2,4]triazin-7-yl)-N-((1r,4r)-4-hydroxy-4-methylcyclohexyl)-4-methylbenzenesulfonamide

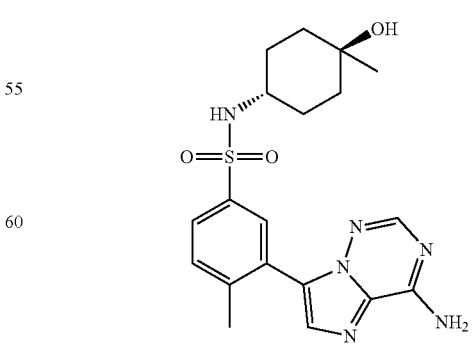

369

Step 1. N-((1r,4r)-4-Hydroxy-4-methylcyclohexyl)-4-methyl-3-(4,4,5,5-tetramethyl-1,3,2-dioxaborolan-2-yl)benzenesulfonamide

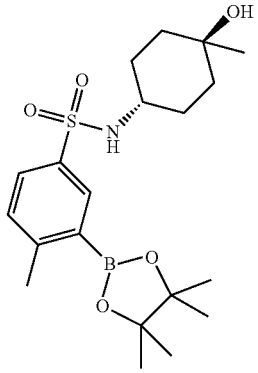 [SMILES: Cc1ccc(S(=O)(=O)N[C@H]2CC[C@](C)(O)CC2)cc1B1OC(C)(C)C(C)(C)O1]

The title compound was synthesized according to experimental procedures analogous to the synthesis of Example 1, steps 1 and 2 substituting (1r,4r)-4-amino-1-methylcyclohexan-1-ol for trans-4-aminocyclohexanol in step 1. LCMS for $C_{20}H_{32}BNO_5S$ (M+H)$^+$: calculated m/z=410.2; found 410.1.

Step 2. 3-(4-Aminoimidazo[2,1-f][1,2,4]triazin-7-yl)-N-((1r,4r)-4-hydroxy-4-methylcyclohexyl)-4-methylbenzenesulfonamide The title compound was synthesized according to experimental procedures analogous to the synthesis of Example 39, substituting N-((1r, 4r)-4-hydroxy-4-methylcyclohexyl)-4-methyl-3-(4,4,5,5-tetramethyl-1,3,2-dioxaborolan-2-yl)benzenesulfonamide for N-(trans-4-hydroxycyclohexyl)-4-methyl-3-(4,4,5,5-tetramethyl-1,3,2-dioxaborolan-2-yl)benzenesulfonamide. $^1$H NMR (600 MHz, d$_6$-DMSO) δ 8.33 (br s, 1H), 8.25 (br s, 1H), 8.07 (s, 1H), 7.93 (d, J=1.9 Hz, 1H), 7.83-7.76 (m, 2H), 7.59 (t, J=8.0 Hz, 2H), 4.12 (s, 1H), 3.10 (s, 1H), 2.34 (s, 3H), 1.60 (m, 2H), 1.49 (m, 2H), 1.27 (m, 4H), 1.05 (s, 3H) LCMS for $C_{19}H_{24}N_6O_3S$ (M+H)$^+$: calculated m/z=417.2; found 417.1.

Example 464. (R)-3-(5-((3-Aminopiperidin-1-yl)sulfonyl)-2-methylphenyl)-6-(trifluoromethyl)imidazo[1,2-a]pyrazin-8-amine tris(2,2,2-trifluoroacetate)

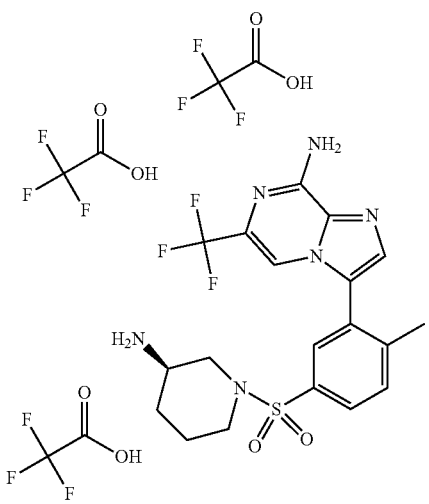

370

Step 1. Tert-Butyl (R)-(1-((3-(8-amino-6-(trifluoromethyl)imidazo[1,2-a]pyrazin-3-yl)-4-methylphenyl)sulfonyl)piperidin-3-yl)carbamate

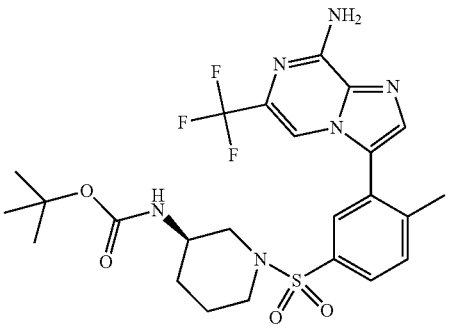 [SMILES: Cc1ccc(S(=O)(=O)N2CCC[C@@H](NC(=O)OC(C)(C)C)C2)cc1-c1cnc2c(N)nc(C(F)(F)F)cn12]

The desired compound was prepared according to the procedure of Example 466, step 2, using 3-(8-amino-6-(trifluoromethyl)imidazo[1,2-a]pyrazin-3-yl)-4-methylbenzenesulfonyl chloride and tert-butyl (R)-piperidin-3-ylcarbamate [Combi-Blocks, AM-1743] as the starting materials. LCMS for $C_{24}H_{30}F_3N_6O_4S$ (M+H)$^+$: m/z=555.2; Found: 555.3.

Step 2. (R)-3-(5-((3-Aminopiperidin-1-yl)sulfonyl)-2-methylphenyl)-6-(trifluoromethyl)imidazo[1,2-a]pyrazin-8-amine tris(2,2,2-trifluoroacetate)

A solution of tert-butyl (R)-(1-((3-(8-amino-6-(trifluoromethyl)imidazo[1,2-a]pyrazin-3-yl)-4-methylphenyl)sulfonyl)piperidin-3-yl)carbamate (0.019 g, 0.034 mmol) in dichloromethane (0.86 mL) was treated with TFA (0.86 mL) and stirred for 1 h. The reaction mixture was concentrated to a residue. Purification by preparative LCMS (XBridge C18 Column, eluting with a gradient of acetonitrile in water with 0.1% trifluoroacetic acid, at flow rate of 60 mL/min) gave the desired product (22 mg, 79%). $^1$H NMR (400 MHz, DMSO-d$_6$) δ 8.08-7.89 (m, 4H), 7.83 (s, 1H), 7.82-7.59 (m, 6H), 3.37 (d, J=11.2 Hz, 1H), 3.34-3.23 (m, 1H), 3.19-3.01 (m, 1H), 2.98-2.72 (m, 2H), 2.30 (s, 3H), 1.87-1.70 (m, 2H), 1.65-1.49 (m, 1H), 1.49-1.31 (m, 1H). LCMS for $C_{19}H_{22}F_3N_6O_2S$ (M+H)$^+$: m/z=455.1; Found: 455.1.

Example 465. 5-(8-Amino-6-methylimidazo[1,2-a]pyrazin-3-yl)-N-((3R,6S)-6-(2-hydroxypropan-2-yl)tetrahydro-2H-pyran-3-yl)-2,4-dimethylbenzenesulfonamide

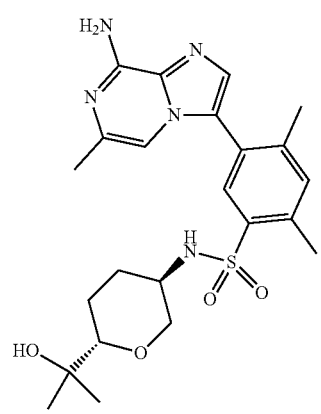 [SMILES: Cc1cn2c(-c3cc(S(=O)(=O)N[C@@H]4CC[C@@H](C(C)(C)O)OC4)c(C)cc3C)cnc2c(N)n1]

Step 1. Methyl (2S,5R)-5-((tert-butoxycarbonyl)amino)tetrahydro-2H-pyran-2-carboxylate

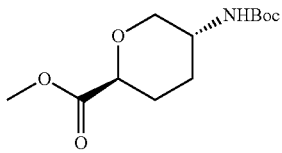 [SMILES: COC(=O)[C@@H]1CC[C@@H](NC(=O)OC(C)(C)C)CO1]

A solution of (2S,5R)-5-((tert-butoxycarbonyl)amino)tetrahydro-2H-pyran-2-carboxylic acid (0.199 g, 0.811 mmol) [Advanced ChemBlocks, I-9006] in methanol (1.62 mL) at 0° C. was treated with (trimethylsilyl)diazomethane solution in diethyl ether (0.811 mL, 1.62 mmol) and stirred for 2 h. The reaction mixture was concentrated to give the desired product (210 mg, 100%) as a white solid that was used without further purification. LCMS for $C_{12}H_{21}NO_5Na$ (M+Na)$^+$: m/z=282.1; Found: 282.0.

Step 2. Tert-Butyl ((3R,6S)-6-(2-hydroxypropan-2-yl)tetrahydro-2H-pyran-3-yl)carbamate

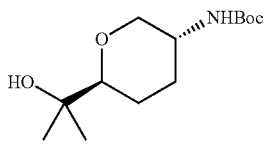 [SMILES: CC(C)(C)OC(=O)N[C@@H]1CC[C@@H](C(C)(C)O)OC1]

A solution of methyl (2S,5R)-5-((tert-butoxycarbonyl)amino)tetrahydro-2H-pyran-2-carboxylate (0.250 g, 0.964 mmol) in tetrahydrofuran (7.42 mL) at 0° C. was treated with methylmagnesium bromide (3.0 M in ether) (1.61 mL, 4.82 mmol) dropwise, and stirred at room temperature for 2 h. The reaction mixture was cooled to 0° C., quenched with saturated ammonium chloride solution (20 mL), and extracted with ethyl acetate. The organic layer was separated, dried over sodium sulfate, filtered, and concentrated to give a crude residue. Purification by flash column chromatography using ethyl acetate in hexanes (0%-60%) gave the desired product (133 mg, 53.2%) as a white solid. LCMS for $C_{13}H_{25}NO_4Na$ (M+Na)$^+$: m/z=282.2; Found: 282.2.

Step 3. 2-((2S,5R)-5-Aminotetrahydro-2H-pyran-2-yl)propan-2-ol Hydrochloride

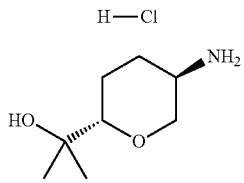

A solution of tert-butyl ((3R,6S)-6-(2-hydroxypropan-2-yl)tetrahydro-2H-pyran-3-yl)carbamate (0.133 g, 0.513 mmol) in dioxane (1.03 mL) was treated with 4 M HCl in dioxane (3.85 mL, 15.4 mmol) and stirred for 3 h. The reaction mixture was concentrated and reconcentrated from acetonitrile (2×) to give the desired product (103 mg, quantitative) as a white solid that was used without further purification. $^1$H NMR (400 MHz, DMSO-d$_6$) δ 7.99 (s, 3H), 4.24 (br s, 1H), 4.01 (d, J=8.0 Hz, 1H), 3.22 (t, J=10.7 Hz, 1H), 3.08-2.97 (m, 1H), 2.93 (d, J=10.8 Hz, 1H), 2.13-1.99 (m, 1H), 1.87-1.69 (m, 1H), 1.55-1.41 (m, 1H), 1.41-1.24 (m, 1H), 1.06 (s, 3H), 1.00 (s, 3H).

Step 4. 5-Bromo-N-((3R,6S)-6-(2-hydroxypropan-2-yl)tetrahydro-2H-pyran-3-yl)-2,4-dimethylbenzenesulfonamide

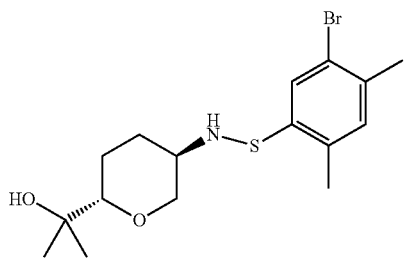 [SMILES: Cc1cc(C)c(SN[C@@H]2CC[C@@H](C(C)(C)O)OC2)cc1Br]

The desired compound was prepared according to the procedure of example 1, step 1, using 5-bromo-2,4-dimethylbenzenesulfonyl chloride and 2-((2S,5R)-5-aminotetrahydro-2H-pyran-2-yl)propan-2-ol hydrochloride as the starting materials. LCMS for $C_{16}H_{24}BrNO_4SNa$ (M+Na)$^+$: m/z=428.1, 430.0; Found: 428.0, 430.0.

Step 5. N-((3R,6S)-6-(2-Hydroxypropan-2-yl)tetrahydro-2H-pyran-3-yl)-2,4-dimethyl-5-(4,4,5,5-tetramethyl-1,3,2-dioxaborolan-2-yl)benzenesulfonamide

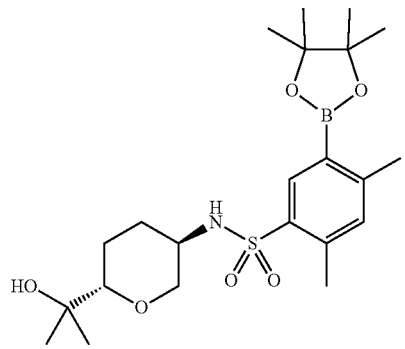 [SMILES: Cc1cc(C)c(S(=O)(=O)N[C@@H]2CC[C@@H](C(C)(C)O)OC2)cc1B1OC(C)(C)C(C)(C)O1]

The desired compound was prepared according to the procedure of example 1, step 2, using 5-bromo-N-((3R,6S)-6-(2-hydroxypropan-2-yl)tetrahydro-2H-pyran-3-yl)-2,4-dimethylbenzenesulfonamide as the starting material. LCMS for $C_{22}H_{36}BNO_6SNa$ (M+Na)$^+$: m/z=476.2; Found: 476.2.

Step 6. 5-(8-Amino-6-methylimidazo[1,2-a]pyrazin-3-yl)-N-((3R,6S)-6-(2-hydroxypropan-2-yl)tetrahydro-2H-pyran-3-yl)-2,4-dimethylbenzenesulfonamide The desired compound was prepared according to the procedure of example 1, step 3, using 3-iodo-6-methylimidazo[1,2-a]pyrazin-8-amine and N-((3R,6S)-6-(2-hydroxypropan-2-yl)tetrahydro-2H-pyran-3-yl)-2,4-dimethyl-5-(4, 4,5,5-tetramethyl-1,3,2-dioxaborolan-2-yl)benzenesulfonamide as the starting materials. $^1$H NMR (400 MHz, DMSO-d$_6$) δ 7.83 (d, J=7.2 Hz, 1H), 7.74 (s, 1H), 7.57 (s, 1H), 7.48 (s, 1H), 7.00 (s, 1H), 6.95 (s, 2H), 4.15 (s, 1H), 3.76-3.60 (m, 1H), 3.02-2.89 (m, 1H), 2.84 (d, J=10.4 Hz, 1H), 2.61 (s, 3H), 2.18 (s, 3H), 2.13 (s, 3H), 1.81-1.55 (m, 2H), 1.45-1.27 (m, 1H), 1.27-1.09 (m, 2H), 1.00 (s, 3H), 0.93 (s, 3H). LCMS for C$_{23}$H$_{32}$N$_5$O$_4$S (M+H)$^+$: m/z=474.2; Found: 474.2.

Example 466. 3-(4-Amino-2-(trifluoromethyl)imidazo[2,1-f][1,2,4]triazin-7-yl)-N-((3S,6R)-6-(cyanomethyl)tetrahydro-2H-pyran-3-yl)-5-fluoro-4-methylbenzenesulfonamide

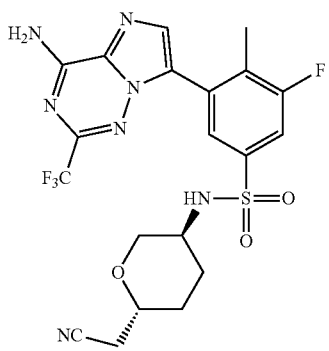 [SMILES: Cc1c(F)cc(S(=O)(=O)N[C@H]2CC[C@H](CC#N)OC2)cc1-c1cnc2c(N)nc(C(F)(F)F)nn12]

Step 1. 3-Bromo-5-fluoro-4-methylbenzenesulfonyl Chloride

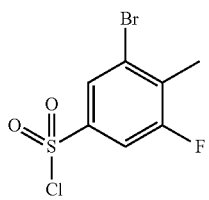

A round-bottom flask was charged with water (80 mL) and placed in an ice bath. To this was added thionyl chloride (13.2 mL, 180 mmol) over 35 min using an addition funnel. The reaction mixture was warmed to room temperature with the aid of a room temperature water bath, treated with copper(I) chloride (0.194 g, 1.96 mmol), and placed in a brine-ice bath. Concurrently in a separate round-bottom flask, 3-bromo-5-fluoro-4-methylaniline (8.00 g, 39.2 mmol) [Oxchem, AX8258142] was added dropwise to concentrated hydrochloric acid (98 mL) (the aniline was melted using a 50° C. oil bath before addition) which gave a free-flowing but thick slurry. The reaction mixture was placed in a brine-ice bath and the slurry became thicker but stirring was maintained with a very large stir bar. The reaction mixture was treated with a solution of sodium nitrite (2.98 g, 43.1 mmol) in water (5.58 mL) over 5 mins at −3 to 0° C. which led to dissolution of most of the solids and a much thinner orange slurry. After stirring for 5 mins, the reaction mixture was added to the chilled thionyl chloride solution dropwise in portions by pipette over 15 mins with gas evolution observed and temperature ranging between −7 to −6° C. The reaction mixture was stirred for 2.5 h, warmed to room temperature and stirred for 1 hr. The reaction mixture was diluted with water (250 mL) and extracted with ethyl acetate (3×200 mL). The combined organic extracts were washed with brine (100 mL), dried with magnesium sulfate, filtered, and concentrated to give the desired product (9.79 g, 87%) as an amber oil that was used without further purification.

Step 2. 3-bromo-N-((3S,6R)-6-(cyanomethyl)tetrahydro-2H-pyran-3-yl)-5-fluoro-4-methylbenzenesulfonamide

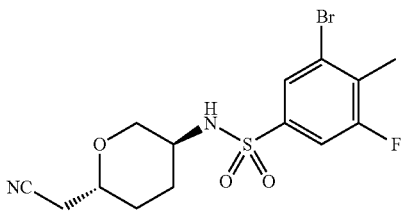 [SMILES: Cc1c(F)cc(S(=O)(=O)N[C@H]2CC[C@H](CC#N)OC2)cc1Br]

A solution of 2-((2R,5S)-5-aminotetrahydro-2H-pyran-2-yl)acetonitrile hydrochloride/2-((2S,5S)-5-aminotetrahydro-2H-pyran-2-yl)acetonitrile hydrochloride (0.184 g, 1.04 mmol) [WO 2015/168246] in dichloromethane (6.96 mL) at 0° C. was treated with triethylamine (0.436 mL, 3.13 mmol) and DMAP (2.55 mg, 0.021 mmol) followed by 3-bromo-5-fluoro-4-methylbenzenesulfonyl chloride (0.30 g, 1.04 mmol) as a solution in dichloromethane (1.00 mL) in one portion at 0° C. and stirred at room temperature for 1 h. The reaction mixture was poured into saturated sodium bicarbonate solution (20 mL) and extracted with dichloromethane (2×20 mL). The combined organic extracts were washed with brine, dried with sodium sulfate, filtered, and concentrated to a residue. Purification by flash column chromatography using ethyl acetate (contained 5% MeOH) in hexanes (0%-60%) gave the desired trans product (185 mg, 45.3%) as a white solid. $^1$H NMR (600 MHz, CDCl$_3$) δ 7.84 (s, 1H), 7.48 (dd, J=8.2, 1.5 Hz, 1H), 4.54 (d, J=8.0 Hz, 1H), 3.96 (ddd, J=11.1, 4.7, 2.2 Hz, 1H), 3.62-3.38 (m, 1H), 3.37-3.20 (m, 1H), 3.08 (dd, J=10.9, 10.9 Hz, 1H), 2.49 (d, J=5.9 Hz, 2H), 2.39 (d, J=2.3 Hz, 3H), 2.11-1.92 (m, 1H), 1.89-1.76 (m, 1H), 1.53-1.43 (m, 1H), 1.42-1.32 (m, 1H). LCMS for C$_{14}$H$_{16}$BrFN$_2$O$_3$SNa (M+Na)$^+$: m/z=413.0, 415.0; Found: 413.0, 415.0.

Step 3. N-((3S,6R)-6-(Cyanomethyl)tetrahydro-2H-pyran-3-yl)-3-fluoro-4-methyl-5-(4,4,5,5-tetramethyl-1,3,2-dioxaborolan-2-yl)benzenesulfonamide

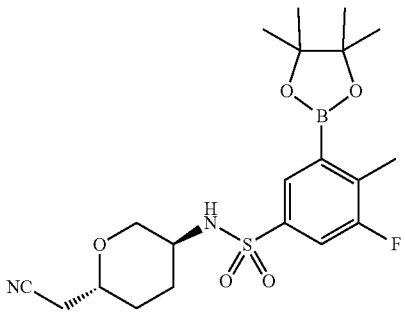 [SMILES: Cc1c(F)cc(S(=O)(=O)N[C@H]2CC[C@H](CC#N)OC2)cc1B1OC(C)(C)C(C)(C)O1]

The desired compound was prepared according to the procedure of example 1, step 2, using 3-bromo-N-((3S,6R)-6-(cyanomethyl)tetrahydro-2H-pyran-3-yl)-5-fluoro-4-methylbenzenesulfonamide as the starting material. LCMS for $C_{20}H_{28}BFN_2O_5SNa$ (M+Na)$^+$: m/z=461.2; Found: 461.2.

Step 4. 3-(4-Amino-2-(trifluoromethyl)imidazo[2,1-f][1,2,4]triazin-7-yl)-N-((3S,6R)-6-(cyanomethyl)tetrahydro-2H-pyran-3-yl)-5-fluoro-4-methylbenzenesulfonamide The desired compound was prepared according to the procedure of example 1, step 3, using 7-bromo-2-(trifluoromethyl)imidazo[2,1-f][1,2,4]triazin-4-amine and N-((3S,6R)-6-(cyanomethyl)tetrahydro-2H-pyran-3-yl)-3-fluoro-4-methyl-5-(4,4,5,5-tetramethyl-1,3,2-dioxaborolan-2-yl)benzenesulfonamide as the starting materials. $^1$H NMR (400 MHz, DMSO-d$_6$) δ 9.11-8.76 (m, 2H), 8.04-7.87 (m, 2H), 7.82 (s, 1H), 7.71 (d, J=8.9 Hz, 1H), 3.81-3.66 (m, 1H), 3.50-3.36 (m, 1H), 3.17-2.90 (m, 2H), 2.70 (dd, J=16.9, 4.0 Hz, 1H), 2.57 (dd, J=16.9, 6.6 Hz, 1H), 2.23 (s, 3H), 1.83-1.54 (m, 2H), 1.51-1.16 (m, 2H). LCMS for $C_{20}H_{20}F_4N_7O_3S$ (M+H)$^+$: m/z=514.1; Found: 514.1.

Example 467. 3-(4-Aminoimidazo[2,1-f][1,2,4]triazin-7-yl)-N-((3S,6R)-6-(fluoromethyl)tetrahydro-2H-pyran-3-yl)-4-methylbenzenesulfonamide

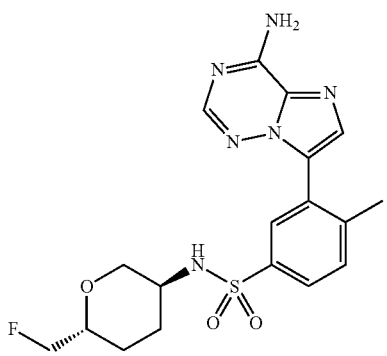 [SMILES: Cc1ccc(S(=O)(=O)N[C@H]2CC[C@H](CF)OC2)cc1-c1cnc2c(N)ncnn12]

Step 1. Tert-Butyl ((3S,6R)-6-(fluoromethyl)tetrahydro-2H-pyran-3-yl)carbamate

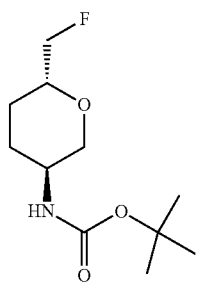 [SMILES: CC(C)(C)OC(=O)N[C@H]1CC[C@H](CF)OC1]

A solution of tert-butyl ((3S,6R)-6-(hydroxymethyl)tetrahydro-2H-pyran-3-yl)carbamate (0.040 g, 0.17 mmol) [J. Med. Chem. (2013), 56, 7396] in dichloromethane (1.7 mL) at −78° C. was treated with diethylaminosulfur trifluoride (0.046 mL, 0.35 mmol) dropwise and stirred at room temperature for 5 h. The reaction mixture was cooled back to −78° C., treated with diethylaminosulfur trifluoride (0.046 mL, 0.35 mmol), and stirred at room temperature for 14 h. The reaction mixture was cooled to 0° C., quenched with saturated sodium bicarbonate (20 mL), and extracted with ethyl acetate (30 mL). The organic layer was separated, washed with brine, dried over sodium sulfate, filtered, and concentrated to a residue. Purification by flash column chromatography using ethyl acetate in hexanes (0%-40%) gave the desired trans product (9.3 mg, 23%) as a white solid. LCMS for $C_{11}H_{20}FNO_3Na$ (M+Na)$^+$: m/z=256.1; Found: 256.1.

Step 2. (3S,6R)-6-(Fluoromethyl)tetrahydro-2H-pyran-3-amine Hydrochloride

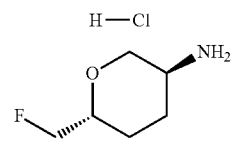

The desired compound was prepared according to the procedure of Example 465, step 3, using tert-butyl ((3S,6R)-6-(fluoromethyl)tetrahydro-2H-pyran-3-yl)carbamate as the starting material. LCMS for $C_6H_{13}FNO$ (M+H)$^+$: m/z=134.1; Found: 134.1.

Step 3. 3-(4-Aminoimidazo[2,1-f][1,2,4]triazin-7-yl)-N-((3S,6R)-6-(fluoromethyl)tetrahydro-2H-pyran-3-yl)-4-methylbenzenesulfonamide The desired compound was prepared according to the procedure of Example 424, step 8, using (3S,6R)-6-(fluoromethyl)tetrahydro-2H-pyran-3-amine hydrochloride as the starting material. $^1$H NMR (400 MHz, DMSO-d$_6$) δ 8.31 (br s, 1H), 8.23 (br s, 1H), 8.05 (s, 1H), 7.93 (d, J=1.5 Hz, 1H), 7.85-7.72 (m, 3H), 7.60 (d, J=8.1 Hz, 1H), 4.48-4.06 (m, 2H), 3.80-3.61 (m, 1H), 3.54-3.35 (m, 1H), 3.15-2.90 (m, 2H), 2.33 (s, 3H), 1.84-1.68 (m, 1H), 1.61-1.49 (m, 1H), 1.46-1.30 (m, 1H), 1.30-1.05 (m, 1H). LCMS for $C_{18}H_{22}FN_6O_3S$ (M+H)$^+$: m/z=421.1; Found: 421.1.

Example 468. 3-(4-Amino-2-methylimidazo[2,1-f][1,2,4]triazin-7-yl)-5-fluoro-N-(2-hydroxy-2-methylpropyl)-4-methylbenzenesulfonamide

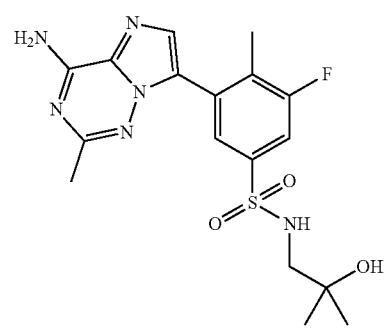 [SMILES: Cc1nc(N)c2ncc(-c3cc(S(=O)(=O)NCC(C)(C)O)cc(F)c3C)n2n1]

Step 1. Ethyl 1-amino-1H-imidazole-2-carboxylate

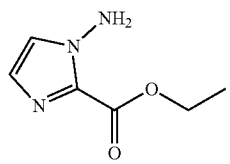

A solution of ethyl 1H-imidazole-2-carboxylate (10.0 g, 71.4 mmol) [Combi-Blocks, SS-7811] in DMF (357 mL) was treated with potassium tert-butoxide (74.9 mL, 74.9 mmol) dropwise and stirred at 20° C. for 1 h. The reaction mixture was then treated with a solution of O-(4-nitrobenzoyl)hydroxylamine (13.7 g, 74.9 mmol) in N,N-dimethylformamide (120 mL) dropwise via an addition funnel and stirred at 20° C. for 3 h. The reaction mixture was filtered and the solid was washed with acetonitrile. The filtrate was evaporated to give the crude product as a slightly oily red solid that was used without further purification.

Step 2. 2-Methylimidazo[2,1-f][1,2,4]triazin-4-ol

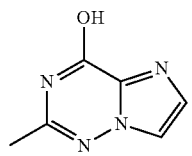

A solution of ethyl 1-amino-1H-imidazole-2-carboxylate (11.1 g, 71.4 mmol) in acetonitrile (179 mL) in a 3-neck round bottom flask equipped with a reflux condenser was cooled to 0° C. and bubbled with HCl gas for 10 min. The reaction mixture was then stirred at 80° C. for 1 h. The reaction mixture was concentrated and the resultant solid was triturated with diethyl ether to give crude intermediate amidine that was used immediately without further purification. A solution of crude intermediate amidine in dioxane (179 mL) was treated carefully with 1.0 M sodium bicarbonate in water (71.4 mL, 71.4 mmol) and stirred at 100° C. for 1 h. The reaction mixture was concentrated and the resultant solid was diluted with acetonitrile and filtered to give the desired product (15.1 g) as an off-white solid that used without further purification (it is assumed that this material contains sodium chloride). LCMS for $C_6H_7N_4O$ (M+H)$^+$: m/z=151.1; Found: 151.0.

Step 3. 7-Bromo-2-methylimidazo[2,1-f][1,2,4]triazin-4-ol

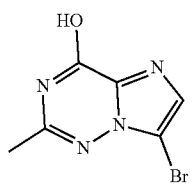

A suspension of 2-methylimidazo[2,1-f][1,2,4]triazin-4-ol (10.7 g, 71.4 mmol) in DMF (238 mL) was treated with N-bromosuccinimide (15.3 g, 86.0 mmol) and stirred at 80° C. for 1 h. The reaction mixture was concentrated and the residue was diluted with DCM, filtered, washed with additional DCM, and dried to give the desired product (14.7 g) as a white solid that was used without further purification (it is assumed that this material contains sodium chloride from the previous step). LCMS for $C_6H_6BrN_4O$ (M+H)$^+$: m/z=229.0, 231.0; Found: 229.0, 230.9.

Step 4. 7-Bromo-N-(4-methoxybenzyl)-2-methyl-imidazo[2,1-f][1,2,4]triazin-4-amine

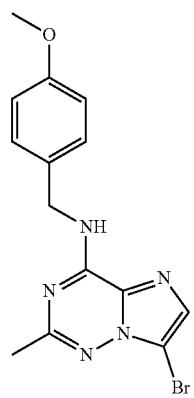 [SMILES: COc1ccc(CNc2nc(C)nn3c(Br)cnc23)cc1]

A heterogeneous mixture of 7-bromo-2-methylimidazo[2,1-f][1,2,4]triazin-4-ol (9.30 g, 40.6 mmol) and (benzotriazol-1-yloxy)tris(dimethylamino)phosphonium hexafluorophosphate (31.1 g, 70.2 mmol) in DCE (203 mL) was treated with 4-methoxybenzylamine (23.1 mL, 177 mmol) and DBU (4.41 mL, 29.2 mmol) and stirred at 20° C. for 20.5 h. The reaction mixture was treated with N,N-diisopropylethylamine (6.84 mL, 39.3 mmol) and stirred at 20° C. for 67 h. The reaction mixture was filtered and washed with DCM. The filtrate was concentrated to give a crude orange oil. Purification by flash column chromatography using ethyl acetate in hexanes (0%-30%) gave the desired product (4.80 g, 33.9%) as a yellow solid. LCMS for $C_{14}H_{15}BrN_5O$ (M+H)$^+$: m/z=348.0, 350.0; Found: 348.0, 350.0.

Step 5. 7-Bromo-2-methylimidazo[2,1-f][1,2,4]triazin-4-amine

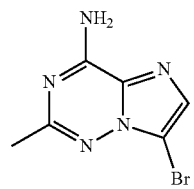

A solution of 7-bromo-N-(4-methoxybenzyl)-2-methyl-imidazo[2,1-f][1,2,4]triazin-4-amine (8.52 g, 24.5 mmol) in TFA (12.4 mL, 161 mmol) was stirred at 80° C. for 18 h. The reaction mixture was treated with additional TFA (12.4 mL, 161 mmol) and stirred at 80° C. for 5 h. The reaction mixture was concentrated and then diluted with toluene and re-concentrated (3×) to give 13.7 g of a crude green solid. The crude material was diluted with ethyl acetate (82 mL) and stirred at 80° C. for 45 min. This material did not completely dissolve. The mixture was cooled to 20° C., diluted with hexanes (82 mL) over 5 min, and stirred overnight. The solids were filtered and washed with hexanes to give the desired product (8.43 g, >99%) as a green solid. LCMS for $C_6H_7BrN_5$ (M+H)$^+$: m/z=228.0, 230.0; Found: 228.0, 230.0.

Step 6. 3-Bromo-5-fluoro-N-(2-hydroxy-2-methylpropyl)-4-methylbenzenesulfonamide

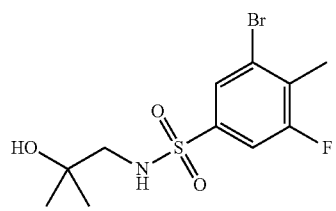 [SMILES: Cc1c(F)cc(S(=O)(=O)NCC(C)(C)O)cc1Br]

The desired compound was prepared according to the procedure of Example 466, step 2, using 1-amino-2-methylpropan-2-ol as the starting material. LCMS for $C_{11}H_{16}BrFNO_3S$ (M+H)$^+$: m/z=340.0, 342.0; Found: 340.0, 342.0.

Step 7. 3-Fluoro-N-(2-hydroxy-2-methylpropyl)-4-methyl-5-(4,4,5,5-tetramethyl-1,3,2-dioxaborolan-2-yl)benzenesulfonamide

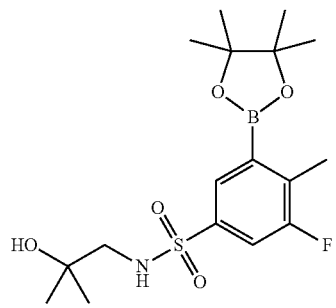 [SMILES: Cc1c(F)cc(S(=O)(=O)NCC(C)(C)O)cc1B1OC(C)(C)C(C)(C)O1]

The desired compound was prepared according to the procedure of Example 1, step 2, using 3-bromo-5-fluoro-N-(2-hydroxy-2-methylpropyl)-4-methylbenzenesulfonamide as the starting material. LCMS for $C_{17}H_{27}BFNO_5SNa$ (M+Na)$^+$: m/z=410.2; Found: 410.1.

Step 8. 3-(4-Amino-2-methylimidazo[2,1-f][1,2,4]triazin-7-yl)-5-fluoro-N-(2-hydroxy-2-methylpropyl)-4-methylbenzenesulfonamide The desired compound was prepared according to the procedure of Example 1, step 3, using 7-bromo-2-methylimidazo[2,1-f][1,2,4]triazin-4-amine and 3-fluoro-N-(2-hydroxy-2-methylpropyl)-4-methyl-5-(4,4,5,5-tetramethyl-1,3,2-dioxaborolan-2-yl)benzenesulfonamide as the starting materials. $^1$H NMR (500 MHz, DMSO-d$_6$) δ 8.22 (br s, 1H), 8.15 (br s, 1H), 7.83-7.71 (m, 2H), 7.71-7.58 (m, 2H), 4.41 (s, 1H), 2.69 (s, 2H), 2.28 (s, 3H), 2.21 (d, J=1.9 Hz, 3H), 1.06 (s, 6H). LCMS for $C_{17}H_{22}FN_6O_3S$ (M+H)$^+$: m/z=409.1; Found: 409.3.

Example 469. 3-(4-Amino-2-(methyl-d$_3$)imidazo[2,1-f][1,2,4]triazin-7-yl)-5-fluoro-N-(2-hydroxy-2-methylpropyl)-4-(methyl-d$_3$)benzenesulfonamide

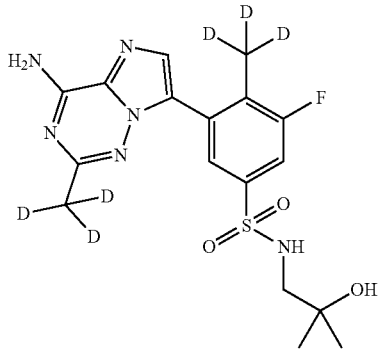 [SMILES: [2H]C([2H])([2H])c1nc(N)c2ncc(-c3cc(S(=O)(=O)NCC(C)(C)O)cc(F)c3C([2H])([2H])[2H])n2n1]

Step 1. 1-Amino-1H-imidazole-2-carbonitrile

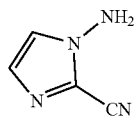

The desired compound was prepared according to the procedure of Example 468, step 1, using 1H-imidazole-2-carbonitrile [PharmaBlock, PBN2011278] as the starting material.

Step 2. 2-(Methyl-d$_3$)imidazo[2,1-f][1,2,4]triazin-4-amine

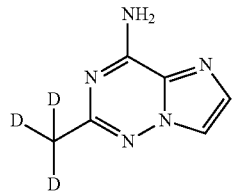 [SMILES: [2H]C([2H])([2H])c1nc(N)c2nccn2n1]

The desired compound was prepared according to the procedure of Example 468, step 2, using 1-amino-1H-imidazole-2-carbonitrile and acetonitrile-d$_3$ as the starting materials. LCMS for $C_6H_5D_3N_5$(M+H)$^+$: m/z=153.1; Found: 153.1.

Step 3. 7-Bromo-2-(methyl-d$_3$)imidazo[2,1-f][1,2,4]triazin-4-amine

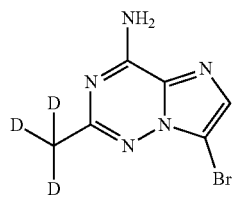 [SMILES: [2H]C([2H])([2H])c1nc(N)c2ncc(Br)n2n1]

The desired compound was prepared according to the procedure of Example 468, step 3, using 2-(methyl-d₃)imidazo[2,1-f][1,2,4]triazin-4-amine as the starting material. LCMS for C₆H₄D₃BrN₅ (M+H)⁺: m/z=231.0, 233.0; Found: 231.1, 233.1.

Step 4. 2-(2-Fluoro-4-nitrophenyl)-4,4,5,5-tetramethyl-1,3,2-dioxaborolane

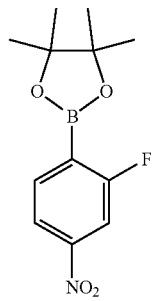 [SMILES: CC1(C)OB(c2ccc([N+](=O)[O-])cc2F)OC1(C)C]

A solution of 2-fluoro-1-iodo-4-nitrobenzene (1.96 g, 7.34 mmol), bis(pinacolato)diboron (1.86 g, 7.34 mmol), dichloro[1,1'-bis(diphenylphosphino)ferrocene]palladium (II) dichloromethane adduct (0.599 g, 0.734 mmol), and potassium acetate (2.38 g, 24.2 mmol) in DMSO (14.7 mL) in a seal-able tube was degassed with nitrogen for 15 min, sealed, and stirred at 100° C. for 2.5 h. The reaction mixture was cooled to room temperature, diluted with water and ethyl acetate, and filtered over Celite. The aqueous layer was separated and re-extracted with ethyl acetate. The combined organic layers were washed with brine, dried over magnesium sulfate, filtered, and concentrated to a brown oil. Purification by flash column chromatography using ethyl acetate in hexanes (0%-20%) gave the desired product (1.60 g, 81.6%).

Step 5. 2-Fluoro-1-(methyl-d₃)-4-nitrobenzene

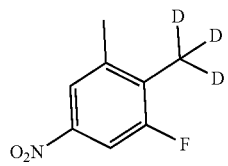

A solution of 2-(2-fluoro-4-nitrophenyl)-4,4,5,5-tetramethyl-1,3,2-dioxaborolane (0.920 g, 3.45 mmol) and cesium fluoride (1.83 g, 12.1 mmol) in DMF (10.6 mL) and water (2.12 mL) in a seal-able tube was treated with iodomethane-d₃ (1.07 mL, 17.2 mmol), degassed with nitrogen for 5 min, and treated with bis(di-tert-butyl(4-dimethylaminophenyl)phosphine)dichloropalladium(II) (0.061 g, 0.086 mmol). The reaction mixture was degassed with nitrogen for another 5 min, sealed, and heated at 45° C. for 21 h. The reaction mixture was cooled to room temperature, diluted with water and ethyl acetate, and filtered over Celite. Three layers were observed during separation. The dark middle layer was filtered again over Celite and combined with the other filtrate. The aqueous layer was separated and re-extracted with ethyl acetate (2×). The combined organic layers were washed with brine, dried over sodium sulfate, filtered, and concentrated to an oil. Purification by flash column chromatography using ethyl acetate in hexanes (0%-10%) gave the desired product (303 mg, 55.6%).

Step 6. 1-Bromo-3-fluoro-2-(methyl-d₃)-5-nitrobenzene

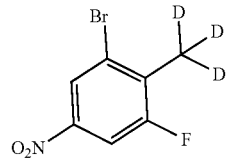

A solution of 2-fluoro-1-(methyl-d₃)-4-nitrobenzene (0.303 g, 1.92 mmol) in sulfuric acid (1.72 mL) and water (0.19 mL) was treated with silver sulfate (0.299 g, 0.958 mmol) followed by bromine (0.099 mL, 1.92 mmol), and stirred at room temperature for 16 h. The reaction mixture was treated with additional bromine (0.099 mL, 1.92 mmol) and stirred at room temperature for 22 h. The reaction mixture was treated with additional silver sulfate (0.299 g, 0.958 mmol) followed by bromine (0.050 mL, 0.958 mmol) and stirred at room temperature for 3 days. The reaction mixture was poured into ice water, diluted with ethyl acetate, warmed to room temp, and filtered to remove solids. The solids were washed with water and ethyl acetate. The layers were separated and the aqueous layer was extracted with ethyl acetate (3×). The combined organic layers were washed with brine, dried over magnesium sulfate, filtered, and concentrated to an amber oil. Purification by flash column chromatography using ethyl acetate in hexanes (0%-10%) gave the desired product (496 mg, 109%).

Step 7. 3-Bromo-5-fluoro-4-(methyl-d₃)aniline

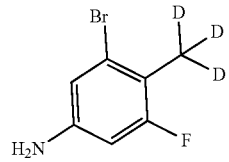

A solution of 1-bromo-3-fluoro-2-(methyl-d₃)-5-nitrobenzene (0.454 g, 1.92 mmol) in ethanol (7.98 mL) was treated with concentrated HCl (2.23 mL, 26.8 mmol) followed by tin(II) chloride (1.09 g, 5.75 mmol) and stirred at room temperature for 15 h. The reaction mixture was filtered to remove solids and the filtrate was quenched with 1 N NaOH until the mixture reached pH 10. There were salts that precipitated and this mixture was diluted with ethyl acetate and filtered over Celite. The aqueous layer from the filtrate was separated and re-extracted with ethyl acetate (2×). The combined organic layers were washed with brine, dried over magnesium sulfate, filtered, and concentrated to an oil. Purification by flash column chromatography using ethyl acetate in hexanes (0%-20%) gave the desired product (32.0 mg, 8.07%). LCMS for C₇H₅D₃BrFN (M+H)⁺: m/z=207.0, 209.0; Found: 206.9, 209.0.

Step 8. 3-Bromo-5-fluoro-4-(methyl-d₃)benzenesulfonyl Chloride

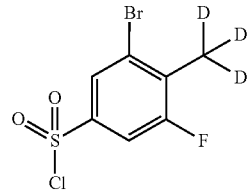 [SMILES: [2H]C([2H])([2H])c1c(F)cc(S(=O)(=O)Cl)cc1Br]

The desired compound was prepared according to the procedure of Example 466, step 1, using 3-bromo-5-fluoro-4-(methyl-d₃)aniline as the starting material.

Step 9. 3-Bromo-5-fluoro-N-(2-hydroxy-2-methylpropyl)-4-(methyl-d)benzenesulfonamide

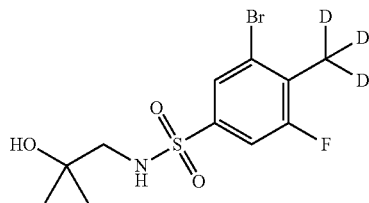 [SMILES: [2H]C([2H])([2H])c1c(F)cc(S(=O)(=O)NCC(C)(C)O)cc1Br]

The desired compound was prepare according to the procedure of Example 466, step 2, using 3-bromo-5-fluoro-4-(methyl-d₃)benzenesulfonyl chloride and 1-amino-2-methylpropan-2-ol as the starting materials. LCMS for $C_{11}H_{12}D_3BrFNO_3SNa$ $(M+Na)^+$: m/z=365.0, 367.0; Found: 364.9, 367.0.

Step 10. 3-Fluoro-N-(2-hydroxy-2-methylpropyl)-4-(methyl-d₃)-5-(4,4,5,5-tetramethyl-1,3,2-dioxaborolan-2-yl)benzenesulfonamide

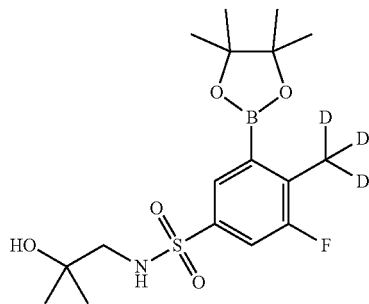 [SMILES: [2H]C([2H])([2H])c1c(F)cc(S(=O)(=O)NCC(C)(C)O)cc1B1OC(C)(C)C(C)(C)O1]

The desired compound was prepared according to the procedure of Example 1, step 2, using 3-bromo-5-fluoro-N-(2-hydroxy-2-methylpropyl)-4-(methyl-d₃)benzenesulfonamide as the starting material. LCMS for $C_{17}H_{24}D_3BrFNO_5SNa$ $(M+Na)^+$: m/z=413.2; Found: 413.2.

Step 11. 3-(4-Amino-2-(methyl-d₃)imidazo[2,1-f][1,2,4]triazin-7-yl)-5-fluoro-N-(2-hydroxy-2-methylpropyl)-4-(methyl-d₃)benzenesulfonamide The desired compound was prepared according to the procedure of Example 1, step 3, using 3-fluoro-N-(2-hydroxy-2-methylpropyl)-4-(methyl-d₃)-5-(4,4,5,5-tetramethyl-1,3,2-dioxaborolan-2-yl)benzenesulfonamide and 7-bromo-2-(methyl-d₃)imidazo[2,1-f][1,2,4]triazin-4-amine as the starting materials. ¹H NMR (400 MHz, DMSO-d₆) δ 8.22 (br s, 1H), 8.15 (br s, 1H), 7.80-7.71 (m, 2H), 7.65 (dd, J=9.0, 1.7 Hz, 1H), 7.62 (s, 1H), 4.41 (s, 1H), 2.68 (s, 2H), 1.05 (s, 6H). LCMS for $C_{17}H_{16}D_6FN_6O_3S$ $(M+H)^+$: m/z=415.2; Found: 415.1.

Example 470. 3-(4-Amino-2-(hydroxymethyl)imidazo[2,1-f][1,2,4]triazin-7-yl)-5-fluoro-N-(2-hydroxy-2-methylpropyl)-4-methylbenzenesulfonamide

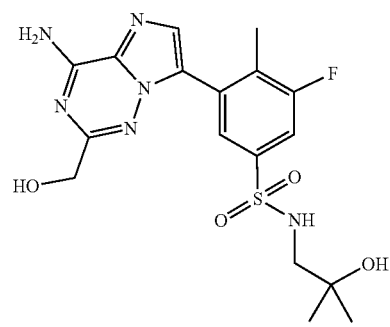 [SMILES: Cc1c(F)cc(S(=O)(=O)NCC(C)(C)O)cc1-c1cnc2c(N)nc(CO)nn12]

Step 1. 2-(Diethoxymethyl)imidazo[2,1-f][1,2,4]triazin-4-amine

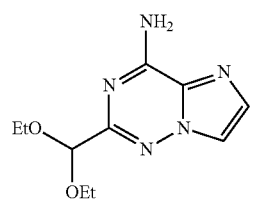 [SMILES: CCOC(OCC)c1nc(N)c2nccn2n1]

A solution of 1-amino-1H-imidazole-2-carbonitrile (0.533 g, 4.93 mmol) in ethanol (7.0 mL) in a microwave vial was treated with a solution of methyl 2,2-diethoxyacetimidate (0.954 g, 5.92 mmol) in ethanol (2.9 mL) over 2-3 min and stirred at room temperature for 10 min. The reaction mixture was treated with triethylamine (0.687 mL, 4.93 mmol) over 1 min and heated in a microwave at 120° C. for 2 h. The reaction mixture was concentrated, diluted with DCM, and concentrated again. The residue was diluted with ethyl acetate and water. Brine was added to help with the emulsion. The aqueous layer was separated and extracted with ethyl acetate. The combined organic layers were washed with brine, dried over magnesium sulfate, filtered, and concentrated to a brown oil. Purification by flash column chromatography using methanol in dichloromethane (0%-5%) gave the desired product (858 mg, 64.6%). LCMS for $C_{10}H_{15}N_5O_2Na$ $(M+Na)^+$: m/z=260.1; Found: 260.1.

Step 2. 7-Bromo-2-(diethoxymethyl)imidazo[2,1-f][1,2,4]triazin-4-amine

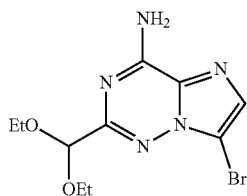 [SMILES: CCOC(OCC)c1nc(N)c2ncc(Br)n2n1]

The desired compound was prepared according to the procedure of Example 468, step 3, using 2-(diethoxymethyl)imidazo[2,1-f][1,2,4]triazin-4-amine as the starting material. LCMS for $C_{10}H_{14}BrN_5O_2Na$ (M+Na)$^+$: m/z=338.0, 340.0; Found: 338.1, 340.1.

Step 3. 4-Amino-7-bromoimidazo[2,1-f][1,2,4]triazine-2-carbaldehyde

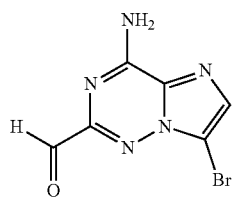 [SMILES: Nc1nc(C=O)nn2c(Br)cnc12]

A solution of 7-bromo-2-(diethoxymethyl)imidazo[2,1-f][1,2,4]triazin-4-amine (0.250 g, 0.791 mmol) in tetrahydrofuran (0.47 mL) was treated with 6 N hydrochloric acid (1.11 mL) and stirred at 90° C. for 1 h. The reaction mixture was concentrated to give the desired product as a white solid that was used without further purification. LCMS for $C_6H_5BrN_5O$ (M+H): m/z=242.0, 244.0; Found: 242.0, 244.0.

Step 4. (4-Amino-7-bromoimidazo[2,1-f][1,2,4]triazin-2-yl)methanol

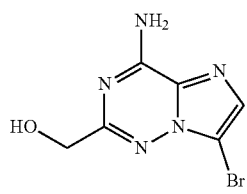 [SMILES: Nc1nc(CO)nn2c(Br)cnc12]

A solution of 4-amino-7-bromoimidazo[2,1-f][1,2,4]triazine-2-carbaldehyde (0.191 g, 0.789 mmol) in methanol (0.99 mL) was treated with sodium borohydride (0.060 g, 1.58 mmol) in portions at room temperature and stirred for 45 min. The reaction mixture was quenched with saturated ammonium chloride, concentrated to remove methanol, and diluted with water and ethyl acetate. The mixture was filtered. The aqueous layer of the filtrate was separated and extracted with ethyl acetate. The combined organic layers were washed with brine, then dried over magnesium sulfate, filtered, and concentrated to a yellow solid. This solid was dissolved in methanol (4-5 mL), stirred at 60° C. for 1 h, cooled to room temperature, and stirred for 105 min.

The solids were isolated by filtration and washed with methanol (1 mL) to give the desired product (54.0 mg, 28.0% for 2 steps). LCMS for $C_6H_7BrN_5O$ (M+H)$^+$: m/z=244.0, 246.0; Found: 243.9, 245.9.

Step 5. 3-(4-Amino-2-(hydroxymethyl)imidazo[2,1-f][1,2,4]triazin-7-yl)-5-fluoro-N-(2-hydroxy-2-methylpropyl)-4-methylbenzenesulfonamide The desired compound was prepared according to the procedure of example 1, step 3, using 3-fluoro-N-(2-hydroxy-2-methylpropyl)-4-methyl-5-(4,4,5,5-tetramethyl-1,3,2-dioxaborolan-2-yl)benzenesulfonamide and (4-amino-7-bromoimidazo[2,1-f][1,2,4]triazin-2-yl)methanol as the starting materials. $^1$H NMR (400 MHz, DMSO-d$_6$) δ 8.29 (br s, 1H), 8.22 (br s, 1H), 7.78 (s, 1H), 7.75 (s, 1H), 7.70-7.64 (m, 1H), 7.61 (s, 1H), 5.15 (t, J=6.3 Hz, 1H), 4.41 (s, 1H), 4.31 (d, J=6.3 Hz, 2H), 2.68 (s, 2H), 2.20 (d, J=2.0 Hz, 3H), 1.06 (s, 6H). LCMS for $C_{17}H_{22}FN_6O_4S$ (M+H)$^+$: m/z=425.1; Found: 425.1.

Example 471. N-(3-(8-Aminoimidazo[1,2-a]pyrazin-3-yl)-4-methylphenyl)tetrahydro-2H-pyran-4-sulfonamide

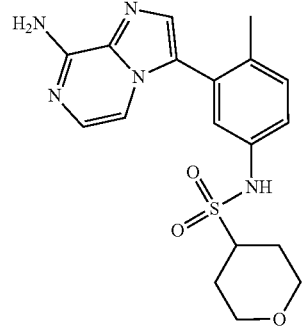 [SMILES: Cc1ccc(NS(=O)(=O)C2CCOCC2)cc1-c1cnc2c(N)nccn12]

Step 1. N-(4-Methyl-3-(4,4,5,5-tetramethyl-1,3,2-dioxaborolan-2-yl)phenyl)tetrahydro-2H-pyran-4-sulfonamide

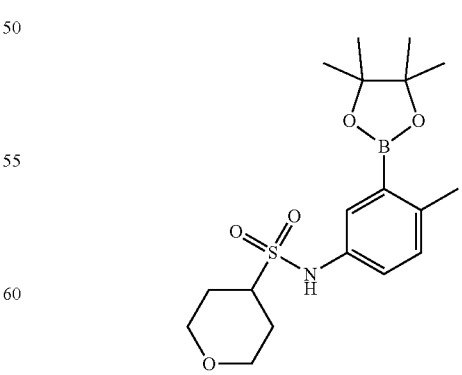

The desired compound was prepared according to the procedure of Example 466, step 2, using tetrahydro-2H-pyran-4-sulfonyl chloride [Aurum Pharmatech, Z-2491] and 4-methyl-3-(4,4,5,5-tetramethyl-1,3,2-dioxaborolan-2-yl) aniline [Boron Molecular, BM139] as the starting materials. LCMS for $C_{18}H_{28}BNO_5SNa$ (M+Na)⁺: m/z=404.2; Found: 404.1.

Step 2. N-(3-(8-Aminoimidazo[1,2-a]pyrazin-3-yl)-4-methylphenyl)tetrahydro-2H-pyran-4-sulfonamide The desired compound was prepared according to the procedure of example 1, step 3, using N-(4-methyl-3-(4,4,5,5-tetramethyl-1,3,2-dioxaborolan-2-yl)phenyl)tetrahydro-2H-pyran-4-sulfonamide and 3-bromoimidazo[1,2-a] pyrazin-8-amine as the starting materials. ¹H NMR (400 MHz, DMSO-d₆) δ 9.90 (br s, 1H), 7.60 (s, 1H), 7.37 (d, J=8.4 Hz, 1H), 7.28 (dd, J=8.2, 2.3 Hz, 1H), 7.25-7.16 (m, 3H), 6.96 (s, 2H), 3.97-3.75 (m, 2H), 3.49-3.13 (m, 3H), 2.11 (s, 3H), 1.94-1.80 (m, 2H), 1.75-1.51 (m, 2H). LCMS for $C_{18}H_{22}N_5O_3S$ (M+H)⁺: m/z=388.1; Found: 388.1.

Example 472. (1-((3-(8-Amino-6-(trifluoromethyl) imidazo[1,2-a]pyrazin-3-yl)-4-methylphenyl)sulfonyl)piperidin-3-yl)methanol

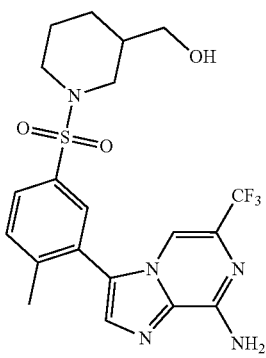 [SMILES: Cc1ccc(S(=O)(=O)N2CCCC(CO)C2)cc1-c1cnc2c(N)nc(C(F)(F)F)cn12]

Step 1. 5-(Trifluoromethyl)pyrazin-2-amine

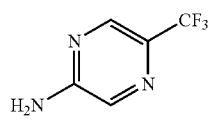

2-Chloro-5-(trifluoromethyl)pyrazine (5.0 g, 27 mmol) (Oakwood Products, 075803) was stirred in ammonium hydroxide (190 mL, 2.7 mol) and heated to 80° C. for 3.5 h in a sealed pressure vessel. After cooling to rt, the aqueous mixture was extracted with DCM (4×). The extracts were combined, dried over sodium sulfate, filtered, and concentrated to afford the title compound as a white solid (4.0 g, 90%). ¹H NMR (400 MHz, CDCl₃) δ 8.34 (s, 1H), 8.01 (s, 1H), 5.01 (br s, 2H). LCMS for $C_5H_5F_3N_3$(M+H)⁺: calculated m/z=164.0; found 164.1.

Step 2. 3-Cloro-5-(trifluoromethyl)pyrazin-2-amine

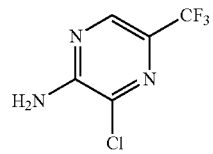

5-(Trifluoromethyl)pyrazin-2-amine (4.56 g, 28.0 mmol) was stirred in NMP (135 mL, 1400 mmol) and N-chlorosuccinimide (3.73 g, 28.0 mmol) was added. The reaction mixture was stirred at rt for 6 h. The reaction mixture was poured into sat. sodium thiosulfate (100 mL) and diluted with water (500 mL). The mixture was extracted with ethyl acetate (4×200 mL). The combined extracts were washed with brine (3×), dried over sodium sulfate, filtered, and concentrated. Purification via silica gel column (0-35% EtOAc/hexanes) afforded the title compound as a white solid (2.32 g, 42.0%). LCMS for $C_5H_4ClF_3N_3$(M+H)⁺: calculated m/z=198.0; found 198.0.

Step 3. 8-Chloro-6-(trifluoromethyl)imidazo[1,2-a] pyrazine

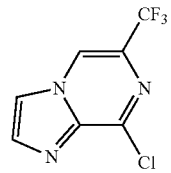

To a solution of 3-chloro-5-(trifluoromethyl)pyrazin-2-amine (2.32 g, 11.7 mmol) in EtOH (84 mL) was slowly added chloroacetaldehyde (37.3 mL, 294 mmol, 50% in H₂O). The reaction mixture was portioned into seven 20-mL microwave vials, and then each was heated at 150° C. for 20 min in a microwave reactor. The reaction mixtures were combined and concentrated, the residue was diluted with DCM, and triethylamine was added cautiously to adjust pH≥7. Purification via silica gel chromatography (0-50% EtOAc/hexanes) afforded the title compound as a brown oil (1.93 g, 74.2%). LCMS for $C_7H_4ClF_3N_3$(M+H)⁺: calculated m/z=222.0; found 221.9.

Step 4. 3-Bromo-8-chloro-6-(trifluoromethyl)imidazo[1,2-a]pyrazine

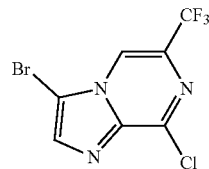 [SMILES: FC(F)(F)c1cn2c(Br)cnc2c(Cl)n1]

To a solution of 8-chloro-6-(trifluoromethyl)imidazo[1,2-a]pyrazine (0.37 g, 1.7 mmol) in DMF (11 mL) was added N-bromosuccinimide (0.30 g, 1.7 mmol). The reaction mixture was heated at 60° C. for 2 h. The reaction mixture was cooled to rt and poured into 40% sat. Na₂S₂O₃ (50 mL). The aqueous mixture was then extracted with DCM (3×40 mL). The combined organic layers were washed with brine (75 mL), dried over Na₂SO₄, filtered, and concentrated. Purification via silica gel chromatography (10-40% EtOAc/hexanes) afforded the title compound as a white solid (0.41 g, 82%). LCMS for $C_7H_3BrClF_3N_3(M+H)^+$: calculated m/z=299.9, 301.9; found 299.9, 301.8.

Step 5. 3-Bromo-N-(4-methoxybenzyl)-6-(trifluoromethyl)imidazo[1,2-a]pyrazin-8-amine

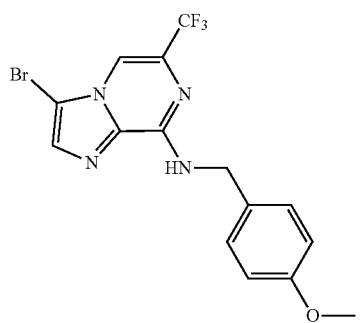 [SMILES: COc1ccc(CNc2nc(C(F)(F)F)cn3c(Br)cnc23)cc1]

A mixture of 3-bromo-8-chloro-6-(trifluoromethyl)imidazo[1,2-a]pyrazine (0.35 g, 1.2 mmol), N,N-diisopropylethylamine (0.40 mL, 2.3 mmol), and 4-methoxybenzylamine (0.17 mL, 1.3 mmol) in iPrOH (5.0 mL) was heated at 110° C. for 15 min in a microwave. The resulting white suspension was washed with water (3×). The resulting white solid was dried in vacuo overnight to afford the title compound as a white solid (0.53 g, >99%). $^1$H NMR (400 MHz, DMSO-d₆) δ 8.71 (t, J=6.0 Hz, 1H), 7.97 (s, 1H), 7.80 (s, 1H), 7.32 (d, J=8.6 Hz, 2H), 6.85 (d, J=8.6 Hz, 2H), 4.59 (d, J=6.0 Hz, 2H), 3.70 (s, 3H). $^{19}$F NMR (376 MHz, DMSO-d₆) δ −66.99. LCMS for $C_{15}H_{13}BrF_3N_4O$ (M+H)⁺: calculated m/z=401.0, 403.0; found 401.0, 403.0.

Step 6. 3-Bromo-6-(trifluoromethyl)imidazo[1,2-a]pyrazin-8-amine

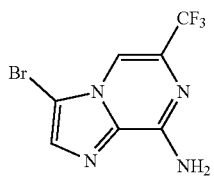 [SMILES: Nc1nc(C(F)(F)F)cn2c(Br)cnc12]

A solution of 3-bromo-N-(4-methoxybenzyl)-6-(trifluoromethyl)imidazo[1,2-a]pyrazin-8-amine (0.53 g, 1.2 mmol) in TFA (2.9 mL) was heated at 55° C. for 1 h. The reaction mixture was concentrated and then diluted with water (3.0 mL). With the reaction vial in a 0° C. bath, the aqueous mixture was basified with 1.0 M NaOH (7.5 mL). The bath was removed, and the aqueous mixture was stirred for 5 min. The resulting white precipitate was collected via filtration, washed with water (2×10 mL) and dried to afford the crude product as a white solid (0.440 g). Purification via silica gel chromatography (5-40% EtOAc/DCM) afforded the title compound as a white solid (0.25 g, 77%). $^1$H NMR (400 MHz, DMSO-d₆) δ 7.98 (s, 1H), 7.81 (s, 1H), 7.73 (br s, 2H). $^{19}$F NMR (376 MHz, DMSO-d₆) δ −66.77. LCMS for $C_7H_5BrF_3N_4(M+H)^+$: calculated m/z=281.0, 283.0; found 280.9, 282.9.

Step 7. 3-(o-Tolyl)-6-(trifluoromethyl)imidazo[1,2-a]pyrazin-8-amine

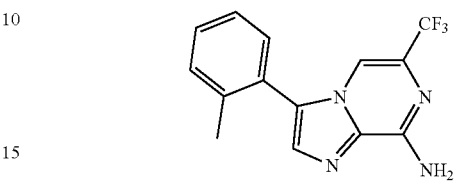

A mixture of dichloro[1,1'-bis(diphenylphosphino)ferrocene]palladium(II) dichloromethane adduct (0.52 g, 0.64 mmol), o-tolylboronic acid (1.4 g, 10 mmol), and 3-bromo-6-(trifluoromethyl)imidazo[1,2-a]pyrazin-8-amine (1.0 g, 3.6 mmol) in THF (36 mL) and 1.0 M potassium carbonate in water (18 mL, 18 mmol) was degassed with N₂ for 5 min and then heated at 80° C. for 5 h. The reaction mixture was filtered through Celite, rinsing with EtOAc and water. The resulting mixture was washed with water (2×75 mL) and brine (70 mL). The organic layer was then dried over sodium sulfate, filtered, and concentrated. Purification via silica gel chromatography (1-88% EtOAc/hexanes) afforded the title compound as a white solid (1.1 g, >99% yield). LCMS for $C_{14}H_{12}F_3N_4$ (M+H)⁺: calculated m/z=293.1; found 293.1.

Step 8. 3-(8-Amino-6-(trifluoromethyl)imidazo[1,2-a]pyrazin-3-yl)-4-methylbenzenesulfonyl Chloride

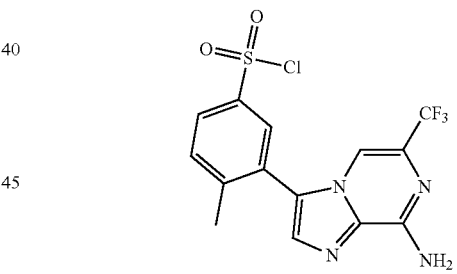

A 45-mL scintillation vial was charged with 3-(o-tolyl)-6-(trifluoromethyl)imidazo[1,2-a]pyrazin-8-amine (0.49 g, 1.7 mmol). The vial was placed under nitrogen, and dichloromethane (20 mL) was added. The reaction vial was placed in an ice bath, and chlorosufluric acid (1.1 mL, 17 mmol) added over 2 min. After 5 min, the ice bath was removed; the mixture was warmed to rt and then heated at 50° C. for 3 h. The reaction mixture was again cooled to 0° C., and an additional portion of chlorosufluric acid (1.1 ml, 17 mmol) was added over 1 min. The mixture was warmed to rt and then heated at 50° C. for 3.5 h. The reaction mixture was cooled to rt and diluted with DCM (20 mL). The mixture added slowly to a stirred mixture of ice water (100 mL) and DCM (80 mL). The organic layer was removed, and the aqueous layer was extracted with DCM (2×100 mL). The combined organic layers were dried over MgSO₄, filtered, and concentrated to afford the title compound as an orange-brown solid (0.53 g, 82%). LCMS for $C_{14}H_{11}ClF_3N_4O_2S$ (M+H)+: calculated m/z=391.0; found 391.0.

Step 9. (1-((3-(8-Amino-6-(trifluoromethyl)imidazo [1,2-a]pyrazin-3-yl)-4-methylphenyl)sulfonyl)piperidin-3-yl)methanol To a mixture of piperidin-3-ylmethanol (3.0 µL, 0.027 mmol), triethylamine (11 µL, 0.080 mmol), and DMAP (0.3 mg, 3 µmol) in DMA (0.24 mL) at 0° C. was added 3-(8-amino-6-(trifluoromethyl)imidazo[1,2-a]pyrazin-3-yl)-4-methylbenzenesulfonyl chloride (10 mg, 0.027 mmol) in a single portion. The reaction mixture was allowed to come to rt and stirred for 2 h. The reaction mixture was again cooled to 0° C., and the reaction was quenched with MeOH. Purification via preparative HPLC on a C-18 column (pH 10, 32-52% MeCN/0.1% NH$_4$OH (aq) over 5 min, 60 mL/min) afforded the desired product as a white solid (7.0 mg, 56%). $^1$H NMR (600 MHz, DMSO-d$_6$) δ 7.84 (s, 1H), 7.78 (dd, J=8.2, 1.9 Hz, 1H), 7.74-7.70 (m, 3H), 7.67 (br s, 2H), 4.55 (t, J=5.3 Hz, 1H), 3.66 (dd, J=11.4, 3.7 Hz, 1H), 3.53 (d, J=10.9 Hz, 1H), 3.37-3.25 (m, 1H), 3.23-3.09 (m, 1H), 2.37-2.30 (m, 1H), 2.30 (s, 3H), 2.08 (t, J=10.8 Hz, 1H), 1.73-1.61 (m, 2H), 1.62-1.56 (m, 1H), 1.55-1.42 (m, 1H), 1.01-0.83 (m, 1H). $^{19}$F NMR (376 MHz, DMSO-d$_6$) δ -66.70. LCMS for $C_{20}H_{23}F_3N_5O_3S$ (M+H)+: calculated m/z=470.1; found 470.2.

Example 473. 3-(2-Methyl-5-(methylsulfonyl)phenyl)-6-(3-methylpyridin-4-yl)imidazo[1,2-a]pyrazin-8-amine Trifluoroacetate

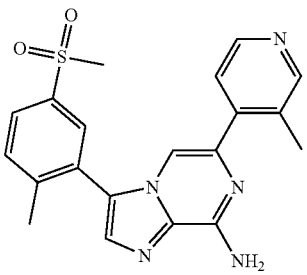 [SMILES: Cc1cnccc1-c1cn2c(-c3cc(S(C)(=O)=O)ccc3C)cnc2c(N)n1]

Step 1. 6-Bromo-3-(2-methyl-5-(methylsulfonyl) phenyl)imidazo[1,2-a]pyrazin-8-amine

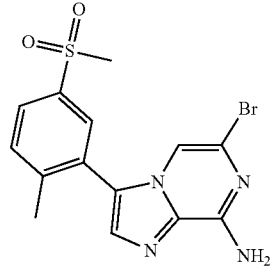 [SMILES: Cc1ccc(S(C)(=O)=O)cc1-c1cnc2c(N)nc(Br)cn12]

A mixture of 6-bromo-3-iodoimidazo[1,2-a]pyrazin-8-amine (680 mg, 2.0 mmol), bis(pinacolato)diboron (490 mg, 1.7 mmol), and tetrakis(triphenylphosphine)palladium(0) (120 mg, 0.10 mmol) in ethanol (10 mL) and 2.0 M Na$_2$CO$_3$ in water (1.7 mL, 3.3 mmol) was degassed for 5 min with N$_2$. The reaction mixture was then heated in a microwave reactor at 130° C. for 20 min. The precipitated solid was collected via filtration, washed with MeOH, and air dried to yield the title compound (620 mg, 74%). $^1$H NMR (400 MHz, DMSO-d$_6$) δ 7.96 (dd, J=8.0, 2.0 Hz, 1H), 7.90 (d, J=1.9 Hz, 1H), 7.71 (d, J=8.4 Hz, 1H), 7.69 (s, 1H), 7.59 (s, 2H), 7.40 (s, 1H), 3.26 (s, 3H), 2.25 (s, 3H). LCMS for $C_{14}H_{14}BrN_4O_2S$ (M+H)+: calculated m/z=381.0, 383.0; found 381.0, 383.0.

Step 2. 3-(2-Methyl-5-(methylsulfonyl)phenyl)-6-(3-methylpyridin-4-yl)imidazo[1,2-a]pyrazin-8-amine Trifluoroacetate A 1-dram vial was charged with 6-bromo-3-(2-methyl-5-(methylsulfonyl)phenyl)imidazo[1,2-a]pyrazin-8-amine (8 mg, 0.02 mmol), dichloro[1,1'-bis(diphenylphosphino)ferrocene]palladium(II) dichloromethane adduct (3 mg, 4 µmol), and (3-methylpyridin-4-yl)boronic acid (11 mg, 0.084 mmol). THF (0.42 mL) and then 1.0 M potassium carbonate (53 µL, 0.052 mmol) were added. The reaction mixture was degassed with N$_2$ briefly and then heated at 80° C. for 16 h. The reaction mixture was diluted with MeOH and filtered through a plug of Na$_2$SO$_4$ and Celite. Purification via preparative HPLC on a C-18 column (pH 2, 11-31% MeCN/ 0.1% TFA (aq) over 5 min, 60 mL/min) afforded the title compound as a yellow semi-solid (3.7 mg, 34%). $^1$H NMR (500 MHz, DMSO-d$_6$) δ 8.72 (s, 1H), 8.67 (d, J=5.7 Hz, 1H), 8.00-7.94 (m, 2H), 7.89-7.82 (m, 2H), 7.72 (d, J=8.8 Hz, 1H), 7.70 (s, 1H), 7.60 (br s, 2H), 3.25 (s, 3H), 2.52 (s, 3H), 2.33 (s, 3H). LCMS for $C_{20}H_{20}N_5O_2S$ (M+H)+: calculated m/z=394.1; found 394.1.

Examples 474 to 486 were synthesized according to procedures analogous to the synthesis of Example 473, and the data are listed in Table 20.

TABLE 20

| Ex. No. | Name / ¹H NMR Spectra | R⁸ | LCMS [M + H]⁺ |
|---|---|---|---|
| 474 | 2-(3-(8-Amino-3-(2-methyl-5-(methylsulfonyl)phenyl)imidazo[1,2-a]pyrazin-6-yl)phenyl)acetonitrile trifluoroacetate | 3-(cyanomethyl)phenyl | 418.1 |
| 475 | 6-(4-(Difluoromethyl)phenyl)-3-(2-methyl-5-(methylsulfonyl)phenyl)imidazo[1,2-a]pyrazin-8-amine trifluoroacetate | 4-(CF₂H)phenyl | 429.1 |
| 476 | 6-(3-Fluoropyridin-4-yl)-3-(2-methyl-5-(methylsulfonyl)phenyl)imidazo[1,2-a]pyrazin-8-amine trifluoroacetate ¹H NMR (500 MHz, DMSO-d₆) δ 8.60 (d, J = 3.3 Hz, 1H), 8.52 (dd, J = 5.0, 1.0 Hz, 1H), 8.06 (dd, J = 7.0, 5.0 Hz, 1H), 7.99 (d, J = 6.9 Hz, 2H), 7.84 (d, J = 1.0 Hz, 2H), 7.76 (d, J = 9.3 Hz, 1H), 7.52 (s, 2H), 3.26 (s, 3H), 2.32 (s, 3H). | 3-fluoropyridin-4-yl | 398.1 |
| 477 | 6-(2-Methoxypyridin-3-yl)-3-(2-methyl-5-(methylsulfonyl)phenyl)imidazo[1,2-a]pyrazin-8-amine trifluoroacetate | 2-methoxypyridin-3-yl | 410.0 |
| 478 | 6-(2-Fluoro-6-methoxyphenyl)-3-(2-methyl-5-(methylsulfonyl)phenyl)imidazo[1,2-a]pyrazin-8-amine trifluoroacetate | 2-fluoro-6-methoxyphenyl | 427.2 |
| 479 | 6-(1-Methyl-1H-pyrazol-5-yl)-3-(2-methyl-5-(methylsulfonyl)phenyl)imidazo[1,2-a]pyrazin-8-amine trifluoroacetate | 1-methyl-1H-pyrazol-5-yl | 383.1 |

TABLE 20-continued

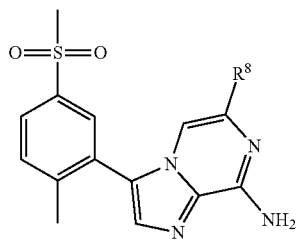

| Ex. No. | Name<br>¹H NMR Spectra | R⁸ | LCMS [M + H]⁺ |
|---|---|---|---|
| 480 | 4-(8-Amino-3-(2-methyl-5-(methylsulfonyl)phenyl)imidazo[1,2-a]pyrazin-6-yl)-3-fluoro-N,N-dimethylbenzamide | | 468.1 |
| 481 | (3-(8-Amino-3-(2-methyl-5-(methylsulfonyl)phenyl)imidazo[1,2-a]pyrazin-6-yl)-2-fluorophenyl)methanol | | 427.1 |
| | ¹H NMR (500 MHz, DMSO-d₆) δ 7.98 (dd, J = 8.1, 2.0 Hz, 1H), 7.95 (d, J = 1.9 Hz, 1H), 7.92 (td, J = 7.8, 1.9 Hz, 1H), 7.79-7.72 (m, 2H), 7.59 (s, 1H), 7.47-7.40 (m, 1H), 7.30-7.22 (m, 3H), 5.25 (t, J = 5.5 Hz, 1H), 4.55 (d, J = 5.5 Hz, 2H), 3.26 (s, 3H), 2.29 (s, 3H). | | |
| 482 | 6-(6-Aminopyridin-3-yl)-3-(2-methyl-5-(methylsulfonyl)phenyl)imidazo[1,2-a]pyrazin-8-amine trifluoroacetate | | 395.1 |
| 483 | 6-(3-Fluoro-2-methoxypyridin-4-yl)-3-(2-methyl-5-(methylsulfonyl)phenyl)imidazo[1,2-a]pyrazin-8-amine trifluoroacetate | | 428.1 |
| 484 | 6-(3-Chloropyridin-4-yl)-3-(2-methyl-5-(methylsulfonyl)phenyl)imidazo[1,2-a]pyrazin-8-amine trifluoroacetate | | 414.0 |
| 485 | 6-(3-Methoxypyridin-4-yl)-3-(2-methyl-5-(methylsulfonyl)phenyl)imidazo[1,2-a]pyrazin-8-amine trifluoroacetate | | 410.1 |

TABLE 20-continued

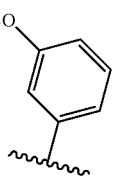

| Ex. No. | Name <br> ¹H NMR Spectra | R⁸ | LCMS [M + H]⁺ |
|---|---|---|---|
| 486 | 2-(3-(8-Amino-3-(2-methyl-5-(methylsulfonyl)phenyl)imidazo[1,2-a]pyrazin-6-yl)phenoxy)acetonitrile trifluoroacetate | NC~O-Ph | 434.2 |

Example 487. 6-(2-Fluoro-4-(pyrrolidin-1-ylmethyl)phenyl)-3-(2-methyl-5-(methylsulfonyl)phenyl)imidazo[1,2-a]pyrazin-8-amine

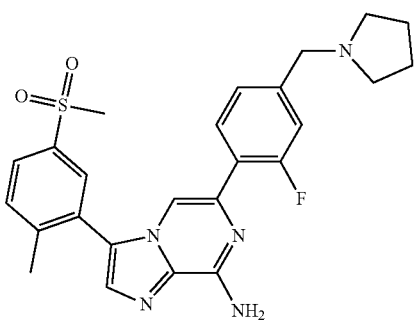 [SMILES: Cc1ccc(S(C)(=O)=O)cc1-c1cnc2c(N)nc(-c3ccc(CN4CCCC4)cc3F)cn12]

Step 1. 4-(8-Amino-3-(2-methyl-5-(methylsulfonyl)phenyl)imidazo[1,2-a]pyrazin-6-yl)-3-fluorobenzaldehyde

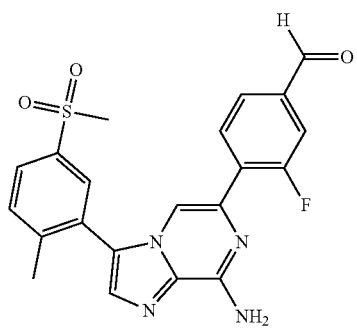 [SMILES: Cc1ccc(S(C)(=O)=O)cc1-c1cnc2c(N)nc(-c3ccc(C=O)cc3F)cn12]

The title compound was synthesized according to experimental procedure analogous to the synthesis of Example 473, Step 1, substituting (2-fluoro-4-formylphenyl)boronic acid for (3-methylpyridin-4-yl)boronic acid. Purification via silica gel chromatography (12-100% EtOAc in DCM) afforded a yellow-orange solid (16 mg), which contained the title compound as a 3:2 mixture with an aldehyde byproduct. This material was carried forward without further purification. LCMS for $C_{21}H_{18}FN_4O_3S$ (M+H)⁺: calculated m/z=425.1; found 425.0.

Step 2. 6-(2-Fluoro-4-(pyrrolidin-1-ylmethyl)phenyl)-3-(2-methyl-5-(methylsulfonyl)phenyl)imidazo[1,2-a]pyrazin-8-amine To a mixture of 4-(8-amino-3-(2-methyl-5-(methylsulfonyl)phenyl)imidazo[1,2-a]pyrazin-6-yl)-3-fluorobenzaldehyde (15 mg, 0.025 mmol, 70% purity) and pyrrolidine (6 μL, 0.07 mmol) in MeOH (0.5 mL) and acetic acid (0.7 μL) was added sodium cyanoborohydride (6 mg, 0.1 mmol). The reaction mixture was stirred overnight. The reaction was quenched with water. Purification via prep LCMS via preparative HPLC on a C-18 column (pH 10, MeCN/0.1% NH₄OH (aq)) afforded the desired product title compound as white solid (2.5 mg, 21%). LCMS for $C_{25}H_{27}FN_5O_2S$ (M+H)⁺: calculated m/z=480.2; found 480.2.

Example 488. 1-(4-(8-Amino-3-(2-methyl-5-(methylsulfonyl)phenyl)imidazo[1,2-a]pyrazin-6-yl)-3-fluorophenyl)ethan-1-ol

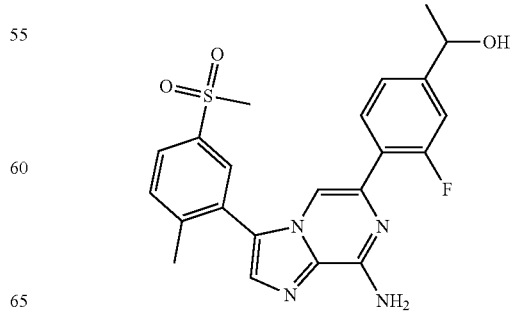

Step 1. 1-(4-Bromo-3-fluorophenyl)ethan-1-ol

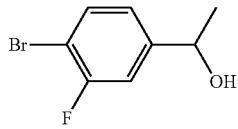

To a solution of 4-bromo-3-fluorobenzaldehyde (0.50 g, 2.5 mmol) in THF (10 mL) at −44° C. was added methylmagnesium bromide (0.99 mL, 3.0 mmol. 3.0 M in Et$_2$O). The reaction mixture was allowed to warm to rt, stirring for 3 h. The reaction was quenched with sat. NH$_4$Cl. The resulting aq. suspension was extracted with EtOAc (3×). The combined organic layers were dried over MgSO$_4$, filtered, and concentrated. Purification via silica gel chromatography (25-69% EtOAc/hexanes) afforded the desired product as a clear liquid (0.51 g, 95%). $^1$H NMR (400 MHz, CDCl$_3$) δ 7.50 (apparent t, J=8.0 Hz, 1H), 7.16 (d, J=9.5 Hz, 1H), 7.02 (d, J=8.4 Hz, 1H), 4.87 (q, J=6.5 Hz, 1H), 1.47 (d, J=6.4 Hz, 3H). $^{19}$F NMR (376 MHz, CDCl$_3$) δ −107.10.

Step 2. 1-(3-Fluoro-4-(4,4,5,5-tetramethyl-1,3,2-dioxaborolan-2-yl)phenyl)ethan-1-ol

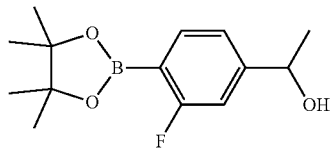 [SMILES: CC(O)c1ccc(B2OC(C)(C)C(C)(C)O2)c(F)c1]

A mixture of 1-(4-bromo-3-fluorophenyl)ethan-1-ol (0.13 g, 0.59 mmol), bis(pinacolato)diboron (0.17 g, 0.65 mmol), potassium acetate (0.17 g, 1.8 mmol), and bis(triphenylphosphine)palladium(II) chloride (15 mg, 0.022 mmol) in THF (4.6 mL) was degassed with N$_2$ for 5 min. The mixture was then heated at 140° C. in a microwave for 20 min. The reaction mixture was diluted with EtOAc and filtered through Celite, rinsing with EtOAc. The filtrate was washed with water and then brine, dried over Na$_2$SO$_4$, filtered, and concentrated. Purification via silica gel chromatography (1-10% MeOH in DCM) afforded a grey-brown solid (0.19 g). This material was a mixture of the title compound and another fluorinated impurity; it was carried on without further purification. LCMS for C$_{14}$H$_{19}$BFO$_2$ (M-OH)$^+$: calculated m/z=249.2; found 249.2.

Step 3. 1-(4-(8-Amino-3-(2-methyl-5-(methylsulfonyl)phenyl)imidazo[1,2-a]pyrazin-6-yl)-3-fluorophenyl)ethan-1-ol The title compound was synthesized according to experimental procedure analogous to the synthesis of Example 473, Step 1, substituting 1-(3-fluoro-4-(4,4,5,5-tetramethyl-1,3,2-dioxaborolan-2-yl)phenyl)ethan-1-ol for (3-methylpyridin-4-yl)boronic acid. $^1$H NMR (500 MHz, DMSO-d$_6$) δ 8.02 (d, J=8.2 Hz, 1H), 8.00-7.98 (m, 1H), 7.98-7.95 (m, 1H), 7.77-7.72 (m, 2H), 7.62 (s, 1H), 7.25 (dd, J=8.5, 1.6 Hz, 1H), 7.23 (br s, 2H), 7.17 (dd, J=13.2, 1.6 Hz, 1H), 5.29 (d, J=4.4 Hz, 1H), 4.85-4.64 (m, 1H), 3.26 (s, 3H), 2.31 (s, 3H), 1.32 (d, J=6.5 Hz, 3H). LCMS for C$_{22}$H$_{22}$FN$_4$O$_3$S (M+H)$^+$: calculated m/z=441.1; found 441.1.

Example 489. 6-(5-Fluoro-2-methylpyridin-4-yl)-3-(2-methyl-5-(methylsulfonyl)phenyl)imidazo[1,2-a]pyrazin-8-amine Trifluoroacetate

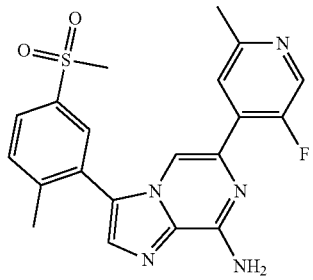 [SMILES: Cc1cc(-c2cn3c(-c4cc(S(C)(=O)=O)ccc4C)cnc3c(N)n2)c(F)cn1]

A mixture of 4-bromo-5-fluoro-2-methylpyridine (16 μL), bis(pinacolato)diboron (40 mg, 0.16 mmol), KOAc (39 mg, 0.395 mmol), and dichloro[1,1'-bis(diphenylphosphino)ferrocene]palladium (II) dichloromethane adduct (4 mg, 5 μmol) in THF (0.37 mL) was degassed with N$_2$ for 3 min. The mixture was then heated at 140° C. in a microwave for 20 min. The reaction mixture was diluted with EtOAc and filtered through Celite, rinsing with EtOAc. The filtrate was washed with water and then brine, dried over Na$_2$SO$_4$, filtered, and concentrated to afford the crude boronate ester.

A 1-dram vial was charged with dichloro[1,1'-bis(diphenylphosphino)ferrocene]palladium (II) dichloromethane adduct (3 mg, 4 μmol) and 6-bromo-3-(2-methyl-5-(methylsulfonyl)phenyl)imidazo[1,2-a]pyrazin-8-amine (8 mg, 0.02 mmol). A solution containing a half portion of the crude boronate ester in THF (0.50 mL) and then 1.0 M potassium carbonate (53 μL, 0.052 mmol) were added. The reaction mixture was degassed with N$_2$ for 5 min and then heated at 80° C. for 3 h. The reaction mixture was partitioned between EtOAc and water. The organic layer was removed, and the aqueous extracted with EtOAc (2×). The combined organic layers were dried over Na$_2$SO$_4$ and filtered. Purification via preparative HPLC on a C-18 column (pH 2, 14-34% MeCN/0.1% TFA (aq) over 5 min, 60 mL/min) afforded the title compound as a yellow solid (6 mg, 60%). LCMS for C$_{20}$H$_{19}$FN$_5$O$_2$S (M+H)$^+$: calculated m/z=412.1; found 412.0.

Example 490. (5-(8-Amino-3-(2-methyl-5-(methylsulfonyl)phenyl)imidazo[1,2-a]pyrazin-6-yl)-6-methoxypyridin-2-yl)methanol Trifluoroacetate

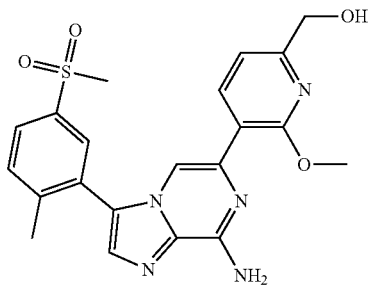 [SMILES: COc1nc(CO)ccc1-c1cn2c(-c3cc(S(C)(=O)=O)ccc3C)cnc2c(N)n1]

Step 1. (5-Bromo-6-methoxypyridin-2-yl)methanol

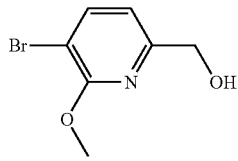

To a suspension of methyl 5-bromo-6-methoxypicolinate (20 mg, 0.079 mmol) (Ark Pharm, AK100459) in ethanol (0.25 mL) was added sodium borohydride (9.6 mg, 0.25 mmol). The reaction mixture was then heated at 50° C. for 2.5 h. An additional portion of sodium borohydride (10 mg, 0.27 mmol) was added, and the reaction mixture was heated at 50° C. for an additional 2 h. The reaction was quenched with water, and the reaction mixture was partitioned between sat. NaHCO$_3$ and EtOAc. The organic layer was removed, and the aqueous mixture was extracted with EtOAc (2×). The combined organic layers were washed with brine, dried over Na$_2$SO$_4$, filtered, and concentrated. Purification via silica gel chromatography (15-55% EtOAc/hexanes) afforded the desired product as a white solid (11 mg, 64%). LCMS for C$_7$H$_9$BrNO$_2$ (M+H)$^+$: calculated m/z=218.0, 220.0; found 217.9, 220.1.

Step 2. (5-(8-Amino-3-(2-methyl-5-(methylsulfonyl) phenyl)imidazo[1,2-a]pyrazin-6-yl)-6-methoxypyridin-2-yl)methanol Trifluoroacetate The title compound was synthesized according to an experimental procedure analogous to the synthesis of Example 489, substituting (5-bromo-6-methoxypyridin-2-yl)methanol for 4-bromo-5-fluoro-2-methylpyridine. LCMS for C$_{21}$H$_{22}$N$_5$O$_4$S (M+H)$^+$: calculated m/z=440.1; found 440.1.

Example 491. 6-(4-Methoxy-1H-pyrazol-5-yl)-3-(2-methyl-5-(methylsulfonyl)phenyl)imidazo[1,2-a] pyrazin-8-amine Trifluoroacetate

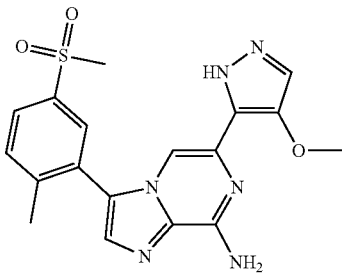 [SMILES: COc1cn[nH]c1-c1cn2c(-c3cc(S(C)(=O)=O)ccc3C)cnc2c(N)n1]

Step 1. 3-Bromo-4-methoxy-1H-pyrazole

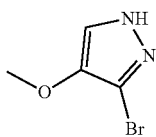

To a solution of 4-methoxy-1H-pyrazole (71 mg, 0.70 mmol) (Synthonix, M20056) in DMF (4.7 mL) was added N-bromosuccinimide (130 mg, 0.70 mmol). After stirring at rt for 2 h, the reaction mixture was diluted with DCM and poured into sat. Na$_2$S$_2$O$_3$. The organic layer was removed, and the aqueous layer was extracted twice more with DCM. The combined organic layers were washed with brine, dried over Na$_2$SO$_4$, filtered, and concentrated. Purification via silica gel chromatography (10-80% EtOAc/hexanes) afforded the title compound as a white solid (77 mg, 62%). LCMS for C$_4$H$_6$BrN$_2$O (M+H)$^+$: calculated m/z=177.0, 179.0; found 177.0, 178.9.

Step 2. 3-Bromo-4-methoxy-1-((2-(trimethylsilyl) ethoxy)methyl)-1H-pyrazole and 5-Bromo-4-methoxy-1-((2-(trimethylsilyl)ethoxy)methyl)-1H-pyrazole

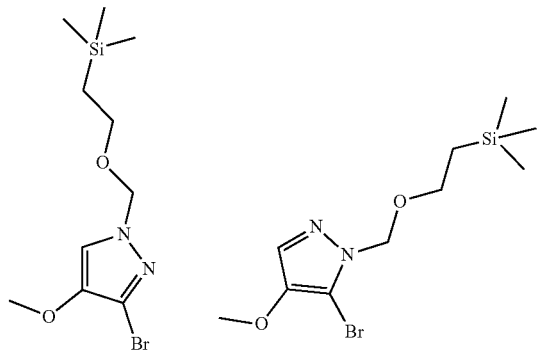

A solution of 3-bromo-4-methoxy-1H-pyrazole (77 mg, 0.44 mmol) in THF (5.4 mL) at 0° C. was treated with 2.0 M NaOtBu in THF (0.28 mL, 0.57 mmol). Upon stirring at 0° C. for 30 min, the reaction mixture was treated with (2-(chloromethoxy)ethyl)trimethylsilane (92 µL, 0.52 mmol) and was then stirred for 2 h during which the reaction mixture came to rt. The reaction was quenched with sat. NH$_4$Cl and diluted with water. The aqueous mixture was extracted with EtOAc (3×). The combined organic layers were dried over Na$_2$SO$_4$, filtered, and concentrated. Purification via silica gel chromatography (10-30% EtOAc in hexanes) afforded the title compounds as 1.3:1 mixture of regioisomers (130 mg, 95%, clear oil). $^1$H NMR (400 MHz, CDCl$_3$) Major isomer: δ 7.16 (s, 1H), 5.29 (s, 2H), 3.81 (s, 3H), 3.62-3.49 (m, 2H), 0.99-0.81 (m, 2H), −0.01 (s, 9H). Minor isomer: δ 7.38 (s, 1H), 5.42 (s, 2H), 3.85 (s, 3H), 3.62-3.49 (m, 2H), 0.99-0.81 (m, 2H), −0.02 (s, 9H). LCMS for C$_{10}$H$_{20}$BrN$_2$O$_2$Si (M+H)$^+$: calculated m/z=307.0, 309.0; found 306.9, 309.0.

Step 3. 6-(4-Methoxy-1H-pyrazol-5-yl)-3-(2-methyl-5-(methylsulfonyl)phenyl)imidazo[,2-a] pyrazin-8-amine Trifluoroacetate A mixture of 3-bromo-4-methoxy-1-((2-(trimethylsilyl) ethoxy)methyl)-1H-pyrazole and 5-bromo-4-methoxy-1-((2-(trimethylsilyl)ethoxy)methyl)-1H-pyrazole (31 mg, 0.10 mmol, mixture of two regioisomers), bis(pinacolato) diboron (32 mg, 0.13 mmol), potassium acetate (32 mg, 0.33 mmol), and dichloro[1,1'-bis(diphenylphosphino)ferrocene] palladium (II) dichloromethane adduct (3 mg, 4 µmol) in THF (0.30 mL) was degassed with N$_2$ for 3 min. The mixture was then heated at 140° C. in a microwave for 20 min and then again for 60 min. Additional portions of bis(pinacolato)diboron (32 mg, 0.13 mmol) and dichloro[1,1'-bis(diphenylphosphino)ferrocene]palladium (II) dichloromethane adduct (3 mg, 4 μmol) were added. The reaction mixture was degassed briefly and then heated at 140° C. in a microwave for 20 min. The reaction mixture was diluted with EtOAc and filtered through Celite, rinsing with EtOAc. The filtrate was washed with water and then brine, dried over $Na_2SO_4$, filtered, and concentrated to afford the crude boronate ester.

A 1-dram vial was charged with 6-bromo-3-(2-methyl-5-(methylsulfonyl)phenyl)imidazo[1,2-a]pyrazin-8-amine (8 mg, 0.02 mmol) and dichloro[1,1'-bis(diphenylphosphino)ferrocene]palladium (II) dichloromethane adduct (3 mg, 4 μmol). A solution of the crude boronate ester in THF (0.50 mL) and then 1.0 M potassium carbonate (53 μL, 0.052 mmol) were added. The reaction mixture was degassed with $N_2$ for 5 min and then heated at 80° C. for 16 h. The reaction mixture was partitioned between EtOAc and water. The organic layer was removed, and the aqueous layer was extracted with EtOAc (2×). The combined organic layers were washed with brine, filtered through a plug of $Na_2SO_4$, and concentrated.

The resulting residue was dissolved in 1:1 DCM/trifluoroacetic acid (0.80 mL) and heated at 40° C. for 1 h. After cooling to rt, the reaction mixture was diluted with MeOH. Purification via preparative HPLC on a C-18 column (pH 2, 19-35% MeCN/0.1% TFA (aq) over 5 min, 60 mL/min) afforded the title compound as a white solid (2 mg, 10%). $^1$H NMR (400 MHz, $CD_3OD$) δ 8.13-8.05 (m, 2H), 7.93 (s, 1H), 7.83 (s, 1H), 7.79 (d, J=8.6 Hz, 1H), 7.55 (s, 1H), 3.81 (s, 3H), 3.20 (s, 3H), 2.42 (s, 3H). LCMS for $C_{18}H_{19}N_6O_3S$ (M+H)$^+$: calculated m/z=399.1; found 399.1.

Example 492. 7-(2-Methyl-5-(((tetrahydro-2H-pyran-4-yl)methyl)sulfonyl)phenyl)imidazo[2,1-f][1,2,4]triazin-4-amine Trifluoroacetate

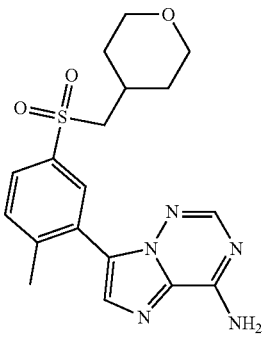 [SMILES: Cc1ccc(S(=O)(=O)CC2CCOCC2)cc1-c1cnc2c(N)ncnn12]

Step 1. Sodium 3-bromo-4-methylbenzenesulfinate

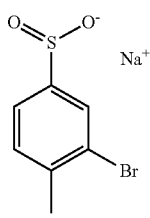

To a mixture of sodium sulfite (0.94 g, 7.4 mmol) and sodium bicarbonate (0.62 g, 7.4 mmol) in water (3.1 mL) at 85° C. was added 3-bromo-4-methylbenzenesulfonyl chloride (0.50 g, 1.9 mmol). Sodium bicarbonate (0.623 g, 7.42 mmol) and then a second portion of 3-bromo-4-methylbenzenesulfonyl chloride (0.52 g, 1.9 mmol) was added to the reaction mixture. [Note: Evolution of $CO_2$ was observed.] The reaction mixture was stirred at 85° C. for 0.5 h before it was concentrated. The resulting solid was triturated with EtOH (4×, 50 mL total). The filtrate was concentrated to afford a white solid (0.99 g, >99%). $^1$H NMR (400 MHz, DMSO-$d_6$) δ 7.57 (d, J=1.7 Hz, 1H), 7.34-7.23 (m, 2H), 2.32 (s, 3H). LCMS for $C_7H_8BrO_2S$ (M+2H)$^+$: calculated m/z=234.9, 236.9; found 235.0, 237.0.

Step 2. 4-(((3-Bromo-4-methylphenyl)sulfonyl)methyl)tetrahydro-2H-pyran

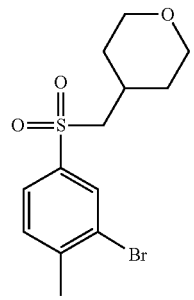 [SMILES: Cc1ccc(S(=O)(=O)CC2CCOCC2)cc1Br]

To a solution of sodium 3-bromo-4-methylbenzenesulfinate (50 mg, 0.19 mmol) in DMF (1 mL) was added 4-(bromomethyl)tetrahydro-2H-pyran (26 μL). The reaction mixture was stirred at 50° C. overnight. An additional portion of 4-(bromomethyl)tetrahydro-2H-pyran (26 μL) was added, and the reaction mixture was stirred at 50° C. for 1 d. The reaction mixture was diluted with water, and the aqueous mixture was extracted with EtOAc (3×). The combined organic layers were washed with brine, dried over $Na_2SO_4$, filtered, and concentrated. Purification via silica gel chromatography (20-80% EtOAc/hexanes) afforded the title compound as a white solid (32 mg, 49%). $^1$H NMR (400 MHz, $CDCl_3$) δ 8.07 (d, J=2.0 Hz, 1H), 7.73 (dd, J=8.0, 1.9 Hz, 1H), 7.43 (d, J=7.9 Hz, 1H), 3.93 (dd, J=12, 2.4 Hz, 2H), 3.41 (td, J=11.7, 1.9 Hz, 2H), 3.01 (d, J=6.4 Hz, 2H), 2.49 (s, 3H), 2.37-2.19 (m, 1H), 1.87-1.75 (m, 2H), 1.53-1.35 (m, 2H). LCMS for $C_{13}H_{18}BrO_3S$ (M+H)$^+$: calculated m/z=333.0, 335.0; found 333.0, 335.0.

Step 3. 4,4,5,5-Tetramethyl-2-(2-methyl-5-(((tetrahydro-2H-pyran-4-yl)methyl)sulfonyl)phenyl)-1,3,2-dioxaborolane

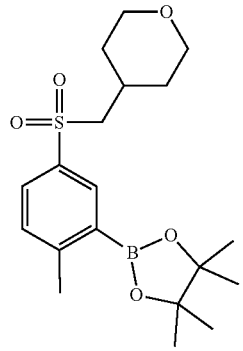 [SMILES: Cc1ccc(S(=O)(=O)CC2CCOCC2)cc1B1OC(C)(C)C(C)(C)O1]

A mixture of 4-(((3-bromo-4-methylphenyl)sulfonyl)methyl)tetrahydro-2H-pyran (32 mg, 0.096 mmol), bis(pinacolato)diboron (32 mg, 0.13 mmol), potassium acetate (32 mg, 0.33 mmol), and dichlorobis(triphenylphosphine)palladium(II) (3 mg, 4 μmol) in THF (0.3 mL) was degassed briefly with $N_2$. The mixture was heated in a microwave at 140° C. for 20 min. The reaction mixture was diluted with EtOAc and filtered through Celite, rinsing with EtOAc. The filtrate was washed with water and then brine, dried over $Na_2SO_4$, filtered, and concentrated to afford the title compound as a crude product, which was utilized without further purification. LCMS for $C_{19}H_{30}BO_5S$ $(M+H)^+$: calculated m/z=381.2; found 381.2.

Step 4. 7-(2-Methyl-5-(((tetrahydro-2H-pyran-4-yl)methyl)sulfonyl)phenyl)imidazo[2,1-f][1,2,4]triazin-4-amine Trifluoroacetate A 1-dram vial was charged with 7-bromoimidazo[2,1-f][1,2,4]triazin-4-amine (17 mg, 0.079 mmol), 4,4,5,5-tetramethyl-2-(2-methyl-5-(((tetrahydro-2H-pyran-4-yl)methyl)sulfonyl)phenyl)-1,3,2-dioxaborolane (crude product from Step 3), and dichloro[1,1'-bis(diphenylphosphino)ferrocene]palladium (II) dichloromethane adduct (13 mg, 0.016 mmol). THF (1.3 mL) and then 1.0 M potassium carbonate (160 μL, 0.16 mmol) were then added. The reaction mixture was degassed with $N_2$ for 5 min and then heated at 80° C. overnight. The reaction mixture was diluted with MeOH and filtered through a plug of $Na_2SO_4$ and Celite. Purification via preparative HPLC on a C-18 column (pH 2, 17-37% MeCN/0.1% TFA (aq) over 5 min, 60 mL/min) afforded the title compound as a white solid (23 mg, 58%). $^1$H NMR (400 MHz, DMSO-$d_6$) δ 8.39 (br s, 1H), 8.29 (br s, 1H), 8.09 (s, 1H), 8.01 (d, J=2.0 Hz, 1H), 7.89 (dd, J=8.1, 2.0 Hz, 1H), 7.83 (s, 1H), 7.68 (d, J=8.1 Hz, 1H), 3.82-3.70 (m, 2H), 3.32 (d, J=6.4 Hz, 2H), 3.27 (td, J=11.7, 2.1 Hz, 2H), 2.36 (s, 3H), 2.04 (ttd, J=10.7, 6.3, 3.1 Hz, 1H), 1.68 (dd, J=12.9, 1.9 Hz, 2H), 1.32 (dtd, J=13.2, 11.4, 4.3 Hz, 2H). LCMS for $C_{18}H_{22}N_5O_3S$ $(M+H)^+$: calculated m/z=388.1; found 388.0.

Example 493. 7-(2-Methyl-5-((3,3,3-trifluoropropyl)sulfonyl)phenyl)imidazo[2,1-f][1,2,4]triazin-4-amine Trifluoroacetate

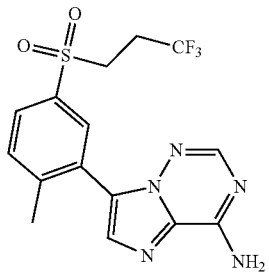 [SMILES: Cc1ccc(S(=O)(=O)CCC(F)(F)F)cc1-c1cnc2c(N)ncnn12]

The title compound was synthesized according to experimental procedures analogous to the synthesis of Example 492, substituting 1,1,1-trifluoro-3-iodopropane for 4-(bromomethyl)tetrahydro-2H-pyran in step 2. LCMS for $C_{15}H_{15}F_3N_5O_2S$ $(M+H)^+$: calculated m/z=386.1; found 386.0.

Example 494. 4-((3-(8-Amino-6-(trifluoromethyl)imidazo[1,2-a]pyrazin-3-yl)-4-methylphenyl)sulfonyl)butan-2-ol

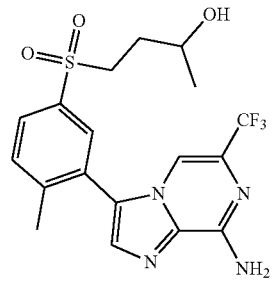 [SMILES: Cc1ccc(S(=O)(=O)CCC(C)O)cc1-c1cnc2c(N)nc(C(F)(F)F)cn12]

Step 1. 4-((3-Bromo-4-methylphenyl)sulfonyl)butan-2-one

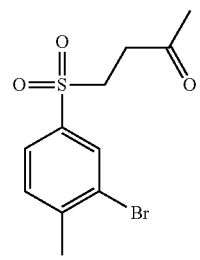 [SMILES: CC(=O)CCS(=O)(=O)c1ccc(C)c(Br)c1]

A mixture of sodium 3-bromo-4-methylbenzenesulfinate (0.20 g, 0.78 mmol) and but-3-en-2-one (70 μL, 0.86 mmol) in AcOH (0.18 mL) and water (1.8 mL) was heated overnight at 110° C. After cooling to rt, the reaction mixture was diluted with water. The aqueous mixture was extracted with EtOAc (3×). The combined organic layers were washed with brine, dried over $Na_2SO_4$, filtered, and concentrated to afford the title compound as a white solid (0.19 g, 80%). ¹H NMR (400 MHz, CDCl₃) δ 8.05 (d, J=1.9 Hz, 1H), 7.73 (dd, J=8.0, 1.9 Hz, 1H), 7.43 (d, J=8.0 Hz, 1H), 3.41-3.32 (m, 2H), 2.97-2.88 (m, 2H), 2.49 (s, 3H), 2.19 (s, 3H). LCMS for C11H14BrO3S (M+H)⁺: calculated m/z=305.0, 307.0; found 304.9, 306.9.

Step 2. 4-((3-Bromo-4-methylphenyl)sulfonyl)butan-2-ol

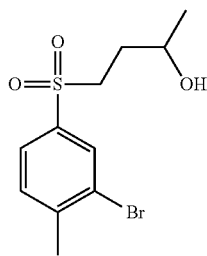 [SMILES: Cc1ccc(S(=O)(=O)CCC(C)O)cc1Br]

Sodium borohydride (2.78 mg, 0.073 mmol) was added to a solution of 4-((3-bromo-4-methylphenyl)sulfonyl)butan-2-one (16 mg, 0.052 mmol) in 1:1 MeOH/THF (1.4 mL) at 0° C. The reaction mixture was stirred for 1.5 h at 0° C. The reaction was quenched with water (0.3 mL). The reaction mixture was warmed to rt, and sat. NaHCO₃ was added. The aqueous mixture was extracted with EtOAc (3×). The combined organic layers were washed with brine, dried over Na₂SO₄, filtered, and concentrated. Purification via silica gel chromatography (10-40% EtOAc in DCM) afforded the title compound as a white residue (15 mg, 93%). LCMS for C11H16BrO3S (M+H)⁺: calculated m/z=307.0, 309.0; found 307.0, 309.0.

Step 3. 4-((4-Methyl-3-(4,4,5,5-tetramethyl-1,3,2-dioxaborolan-2-yl)phenyl)sulfonyl)butan-2-ol

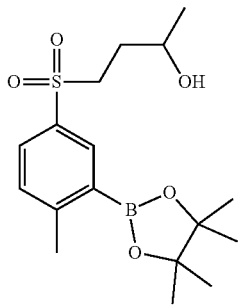 [SMILES: Cc1ccc(S(=O)(=O)CCC(C)O)cc1B1OC(C)(C)C(C)(C)O1]

The title compound was synthesized according to an experimental procedure analogous to the synthesis of Example 492, Step 3, substituting 4-((3-bromo-4-methylphenyl)sulfonyl)butan-2-ol for 4-(((3-bromo-4-methylphenyl)sulfonyl)methyl)tetrahydro-2H-pyran. LCMS for C17H28BO5S (M+H)⁺: calculated m/z=355.2; found 355.2.

Step 4. 4-((3-(8-Amino-6-(trifluoromethyl)imidazo[1,2-a]pyrazin-3-yl)-4-methylphenyl)sulfonyl)butan-2-ol The title compound was synthesized according to an experimental procedure analogous to the synthesis of Example 492, Step 4, substituting 3-bromo-6-(trifluoromethyl)imidazo[1,2-a]pyrazin-8-amine for 7-bromoimidazo[2,1-][1,2,4]triazin-4-amine and substituting 4-((4-methyl-3-(4,4,5,5-tetramethyl-1,3,2-dioxaborolan-2-yl)phenyl)sulfonyl)butan-2-ol for 4,4,5,5-tetramethyl-2-(2-methyl-5-(((tetrahydro-2H-pyran-4-yl)methyl)sulfonyl)phenyl)-1,3,2-dioxaborolane. ¹H NMR (600 MHz, DMSO-d₆) δ 7.94 (dd, J=8.1, 2.0 Hz, 1H), 7.91 (d, J=1.9 Hz, 1H), 7.83 (s, 1H), 7.74 (d, J=8.1 Hz, 1H), 7.68 (br s, 3H), 4.63 (d, J=4.7 Hz, 1H), 3.62 (s, 1H), 3.41-3.28 (m, 2H), 2.28 (s, 3H), 1.70-1.50 (m, 2H), 1.02 (d, J=6.2 Hz, 3H). LCMS for C18H20F3N4O3S (M+H)⁺: calculated m/z=429.1; found 429.2.

Example 495. 4-((3-(8-Amino-6-(trifluoromethyl)imidazo[1,2-a]pyrazin-3-yl)-4-methylphenyl)sulfonyl)-2-methylbutan-2-ol

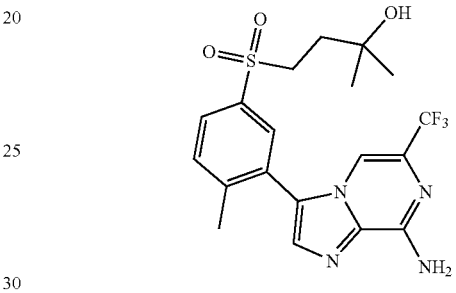

Step 1. 4-((3-Bromo-4-methylphenyl)sulfonyl)-2-methylbutan-2-ol

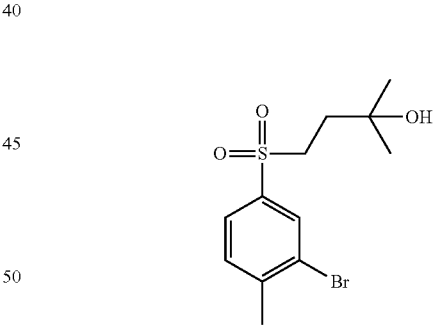

Methylmagnesium bromide (40 μL, 0.1 mmol, 3 M in Et₂O) was added dropwise to a solution of 4-((3-bromo-4-methylphenyl)sulfonyl)butan-2-one (12 mg, 0.039 mmol) in THF (1.0 mL) at −78° C. The reaction mixture was stirred overnight during which it came to rt. The reaction mixture was cooled to 0° C., and the reaction was quenched with NH₄Cl and water. The mixture was extracted with EtOAc (3×). The organic layers were filtered through a plug of Na₂SO₄, combined, and concentrated to afford the title compound (8.2 mg, 65%). ¹H NMR (400 MHz, CDCl₃) δ 8.07 (d, J=1.9 Hz, 1H), 7.73 (dd, J=8.0, 2.0 Hz, 1H), 7.43 (d, J=7.9 Hz, 1H), 3.28-3.19 (m, 2H), 2.49 (s, 3H), 1.91-1.83 (m, 2H), 1.23 (s, 6H). LCMS for C12H16BrO2S (M-OH)⁺: calculated m/z=303.0, 305.0; found 303.0, 305.0.

Step 2. 2-Methyl-4-((4-methyl-3-(4,4,5,5-tetramethyl-1,3,2-dioxaborolan-2-yl)phenyl)sulfonyl)butan-2-ol

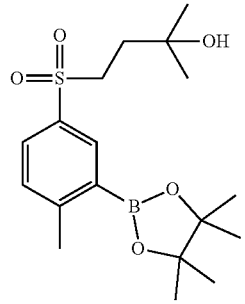 [SMILES: Cc1ccc(S(=O)(=O)CCC(C)(C)O)cc1B1OC(C)(C)C(C)(C)O1]

The title compound was synthesized according to an experimental procedure analogous to the synthesis of Example 492, Step 3 substituting 4-((3-bromo-4-methylphenyl)sulfonyl)-2-methylbutan-2-ol for 4-(((3-bromo-4-methylphenyl)sulfonyl)methyl)tetrahydro-2H-pyran. LCMS for $C_{18}H_{28}BO_4S$ (M-OH)$^+$: calculated m/z=351.2; found 351.1.

Step 4. 4-((3-(8-Amino-6-(trifluoromethyl)imidazo[1,2-a]pyrazin-3-yl)-4-methylphenyl)sulfonyl)-2-methylbutan-2-ol The title compound was synthesized according to an experimental procedure analogous to the synthesis of Example 492, Step 4, substituting 3-bromo-6-(trifluoromethyl)imidazo[1,2-a]pyrazin-8-amine for 7-bromoimidazo[2,1-f][1,2,4]triazin-4-amine and substituting 2-methyl-4-((4-methyl-3-(4,4,5,5-tetramethyl-1,3,2-dioxaborolan-2-yl)phenyl)sulfonyl)butan-2-ol for 4,4,5,5-tetramethyl-2-(2-methyl-5-(((tetrahydro-2H-pyran-4-yl)methyl)sulfonyl)phenyl)-1,3,2-dioxaborolane. $^1$H NMR (400 MHz, DMSO-d$_6$) δ 7.98-7.89 (m, 2H), 7.83 (s, 1H), 7.74 (d, J=8.0 Hz, 1H), 7.68 (s, 3H), 4.42 (s, 1H), 3.40-3.20 (m, 2H), 2.28 (s, 3H), 1.73-1.58 (m, 2H), 1.05 (s, 6H). LCMS for $C_{19}H_{22}F_3N_4O_3S$ (M+H)$^+$: calculated m/z=443.1; found 443.1.

Example 496. 1-((3-(8-Amino-6-(trifluoromethyl)imidazo[1,2-a]pyrazin-3-yl)-4-methylphenyl)sulfonyl)propan-2-ol Trifluoroacetate

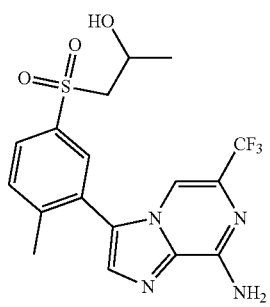 [SMILES: Cc1ccc(S(=O)(=O)CC(C)O)cc1-c1cnc2c(N)nc(C(F)(F)F)cn12]

Step 1. 1-((3-Bromo-4-methylphenyl)sulfonyl)propan-2-one

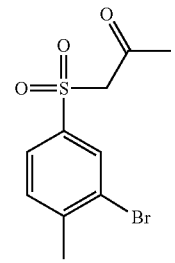

A mixture of sodium 3-bromo-4-methylbenzenesulfinate (20 mg, 0.078 mmol) and chloroacetone (6.5 µL, 0.078 mmol) in DMF (230 µL) was heated at 100° C. for 5 min in a microwave. The reaction mixture was diluted with water. The aqueous mixture was extracted with EtOAc (3×). The organic layers were filtered through a plug of Na$_2$SO$_4$, combined, and concentrated to afford the title compound (15 mg, 64%). $^1$H NMR (400 MHz, CDCl$_3$) δ 8.04 (s, 1H), 7.71 (d, J=8.0 Hz, 1H), 7.43 (d, J=7.9 Hz, 1H), 4.15 (s, 2H), 2.49 (s, 3H), 2.41 (s, 3H). LCMS for $C_{10}H_{15}BrNO_3S$ (M+NH$_4$)$^+$: calculated m/z=308.0, 310.0; found 308.0, 310.0.

Step 2. 1-((3-Bromo-4-methylphenyl)sulfonyl)propan-2-ol

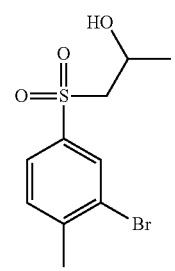

The title compound was synthesized according to an experimental procedure analogous to the synthesis of Example 494, Step 2, substituting 1-((3-bromo-4-methylphenyl)sulfonyl)propan-2-one for 4-((3-bromo-4-methylphenyl)sulfonyl)butan-2-one. $^1$H NMR (400 MHz, CDCl$_3$) δ 8.08 (s, 1H), 7.75 (d, J=7.7 Hz, 1H), 7.44 (d, J=8.0 Hz, 1H), 4.33 (s, 1H), 3.36-3.05 (m, 3H), 2.50 (s, 3H), 1.26 (d, J=6.3 Hz, 3H). LCMS for $C_{10}H_{14}BrO_3S$ (M+H)$^+$: calculated m/z=293.0, 295.0; found 293.0, 294.9.

Step 3. 1-((4-Methyl-3-(4,4,5,5-tetramethyl-1,3,2-dioxaborolan-2-yl)phenyl)sulfonyl)propan-2-ol

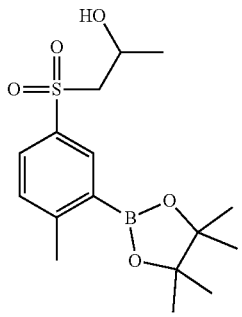 [SMILES: Cc1ccc(S(=O)(=O)CC(C)O)cc1B1OC(C)(C)C(C)(C)O1]

The title compound was synthesized according to an experimental procedure analogous to the synthesis of Example 492, Step 3 substituting 1-((3-bromo-4-methylphenyl)sulfonyl)propan-2-ol for 4-(((3-bromo-4-methylphenyl)sulfonyl)methyl)tetrahydro-2H-pyran. LCMS for $C_{16}H_{26}BO_5S$ (M+H)$^+$: calculated m/z=341.2; found 341.1.

Step 4. 1-((3-(8-Amino-6-(trifluoromethyl)imidazo[1,2-a]pyrazin-3-yl)-4-methylphenyl)sulfonyl)propan-2-ol Trifluoroacetate The title compound was synthesized according to an experimental procedure analogous to the synthesis of Example 492, Step 4, substituting 3-bromo-6-(trifluoromethyl)imidazo[1,2-a]pyrazin-8-amine for 7-bromoimidazo[2,1-f][1,2,4]triazin-4-amine and substituting 1-((4-methyl-3-(4,4,5,5-tetramethyl-1,3,2-dioxaborolan-2-yl)phenyl)sulfonyl)propan-2-ol for 4,4,5,5-tetramethyl-2-(2-methyl-5-(((tetrahydro-2H-pyran-4-yl)methyl)sulfonyl)phenyl)-1,3,2-dioxaborolane. LCMS for $C_{17}H_{18}F_3N_4O_3S$ (M+H)$^+$: calculated m/z=415.1; found 415.2.

Example 497. 1-((3-(8-Amino-6-(trifluoromethyl)imidazo[1,2-a]pyrazin-3-yl)-4-methylphenyl)sulfonyl)propan-2-ol

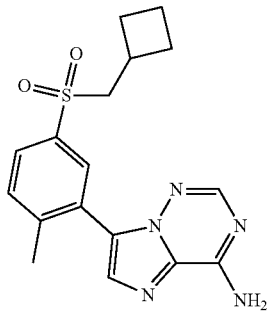 [SMILES: Cc1ccc(S(=O)(=O)CC2CCC2)cc1-c1cnc2c(N)ncnn12]

Step 1. Sodium 3-(4-aminoimidazo[2,1-f][1,2,4]triazin-7-yl)-4-methylbenzenesulfinate

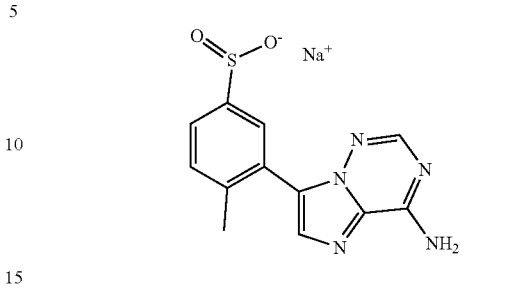

The title compound was synthesized according to an experimental procedure analogous to the synthesis of Example 492, Step 1, substituting 3-(4-aminoimidazo[2,1-f][1,2,4]triazin-7-yl)-4-methylbenzenesulfonyl chloride for 3-bromo-4-methylbenzenesulfonyl chloride. LCMS for $C_{12}H_{12}N_5O_2S$ (M+2H)$^+$: calculated m/z=290.1; found 290.0.

Step 2. 1-((3-(8-Amino-6-(trifluoromethyl)imidazo[1,2-a]pyrazin-3-yl)-4-methylphenyl)sulfonyl)propan-2-ol To a solution of sodium 3-(4-aminoimidazo[2,1-f][1,2,4]triazin-7-yl)-4-methylbenzenesulfinate (15 mg, 0.048 mmol) in DMF (240 µL) was added (bromomethyl)cyclobutane (5.4 µL, 0.048 mmol). The reaction mixture was stirred at 50° C. overnight. The reaction mixture was diluted with MeOH and filtered. Purification via preparative HPLC on a C-18 column (pH 10, 33-55% MeCN/0.1% NH$_4$OH (aq) over 5 min, 60 mL/min) afforded the title compound as a white solid (7.5 mg, 44%). LCMS for $C_{17}H_{20}N_5O_2S$ (M+H)$^+$: calculated m/z=358.1; found 358.2.

Example 498. Cis-4-(((3-(4-Aminoimidazo[2,1-f][1,2,4]triazin-7-yl)-4-methylphenyl)sulfonyl)methyl)cyclohexan-1-ol

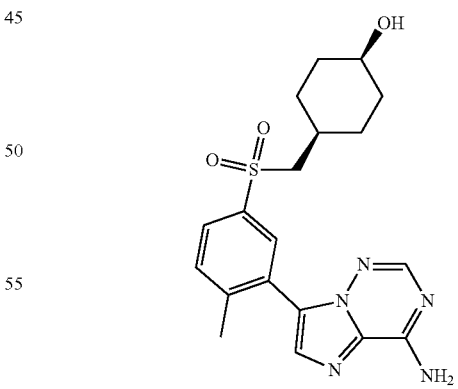

To a solution of sodium 3-(4-aminoimidazo[2,1-f][1,2,4]triazin-7-yl)-4-methylbenzenesulfinate (17 mg, 0.055 mmol) in DMF (0.27 mL) was added cis-(4-(bromomethyl)cyclohexyloxy)(tert-butyl)dimethylsilane (17 mg, 0.055 mmol) (prepared as described by Liu, J. et al. *ACS Med. Chem. Lett.* 2012, 3, 129). The reaction mixture was stirred at 50° C. overnight. After cooling to rt, an additional portion of cis-(4-(bromomethyl)cyclohexyloxy)(tert-butyl)dimethylsilane (17 mg, 0.055 mmol) in DMF (0.10 mL) was added, and the reaction mixture was stirred at 50° C. for 1 d. The reaction mixture was diluted with water. The aqueous mixture was extracted with EtOAc (3×). The combined organic layers were washed with brine, dried over Na$_2$SO$_4$, filtered, and concentrated to afford the unpurified TBS-protected intermediate (31 mg). LCMS for C$_{25}$H$_{38}$N$_5$O$_3$SSi (M+H)$^+$: calculated m/z=516.2; found 516.2.

This crude product was dissolved in MeOH (2.5 mL), and conc. HCl (0.23 mL, 2.7 mmol, 12 M) was added. The reaction mixture was stirred at rt for 3 h and then concentrated. Purification via preparative HPLC on a C-18 column (pH 2, 21-33% MeCN/0.1% TFA (aq) over 5 min, 60 mL/min) and then repurification via preparative HPLC on a C-18 column (pH 10, 20-40% MeCN/0.1% NH$_4$OH (aq) over 5 min, 60 mL/min) afforded the title compound (1.3 mg, 5.9%). LCMS for C$_{19}$H$_{24}$N$_5$O$_3$S (M+H)$^+$: calculated m/z=402.2; found 402.1.

Examples 499 to 500 were synthesized according to procedures analogous to the synthesis of Example 492, and the data are listed in Table 21.

TABLE 21

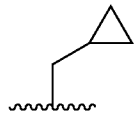 [SMILES: *CC1CC1]

| Ex. No. | Name | R$^{10}$ | LCMS [M+H]$^+$ |
|---|---|---|---|
| 499 | 7-(5-((Cyclopropylmethyl)-sulfonyl)-2-ethylphenyl)-imidazo[2,1-f][1,2,4]triazin-4-amine | 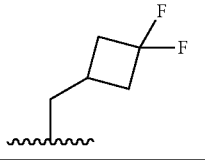 | 344.1 |
| 500 | 7-(5-(((3,3-Difluorocyclobutyl)-methyl)sulfonyl)-2-methylphenyl)imidazo[2,1-f][1,2,4]triazin-4-amine | | 394.1 |

Example 501. Cis-3-((3-(4-Aminoimidazo[2,1-f][1,2,4]triazin-7-yl)-4-methylphenyl)sulfonyl)cyclohexan-1-ol

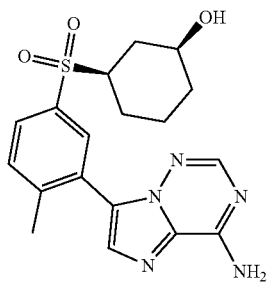 [SMILES: Cc1ccc(S(=O)(=O)[C@@H]2CCC[C@H](O)C2)cc1-c1cnc2c(N)ncnn12]

A mixture of sodium 3-(4-aminoimidazo[2,1-f][1,2,4]triazin-7-yl)-4-methylbenzenesulfinate (50 mg, 0.16 mmol) and cyclohex-2-en-1-one (17 µL, 0.18 mmol) in AcOH (37 µL) and water (370 µL) was heated 1 d at 110° C. After cooling to rt, the reaction mixture was diluted with water. The aqueous mixture was extracted with EtOAc (3×). The combined organic layers were washed with brine, dried over Na$_2$SO$_4$, filtered and concentrated to afford the crude ketone intermediate. LCMS for C$_{18}$H$_{20}$N$_5$O$_3$S (M+H)$^+$: calculated m/z=386.1; found 386.1.

The crude ketone intermediate was dissolved in 1:1 iPrOH/THF (4.0 mL), and the solution was cooled to 0° C. Sodium borohydride (8.5 mg, 0.23 mmol) was then added, and the reaction mixture was stirred for 1 h at 0° C. The reaction was quenched with H$_2$O (1 mL). Purification via preparative HPLC on a C-18 column (pH 10, 18-38% MeCN/0.1% NH$_4$OH (aq) over 5 min, 60 mL/min) afforded the title compound as a white solid (17 mg, 27%). $^1$H NMR (500 MHz, DMSO-d$_6$) δ 8.06 (s, 1H), 8.02 (s, 2H), 7.94 (d, J=2.0 Hz, 1H), 7.81 (dd, J=8.0, 2.0 Hz, 1H), 7.79 (s, 1H), 7.67 (d, J=8.2 Hz, 1H), 4.58 (d, J=4.8 Hz, 1H), 3.47-3.35 (m, 1H), 3.29-3.21 (m, 1H), 2.38 (s, 3H), 2.11 (d, J=12.2 Hz, 1H), 1.88 (d, J=11.5 Hz, 1H), 1.78 (d, J=12.7 Hz, 2H), 1.34-1.11 (m, 3H), 1.10-0.94 (m, 1H). LCMS for C$_{18}$H$_{22}$N$_5$O$_3$S (M+H)$^+$: calculated m/z=388.1; found 388.1.

Example 502. 3-((3-(8-Amino-6-(2-methoxypyridin-3-yl)imidazo[1,2-a]pyrazin-3-yl)-4-methylphenyl)sulfonyl)-3-methylbutan-2-ol Trifluoroacetate

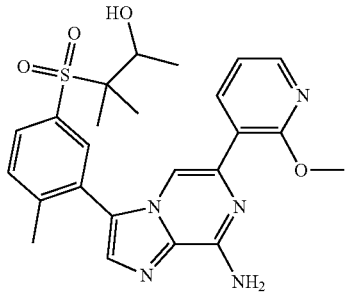 [SMILES: COc1ncccc1-c1cn2c(-c3cc(S(=O)(=O)C(C)(C)C(C)O)ccc3C)cnc2c(N)n1]

Step 1. 3-((3-Bromo-4-methylphenyl)sulfonyl)-3-methylbutan-2-one

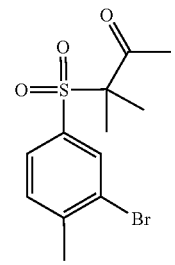 [SMILES: CC(=O)C(C)(C)S(=O)(=O)c1ccc(C)c(Br)c1]

To a mixture of 1-((3-bromo-4-methylphenyl)sulfonyl)propan-2-one (70 mg, 0.24 mmol) (from Example 496, Step 1) and potassium carbonate (73 mg, 0.53 mmol) in DMF (2.4 mL) was added iodomethane (37 µL, 0.60 mmol). The reaction mixture was stirred at rt for 2 h. The reaction mixture was diluted with water, and the aqueous mixture was extracted with EtOAc (3×). The combined organic layers were washed with brine, dried over Na$_2$SO$_4$, filtered, and concentrated. Purification via silica gel chromatography (1-50% EtOAc/hexanes) afforded the title compound as a white solid (42 mg, 55%). $^1$H NMR (400 MHz, CDCl$_3$) δ 7.92 (d, J=1.9 Hz, 1H), 7.57 (dd, J=8.0, 1.9 Hz, 1H), 7.40 (d, J=8.0 Hz, 1H), 2.49 (s, 6H), 1.55 (s, 6H). LCMS for C$_{12}$H$_{15}$BrNaO$_3$S (M+Na)$^+$: calculated m/z=341.0, 343.0; found 340.9, 342.9.

Step 2. 3-((3-Bromo-4-methylphenyl)sulfonyl)-3-methylbutan-2-ol

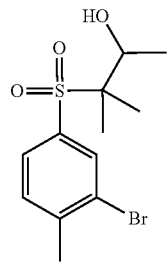 [SMILES: Cc1ccc(S(=O)(=O)C(C)(C)C(C)O)cc1Br]

The title compound was synthesized according to an experimental procedure analogous to the synthesis of Example 494, Step 2, substituting 3-((3-bromo-4-methylphenyl)sulfonyl)-3-methylbutan-2-one for 4-((3-bromo-4-methylphenyl)sulfonyl)butan-2-one. LCMS for C$_{12}$H$_{18}$BrO$_3$S (M+H)$^+$: calculated m/z=321.0, 323.0; found 321.0, 323.0.

Step 3. 3-Methyl-3-((4-methyl-3-(4,4,5,5-tetramethyl-1,3,2-dioxaborolan-2-yl)phenyl)sulfonyl)butan-2-ol

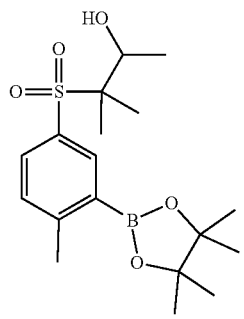 [SMILES: Cc1ccc(S(=O)(=O)C(C)(C)C(C)O)cc1B1OC(C)(C)C(C)(C)O1]

The title compound was synthesized according to an experimental procedure analogous to the synthesis of Example 492, Step 3 substituting 3-((3-bromo-4-methylphenyl)sulfonyl)-3-methylbutan-2-ol for 4-(((3-bromo-4-methylphenyl)sulfonyl)methyl)tetrahydro-2H-pyran. LCMS for C$_{18}$H$_{30}$BO$_5$S (M+H)$^+$: calculated m/z=369.2; found 369.2.

Step 4. 3-((3-(8-Amino-6-(2-methoxypyridin-3-yl)imidazo[1,2-a]pyrazin-3-yl)-4-methylphenyl)sulfonyl)-3-methylbutan-2-ol Trifluoroacetate The title compound was synthesized according to an experimental procedure analogous to the synthesis of Example 40, Step 2, substituting 3-methyl-3-((4-methyl-3-(4,4,5,5-tetramethyl-1,3,2-dioxaborolan-2-yl)phenyl)sulfonyl)butan-2-ol for 4,4,5,5-tetramethyl-2-[2-methyl-5-(methylsulfonyl)phenyl]-1,3,2-dioxaborolane and substituting (2-methoxypyridin-3-yl)boronic acid for (2-fluorophenyl)boronic acid. $^1$H NMR (400 MHz, DMSO-d$_6$) δ 8.24 (s, 1H), 8.21 (dd, J=4.9, 1.9 Hz, 1H), 7.96-7.83 (m, 4H), 7.71 (d, J=8.1 Hz, 1H), 7.14 (dd, J=7.5, 4.9 Hz, 1H), 4.04-3.93 (m, 1H), 3.88 (s, 3H), 2.36 (s, 3H), 1.19 (d, J=4.1 Hz, 6H), 1.10 (d, J=6.3 Hz, 3H). LCMS for C$_{24}$H$_{28}$N$_5$O$_4$S (M+H)$^+$: calculated m/z=482.2; found 482.1.

Example 503. 1-(((3-(8-Amino-6-(3-fluoropyridin-4-yl)imidazo[1,2-a]pyrazin-3-yl)-4-methylphenyl)sulfonyl)methyl)cyclobutan-1-ol

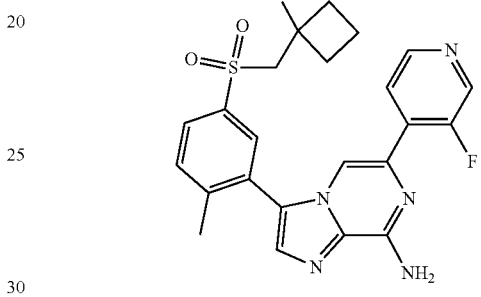

Step 1. 1-(((3-Bromo-4-methylphenyl)sulfonyl)methyl)cyclobutan-1-ol

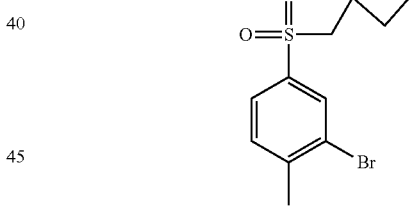

To a solution of 2-bromo-1-methyl-4-(methylsulfonyl)benzene (50 mg, 0.20 mmol) in THF (1.0 mL) at −78° C. was added dropwise n-butyllithium (80 μL, 0.20 mmol, 2.5 M in hexanes), and the reaction mixture was stirred at −78° C. for 30 min. The reaction mixture was then added dropwise to a solution of cyclobutanone (16 μL, 0.22 mmol) in THF (2.0 mL) at −78° C. After 10 min, the −78° C. bath was removed, and the reaction mixture was stirred for 4 h, during which it came to rt. The reaction mixture was then cooled to 0° C., and the reaction was quenched with sat. NH$_4$C$_1$. The mixture was partitioned between water and DCM. The organic layer was removed, and the aqueous layer was extracted with DCM (2×). The combined organic layers were dried over Na$_2$SO$_4$, filtered, and concentrated. Purification via preparative HPLC on a C-18 column (pH 2, 26-51% MeCN/0.1% TFA (aq) over 5 min, 60 mL/min) afforded the title compound as a white solid (11 mg, 14%). $^1$H NMR (400 MHz, CDCl$_3$) δ 8.08 (d, J=1.9 Hz, 1H), 7.76 (dd, J=7.9, 1.9 Hz, 1H), 7.43 (d, J=8.0 Hz, 1H), 3.46 (s, 2H), 2.50 (s, 4H), 2.37-2.07 (m, 3H), 2.04-1.78 (m, 1H), 1.78-1.49 (m, 1H). LCMS for $C_{12}H_{19}BrNO_3S$ (M+NH$_4$)$^+$: calculated m/z=336.0, 338.0; found 336.0, 338.0.

Step 2. 1-(((4-Methyl-3-(4,4,5,5-tetramethyl-1,3,2-dioxaborolan-2-yl)phenyl)sulfonyl)methyl)cyclobutan-1-ol

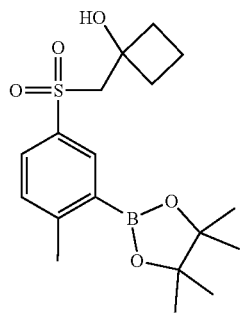 [SMILES: Cc1ccc(S(=O)(=O)CC2(O)CCC2)cc1B1OC(C)(C)C(C)(C)O1]

The title compound was synthesized according to an experimental procedure analogous to the synthesis of Example 492, Step 3, substituting 1-(((3-bromo-4-methylphenyl)sulfonyl)methyl)cyclobutan-1-ol for 4-(((3-bromo-4-methylphenyl)sulfonyl)methyl)tetrahydro-2H-pyran. LCMS for $C_{17}H_{26}BO_4S$ (M-OH)$^+$: calculated m/z=349.2; found 349.1.

Step 3. 1-(((3-(8-Amino-6-(3-fluoropyridin-4-yl)imidazo[1,2-a]pyrazin-3-yl)-4-methylphenyl)sulfonyl)methyl)cyclobutan-1-ol The title compound was synthesized according to an experimental procedure analogous to the synthesis of Example 40, Step 2, substituting 1-(((4-methyl-3-(4,4,5,5-tetramethyl-1,3,2-dioxaborolan-2-yl)phenyl)sulfonyl)methyl)cyclobutan-1-ol for 4,4,5,5-tetramethyl-2-[2-methyl-5-(methylsulfonyl)phenyl]-1,3,2-dioxaborolane and substituting 3-fluoro-4-(4,4,5,5-tetramethyl-1,3,2-dioxaborolan-2-yl)pyridine for (2-fluorophenyl)boronic acid. LCMS for $C_{23}H_{23}FN_5O_3S$ (M+H)$^+$: calculated m/z=468.1; found 468.1.

Example 504. 3-(8-Amino-6-isopropylimidazo[1,2-a]pyrazin-3-yl)-N-(trans-4-hydroxycyclohexyl)-4-methylbenzenesulfonamide

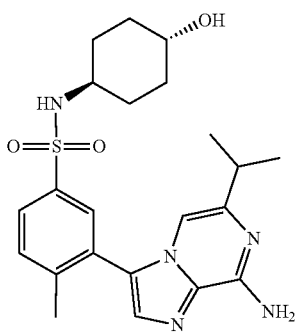 [SMILES: Cc1ccc(S(=O)(=O)N[C@H]2CC[C@H](O)CC2)cc1-c1cnc2c(N)nc(C(C)C)cn12]

The title compound was synthesized according to experimental procedures analogous to the synthesis of Example 38, substituting potassium isopropenyltrifluoroborate for potassium vinyltrifluoroborate in Step 1. LCMS for $C_{22}H_{30}N_5O_3S$ (M+H)$^+$: calculated m/z=444.2; found 444.2.

Example 505. 3-(8-Amino-6-methylimidazo[1,2-a]pyrazin-3-yl)-N-((1r,4r)-4-hydroxy-4-methylcyclohexyl)-4-methylbenzenesulfonamide

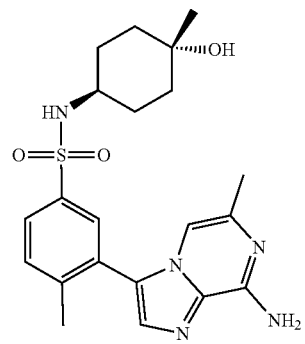 [SMILES: Cc1cn2c(-c3cc(S(=O)(=O)N[C@H]4CC[C@](C)(O)CC4)ccc3C)cnc2c(N)n1]

Step 1. N-((1r,4r)-4-Hydroxy-4-methylcyclohexyl)-4-methyl-3-(4,4,5,5-tetramethyl-1,3,2-dioxaborolan-2-yl)benzenesulfonamide

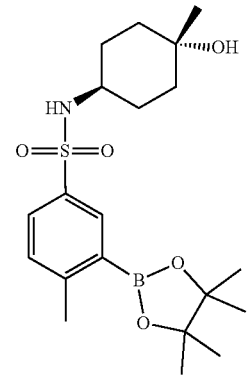 [SMILES: Cc1ccc(S(=O)(=O)N[C@H]2CC[C@](C)(O)CC2)cc1B1OC(C)(C)C(C)(C)O1]

The title compound was synthesized according to experimental procedures analogous to the synthesis of Example 1, Steps 1 and 2, substituting trans-4-amino-1-methylcyclohexanol for trans-4-aminocyclohexanol in Step 1. LCMS for $C_{20}H_{33}BNO_5S$ (M+H)$^+$: calculated m/z=410.2; found 410.2.

Step 2. 3-Iodo-6-methylimidazo[1,2-a]pyrazin-8-amine

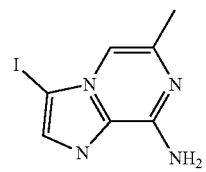

The title compound was synthesized according to experimental procedures analogous to the synthesis of Example 16, Steps 1 and 2, substituting 8-bromo-6-methylimidazo[1,2-a]pyrazine (Frontier, B12886) for 6,8-dibromoimidazo[1,2-a]pyrazine in Step 1. $^1$H NMR (400 MHz, DMSO-d$_6$) δ 7.58 (s, 1H), 7.38 (s, 1H), 6.95 (s, 2H), 2.23 (s, 3H). LCMS for C$_7$H$_8$IN$_4$ (M+H)$^+$: calculated m/z=275.0; found 275.0.

Step 3. 3-(8-Amino-6-methylimidazo[1,2-a]pyrazin-3-yl)-N-((1r,4r)-4-hydroxy-4-methylcyclohexyl)-4-methylbenzenesulfonamide The title compound was synthesized according to an experimental procedure analogous to the synthesis of Example 1, Step 3, substituting N-((1r,4r)-4-hydroxy-4-methylcyclohexyl)-4-methyl-3-(4,4,5,5-tetramethyl-1,3,2-dioxaborolan-2-yl)benzenesulfonamide for N-(trans-4-hydroxycyclohexyl)-4-methyl-3-(4,4,5,5-tetramethyl-1,3,2-dioxaborolan-2-yl)benzenesulfonamide and substituting 3-iodo-6-methylimidazo[1,2-a]pyrazin-8-amine for 3-bromoimidazo[1,2-a]pyridin-8-amine. $^1$H NMR (600 MHz, DMSO-d$_6$) δ 7.83 (dd, J=8.1, 2.0 Hz, 1H), 7.75 (d, J=2.0 Hz, 1H), 7.64 (d, J=8.2 Hz, 1H), 7.61 (s, 1H), 7.60 (s, 1H), 7.00 (d, J=0.9 Hz, 1H), 6.98 (s, 2H), 4.12 (s, 1H), 3.09 (s, 1H), 2.23 (s, 3H), 2.15 (d, J=0.8 Hz, 3H), 1.66-1.55 (m, 2H), 1.52-1.43 (m, 2H), 1.32-1.17 (m, 4H), 1.05 (s, 3H). LCMS for C$_{22}$H$_{28}$N$_5$O$_3$S (M+H)$^+$: calculated m/z=430.2; found 430.2.

Example 506. (S)-1-((3-(8-Amino-6-(2-fluoro-4-(hydroxymethyl)phenyl)imidazo[1,2-a]pyrazin-3-yl)-4-methylphenyl)sulfonyl)pyrrolidin-3-ol

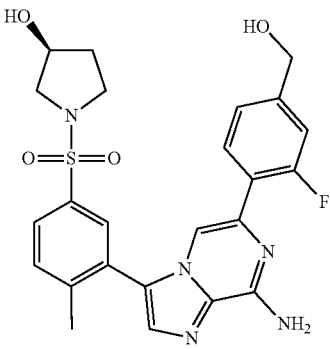 [SMILES: Cc1ccc(S(=O)(=O)N2CC[C@H](O)C2)cc1-c1cnc2c(N)nc(-c3ccc(CO)cc3F)cn12]

Step 1. (S)-1-((4-Methyl-3-(4,4,5,5-tetramethyl-1,3,2-dioxaborolan-2-yl)phenyl)sulfonyl)pyrrolidin-3-ol

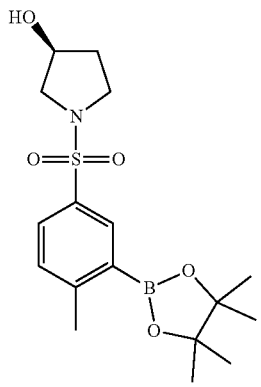 [SMILES: Cc1ccc(S(=O)(=O)N2CC[C@H](O)C2)cc1B1OC(C)(C)C(C)(C)O1]

The title compound was synthesized according to experimental procedures analogous to the synthesis of Example 1, Steps 1 and 2, substituting (S)-pyrrolidin-3-ol for trans-4-aminocyclohexanol in Step 1. LCMS for C$_{17}$H$_{27}$BNO$_5$S (M+H)$^+$: calculated m/z=368.2; found 368.1.

Step 2. (S)-1-((3-(8-Amino-6-bromoimidazo[1,2-a]pyrazin-3-yl)-4-methylphenyl)sulfonyl)pyrrolidin-3-ol

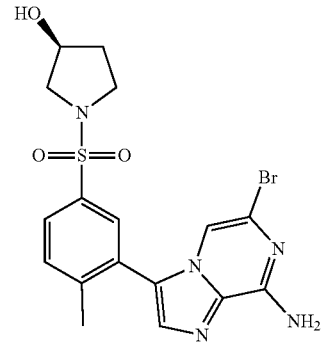 [SMILES: Cc1ccc(S(=O)(=O)N2CC[C@H](O)C2)cc1-c1cnc2c(N)nc(Br)cn12]

The title compound was synthesized according to an experimental procedure analogous to the synthesis of Example 16, Step 3, substituting (S)-1-((4-methyl-3-(4,4,5,5-tetramethyl-1,3,2-dioxaborolan-2-yl)phenyl)sulfonyl)pyrrolidin-3-ol for N-(trans-4-hydroxycyclohexyl)-4-methyl-3-(4,4,5,5-tetramethyl-1,3,2-dioxaborolan-2-yl)benzenesulfonamide. LCMS for C$_{17}$H$_{19}$BrN$_5$O$_3$S (M+H)$^+$: calculated m/z=452.0, 454.0; found 452.1, 454.1.

Step 3. (S)-1-((3-(8-Amino-6-(2-fluoro-4-(hydroxymethyl)phenyl)imidazo[1,2-a]pyrazin-3-yl)-4-methylphenyl)sulfonyl)pyrrolidin-3-ol The title compound was synthesized according to an experimental procedure analogous to the synthesis of Example 17, substituting (S)-1-((3-(8-amino-6-bromoimidazo[1,2-a]pyrazin-3-yl)-4-methylphenyl)sulfonyl)pyrrolidin-3-ol for 3-(8-amino-6-bromoimidazo[1,2-a]pyrazin-3-yl)-N-(trans-4-hydroxycyclohexyl)-4-methylbenzenesulfonamide and substituting (2-fluoro-4-(hydroxymethyl)phenyl)boronic acid for (2-methylphenyl)boronic acid. LCMS for C$_{24}$H$_{25}$FN$_5$O$_4$S (M+H)$^+$: calculated m/z=498.2; found 498.2.

Example 507. 3-(4-Aminoimidazo[2,1-f][1,2,4]triazin-7-yl)-N-((1s,4s)-4-hydroxy-4-methylcyclohexyl-1-d)-4-methylbenzenesulfonamide

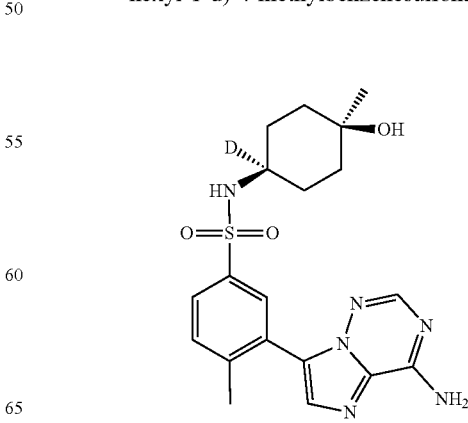

Step 1. (R)-2-Methyl-N-(8-deutero-1,4-dioxaspiro[4.5]decan-8-yl)propane-2-sulfinamide

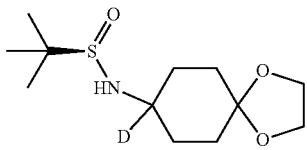 [SMILES: [2H]C1(N[S@](=O)C(C)(C)C)CCC2(CC1)OCCO2]

A mixture of 1,4-dioxaspiro[4.5]decan-8-one (2.5 g, 16 mmol), (R)-(+)-2-methyl-2-propanesulfinamide (1.9 g, 16 mmol), and titanium(IV) ethoxide (6.7 ml, 32 mmol) in THF (32 mL) was heated at reflux for 2 h. After cooling to rt, the reaction mixture was added dropwise via cannula to a suspension of sodium borodeuteride (2.0 g, 48 mmol) (Aldrich, 205591) in THF (12 mL) at −44° C. The original flask, which had contained the reaction mixture from the imine condensation, was rinsed with THF (2×6 mL), and this mixture was added dropwise to the flask containing the sodium borodeuteride reaction mixture. The reaction mixture was then allowed to warm to rt, stirring for 3 h. The reaction mixture was cooled to 0° C., and the reaction quenched by dropwise addition of methanol (13 mL, 320 mmol). After stirring for 10 min, the mixture was warmed to rt while stirring 30 min. The mixture was then diluted with EtOAc (80 mL) and poured into brine (5 mL). The resulting slurry was stirred rapidly for 20 min. The slurry was filtered through Celite, rinsing the filter cake generously with EtOAc. The filtrate was then concentrated. Purification via silica gel chromatography (3-7% MeOH in DCM) afforded the title compound as a white solid (3.8 g, 90%). $^1$H NMR (400 MHz, CDCl$_3$) δ 3.94 (s, 4H), 3.00 (s, 1H), 2.05-1.90 (m, 2H), 1.83-1.70 (m, 2H), 1.68-1.51 (m, 4H), 1.20 (s, 9H). LCMS for C$_{12}$H$_{23}$DNO$_3$S (M+H)$^+$: calculated m/z=263.2; found 263.1.

Step 2. (R)-2-Methyl-N-(1-deutero-4-oxocyclohexyl)propane-2-sulfinamide

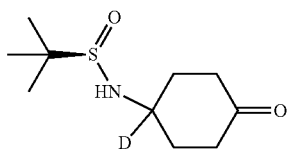

A solution of p-toluenesulfonic acid monohydrate (0.13 g, 0.71 mmol) in water (4.9 mL) was added to a solution of ((R)-2-methyl-N-(8-deutero-1,4-dioxaspiro[4.5]decan-8-yl)propane-2-sulfinamide (3.7 g, 14 mmol) in acetone (9.8 mL). The reaction mixture was then heated at 100° C. for 15 min in a microwave. The reaction mixture was diluted with EtOAc and washed with sat. NaHCO$_3$. The organic layer was removed, and the aqueous layer was extracted with EtOAc (2×). The combined organic layers were dried over Na$_2$SO$_4$, filtered, and concentrated. Purification via silica gel chromatography (70-100% EtOAc in DCM, then 0-5% MeOH in EtOAc) afforded the title compound as an off-white solid (2.3 g, 75%). $^1$H NMR (400 MHz, CDCl$_3$) δ 3.12 (s, 1H), 2.55-2.30 (m, 4H), 2.30-2.14 (m, 2H), 1.98-1.75 (m, 2H), 1.24 (s, 9H). LCMS for C$_{10}$H$_{19}$DNO$_2$S (M+H)$^+$: calculated m/z=219.1; found 219.1.

Step 3. (R)-N-((1r,4R)-4-hydroxy-4-methylcyclohexyl-1-d)-2-methylpropane-2-sulfinamide and (R)-N-((1s,4S)-4-hydroxy-4-methylcyclohexyl-1-d)-2-methylpropane-2-sulfinamide

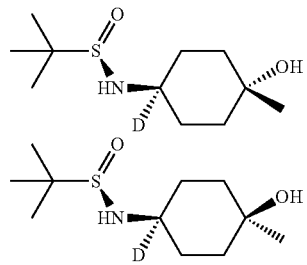

To a solution of (R)-2-methyl-N-(1-deutero-4-oxocyclohexyl)propane-2-sulfinamide (1.0 g, 4.6 mmol) in THF (46 mL) at −78° C. was added dropwise methyllithium (8.6 mL, 14 mmol, 1.6 M in diethyl ether). Upon addition, the reaction mixture was allowed to come to rt and was stirred for 3 h at rt. The reaction mixture was cooled to 0° C., and the reaction was quenched with sat. NH$_4$Cl solution (20 mL). The bath was removed. After stirring for 5 min, the mixture was then partitioned between water and EtOAc. The organic layer was removed, and the aqueous layer was extracted with EtOAc (2×). The combined organic layers were dried over Na$_2$SO$_4$, filtered, and concentrated. Purification via silica gel chromatography (1-12% MeOH in DCM) afforded a mixture of the title compounds as a white solid (0.30 g). Repurification via preparative HPLC on a C-18 column (pH 10, 14-28% MeCN/0.1% NH$_4$OH (aq) over 5 min, 60 mL/min) afforded the separated isomers: (R)-N-((1r,4R)-4-hydroxy-4-methylcyclohexyl-1-d)-2-methylpropane-2-sulfinamide (first eluting, t$_R$=4.86 min, minor isomer) as white solid (53 mg, 4.9%) and (R)-N-((1s,4S)-4-hydroxy-4-methylcyclohexyl-1-d)-2-methylpropane-2-sulfinamide (second eluting, t$_R$=5.62 min, major isomer) as a white solid (0.12 g, 11%). First eluting: LCMS for C$_{11}$H$_{23}$DNO$_2$S (M+H)$^+$: calculated m/z=235.2; found 235.2. Second eluting: $^1$H NMR (400 MHz, CDCl$_3$) δ 3.04 (br s, 1H), 1.91-1.78 (m, 2H), 1.76-1.34 (m, 8H), 1.23 (s, 3H), 1.20 (s, 9H). LCMS for C$_{11}$H$_{23}$DNO$_2$S (M+H)$^+$: calculated m/z=235.2; found 235.1.

Step 4. (1s,4s)-4-Amino-1-methylcyclohexan-4-d-1-ol Hydrochloride

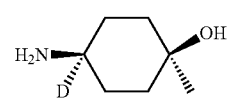

To a solution of (R)-N-((1s,4S)-4-hydroxy-4-methylcyclohexyl-1-d)-2-methylpropane-2-sulfinamide (10 mg, 0.043 mmol) in MeOH (0.50 mL) was added HCl (50 μL, 0.2 mmol, 4.0 M in 1,4-dioxane) while the reaction flask was in a rt water bath. The bath was removed, and the reaction mixture was stirred at rt for 30 min. The reaction mixture was concentrated to afford the title compound. $^1$H NMR (600 MHz, DMSO-d$_6$) δ 8.10 (s, 3H), 1.70-1.62 (m, 4H), 1.55 (d, J=11.7 Hz, 2H), 1.35-1.25 (m, 2H), 1.09 (s, 3H). LCMS for $C_7H_{15}DNO$ (M+H)$^+$: calculated m/z=131.1; found 131.2.

Step 5. 3-(4-Aminoimidazo[2,1-f][1,2,4]triazin-7-yl)-N-((1s,4s)-4-hydroxy-4-methylcyclohexyl-1-d)-4-methylbenzenesulfonamide To a solution of (1s,4s)-4-amino-1-methylcyclohexan-4-d-1-ol hydrochloride (7.1 mg, 0.043 mmol), triethylamine (18 µL, 0.128 mmol), and DMAP (0.5 mg, 4 µmol) in DMA (350 µL) at 0° C. was added 3-(4-aminoimidazo[2,1-f][1,2,4]triazin-7-yl)-4-methylbenzenesulfonyl chloride (14 mg, 0.043 mmol) in a single portion. The reaction mixture was allowed to come to rt, stirring for 2 h. The reaction mixture was again cooled to 0° C., and the reaction was quenched with MeOH. Purification via preparative HPLC on a C-18 column (pH 10, 26-38% MeCN/0.1% NH$_4$OH (aq) over 5 min, 60 mL/min) afforded the title compound as a white solid (4.1 mg, 23%). LCMS for $C_{19}H_{24}DN_6O_3S$ (M+H)$^+$: calculated m/z=418.2; found 418.1.

Example 508. 3-(4-Aminoimidazo[2,1-f][1,2,4]triazin-7-yl)-N-((1r,4r)-4-hydroxy-4-methylcyclohexyl-1-d)-4-methylbenzenesulfonamide Trifluoroacetate

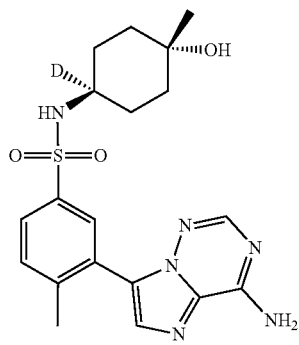 [SMILES: [2H][C@]1(NS(=O)(=O)c2ccc(C)c(-c3cnc4c(N)ncnn34)c2)CC[C@](C)(O)CC1]

Step 1. (1r,4r)-4-Amino-1-methylcyclohexan-4-d-1-ol Hydrochloride

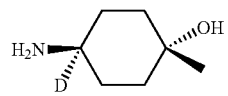

The title compound was synthesized according to experimental procedures analogous to the synthesis of Example 507, Step 4 substituting (R)-N-((1r,4R)-4-hydroxy-4-methylcyclohexyl-1-d)-2-methylpropane-2-sulfinamide (from Example 507, Step 3) for (R)-N-((1s,4S)-4-hydroxy-4-methylcyclohexyl-1-d)-2-methylpropane-2-sulfinamide. LCMS for $C_7H_{15}DNO$ (M+H)$^+$: calculated m/z=131.1; found 131.1.

Step 2. 3-(4-Aminoimidazo[2,1-f][1,2,4]triazin-7-yl)-N-((1r,4r)-4-hydroxy-4-methylcyclohexyl-1-d)-4-methylbenzenesulfonamide Trifluoroacetate The title compound was synthesized according to experimental procedures analogous to the synthesis of Example 507, Step 5 substituting (1r,4r)-4-amino-1-methylcyclohexan-4-d-1-ol hydrochloride for (1s,4s)-4-amino-1-methylcyclohexan-4-d-1-ol hydrochloride. $^1$H NMR (500 MHz, CD$_3$CN) δ 8.07 (s, 1H), 7.96 (d, J=2.0 Hz, 1H), 7.83 (dd, J=8.1, 2.1 Hz, 1H), 7.70 (s, 1H), 7.56 (d, J=8.1 Hz, 1H), 6.99 (br s, 2H), 5.66 (s, 1H), 2.35 (s, 3H), 1.77-1.64 (m, 2H), 1.58-1.46 (m, 2H), 1.44-1.27 (m, 4H), 1.12 (s, 3H). LCMS for $C_{19}H_{24}DN_6O_3S$ (M+H)$^+$: calculated m/z=418.2; found 418.2.

Example 509. Ethyl 1-((3-(8-amino-6-(trifluoromethyl)imidazo[1,2-a]pyrazin-3-yl)-4-methylphenyl)sulfonyl)piperidine-3-carboxylate

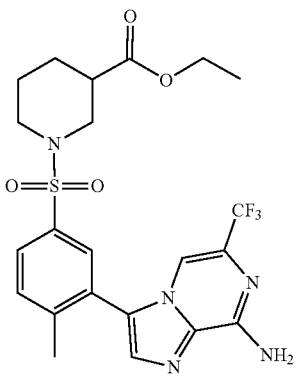 [SMILES: CCOC(=O)C1CCCN(S(=O)(=O)c2ccc(C)c(-c3cnc4c(N)nc(C(F)(F)F)cn34)c2)C1]

Step 1. Ethyl 1-((4-methyl-3-(4,4,5,5-tetramethyl-1,3,2-dioxaborolan-2-yl)phenyl)sulfonyl)piperidine-3-carboxylate

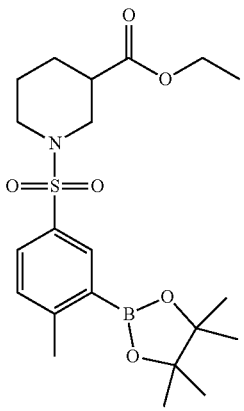 [SMILES: CCOC(=O)C1CCCN(S(=O)(=O)c2ccc(C)c(B3OC(C)(C)C(C)(C)O3)c2)C1]

The title compound was synthesized according to experimental procedures analogous to the synthesis of Example 1, Steps 1 and 2, substituting ethyl piperidine-3-carboxylate for trans-4-aminocyclohexanol in Step 1. LCMS for $C_{21}H_{33}BNO_6S$ (M+H)$^+$: calculated m/z=438.2; found 438.2.

Step 2. Ethyl 1-((3-(8-amino-6-(trifluoromethyl)imidazo[1,2-a]pyrazin-3-yl)-4-methylphenyl)sulfonyl)piperidine-3-carboxylate The title compound was synthesized according to an experimental procedure analogous to the synthesis of Example 1, Step 3, substituting ethyl 1-((4-methyl-3-(4,4,5,5-tetramethyl-1,3,2-dioxaborolan-2-yl)phenyl)sulfonyl)piperidine-3-carboxylate for N-(trans-4-hydroxycyclohexyl)-4-methyl-3-(4,4,5,5-tetramethyl-1,3,2-dioxaborolan-2-yl)benzenesulfonamide and substituting 3-bromo-6-(trifluoromethyl)imidazo[1,2-a]pyrazin-8-amine for 3-bromoimidazo[1,2-a]pyridin-8-amine. LCMS for $C_{22}H_{25}F_3N_5O_4S$ (M+H)$^+$: calculated m/z=512.2; found 512.2.

Example 510. 1-((3-(8-Amino-6-(trifluoromethyl)imidazo[1,2-a]pyrazin-3-yl)-4-methylphenyl)sulfonyl)piperidine-3-carboxylic Acid Trifluoroacetate

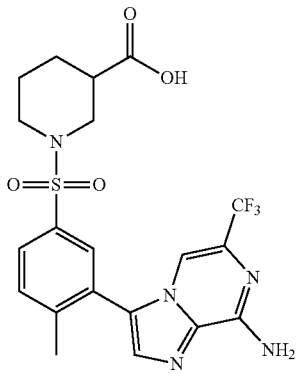 [SMILES: Cc1ccc(S(=O)(=O)N2CCCC(C(=O)O)C2)cc1-c1cnc2c(N)nc(C(F)(F)F)cn12]

To a solution of ethyl 1-((3-(8-amino-6-(trifluoromethyl)imidazo[1,2-a]pyrazin-3-yl)-4-methylphenyl)sulfonyl)piperidine-3-carboxylate (22 mg, 0.043 mmol) in THF (0.31 mL) was added 1.0 M sodium hydroxide (95 µL, 0.095 mmol). The reaction mixture was stirred overnight at rt; diluted with MeOH, MeCN, and water; and filtered. Purification via preparative HPLC on a C-18 column (pH 2, 33-53% MeCN/0.1% TFA (aq) over 5 min, 60 mL/min) afforded the title compound as a white solid (7.7 mg, 30%). LCMS for $C_{20}H_{21}F_3N_5O_4S$ (M+H)$^+$: calculated m/z=484.1; found 484.1.

Example 511. (1-((3-(8-Amino-6-(trifluoromethyl)imidazo[1,2-a]pyrazin-3-yl)-4-methylphenyl)sulfonyl)piperidin-3-yl)((R)-2-(methoxymethyl)pyrrolidin-1-yl)methanone

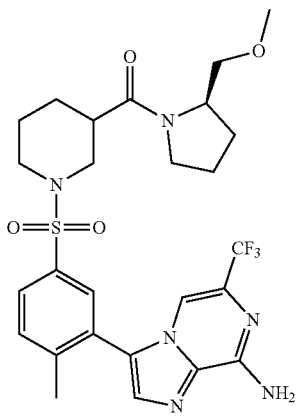 [SMILES: COC[C@H]1CCCN1C(=O)C1CCCN(S(=O)(=O)c2ccc(C)c(-c3cnc4c(N)nc(C(F)(F)F)cn34)c2)C1]

To a mixture of (R)-2-(methoxymethyl)pyrrolidine (5 µL, 0.04 mmol), 1-((3-(8-amino-6-(trifluoromethyl)imidazo[1,2-a]pyrazin-3-yl)-4-methylphenyl)sulfonyl)piperidine-3-carboxylic acid (10 mg, 0.021 mmol), and N,N,N,N-tetramethyl-O-(7-azabenzotriazol-1-yl)uronium hexafluorophosphate (9.4 mg, 0.026 mmol) in DMF (0.20 mL) was added dropwise N,N-diisopropylethylamine (5.0 µL, 0.029 mmol). The reaction mixture was stirred 1 h at rt. The reaction mixture was diluted with MeOH and purified via preparative HPLC on a C-18 column (pH 10, 35-55% MeCN/0.1% NH$_4$OH (aq) over 5 min, 60 mL/min) to afford the title compound (2.9 mg, 24%). LCMS for $C_{26}H_{32}F_3N_6O_4S$ (M+H)$^+$: calculated m/z=581.2; found 581.3.

Example 512. tert-Butyl ((1-((3-(8-amino-6-(trifluoromethyl)imidazo[1,2-a]pyrazin-3-yl)-4-methylphenyl)sulfonyl)piperidin-3-yl)methyl)carbamate

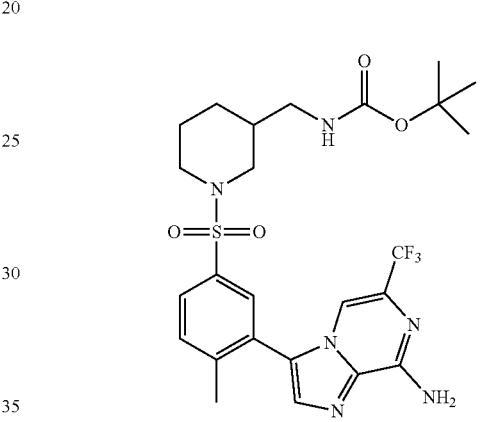

The title compound was synthesized according to experimental procedures analogous to the synthesis of Example 472, Step 9 substituting tert-butyl (piperidin-3-ylmethyl)carbamate for piperidin-3-ylmethanol. LCMS for $C_{25}H_{31}F_3N_6NaO_4S$ (M+Na)$^+$: calculated m/z=591.2; found 591.3.

Example 513. 3-(5-((3-(Aminomethyl)piperidin-1-yl)sulfonyl)-2-methylphenyl)-6-(trifluoromethyl)imidazo[1,2-a]pyrazin-8-amine Trifluoroacetate

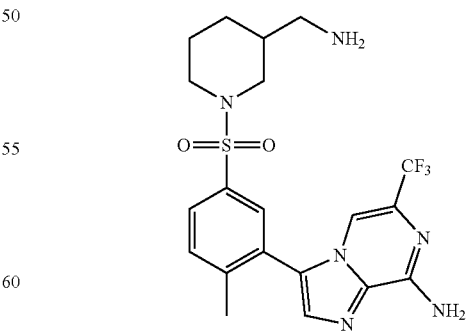

A solution of tert-butyl ((1-((3-(8-amino-6-(trifluoromethyl)imidazo[1,2-a]pyrazin-3-yl)-4-methylphenyl)sulfonyl)piperidin-3-yl)methyl)carbamate (40. mg, 0.070 mmol) in trifluoroacetic acid (1.1 mL) was stirred at rt for 1 h. The reaction mixture was diluted with DCM and concentrated to afford the crude product. A quarter of the crude product was purified via preparative HPLC on a C-18 column (pH 2, 36-56% MeCN/0.1% TFA (aq) over 5 min, 60 mL/min) to afford the title compound as a pink solid (13 mg). LCMS for $C_{20}H_{24}F_3N_6O_2S$ (M+H)+: calculated m/z=469.2; found 469.3.

Example 514. N-((1-((3-(8-Amino-6-(trifluoromethyl)imidazo[1,2-a]pyrazin-3-yl)-4-methylphenyl)sulfonyl)piperidin-3-yl)methyl)-2-(dimethylamino)acetamide

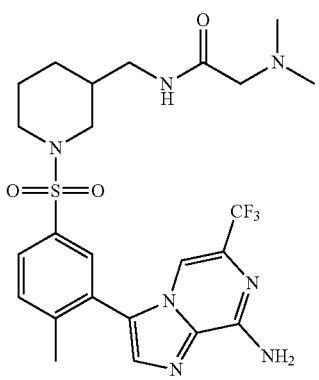

The title compound was synthesized according to experimental procedures analogous to the synthesis of Example 511, substituting 3-(5-((3-(aminomethyl)piperidin-1-yl)sulfonyl)-2-methylphenyl)-6-(trifluoromethyl)imidazo[1,2-a]pyrazin-8-amine trifluoroacetate for (R)-2-(methoxymethyl)pyrrolidine and substituting dimethylglycine for 1-((3-(8-amino-6-(trifluoromethyl)imidazo [1,2-a]pyrazin-3-yl)-4-methylphenyl)sulfonyl)piperidine-3-carboxylic acid. LCMS for $C_{24}H_{31}F_3N_7O_3S$ (M+H)+: calculated m/z=554.2; found 554.1.

Example 515. tert-Butyl (1-((3-(8-amino-6-(trifluoromethyl)imidazo[1,2-a]pyrazin-3-yl)-4-methylphenyl)sulfonyl)piperidin-3-yl)carbamate

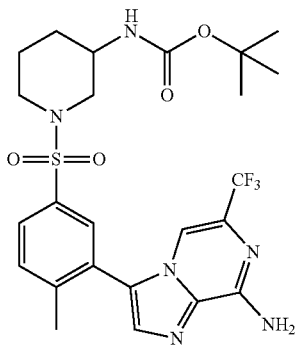

The title compound was synthesized according to experimental procedures analogous to the synthesis of Example 472, Step 9 substituting tert-butyl (piperidin-3-ylmethyl)carbamate for piperidin-3-ylmethanol. LCMS for $C_{24}H_{29}F_3N_6NaO_4S$ (M+Na)+: calculated m/z=577.2; found 577.1.

Example 516. 3-(5-((3-Aminopiperidin-1-yl)sulfonyl)-2-methylphenyl)-6-(trifluoromethyl)imidazo[1,2-a]pyrazin-8-amine Trifluoroacetate

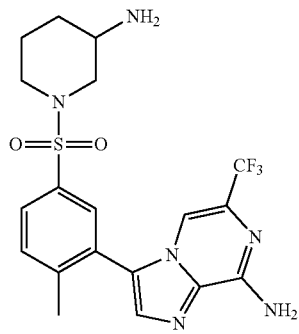 [SMILES: Cc1ccc(S(=O)(=O)N2CCCC(N)C2)cc1-c1cnc2c(N)nc(C(F)(F)F)cn12]

The title compound was synthesized according to experimental procedures analogous to the synthesis of Example 513, substituting tert-butyl (1-((3-(8-amino-6-(trifluoromethyl)imidazo[1,2-a]pyrazin-3-yl)-4-methylphenyl)sulfonyl)piperidin-3-yl)carbamate for tert-butyl ((1-((3-(8-amino-6-(trifluoromethyl)imidazo[1,2-a]pyrazin-3-yl)-4-methylphenyl)sulfonyl)piperidin-3-yl)methyl)carbamate. LCMS for $C_{19}H_{22}F_3N_6O_2S$ (M+H)+: calculated m/z=455.1; found 455.1.

Example 517. N-(1-((3-(8-Amino-6-(trifluoromethyl)imidazo[1,2-a]pyrazin-3-yl)-4-methylphenyl)sulfonyl)piperidin-3-yl)cyclopropanecarboxamide Trifluoroacetate

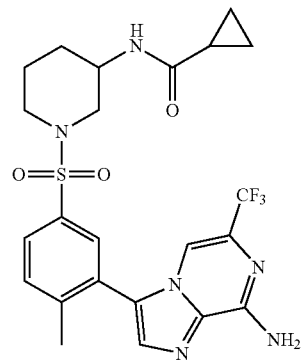

The title compound was synthesized according to experimental procedures analogous to the synthesis of Example 511, substituting 3-(5-((3-aminopiperidin-1-yl)sulfonyl)-2-methylphenyl)-6-(trifluoromethyl)imidazo[1,2-a]pyrazin-8-amine trifluoroacetate for (R)-2-(methoxymethyl)pyrrolidine and substituting cyclopropanecarboxylic acid for 1-((3-(8-amino-6-(trifluoromethyl)imidazo[1,2-a]pyrazin-3-yl)-4-methylphenyl)sulfonyl)piperidine-3-carboxylic acid. $^1$H NMR (600 MHz, DMSO-d$_6$) δ 8.02 (d, J=7.6 Hz, 1H), 7.84 (s, 1H), 7.79 (dd, J=8.0, 2.0 Hz, 1H), 7.76 (d, J=2.0 Hz, 1H), 7.71 (d, J=8.2 Hz, 1H), 7.69 (s, 1H), 7.66 (br s, 2H), 3.85-3.66 (m, 1H), 3.53-3.37 (m, 1H), 3.37-3.27 (m, 1H), 2.63-2.54 (m, 1H), 2.35-2.26 (m, 1H), 2.29 (s, 3H), 1.82-1.73 (m, 1H), 1.73-1.65 (m, 1H), 1.58-1.45 (m, 2H), 1.32-

1.19 (m, 1H), 0.72-0.57 (m, 4H). LCMS for $C_{23}H_{26}F_3N_6O_3S$ (M+H)$^+$: calculated m/z=523.2; found 523.2.

Example 518. 3-(8-Aminoimidazo[1,2-b]pyridazin-3-yl)-N-((1r,4r)-4-hydroxy-4-methylcyclohexyl)-4-methylbenzenesulfonamide

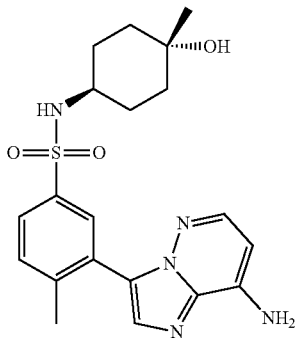 [SMILES: Cc1ccc(S(=O)(=O)N[C@H]2CC[C@](C)(O)CC2)cc1-c1cnc2c(N)ccnn12]

Step 1. 3-Bromo-6-chloroimidazo[1,2-b]pyridazin-8-amine

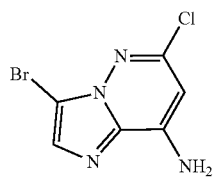 [SMILES: Nc1cc(Cl)nn2c(Br)cnc12]

The title compound was synthesized according to an experimental procedure analogous to Example 16, Step 2 substituting 3,8-dibromo-6-chloroimidazo[1,2-b]pyridazine (AstaTech, 50987) for 6,8-dibromoimidazo[1,2-a]pyrazine. LCMS for $C_6H_5BrClN_4$ (M+H)$^+$: calculated m/z 10=246.9, 248.9; found 247.0, 249.0.

Step 2. 3-(8-Amino-6-chloroimidazo[1,2-b]pyridazin-3-yl)-N-((1r,4r)-4-hydroxy-4-methylcyclohexyl)-4-methylbenzenesulfonamide

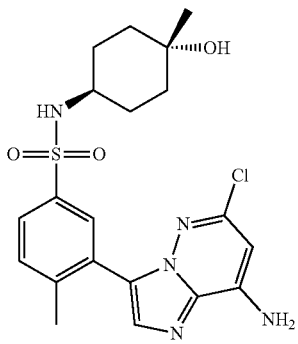 [SMILES: Cc1ccc(S(=O)(=O)N[C@H]2CC[C@](C)(O)CC2)cc1-c1cnc2c(N)cc(Cl)nn12]

The title compound was synthesized according to an experimental procedure analogous to Example 1, Step 3, substituting 3-bromo-6-chloroimidazo[1,2-b]pyridazin-8-amine for 3-bromoimidazo[1,2-a]pyridin-8-amine and substituting N-((1r,4r)-4-hydroxy-4-methylcyclohexyl)-4-methyl-3-(4,4,5,5-tetramethyl-1,3,2-dioxaborolan-2-yl)benzenesulfonamide for N-(trans-4-hydroxycyclohexyl)-4-methyl-3-(4,4,5,5-tetramethyl-1,3,2-dioxaborolan-2-yl)benzenesulfonamide. LCMS for $C_{20}H_{25}ClN_5O_3S$ (M+H)$^+$: calculated m/z=450.1; found 450.2.

Step 3. 3-(8-Aminoimidazo[1,2-b]pyridazin-3-yl)-N-((1r,4r)-4-hydroxy-4-methylcyclohexyl)-4-methylbenzenesulfonamide To a solution of 3-(8-amino-6-chloroimidazo[1,2-b]pyridazin-3-yl)-N-((1r,4r)-4-hydroxy-4-methylcyclohexyl)-4-methylbenzenesulfonamide (12 mg, 0.027 mmol) and triethylamine (7.4 µL, 0.053 mmol) in MeOH (0.43 mL) under a N$_2$ atmosphere was added Pd/C (11 mg, 5.3 µmol, 10% Pd, ~50% H$_2$O) (Sigma-Aldrich 330108, lot 03014DC). The atmosphere was replaced with H$_2$. After stirring overnight at rt, the reaction mixture was filtered through Celite, and the Celite pad was washed with MeOH. The filtrate was concentrated. Purification via preparative HPLC on a C-18 column (pH 10, 23-37% MeCN/0.1% NH$_4$OH (aq) over 5 min, 60 mL/min) afforded the title compound as a white solid (3.0 mg, 27%). $^1$H NMR (600 MHz, DMSO-d$_6$) δ 7.97 (d, J=5.4 Hz, 1H), 7.92 (d, J=2.1 Hz, 1H), 7.75 (dd, J=8.0, 2.1 Hz, 1H), 7.68 (s, 1H), 7.56 (d, J=8.3 Hz, 1H), 7.04 (s, 2H), 6.18 (d, J=5.4 Hz, 1H), 4.12 (s, 1H), 3.11-2.98 (m, 1H), 2.30 (s, 3H), 1.66-1.56 (m, 2H), 1.48 (t, J=8.9 Hz, 2H), 1.34-1.20 (m, 4H), 1.05 (s, 3H). LCMS for $C_{20}H_{26}N_5O_3S$ (M+H)$^+$: calculated m/z=416.1; found 416.2.

Example 519. 3-(8-(Benzylamino)-6-(trifluoromethyl)imidazo[1,2-a]pyrazin-3-yl)-N-(2-hydroxy-2-methylpropyl)-4-methylbenzenesulfonamide

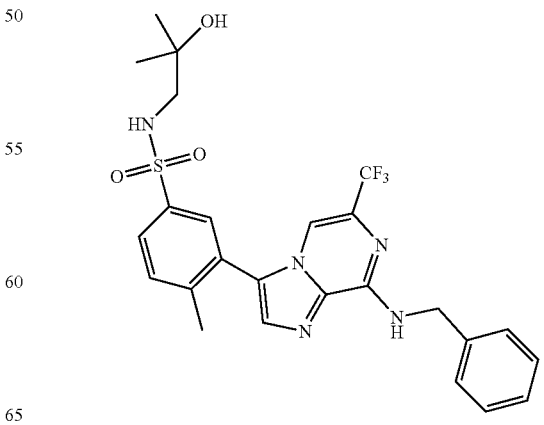

Step 1. 8-Chloro-3-iodo-6-(trifluoromethyl)imidazo[1,2-a]pyrazine

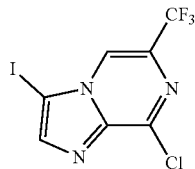 [SMILES: FC(F)(F)c1cn2c(I)cnc2c(Cl)n1]

The title compound was synthesized according to an experimental procedure analogous to Example 472, Step 4, substituting N-iodosuccinimide for N-bromosuccinimide. LCMS for $C_7H_3CF_3IN_3$ (M+H)$^+$: calculated m/z=347.9; found 347.9.

Step 2. N-Benzyl-3-iodo-6-(trifluoromethyl)imidazo[1,2-a]pyrazin-8-amine

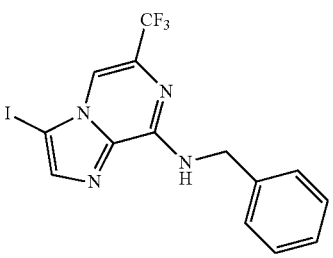

The title compound was synthesized according to an experimental procedure analogous to Example 472, Step 5, substituting benzylamine for 4-methoxybenzylamine and substituting 8-chloro-3-iodo-6-(trifluoromethyl)imidazo[1,2-a]pyrazine for 3-bromo-8-chloro-6-(trifluoromethyl)imidazo[1,2-a]pyrazine. LCMS for $C_{14}H_{11}F_3IN_4$ (M+H)$^+$: calculated m/z=419.0; found 419.0.

Step 3. N-(2-hydroxy-2-methylpropyl)-4-methyl-3-(4,4,5,5-tetramethyl-1,3,2-dioxaborolan-2-yl)benzenesulfonamide

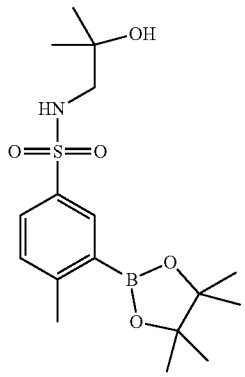 [SMILES: Cc1ccc(S(=O)(=O)NCC(C)(C)O)cc1B1OC(C)(C)C(C)(C)O1]

The title compound was synthesized according to experimental procedures analogous to Example 1, Steps 1 and 2, substituting 1-amino-2-methylpropan-2-ol for trans-4-aminocyclohexanol in Step 1. LCMS for $C_{17}H_{27}BNO_4S$ (M-OH)$^+$: calculated m/z=352.2; found 352.1.

Step 4. 3-(8-(Benzylamino)-6-(trifluoromethyl)imidazo[1,2-a]pyrazin-3-yl)-N-(2-hydroxy-2-methylpropyl)-4-methylbenzenesulfonamide The title compound was synthesized according to an experimental procedure analogous to Example 1, Step 3, substituting N-benzyl-3-iodo-6-(trifluoromethyl)imidazo[1,2-a]pyrazin-8-amine for 3-bromoimidazo[1,2-a]pyridin-8-amine and substituting N-(2-hydroxy-2-methylpropyl)-4-methyl-3-(4,4,5,5-tetramethyl-1,3,2-dioxaborolan-2-yl)benzenesulfonamide for N-(trans-4-hydroxycyclohexyl)-4-methyl-3-(4,4,5,5-tetramethyl-1,3,2-dioxaborolan-2-yl)benzenesulfonamide. $^1$H NMR (400 MHz, DMSO-d$_6$) δ 8.78 (t, J=6.3 Hz, 1H), 7.84 (d, J=8.0 Hz, 1H), 7.81 (s, 2H), 7.65 (d, J=8.1 Hz, 1H), 7.62 (s, 1H), 7.51 (s, 1H), 7.43 (d, J=7.4 Hz, 2H), 7.31 (t, J=7.6 Hz, 2H), 7.23 (t, J=7.3 Hz, 1H), 4.70 (d, J=6.3 Hz, 2H), 4.38 (s, 1H), 2.65 (s, 2H), 2.25 (s, 3H), 1.04 (s, 6H). LCMS for $C_{25}H_{27}F_3N_5O_3S$ (M+H)$^+$: calculated m/z=534.2; found 534.1.

Example 520. 3-(4-Aminoimidazo[2,1-f][1,2,4]triazin-7-yl)-N-(5-cyanobicyclo[3.1.1]heptan-1-yl)-4-methylbenzenesulfonamide Trifluoroacetate

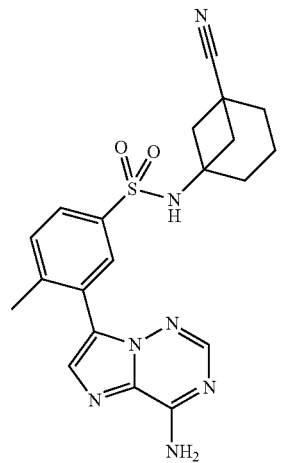

Step 1. tert-butyl (5-carbamoylbicyclo[3.1.1]heptan-1-yl)carbamate

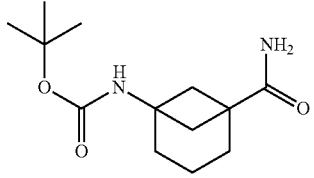

A mixture of 5-((tert-butoxycarbonyl)amino)bicyclo[3.1.1]heptane-1-carboxylic acid (40 mg, 0.157 mmol), ammonium carbonate (75 mg, 0.78 mmol), HATU (89 mg, 0.24 mmol), and DIEA (0.055 mL, 0.31 mmol) in DCE (0.6 mL) was stirred at ambient temperature for 5 h. The reaction mixture was diluted with ethyl acetate (20 mL) and water (3 mL). The layers were separated and the organic layer was washed with water (3×3 mL) and the combined aqueous phases were extracted with ethyl acetate (5 mL). The combined organic layers were washed with brine (5 mL), dried over Na$_2$SO$_4$, filtered and concentrated in-vacuo. The crude product was used directly in the next step without further purification. LCMS for C$_{13}$H$_{22}$N$_2$O$_3$ (M+Na)$^+$: calculated m/z=277.3; found 277.2.

Step 2. 5-aminobicyclo[3.1.1]heptane-1-carbonitrile Hydrochloride

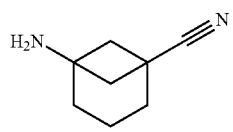

To a 0° C. solution of tert-butyl (5-carbamoylbicyclo[3.1.1]heptan-1-yl)carbamate (40. mg, 0.16 mmol) and triethylamine (0.088 mL, 0.63 mmol) was added trifluoroacetic anhydride (0.027 mL, 0.19 mmol) and the resulting solution was stirred at ambient temperature for 4 h. LCMS data indicated the presence of starting material, so a second aliquot of trifluoroacetic anhydride (30 μL) was added and stirring was continued overnight. 4 N hydrogen chloride in 1,4-dioxane (1.0 mL, 4.0 mmol) was added to the crude reaction mixture to remove the Boc protecting group and the solution was stirred overnight. The volatiles were removed in-vacuo and the residue was placed under high vacuum and used in the next step without further purification. LCMS for C$_8$H$_{12}$N$_2$(M+H)$^+$: calculated m/z=137.2; found 137.1.

Step 3. 3-(4-Aminoimidazo[2,1-f][1,2,4]triazin-7-yl)-N-(5-cyanobicyclo[3.1.1]heptan-1-yl)-4-methylbenzenesulfonamide Trifluoroacetate

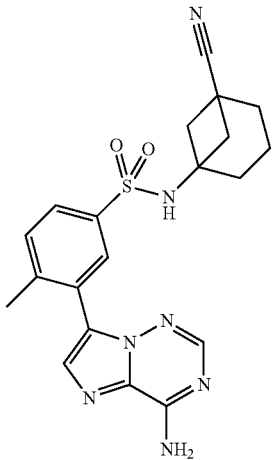

To a solution of 5-aminobicyclo[3.1.1]heptane-1-carbonitrile hydrochloride (8.4 mg, 0.049 mmol) and 3-(4-aminoimidazo[2,1-f][1,2,4]triazin-7-yl)-4-methylbenzenesulfonyl chloride (10 mg, 0.031 mmol) in DCM (0.5 mL) was added sequentially triethylamine (0.017 mL, 0.12 mmol), and DMAP (1.5 mg, 0.012 mmol). After 15 min., NMP (0.2 mL) was added and the resulting solution was stirred at ambient temperature overnight. The crude reaction mixture was diluted with MeOH and acidified by the addition of a couple of drops of 4 N HCl (aq) and purified by preparative HPLC on a C-18 column (pH 2, 15-35% MeCN/0.1% TFA (aq) over 5 min, 60 mL/min) to afford the title compound. LCMS for C$_{20}$H$_{21}$N$_7$O$_2$S (M+H)$^+$: calculated m/z=424.5; found 424.2.

Example 521. 3-(4-Aminoimidazo[2,1-f][1,2,4]triazin-7-yl)-N-(5-(1-hydroxyethyl)bicyclo[3.1.1]heptan-1-yl)-4-methylbenzenesulfonamide Trifluoroacetate

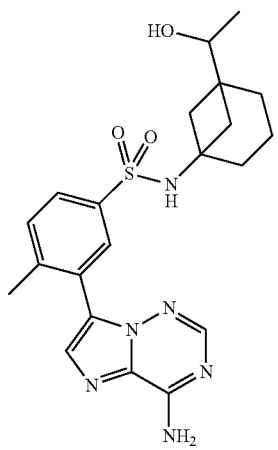

Step 1. Tert-Butyl (5-(methoxy(methyl)carbamoyl)bicyclo[3.1.1]heptan-1-yl)carbamate

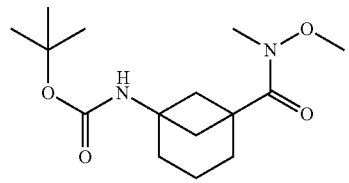

A solution of 5-((tert-butoxycarbonyl)amino)bicyclo[3.1.1]heptane-1-carboxylic acid (200 mg, 0.78 mmol), N,O-dimethylhydroxylamine hydrochloride (153 mg, 1.57 mmol), HATU (357 mg, 0.94 mmol), and DIEA (0.274 mL, 1.57 mmol) in DCE (4 mL) was stirred at ambient temperature overnight. LCMS data indicated that the major reaction component was the desired product. The reaction mixture was diluted with EtOAc (50 mL) and H$_2$O (5 mL). The layers were separated and the organic layer was washed with H$_2$O (3×5 mL) and the combined aqueous phases were extracted with EtOAc (10 mL). The combined organic layers were washed with brine (5 mL), dried over Na$_2$SO$_4$, filtered, and concentrated in-vacuo. The crude product was used directly in the next step without any further purification. LCMS for C$_{15}$H$_{26}$N$_2$O$_4$ (M+Na)$^+$: calculated m/z=321.4; found 321.2.

Step 2. 5-amino-N-methoxy-N-methylbicyclo[3.1.1]heptane-1-carboxamide Hydrochloride

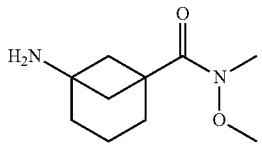

To a solution of tert-butyl (5-(methoxy(methyl)carbamoyl)bicyclo[3.1.1]heptan-1-yl)carbamate (145 mg, 0.485 mmol) in THF was added 4 N HCl in 1,4-dioxane (2.0 mL, 8.0 mmol) and the solution was stirred at ambient temperature for 4 h. The volatiles were removed in-vacuo and the residue was placed on the high vacuum and used in the next step without further purification. LCMS for $C_{10}H_{18}N_2O_2$ (M+H)$^+$: calculated m/z=199.3; found 199.2.

Step 3. 5-((3-(4-aminoimidazo[2,1-f][1,2,4]triazin-7-yl)-4-methylphenyl)sulfonamido)-N-methoxy-N-methylbicyclo[3.1.1]heptane-1-carboxamide

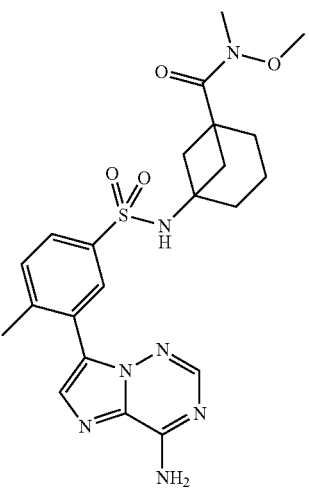

To a solution of 5-amino-N-methoxy-N-methylbicyclo[3.1.1]heptane-1-carboxamide hydrochloride (115 mg, 0.49 mmol), triethylamine (0.172 mL, 1.24 mmol), and DMAP (3.8 mg, 0.031 mmol) in DCM (2 mL) was added 3-(4-aminoimidazo[2,1-f][1,2,4]triazin-7-yl)-4-methylbenzenesulfonyl chloride (100. mg, 0.309 mmol) and the resulting solution was stirred at ambient temperature overnight. LCMS data indicated that some of the amine starting material was present, so a second aliquot of sulfonyl chloride (40 mg) and DMAP (2 mg) were added and stirring was continued overnight. LCMS data indicated that some of the amine starting material was present, so an additional aliquot of sulfonyl chloride (30 mg), Et$_3$N (100 µL), NMP (100 µL) and DMAP (2 mg) were added and stirring was continued for 3 h. The crude product was purified by CombiFlash chromatography (25 g silica gel column, eluting with 0-20% methanol/dichloromethane) to afford the desired product (62 mg, 42%). LCMS for $C_{22}H_{27}N_7O_4S$ (M+H)$^+$: calculated m/z=486.6; found 486.2.

Step 4. N-(5-acetylbicyclo[3.1.1]heptan-1-yl)-3-(4-aminoimidazo[2,1-f][1,2,4]triazin-7-yl)-4-methyl-benzenesulfonamide

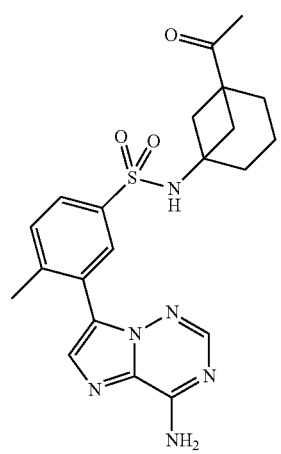

To a 0° C. solution of 5-((3-(4-aminoimidazo[2,1-f][1,2,4]triazin-7-yl)-4-methylphenyl)sulfonamido)-N-methoxy-N-methylbicyclo[3.1.1]heptane-1-carboxamide (62 mg, 0.128 mmol) in anhydrous THF (1. mL) was added 3 M methylmagnesium bromide in Et$_2$O (0.20 mL, 0.60 mmol) drop-wise and the resulting solution was allowed to gradually warm to ambient temperature. After 4 h, LCMS data indicated that the reaction was complete. The crude reaction mixture was cooled to 0° C. and quenched by the addition of saturated ammonium chloride (aq). The reaction mixture was diluted with EtOAc (30 mL) and washed successively with water (2×3 mL) and brine (2×3 mL). The organic layer was dried over Na$_2$SO$_4$, filtered, and concentrated in-vacuo. The crude product was purified by CombiFlash chromatography (12 g silica gel column, eluting with 0-15% methanol/dichloromethane) to afford the desired product. LCMS for $C_{21}H_{24}N_6O_3S$ (M+H)$^+$: calculated m/z=441.5; found 441.1.

Step 5. 3-(4-aminoimidazo[2,1-f][1,2,4]triazin-7-yl)-N-(5-(1-hydroxyethyl)bicyclo[3.1.1]heptan-1-yl)-4-methylbenzenesulfonamide Trifluoroacetate To a solution of N-(5-acetylbicyclo[3.1.1]heptan-1-yl)-3-(4-aminoimidazo[2,1-f][1,2,4]triazin-7-yl)-4-methylbenzenesulfonamide (18 mg, 0.041 mmol) in THF (1.0 mL) was added NaBH$_4$ (7.7 mg, 0.20 mmol) and the resulting mixture was stirred at ambient temperature overnight. LCMS data indicated that the major reaction component was the desired product. The reaction mixture was diluted with MeOH and purified by preparative HPLC on a C-18 column (pH 2, 18.7-36.7% MeCN/0.1% TFA (aq) over 12 min, 60 mL/min) to afford the title compound. LCMS for $C_{21}H_{26}N_6O_3S$ (M+H)$^+$: calculated m/z=443.5; found 443.2.

Example 522. 3-(4-Aminoimidazo[2,1-f][1,2,4]triazin-7-yl)-N-(5-(1-(3-cyanoazetidin-1-yl)ethyl)bicyclo[3.1.1]heptan-1-yl)-4-methylbenzenesulfonamide Trifluoroacetate

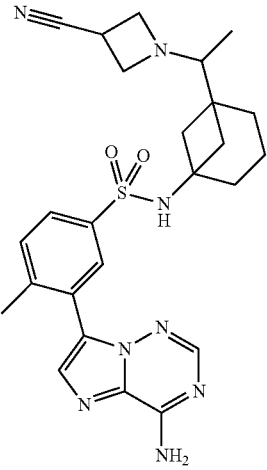

To a pre-stirred solution of N-(5-acetylbicyclo[3.1.1]heptan-1-yl)-3-(4-aminoimidazo[2,1-f][1,2,4]triazin-7-yl)-4-methylbenzenesulfonamide (18 mg, 0.041 mmol, prepared in Example 521, Step 4), azetidine-3-carbonitrile hydrochloride (24 mg, 0.20 mmol), and Et₃N (0.028 mL, 0.20 mmol) was added sodium triacetoxyborohydride (14 mg, 0.069 mmol) and the resulting solution was stirred at 60° C. overnight. The reaction mixture was diluted with MeOH and purified via preparative HPLC on a C-18 column (pH 2, 12-30% MeCN/0.1% TFA (aq) over 12 min, 60 mL/min) to afford the title compound. LCMS for $C_{25}H_{30}N_8O_2S$ (M+H)⁺: calculated m/z=507.6; found 507.2.

Example 523. 3-(4-Aminoimidazo[2,1-f][1,2,4]triazin-7-yl)-4-methyl-N-(3-methyl-3-azabicyclo[3.1.1]heptan-1-yl)benzenesulfonamide Trifluoroacetate

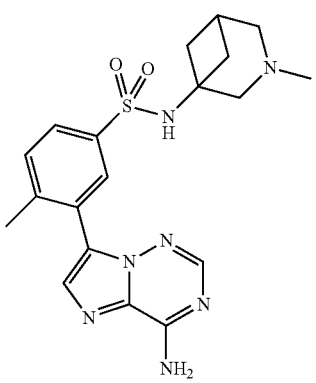

Step 1. 3-((benzyloxy)carbonyl)-3-azabicyclo[3.1.1]heptane-1-carboxylic Acid

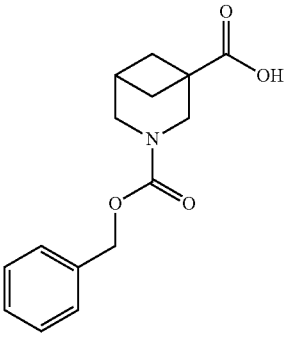 [SMILES: O=C(OCc1ccccc1)N1CC2CC(C(=O)O)(C2)C1]

To a solution of 3-azabicyclo[3.1.1]heptane-1-carboxylic acid (0.522 g, 3.70 mmol) and N-(benzyloxycarbonyloxy)succinimide (1.01 g, 4.07 mmol) in DCM (15 mL) was added DIEA (0.97 mL, 5.6 mmol) and the resulting solution was stirred at ambient temperature overnight. The reaction mixture was diluted with dichloromethane (50 mL) and acidified by the addition of 1 N HCl (aq) (10 mL). The layers were separated and the organic layer was washed with H₂O (3×5 mL) and the combined aqueous phases were extracted with dichloromethane (10 mL). The combined organic layers were washed with brine (10 mL), dried over Na₂SO₄, filtered, and concentrated in-vacuo to afford an off-white solid (1.00 g, 98%). LCMS for $C_{15}H_{17}NO_4$ (M+H)⁺: calculated m/z=276.3; found 276.1.

Step 2. Benzyl 1-((tert-butoxycarbonyl)amino)-3-azabicyclo[3.1.1]heptane-3-carboxylate

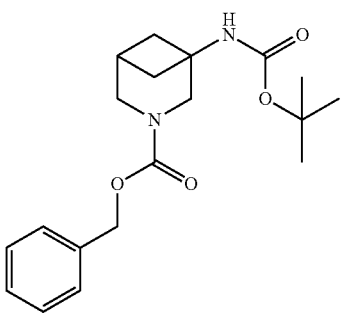

To a solution of 3-((benzyloxy)carbonyl)-3-azabicyclo[3.1.1]heptane-1-carboxylic acid (150 mg, 0.545 mmol) and triethylamine (0.091 mL, 0.65 mmol) in tert-butanol (3.0 mL) was added diphenyl phosphoryl azide (0.129 mL, 0.599 mmol) and the solution was heated at 85° C. in a sealed vial overnight. LCMS data indicated that the major reaction component was the desired product. The crude reaction mixture was concentrated in-vacuo and the residue was purified by CombiFlash chromatography (25 g column, eluting with 0-50% ethyl acetate/hexanes) to afford the desired product (45 mg, 24%). LCMS for $C_{19}H_{26}N_2O_4$ (M+Na)⁺: calculated m/z=369.4; found 369.1.

Step 3. Benzyl 1-amino-3-azabicyclo[3.1.1]heptane-3-carboxylate Hydrochloride

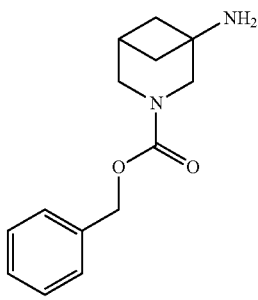 [SMILES: NC12CC(CN(C(=O)OCc3ccccc3)C1)C2]

To a solution of benzyl 1-((tert-butoxycarbonyl)amino)-3-azabicyclo[3.1.1]heptane-3-carboxylate (45 mg, 0.130 mmol) in THF (1 mL) was added 4 N HCl in 1,4-dioxane (2 mL, 8.00 mmol) and the solution was stirred at ambient temperature for 2 h. The volatiles were removed in-vacuo and the residue was placed under high vacuum prior to using in the subsequent reaction. LCMS for $C_{14}H_{18}N_2O_2$ (M+H)$^+$: calculated m/z=247.3; found 247.2.

Step 4. Benzyl 1-((3-(4-aminoimidazo[2,1-f][1,2,4]triazin-7-yl)-4-methylphenyl)sulfonamido)-3-azabicyclo[3.1.1]heptane-3-carboxylate

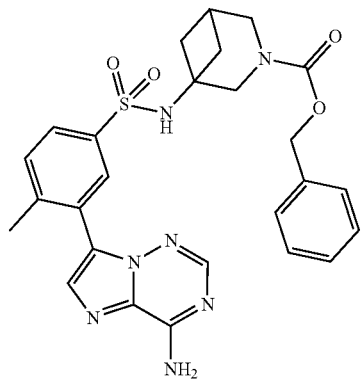 [SMILES: Cc1ccc(S(=O)(=O)NC23CC(CN(C(=O)OCc4ccccc4)C2)C3)cc1-c1cnc2c(N)ncnn12]

To a solution of benzyl 1-amino-3-azabicyclo[3.1.1]heptane-3-carboxylate hydrochloride (34 mg, 0.12 mmol), Et$_3$N (0.069 mL, 0.49 mmol), and DMAP (1.5 mg, 0.012 mmol) in DCM (0.5 mL) was added 3-(4-aminoimidazo[2,1-f][1,2,4]triazin-7-yl)-4-methylbenzenesulfonyl chloride (40. mg, 0.12 mmol) and the resulting mixture was stirred at ambient temperature overnight. The crude reaction mixture was purified by CombiFlash chromatography (12 g silica gel column, eluting with 0-15% methanol/dichloromethane) to afford the desired product (18 mg, 27%). LCMS for $C_{26}H_{27}N_7O_4S$ (M+H)$^+$: calculated m/z=534.6; found 534.1.

Step 5. 3-(4-aminoimidazo[2,1-f][1,2,4]triazin-7-yl)-N-(3-azabicyclo[3.1.1]heptan-1-yl)-4-methylbenzenesulfonamide

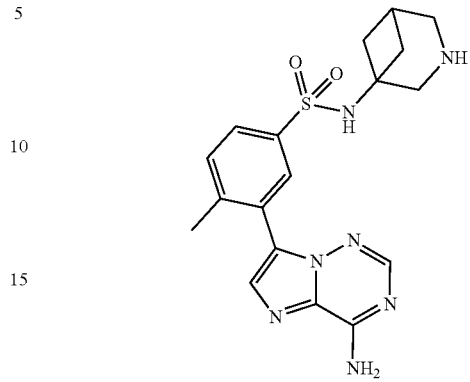

A mixture of benzyl 1-((3-(4-aminoimidazo[2,1-f][1,2,4]triazin-7-yl)-4-methylphenyl)sulfonamido)-3-azabicyclo[3.1.1]heptane-3-carboxylate (18 mg, 0.034 mmol) and 10% palladium (dry basis) on activated carbon, wet, Degussa type E101 NE/W (4 mg) in MeOH (3 mL) was stirred for 16 h under an atmosphere of hydrogen. The crude reaction mixture was purged with nitrogen, diluted with EtOAc (20 mL), and filtered through a pad of celite. The inorganics were washed thoroughly with EtOAc. The volatiles were removed in-vacuo and the crude product was used in the subsequent step without further purification. LCMS for $C_{18}H_{21}N_7O_2S$ (M+H)$^+$: calculated m/z=400.5; found 400.1.

Step 6. 3-(4-aminoimidazo[2,1-f][1,2,4]triazin-7-yl)-4-methyl-N-(3-methyl-3-azabicyclo[3.1.1]heptan-1-yl)benzenesulfonamide Trifluoroacetate A mixture of 3-(4-aminoimidazo[2,1-f][1,2,4]triazin-7-yl)-N-(3-azabicyclo[3.1.1]heptan-1-yl)-4-methylbenzenesulfonamide (14 mg, 0.035 mmol), paraformaldehyde (2.1 mg, 0.070 mmol), and sodium triacetoxyborohydride (15 mg, 0.070 mmol) in DCE (0.6 mL) was stirred at ambient temperature for 4 h. The reaction mixture was diluted with MeOH and purified via preparative HPLC on a C-18 column (pH 2, 5-23% MeCN/0.1% TFA (aq) over 12 min, 60 mL/min) to afford the title compound. LCMS for $C_{19}H_{23}N_7O_2S$ (M+H)$^+$: calculated m/z=414.5; found 414.2.

Example 524. 3-(4-Amino-2-(trifluoromethyl)imidazo[2,1-f][1,2,4]triazin-7-yl)-N-(3-isopropyl-3-azabicyclo[3.1.1]heptan-1-yl)-4-methylbenzenesulfonamide Trifluoroacetate

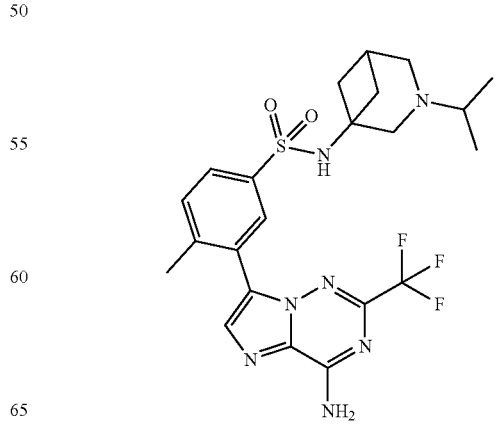

Step 1. Tert-Butyl (3-azabicyclo[3.1.1]heptan-1-yl) carbamate

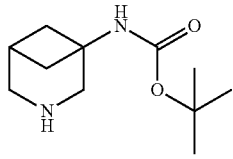

A mixture of benzyl 1-((tert-butoxycarbonyl)amino)-3-azabicyclo[3.1.1]heptane-3-carboxylate (236 mg, 0.681 mmol, prepared in Example 523, Step 2) and palladium hydroxide 20% (dry basis), wet (24 mg, 0.034 mmol) in MeOH (5 mL) was stirred under an atmosphere of H$_2$ (g) while stirring at ambient temperature. The crude reaction mixture was purged with nitrogen, diluted with EtOAc (20 mL), and filtered through a pad of celite. The inorganics were washed thoroughly with EtOAc. The volatiles were removed in-vacuo and the crude product was used in the subsequent step without further purification. LCMS for C$_{11}$H$_{20}$N$_2$O$_2$ (M+H)$^+$: calculated m/z=213.3; found 213.2.

Step 2. 3-isopropyl-3-azabicyclo[3.1.1]heptan-1-amine Hydrochloride

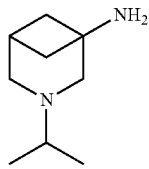

A mixture of tert-butyl (3-azabicyclo[3.1.1]heptan-1-yl) carbamate (25 mg, 0.12 mmol), acetone (0.043 mL, 0.59 mmol), and sodium triacetoxyborohydride (42. mg, 0.20 mmol) in DCE (0.5 mL) was stirred at ambient temperature overnight. 4 N HCl in 1,4-dioxane (1 mL) was added and the resultant solution was stirred at ambient temperature for 5 h. The volatiles were removed in-vacuo and the residue was azeotropically washed with acetonitrile prior to placing it under high vacuum. The crude product was used in the subsequent reaction without further purification. LCMS for C$_9$H$_{18}$N$_2$ (M+H)$^+$: calculated m/z=155.3; found 155.1.

Step 3. 3-(4-amino-2-(trifluoromethyl)imidazo[2,1-f][1,2,4]triazin-7-yl)-N-(3-isopropyl-3-azabicyclo[3.1.1]heptan-1-yl)-4-methylbenzenesulfonamide Trifluoroacetate To a solution of 3-isopropyl-3-azabicyclo[3.1.1]heptan-1-amine hydrochloride (12 mg, 0.064 mmol) and 3-(4-amino-2-(trifluoromethyl)imidazo[2,1-f][1,2,4]triazin-7-yl)-4-methylbenzenesulfonyl chloride (10. mg, 0.026 mmol) in DCM (0.5 mL) was added sequentially Et$_3$N (0.014 mL, 0.10 mmol), and DMAP (1.5 mg, 0.012 mmol). After 15 min. NMP (0.2 mL) was added and the resulting solution was stirred at ambient temperature overnight. The reaction mixture was quenched by the addition of 4 N HCl (aq) (0.5 mL), diluted with MeOH, and purified via preparative HPLC on a C-18 column (pH 2, 17-35% MeCN/0.1% TFA (aq) over 12 min, 60 mL/min) to afford the title compound. LCMS for C$_{22}$H$_{26}$F$_3$N$_7$O$_2$S (M+H)$^+$: calculated m/z=510.6; found 510.2.

Example 525. 3-(4-Aminoimidazo[2,1-f][1,2,4]triazin-7-yl)-N-(3-cyclobutyl-3-azabicyclo[3.1.1]heptan-1-yl)-4-methylbenzenesulfonamide Trifluoroacetate

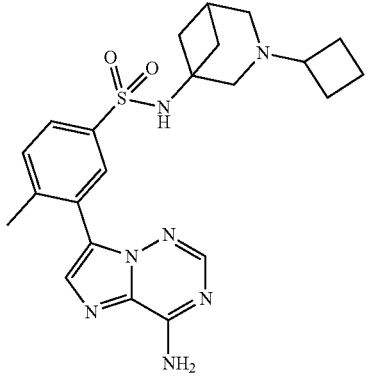 [SMILES: Cc1ccc(S(=O)(=O)NC23CC(CN(C4CCC4)C2)C3)cc1-c1cnc2c(N)ncnn12]

To a solution of 3-cyclobutyl-3-azabicyclo[3.1.1]heptan-1-amine hydrochloride (13 mg, 0.064 mmol, prepared by using a procedure analogous to that in Example 524, Steps 1-2) in DCE (1 mL) was added sequentially 1 N Na$_2$CO$_3$ (aq) (1 mL) and 3-(4-aminoimidazo[2,1-f][1,2,4]triazin-7-yl)-4-methylbenzenesulfonyl chloride (8. mg, 0.03 mmol) and the resulting mixture was stirred at ambient temperature overnight. The reaction mixture was quenched by the addition of 4 N HCl (aq) (0.5 mL), diluted with MeOH, and purified via preparative HPLC on a C-18 column (pH 2, 14-34% MeCN/0.1% TFA (aq) over 5 min, 60 mL/min) to afford the title compound. LCMS for C$_{22}$H$_{27}$N$_7$O$_2$S (M+H)$^+$: calculated m/z=454.6; found 454.3.

Example 526. 3-(4-Amino-2-(trifluoromethyl)imidazo[2,1-f][1,2,4]triazin-7-yl)-N-(1,3-dimethylpiperidin-3-yl)-4-methylbenzenesulfonamide Trifluoroacetate

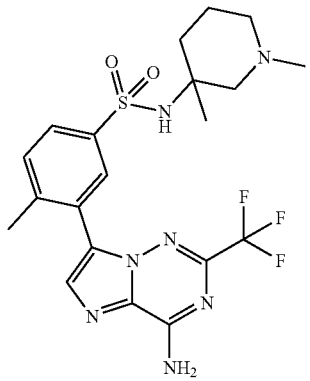

Step 1. 1,3-dimethylpiperidin-3-amine Hydrochloride

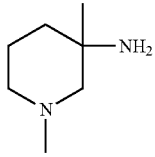

A mixture of tert-butyl (3-methylpiperidin-3-yl) carbamate (50. mg, 0.23 mmol), paraformaldehyde (35 mg, 1.2 mmol), and sodium triacetoxyborohydride (84 mg, 0.40 mmol) in DCE (1.0 mL) was stirred at ambient temperature overnight. 4 N HCl in 1,4-dioxane (1 mL) was added and the resultant solution was stirred at ambient temperature for 5 h. The volatiles were removed in-vacuo and the residue was azeotropically washed with acetonitrile prior to placing it under high vacuum. The crude product was used in the subsequent reaction without further purification. LCMS for $C_7H_{16}N_2(M+H)^+$: calculated m/z=129.2; found 129.1.

Step 2. 3-(4-amino-2-(trifluoromethyl)imidazo[2,1-f][1,2,4]triazin-7-yl)-N-(1,3-dimethylpiperidin-3-yl)-4-methylbenzenesulfonamide trifluoroacetate

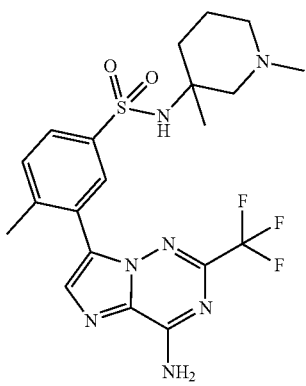

To a solution of 1,3-dimethylpiperidin-3-amine hydrochloride (10. mg, 0.064 mmol) in DCE (1 mL) was added sequentially 1 N $Na_2CO_3$ (aq) (1 mL) and 3-(4-amino-2-(trifluoromethyl)imidazo[2,1-f][1,2,4]triazin-7-yl)-4-methylbenzenesulfonyl chloride (10. mg, 0.026 mmol) and the resulting mixture was stirred at ambient temperature overnight. The reaction mixture was quenched by the addition of 4 N HCl (aq) (0.5 mL), diluted with MeOH, and purified via preparative HPLC on a C-18 column (pH 2, 8-26% MeCN/ 0.1% TFA (aq) over 12 min, 60 mL/min) to afford the title compound. LCMS for $C_{20}H_{24}F_3N_7O_2S$ (M+H)$^+$: calculated m/z=484.5; found 484.2.

Example 527. 3-(4-Amino-2-(trifluoromethyl)imidazo[2,1-f][1,2,4]triazin-7-yl)-N-(1-isopropyl-3-methylpiperidin-3-yl)-4-methylbenzenesulfonamide Trifluoroacetate

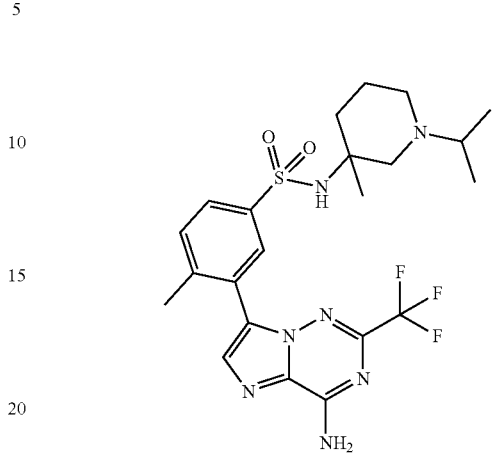

A procedure analogous to that outlined in Example 526 was used with the exception that 1-isopropyl-3-methylpiperidin-3-amine hydrochloride (12 mg, 0.064 mmol) was used as the amine. LCMS for $C_{22}H_{28}F_3N_7O_2S$ (M+H)$^+$: calculated m/z=512.6; found 512.3.

Example 528. 3-(4-Amino-2-(trifluoromethyl)imidazo[2,1-f][1,2,4]triazin-7-yl)-N-(1,4-dimethylpiperidin-4-yl)-4-methylbenzenesulfonamide Trifluoroacetate

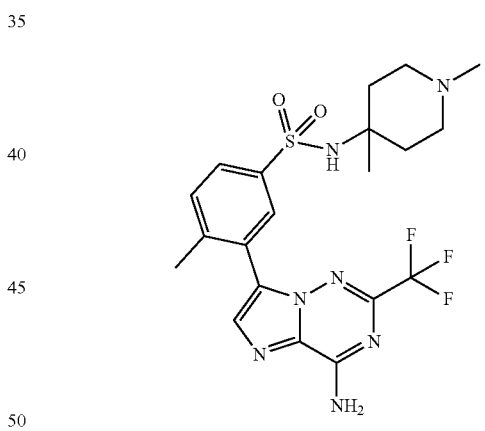

To a vial containing 3-(4-amino-2-(trifluoromethyl)imidazo[2,1-f][1,2,4]triazin-7-yl)-4-methylbenzenesulfonyl chloride (10 mg, 0.026 mmol) and DMAP (2.0 mg, 0.016 mmol) was added a solution of 1,4-dimethylpiperidin-4-amine hydrochloride (9.2 mg, 0.056 mmol, prepared in a manner similar to that outlined in Example 526, step 1) and $Et_3N$ (0.014 mL, 0.10 mmol) in DCM (0.6 mL) and NMP (0.4 mL) and the resulting mixture was stirred at ambient temperature overnight. A second aliquot of sulfonyl chloride was added and stirring was continued overnight. The reaction was diluted with methanol (4 mL), acidified by the addition of 4 N HCl (aq) (0.5 mL), syringe filtered, and purified via preparative HPLC on a C-18 column (pH 2, 16-34% MeCN/0.1% TFA (aq) over 12 min, 60 mL/min) to afford the title compound. LCMS for $C_{20}H_{24}F_3N_7O_2S$ (M+H): calculated m/z=484.5; found 484.2.

445

Example 529. 3-(4-Amino-2-(trifluoromethyl)imidazo[2,1-f][1,2,4]triazin-7-yl)-N-(1-(3-cyanocyclobutyl)-4-methylpiperidin-4-yl)-4-methylbenzenesulfonamide Trifluoroacetate

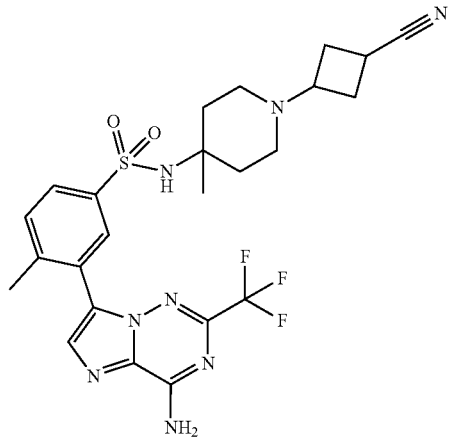 [SMILES: Cc1ccc(S(=O)(=O)NC2(C)CCN(C3CC(C#N)C3)CC2)cc1-c1cnc2c(N)nc(C(F)(F)F)nn12]

A procedure analogous to that outlined in Example 528 was used with the exception that 3-(4-amino-4-methylpiperidin-1-yl)cyclobutane-1-carbonitrile hydrochloride (13 mg, 0.056 mmol) was used as the amine. LCMS for $C_{24}H_{27}F_3N_8O_2S$ (M+H)$^+$: calculated m/z=549.6; found 549.1.

Example 530. 3-(4-Amino-2-(trifluoromethyl)imidazo[2,1-f][1,2,4]triazin-7-yl)-4-methyl-N-(4-methyl-1-(tetrahydrofuran-3-yl)piperidin-4-yl)benzenesulfonamide Trifluoroacetate

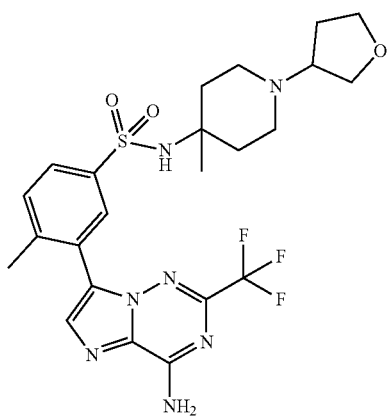 [SMILES: Cc1ccc(S(=O)(=O)NC2(C)CCN(C3CCOC3)CC2)cc1-c1cnc2c(N)nc(C(F)(F)F)nn12]

A procedure analogous to that outlined in Example 528 was used with the exception that 4-methyl-1-(tetrahydrofuran-3-yl)piperidin-4-amine hydrochloride (12 mg, 0.056 mmol) was used as the amine. LCMS for $C_{23}H_{28}F_3N_7O_3S$ (M+H)f: calculated m/z=540.6; found 540.1.

446

Example 531. 3-(4-Amino-2-(trifluoromethyl)imidazo[2,1-f][1,2,4]triazin-7-yl)-4-methyl-N-(3-methylazetidin-3-yl)benzenesulfonamide Trifluoroacetate

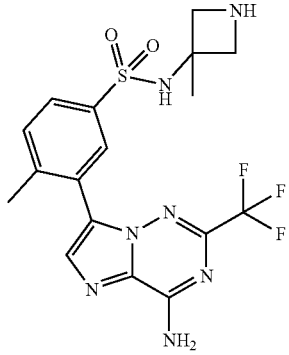 [SMILES: Cc1ccc(S(=O)(=O)NC2(C)CNC2)cc1-c1cnc2c(N)nc(C(F)(F)F)nn12]

Step 1. Benzyl 3-((tert-butoxycarbonyl)amino)-3-methylazetidine-1-carboxylate

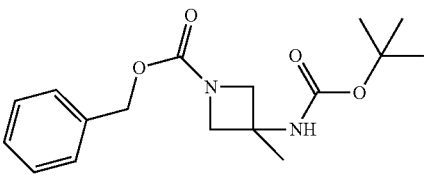 [SMILES: CC1(NC(=O)OC(C)(C)C)CN(C(=O)OCc2ccccc2)C1]

To a 0° C. solution of tert-butyl (3-methylazetidin-3-yl) carbamate (200 mg, 1.074 mmol) and Et$_3$N (0.299 mL, 2.15 mmol) in DCM (6 mL) was added benzyl chloroformate (0.18 mL, 1.3 mmol) drop-wise. The solution was allowed to gradually warm to ambient temperature while stirring for 3 h. The crude reaction mixture was purified by CombiFlash chromatography (25 g silica gel column, eluting with 0-15% methanol/dichloromethane) to afford the desired product (183 mg, 53%). LCMS for $C_{17}H_{24}N_2O_4$ (M+Na)$^+$: calculated m/z=343.4; found 343.1.

Step 2. Benzyl 3-amino-3-methylazetidine-1-carboxylate Trifluoroacetate

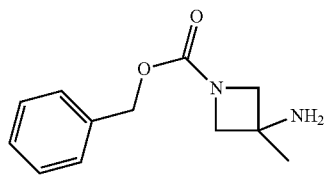 [SMILES: CC1(N)CN(C(=O)OCc2ccccc2)C1]

Benzyl 3-((tert-butoxycarbonyl)amino)-3-methylazetidine-1-carboxylate (56 mg, 0.18 mmol) was dissolved in DCM (1 mL) and to this was added TFA (1 mL) and the resulting solution was stirred at ambient temperature for 4 h. The volatiles were removed in-vacuo and the crude product was azeotropically washed with acetonitrile and placed under high vacuum prior to use in the subsequent reaction. LCMS for $C_{12}H_{16}N_2O_2$ (M+H)+: calculated m/z=221.3; found 221.1.

Step 3. 3-(4-amino-2-(trifluoromethyl)imidazo[2,1-f][1,2,4]triazin-7-yl)-4-methyl-N-(3-methylazetidin-3-yl)benzenesulfonamide Trifluoroacetate A procedure analogous to that outlined in Example 523 steps 4-5 was used with the exception that benzyl 3-amino-3-methylazetidine-1-carboxylate trifluoroacetate (33 mg, 0.130 mmol) was used as the amine. LCMS for $C_{17}H_{18}F_3N_7O_2S$ (M+H)+: calculated m/z=442.4; found 442.2.

Example 532. 3-(4-Amino-2-(trifluoromethyl)imidazo[2,1-f][1,2,4]triazin-7-yl)-N-(1,3-dimethylazetidin-3-yl)-4-methylbenzenesulfonamide

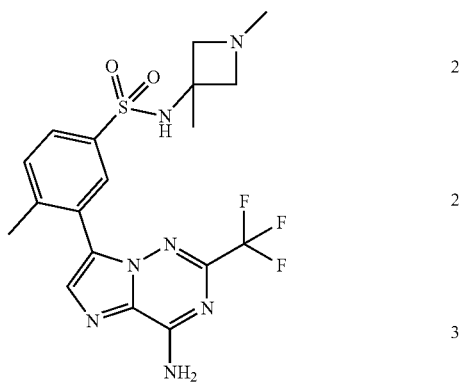

A procedure analogous to that outlined in Example 523 step 6 was used with the exception that 3-(4-amino-2-(trifluoromethyl)imidazo[2,1-f][1,2,4]triazin-7-yl)-4-methyl-N-(3-methylazetidin-3-yl)benzenesulfonamide (18 mg, 0.041 mmol) was used as the amine. The reaction mixture was diluted with MeOH and purified via preparative HPLC on a C-18 column (pH 10, 20-38% MeCN/NH4OH (aq) over 12 min, 60 mL/min) to afford the title compound. LCMS for $C_{18}H_{20}F_3N_7O_2S$ (M+H)+: calculated m/z=456.5; found 456.1.

Example 533. 3-(4-Amino-2-(trifluoromethyl)imidazo[2,1-f][1,2,4]triazin-7-yl)-N-(1,3-dimethylpyrrolidin-3-yl)-4-methylbenzenesulfonamide Trifluoroacetate

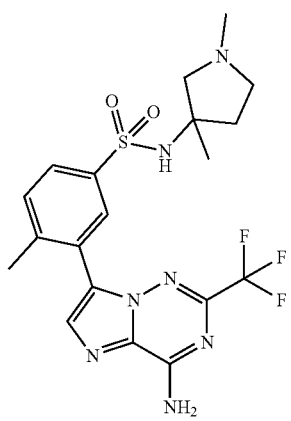 [SMILES: Cc1ccc(S(=O)(=O)NC2(C)CCN(C)C2)cc1-c1cnc2c(N)nc(C(F)(F)F)nn12]

A procedure analogous to that outlined in Example 526 steps 1-2 was used with the exception that tert-butyl (3-methylpyrrolidin-3-yl)carbamate was used as the starting amine. LCMS for $C_{19}H_{22}F_3N_7O_2S$ (M+H)+: calculated m/z=470.5; found 470.2.

Example 534. 3-(4-Aminoimidazo[2,1-f][1,2,4]triazin-7-yl)-N-(4-cyanocuban-1-yl)-4-methylbenzenesulfonamide Trifluoroacetate

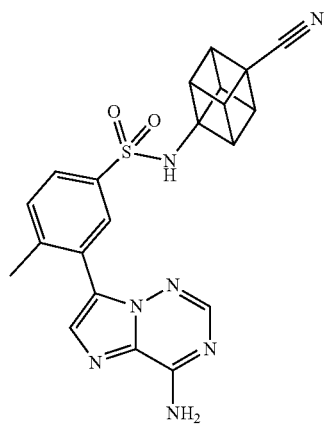 [SMILES: Cc1ccc(S(=O)(=O)NC23C4C5C2C2C3C4C52C#N)cc1-c1cnc2c(N)ncnn12]

Step 1. Methyl-4-aminocubane-1-carboxylate Hydrochloride

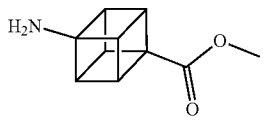

To a solution of methyl-4-((tert-butoxycarbonyl)amino)cubane-1-carboxylate (150 mg, 0.541 mmol) in THF (2.0 mL) was added 4 N HCl in 1,4-dioxane (2.0 mL, 8.0 mmol) and the solution was stirred at ambient temperature overnight. The volatiles were removed in-vacuo and the residue was placed under high vacuum prior to using in the subsequent reaction. LCMS for $C_{10}H_{11}NO_2$ (M+H)+: calculated m/z=178.2; found 178.1.

Step 2. methyl 4-((3-(4-aminoimidazo[2,1-f][1,2,4]triazin-7-yl)-4-methylphenyl)sulfonamido)cubane-1-carboxylate

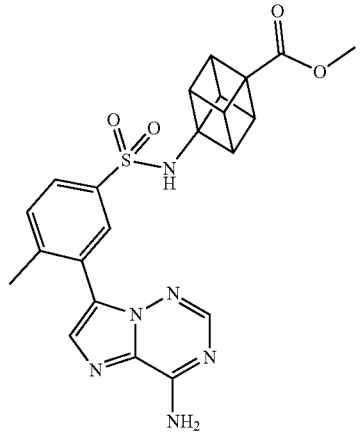

To a solution of methyl-4-aminocubane-1-carboxylate (96 mg, 0.54 mmol), Et₃N (0.30 mL, 2.2 mmol), and DMAP (6.6 mg, 0.054 mmol) in DCM (0.5 mL) was added 3-(4-aminoimidazo[2,1-f][1,2,4]triazin-7-yl)-4-methylbenzenesulfonyl chloride (175 mg, 0.541 mmol) and the resulting solution was stirred at ambient temperature for 6 h. The crude reaction mixture was purified by CombiFlash chromatography (25 g silica gel column, eluting with 0-15% methanol/dichloromethane) to afford the desired product (93 mg, 38%). LCMS for $C_{22}H_{20}N_6O_4S$ $(M+H)^+$: calculated m/z=465.5; found 465.2.

Step 3. 4-((3-(4-aminoimidazo[2,1-f][1,2,4]triazin-7-yl)-4-methylphenyl)sulfonamido)cubane-1-carboxamide

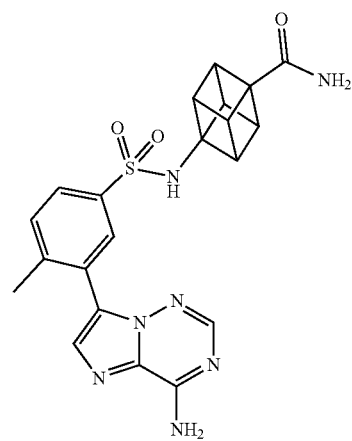 [SMILES: Cc1ccc(S(=O)(=O)NC23C4C5C2C2C3C4C52C(N)=O)cc1-c1cnc2c(N)ncnn12]

A solution of methyl 4-((3-(4-aminoimidazo[2,1-f][1,2,4]triazin-7-yl)-4-methylphenyl)sulfonamido)cubane-1-carboxylate (20 mg, 0.043 mmol) in ammonia in methanol 7 N (1.0 mL, 7.0 mmol) was stirred at ambient temperature overnight. The volatiles were removed in-vacuo and the crude product was used in the subsequent reaction without further purification. LCMS for $C_{21}H_{19}N_7O_3S$ $(M+H)^+$: calculated m/z=450.5; found 450.2.

Step 4. 3-(4-aminoimidazo[2,1-f][1,2,4]triazin-7-yl)-N-(4-cyanocuban-1-yl)-4-methylbenzenesulfonamide Trifluoroacetate

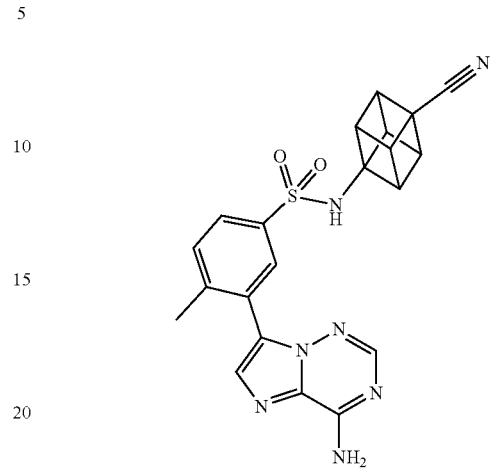

4-((3-(4-aminoimidazo[2,1-f][1,2,4]triazin-7-yl)-4-methylphenyl)sulfonamido)cubane-1-carboxamide formed above was dissolved in anhydrous DCM (1.0 mL) and to this was added sequentially Et₃N (0.024 mL, 0.17 mmol) and trifluoroacetic anhydride (7.0 μL, 0.050 mmol) and the resulting solution was stirred at ambient temperature. After 2 h, a second aliquot of Et₃N and TFAA were added and stirring was continued for an additional 2 h. The reaction mixture was diluted with MeOH and purified via preparative HPLC on a C-18 column (pH 2, eluting with MeCN/0.1% TFA (aq)). LCMS for $C_{21}H_{17}N_7O_2S$ $(M+H)^+$: calculated m/z=432.5; found 432.1.

Example 535. 3-(4-Aminoimidazo[2,1-f][1,2,4]triazin-7-yl)-N-(4-(2-hydroxypropan-2-yl)cuban-1-yl)-4-methylbenzenesulfonamide Trifluoroacetate

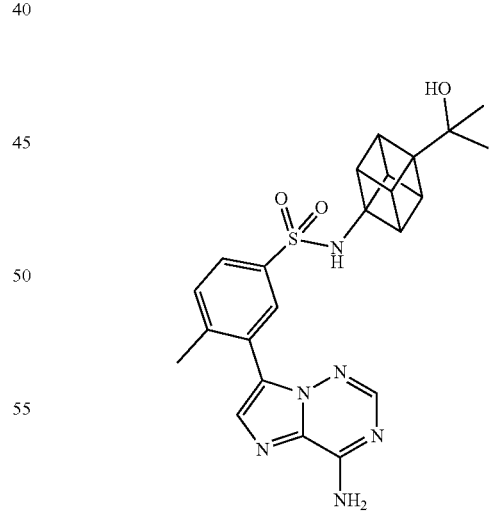

To a solution of methyl 4-((3-(4-aminoimidazo[2,1-][1,2,4]triazin-7-yl)-4-methylphenyl)sulfonamido)cubane-1-carboxylate (20 mg, 0.043 mmol) in anhydrous THF (1.0 mL) was added 3 M methylmagnesium bromide in ether (0.072 mL, 0.22 mmol) and the resulting solution was stirred at ambient temperature overnight. The reaction mixture was diluted with MeOH and purified via preparative HPLC on a C-18 column (pH 2, 16-34% MeCN/0.1% TFA (aq) over 12 min, 60 mL/min) afforded the title compound. LCMS for $C_{23}H_{24}N_6O_3S$ (M+H)$^+$: calculated m/z=465.5; found 465.3.

Example 536. 3-(2-Methyl-5-(methylsulfonyl)phenyl)-6-(tetrahydro-2H-pyran-4-yl)imidazo[1,2-a]pyrazin-8-amine Trifluoroacetate

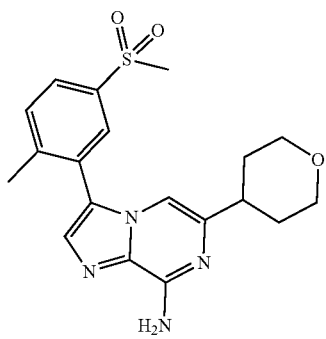 [SMILES: Cc1ccc(S(C)(=O)=O)cc1-c1cnc2c(N)nc(C3CCOCC3)cn12]

Step 1. 6-(3,6-dihydro-2H-pyran-4-yl)-3-(2-methyl-5-(methylsulfonyl)phenyl)imidazo[1,2-a]pyrazin-8-amine

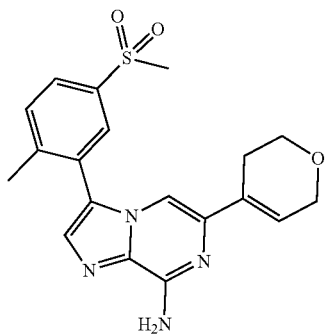 [SMILES: Cc1ccc(S(C)(=O)=O)cc1-c1cnc2c(N)nc(C3=CCOCC3)cn12]

A mixture of 2-(3,6-dihydro-2H-pyran-4-yl)-4,4,5,5-tetramethyl-1,3,2-dioxaborolane (28 mg, 0.13 mmol), 6-bromo-3-(2-methyl-5-(methylsulfonyl)phenyl)imidazo[1,2-a]pyrazin-8-amine (25 mg, 0.065 mmol), Pd(Ph$_3$P)$_4$ (7.5 mg, 0.006 mmol), and K$_2$CO$_3$ (27 mg, 0.20 mmol) in 1,4-dioxane (1.0 mL) was de-gassed and purged with nitrogen several times prior to heating at 110° C. in a sealed vial overnight. The crude reaction mixture was diluted with EtOAc (20 mL) and filtered through a pad of celite. The inorganics were washed thoroughly with EtOAc. The volatiles were removed in-vacuo and the crude product was purified by CombiFlash chromatography (12 g silica gel column, eluting with 0-20% methanol/dichloromethane) to afford the desired product (11 mg, 44%). LCMS for $C_{19}H_{20}N_4O_3S$ (M+H)$^+$: calculated m/z=385.5; found 385.2.

Step 2. 3-(2-Methyl-5-(methylsulfonyl)phenyl)-6-(tetrahydro-2H-pyran-4-yl)imidazo[1,2-a]pyrazin-8-amine Trifluoroacetate A mixture of 6-(3,6-dihydro-2H-pyran-4-yl)-3-(2-methyl-5-(methylsulfonyl)phenyl)imidazo[1,2-a]pyrazin-8-amine (5.5 mg, 0.014 mmol) and palladium hydroxide (2.0 mg, 2.9 μmol) in MeOH (2 mL) and THF (1 mL) was stirred under an atmosphere of H$_2$ (g) via a balloon. The crude reaction mixture was purged with nitrogen, diluted with EtOAc (10 mL), and filtered through a pad of celite. The inorganics were washed thoroughly with EtOAc. The volatiles were removed in-vacuo and the crude product was diluted with MeOH and purified via preparative HPLC on a C-18 column (pH 2, 13-33% MeCN/0.1% TFA (aq) over 5 min, 60 mL/min) to afford the title compound. LCMS for $C_{19}H_{22}N_4O_3S$ (M+H)$^+$: calculated m/z=387.5; found 387.1.

Example 537. 1-(4-(8-Amino-3-(2-methyl-5-(methylsulfonyl)phenyl)imidazo[1,2-a]pyrazin-6-yl)piperidin-1-yl)ethan-1-one Trifluoroacetate

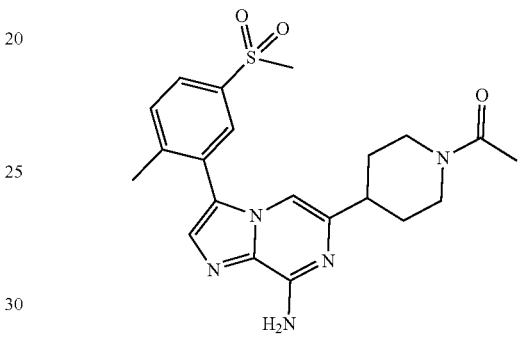

Step 1. 3-(2-methyl-5-(methylsulfonyl)phenyl)-6-(piperidin-4-yl)imidazo[1,2-a]pyrazin-8-amine

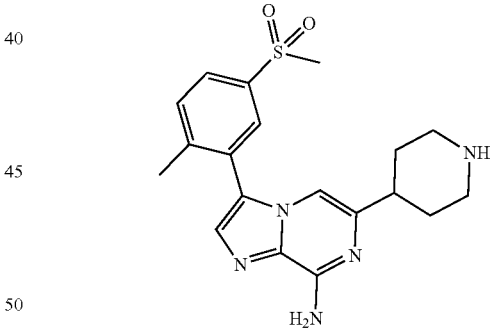

A procedure analogous to that outlined in Example 536, steps 1-2 was used with the exception that benzyl 4-(4,4,5,5-tetramethyl-1,3,2-dioxaborolan-2-yl)-3,6-dihydropyridine-1(2H)-carboxylate (90 mg, 0.26 mmol) was used as the starting boronic ester. LCMS for $C_{19}H_{23}N_5O_2S$ (M+H)$^+$: calculated m/z=386.5; found 386.2.

Step 2. 1-(4-(8-amino-3-(2-methyl-5-(methylsulfonyl)phenyl)imidazo[1,2-a]pyrazin-6-yl)piperidin-1-yl)ethan-1-one Trifluoroacetate To a 0° C. solution of 3-(2-methyl-5-(methylsulfonyl)phenyl)-6-(piperidin-4-yl)imidazo[1,2-a]pyrazin-8-amine (15 mg, 0.039 mmol) in DCM (1 mL) was added a solution of acetyl chloride (3.0 μL, 0.043 mmol) in DCM (0.5 mL)

and the resulting solution was allowed to gradually warm to ambient temperature overnight. The reaction mixture was diluted with MeOH and purified via preparative HPLC on a C-18 column (pH 2, 11-31% MeCN/0.1% TFA (aq) over 5 min, 60 mL/min) to afford the title compound. LCMS for $C_{21}H_{25}N_5O_3S$ (M+H)$^+$: calculated m/z=428.5; found 428.2.

Example 538. Methyl 3-(8-amino-3-(2-methyl-5-(methylsulfonyl)phenyl)imidazo[1,2-a]pyrazin-6-yl)pyrrolidine-1-carboxylate Trifluoroacetate

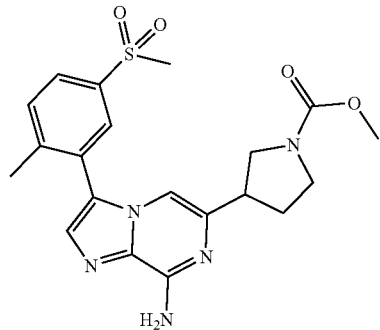

A procedure analogous to that outlined in Example 537 steps 1-2 was used with the exception that tert-butyl 3-(4,4,5,5-tetramethyl-1,3,2-dioxaborolan-2-yl)-2,5-dihydro-1H-pyrrole-1-carboxylate (77 mg, 0.26 mmol) was used as the starting boronic ester in step 1 and methyl chloroformate was used as the acylating reagent in step 2. LCMS for $C_{20}H_{23}N_5O_4S$ (M+H)$^+$: calculated m/z=430.5; found 430.1.

Example 539. 5-((3-(4-Aminoimidazo[2,1-f][1,2,4]triazin-7-yl)-4-methylphenyl)sulfonamido)-N-(2,2,2-trifluoroethyl)picolinamide Trifluoroacetate

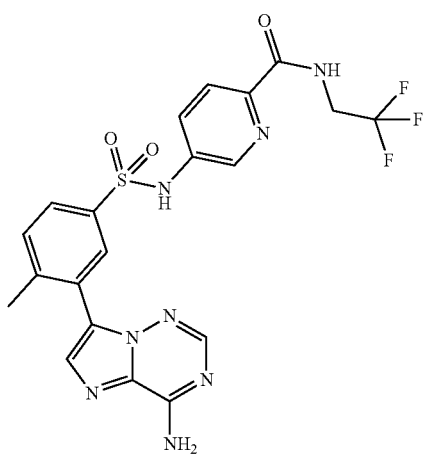 [SMILES: Cc1ccc(S(=O)(=O)Nc2ccc(C(=O)NCC(F)(F)F)nc2)cc1-c1cnc2c(N)ncnn12]

To a solution of 2,2,2-trifluoroethylamine (0.015 mL, 0.19 mmol) in anhydrous DCM (0.5 mL) was added 2.0 M trimethylaluminum in toluene (0.10 mL, 0.20 mmol) and the resulting solution was stirred at ambient temperature for 30 min. This solution was added via syringe to a cloudy solution of methyl 5-((3-(4-aminoimidazo[2,1-f][1,2,4]triazin-7-yl)-4-methylphenyl)sulfonamido)picolinate (14 mg, 0.032 mmol) in anhydrous DCM (0.5 mL). The resulting mixture was stirred overnight. The crude reaction mixture was diluted with DCM (10 mL) and quenched by the careful addition of MeOH followed by saturated NH$_4$Cl (aq) and the resulting slurry was stirred for 10 min. The crude reaction mixture was filtered through a pad of celite and the inorganics were washed thoroughly with DCM. The volatiles were removed in-vacuo and the crude product was diluted with MeOH and purified via preparative HPLC on a C-18 column (pH 2, 23-41% MeCN/0.1% TFA (aq) over 12 min, 60 mL/min) to afford the title compound. LCMS for $C_{20}H_{17}F_3N_8O_3S$ (M+H)$^+$: calculated m/z=507.5; found 507.2.

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, VA) and maintained in RPMI with 10% FBS (Gibco/Life Technologies, Carlsbad, CA). For the assay, THP-1 cells are serum starved overnight in RPMI, then plated in RPMI ($2 \times 10^5$ cells/well in 90 μL) into 96-well flat-bottom tissue culture treated plates (Corning, Corning, NY), in the presence or absence of a concentration range of test compounds. Covered plates are incubated for 2 hours at 37° C., 5% CO$_2$ then treated with or without 10 nM MCP-1(MYBioSource, San Diego, CA) for 15 minutes at 37° C., 5% CO$_2$. Plates are centrifuged at 1600 RPM and supernatants are removed. Cells are lysed in Lysis Buffer (Cell Signaling, Danvers, MA) with Protease Inhibitor (Calbiochem/EMD, Germany), PMSF (Sigma, St Louis MO), HALTS (Thermo Fisher, Rockford, IL) for 30 min on wet ice. Cell lysates are frozen at −80° C. before testing. The lysates are tested in the Human/Mouse/Rat Phospho-RPS6 ELISA (R&D Systems, Inc. Minn, MN). The plate is measured using a microplate reader (SpectraMax M5-Molecular Devices, LLC Sunnyvale, CA) set to 450 nm with a wavelength correction of 540. IC$_{50}$ determination is performed by fitting the curve of inhibitor percent inhibition versus the log of the inhibitor concentration using the GraphPad Prism 5.0 software.

Example B. PI3K-γ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, MA). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, UT). PI3Kγ (p110γ) Recombinant Human Protein was purchased from Life technology (Grand Island, NY). ATP, MgCl$_2$, DTT, EDTA, MOPS and CHAPS were purchased from Sigma-Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of M PIP2, 2 μM ATP, 0.5 μCi [γ-$^{33}$P] ATP, 13 nM PI3Kγ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software. Data for the Examples, obtained using the methods described in Example B, are provided in Table 22.

Example C. PI3Kδ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, MA). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, UT). PI3Kδ (p110δ/p85α) Recombinant Human Protein was purchased from Eurofins (St Charles, MO). ATP, $MgCl_2$, DTT, EDTA, MOPS and CHAPS were purchased from Sigma-Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM $MgCl_2$, 5 mM DTT and CHAPS 0.0300. Reactions were initiated by the addition of ATP, the final reaction mixture consisted of M PIP2, 2 μM ATP, 0.5 μCi [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software.

Data for the Examples, obtained using the methods described in Examples A, B and C, are provided in Table 22.

TABLE 22

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 1 | ++ | +++ | #### |
| 2 | ++ | +++ | #### |
| 3 | ++ | ++++ | — |
| 4 | + | ++ | # |
| 5 | + | ++ | ## |
| 6 | +++ | ++++ | — |
| 7 | ++ | +++ | — |
| 8 | + | ++ | #### |
| 9 | + | +++ | #### |
| 10 | + | ++ | #### |
| 11 | + | +++ | # |
| 12 | + | ++ | ## |

TABLE 22-continued

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 13 | + | ++ | ## |
| 14 | + | + | #### |
| 15 | + | +++ | #### |
| 16 | + | + | # |
| 17 | + | ++ | ## |
| 18 | + | ++ | # |
| 19 | + | ++ | # |
| 20 | + | + | # |
| 21 | + | + | # |
| 22 | + | + | # |
| 23 | + | + | # |
| 24 | + | + | ## |
| 25 | + | ++ | ## |
| 26 | + | + | ## |
| 27 | + | ++ | # |
| 28 | + | ++ | ## |
| 29 | + | ++ | #### |
| 30 | + | + | # |
| 31 | + | + | #### |
| 32 | + | + | # |
| 33 | + | ++ | ### |
| 34 | + | ++ | ## |
| 35 | + | ++ | # |
| 36 | + | + | # |
| 37 | + | + | ## |
| 38 | + | + | # |
| 39 | + | ++ | ## |
| 40 | + | ++ | — |
| 41 | + | ++ | #### |
| 42 | + | +++ | ### |
| 43 | ++ | + | — |
| 44 | +++ | ++++ | — |
| 45 | + | +++ | — |
| 46 | + | ++ | — |
| 47 | + | +++ | #### |
| 48 | + | +++ | #### |
| 49 | + | +++ | #### |
| 50 | + | +++ | #### |
| 51 | + | +++ | #### |
| 52 | + | ++ | ### |
| 53 | + | +++ | #### |
| 54 | + | ++ | #### |
| 55 | + | ++++ | #### |
| 56 | + | +++ | #### |
| 57 | + | +++ | #### |
| 58 | ++ | +++ | #### |
| 59 | + | +++ | #### |
| 60 | + | ++ | ## |
| 61 | + | +++ | ### |
| 62 | + | ++ | ## |
| 63 | + | ++ | ## |
| 64 | + | ++++ | #### |
| 65 | + | ++++ | #### |
| 66 | ++ | ++++ | — |
| 67 | ++ | ++++ | |
| 68 | + | +++ | ### |
| 69 | + | +++ | ## |
| 70 | + | +++ | #### |
| 71 | + | ++++ | ## |
| 72 | + | ++++ | #### |
| 73 | + | +++ | #### |
| 74 | + | +++ | #### |
| 75 | + | + | ## |
| 76 | + | ++ | ## |
| 77 | + | ++ | ## |
| 78 | + | ++ | ### |
| 79 | + | + | ## |
| 80 | + | ++ | ## |
| 81 | + | + | # |
| 82 | + | + | # |
| 83 | ++ | + | #### |
| 84 | + | +++ | #### |
| 85 | + | +++ | ## |
| 86 | + | +++ | #### |
| 87 | + | ++ | ## |
| 88 | + | ++ | # |
| 89 | + | ++ | # |

TABLE 22-continued

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 90 | + | ++ | # |
| 91 | + | ++ | ## |
| 92 | + | ++ | # |
| 93 | + | ++ | ## |
| 94 | + | ++ | ### |
| 95 | + | ++ | ## |
| 96 | + | ++ | #### |
| 97 | + | ++ | ## |
| 98 | + | +++ | ## |
| 99 | + | +++ | #### |
| 100 | + | +++ | ### |
| 101 | + | +++ | #### |
| 102 | + | ++ | ## |
| 103 | + | +++ | #### |
| 104 | + | +++ | ### |
| 105 | + | +++ | — |
| 106 | + | +++ | #### |
| 107 | + | ++ | ### |
| 108 | + | ++ | ## |
| 109 | + | +++ | #### |
| 110 | + | ++ | #### |
| 111 | + | ++ | ## |
| 112 | + | ++ | ## |
| 113 | + | +++ | ## |
| 114 | + | ++ | ## |
| 115 | + | +++ | ## |
| 116 | + | +++ | ## |
| 117 | + | +++ | ## |
| 118 | + | ++ | #### |
| 119 | ++ | ++++ | — |
| 120 | + | ++ | — |
| 121 | ++ | ++++ | #### |
| 122 | + | +++ | ## |
| 123 | + | +++ | ### |
| 124 | + | ++ | ## |
| 125 | + | +++ | #### |
| 126 | + | +++ | ## |
| 127 | + | +++ | ## |
| 128 | + | ++ | ## |
| 129 | + | ++ | # |
| 130 | + | +++ | ### |
| 131 | ++ | +++ | #### |
| 132 | + | ++ | ## |
| 133 | + | +++ | #### |
| 134 | + | +++ | ## |
| 135 | + | ++ | #### |
| 136 | ++ | ++++ | #### |
| 137 | + | +++ | #### |
| 138 | + | +++ | #### |
| 139 | + | +++ | #### |
| 140 | + | +++ | ## |
| 141 | + | ++ | ## |
| 142 | + | +++ | ## |
| 143 | + | ++ | #### |
| 144 | + | ++ | ### |
| 145 | + | ++ | ## |
| 146 | + | ++ | — |
| 147 | + | ++ | ## |
| 148 | ++ | +++ | — |
| 149 | + | ++ | — |
| 150 | + | +++ | — |
| 151 | + | ++ | — |
| 152 | + | +++ | — |
| 153 | + | +++ | — |
| 154 | + | ++++ | — |
| 155 | + | ++ | ## |
| 156 | + | +++ | ### |
| 157 | + | +++ | ### |
| 158 | + | +++ | — |
| 159 | ++ | ++++ | — |
| 160 | ++ | +++ | — |
| 161 | + | ++ | — |
| 162 | + | +++ | — |
| 163 | + | +++ | — |
| 164 | + | +++ | — |
| 165 | + | ++ | ### |
| 166 | + | ++ | ## |
| 167 | ++ | ++++ | — |
| 168 | + | +++ | — |
| 169 | ++ | ++++ | — |
| 170 | + | +++ | — |
| 171 | ++ | +++ | — |
| 172 | ++ | +++ | — |
| 173 | ++ | ++++ | — |
| 174 | ++ | ++++ | — |
| 175 | + | ++ | ## |
| 176 | ++ | ++++ | — |
| 177 | + | +++ | — |
| 178 | + | +++ | — |
| 179 | + | +++ | — |
| 180 | + | ++ | ## |
| 181 | + | + | ## |
| 182 | + | +++ | ### |
| 183 | + | ++ | # |
| 184 | + | + | # |
| 185 | + | ++ | ## |
| 186 | + | ++ | ## |
| 187 | + | ++ | ## |
| 188 | + | + | ## |
| 189 | + | +++ | ### |
| 190 | + | +++ | #### |
| 191 | + | +++ | — |
| 192 | + | ++ | ### |
| 193 | + | +++ | — |
| 194 | + | +++ | ## |
| 195 | + | ++ | — |
| 196 | + | +++ | — |
| 197 | + | +++ | ### |
| 198 | ++ | +++ | — |
| 199 | + | +++ | ### |
| 200 | + | +++ | — |
| 201 | + | +++ | — |
| 202 | ++ | +++ | — |
| 203 | + | ++ | ### |
| 204 | ++ | +++ | — |
| 205 | + | +++ | #### |
| 206 | + | +++ | #### |
| 207 | + | ++ | — |
| 208 | + | +++ | ### |
| 209 | + | +++ | — |
| 210 | + | ++ | ## |
| 211 | + | +++ | ### |
| 212 | + | +++ | ### |
| 213 | + | +++ | — |
| 214 | + | − | — |
| 215 | + | − | — |
| 216 | + | − | — |
| 217 | + | − | — |
| 218 | + | − | — |
| 219 | ++ | − | — |
| 220 | + | − | — |
| 221 | + | − | — |
| 222 | + | − | — |
| 223 | + | − | — |
| 224 | + | − | — |
| 225 | + | − | — |
| 226 | + | − | — |
| 227 | + | − | — |
| 228 | + | − | — |
| 229 | + | − | — |
| 230 | + | − | — |
| 231 | + | − | — |
| 232 | + | − | — |
| 233 | + | − | — |
| 234 | ++ | − | — |
| 235 | + | − | — |
| 236 | + | − | — |
| 237 | + | − | — |
| 238 | ++ | − | — |
| 239 | +++ | − | — |
| 240 | + | − | — |
| 241 | + | − | — |
| 242 | + | − | — |
| 243 | + | − | — |

TABLE 22-continued

| Ex. No. | PI3Kγ IC₅₀ (nM) | PI3Kδ IC₅₀ (nM) | PI3Kγ_THP1_RPS6_ELISA IC₅₀ (nM) |
|---|---|---|---|
| 244 | + | − | — |
| 245 | + | − | — |
| 246 | + | − | — |
| 247 | + | − | — |
| 248 | + | − | — |
| 249 | + | ++ | ## |
| 250 | + | ++ | ## |
| 251 | + | ++ | # |
| 252 | + | ++ | ## |
| 253 | + | ++ | # |
| 254 | + | ++ | # |
| 255 | + | ++ | # |
| 256 | + | ++ | ## |
| 257 | + | +++ | #### |
| 258 | + | ++ | ### |
| 259 | + | ++ | # |
| 260 | + | +++ | — |
| 261 | + | +++ | # |
| 262 | + | + | ## |
| 263 | + | ++ | ## |
| 264 | + | ++ | ## |
| 265 | + | + | # |
| 266 | + | ++ | ## |
| 267 | + | ++ | ## |
| 268 | + | ++ | ## |
| 269 | + | ++ | ## |
| 270 | + | ++ | # |
| 271 | + | ++ | # |
| 272 | + | ++ | ## |
| 273 | + | +++ | ## |
| 274 | + | ++ | # |
| 275 | + | ++ | ## |
| 276 | + | ++ | # |
| 277 | + | ++ | # |
| 278 | + | ++ | # |
| 279 | + | + | # |
| 280 | + | ++ | ## |
| 281 | + | ++ | ## |
| 282 | + | ++ | # |
| 283 | + | ++ | ## |
| 284 | + | ++ | ## |
| 285 | + | ++ | ## |
| 286 | + | ++ | # |
| 287 | + | ++ | # |
| 288 | + | ++ | ## |
| 289 | + | ++ | ## |
| 290 | + | +++ | #### |
| 291 | + | ++ | ### |
| 292 | + | +++ | #### |
| 293 | + | ++ | ## |
| 294 | + | +++ | #### |
| 295 | + | +++ | #### |
| 296 | + | +++ | ## |
| 297 | + | +++ | — |
| 298 | + | +++ | — |
| 299 | + | ++ | ## |
| 300 | + | +++ | — |
| 301 | + | +++ | ## |
| 302 | + | +++ | — |
| 303 | + | +++ | — |
| 304 | + | +++ | — |
| 305 | + | ++ | #### |
| 306 | + | + | # |
| 307 | + | + | ## |
| 308 | + | + | # |
| 309 | + | +++ | ## |
| 310 | + | ++ | # |
| 311 | + | ++ | # |
| 312 | + | ++ | ## |
| 313 | + | ++ | — |
| 314 | + | ++ | ## |
| 315 | + | + | # |
| 316 | + | ++ | # |
| 317 | + | ++ | # |
| 318 | + | ++ | # |
| 319 | + | ++ | # |
| 320 | + | ++ | ## |
| 321 | + | + | # |
| 322 | + | ++ | # |
| 323 | + | ++ | # |
| 324 | + | ++ | # |
| 325 | + | + | ## |
| 326 | + | ++ | # |
| 327 | + | ++ | ## |
| 328 | + | ++ | # |
| 329 | + | ++ | ## |
| 330 | + | + | # |
| 331 | + | ++ | ## |
| 332 | + | ++ | # |
| 333 | + | ++ | # |
| 334 | + | ++ | # |
| 335 | + | ++ | ## |
| 336 | + | ++ | ## |
| 337 | + | ++ | ## |
| 338 | + | ++ | ## |
| 339 | + | ++ | ## |
| 340 | + | ++ | ## |
| 341 | + | ++ | ## |
| 342 | + | ++ | ## |
| 343 | + | + | # |
| 344 | + | + | ## |
| 345 | + | ++ | #### |
| 346 | + | ++ | ## |
| 347 | + | ++ | # |
| 348 | + | + | ## |
| 349 | + | +++ | — |
| 350 | ++ | +++ | — |
| 351 | + | +++ | — |
| 352 | + | +++ | — |
| 353 | + | +++ | #### |
| 354 | + | +++ | #### |
| 355 | + | ++ | ## |
| 356 | + | ++ | # |
| 357 | + | − | — |
| 358 | + | − | — |
| 359 | + | ++ | #### |
| 360 | ++ | ++ | #### |
| 361 | ++ | ++ | — |
| 362 | + | ++ | # |
| 363 | + | +++ | ## |
| 364 | + | ++ | # |
| 365 | + | ++ | ## |
| 366 | + | ++ | — |
| 367 | + | ++ | #### |
| 368 | + | ++ | — |
| 369 | + | ++ | — |
| 370 | + | ++ | # |
| 371 | + | ++ | ## |
| 372 | + | +++ | — |
| 373 | +++ | +++ | — |
| 374 | + | +++ | ### |
| 375 | + | ++ | # |
| 376 | + | ++ | #### |
| 377 | + | + | # |
| 378 | + | ++ | # |
| 379 | + | ++ | # |
| 380 | + | +++ | #### |
| 381 | + | ++ | ## |
| 382 | ++ | +++ | — |
| 383 | + | + | # |
| 384 | + | + | ### |
| 385 | + | + | ## |
| 386 | + | ++ | # |
| 387 | + | ++ | # |
| 388 | + | ++ | #### |
| 389 | + | + | # |
| 390 | + | ++ | ## |
| 391 | + | ++ | # |
| 392 | + | + | ## |
| 393 | + | +++ | ## |
| 394 | + | ++ | ## |
| 395 | + | ++ | ## |
| 396 | + | ++ | ### |
| 397 | + | ++ | # |

TABLE 22-continued

| Ex. No. | PI3Kγ IC₅₀ (nM) | PI3Kδ IC₅₀ (nM) | PI3Kγ_THP1_RPS6_ELISA IC₅₀ (nM) |
|---|---|---|---|
| 398 | + | ++ | ### |
| 399 | + | + | #### |
| 400 | + | + | # |
| 401 | + | ++++ | — |
| 402 | + | ++ | ## |
| 403 | + | ++ | # |
| 404 | + | + | # |
| 405 | + | ++ | # |
| 406 | + | + | # |
| 407 | +++ | ++++ | — |
| 408 | + | ++ | #### |
| 409 | + | ++ | ## |
| 410 | + | + | # |
| 411 | + | ++ | ## |
| 412 | + | ++ | # |
| 413 | + | ++ | # |
| 414 | + | + | ## |
| 415 | + | ++ | # |
| 416 | + | ++ | # |
| 417 | + | ++ | ### |
| 418 | + | ++ | #### |
| 419 | + | = | #### |
| 420 | + | ++ | ## |
| 421 | + | + | # |
| 422 | + | + | # |
| 423 | + | + | # |
| 424 | + | ++ | ## |
| 425 | + | ++ | # |
| 426 | + | ++ | ## |
| 427 | + | ++ | ## |
| 428 | + | ++ | ## |
| 429 | + | ++ | ## |
| 430 | + | ++ | ## |
| 431 | + | ++ | ## |
| 432 | + | ++ | ## |
| 433 | + | ++ | ## |
| 434 | + | ++ | ## |
| 435 | + | ++ | ### |
| 436 | + | ++ | ## |
| 437 | + | ++ | ## |
| 438 | + | ++ | # |
| 439 | + | +++ | ### |
| 440 | + | ++ | ## |
| 441 | + | ++ | ## |
| 442 | + | +++ | ## |
| 443 | + | + | ## |
| 444 | + | + | ## |
| 445 | + | ++ | ## |
| 446 | + | ++ | ## |
| 447 | + | +++ | ### |
| 448 | + | +++ | ## |
| 449 | + | ++ | #### |
| 450 | + | ++ | ### |
| 451 | + | ++ | ### |
| 452 | ++++ | ++ | — |
| 453 | ++ | ++ | — |
| 454 | ++ | +++ | — |
| 455 | +++ | +++ | — |
| 456 | ++ | ++ | — |
| 457 | ++ | ++ | — |
| 458 | +++ | ++++ | — |
| 459 | ++ | ++++ | — |
| 460 | +++ | ++++ | — |
| 461 | ++ | +++ | — |
| 462 | + | +++ | — |
| 463 | + | ++ | ## |
| 464 | + | + | # |
| 465 | + | +++ | ## |
| 466 | + | + | # |
| 467 | + | ++ | # |
| 468 | + | ++ | ## |
| 469 | + | ++ | ## |
| 470 | + | +++ | — |
| 471 | ++ | +++ | #### |
| 472 | + | ++ | ## |
| 473 | + | +++ | — |
| 474 | + | ++ | ## |
| 475 | + | ++ | ### |
| 476 | + | ++ | ## |
| 477 | + | ++ | ## |
| 478 | ++ | +++ | — |
| 479 | + | ++ | — |
| 480 | + | ++ | — |
| 481 | + | ++ | ## |
| 482 | + | +++ | #### |
| 483 | + | + | #### |
| 484 | + | ++ | ## |
| 485 | + | ++ | ## |
| 486 | + | ++ | ## |
| 487 | + | ++ | — |
| 488 | + | ++ | ## |
| 489 | + | ++ | ## |
| 490 | + | ++ | # |
| 491 | + | ++ | ## |
| 492 | + | +++ | ### |
| 493 | ++ | ++++ | #### |
| 494 | + | +++ | #### |
| 495 | + | +++ | #### |
| 496 | + | +++ | ### |
| 497 | ++ | +++ | — |
| 498 | + | +++ | — |
| 499 | ++ | +++ | — |
| 500 | + | +++ | ## |
| 501 | + | +++ | — |
| 502 | + | + | ## |
| 503 | + | + | ## |
| 504 | + | + | # |
| 505 | + | + | ## |
| 506 | + | + | # |
| 507 | + | ++ | ### |
| 508 | + | ++ | ### |
| 509 | + | +++ | #### |
| 510 | + | ++ | #### |
| 511 | +++ | ++++ | — |
| 512 | + | ++++ | — |
| 513 | + | ++ | ## |
| 514 | ++ | +++ | — |
| 515 | ++ | ++++ | — |
| 516 | + | + | # |
| 517 | + | +++ | — |
| 518 | ++ | +++ | ## |
| 519 | ++ | + | #### |
| 520 | + | − | — |
| 521 | + | − | — |
| 522 | + | − | — |
| 523 | + | − | — |
| 524 | + | − | — |
| 525 | ++ | − | — |
| 526 | + | − | — |
| 527 | + | − | — |
| 528 | + | − | — |
| 529 | ++ | − | — |
| 530 | ++ | − | — |
| 531 | + | − | — |
| 532 | + | − | — |
| 533 | + | − | — |
| 534 | + | − | — |
| 535 | + | − | — |
| 536 | + | − | — |
| 537 | + | − | — |
| 538 | ++ | − | — |
| 539 | + | − | — |

+ refers to IC₅₀ of ≤100 nM;
++ refers to IC₅₀ of ≤500 nM;
+++ refers to an IC₅₀ of <2000 nM;
++++ refers to an IC₅₀ of ≥2000 nM.
# refers to IC₅₀ of ≤100 nM;
## refers to IC₅₀ of ≤500 nM;
### refers to IC₅₀ of <1000 nM;
#### refers to an IC₅₀ of ≥1000 nM.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound, which is 3-(4-aminoimidazo[2,1-f][1,2,4]triazin-7-yl)-N-(4-cyanobicyclo[2.1.1]hexan-1-yl)-4-(methyl-$d_3$)benzenesulfonamide, or a pharmaceutically acceptable salt thereof.

2. The compound of claim 1, which is 3-(4-aminoimidazo[2,1-f][1,2,4]triazin-7-yl)-N-(4-cyanobicyclo[2.1.1]hexan-1-yl)-4-(methyl-$d_3$)benzenesulfonamide.

3. The compound of claim 1, which is a crystalline free base of 3-(4-aminoimidazo[2,1-f][1,2,4]triazin-7-yl)-N-(4-cyanobicyclo[2.1.1]hexan-1-yl)-4-(methyl-$d_3$)benzenesulfonamide.

4. The compound of claim 3, having at least one XRPD peak, in terms of 2θ, selected from 8.4°±0.2°, 15.3°±0.2°, 16.9°±0.2°, 17.3°±0.2°, 17.4°±0.2°, 17.6°±0.2°, 19.4°±0.2°, 20.6°±0.2°, 24.9°±0.2°, and 26.5°±0.2°.

5. The compound of claim 3, having at least two XRPD peaks, in terms of 2θ, selected from 8.4°±0.2°, 15.3°±0.2°, 16.9°±0.2°, 17.3°±0.2°, 17.4°±0.2°, 17.6°±0.2°, 19.4°±0.2°, 20.6°±0.2°, 24.9°±0.2°, and 26.5°±0.2°.

6. The compound of claim 3, having at least three XRPD peaks, in terms of 2θ, selected from 8.4°±0.2°, 15.3°±0.2°, 16.9°±0.2°, 17.3°±0.2°, 17.4°±0.2°, 17.6°±0.2°, 19.4°±0.2°, 20.6°±0.2°, 24.9°±0.2°, and 26.5°±0.2°.

7. A pharmaceutical composition comprising the compound of claim 1, or a pharmaceutically acceptable salt thereof, and a pharmaceutically acceptable carrier.

8. A compound, which is 3-(4-aminoimidazo[2,1-f][1,2,4]triazin-7-yl)-N-(4-cyanobicyclo[2.1.1]hexan-1-yl)-4-(methyl-$d_3$)benzenesulfonamide crystalline benzenesulfonic acid salt.

9. The compound of claim 8, having at least one XRPD peak, in terms of 2θ, selected from 14.8°±0.2°, 15.8°±0.2°, 16.5°±0.2°, 16.7°±0.2°, 17.1°±0.2°, 18.6°±0.2°, 18.9°±0.2°, 19.2°±0.2°, 19.8°±0.2°, 22.2°±0.2°, 22.8°±0.2°, 23.6°±0.2°, 24.5°±0.2°, 24.9°±0.2°, and 25.9°±0.2°.

10. The compound of claim 8, having at least two XRPD peaks, in terms of 2θ, selected from 14.8°±0.2°, 15.8°±0.2°, 16.5°±0.2°, 16.7°±0.2°, 17.1°±0.2°, 18.6°±0.2°, 18.9°±0.2°, 19.2°±0.2°, 19.8°±0.2°, 22.2°±0.2°, 22.8°±0.2°, 23.6°±0.2°, 24.5°±0.2°, 24.9°±0.2°, and 25.9°±0.2°.

11. The compound of claim 8, having at least three XRPD peaks, in terms of 2θ, selected from 14.8°±0.2°, 15.8°±0.2°, 16.5°±0.2°, 16.7°±0.2°, 17.1°±0.2°, 18.6°±0.2°, 18.9°±0.2°, 19.2°±0.2°, 19.8°±0.2°, 22.2°±0.2°, 22.8°±0.2°, 23.6°±0.2°, 24.5°±0.2°, 24.9°±0.2°, and 25.9°±0.2°.

12. A pharmaceutical composition comprising the compound of claim 8 and a pharmaceutically acceptable carrier.

13. A compound, which is 3-(4-aminoimidazo[2,1-f][1,2,4]triazin-7-yl)-N-(4-cyanobicyclo[2.1.1]hexan-1-yl)-4-(methyl-$d_3$)benzenesulfonamide crystalline hydrochloric acid salt.

14. The compound of claim 13, having at least one XRPD peak, in terms of 2θ, selected from 9.9°±0.2°, 13.4°±0.2°, 14.1°±0.2°, 15.8°±0.2°, 16.1°±0.2°, 16.2°±0.2°, 17.4°±0.2°, 18.0°±0.2°, 21.7°±0.2°, 22.0°±0.2°, 22.4°±0.2°, 23.4°±0.2°, 24.5°±0.2°, 25.3°±0.2°, 26.4°±0.2°, 26.8°±0.2°, and 27.9°±0.2°.

15. The compound of claim 13, having at least two XRPD peaks, in terms of 2θ, selected from 9.9°±0.2°, 13.4°±0.2°, 14.1°±0.2°, 15.8°±0.2°, 16.1°±0.2°, 16.2°±0.2°, 17.4°±0.2°, 18.0°±0.2°, 21.7°±0.2°, 22.0°±0.2°, 22.4°±0.2°, 23.4°±0.2°, 24.5°±0.2°, 25.3°±0.2°, 26.4°±0.2°, 26.8°±0.2°, and 27.9°±0.2°.

16. The compound of claim 13, having at least three XRPD peaks, in terms of 2θ, selected from 9.9°±0.2°, 13.4°±0.2°, 14.1°±0.2°, 15.8°±0.2°, 16.1°±0.2°, 16.2°±0.2°, 17.4°±0.2°, 18.0°±0.2°, 21.7°±0.2°, 22.0°±0.2°, 22.4°±0.2°, 23.4°±0.2°, 24.5°±0.2°, 25.3°±0.2°, 26.4°±0.2°, 26.8°±0.2°, and 27.9°±0.2°.

17. A pharmaceutical composition comprising the compound of claim 13 and a pharmaceutically acceptable carrier.

18. A compound, which is 3-(4-aminoimidazo[2,1-f][1,2,4]triazin-7-yl)-N-(3-cyanobicyclo[1.1.1]pentan-1-yl)-4-methylbenzenesulfonamide, or a pharmaceutically acceptable salt thereof.

19. The compound of claim 18, which is 3-(4-aminoimidazo[2,1-f][1,2,4]triazin-7-yl)-N-(3-cyanobicyclo[1.1.1]pentan-1-yl)-4-methylbenzenesulfonamide.

20. A pharmaceutical composition comprising the compound of claim 18, or a pharmaceutically acceptable salt thereof, and a pharmaceutically acceptable carrier.

* * * * *